United States Patent
Costa et al.

(10) Patent No.: US 12,268,741 B2
(45) Date of Patent: Apr. 8, 2025

(54) ANTIBODIES AND CHIMERIC ANTIGEN RECEPTORS SPECIFIC FOR RECEPTOR TYROSINE KINASE LIKE ORPHAN RECEPTOR 1 (ROR1)

(71) Applicant: Juno Therapeutics, Inc., Seattle, WA (US)

(72) Inventors: Andreia Costa, Seattle, WA (US); Rupesh Amin, Seattle, WA (US); Jenna Bailey, Seattle, WA (US); Samriti Bedi, Newcastle, WA (US); Brian Belmont, Seattle, WA (US); Aye Chen, Seattle, WA (US); Stephen Jacob Goldfless, Seattle, WA (US); Eric Jeffery, Seattle, WA (US); Yue Jiang, Seattle, WA (US); Yeonjoo Oh, Seattle, WA (US); Madeline Williams, Seattle, WA (US); Collin Hauskins, Seattle, WA (US); Catherine Sierra, Seattle, WA (US)

(73) Assignee: Juno Therapeutics, Inc., Seattle, WA (US)

( * ) Notice: Subject to any disclaimer, the term of this patent is extended or adjusted under 35 U.S.C. 154(b) by 668 days.

(21) Appl. No.: 17/421,365

(22) PCT Filed: Jan. 28, 2020

(86) PCT No.: PCT/US2020/015489
§ 371 (c)(1),
(2) Date: Jul. 7, 2021

(87) PCT Pub. No.: WO2020/160050
PCT Pub. Date: Aug. 6, 2020

(65) Prior Publication Data
US 2022/0096651 A1    Mar. 31, 2022

Related U.S. Application Data

(60) Provisional application No. 62/798,456, filed on Jan. 29, 2019.

(51) Int. Cl.
| | |
|---|---|
| A61K 47/68 | (2017.01) |
| A61K 35/17 | (2015.01) |
| A61K 39/00 | (2006.01) |
| A61K 39/395 | (2006.01) |
| A61P 35/00 | (2006.01) |
| C12N 5/0783 | (2010.01) |
| C12N 5/10 | (2006.01) |
| C12N 15/62 | (2006.01) |
| C12N 15/63 | (2006.01) |

(52) U.S. Cl.
CPC .... *A61K 39/39558* (2013.01); *A61K 39/4611* (2023.05); *A61K 39/4631* (2023.05); *A61K 39/464402* (2023.05); *A61K 47/6851* (2017.08); *A61P 35/00* (2018.01); *C12N 5/0636* (2013.01); *C12N 5/10* (2013.01); *C12N 15/62* (2013.01); *C12N 15/63* (2013.01); *A61K 2239/31* (2023.05); *A61K 2239/38* (2023.05); *A61K 2239/48* (2023.05); *A61K 2239/49* (2023.05); *A61K 2239/55* (2023.05)

(58) Field of Classification Search
None
See application file for complete search history.

(56) References Cited

U.S. PATENT DOCUMENTS

| | | |
|---|---|---|
| 4,235,871 A | 11/1980 | Papahadjopoulos et al. |
| 4,452,773 A | 6/1984 | Molday |
| 4,501,728 A | 2/1985 | Geho et al. |
| 4,690,915 A | 9/1987 | Rosenberg |
| 4,795,698 A | 1/1989 | Owen et al. |
| 4,837,028 A | 6/1989 | Allen |
| 5,019,369 A | 5/1991 | Presant et al. |
| 5,087,616 A | 2/1992 | Myers et al. |
| 5,200,084 A | 4/1993 | Liberti et al. |
| 5,208,020 A | 5/1993 | Chari et al. |
| 5,219,740 A | 6/1993 | Miller et al. |
| 5,283,173 A | 2/1994 | Fields et al. |
| 5,416,064 A | 5/1995 | Chari et al. |
| 5,424,297 A | 6/1995 | Rubio et al. |

(Continued)

FOREIGN PATENT DOCUMENTS

| | | |
|---|---|---|
| CN | 107557337 | 1/2018 |
| EP | 0452342 | 10/1991 |

(Continued)

OTHER PUBLICATIONS

US 8,252,592 B2, 08/2012, Sadelain (withdrawn)
(Continued)

*Primary Examiner* — Amy E Juedes
*Assistant Examiner* — Peter Johansen
(74) *Attorney, Agent, or Firm* — Morrison & Foerster LLP

(57) ABSTRACT

Provided are receptor tyrosine kinase-like orphan receptor 1 (ROR1)-binding molecules, in particular, to human antibodies specific for ROR1, including antibody fragments. The present disclosure further relates to recombinant receptors, including chimeric antigen receptors (CARs) that contain such antibodies or fragments, and polynucleotides that encode the antibodies, antigen-binding fragments or receptors specific for ROR1. The disclosure further relates to genetically engineered cells, containing such ROR1-binding proteins and receptors, and related methods and uses thereof in adoptive cell therapy.

49 Claims, 45 Drawing Sheets
Specification includes a Sequence Listing.

(56) References Cited

U.S. PATENT DOCUMENTS

| | | |
|---|---|---|
| 5,468,614 A | 11/1995 | Fields et al. |
| 5,504,090 A | 4/1996 | Neely et al. |
| 5,545,627 A | 8/1996 | Jacobson et al. |
| 5,565,566 A | 10/1996 | Olsson |
| 5,635,483 A | 6/1997 | Pettit et al. |
| 5,635,517 A | 6/1997 | Muller et al. |
| 5,670,501 A | 9/1997 | Peck et al. |
| 5,712,291 A | 1/1998 | D'Amato |
| 5,712,374 A | 1/1998 | Kuntsmann et al. |
| 5,714,586 A | 2/1998 | Kunstmann et al. |
| 5,739,116 A | 4/1998 | Hamann et al. |
| 5,767,285 A | 6/1998 | Hamann et al. |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,786,360 A | 7/1998 | Neely |
| 5,798,368 A | 8/1998 | Muller et al. |
| 5,861,405 A | 1/1999 | Jacobson et al. |
| 5,877,296 A | 3/1999 | Hamann et al. |
| 5,981,524 A | 11/1999 | Peck et al. |
| 6,040,177 A | 3/2000 | Riddell et al. |
| 6,060,273 A | 5/2000 | Dirks et al. |
| 6,066,642 A | 5/2000 | Jacobson et al. |
| 6,111,090 A | 8/2000 | Gorman et al. |
| 6,117,998 A | 9/2000 | Neely |
| 6,207,453 B1 | 3/2001 | Maass et al. |
| 6,232,297 B1 | 5/2001 | Linden et al. |
| 6,281,230 B1 | 8/2001 | Muller et al. |
| 6,313,131 B1 | 11/2001 | Lawyer |
| 6,316,471 B1 | 11/2001 | Muller et al. |
| 6,322,771 B1 | 11/2001 | Linden et al. |
| 6,326,390 B1 | 12/2001 | Leung et al. |
| 6,335,349 B1 | 1/2002 | Muller et al. |
| 6,380,239 B1 | 4/2002 | Muller et al. |
| 6,395,754 B1 | 5/2002 | Muller et al. |
| 6,403,613 B1 | 6/2002 | Man et al. |
| 6,410,319 B1 | 6/2002 | Raubitschek et al. |
| 6,451,995 B1 | 9/2002 | Cheung et al. |
| 6,458,810 B1 | 10/2002 | Muller et al. |
| 6,476,052 B1 | 11/2002 | Muller et al. |
| 6,602,684 B1 | 8/2003 | Umana et al. |
| 6,630,579 B2 | 10/2003 | Chari et al. |
| 7,025,962 B1 | 4/2006 | Gorman et al. |
| 7,070,995 B2 | 7/2006 | Jensen |
| 7,091,353 B2 | 8/2006 | Robarge et al. |
| 7,132,255 B2 | 11/2006 | Blumberg |
| 7,141,575 B2 | 11/2006 | Gillespie et al. |
| 7,244,759 B2 | 7/2007 | Muller et al. |
| 7,265,209 B2 | 9/2007 | Jensen |
| 7,320,991 B2 | 1/2008 | Figg et al. |
| 7,354,762 B2 | 4/2008 | Jensen |
| 7,405,219 B2 | 7/2008 | Gillespie et al. |
| 7,446,179 B2 | 11/2008 | Jensen et al. |
| 7,446,190 B2 | 11/2008 | Sadelain et al. |
| 7,446,191 B2 | 11/2008 | Jensen |
| 7,498,298 B2 | 3/2009 | Doronina et al. |
| 7,521,541 B2 | 4/2009 | Eigenbrot et al. |
| 7,618,632 B2 | 11/2009 | Collins et al. |
| 7,812,135 B2 | 10/2010 | Smith et al. |
| 7,855,275 B2 | 12/2010 | Eigenbrot et al. |
| 7,943,743 B2 | 5/2011 | Korman et al. |
| 8,008,449 B2 | 8/2011 | Korman et al. |
| 8,080,554 B2 | 12/2011 | Sitkovsky et al. |
| 8,124,084 B2 | 2/2012 | Lefrancois et al. |
| 8,324,353 B2 | 12/2012 | Jensen |
| 8,339,645 B2 | 12/2012 | Jun |
| 8,354,509 B2 | 1/2013 | Carven et al. |
| 8,388,967 B2 | 3/2013 | Smith et al. |
| 8,389,282 B2 | 3/2013 | Sadelain et al. |
| 8,497,118 B2 | 7/2013 | Jensen |
| 8,586,023 B2 | 11/2013 | Shiku et al. |
| 8,591,886 B2 | 11/2013 | Ponath et al. |
| 8,609,089 B2 | 12/2013 | Langermann et al. |
| 8,716,301 B2 | 5/2014 | Sitkovsky et al. |
| 8,716,315 B2 | 5/2014 | Figg et al. |
| 8,802,374 B2 | 8/2014 | Jensen |
| 8,883,500 B2 | 11/2014 | Sitkovsky et al. |
| 8,911,993 B2 | 12/2014 | June et al. |
| 8,987,279 B2 | 3/2015 | Bamford et al. |
| 10,736,918 B2 | 8/2020 | Jensen et al. |
| 10,780,118 B2 | 9/2020 | Jensen et al. |
| 10,865,242 B2 | 12/2020 | Jensen |
| 10,869,889 B2 | 12/2020 | Jenen et al. |
| 10,889,652 B2 | 1/2021 | Chen et al. |
| 10,968,275 B2 | 4/2021 | Balakrishnan et al. |
| 11,149,073 B2 | 10/2021 | Hudecek et al. |
| 11,919,970 B2 | 3/2024 | Chen et al. |
| 11,932,691 B2 | 3/2024 | Balakrishnan et al. |
| 2002/0131960 A1 | 9/2002 | Sadelain et al. |
| 2002/0164328 A1 | 11/2002 | Shinkawa et al. |
| 2003/0045552 A1 | 3/2003 | Robarge et al. |
| 2003/0115614 A1 | 6/2003 | Kanda et al. |
| 2003/0157108 A1 | 8/2003 | Presta |
| 2003/0148982 A1 | 9/2003 | Brenner et al. |
| 2003/0170238 A1 | 9/2003 | Gruenberg et al. |
| 2004/0047858 A1 | 3/2004 | Blumberg et al. |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0132140 A1 | 7/2004 | Satoh et al. |
| 2004/0259150 A1 | 12/2004 | Nakamura |
| 2005/0031613 A1 | 2/2005 | Nakamura |
| 2005/0123546 A1 | 6/2005 | Umana et al. |
| 2005/0272916 A1 | 12/2005 | Hanai |
| 2006/0270045 A1 | 11/2006 | Cregg et al. |
| 2007/0116690 A1 | 5/2007 | Yang et al. |
| 2007/0134759 A1 | 6/2007 | Nishiya |
| 2008/0241884 A1 | 10/2008 | Shitara |
| 2009/0082299 A1 | 3/2009 | Felber et al. |
| 2009/0203078 A1 | 8/2009 | Ogawa et al. |
| 2010/0028330 A1 | 2/2010 | Collins et al. |
| 2010/0247521 A1 | 9/2010 | Jones et al. |
| 2011/0003380 A1 | 1/2011 | Miltenyi et al. |
| 2011/0081311 A1 | 4/2011 | Pavlakis et al. |
| 2011/0129478 A1 | 6/2011 | Okano et al. |
| 2012/0039906 A1 | 2/2012 | Olive |
| 2012/0058051 A1 | 3/2012 | Rader et al. |
| 2012/0114649 A1 | 5/2012 | Langermann et al. |
| 2012/0141413 A1 | 6/2012 | Pavlakis et al. |
| 2012/0177598 A1 | 7/2012 | Lefrancois et al. |
| 2013/0149337 A1 | 6/2013 | Cooper et al. |
| 2013/0156774 A1 | 6/2013 | Kuchroo et al. |
| 2013/0251642 A1 | 9/2013 | Rader et al. |
| 2013/0251723 A1 | 9/2013 | Rohlff et al. |
| 2013/0287748 A1 | 10/2013 | June et al. |
| 2014/0056922 A1 | 2/2014 | Sitkovsky et al. |
| 2014/0271618 A1 | 9/2014 | Markel et al. |
| 2014/0377240 A1 | 12/2014 | Sitkovsky et al. |
| 2015/0210769 A1 | 7/2015 | Freeman et al. |
| 2015/0218274 A1 | 8/2015 | Sabatos-Peyton et al. |
| 2015/0259420 A1 | 9/2015 | Triebel et al. |
| 2016/0208018 A1 | 7/2016 | Chen et al. |
| 2016/0313300 A1 | 10/2016 | Trotter et al. |
| 2018/0265593 A1 | 9/2018 | Chen et al. |
| 2018/0340026 A1 | 11/2018 | Rader et al. |
| 2021/0052649 A1 | 2/2021 | Jensen et al. |
| 2023/0324408 A1 | 10/2023 | Hauskins et al. |

FOREIGN PATENT DOCUMENTS

| | | |
|---|---|---|
| EP | 1866339 | 12/2007 |
| EP | 2537416 | 12/2012 |
| JP | WO 2005/053742 | 6/2007 |
| WO | WO 1992/008796 | 5/1992 |
| WO | WO 1992/015322 | 9/1992 |
| WO | WO 1994/011026 | 5/1994 |
| WO | WO 1994/028143 | 12/1994 |
| WO | WO 1995/021528 | 8/1995 |
| WO | WO 1997/030087 | 8/1997 |
| WO | WO 1998/003502 | 1/1998 |
| WO | WO 1998/054170 | 12/1998 |
| WO | WO 1998/058964 | 12/1998 |

(56) References Cited

FOREIGN PATENT DOCUMENTS

| | | |
|---|---|---|
| WO | WO 1999/20758 | 4/1999 |
| WO | WO 1999/022764 | 5/1999 |
| WO | WO 1999/040196 | 8/1999 |
| WO | WO 1999/052552 | 10/1999 |
| WO | WO 2000/014257 | 3/2000 |
| WO | WO 2000/061739 | 10/2000 |
| WO | WO 2001/03720 | 1/2001 |
| WO | WO 2002/055083 | 7/2002 |
| WO | WO 2002/059106 | 8/2002 |
| WO | WO 2002/068414 | 9/2002 |
| WO | WO 2002/077029 | 10/2002 |
| WO | WO 2003/011878 | 2/2003 |
| WO | WO 2003/084570 | 10/2003 |
| WO | WO 2003/085107 | 10/2003 |
| WO | WO 2003/085119 | 10/2003 |
| WO | WO 2004/056312 | 7/2004 |
| WO | WO 2005/007190 | 1/2005 |
| WO | WO 2005/035586 | 4/2005 |
| WO | WO 2005/035778 | 4/2005 |
| WO | WO 2005/055808 | 6/2005 |
| WO | WO 2005/115451 | 12/2005 |
| WO | WO 2006/083289 | 8/2006 |
| WO | WO 2006/121168 | 11/2006 |
| WO | WO 2007/005874 | 1/2007 |
| WO | WO 2007/133822 | 11/2007 |
| WO | WO 2008/147482 | 12/2008 |
| WO | WO 2008/154252 | 12/2008 |
| WO | WO 2009/072003 | 6/2009 |
| WO | WO 2009/101611 | 8/2009 |
| WO | WO 2009/114335 | 9/2009 |
| WO | WO 2010/003118 | 1/2010 |
| WO | WO 2010/019570 | 2/2010 |
| WO | WO 2010/025177 | 3/2010 |
| WO | WO 2010/027827 | 3/2010 |
| WO | WO 2010/033140 | 3/2010 |
| WO | WO 2010/077634 | 7/2010 |
| WO | WO 2010/124188 | 10/2010 |
| WO | WO 2010/125571 | 11/2010 |
| WO | WO 2011/014469 | 2/2011 |
| WO | WO 2011/028683 | 3/2011 |
| WO | WO 2011/051726 | 5/2011 |
| WO | WO 2011/056894 | 5/2011 |
| WO | WO 2011/066342 | 6/2011 |
| WO | WO 2011/159847 | 12/2011 |
| WO | WO 2012/012695 | 1/2012 |
| WO | WO 2012/045085 | 4/2012 |
| WO | WO 2012/048340 | 4/2012 |
| WO | WO 2012/048341 | 4/2012 |
| WO | WO 2012/076066 | 6/2012 |
| WO | WO 2012/079000 | 6/2012 |
| WO | WO 2012/129514 | 9/2012 |
| WO | WO 2013/006490 | 1/2013 |
| WO | WO 2013/039954 | 3/2013 |
| WO | WO 2013/054331 | 4/2013 |
| WO | WO 2013/071154 | 5/2013 |
| WO | WO 2013/082366 | 6/2013 |
| WO | WO 2013/123061 | 8/2013 |
| WO | WO 2013/126712 | 8/2013 |
| WO | WO 2013/126726 | 8/2013 |
| WO | WO 2013/166321 | 11/2013 |
| WO | WO 2014/022332 | 2/2014 |
| WO | WO 2014/031174 | 2/2014 |
| WO | WO 2014/055668 | 4/2014 |
| WO | WO 2014/059251 | 4/2014 |
| WO | WO 2014/190273 | 11/2014 |
| WO | WO 2015/079417 | 6/2015 |
| WO | WO 2015/095895 | 6/2015 |
| WO | WO 2015/157399 | 10/2015 |
| WO | WO 2015/184203 | 12/2015 |
| WO | WO 2016/016344 | 2/2016 |
| WO | WO 2016/044227 | 3/2016 |
| WO | WO 2016/115559 | 7/2016 |
| WO | WO 2016/176322 | 11/2016 |
| WO | WO 2014/031687 | 2/2017 |
| WO | WO 2017/072361 | 5/2017 |
| WO | WO 2017/136607 | 8/2017 |
| WO | WO 2018/197675 | 11/2018 |
| WO | WO 2019/089982 | 5/2019 |
| WO | WO 2020/160050 | 8/2020 |
| WO | WO 2022/029660 | 2/2022 |

OTHER PUBLICATIONS

Berger et al. "Safety of targeting ROR1 in primates with chimeric antigen receptor-modified T cells", Cancer Immunol Res. Feb. 2015;3(2):206-16 (Year: 2015).*

Allard et al., "Targeting CD73 Enhances the Antitumor Activity of Anti-PD-1 and Anti-CTLA-4 mAbs," Clin Cancer Res (2013) 19(20):5626-5635.

Al-Lazikani et al., "Standard conformations for the canonical structures of immunoglobulins," JMB (1997) 273:927-948.

Alonso-Camino et al., "CARbodies: Human Antibodies Against Cell Surface Tumor Antigens Selected From Repertoires Displayed on T Cell Chimeric Antigen Receptors," Mol Ther Nucl Acids (2013) 2: e93.

Amado et al., "Lentiviral vectors—the promise of gene therapy within reach?" Science (1999) 285(5428):674-676.

Baskar et al., "Targeting malignant B cells with an immunotoxin against ROR1," MAbs. May-Jun. 2012;4(3):349-61.

Beavis et al., "Blockade of A2A receptors potently suppresses the metastasis of CD73+ tumors," PNAS (2013) 110(36):14711-14716.

Berger et al., "Phase I safety and pharmacokinetic study of CT-011, a humanized antibody interacting with PD-1, in patients with advanced hematologic malignancies," Clin Cancer Res (2008) 14(10):3044-3051.

Bertilaccio et al., "Low-Dose Lenalidomide Improves CAR-Based Immunotherapy in CLL By Reverting T-Cell Defects In Vivo," Blood (2013) 122:4171.

Blank et al., "Contribution of the PD-L1/PD-1 pathway to T-cell exhaustion: an update on implications for chronic infections and tumor evasion," Cancer Immunol Immunother (2007) 56(5):739-745.

Boris-Lawrie et al., "Recent advances in retrovirus vector technology," Cur. Opin. Genet. Develop. (1993) 3:102-109.

Brahmer et al., "Safety and Activity of Anti-PD-L1 Antibody in Patients with Advanced Cancer," N Engl J Med (2012) 366:2455-2465.

Brash et al., "Strontium phosphate transfection of human cells in primary culture: stable expression of the simian virus 40 large-T-antigen gene in primary human bronchial epithelial cells," Mol. Cell Biol. (1987) 7: 2031-2034.

Brentjens et al., "CD19-targeted T cells rapidly induce molecular remissions in adults with chemotherapy-refractory acute lymphoblastic leukemia," Sci Transl Med. (2013) 5(177): 177ra38.

Brummelkamp et al., "A system for stable expression of short interfering RNAs in mammalian cells," Science (2002) 296(5567):550-553.

Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA (1993) 90:8033-8037.

Carlens et al., "Ex vivo T lymphocyte expansion for retroviral transduction: influence of serum-free media on variations in cell expansion rates and lymphocyte subset distribution," Exp Hematol (2000) 28(10): 1137-46.

Carroll et al., "Targeting the molecular basis for tumour hypoxia," Expert Rev Mol Med (2005) 7(6):1-16.

Cavalieri et al., "Human T lymphocytes transduced by lentiviral vectors in the absence of TCR activation maintain an intact immune competence," Blood (2003) 102(2): 497-505.

Chari et al., "Immunoconjugates containing novel maytansinoids: promising anticancer drugs," Cancer Res. (1992) 52:127-131.

Chicaybam et al., "An efficient low cost method for gene transfer to T lymphocytes," PLoS ONE (2013) 8(3): e60298.

Cho et al., "Human mammalian cell sorting using a highly integrated micro-fabricated fluorescence-activated cell sorter (microFACS)," Lab Chip (2010) 10: 1567-1573.

(56) References Cited

OTHER PUBLICATIONS

Clackson et al., "Making antibody fragments using phage display libraries," Nature (1991) 352:624-628.
Clarke and Davies in: Methods in Molecular Medicine, vol. 58: Metastasis Research Protocols, vol. 2: Cell Behavior In Vitro and In Vivo, Edited by: S. A. Brooks and U. Schumacher © Humana Press Inc., Totowa, NJ (2001) pp. 17-25.
Collins et al., "Chemical approaches to targeted protein degradation through modulation of the ubiquitin-proteasome pathway," Biochem J (2017) 474(7):1127-1147.
Cooper et al., "T-cell clones can be rendered specific for CD19: toward the selective augmentation of the graft-versus-B-lineage leukemia effect," Blood. (2003) 101:1637-1644.
Cronstein et al., "Adenosine modulates the generation of superoxide anion by stimulated human neutrophils via interaction with a specific cell surface receptor," Ann N Y Acad Sci (1985) 451:291-301.
Cronstein et al., "Engagement of adenosine receptors inhibits hydrogen peroxide (H2O2-) release by activated human neutrophils," Clin Immunol Immunopathol (1987) 42(1):76-85.
Davila et al., "CD19 CAR-targeted T cells induce long-term remission and B Cell Aplasia in an immunocompetent mouse model of B cell acute lymphoblastic leukemia," PLoS ONE (2013) 8(4): e61338.
De Felipe et al., "Skipping the co-expression problem: the new 2A "CHYSEL" technology," Genetics Vaccines and Therapy (2004) 2:13.
De Felipe et al., "Targeting of proteins derived from self-processing polyproteins containing multiple signal sequences," Traffic (2004) 5(8):616-626.
Dubowchik et al., "Doxorubicin immunoconjugates containing bivalent, lysosomally-cleavable dipeptide linkages," Bioorg. & Med. Chem. Letters (2002) 12:1529-1532.
Endo et al., "High-throughput, genome-scale protein production method based on the wheat germ cell-free expression system," Biotechnol. Adv. (2003) 21: 695-713.
Fecteau et al., "Lenalidomide inhibits the proliferation of CLL cells via a cereblon/p21WAF1/Cip1-dependent mechanism independent of functional p53," Blood (2014) 124:1637-1644.
Fedorov et al., "PD-1- and CTLA-4-based inhibitory chimeric antigen receptors (iCARs) divert off-target immunotherapy responses," Sci. Transl. Medicine (2013) 5(215).
Finger et al., "The human PD-1 gene: complete cDNA, genomic organization, and developmentally regulated expression in B cell progenitors," Gene (1997) 197(1-2):177-187.
Flatman et al., "Process analytics for purification of monoclonal antibodies," J. Chromatogr. (2007) B 848:79-87.
Gerngross et al, "Advances in the production of human therapeutic proteins in yeasts and filamentous fungi," Nat. Biotech. (2004) 22:1409-1414.
Gildener-Leapman et al., "Promising systemic immunotherapies in head and neck squamous cell carcinoma," Oral Oncol (2013) 49(12):1089-1096.
Godin et al., "Microfluidics and photonics for Bio-System-on-a-Chip: a review of advancements in technology towards a microfluidic flow cytometry chip," J Biophoton. (2008) 1(5):355-376.
Gorgun et al., "Chronic lymphocytic leukemia cells induce changes in gene expression of CD4 and CD8 T cells," J Clin Invest. (2005) 115(7): 1797-805.
Hausler et al., "Anti-CD39 and anti-CD73 antibodies A1 and 7G2 improve targeted therapy in ovarian cancer by blocking adenosine-dependent immune evasion," Am J transl Res (2014) 6(2):129-139.
Hermans et al., "The VITAL assay: a versatile fluorometric technique for assessing CTL- and NKT-mediated cytotoxicity against multiple targets in vitro and in vivo," J. Immunological Methods (2004) 285(1): 25-40.
Hershfield, "PEG-ADA: an alternative to haploidentical bone marrow transplantation and an adjunct to gene therapy for adenosine deaminase deficiency," Hum Mutat (1995) 5(2):107-112.

Hinman et al., "Preparation and characterization of monoclonal antibody conjugates of the calicheamicins: a novel and potent family of antitumor antibiotics," Cancer Res. (1993) 53:3336-3342.
Honegger A and Plückthun A, "Yet another numbering scheme for immunoglobulin variable domains: an automatic modeling and analysis tool," J Mol Biol, (2001) 8;309(3):657-70.
Hoogenboom et al., "Overview of antibody phage-display technology and its applications," Methods in Molecular Biology (2002) 178:1-37.
Huang et al., "DNA transposons for modification of human primary T lymphocytes," Methods Mol Biol (2009) 506: 115-126.
Hudecek et al., "Receptor affinity and extracellular domain modifications affect tumor recognition by ROR1-specific chimeric antigen receptor T cells," Clin. Cancer Res. (2013) 19:3153.
Hudecek et al., "The nonsignaling extracellular spacer domain of chimeric antigen receptors is decisive for in vivo antitumor activity," Cancer Immunol Res (2015) 3(2):125-135.
Ito et al., "Identification of a primary target of thalidomide teratogenicity," Science (2010) 327:1345-1350.
Jeffrey et al., "Dipeptide-based highly potent doxorubicin antibody conjugates," Bioorganic & Med. Chem. Letters (2006) 16:358-362.
Jin et al., "CD73 on tumor cells impairs antitumor T-cell responses: a novel mechanism of tumor-induced immune suppression," Cancer Res (2010) 70(6):2245-2255.
Johnston, et al., "Biolistic transformation: microbes to mice," Nature (1990) 346: 776-777.
Junghans et al., "Anti-Tac-H, a humanized antibody to the interleukin 2 receptor with new features for immunotherapy in malignant and immune disorders," Cancer Res. (1990) 50:1495-1502.
Kanda, Y. et al., "Comparison of cell lines for stable production of fucose-negative antibodies with enhanced ADCC," Biotechnol. Bioeng. (2006) 94(4):680-688.
Kindt et al., Kuby Immunology 6th ed., W.H. Freeman and Co. (2007) p. 91.
King et al., "Monoclonal antibody conjugates of doxorubicin prepared with branched peptide linkers: inhibition of aggregation by methoxytriethyleneglycol chains," J. Med. Chem. (2002) 45:4336-4343.
Klebanoff et al., "Sorting through subsets: which T-cell populations mediate highly effective adoptive immunotherapy?," J Immunother. (2012) 35(9): 651-660.
Kochenderfer et al., "Construction and preclinical evaluation of an anti-CD19 chimeric antigen receptor," J. Immunotherapy (2009) 32(7): 689-702.
Koste et al., "T-cell receptor transfer into human T cells with ecotropic retroviral vectors," Gene Therapy (2014) 21: 533-538.
Kratz et al., "Prodrugs of anthracyclines in cancer chemotherapy," Current Med. Chem. (2006) 13:477-523.
Kuramitsu et al., "Lenalidomide enhances the function of chimeric antigen receptor T cells against the epidermal growth factor receptor variant III by enhancing immune synapses," Cancer Gene Therapy (2015) 22(10):487-495.
Lefranc et al., "IMGT unique numbering for immunoglobulin and T cell receptor variable domains and Ig superfamily V-like domains," Dev Comp Immunol (2003) 27(1):55-77.
Leone et al., "A2aR antagonists: Next generation checkpoint blockade for cancer immunotherapy," Comput Struct Biotechnol J. (2015) 13:265-272.
Li et al., "Optimization of humanized IgGs in glycoengineered Pichia pastoris," Nat. Biotech. (2006) 24:210-215.
Lim et al., "Anti-CD20 monoclonal antibodies: historical and future perspectives," Haematologica (2010) 95(1):135-143.
Lipson et al., "Durable cancer regression off-treatment and effective reinduction therapy with an anti-PD-1 antibody," Clin Cancer Res (2013) 19(2):462-468.
Liu et al., "Inclusion of Strep-tag II in design of antigen receptors for T-cell immunotherapy," Nat Biotechnol (2016) 34(4):430-434.
Lode et al., "Targeted therapy with a novel enediyene antibiotic calicheamicin theta(I)1 effectively suppresses growth and dissemination of liver metastases in a syngeneic model of murine neuroblastoma," Cancer Res. (1998) 58:2925-2928.

(56) References Cited

OTHER PUBLICATIONS

Lopez-Girona et al., "Cereblon is a direct protein target for immunomodulatory and antiproliferative activities of lenalidomide and pomalidomide," Leukemia (2012) 26:2326-2335.
Lupton S. D. et al., "Dominant positive and negative selection using a hygromycin phosphotransferase-thymidine kinase fusion gene," Mol. and Cell Biol. (1991) 11:6.
Maccallum et al., "Antibody-antigen interactions: Contact analysis and binding site topography," J. Mol. Biol. (1996) 262, 732-745.
Manuri et al., "piggyBac transposon/transposase system to generate CD19-specific T cells for the treatment of B-lineage malignancies," Hum Gene Ther (2010) 21(4): 427-437.
Martin et al., "Modeling antibody hypervariable loops: a combined algorithm," Proc Natl Acad Sci U S A. Dec. 1989;86(23):9268-72.
Menzies et al., "New combinations and immunotherapies for melanoma: latest evidence and clinical utility," Ther Adv Med Oncol (2013) 5(5):278-285.
Miller et al., "Improved retroviral vectors for gene transfer and expression," BioTechniques (1989) 7:980-990.
Miller et al., "Retrovirus packaging cells," Human Gene Therapy (1990) 1:5-14.
Millrine et al., "A brighter side to thalidomide: It's potential use in immunological Disorders," Trends in Mol Medicine (2017) 23(4):348-364.
Miyagishi et al., "U6 promoter-driven siRNAs with four uridine 3' overhangs efficiently suppress targeted gene expression in mammalian cells" Nat Biotechnol (2002) 20(5):497-500.
Monney et al., "Th1-specific cell surface protein Tim-3 regulates macrophage activation and severity of an autoimmune disease," Nature (2002) 415(6871):536-541.
Mullen et al., "Transfer of the bacterial gene for cytosine deaminase to mammalian cells confers lethal sensitivity to 5-fluorocytosine: a negative selection system," Proc. Natl. Acad. Sci. USA (1992) 89:33.
Nagy et al., "Stability of cytotoxic luteinizing hormone-releasing hormone conjugate (AN-152) containing doxorubicin 14-O-hemiglutarate in mouse and human serum in vitro: implications for the design of preclinical studies," Proc. Natl. Acad. Sci. USA (2000) 97:829-834.
Ngiow et al., "Anti-TIM3 Antibody Promotes T Cell IFN-γ-Mediated Antitumor Immunity and Suppresses Established Tumors," Cancer Res (2011) 71(10):3540-3551.
Ohta et al., "A2A adenosine receptor protects tumors from antitumor T cells," PNAS U.S.A. (2006) 103(35):13132-13137.
Okazaki et al., "Fucose depletion from human IgG1 oligosaccharide enhances binding enthalpy and association rate between IgG1 and FcgammaRIIIa," J. Mol. Biol. (2004) 336:1239-1249.
Oshima et al., "Immunomodulatory Drugs (IMiDs)," Nihon Rinsho (2014) 72(6):1130-1135.
Otahal et al., "Lenalidomide enhances antitumor functions of chimeric antigen receptor modified T cells," Oncoimmunology (2015) 5(4):e1115940.
Ott et al., "CTLA-4 and PD-1/PD-L1 Blockade: New Immunotherapeutic Modalities with Durable Clinical Benefit in Melanoma Patients," Clin Cancer Res (2013) 19(19):5300.
Pardoll, "The blockade of immune checkpoints in cancer immunotherapy," Nature (2012) 12:252-264.
Park et al., "Treating cancer with genetically engineered T cells," Trends Biotechnol. (2011) 29(11): 550-557.
Pinna et al., "Novel investigational adenosine A2A receptor antagonists for Parkinson's disease," Expert Opin Investig Drugs (2009) 18:1619-1631.
Portolano et al., "Lack of promiscuity in autoantigen-specific H and L chain combinations as revealed by human H and L chain "roulette"," J. Immunol. (1993) 150:880-887.
Radvanyi et al., "Antagonist antibodies to PD-1 and B7-H1 (PD-L1) in the treatment of advanced human cancer—letter," Clin Cancer Res (2013) 19(19):5541.

Ramsay et al., "Chronic lymphocytic leukemia T cells show impaired immunological synapse formation that can be reversed with an immunomodulating drug," J Clin Invest. (2008) 118(7):2427-37.
Riches, "Advances in Chimeric Antigen Receptor Immunotherapy for Chronic Lymphocytic Leukemia." Discovery Medicine (2013) 16(90):295-302.
Riddell et al., "Phase I study of cellular adoptive immunotherapy using genetically modified CD8+ HIV-specific T cells for HIV seropositive patients undergoing allogeneic bone marrow transplant," Human Gene Therapy (1992) 3:319-338.
Ripka et al., "Two Chinese hamster ovary glycosylation mutants affected in the conversion of GDP-mannose to GDP-fucose," Arch. Biochem. Biophys. (1986) 249:533-545.
Robert et al., "What is the role of cytotoxic T lymphocyte-associated antigen 4 blockade in patients with metastatic melanoma?," Oncologist (2009) 14(8):848-861.
Roberts et al., "Inhibition by adenosine of reactive oxygen metabolite production by human polymorphonuclear leucocytes," Biochem J (1985) 227(2):669-674.
Rosenberg, et al., "Cell transfer immunotherapy for metastatic solid cancer—what clinicians need to know," Nat Rev Clin Oncol. (2011) 8(10):577-85).
Sadelain et al., "The basic principles of chimeric antigen receptor design," Cancer Discov. (2013) 3(4): 388-398.
Scarpa et al., "Characterization of recombinant helper retroviruses from Moloney-based vectors in ecotropic and amphotropic packaging cell lines," Virology (1991) 180:849-852.
Scatchard, "The attractions of proteins for small molecules and ions," Annals of the New York Academy of Sciences (1949) 51(4):660-672.
Schrier et al., "The effects of adenosine agonists on human neutrophil function," J Immunol (1986) 137(10):3284-3289.
Sharma et al., "Efficient sleeping beauty DNA transposition from DNA minicircles," Molec Ther Nucl Acids (2013) 2, e74.
Shinohara et al., "Structure and chromosomal localization of the human PD-1 gene (PDCD1)," Genomics (1994) 23:704-706.
Sitaraman et al., "High-throughput protein expression using cell-free system," Methods Mol. Biol. (2009) 498: 229-44.
Sitkovsky et al., "Hostile, hypoxia-A2-adenosinergic tumor biology as the next barrier to overcome for tumor immunologists," Cancer Immunol Re (2014) 2(7):598-605.
Spirin, et al., "High-throughput cell-free systems for synthesis of functionally active proteins," Trends Biotechnol. (2004) 22: 538-45.
Szoka et al., "Comparative properties and methods of preparation of lipid vesicles (liposomes)," Ann. Rev. Biophys. Bioeng. (1980) 9: 467.
Terakura et al., "Generation of CD19-chimeric antigen receptor modified CD8+ T cells derived from virus-specific central memory T cells," Blood (2012) 1:72-82.
Themeli et al., "Generation of tumor-targeted human T lymphocytes from induced pluripotent stem cells for cancer therapy," Nat Biotechnol. (2013) 31(10): 928-933.
Timmerman et al., "Functional reconstruction and synthetic mimicry of a conformational epitope using CLIPS technology," J Mol Recognit (2007) 20(5):283-299.
Topalian et al., "Safety, Activity, and Immune Correlates of Anti-PD-1 Antibody in Cancer," N Engl J Med (2012) 366:2443-2454.
Torgov et al., "Generation of an intensely potent anthracycline by a monoclonal antibody-beta-galactosidase conjugate," Bioconj. Chem. (2005) 16:717-721.
Tsukahara et al., "CD19 target-engineered T-cells accumulate at tumor lesions in human B-cell lymphoma xenograft mouse models," Biochem Biophys Res Commun (2013) 438(1): 84-9.
Turtle et al., "Engineered T cells for anti-cancer therapy," Curr. Opin. Immunol. (2012) 24(5): 633-39.
Van Tendeloo et al., "High-level transgene expression in primary human T lymphocytes and adult bone marrow CD34+ cells via electroporation-mediated gene delivery," Gene Therapy (2000) 7(16): 1431-1437).
Verhoeyen et al., "Lentiviral vector gene transfer into human T cells," Methods Mol Biol. (2009) 506: 97-114.
Vitetta et al., "Redesigning nature's poisons to create anti-tumor reagents," Science (1987) 238:1098.

(56) References Cited

OTHER PUBLICATIONS

Wada et al., "Sequencing CTLA-4 blockade with cell-based immunotherapy for prostate cancer," J Transl Med (2013) 11:89.
Wadhwa et al., "Receptor mediated glycotargeting," J. Drug Targeting (1995) 3: 111.
Wang et al., "Phenotypic and functional attributes of lentivirus-modified CD19-specific human CD8+ central memory T cells manufactured at clinical scale," J Immunother. (2012) 35(9):689-701.
Weber, "Review: anti-CTLA-4 antibody ipilimumab: case studies of clinical response and immune-related adverse events," Oncologist (2007) 12(7):864-872.
Wigler et al., "Transfer of purified herpes virus thymidine kinase gene to cultured mouse cells," Cell (1997) 11: 223-232.
Wilson, "Tech.Sight. Analyzing biomolecular interactions," Science (2002) 295(5562):2103-2105.
Wolff et al., "Monoclonal Antibody Homodimers: Enhanced Antitumor Activity in Nude Mice," Can Res (1993) 53:2560-2565.
Wu et al., "Adoptive T-cell therapy using autologous tumor-infiltrating lymphocytes for metastatic melanoma: current status and future outlook," Cancer (2012) 18(2): 160-75.
Yamane-Ohnuki et al., "Establishment of FUT8 knockout Chinese hamster ovary cells: an ideal host cell line for producing completely defucosylated antibodies with enhanced antibody-dependent cellular cytotoxicity," Biotech. Bioeng. (2004) 87: 614.
Yang et al., "Therapeutic potential and challenges of targeting receptor tyrosine kinase ROR1 with monoclonal antibodies in B-cell malignancies," PLoS One. (2011);6(6):e21018.
Ye et al., "IgBLAST: an immunoglobulin variable domain sequence analysis tool," Nucleic Acids Res. Jul. 2013; 41(Web Server issue): W34-W40.
Zhang et al., "CD73: a novel target for cancer immunotherapy," Cancer Res (2010) 70(16):6407-6411.
Zheng et al., "A novel anti-CEACAM5 monoclonal antibody, CC4, suppresses colorectal tumor growth and enhances NK cells-mediated tumor immunity," PLoS One (2011) 6(6):e21146.
Zheng et al., "Protein L: a novel reagent for the detection of chimeric antigen receptor (CAR) expression by flow cytometry," J Transl Med (2012) 10:29.
Zola in: Monoclonal Antibodies: A Manual of Techniques, © CRC Press Inc., Boca Raton, FL (1987) pp. 147-158.
U.S. Appl. No. 18/433,277, filed Aug. 20, 2013, by Jensen et al. (Copy not provided). (Copy not submitted herewith pursuant to the waiver of 37 C.F. R. § 1.98(a)(2)(iii) issued by the Office on Sep. 21, 2004).
U.S. Appl. No. 18/435,933, filed Feb. 7, 2024, by Balakrishnan et al. (Copy not provided). (Copy not submitted herewith pursuant to the waiver of 37 C.F. R. § 1.98(a)(2)(iii) issued by the Office on Sep. 21, 2004).
Aalberse et al., "IgG4 breaking the rules", Immunology. (2002) 105(1): 9-19.
Adlersberg, Jay B., "The Immunoglobulin Hinge (Interdomain) Region," La Ricerca Clin. Lab, 6: 191-205, 1976.
Anonymous, "A ROR1 antibody (Receptor Tyrosine Kinase-Like Orphan Receptor 1) (C-Term) Antigen: Receptor Tyrosine Kinase-Like Orphan Receptor 1(ROR1)" retrieved from the internet www.antibodies-online.com [retrieved Sep. 10, 2019]. 5 pages.
Anonymous, "Anti ROR1 Antibody (Receptor Tyrosine Kinase Like Orphan Receptor 1) (C Term)," Online, Sep. 1, 2008, pp. 1-4, URL, https://www.antibodiesonline.com/productsheets/ABIN5539753.pdf.
Anonymous, "Product Data sheet:ARP63925 P050—RORI Antibody—C-terminal. Region (ARP63925 P050)—Aviva Systems Biology" 2 p. Retrieved from the internet: URL:http://www.avivasysbio.com/sd/tds/html_datasheet.php?sku=ARP63925_P050 [retrieved on Apr. 19, 2017].
Balakrishnan et al., "Analysis of ROR1 Protein Expression in Human Cancer and Normal Tissues," Clin Cancer Res (2017) 23(12):3061-3071.

Baskar et al., "Monoclonal Antibody Against The Receptor Tyrosine Kinase ROR1 as a Potential Therapeutic Drug for Human B Cell Chronic Lymphocytic Leukemia," XIII International Workshop on Chronic Lymphocytic Leukemia, 2009, Abstract 9.1., p. S78.
Berasain et al., "Specific cleavage sites on human IgG subclasses by cruzipain, the major cysteine proteinase from Trypanosoma cruzi," Molecular & Biochemical Parasitology, p. 1-7 (2003).
Bridgeman et al., "Building better chimeric antigen receptors for adoptive T cell therapy." Curr. Gene Ther. (2010) 10(2): 77-90.
Bruggemann et al., "Human antibody production in transgenic animals," Arch Immunol. Ther. Exp. (2015) 63:101-108.
Brummell et al., "Probing the combining site of an anti-carbohydrate antibody by saturation-mutagenesis: role of the heavy-chain CDR3 residues," Biochemistry (1993) 32(4): 1180-1187.
Burks et al., "In vitro scanning saturation mutagenesis of an antibody binding pocket," PNAS (1997) 94:412-417.
Cartellieri et al. "Chimeric Antigen Receptor-Engineered T Cells for Immunotherapy of Cancer," Journal of Biomedicine and Biotechnology, vol. 2010, Article ID 956304 (13 pages) (2010).
Casset et al., "A peptide mimetic of an anti-CD4 monoclonal antibody by rational design," BBRC (2003) 307:198-205.
Cheadle E.J. et al., "Natural Expression of the CD19 Antigen Impacts the Long-Term Engraftment but Not Antitumor Activity of CD19-Specific Engineered T Cells, The Journal of Immunology." (2010) 184, p. 1885-1896.
Chen et al., "Selection and analysis of an optimized anti-VEGF antibody: crystal structure of an affinity-matured Fab in complex with antigen," J. Mol. Bio. (1999) 293:865- 881.
Chen et al., "Cirmtuzumab blocks Wnt5a/ROR1 stimulation of NF-KB to repress autocrine STAT3 activation in chronic lymphocytic leukemia," Blood (2019) 134(13): 1084- 94.
Chen et al., "Generation and Analysis of Random Point Mutations in an Antibody CDR2 Sequence: Many Mutated Antibodies Lose Their Ability to Bind Antigen," J Exp. Med. 176:855-866, 1992.
Chmielewski et al., "CD28 cosignalling does not affect the activation threshold in a chimeric antigen receptor-redirected T-cell attack," Gene Therapy 18:62-72 (2011).
Choi et al., "Phase I Trial: Cirmtuzumab Inhibits ROR1 Signaling and Stemness Signatures in Patients with Chronic Lymphocytic Leukemia," Cell Stem Cell (2018) 22(6);951-9.
Colman, "Effects of amino acid sequence changes on antibody-antigen interactions," Research in Immunol. (1994) 145:33-36.
Daneshmanesh et al., "Monoclonal antibodies against ROR1 induce apoptosis of chronic lymphocytic leukemia (CLL) cells," Leukemia. (2012) Jun. 26(6):1348-55.
Daneshmanesh et al., "Ror1, a cell surface receptor tyrosine kinase is expressed in chronic lymphocytic leukemia and may serve as a putative target for therapy," International Journal of Cancer (2008) 123:1190-1195.
De Pascalis et al., "Grafting of "Abbreviated" Complementarity-Determining Regions Containing Specificity-Determining Residues Essential for Ligand Contact to Engineer a Less Immunogenic Humanized Monoclonal Antibody," The Journal of Immunology 169:3076-3084 (2002).
George et al., "Differential Effects of Anti-B2-Glycoprotein I Antibodies on Endothelial Cells and on the Manifestations of Experimental Antiphospholipid Syndrome," Circulation (1998) 97:900-906.
Guest et al., "The Role of Extracellular Spacer Regions in the Optimal Design of Chimeric Immune Receptors," J Immunother 28:203-211 (May/Jun. 2005).
Hojjat-Farsangi et al., "Inhibition of the receptor tyrosine kinase ROR1 by anti-ROR1 monoclonal antibodies and siRNA induced apoptosis of melanoma cells," PLoS One. (2013) Apr. 8;8(4): e61167, 10 pages.
Holm et al., "Functional mapping and single chain construction of the anti-cytokeratin 8 monoclonal antibody TS1" Mol. Immunol. (2007) 44: 1075-1084.
Hombach et al., "Adoptive immunotherapy with genetically engineered T cells: modification of the IgG1 Fc 'spacer' domain in the extracellular moiety of chimeric antigen receptors avoids 'off-target' activation and unintended initiation of an innate immune response," Gene Ther. 17: 1206-1213, 2010.

(56) References Cited

OTHER PUBLICATIONS

Hu et al., "The Chimeric Antigen Receptor Detection Toolkit," Front Immunol (Aug. 11, 2020) 11:1770, 16 pages.
Hudecek et al., "CD8+ T Cells Engineered to Express a ROR1-Specific Chimeric Antigen Receptor Specifically Recognize ROR1 Positive B Cell Tumors," Blood (2009) 114 (22): 930, 5 pages.
Hudecek et al., "The anti-tumor reactivity of ROR1-CAR modified T cells depends on the targeted epitope, CAR affinity and design of the CAR extracellular domain," Clinical Lymphoma, Myeloma and Leukemia Supplement (2011) 11(2):s280-s281.
Hudecek et al., "The B-cell tumor-associated antigen ROR1 can be targeted with T cells modified to express a ROR1-specific chimeric antigen receptor," Blood. (2010) Nov. 25;116(22):4532-41.
Jakka, "Functional Characterization of Anti-idiotypic Antibody Expanded Chimeric Antigen Receptor (CAR) Expressing Redirected T Cells," Dissertation, Zurich Open Repository and Archive (2012), University of Zurich, Faculty of Science, 88 pages.
Jensen et al., "Antitransgene Rejection Responses Contribute to Attenuated Persistence of Adoptively Transferred CD20/CD19-specific Chimeric Antigen Receptor Redirected T Cells in Humans," Biol Blood Marrow Transplant (2010) 16 (9); 1245-1256.
Kobayashi et al., "Tryptophan H33 plays an important role in pyrimidine (6-4) pyrimidone photoproduct binding by a high-affinity antibody," Protein Engineering (1999) 12(10):879-884.
Koehler et al., "Engineered T Cells for the Adoptive Therapy of B-Cell Chronic Lymphocytic Leukaemia." Advances in Hematology. (2011) v.2012:595060, p. 1-13.
Kowolik et al., "CD28 Costimulation Provided through a CD19-Specific Chimeric Antigen Receptor Enhances In vivo Persistence and Antitumor Efficacy of Adoptively Transferred T Cells," Cancer Res., 2006, 66: 10995-11004.
Kumar et al., "Molecular cloning and expression of the Fabs of human autoantibodies in *Escherichia coli*. Determination of the heavy or light chain contribution to the anti-DNA/-cardiolipin activity of the Fab," J. Biol. Chem. (2000) 275(45): 35129-35136.
Kunik et al., "Structural consensus among antibodies defines the antigen binding site," PLOS Comput Biol. (2012) 8(2): e1002388, 12 pages.
Kussie et al., "Single Engineered Amino Acid Substitution Changes Antibody Fine Specificity," J Immunol. (1994) 152(1):146-52.
Matsumoto, "How far has the development and application of human antibodies progressed," Chemistry and Biology (1998) vol. 38, No. 7, pp. 448-456 (Including English translation).
Moritz et al., "A spacer region between the single chain antibody- and the CD3 zeta-chain domain of chimeric T cell receptor components is required for efficient ligand binding and signaling activity." Gene Ther. Oct. 1995;2(8):539-46.
Nicholson et al., "Construction and characterisation of a functional CD19 specific single chain Fv fragment for immunotherapy of B lineage leukaemia and lymphoma." Molecular Immunology 24(16-17): 1157-1165, 1997.
Patel et al., "Impact of chimeric immune receptor extracellular protein domains on T cell function," Gene Thercmv 6:412-419 (1999).
Pule et al., "A Chimeric T Cell Antigen Receptor That Augments Cytokine Release and Supports Clonal Expansion of Primary Human T Cells," Mol. Ther. (2005) 12(5):933-941.
Ramos et al., "Chimeric Antigen Receptor (CAR)-Engineered Lymphocytes for Cancer Therapy," Expert Opin Biol Ther. 11 (7): 855-873, 2011. (32 pages).
Rudikoff et al., "Single amino acid substitution altering antigen-binding specificity," PNAS (1982) 79(6): 1979-1983.
Savoldo et al., "CD28 costimulation improves expansion and persistence of chimeric antigen receptor-modified T cells in lymphoma patients," JCI (2011) 121(5): 1822-1826.
Sequence alignment 1, Retrieved Jul. 5, 2019, Result 1, US-15-302-403A-17, 1 page.
Sequence alignment 2, Retrieved Jul. 5, 2019, Result 1, US-10-093-958-35, 1 page.
Smith-Gill et al., "Contributions of immunoglobulin heavy and light chains to antibody specificity for lysozyme and two haptens," J. Immunol. (1987) 139:4135-4144.
Solomon et al., "Proteolytic cleavage of human IgG molecules by neutral proteases of polymorphonuclear leukocytes," Eur. J Immunol. 8: 782-785, 1978.
Song et al., "Light chain of natural antibody plays a dominant role in protein antigen binding," Biochem Biophys Res Comm (2000) 268:390-394.
Specht et al., "Abstract CT131: A phase I study of adoptive immunotherapy for advanced ROR1+ malignancies with defined subsets of autologous T cells expressing a ROR1-specific chimeric antigen receptor (ROR1-CAR)," Meeting Info: 2018 Annual Meeting of the American Association for Cancer Research, AACR 2018. Chicago, IL, United States, Apr. 2018, Cancer Research (Jul. 2018) 78(13):Supplement 1, Abstract No. CT131, 4 pages.
Specht et al., "Abstract P2-09-13: A phase I study of adoptive immunotherapy for ROR1+ advanced triple negative breast cancer (TNBC) with defined subsets of autologous T cells expressing a ROR1-specific chimeric antigen receptor (ROR1-CAR)," Meeting Info: 2018 San Antonio Breast Cancer Symposium. San Antonio, TX, United States, Dec. 2018, Cancer Research (Feb. 2019) 79(4): Supplement 1, Abstract No. P2-09-13, 4 pages.
Till et al., "Adoptive immunotherapy for indolent non-Hodgkin lymphoma and mantle cell lymphoma using genetically modified autologous CD20-specific T cells." Blood. (2008) 112(6):2261-2271.
Vajdos et al. "Comprehensive functional maps of the antigen-binding site of an anti-ErbB2 antibody obtained with shotgun scanning mutagenesis." J. Mol. Biol. 320, 415-428 (2002).
Vera et al., "T lymphocytes redirected against the light chain of human immunoglobulin efficiently kill mature B lymphocyte-derived malignant cells" Blood. (2006) 108:3890-3897.
Wallstabe et al., "ROR1-CAR T cells are effective against lung and breast cancer in advanced microphysiologic 3D tumor models," JCI Insight (2019) 4(18): e126345, 14 pages.
Wang et al., "A transgene-encoded cell surface polypeptide for selection, in vivo tracking, and ablation of engineering cells." Blood. (2011) 118(5):1255-63.
Ward et al., "Binding activities of a repertoire of single immunoglobulin variable domains secreted from *Escherichia coli*," Nature (1989) 341:544-546.
Wilkie et al., "Retargeting of Human T Cells to Tumor-Associated MUC I: The Evolution of a Chimeric Antigen Receptor," Journal of Immunology 180:4901-4909, 2008.
Winkler et al., "Changing the antigen binding specificity by single point mutations of an anti-p24 (HIV-1) antibody," J. Immunol. (2000) 165(8):4505-14.
Wu et al. "Humanization of a murine monoclonal antibody by simultaneous optimization of framework and CDR residues." J. Mol. Biol. 294, 151-162 (1999).
Yu et al., "Cirmtuzumab inhibits Wnt5a-induced Rac1 activation in chronic lymphocytic leukemia treated with ibrutinib," Leukemia (2017) 31(6):1333-9.
Yvon et al., "Immunotherapy of metastatic melanoma using genetically engineered GD2-specific T cells," Clin Cancer Res (2009) 15(18):5852-5860.
Zhao et al., "A Herceptin-Based Chimeric Antigen Receptor with Modified Signaling Domains Leads to Enhanced Survival of Transduced T Lymphocytes and Anti tumor Activity," The Journal of Immunology 183:5563-5574 (2009), 29 pages.

\* cited by examiner

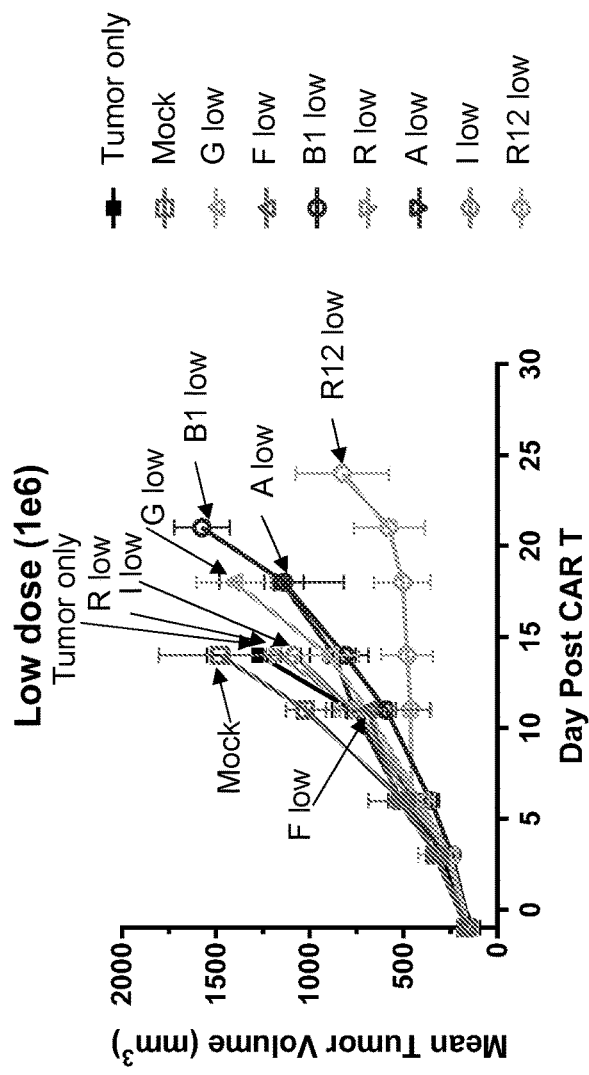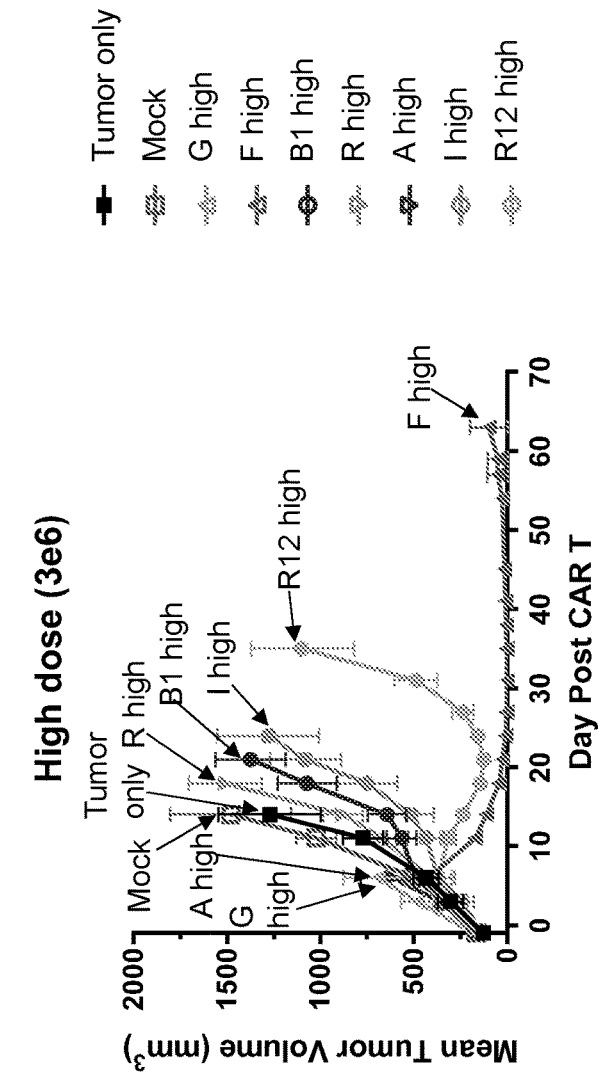
FIG. 5A
FIG. 5B

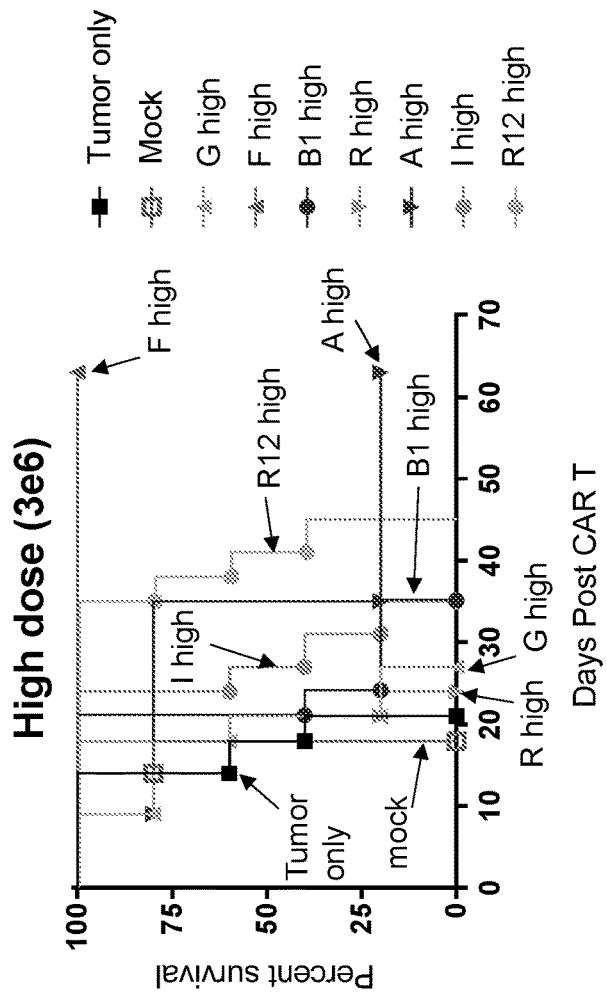
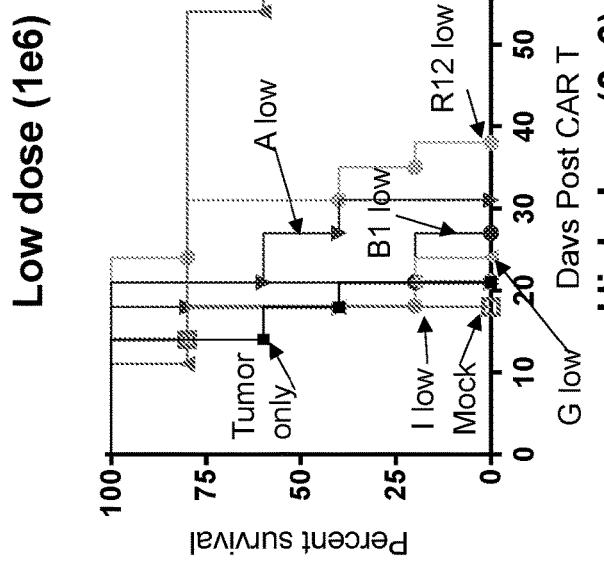
FIG. 6A
FIG. 6B

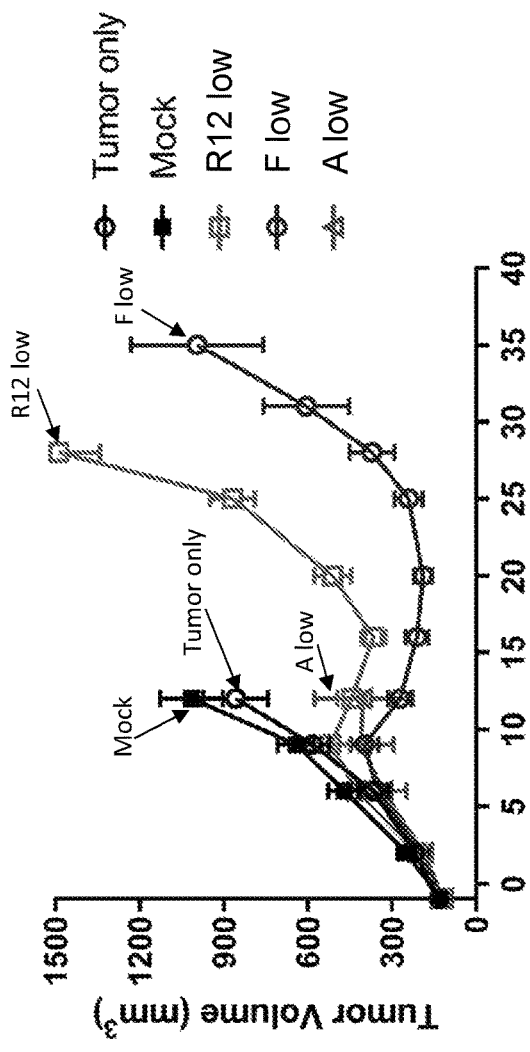
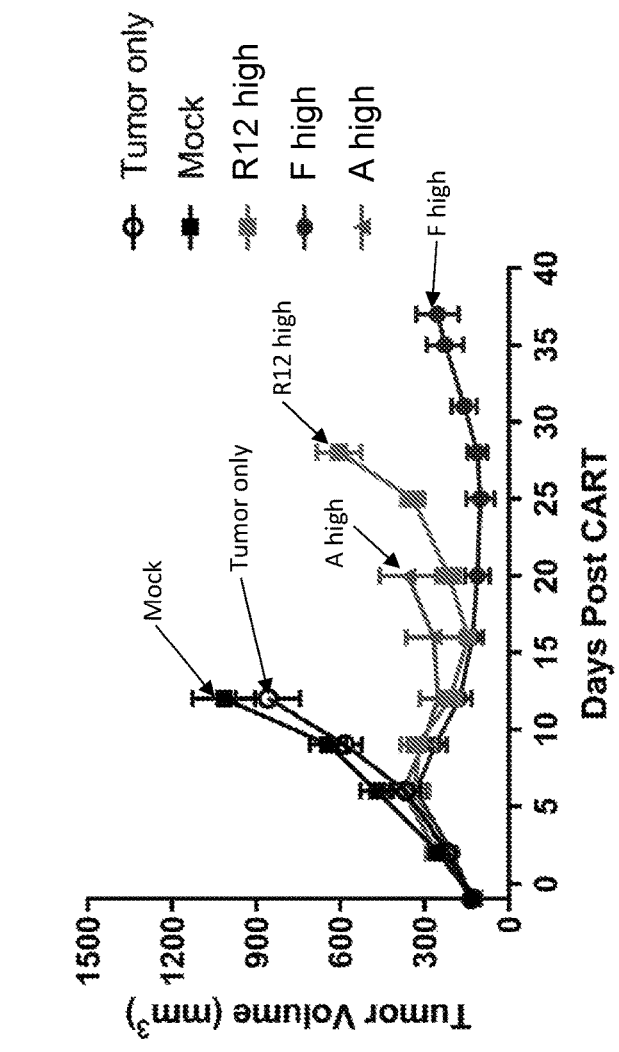
FIG. 8A
FIG. 8B

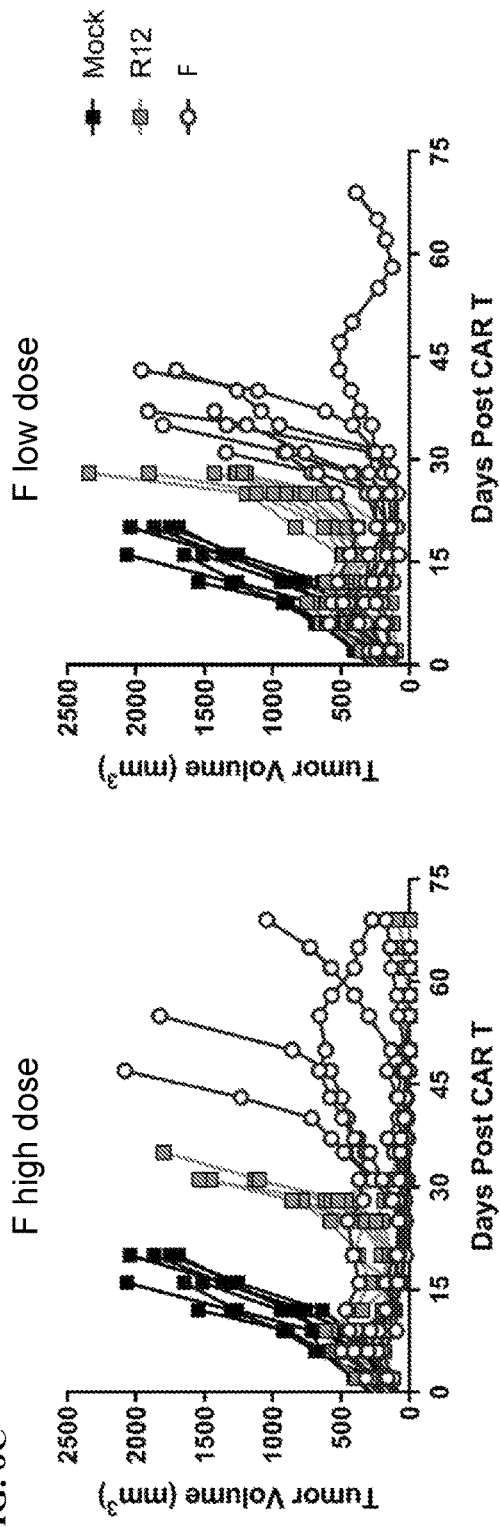
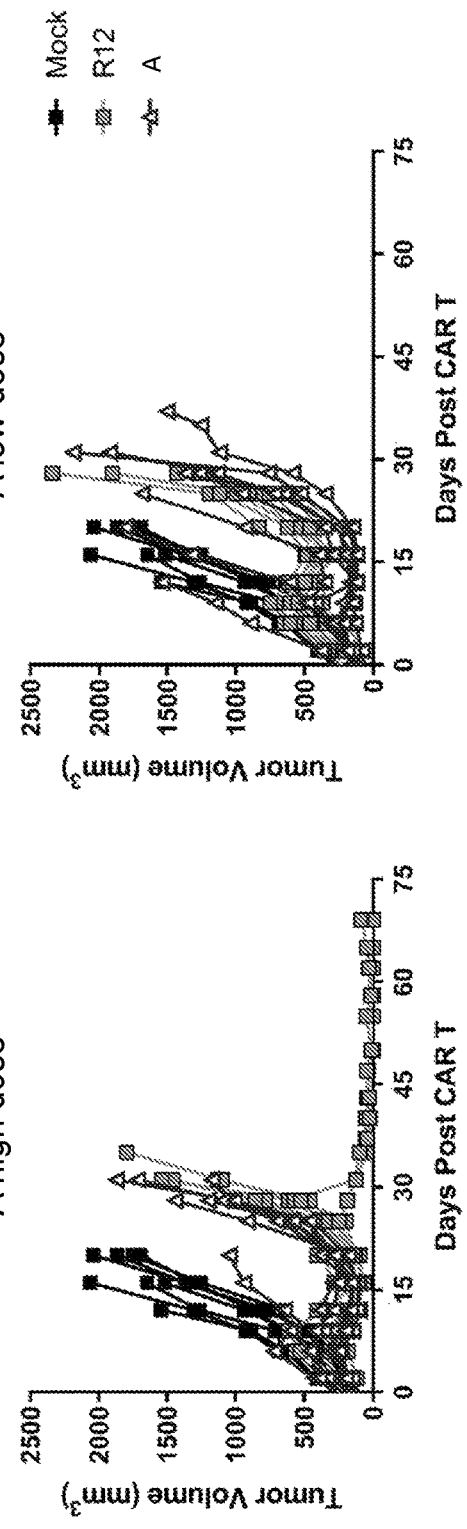
FIG. 8C

FIG. 13C
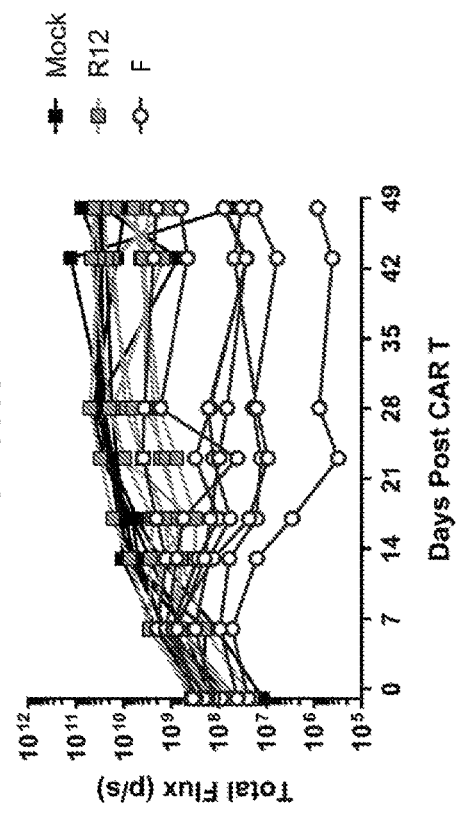
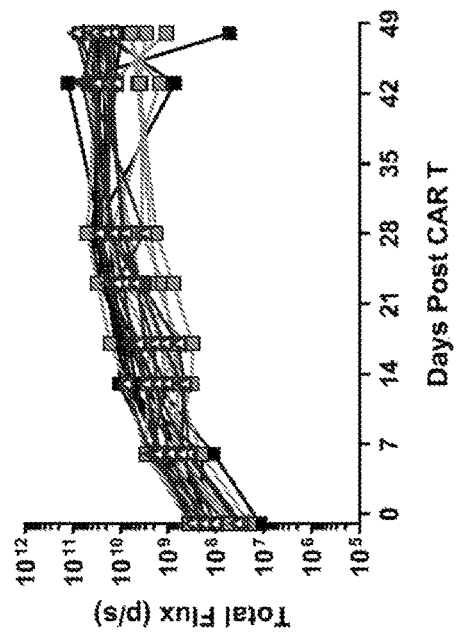
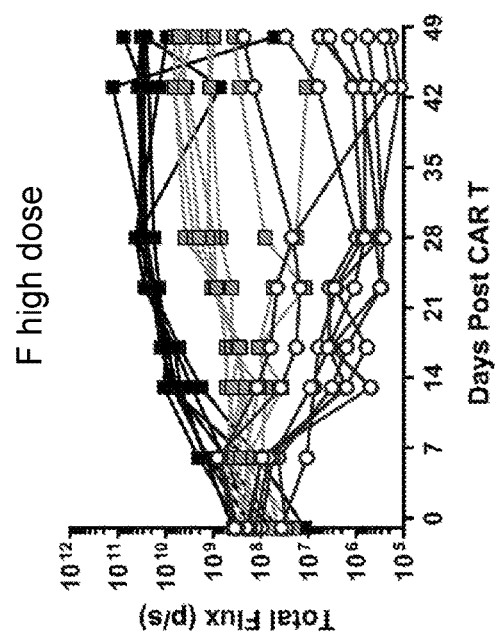
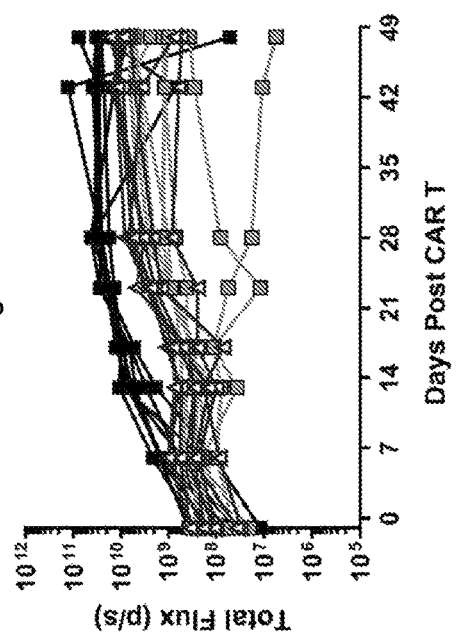

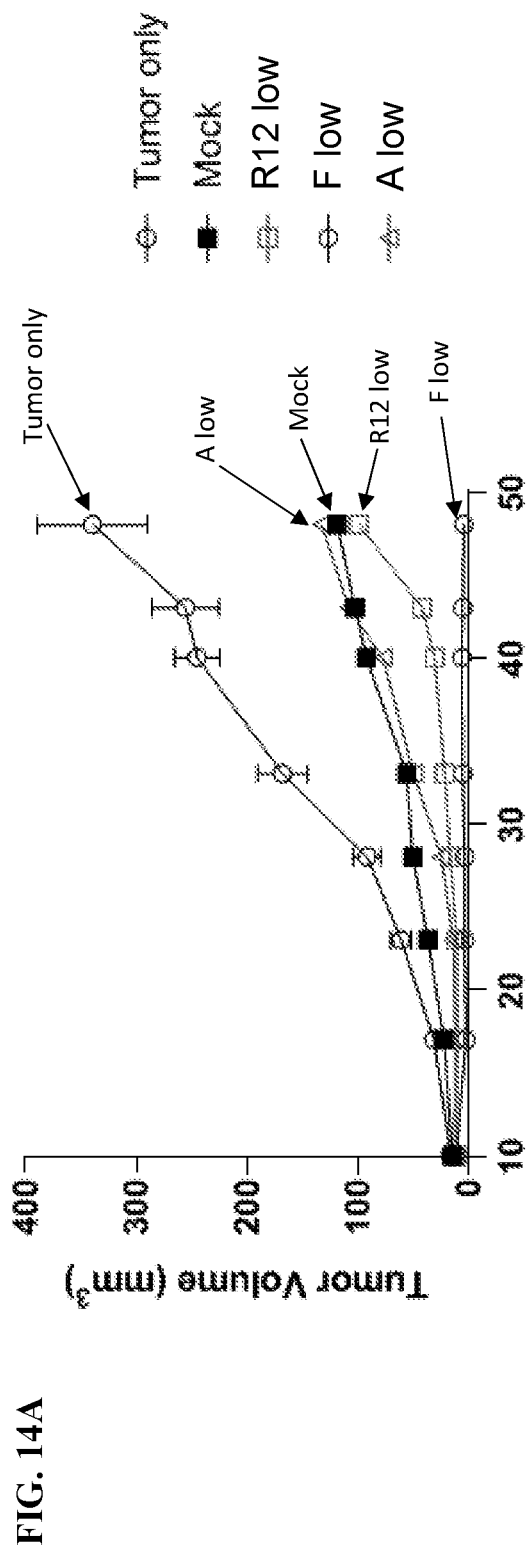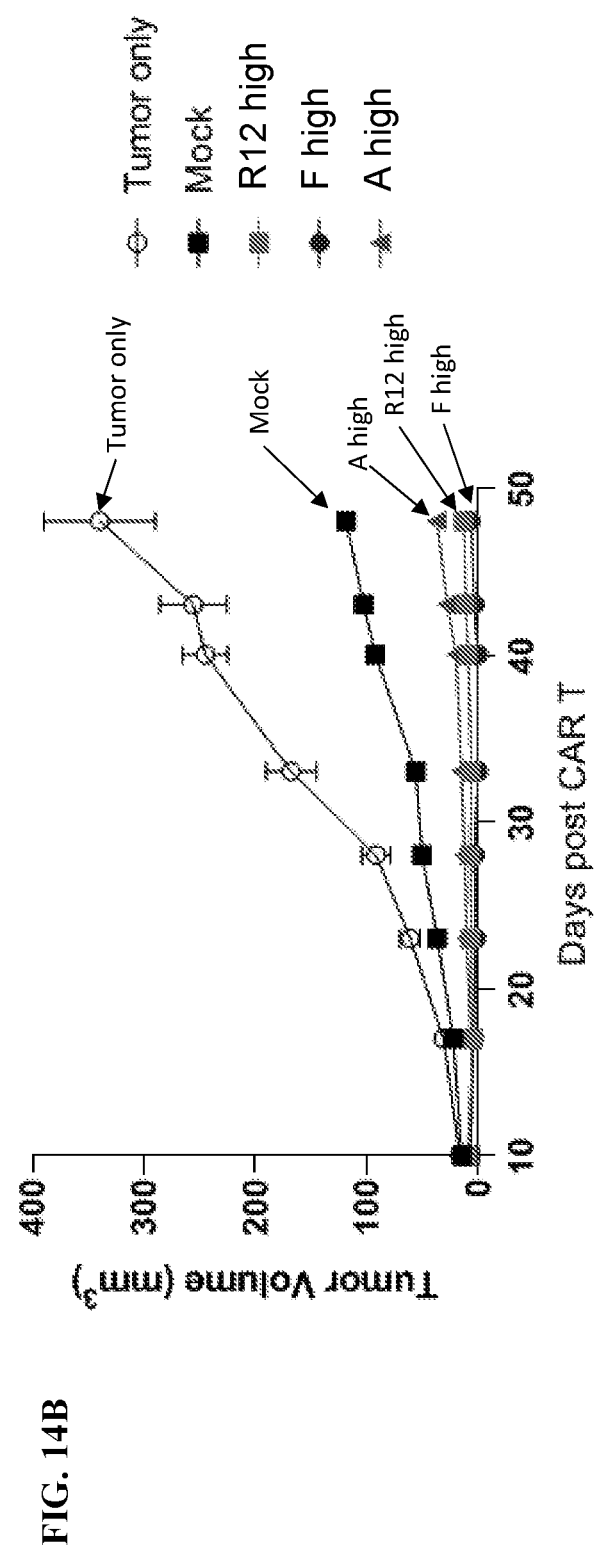
FIG. 14A
FIG. 14B

FIG. 14E
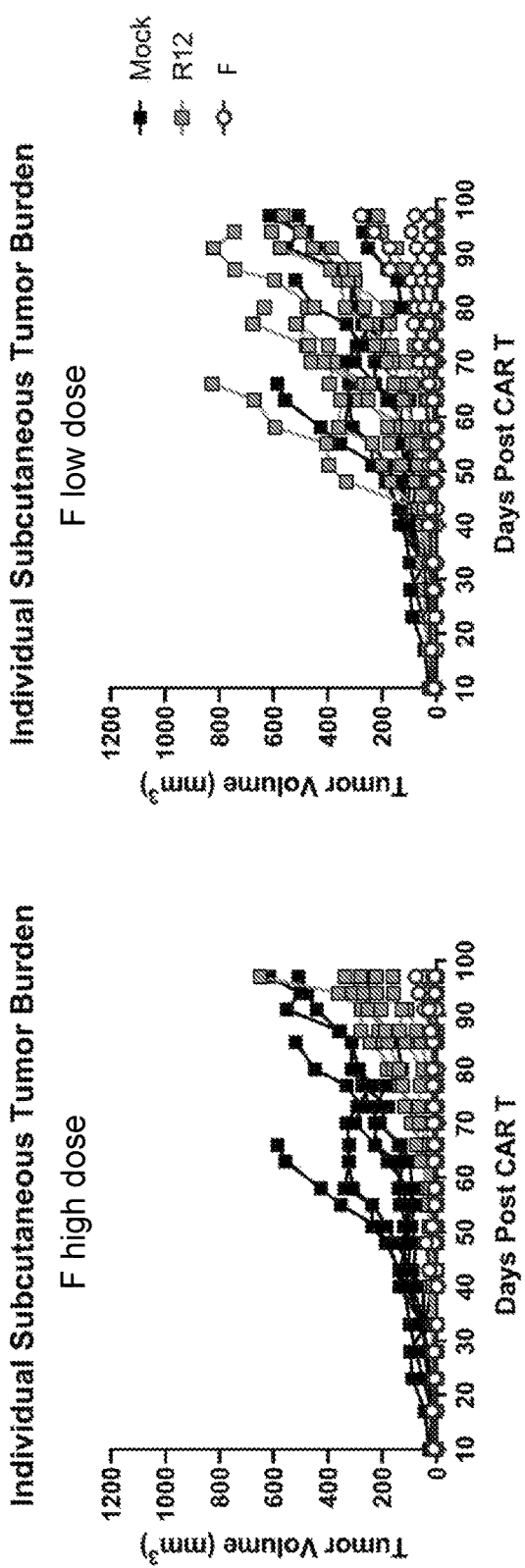
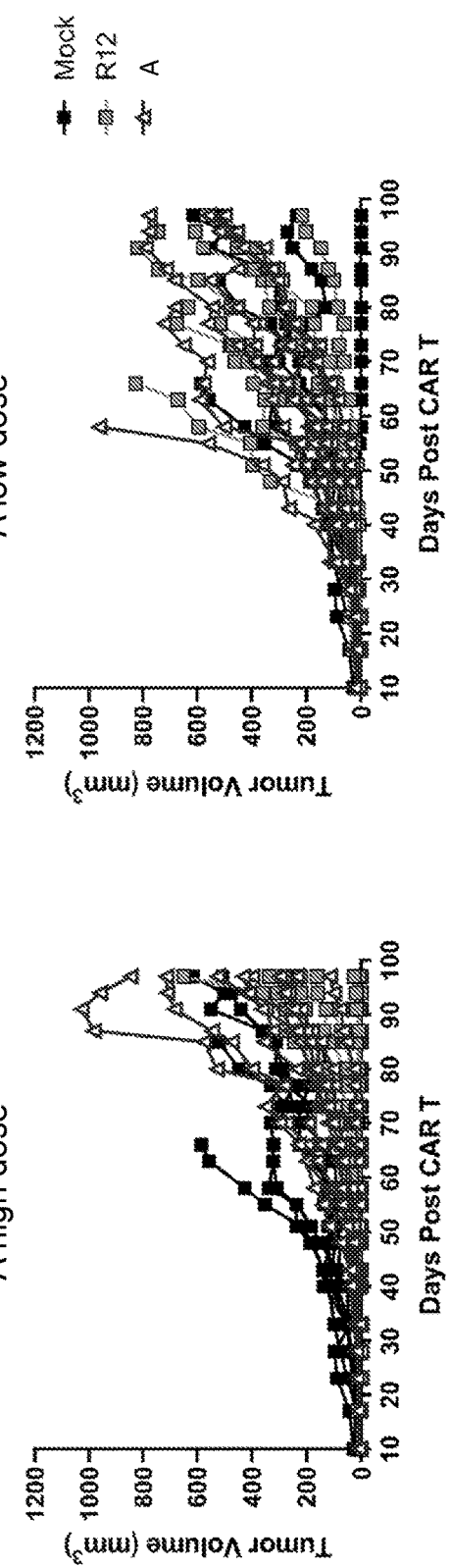

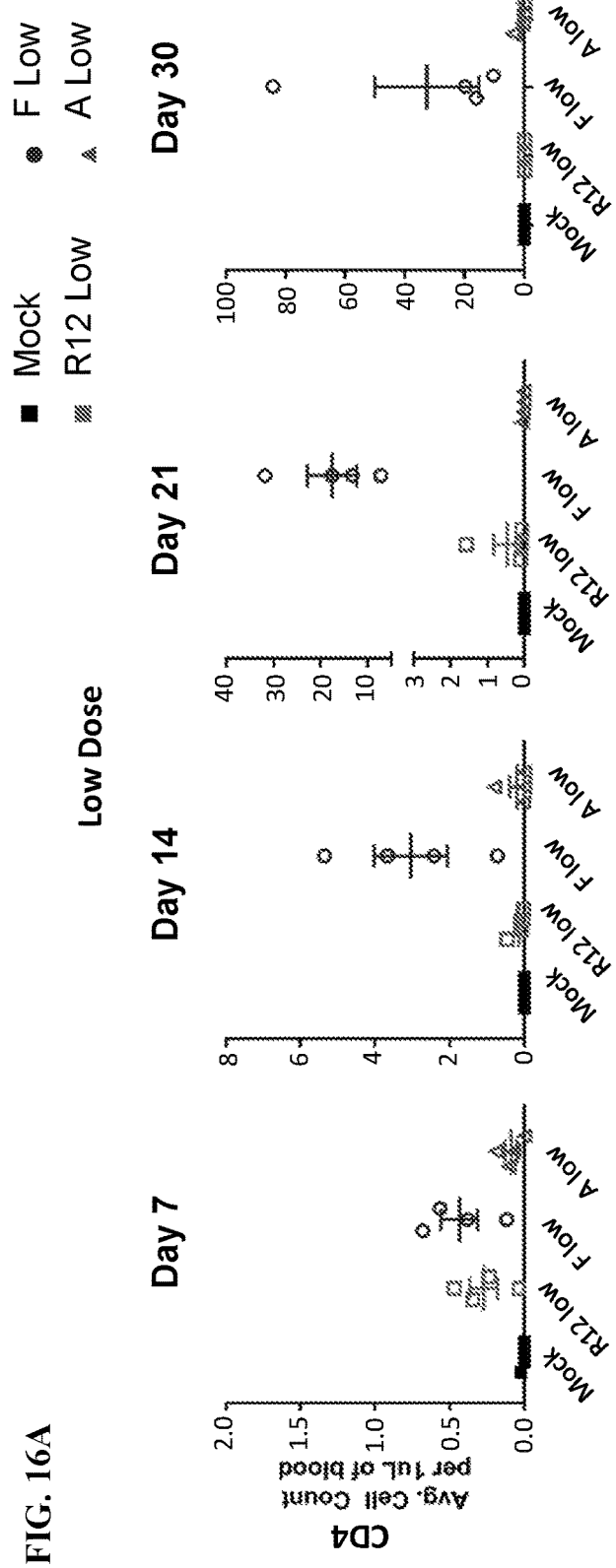
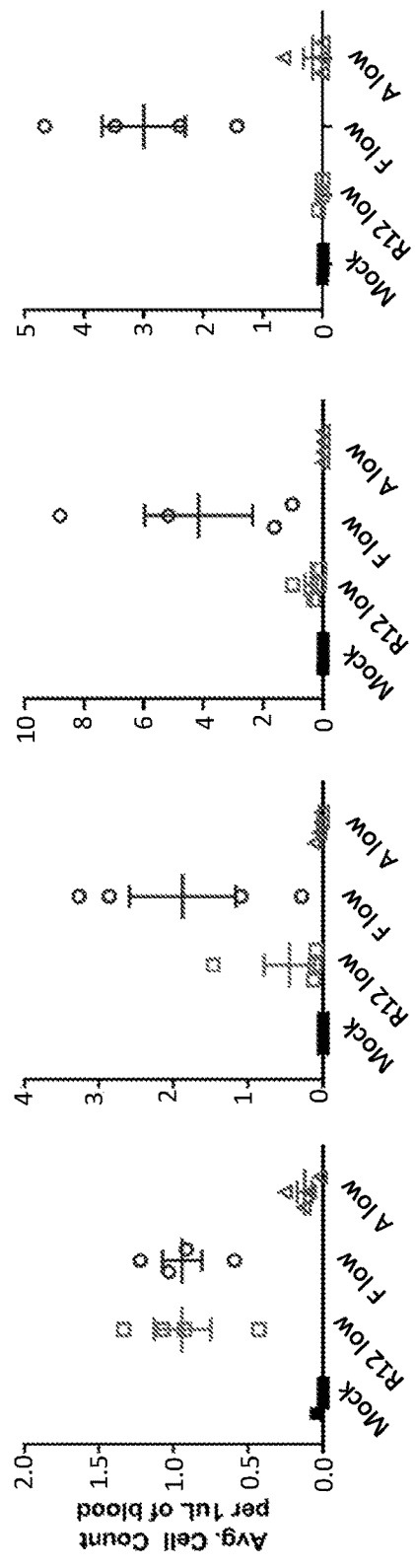
FIG. 16A
FIG. 16B

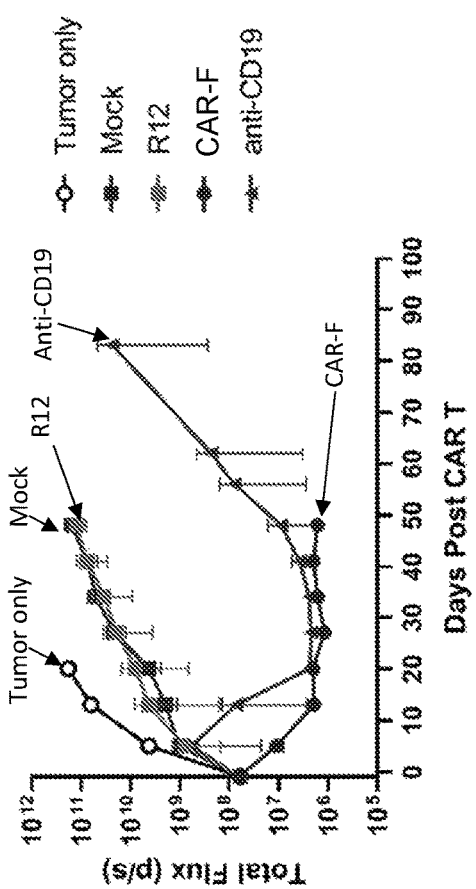
FIG. 19A Mean BLI Tumor Burden (3.0E+06 Dose)
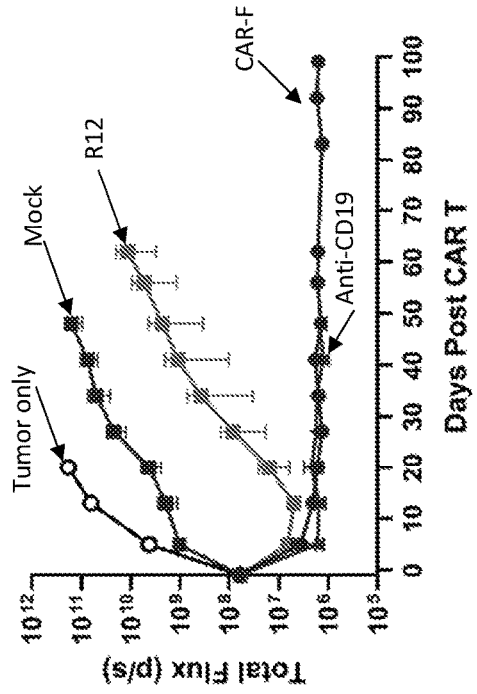
FIG. 19B Mean BLI Tumor Burden (1.0E+06 Dose)
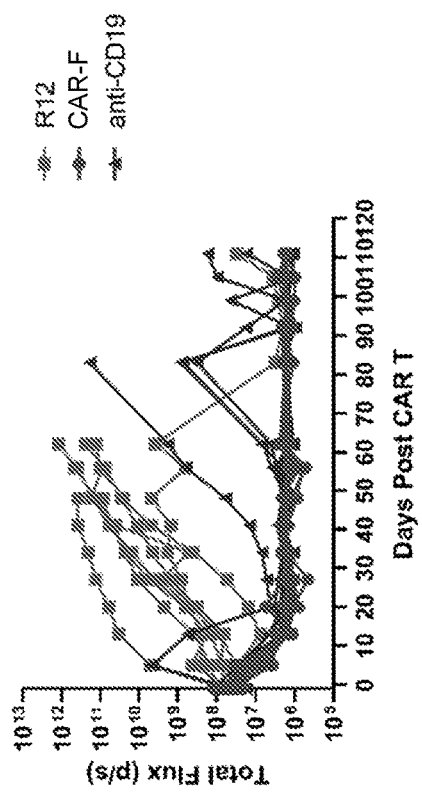
FIG. 19C Individual BLI Tumor Burden (3.0E+06 Dose)
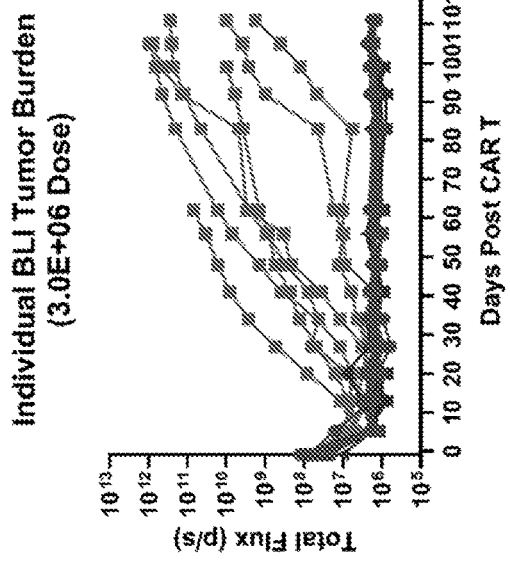
FIG. 19D Individual BLI Tumor Burden (1.0E+06 Dose)

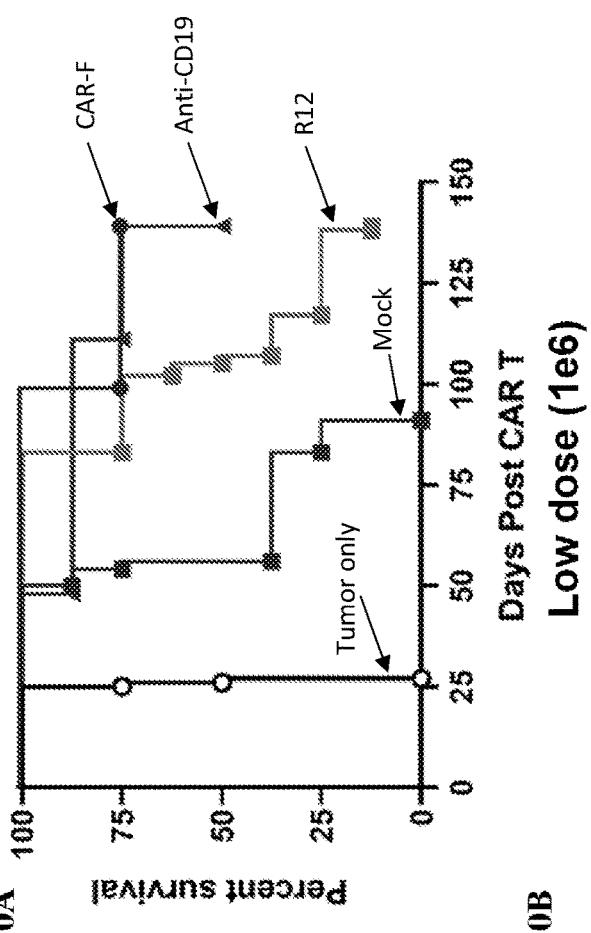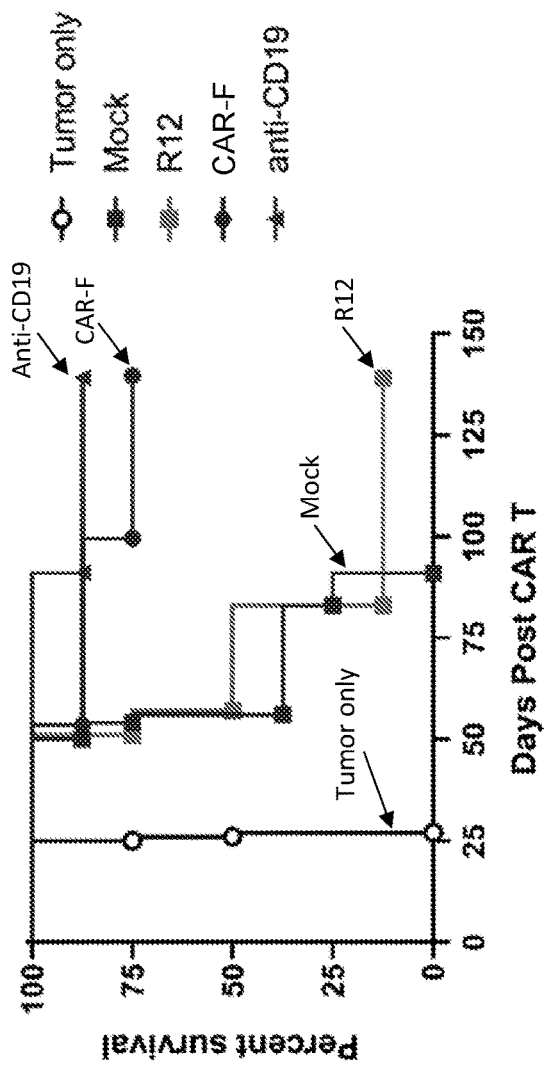
FIG. 20A
FIG. 20B

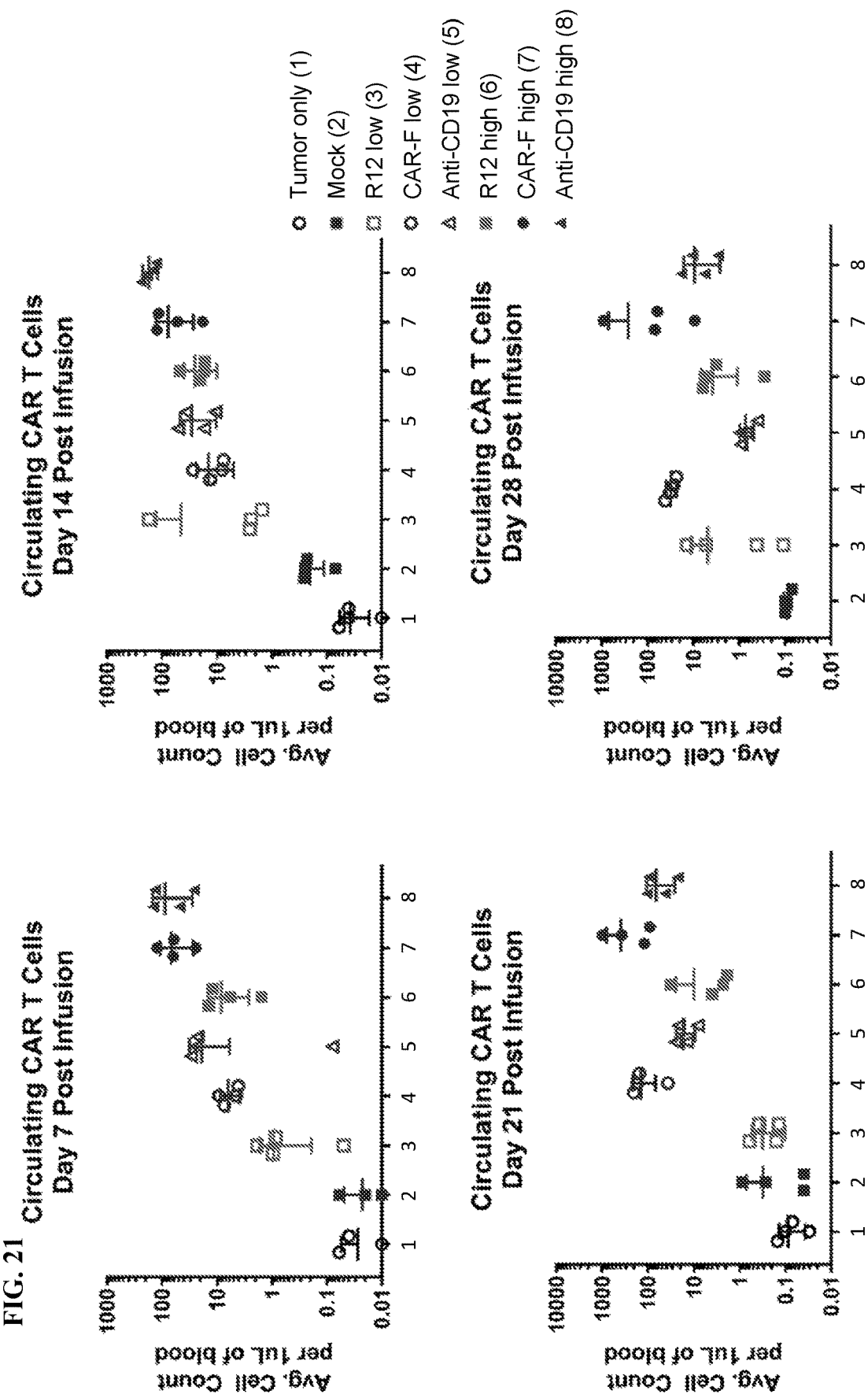

ROR1-1 mFc

ROR1-2 mFc

US 12,268,741 B2

ANTIBODIES AND CHIMERIC ANTIGEN RECEPTORS SPECIFIC FOR RECEPTOR TYROSINE KINASE LIKE ORPHAN RECEPTOR 1 (ROR1)

CROSS-REFERENCE TO RELATED APPLICATIONS

This application is a National Stage application under 35 U.S.C. § 371 of International Application No. PCT/US2020/015489, filed on Jan. 28, 2020, which claims priority from U.S. provisional application No. 62/798,456, filed Jan. 29, 2019, entitled "ANTIBODIES AND CHIMERIC ANTIGEN RECEPTORS SPECIFIC FOR RECEPTOR TYROSINE KINASE LIKE ORPHAN RECEPTOR 1 (ROR1)," the contents of which are incorporated by reference in their entirety.

INCORPORATION BY REFERENCE OF SEQUENCE LISTING

The present application is being filed along with a Sequence Listing in electronic format. The Sequence Listing is provided as a file entitled 735042017700SeqList.txt, created Jul. 7, 2021 which is 225 kilobytes in size. The information in the electronic format of the Sequence Listing is incorporated by reference in its entirety.

FIELD

The present disclosure relates in some aspects to receptor tyrosine kinase-like orphan receptor 1 (ROR1)-binding molecules, in particular, to human antibodies specific for ROR1, including antibody fragments. The present disclosure further relates to recombinant receptors, including chimeric antigen receptors (CARs) that contain such antibodies or fragments, and polynucleotides that encode the antibodies, antigen-binding fragments or receptors specific for ROR1. The disclosure further relates to genetically engineered cells, containing such ROR1-binding proteins and receptors, and related methods and uses thereof in adoptive cell therapy.

BACKGROUND

Receptor tyrosine kinase-like orphan receptor 1 (ROR1) is a transmembrane receptor expressed during embryogenesis, but typically not in normal adult cells. ROR1, however, is expressed in the context of a variety of different cancers, and in some cases, involved in cell signaling to promote tumor cell survival. Based on its expression, ROR1 could be a tumor-specific and/or tumor-associated target for therapy. ROR1-binding molecules, receptors and cells expressing such molecules are available. Improved ROR1-binding molecules and engineered ROR1-binding receptor-expressing cells are needed. Provided are embodiments that meet such needs.

SUMMARY

Provided herein is an anti-ROR1 antibody or antigen-binding fragment thereof, containing: a heavy chain variable ($V_H$) region, and a light chain variable ($V_L$) region, wherein: (i) the $V_H$ region contains a heavy chain complementarity determining region 1 (CDR-H1) containing the sequence set forth in SEQ ID NO: 67, 82 or 52, a heavy chain complementarity determining region 2 (CDR-H2) containing the sequence set forth in SEQ ID NO: 71, 86, 56 or 97, and a heavy chain complementarity determining region 3 (CDR-H3) containing the sequence set forth in SEQ ID NO: 73, 88, 58 or 99, and the $V_L$ region contains a light chain complementarity determining region 1 (CDR-L1) containing the sequence set forth in SEQ ID NO: 75, 90 or 60, a light chain complementarity determining region 2 (CDR-L2) containing the sequence set forth in SEQ ID NO: 77, 92 or 62; and a light chain complementarity determining region 3 (CDR-L3) containing the sequence set forth in SEQ ID NO: 79, 94 or 64; or (ii) the $V_H$ region contains a CDR-H1 containing the sequence set forth in SEQ ID NO: 65, 80 or 50, a CDR-H2 containing the sequence set forth in SEQ ID NO: 69, 84, 54 or 95, and a CDR-H3 containing the sequence set forth in SEQ ID NO: 73, 88, 58 or 99, and the $V_L$ region contains a CDR-L1 containing the sequence set forth in SEQ ID NO: 75, 90 or 60, a CDR-L2 containing the sequence set forth in SEQ ID NO: 77, 92 or 62; and a CDR-L3 containing the sequence set forth in SEQ ID NO: 79, 94 or 64; or (iii) the $V_H$ region contains a CDR-H1 containing the sequence set forth in SEQ ID NO: 66, 81 or 51, a CDR-H2 containing the sequence set forth in SEQ ID NO: 70, 85, 55 or 96, and a CDR-H3 containing the sequence set forth in SEQ ID NO: 73, 88, 58 or 99, and the $V_L$ region contains a CDR-L1 containing the sequence set forth in SEQ ID NO: 75, 90 or 60, a CDR-L2 containing the sequence set forth in SEQ ID NO: 77, 92 or 62; and a CDR-L3 containing the sequence set forth in SEQ ID NO: 79, 94 or 64; or (iv) the $V_H$ region contains a CDR-H1 containing the sequence set forth in SEQ ID NO: 68, 83 or 53, a CDR-H2 containing the sequence set forth in SEQ ID NO: 72, 87, 57 or 98, and a CDR-H3 containing the sequence set forth in SEQ ID NO: 74, 89, 59 or 100, and the $V_L$ region contains a CDR-L1 containing the sequence set forth in SEQ ID NO: 76, 91 or 61, a CDR-L2 containing the sequence set forth in SEQ ID NO: 78, 93 or 63; and a CDR-L3 containing the sequence set forth in SEQ ID NO: 79, 94 or 64.

Also provided herein is an anti-ROR1 antibody or antigen-binding fragment thereof, containing: a heavy chain variable ($V_H$) region, and a light chain variable ($V_L$) region, wherein: (i) the $V_H$ region contains a heavy chain complementarity determining region 1 (CDR-H1), a heavy chain complementarity determining region 2 (CDR-H2) and a heavy chain complementarity determining region 3 (CDR-H3) containing the sequence set forth in SEQ ID NOS:67, 71 and 73, respectively, and the $V_L$ region contains a light chain complementarity determining region 1 (CDR-L1), a light chain complementarity determining region 2 (CDR-L2) and a light chain complementarity determining region 3 (CDR-L3) containing the sequence set forth in SEQ ID NOS:75, 77 and 79, respectively; the $V_H$ region contains a CDR-H1, a CDR-H2 and a CDR-H3 containing the sequence set forth in SEQ ID NOS:82, 86 and 88, respectively, and the $V_L$ region contains a CDR-L1, a CDR-L2 and a CDR-L3 containing the sequence set forth in SEQ ID NOS:90, 92 and 94, respectively; the $V_H$ region contains a CDR-H1, a CDR-H2 and a CDR-H3 containing the sequence set forth in SEQ ID NOS:52, 56 and 58, respectively, and the $V_L$ region contains a CDR-L1, a CDR-L2 and a CDR-L3 containing the sequence set forth in SEQ ID NOS:60, 62 and 64, respectively; or the $V_H$ region contains a CDR-H1, a CDR-H2 and a CDR-H3 containing the sequence set forth in SEQ ID NOS:52, 97 and 99, respectively, and the $V_L$ region contains a CDR-L1, a CDR-L2 and a CDR-L3 containing the sequence set forth in SEQ ID NOS:60, 62 and 64, respectively; (ii) the $V_H$ region contains a CDR-H1, a CDR-H2 and a CDR-H3 containing the sequence set forth in SEQ ID NOS:65, 69 and 73, respectively, and the $V_L$ region contains a CDR-L1, a CDR-L2 and a CDR-L3 containing the sequence set forth in SEQ ID NOS:75, 77 and 79, respectively; the $V_H$ region contains a CDR-H1, a CDR-H2 and a CDR-H3 containing the sequence set forth in SEQ ID NOS:80, 84 and 88, respectively, and the $V_L$ region contains a CDR-L1, a CDR-L2 and a CDR-L3 containing the sequence set forth in SEQ ID NOS:90, 92 and 94, respectively; the $V_H$ region contains a CDR-H1, a CDR-H2 and a CDR-H3 containing the sequence set forth in SEQ ID NOS:50, 54 and 58, respectively, and the $V_L$ region contains a CDR-L1, a CDR-L2 and a CDR-L3 containing the sequence set forth in SEQ ID NOS:60, 62 and 64, respectively; or the $V_H$ region contains a CDR-H1, a CDR-H2 and a CDR-H3 containing the sequence set forth in SEQ ID NOS:50, 95 and 99, respectively, and the $V_L$ region contains a CDR-L1, a CDR-L2 and a CDR-L3 containing the sequence set forth in SEQ ID NOS:60, 62 and 64, respectively; (iii) the $V_H$ region contains a CDR-H1, a CDR-H2 and a CDR-H3 containing the sequence set forth in SEQ ID NOS:66, 70 and 73, respectively, and the $V_L$ region contains a CDR-L1, a CDR-L2 and a CDR-L3 containing the sequence set forth in SEQ ID NOS:75, 77 and 79, respectively; the $V_H$ region contains a CDR-H1, a CDR-H2 and a CDR-H3 containing the sequence set forth in SEQ ID NOS:81, 85 and 88, respectively, and the $V_L$ region contains a CDR-L1, a CDR-L2 and a CDR-L3 containing the sequence set forth in SEQ ID NOS:90, 92 and 94, respectively; the $V_H$ region contains a CDR-H1, a CDR-H2 and a CDR-H3 containing the sequence set forth in SEQ ID NOS:51, 55 and 58, respectively, and the $V_L$ region contains a CDR-L1, a CDR-L2 and a CDR-L3 containing the sequence set forth in SEQ ID NOS:60, 62 and 64, respectively; or the $V_H$ region contains a CDR-H1, a CDR-H2 and a CDR-H3 containing the sequence set forth in SEQ ID NOS:51, 96 and 99, respectively, and the $V_L$ region contains a CDR-L1, a CDR-L2 and a CDR-L3 containing the sequence set forth in SEQ ID NOS:60, 62 and 64, respectively; (iv) the $V_H$ region contains a CDR-H1, a CDR-H2 and a CDR-H3 containing the sequence set forth in SEQ ID NOS:68, 72 and 74, respectively, and the $V_L$ region contains a CDR-L1, a CDR-L2 and a CDR-L3 containing the sequence set forth in SEQ ID NOS:76, 78 and 79, respectively; or the $V_H$ region contains a CDR-H1, a CDR-H2 and a CDR-H3 containing the sequence set forth in SEQ ID NOS:83, 87 and 89, respectively, and the $V_L$ region contains a CDR-L1, a CDR-L2 and a CDR-L3 containing the sequence set forth in SEQ ID NOS:91, 93 and 94, respectively; the $V_H$ region contains a CDR-H1, a CDR-H2 and a CDR-H3 containing the sequence set forth in SEQ ID NOS:53, 57 and 59, respectively, and the $V_L$ region contains a CDR-L1, a CDR-L2 and a CDR-L3 containing the sequence set forth in SEQ ID NOS:60, 63 and 64, respectively; or the $V_H$ region contains a CDR-H1, a CDR-H2 and a CDR-H3 containing the sequence set forth in SEQ ID NOS:53, 98 and 100, respectively, and the $V_L$ region contains a CDR-L1, a CDR-L2 and a CDR-L3 containing the sequence set forth in SEQ ID NOS:61, 63 and 64, respectively.

In some of any such embodiments: (i) the $V_H$ region contains a CDR-H1, a CDR-H2 and a CDR-H3 containing the sequence set forth in SEQ ID NOS:67, 71 and 73, respectively, and the $V_L$ region contains a CDR-L1, a CDR-L2 and a CDR-L3 containing the sequence set forth in SEQ ID NOS:75, 77 and 79, respectively; (ii) the $V_H$ region contains a CDR-H1, a CDR-H2 and a CDR-H3 containing the sequence set forth in SEQ ID NOS:65, 69 and 73, respectively, and the $V_L$ region contains a CDR-L1, a CDR-L2 and a CDR-L3 containing the sequence set forth in SEQ ID NOS:75, 77 and 79, respectively; (iii) the $V_H$ region contains a CDR-H1, a CDR-H2 and a CDR-H3 containing the sequence set forth in SEQ ID NOS:66, 70 and 73, respectively, and the $V_L$ region contains a CDR-L1, a CDR-L2 and a CDR-L3 containing the sequence set forth in SEQ ID NOS:75, 77 and 79, respectively; or (iv) the $V_H$ region contains a CDR-H1, a CDR-H2 and a CDR-H3 containing the sequence set forth in SEQ ID NOS:68, 72 and 74, respectively, and the $V_L$ region contains a CDR-L1, a CDR-L2 and a CDR-L3 containing the sequence set forth in SEQ ID NOS:76, 78 and 79, respectively.

In some of any such embodiments: (i) the $V_H$ region contains a CDR-H1, a CDR-H2 and a CDR-H3 containing the sequence set forth in SEQ ID NOS:82, 86 and 88, respectively, and the $V_L$ region contains a CDR-L1, a CDR-L2 and a CDR-L3 containing the sequence set forth in SEQ ID NOS:90, 92 and 94, respectively; (ii) the $V_H$ region contains a CDR-H1, a CDR-H2 and a CDR-H3 containing the sequence set forth in SEQ ID NOS:80, 84 and 88, respectively, and the $V_L$ region contains a CDR-L1, a CDR-L2 and a CDR-L3 containing the sequence set forth in SEQ ID NOS:90, 92 and 94, respectively; (iii) the $V_H$ region contains a CDR-H1, a CDR-H2 and a CDR-H3 containing the sequence set forth in SEQ ID NOS:81, 85 and 88, respectively, and the $V_L$ region contains a CDR-L1, a CDR-L2 and a CDR-L3 containing the sequence set forth in SEQ ID NOS:90, 92 and 94, respectively; or (iv) the $V_H$ region contains a CDR-H1, a CDR-H2 and a CDR-H3 containing the sequence set forth in SEQ ID NOS:83, 87 and 89, respectively, and the $V_L$ region contains a CDR-L1, a CDR-L2 and a CDR-L3 containing the sequence set forth in SEQ ID NOS:91, 93 and 94, respectively.

In some of any embodiments, the $V_H$ region comprises a CDR-H1, a CDR-H2 and a CDR-H3 comprising the sequence set forth in SEQ ID NOS:67, 71 and 73, respectively, and the $V_L$ region comprises a CDR-L1, a CDR-L2 and a CDR-L3 comprising the sequence set forth in SEQ ID NOS:75, 77 and 79, respectively. In some of any embodiments, the $V_H$ region comprises a CDR-H1, a CDR-H2 and a CDR-H3 comprising the sequence set forth in SEQ ID NOS:82, 86 and 88, respectively, and the $V_L$ region comprises a CDR-L1, a CDR-L2 and a CDR-L3 comprising the sequence set forth in SEQ ID NOS:90, 92 and 94, respectively. In some of any such embodiments, the $V_H$ region comprises a CDR-H1, a CDR-H2 and a CDR-H3 comprising the sequence set forth in SEQ ID NOS:52, 56 and 58, respectively, and the $V_L$ region comprises a CDR-L1, a CDR-L2 and a CDR-L3 comprising the sequence set forth in SEQ ID NOS:60, 62 and 64, respectively. In some of any such embodiments, the $V_H$ region comprises a CDR-H1, a CDR-H2 and a CDR-H3 comprising the sequence set forth in SEQ ID NOS:52, 97 and 99, respectively, and the $V_L$ region comprises a CDR-L1, a CDR-L2 and a CDR-L3 comprising the sequence set forth in SEQ ID NOS:60, 62 and 64, respectively.

Also provided herein is an anti-ROR1 antibody or antigen-binding fragment thereof, containing: a heavy chain variable ($V_H$) region and a light chain variable ($V_L$) region, wherein: the $V_H$ region contains a heavy chain complementarity determining region 1 (CDR-H1), a heavy chain complementarity determining region 2 (CDR-H2) and a heavy chain complementarity determining region 3 (CDR-H3) contained within SEQ ID NO: 112, 121, 103 or 130, and the $V_L$ region contains a light chain complementarity determining region 1 (CDR-L1), a light chain complementarity determining region 2 (CDR-L2) and a light chain complementarity determining region 3 (CDR-L3) contained within SEQ ID NO: 115, 124 or 106.

Also provided herein is an anti-ROR1 antibody or antigen-binding fragment thereof, containing: a heavy chain variable ($V_H$) region and a light chain variable ($V_L$) region, wherein: the $V_H$ region contains a heavy chain complementarity determining region 1 (CDR-H1), a heavy chain complementarity determining region 2 (CDR-H2) and a heavy chain complementarity determining region 3 (CDR-H3) contained within SEQ ID NO:112, and the $V_L$ region contains a light chain complementarity determining region 1 (CDR-L1), a light chain complementarity determining region 2 (CDR-L2) and a light chain complementarity determining region 3 (CDR-L3) contained within SEQ ID NO:115; the $V_H$ region contains a CDR-H1, a CDR-H2 and a CDR-H3 contained within SEQ ID NO:121, and the $V_L$ region contains a CDR-L1, a CDR-L2 and a CDR-L3 contained within SEQ ID: NO 124; the $V_H$ region contains a CDR-H1, a CDR-H2 and a CDR-H3 contained within SEQ ID NO:103, and the $V_L$ region contains a CDR-L1, a CDR-L2 and a CDR-L3 contained within SEQ ID: NO 106; or the $V_H$ region contains a CDR-H1, a CDR-H2 and a CDR-H3 contained within SEQ ID NO:130, and the $V_L$ region contains a CDR-L1, a CDR-L2 and a CDR-L3 contained within SEQ ID: NO 106.

In some of any such embodiments, the $V_H$ region contains a CDR-H1, a CDR-H2 and a CDR-H3 contained within SEQ ID NO:112, and the $V_L$ region contains a CDR-L1, a CDR-L2 and a CDR-L3 contained within SEQ ID: NO 115. In some of any such embodiments, the $V_H$ region contains a CDR-H1, a CDR-H2 and a CDR-H3 contained within SEQ ID NO:121, and the $V_L$ region contains a CDR-L1, a CDR-L2 and a CDR-L3 contained within SEQ ID: NO 124. In some of any embodiments, the $V_H$ region comprises a CDR-H1, a CDR-H2 and a CDR-H3 contained within SEQ ID NO:103, and the $V_L$ region comprises a CDR-L1, a CDR-L2 and a CDR-L3 contained within SEQ ID: NO 106. In some of any embodiments, the $V_H$ region comprises a CDR-H1, a CDR-H2 and a CDR-H3 contained within SEQ ID NO:130, and the $V_L$ region comprises a CDR-L1, a CDR-L2 and a CDR-L3 contained within SEQ ID: NO 106.

In some of any such embodiments, the $V_H$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO: 112, 121, 103 or 130, and the $V_L$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO: 115, 124 or 106. In some of any such embodiments, the $V_H$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO:112, and the $V_L$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO: 115; the $V_H$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO:121, and the $V_L$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO:124; the $V_H$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO:103, and the $V_L$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO:106; or the $V_H$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO:130, and the $V_L$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO:106.

In some of any such embodiments, the $V_H$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO:112, and the $V_L$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO: 115. In some of any such embodiments, the $V_H$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO:121, and the $V_L$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO:124. In some of any embodiments, the $V_H$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:103, and the $V_L$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:106. In some of any embodiments, the $V_H$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:130, and the $V_L$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:106.

Also provided herein is an anti-ROR1 antibody or antigen-binding fragment thereof, containing: a heavy chain variable ($V_H$) region and a light chain variable ($V_L$) region, wherein: the $V_H$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO: 112, 121, 103 or 130, and the $V_L$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO: 115, 124 or 106.

Also provided herein is an anti-ROR1 antibody or antigen-binding fragment thereof, containing: a heavy chain variable ($V_H$) region and a light chain variable ($V_L$) region, wherein: the $V_H$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO:112, and the $V_L$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO: 115; the $V_H$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO:121, and the $V_L$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO:124; the $V_H$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO:103, and the $V_L$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO:106; or the $V_H$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO:130, and the $V_L$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO:106.

In some of any such embodiments, the $V_H$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO:112, and the $V_L$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO: 115. In some of any such embodiments, the $V_H$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO:121, and the $V_L$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO:124.

In some of any such embodiments: the $V_H$ region is or contains the sequence set forth in SEQ ID NO: 112, 121, 103 or 130, and the $V_L$ region is or contains the sequence set forth in SEQ ID NO: 115, 124 or 106. In some of any such embodiments: the $V_H$ region and the $V_L$ region are or contain the sequence set forth in SEQ ID NOS: 112 and 115, respectively; the $V_H$ region and the $V_L$ region are or contain the sequence set forth in SEQ ID NOS: 121 and 124, respectively; the $V_H$ region and the $V_L$ region are or contain the sequence set forth in SEQ ID NOS: 103 and 106, respectively; or the $V_H$ region and the $V_L$ region are or contain the sequence set forth in SEQ ID NOS: 130 and 106, respectively.

Also provided herein is an anti-ROR1 antibody or antigen-binding fragment thereof, containing: a heavy chain variable ($V_H$) region and a light chain variable ($V_L$) region, wherein: the $V_H$ region is or contains the sequence set forth in SEQ ID NO: 112, 121, 103 or 130, and the $V_L$ region is or contains the sequence set forth in SEQ ID NO: 115, 124 or 106.

Also provided herein is an anti-ROR1 antibody or antigen-binding fragment thereof, containing: a heavy chain variable ($V_H$) region and a light chain variable ($V_L$) region, wherein: the $V_H$ region and the $V_L$ region are or contain the sequence set forth in SEQ ID NOS: 112 and 115, respectively; the $V_H$ region and the $V_L$ region are or contain the sequence set forth in SEQ ID NOS: 121 and 124, respectively; the $V_H$ region and the $V_L$ region are or contain the sequence set forth in SEQ ID NOS: 103 and 106, respectively; or the $V_H$ region and the $V_L$ region are or contain the sequence set forth in SEQ ID NOS: 130 and 106, respectively.

In some of any such embodiments, the $V_H$ region and the $V_L$ region are or contain the sequence set forth in SEQ ID NOS: 112 and 115, respectively. In some of any such embodiments, the $V_H$ region and the $V_L$ region are or contain the sequence set forth in SEQ ID NOS:121 and 124, respectively. In some of any embodiments, the $V_H$ region and the $V_L$ region are or comprise the sequence set forth in SEQ ID NOS: 103 and 106, respectively. In some of any embodiments, the $V_H$ region and the $V_L$ region are or comprise the sequence set forth in SEQ ID NOS:130 and 106, respectively.

In some of any such embodiments, the $V_H$ region is or contains the amino acid sequence encoded by SEQ ID NO: 110, 119, 101 or 128 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 110, 119, 101 or 128, and the $V_L$ region is or contains the amino acid sequence encoded by SEQ ID NO: 113, 122 or 104, or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 113, 122 or 104. In some of any such embodiments, the $V_H$ region is or contains the amino acid sequence encoded by SEQ ID NO: 111, 120, 102 or 129, and the $V_L$ region is or contains the amino acid sequence encoded by SEQ ID NO: 114, 123, 105 or 131. In some of any such embodiments, the $V_H$ region is or contains the amino acid sequence encoded by SEQ ID NO: 110 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 110, and the $V_L$ region is or contains the amino acid sequence encoded by SEQ ID NO: 113, or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 113. In some of any such embodiments, the $V_H$ region is or contains the amino acid sequence encoded by SEQ ID NO: 111, and the $V_L$ region is or contains the amino acid sequence encoded by SEQ ID NO: 114. In some of any such embodiments, the $V_H$ region is or contains the amino acid sequence encoded by SEQ ID NO: 119 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 119, and the $V_L$ region is or contains the amino acid sequence encoded by SEQ ID NO: 122, or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 122. In some of any such embodiments, the $V_H$ region is or contains the amino acid sequence encoded by SEQ ID NO: 120, and the $V_L$ region is or contains the amino acid sequence encoded by SEQ ID NO: 123.

In some of any embodiments, the antibody is a full length antibody. In some of any embodiments, the antibody is an antigen-binding fragment. In some of any such embodiments, said anti-ROR1 antibody or antigen-binding fragment thereof is isolated. In some of any such embodiments, said anti-ROR1 antibody or antigen-binding fragment thereof is recombinant. In some of any such embodiments, at least a portion of the $V_H$ region and the $V_L$ region is human or is from a human protein. In some of any such embodiments, the antigen-binding fragment thereof is or contains a single chain fragment. In some of any such embodiments, the antigen-binding fragment thereof is or contains a single chain Fv (scFv).

In some of any such embodiments, the $V_H$ region is amino-terminal to the $V_L$ region. In some of any such embodiments, the $V_H$ region is carboxy-terminal to the $V_L$ region. In some of any such embodiments, the $V_H$ region and the $V_L$ region are joined by a flexible linker. In some of any such embodiments, the flexible linker contains the sequence set forth in SEQ ID NO:41.

In some of any such embodiments, the scFv is or contains the sequence set forth in SEQ ID NO: 118, 127, 109 or 134, or an amino acid sequence having at least at or about 85%, 86%, 87%, 88%, 89%, 90%, 91%, 92%, 93%, 94%, 95%, 96%, 97%, 98% or 99% sequence identity to SEQ ID NO: 118, 127, 109 or 134. In some of any such embodiments, the scFv is or contains the sequence set forth in SEQ ID NO: 118. In some of any such embodiments, the scFv is or contains the sequence set forth in SEQ ID NO: 127. In some of any embodiments, the scFv is or comprises the sequence set forth in SEQ ID NO: 109. In some of any embodiments, the scFv is or comprises the sequence set forth in SEQ ID NO: 134.

In some of any such embodiments, the scFv is or contains the amino acid sequence encoded by SEQ ID NO: 116, 125, 107 or 132 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 116, 125, 107 or 132. In some of any such embodiments, the scFv is or contains the amino acid sequence encoded by SEQ ID NO: 117, 126, 108 or 133. In some of any such embodiments, the scFv is or contains the amino acid sequence encoded by SEQ ID NO: 116 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 116. In some of any such embodiments, the scFv is or contains the amino acid sequence encoded by SEQ ID NO: 117. In some of any such embodiments, the scFv is or contains the amino acid sequence encoded by SEQ ID NO: 125 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 125. In some of any such embodiments, the scFv is or contains the amino acid sequence encoded by SEQ ID NO: 126.

In some of any such embodiments, the anti-ROR1 antibody or fragment further contains at least a portion of an immunoglobulin constant region or a variant thereof. In some of any such embodiments, the portion of an immunoglobulin constant region contains at least a portion of a hinge region or a variant thereof. In some of any such embodiments, the at least a portion of an immunoglobulin constant region or a variant thereof contains at least a portion of a $C_H2$ region or a variant thereof. In some of any such embodiments, the at least a portion of an immunoglobulin constant region or a variant thereof contains at least a portion of a $C_H3$ region or a variant thereof. In some of any such embodiments, the at least a portion of an immunoglobulin constant region or a variant thereof contains at least a portion of a $C_H2$ region and/or a $C_H3$ region or a variant thereof. In some of any such embodiments, the at least a portion of an immunoglobulin constant region or a variant thereof is human or from a human protein or a variant thereof.

In some of any such embodiments, said anti-ROR1 antibody or antigen-binding fragment thereof specifically binds to a Receptor tyrosine kinase-like orphan receptor 1 (ROR1) protein. In some of any such embodiments, said anti-ROR1 antibody or antigen-binding fragment thereof specifically binds to a human ROR1 protein. In some of any such embodiments, the human ROR1 protein contains an amino acid sequence set forth in SEQ ID NO: 144, 145 or 146.

In some of any embodiments, the anti-ROR1 antibody or antigen-binding fragment thereof specifically binds to an epitope consisting of the sequence set forth in SEQ ID NO:199 or an epitope present within the sequence set forth in SEQ ID NO:199. In some of any embodiments, the antibody or antigen-binding fragment thereof further binds to one or more epitopes consisting of a sequence selected from among any one of SEQ ID NOS: 200-214 or an epitope present within a sequence selected from among any one of SEQ ID NOS: 200-214. In some of any embodiments, the one or more epitopes comprises a conformational epitope.

In some of any such embodiments, said anti-ROR1 antibody or antigen-binding fragment thereof does not bind to, is not cross-reactive to, or binds at a lower level or degree or affinity to a Receptor tyrosine kinase-like orphan receptor 2 (ROR2) protein. In some of any such embodiments, said anti-ROR1 antibody or antigen-binding fragment thereof does not bind to, is not cross-reactive to, or binds at a lower level or degree or affinity to a human ROR2 protein. In some of any such embodiments, the extent, level or degree or affinity of binding of said anti-ROR1 antibody or antigen-binding fragment thereof to a human ROR2 is at least at or about 75%, 80%, 90%, 95% or 99% less than the extent, level or degree or affinity of binding to a human ROR1 protein.

In some of any embodiments, the antibody or antigen-binding fragment thereof binds to human ROR1 protein with an equilibrium dissociation constant ($K_D$) of from about $1 \times 10^{-11}$ M to about $1 \times 10^{-7}$ M. In some of any embodiments, the antibody or antigen-binding fragment thereof binds to human ROR1 protein with an equilibrium dissociation constant ($K_D$) of from about $1 \times 10^{-8}$ M to about $1 \times 10^{-7}$ M. In some of any embodiments, the antibody or antigen-binding fragment thereof binds to human ROR1 protein with an equilibrium dissociation constant ($K_D$) of from about $5 \times 10^{-11}$ M to about $1 \times 10^{10}$ M.

In some of any embodiments, the antibody or antigen-binding fragment thereof binds to human ROR1 protein with an dissociation rate constant ($k_d$ or $k_{off}$) of from about $1 \times 10^{-5}$ 1/s to about $1 \times 10^{-2}$ 1/s. In some of any embodiments, the antibody or antigen-binding fragment thereof binds to human ROR1 protein with an dissociation rate constant ($k_d$ or $k_{off}$) of from about $1 \times 10^{-3}$ 1/s to about $1 \times 10^{-2}$ 1/s. In some of any embodiments, the antibody or antigen-binding fragment thereof binds to human ROR1 protein with an dissociation rate constant ($k_d$ or $k_{off}$) of from about $1 \times 10^{-5}$ 1/s to about $1 \times 10^{-4}$ 1/s.

Also provided herein is a single chain cell-surface protein, containing the anti-ROR1 antibody or antigen-binding fragment thereof of any of the embodiments provided herein.

Also provided herein is a conjugate, containing the anti-ROR1 antibody or antigen-binding fragment thereof of any of the embodiments provided herein and a heterologous molecule or moiety. In some of any such embodiments, the heterologous molecule or moiety is a therapeutic moiety.

Also provided herein is an anti-ROR1 chimeric antigen receptor (CAR) containing an extracellular antigen-binding domain containing the anti-ROR1 antibody or antigen-binding fragment thereof of any of the embodiments provided herein and an intracellular signaling region.

Also provided herein is an anti-ROR1 chimeric antigen receptor (CAR) containing an extracellular antigen-binding domain containing the anti-ROR1 antibody or antigen-binding fragment thereof of any of the embodiments provided herein, a transmembrane region and an intracellular signaling region.

Also provided herein is an anti-ROR1 chimeric antigen receptor (CAR) containing: an extracellular antigen-binding domain containing a heavy chain variable ($V_H$) region, and a light chain variable (V$_L$) region, and an intracellular signaling region, wherein: (i) the V$_H$ region contains a heavy chain complementarity determining region 1 (CDR-H1) containing the sequence set forth in SEQ ID NO: 67, 82 or 52, a heavy chain complementarity determining region 2 (CDR-H2) containing the sequence set forth in SEQ ID NO: 71, 86, 56 or 97, and a heavy chain complementarity determining region 3 (CDR-H3) containing the sequence set forth in SEQ ID NO: 73, 88, 58 or 99, and the V$_L$ region contains a light chain complementarity determining region 1 (CDR-L1) containing the sequence set forth in SEQ ID NO: 75, 90 or 60, a light chain complementarity determining region 2 (CDR-L2) containing the sequence set forth in SEQ ID NO: 77, 92 or 62; and a light chain complementarity determining region 3 (CDR-L3) containing the sequence set forth in SEQ ID NO: 79, 94 or 64; or (ii) the V$_H$ region contains a CDR-H1 containing the sequence set forth in SEQ ID NO: 65, 80 or 50, a CDR-H2 containing the sequence set forth in SEQ ID NO: 69, 84, 54 or 95, and a CDR-H3 containing the sequence set forth in SEQ ID NO: 73, 88, 58 or 99, and the V$_L$ region contains a CDR-L1 containing the sequence set forth in SEQ ID NO: 75, 90 or 60, a CDR-L2 containing the sequence set forth in SEQ ID NO: 77, 92 or 62; and a CDR-L3 containing the sequence set forth in SEQ ID NO: 79, 94 or 64; or (iii) the V$_H$ region contains a CDR-H1 containing the sequence set forth in SEQ ID NO: 66, 81 or 51, a CDR-H2 containing the sequence set forth in SEQ ID NO: 70, 85, 55 or 96, and a CDR-H3 containing the sequence set forth in SEQ ID NO: 73, 88, 58 or 99, and the V$_L$ region contains a CDR-L1 containing the sequence set forth in SEQ ID NO: 75, 90 or 60, a CDR-L2 containing the sequence set forth in SEQ ID NO: 77, 92 or 62; and a CDR-L3 containing the sequence set forth in SEQ ID NO: 79, 94 or 64; or (iv) the V$_H$ region contains a CDR-H1 containing the sequence set forth in SEQ ID NO: 68, 83 or 53, a CDR-H2 containing the sequence set forth in SEQ ID NO: 72, 87, 57 or 98, and a CDR-H3 containing the sequence set forth in SEQ ID NO: 74, 89, 59 or 100, and the V$_L$ region contains a CDR-L1 containing the sequence set forth in SEQ ID NO: 76, 91 or 61, a CDR-L2 containing the sequence set forth in SEQ ID NO: 78, 93 or 63; and a CDR-L3 containing the sequence set forth in SEQ ID NO: 79, 94 or 64.

Also provided herein is an anti-ROR1 chimeric antigen receptor (CAR) containing: an extracellular antigen-binding domain containing a heavy chain variable (V$_H$) region, and a light chain variable (V$_L$) region, and an intracellular signaling region, wherein: (i) the V$_H$ region contains a heavy chain complementarity determining region 1 (CDR-H1), a heavy chain complementarity determining region 2 (CDR-H2) and a heavy chain complementarity determining region 3 (CDR-H3) containing the sequence set forth in SEQ ID NOS:67, 71 and 73, respectively, and the V$_L$ region contains a light chain complementarity determining region 1 (CDR-L1), a light chain complementarity determining region 2 (CDR-L2) and a light chain complementarity determining region 3 (CDR-L3) containing the sequence set forth in SEQ ID NOS:75, 77 and 79, respectively; the V$_H$ region contains a CDR-H1, a CDR-H2 and a CDR-H3 containing the sequence set forth in SEQ ID NOS:82, 86 and 88, respectively, and the V$_L$ region contains a CDR-L1, a CDR-L2 and a CDR-L3 containing the sequence set forth in SEQ ID NOS:90, 92 and 94, respectively; the V$_H$ region contains a CDR-H1, a CDR-H2 and a CDR-H3 containing the sequence set forth in SEQ ID NOS:52, 56 and 58, respectively, and the V$_L$ region contains a CDR-L1, a CDR-L2 and a CDR-L3 containing the sequence set forth in SEQ ID NOS:60, 62 and 64, respectively; or the V$_H$ region contains a CDR-H1, a CDR-H2 and a CDR-H3 containing the sequence set forth in SEQ ID NOS:52, 97 and 99, respectively, and the V$_L$ region contains a CDR-L1, a CDR-L2 and a CDR-L3 containing the sequence set forth in SEQ ID NOS:60, 62 and 64, respectively; (ii) the V$_H$ region contains a CDR-H1, a CDR-H2 and a CDR-H3 containing the sequence set forth in SEQ ID NOS:65, 69 and 73, respectively, and the V$_L$ region contains a CDR-L1, a CDR-L2 and a CDR-L3 containing the sequence set forth in SEQ ID NOS:75, 77 and 79, respectively; the V$_H$ region contains a CDR-H1, a CDR-H2 and a CDR-H3 containing the sequence set forth in SEQ ID NOS:80, 84 and 88, respectively, and the V$_L$ region contains a CDR-L1, a CDR-L2 and a CDR-L3 containing the sequence set forth in SEQ ID NOS:90, 92 and 94, respectively; the V$_H$ region contains a CDR-H1, a CDR-H2 and a CDR-H3 containing the sequence set forth in SEQ ID NOS:50, 54 and 58, respectively, and the V$_L$ region contains a CDR-L1, a CDR-L2 and a CDR-L3 containing the sequence set forth in SEQ ID NOS:60, 62 and 64, respectively; or the V$_H$ region contains a CDR-H1, a CDR-H2 and a CDR-H3 containing the sequence set forth in SEQ ID NOS:50, 95 and 99, respectively, and the V$_L$ region contains a CDR-L1, a CDR-L2 and a CDR-L3 containing the sequence set forth in SEQ ID NOS:60, 62 and 64, respectively; (iii) the V$_H$ region contains a CDR-H1, a CDR-H2 and a CDR-H3 containing the sequence set forth in SEQ ID NOS:66, 70 and 73, respectively, and the V$_L$ region contains a CDR-L1, a CDR-L2 and a CDR-L3 containing the sequence set forth in SEQ ID NOS:75, 77 and 79, respectively; the V$_H$ region contains a CDR-H1, a CDR-H2 and a CDR-H3 containing the sequence set forth in SEQ ID NOS:81, 85 and 88, respectively, and the V$_L$ region contains a CDR-L1, a CDR-L2 and a CDR-L3 containing the sequence set forth in SEQ ID NOS:90, 92 and 94, respectively; the V$_H$ region contains a CDR-H1, a CDR-H2 and a CDR-H3 containing the sequence set forth in SEQ ID NOS:51, 55 and 58, respectively, and the V$_L$ region contains a CDR-L1, a CDR-L2 and a CDR-L3 containing the sequence set forth in SEQ ID NOS:60, 62 and 64, respectively; or the V$_H$ region contains a CDR-H1, a CDR-H2 and a CDR-H3 containing the sequence set forth in SEQ ID NOS:51, 96 and 99, respectively, and the V$_L$ region contains a CDR-L1, a CDR-L2 and a CDR-L3 containing the sequence set forth in SEQ ID NOS:60, 62 and 64, respectively; (iv) the V$_H$ region contains a CDR-H1, a CDR-H2 and a CDR-H3 containing the sequence set forth in SEQ ID NOS:68, 72 and 74, respectively, and the V$_L$ region contains a CDR-L1, a CDR-L2 and a CDR-L3 containing the sequence set forth in SEQ ID NOS:76, 78 and 79, respectively; or the V$_H$ region contains a CDR-H1, a CDR-H2 and a CDR-H3 containing the sequence set forth in SEQ ID NOS:83, 87 and 89, respectively, and the V$_L$ region contains a CDR-L1, a CDR-L2 and a CDR-L3 containing the sequence set forth in SEQ ID NOS:91, 93 and 94, respectively; the V$_H$ region contains a CDR-H1, a CDR-H2 and a CDR-H3 containing the sequence set forth in SEQ ID NOS:53, 57 and 59, respectively, and the V$_L$ region contains a CDR-L1, a CDR-L2 and a CDR-L3 containing the sequence set forth in SEQ ID NOS:60, 63 and 64, respectively; or the V$_H$ region contains a CDR-H1, a CDR-H2 and a CDR-H3 containing the sequence set forth in SEQ ID NOS:53, 98 and 100, respectively, and the V$_L$ region contains a CDR-L1, a CDR-L2 and a CDR-L3 containing the sequence set forth in SEQ ID NOS:61, 63 and 64, respectively.

In some of any such embodiments: (i) the $V_H$ region contains a CDR-H1, a CDR-H2 and a CDR-H3 containing the sequence set forth in SEQ ID NOS:67, 71 and 73, respectively, and the $V_L$ region contains a CDR-L1, a CDR-L2 and a CDR-L3 containing the sequence set forth in SEQ ID NOS:75, 77 and 79, respectively; (ii) the $V_H$ region contains a CDR-H1, a CDR-H2 and a CDR-H3 containing the sequence set forth in SEQ ID NOS:65, 69 and 73, respectively, and the $V_L$ region contains a CDR-L1, a CDR-L2 and a CDR-L3 containing the sequence set forth in SEQ ID NOS:75, 77 and 79, respectively; (iii) the $V_H$ region contains a CDR-H1, a CDR-H2 and a CDR-H3 containing the sequence set forth in SEQ ID NOS:66, 70 and 73, respectively, and the $V_L$ region contains a CDR-L1, a CDR-L2 and a CDR-L3 containing the sequence set forth in SEQ ID NOS:75, 77 and 79, respectively; or (iv) the $V_H$ region contains a CDR-H1, a CDR-H2 and a CDR-H3 containing the sequence set forth in SEQ ID NOS:68, 72 and 74, respectively, and the $V_L$ region contains a CDR-L1, a CDR-L2 and a CDR-L3 containing the sequence set forth in SEQ ID NOS:76, 78 and 79, respectively.

In some of any such embodiments: (i) the $V_H$ region contains a CDR-H1, a CDR-H2 and a CDR-H3 containing the sequence set forth in SEQ ID NOS:82, 86 and 88, respectively, and the $V_L$ region contains a CDR-L1, a CDR-L2 and a CDR-L3 containing the sequence set forth in SEQ ID NOS:90, 92 and 94, respectively; (ii) the $V_H$ region contains a CDR-H1, a CDR-H2 and a CDR-H3 containing the sequence set forth in SEQ ID NOS:80, 84 and 88, respectively, and the $V_L$ region contains a CDR-L1, a CDR-L2 and a CDR-L3 containing the sequence set forth in SEQ ID NOS:90, 92 and 94, respectively; (iii) the $V_H$ region contains a CDR-H1, a CDR-H2 and a CDR-H3 containing the sequence set forth in SEQ ID NOS:81, 85 and 88, respectively, and the $V_L$ region contains a CDR-L1, a CDR-L2 and a CDR-L3 containing the sequence set forth in SEQ ID NOS:90, 92 and 94, respectively; or (iv) the $V_H$ region contains a CDR-H1, a CDR-H2 and a CDR-H3 containing the sequence set forth in SEQ ID NOS:83, 87 and 89, respectively, and the $V_L$ region contains a CDR-L1, a CDR-L2 and a CDR-L3 containing the sequence set forth in SEQ ID NOS:91, 93 and 94, respectively.

Also provided herein is an anti-ROR1 chimeric antigen receptor (CAR) containing: an extracellular antigen-binding domain containing a heavy chain variable ($V_H$) region and a light chain variable ($V_L$) region, and an intracellular signaling region, wherein: the $V_H$ region contains a heavy chain complementarity determining region 1 (CDR-H1), a heavy chain complementarity determining region 2 (CDR-H2) and a heavy chain complementarity determining region 3 (CDR-H3) contained within SEQ ID NO: 112, 121, 103 or 130, and the $V_L$ region contains a light chain complementarity determining region 1 (CDR-L1), a light chain complementarity determining region 2 (CDR-L2) and a light chain complementarity determining region 3 (CDR-L3) contained within SEQ ID NO: 115, 124 or 106.

Also provided herein is an anti-ROR1 chimeric antigen receptor (CAR) containing: an extracellular antigen-binding domain containing a heavy chain variable ($V_H$) region and a light chain variable ($V_L$) region, and an intracellular signaling region, wherein: the $V_H$ region contains a heavy chain complementarity determining region 1 (CDR-H1), a heavy chain complementarity determining region 2 (CDR-H2) and a heavy chain complementarity determining region 3 (CDR-H3) contained within SEQ ID NO:112, and the $V_L$ region contains a light chain complementarity determining region 1 (CDR-L1), a light chain complementarity determining region 2 (CDR-L2) and a light chain complementarity determining region 3 (CDR-L3) contained within SEQ ID NO:115; the $V_H$ region contains a CDR-H1, a CDR-H2 and a CDR-H3 contained within SEQ ID NO:121, and the $V_L$ region contains a CDR-L1, a CDR-L2 and a CDR-L3 contained within SEQ ID: NO 124; the $V_H$ region contains a CDR-H1, a CDR-H2 and a CDR-H3 contained within SEQ ID NO:103, and the $V_L$ region contains a CDR-L1, a CDR-L2 and a CDR-L3 contained within SEQ ID: NO 106; or the $V_H$ region contains a CDR-H1, a CDR-H2 and a CDR-H3 contained within SEQ ID NO:130, and the $V_L$ region contains a CDR-L1, a CDR-L2 and a CDR-L3 contained within SEQ ID: NO 106.

In some of any such embodiments, the $V_H$ region contains a CDR-H1, a CDR-H2 and a CDR-H3 contained within SEQ ID NO:112, and the $V_L$ region contains a CDR-L1, a CDR-L2 and a CDR-L3 contained within SEQ ID NO: 115. In some of any such embodiments, the $V_H$ region contains a CDR-H1, a CDR-H2 and a CDR-H3 contained within SEQ ID NO:121, and the $V_L$ region contains a CDR-L1, a CDR-L2 and a CDR-L3 contained within SEQ ID: NO 124.

In some of any such embodiments: the $V_H$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO: 112, 121, 103 or 130, and the $V_L$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO: 115, 124 or 106. In some of any such embodiments: the $V_H$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO:112, and the $V_L$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO: 115; the $V_H$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO:121, and the $V_L$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO:124; the $V_H$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO:103, and the $V_L$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO:106; or the $V_H$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO:130, and the $V_L$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO:106.

In some of any such embodiments, the $V_H$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO:112, and the $V_L$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO: 115. In some of any such embodiments, the $V_H$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO:121, and the $V_L$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO:124.

Also provided herein is an anti-ROR1 chimeric antigen receptor (CAR) containing: an extracellular antigen-binding domain containing a heavy chain variable ($V_H$) region and a light chain variable ($V_L$) region, and an intracellular signaling region, wherein: the $V_H$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO: 112, 121, 103 or 130, and the $V_L$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO: 115, 124 or 106.

Also provided herein is an anti-ROR1 chimeric antigen receptor (CAR) containing: an extracellular antigen-binding domain containing a heavy chain variable ($V_H$) region and a light chain variable ($V_L$) region, and an intracellular signaling region, wherein: the $V_H$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO:112, and the $V_L$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO: 115; the $V_H$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO:121, and the $V_L$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO:124; the $V_H$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO:103, and the $V_L$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO:106; or the $V_H$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO:130, and the $V_L$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO:106.

In some of any such embodiments, the $V_H$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO:112, and the $V_L$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO: 115. In some of any such embodiments, the $V_H$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO:121, and the $V_L$ region is or contains an amino acid sequence having at least at or about 85%, 86%, 87%, 88%, 89%, 90%, 91%, 92%, 93%, 94%, 95%, 96%, 97%, 98% or 99% identity to SEQ ID NO:124.

In some of any such embodiments: the $V_H$ region is or contains the sequence set forth in SEQ ID NO: 112, 121, 103 or 130, and the $V_L$ region is or contains the sequence set forth in SEQ ID NO: 115, 124 or 106.

In some of any such embodiments: the $V_H$ region and the $V_L$ region are or contain the sequence set forth in SEQ ID NOS: 112 and 115, respectively; the $V_H$ region and the $V_L$ region are or contain the sequence set forth in SEQ ID NOS: 121 and 124, respectively; the $V_H$ region and the $V_L$ region are or contain the sequence set forth in SEQ ID NOS: 103 and 106, respectively; or the $V_H$ region and the $V_L$ region are or contain the sequence set forth in SEQ ID NOS: 130 and 106, respectively.

Also provided herein is an anti-ROR1 chimeric antigen receptor (CAR) containing: an extracellular antigen-binding domain containing a heavy chain variable ($V_H$) region and a light chain variable ($V_L$) region, and an intracellular signaling region, wherein: the $V_H$ region is or contains the sequence set forth in SEQ ID NO: 112, 121, 103 or 130, and the $V_L$ region is or contains the sequence set forth in SEQ ID NO: 115, 124 or 106.

Also provided herein is an anti-ROR1 chimeric antigen receptor (CAR) containing: an extracellular antigen-binding domain containing a heavy chain variable ($V_H$) region and a light chain variable ($V_L$) region, and an intracellular signaling region, wherein: the $V_H$ region and the $V_L$ region are or contain the sequence set forth in SEQ ID NOS: 112 and 115, respectively; the $V_H$ region and the $V_L$ region are or contain the sequence set forth in SEQ ID NOS: 121 and 124, respectively; the $V_H$ region and the $V_L$ region are or contain the sequence set forth in SEQ ID NOS: 103 and 106, respectively; or the $V_H$ region and the $V_L$ region are or contain the sequence set forth in SEQ ID NOS: 130 and 106, respectively.

In some of any such embodiments, the $V_H$ region and the $V_L$ region are or contain the sequence set forth in SEQ ID NOS: 112 and 115, respectively. In some of any such embodiments, the $V_H$ region and the $V_L$ region are or contain the sequence set forth in SEQ ID NOS:121 and 124, respectively.

In some of any such embodiments, the $V_H$ region is or contains the amino acid sequence encoded by SEQ ID NO: 110, 119, 101 or 128 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 110, 119, 101 or 128, and the $V_L$ region is or contains the amino acid sequence encoded by SEQ ID NO: 113, 122 or 104, or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 113, 122 or 104. In some of any such embodiments, the $V_H$ region is or contains the amino acid sequence encoded by SEQ ID NO: 111, 120, 102 or 129, and the $V_L$ region is or contains the amino acid sequence encoded by SEQ ID NO: 114, 123, 105 or 131. In some of any such embodiments, the $V_H$ region is or contains the amino acid sequence encoded by SEQ ID NO: 110 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 110, and the $V_L$ region is or contains the amino acid sequence encoded by SEQ ID NO: 113, or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 113. In some of any such embodiments, the $V_H$ region is or contains the amino acid sequence encoded by SEQ ID NO: 111, and the $V_L$ region is or contains the amino acid sequence encoded by SEQ ID NO: 114. In some of any such embodiments, the V$_H$ region is or contains the amino acid sequence encoded by SEQ ID NO: 119 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 119, and the V$_L$ region is or contains the amino acid sequence encoded by SEQ ID NO: 122, or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 122. In some of any such embodiments, the V$_H$ region is or contains the amino acid sequence encoded by SEQ ID NO: 120, and the V$_L$ region is or contains the amino acid sequence encoded by SEQ ID NO: 123.

In some of any such embodiments, said anti-ROR1 antibody or antigen-binding fragment thereof is isolated. In some of any such embodiments, said anti-ROR1 antibody or antigen-binding fragment thereof is recombinant. In some of any such embodiments, at least a portion of the V$_H$ region and the V$_L$ region is human or is from a human protein.

In some of any such embodiments, the antigen-binding fragment thereof is or contains a single chain fragment. In some of any such embodiments, the antigen-binding fragment thereof is or contains a single chain Fv (scFv).

In some of any such embodiments, the V$_H$ region is amino-terminal to the V$_L$ region. In some of any such embodiments, the V$_H$ region is carboxy-terminal to the V$_L$ region. In some of any such embodiments, the V$_H$ region and the V$_L$ region are joined by a flexible linker. In some of any such embodiments, the flexible linker contains the sequence set forth in SEQ ID NO:41.

In some of any such embodiments, the scFv is or contains the sequence set forth in SEQ ID NO: 118, 127, 109 or 134, or an amino acid sequence having at least at or about 85%, 86%, 87%, 88%, 89%, 90%, 91%, 92%, 93%, 94%, 95%, 96%, 97%, 98% or 99% sequence identity to SEQ ID NO: 118, 127, 109 or 134. In some of any such embodiments, the scFv is or contains the sequence set forth in SEQ ID NO: 118. In some of any such embodiments, the scFv is or contains the sequence set forth in SEQ ID NO: 127. In some of any such embodiments, the scFv is or contains the amino acid sequence encoded by SEQ ID NO: 116, 125, 107 or 132 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 116, 125, 107 or 132. In some of any such embodiments, the scFv is or contains the amino acid sequence encoded by SEQ ID NO: 117, 126, 108 or 133. In some of any such embodiments, the scFv is or contains the amino acid sequence encoded by SEQ ID NO: 116 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 116. In some of any such embodiments, the scFv is or contains the amino acid sequence encoded by SEQ ID NO: 117. In some of any such embodiments, the scFv is or contains the amino acid sequence encoded by SEQ ID NO: 125 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 125. In some of any such embodiments, the scFv is or contains the amino acid sequence encoded by SEQ ID NO: 126.

In some of any such embodiments, the anti-ROR1 chimeric antigen receptor further contains a spacer between the extracellular antigen-binding domain and the transmembrane domain. In some of any such embodiments, the spacer contains at least a portion of an immunoglobulin or a variant thereof. In some of any such embodiments, the spacer contains at least a portion of a hinge region of an immunoglobulin or a variant thereof. In some of any such embodiments, the spacer is less than at or about 15 amino acids in length. In some of any such embodiments, the spacer is or contains an amino acid sequence having at least at or about 85%, 86%, 87%, 88%, 89%, 90%, 91%, 92%, 93%, 94%, 95%, 96%, 97%, 98% or 99% identity to SEQ ID NO:1, 26, 27, 29, 31, 32, 33 or 135.

In some of any such embodiments, the at least a portion of a hinge region contains all or a portion of an IgG4 hinge region. In some of any such embodiments, the at least a portion of a hinge region contains all or a portion of a human IgG4 hinge region, or a variant thereof. In some of any such embodiments, the at least a portion of a hinge region contains all or a portion of an IgG2 hinge region. In some of any such embodiments, the at least a portion of a hinge region contains all or a portion of a human IgG2 hinge region, or a variant thereof.

In some of any such embodiments, the spacer is or contains the sequence set forth in SEQ ID NO:1. In some of any such embodiments, the spacer is or contains the amino acid sequence encoded by SEQ ID NO: 2 or 30 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 2 or 30. In some of any such embodiments, the spacer is or contains the amino acid sequence encoded by SEQ ID NO: 30.

In some of any such embodiments, the spacer is or contains the sequence set forth in SEQ ID NO:135. In some of any such embodiments, the spacer is or contains the amino acid sequence encoded by SEQ ID NO: 192 or 136 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 192 or 136. In some of any such embodiments, the spacer is or contains the amino acid sequence encoded by SEQ ID NO: 136.

In some of any such embodiments, the spacer contains at least a portion of a C$_H$3 region of an immunoglobulin or a variant thereof. In some of any such embodiments, the at least a portion of a C$_H$3 region contains all or a portion of an IgG4 C$_H$3. In some of any such embodiments, the at least a portion of a C$_H$3 region contains all or a portion of an IgG2 C$_H$3. In some of any such embodiments, the at least a portion of a C$_H$3 region contains all or a portion of an IgG4 C$_H$3 and/or an IgG2 C$_H$3. In some of any such embodiments, the IgG4 C$_H$3 is a human IgG4 C$_H$3 and the IgG2 C$_H$3 is a human IgG2 C$_H$3. In some of any such embodiments, the spacer contains at least a portion of a hinge region and at least a portion of a C$_H$3 region of an immunoglobulin or a variant thereof. In some of any such embodiments, the spacer is at or about 111, 112, 113, 114, 115, 116, 117, 118, 119, 120, 121, 122, 123, 124 or 125 amino acids in length, or has a length between any of the foregoing. In some of any such embodiments, the spacer is at or about 120 amino acids in length.

In some of any such embodiments, the spacer is or contains an amino acid sequence having at least at or about 85%, 86%, 87%, 88%, 89%, 90%, 91%, 92%, 93%, 94%, 95%, 96%, 97%, 98% or 99% identity to SEQ ID NO: 138. In some of any such embodiments, the spacer is or contains the sequence set forth in SEQ ID NO:138. In some of any such embodiments, the spacer is or contains the amino acid sequence encoded by SEQ ID NO: 193 or 139 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 193 or 139. In some of any such embodiments, the spacer is or contains the amino acid sequence encoded by SEQ ID NO: 139.

In some of any such embodiments, the spacer is at or about 120 amino acids in length. In some of any such embodiments, the spacer is or contains an amino acid sequence having at least at or about 85%, 86%, 87%, 88%, 89%, 90%, 91%, 92%, 93%, 94%, 95%, 96%, 97%, 98% or 99% identity to SEQ ID NO: 3. In some of any such embodiments, the spacer is or contains the sequence set forth in SEQ ID NO:3. In some of any such embodiments, the spacer is or contains the amino acid sequence encoded by SEQ ID NO: 4 or 137 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 4 or 137. In some of any such embodiments, the spacer is or contains the amino acid sequence encoded by SEQ ID NO: 137.

In some of any such embodiments, the spacer contains at least a portion of a $C_H2$ of an immunoglobulin or a variant thereof. In some of any such embodiments, the at least a portion of a $C_H2$ region contains all or a portion of an IgG4 $C_H2$. In some of any such embodiments, the at least a portion of a $C_H2$ region contains all or a portion of an IgG2 $C_H2$. In some of any such embodiments, the at least a portion of a $C_H2$ region contains all or a portion of an IgG4 $C_H2$ and/or an IgG2 $C_H2$. In some of any such embodiments, the IgG4 $C_H2$ is a human IgG4 $C_H2$ and the IgG2 $C_H2$ is a human IgG2 $C_H2$. In some of any such embodiments, the spacer contains at least a portion of a hinge region, at least a portion of a $C_H2$ and at least a portion of a $C_H3$ region of an immunoglobulin or a variant thereof. In some of any such embodiments, the spacer is at or about 130, 140, 150, 160, 170, 180, 190, 200, 210, 220, 221, 222, 223, 224, 225, 226, 227, 228, 229 or 230 amino acids in length, or has a length between any of the foregoing. In some of any such embodiments, one or more of the hinge region, the $C_H2$ region and the $C_H3$ region contains all or a portion of a $C_H2$ region and all or a portion of a $C_H3$ region from human IgG4. In some of any such embodiments, one or more of the hinge region, the $C_H2$ region and the $C_H3$ region is chimeric and contains a hinge, a $C_H2$ region and a $C_H3$ region from human IgG4 and human IgG2.

In some of any such embodiments, the spacer contains a IgG4/2 chimeric hinge region or a modified IgG4 hinge region containing at least one amino acid replacement compared to a human IgG4 hinge; an IgG2/4 chimeric $C_H2$ region; and an IgG4 $C_H3$ region.

In some of any such embodiments, the spacer is or contains an amino acid sequence having at least at or about 85%, 86%, 87%, 88%, 89%, 90%, 91%, 92%, 93%, 94%, 95%, 96%, 97%, 98% or 99% identity to SEQ ID NO:194. In some of any such embodiments, the spacer is or contains the sequence set forth in SEQ ID NO: 194. In some of any such embodiments, the spacer is or contains the amino acid sequence encoded by SEQ ID NO: 195 or 196 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 195 or 196. In some of any such embodiments, the spacer is or contains the amino acid sequence encoded by SEQ ID NO: 196.

In some of any such embodiments, the spacer is or contains an amino acid sequence having at least at or about 85%, 86%, 87%, 88%, 89%, 90%, 91%, 92%, 93%, 94%, 95%, 96%, 97%, 98% or 99% identity to SEQ ID NO:37. In some of any such embodiments, the spacer is or contains the sequence set forth in SEQ ID NO: 37. In some of any such embodiments, the spacer is or contains the amino acid sequence encoded by SEQ ID NO: 38 or 140 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 38 or 140. In some of any such embodiments, the spacer is or contains the amino acid sequence encoded by SEQ ID NO: 140.

In some of any such embodiments, the intracellular signaling region contains an intracellular signaling domain. In some of any such embodiments, the intracellular signaling domain is capable of inducing a primary activation signal in a T cell, is a T cell receptor (TCR) component or contains an immunoreceptor tyrosine-based activation motif (ITAM). In some of any such embodiments, the intracellular signaling domain is or contains a cytoplasmic signaling domain of a CD3-zeta (CD3ζ) chain or a functional variant or signaling portion thereof. In some of any such embodiments, the intracellular signaling domain is human or is from a human protein. In some of any such embodiments, the intracellular signaling domain is or contains the sequence set forth in SEQ ID NO:13, 14 or 15, or an amino acid sequence having at least at or about 90%, 91%, 92%, 93%, 94%, 95%, 96%, 97%, 98% or 99% sequence identity to SEQ ID NO:13, 14 or 15. In some of any such embodiments, the intracellular signaling domain is or contains the sequence set forth in SEQ ID NO:13.

In some of any such embodiments, the intracellular signaling region further contains a costimulatory signaling region. In some of any such embodiments, the costimulatory signaling region contains an intracellular signaling domain of a T cell costimulatory molecule or a signaling portion thereof. In some of any such embodiments, the costimulatory signaling region contains an intracellular signaling domain of CD28, 4-1BB, or ICOS, or a signaling portion thereof. In some of any such embodiments, the costimulatory signaling region is human or is from a human protein. In some of any such embodiments, the costimulatory signaling region contains an intracellular signaling domain of CD28. In some of any such embodiments, the costimulatory signaling region is or contains the sequence set forth in SEQ ID NO:10 or an amino acid sequence having at least at or about 90%, 91%, 92%, 93%, 94%, 95%, 96%, 97%, 98% or 99% sequence identity to SEQ ID NO:10. In some of any such embodiments, the costimulatory signaling region contains an intracellular signaling domain of 4-1BB. In some of any such embodiments, the costimulatory signaling region is or contains the sequence set forth in SEQ ID NO:12 or an amino acid sequence having at least at or about 90%, 91%, 92%, 93%, 94%, 95%, 96%, 97%, 98% or 99% sequence identity to SEQ ID NO: 12.

In some of any such embodiments, the anti-ROR1 chimeric antigen receptor further contains a transmembrane region. In some of any such embodiments, the costimulatory signaling region is between the transmembrane region and the intracellular signaling domain. In some of any such embodiments, the transmembrane region is or contains a transmembrane domain from CD4, CD28, or CD8. In some of any such embodiments, the transmembrane region is or contains a transmembrane domain from CD28. In some of any such embodiments, the transmembrane region is human or is from a human protein.

In some of any such embodiments, the transmembrane domain is or contains SEQ ID NO: 8 or an amino acid sequence having at least at or about 90%, 91%, 92%, 93%, 94%, 95%, 96%, 97%, 98% or 99% sequence identity to SEQ ID NO: 8. In some of any such embodiments, the transmembrane domain is or contains the sequence set forth in SEQ ID NO: 8. In some of any such embodiments, the transmembrane domain is or contains the amino acid sequence encoded by SEQ ID NO: 197 or 198 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 197 or 198. In some of any such embodiments, the transmembrane domain is or contains the amino acid sequence encoded by SEQ ID NO: 198.

In some of any such embodiments, the transmembrane domain is or contains SEQ ID NO: 149 or an amino acid sequence having at least at or about 90%, 91%, 92%, 93%, 94%, 95%, 96%, 97%, 98% or 99% sequence identity to SEQ ID NO: 149. In some of any such embodiments, the transmembrane domain is or contains the sequence set forth in SEQ ID NO: 149. In some of any such embodiments, the transmembrane domain is or contains the amino acid sequence encoded by SEQ ID NO: 147 or 148 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 147 or 148. In some of any such embodiments, the transmembrane domain is or contains the amino acid sequence encoded by SEQ ID NO: 148.

In some of any such embodiments, the encoded chimeric antigen receptor contains from its N to C terminus in order: the extracellular antigen-binding domain, the spacer, the transmembrane region and the intracellular signaling region. In some of any such embodiments, the encoded chimeric antigen receptor contains, from its N to C terminus in order: an extracellular antigen-binding domain containing an scFv, a spacer containing a modified IgG4 hinge; a transmembrane domain; and an intracellular signaling region containing a cytoplasmic signaling domain of a CD3-zeta (CD3ζ) chain and an intracellular signaling domain of a costimulatory signaling region. In some of any such embodiments, the encoded chimeric antigen receptor contains, from its N to C terminus in order: an extracellular antigen-binding domain containing an scFv, a spacer containing a modified IgG4 hinge containing the sequence set forth in SEQ ID NO:135; a transmembrane domain from a human CD28; and an intracellular signaling region containing a cytoplasmic signaling domain of a CD3-zeta (CD3ζ) chain and an intracellular signaling domain of a costimulatory signaling region containing an intracellular signaling domain of 4-1BB. In some of any such embodiments, the encoded chimeric antigen receptor contains, from its N to C terminus in order: an extracellular antigen-binding domain containing an scFv, a spacer containing a modified IgG4 hinge-$C_H 3$; a transmembrane domain; and an intracellular signaling region containing a cytoplasmic signaling domain of a CD3-zeta (CD3ζ) chain and an intracellular signaling domain of a costimulatory signaling region. In some of any such embodiments, the encoded chimeric antigen receptor contains, from its N to C terminus in order: an extracellular antigen-binding domain containing an scFv, a spacer containing a modified IgG4 hinge-$C_H 3$ containing the sequence set forth in SEQ ID NO: 138; a transmembrane domain from a human CD28; and an intracellular signaling region containing a cytoplasmic signaling domain of a CD3-zeta (CD3ζ) chain and an intracellular signaling domain of a costimulatory signaling region containing an intracellular signaling domain of 4-1BB. In some of any such embodiments, the extracellular antigen-binding domain is an scFv.

In some of any such embodiments, the anti-ROR1 chimeric antigen receptor is or contains the sequence set forth in SEQ ID NO: 184, 185, 186, 187, 188 or 189 or a sequence that exhibits at least 85%, 86%, 87%, 88%, 89%, 90%, 91%, 92%, 93%, 94%, 95%, 96%, 97%, 98%, or 99% sequence identity to the sequence set forth in SEQ ID NO: 184, 185, 186, 187, 188 or 189.

In some of any such embodiments, the anti-ROR1 chimeric antigen receptor is or contains the sequence set forth in SEQ ID NO: 184 or a sequence that exhibits at least 85%, 86%, 87%, 88%, 89%, 90%, 91%, 92%, 93%, 94%, 95%, 96%, 97%, 98%, or 99% sequence identity to the sequence set forth in SEQ ID NO: 184. In some of any such embodiments, the anti-ROR1 chimeric antigen receptor is or contains the sequence set forth in SEQ ID NO: 184. In some of any such embodiments, the anti-ROR1 chimeric antigen receptor is or contains the sequence set forth in SEQ ID NO: 185 or a sequence that exhibits at least 85%, 86%, 87%, 88%, 89%, 90%, 91%, 92%, 93%, 94%, 95%, 96%, 97%, 98%, or 99% sequence identity to the sequence set forth in SEQ ID NO:185. In some of any such embodiments, the anti-ROR1 chimeric antigen receptor is or contains the sequence set forth in SEQ ID NO: 185. In some of any embodiments, the anti-ROR1 chimeric antigen receptor is or comprises the sequence set forth in SEQ ID NO: 186 or a sequence that exhibits at least 85%, 86%, 87%, 88%, 89%, 90%, 91%, 92%, 93%, 94%, 95%, 96%, 97%, 98%, or 99% sequence identity to the sequence set forth in SEQ ID NO: 186. In some of any embodiments, the anti-ROR1 chimeric antigen receptor is or comprises the sequence set forth in SEQ ID NO: 186. In some of any embodiments, the anti-ROR1 chimeric antigen receptor is or comprises the sequence set forth in SEQ ID NO: 187 or a sequence that exhibits at least 85%, 86%, 87%, 88%, 89%, 90%, 91%, 92%, 93%, 94%, 95%, 96%, 97%, 98%, or 99% sequence identity to the sequence set forth in SEQ ID NO:187. In some of any embodiments, the anti-ROR1 chimeric antigen receptor is or comprises the sequence set forth in SEQ ID NO: 187. In some of any embodiments, the anti-ROR1 chimeric antigen receptor is or comprises the sequence set forth in SEQ ID NO: 188 or a sequence that exhibits at least 85%, 86%, 87%, 88%, 89%, 90%, 91%, 92%, 93%, 94%, 95%, 96%, 97%, 98%, or 99% sequence identity to the sequence set forth in SEQ ID NO: 188. In some of any embodiments, the anti-ROR1 chimeric antigen receptor is or comprises the sequence set forth in SEQ ID NO: 188. In some of any embodiments, the anti-ROR1 chimeric antigen receptor is or comprises the sequence set forth in SEQ ID NO: 189 or a sequence that exhibits at least 85%, 86%, 87%, 88%, 89%, 90%, 91%, 92%, 93%, 94%, 95%, 96%, 97%, 98%, or 99% sequence identity to the sequence set forth in SEQ ID NO:189. In some of any embodiments, the anti-ROR1 chimeric antigen receptor is or comprises the sequence set forth in SEQ ID NO: 189.

In some of any such embodiments, the anti-ROR1 chimeric antigen receptor is encoded by the sequence set forth in SEQ ID NO: 156, 157, 158, 159, 160 or 161 or a sequence that exhibits at least 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 156, 157, 158, 159, 160 or 161. In some of any such embodiments, the anti-ROR1 chimeric antigen receptor is encoded by the sequence set forth in SEQ ID NO: 156 or a sequence that exhibits at least 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 156. In some of any such embodiments, the anti-ROR1 chimeric antigen receptor is encoded by the sequence set forth in SEQ ID NO: 156. In some of any such embodiments, the anti-ROR1 chimeric antigen receptor is encoded by the sequence set forth in SEQ ID NO: 157 or a sequence that exhibits at least 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 157. In some of any such embodiments, the anti-ROR1 chimeric antigen receptor is encoded by the sequence set forth in SEQ ID NO: 157.

In some of any such embodiments, said anti-ROR1 chimeric antigen receptor specifically binds to a receptor tyrosine kinase-like orphan receptor 1 (ROR1) protein. In some of any such embodiments, said anti-ROR1 chimeric antigen receptor specifically binds to a human ROR1 protein. In some of any such embodiments, the human ROR1 protein contains an amino acid sequence set forth in SEQ ID NO: 144, 145 or 146. In some of any such embodiments, said anti-ROR1 chimeric antigen receptor does not bind to, is not cross-reactive to, or binds at a lower level or degree or affinity to a receptor tyrosine kinase-like orphan receptor 2 (ROR2) protein. In some of any such embodiments, said anti-ROR1 chimeric antigen receptor does not bind to, is not cross-reactive to, or binds at a lower level or degree or affinity to a human ROR2.

In some of any such embodiments, the extent, level or degree or affinity of binding of said anti-ROR1 chimeric antigen receptor to a human ROR2 is at least at or about 75%, 80%, 90%, 95% or 99% less than the extent, level or degree or affinity of binding to a human ROR1. In some of any such embodiments, binding is compared under the same or substantially the same conditions or assay. In some of any such embodiments, said anti-ROR1 chimeric antigen receptor exhibits the same, substantially the same or lower level or degree of signaling or activity in the presence of a ROR2 protein, compared to the level or degree of signaling or activity in the presence of a ROR1 protein. In some of any such embodiments, said anti-ROR1 chimeric antigen receptor exhibits the same, substantially the same or lower level or degree of signaling or activity in the presence of a human ROR2 protein, compared to the level or degree of signaling or activity in the presence of a human ROR1 protein. In some of any such embodiments, activity is compared under the same or substantially the same conditions or assay. In some of any such embodiments, said anti-ROR1 chimeric antigen receptor exhibits a level or degree of signaling or activity in the presence of a human ROR2 that is at least at or about 75%, 80%, 90%, 95% or 99% less than the level or degree of signaling or activity in the presence of a human ROR1. In some of any such embodiments, activity is compared under the same or substantially the same conditions or assay.

In some of any such embodiments, said anti-ROR1 chimeric antigen receptor exhibits the same, substantially the same or lower level or degree of signaling or activity in the presence of a ROR2 protein compared to a reference ROR1-specific chimeric antigen receptor. In some of any such embodiments, said anti-ROR1 chimeric antigen receptor exhibits the same, substantially the same or lower level or degree of signaling or activity in the presence of a human ROR2, compared to a reference ROR1-specific chimeric antigen receptor. In some of any embodiments, activity is compared under the same or substantially the same conditions or assay.

In some of any such embodiments, said anti-ROR1 chimeric antigen receptor exhibits the same, substantially the same or lower level or degree of signaling or activity in the presence of a ROR2 protein, compared to a reference ROR1-specific chimeric antigen receptor. In some of any such embodiments, said anti-ROR1 chimeric antigen receptor exhibits the same, substantially the same or lower level or degree of signaling or activity in the presence of a human ROR2 protein, compared to a reference ROR1-specific chimeric antigen receptor. In some of any such embodiments, activity is compared under the same or substantially the same conditions or assay. In some of any such embodiments, said anti-ROR1 chimeric antigen receptor exhibits the same, substantially the same or higher antigen-specific signaling or antigen dependent activity or signaling compared to a reference ROR1-specific chimeric antigen receptor. In some of any such embodiments, activity is compared under the same or substantially the same conditions or assay. In some of any such embodiments, said anti-ROR1 chimeric antigen receptor exhibits the same, substantially the same or lower tonic signaling or antigen independent activity or signaling compared to a reference ROR1-specific chimeric antigen receptor. In some of any such embodiments, activity is compared under the same or substantially the same conditions or assay. In some of any such embodiments, said anti-ROR1 chimeric antigen receptor exhibits a level or degree of tonic signaling or antigen independent activity or signaling that is at least at or about 75%, 80%, 90%, 95% or 99% less than the level or degree of tonic signaling or antigen independent activity of a reference ROR1-specific chimeric antigen receptor. In some of any such embodiments, activity is compared under the same or substantially the same conditions or assay.

In some of any such embodiments, the reference ROR1-specific chimeric antigen receptor contains the anti-ROR1 antibody R12 or the anti-ROR1 antibody 2A2 or an antigen-binding fragment thereof. In some of any such embodiments, the reference ROR1-specific chimeric antigen receptor contains an scFv from R12 or 2A2. In some of any such embodiments, the reference ROR1-specific chimeric antigen receptor contains the anti-ROR1 antibody R12 or an scFv from R12 or 2A2.

Also provided herein is a polynucleotide containing a nucleic acid encoding all or a portion of the anti-ROR1 antibody or antigen-binding domain thereof of any of the embodiments provided herein, the single chain cell surface protein of any of the embodiments provided herein, the conjugate of any of the embodiments provided herein, or the anti-ROR1 chimeric antigen receptor of any of the embodiments provided herein.

In some of any such embodiments, said polynucleotide contains a nucleic acid encoding the $V_H$ containing the sequence set forth in SEQ ID NO: 110, 119, 101 or 128 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 110, 119, 101 or 128, and a nucleic acid encoding the $V_L$ containing the sequence set forth in SEQ ID NO: 113, 122 or 104, or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 113, 122 or 104. In some of any such embodiments, said polynucleotide contains a nucleic acid encoding the $V_H$ containing the sequence set forth in SEQ ID NO: 110 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 110, and a nucleic acid encoding the $V_L$ containing the sequence set forth in SEQ ID NO: 113, or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 113. In some of any such embodiments, said polynucleotide contains a nucleic acid encoding the $V_H$ containing the sequence set forth in SEQ ID NO: 119 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 119, and a nucleic acid encoding the $V_L$ containing the sequence set forth in SEQ ID NO: 122, or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 122.

In some of any such embodiments, said polynucleotide contains a nucleic acid encoding the scFv containing the sequence set forth in SEQ ID NO: 116, 125, 107 or 132 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 116, 125, 107 or 132. In some of any such embodiments, said polynucleotide contains a nucleic acid encoding the scFv containing the sequence set forth in SEQ ID NO: 116 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 116. In some of any such embodiments, said polynucleotide contains a nucleic acid encoding the scFv containing the sequence set forth in SEQ ID NO: 125 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 125.

In some of any such embodiments, said polynucleotide contains a nucleic acid encoding the spacer containing the sequence set forth in SEQ ID NO: 192 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 192. In some of any such embodiments, said polynucleotide contains a nucleic acid encoding the spacer containing the sequence set forth in SEQ ID NO: 193 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 193. In some of any such embodiments, said polynucleotide contains a nucleic acid encoding the spacer containing the sequence set forth in SEQ ID NO: 195 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 195.

In some of any such embodiments, the nucleic acid encoding the anti-ROR1 antibody or antigen-binding domain thereof, the single chain cell surface protein, the conjugate or the anti-ROR1 chimeric antigen receptor contains at least one modified splice donor or splice acceptor site or both, said modified splice donor and/or acceptor site containing one or more nucleotide modifications corresponding to a reference splice donor site and/or reference splice acceptor site. In some of any such embodiments, the one or more nucleotide modifications contain a nucleic acid substitution. In some of any such embodiments, the reference splice donor and/or reference splice acceptor sites are canonical, non-canonical, or cryptic splice sites. In some of any embodiments, the polynucleotide is optimized by splice site elimination.

In some of any such embodiments: the reference splice donor or reference splice acceptor site(s) or both has a splice site prediction score of at least at or about 0.4, 0.5, 0.6, 0.70, 0.75, 0.80, 0.85, 0.90, 0.95, 0.99 or 1.0; or the reference splice donor or reference splice acceptor site(s) or both is/are predicted to be involved in a splice event with a probability of at least at or about 40%, 50%, 60%, 70%, 75%, 80%, 85%, 90%, 95%, 99% or 100%.

In some of any such embodiments: the reference splice donor or reference splice acceptor site(s) or both has a splice site prediction score of at least at or about 0.70, 0.75, 0.80, 0.85, 0.90, 0.95, 0.99 or 1.0; and/or the reference splice donor or reference splice acceptor site(s) or both is/are predicted to be involved in a splice event with a probability of at least at or about 70%, 75%, 80%, 85%, 90%, 95%, 99% or 100%.

In some of any such embodiments, at least one of the one or more nucleotide modifications are within 1, 2, 3, 4, 5, 6, 7, 8, 9 or 10 residues of the splice site junction of the reference splice acceptor and/or reference splice donor site. In some of any such embodiments, the one or more nucleotide modifications is silent or results in a degenerate codon or does not change the amino acid sequence of the encoded protein, or one or more or all of the foregoing.

In some of any such embodiments, upon expression of the polynucleotide in a cell, the transcribed RNA from the polynucleotide, exhibits at least at or about 70%, at or about 75%, at or about 80%, at or about 85%, at or about 90%, or at or about 95% RNA homogeneity. In some of any such embodiments, upon expression in a cell, the transcribed RNA from the polynucleotide exhibits reduced heterogeneity compared to the heterogeneity of the mRNA transcribed from a reference polynucleotide, said reference polynucleotide encoding the same amino acid sequence as the polynucleotide, wherein the reference polynucleotide differs by the presence of one or more splice donor site or one or more splice acceptor site or both, in the nucleic acid encoding the spacer or contains one or more nucleotide modifications compared to the polynucleotide. In some of any such embodiments, the RNA heterogeneity is reduced by greater than at or about 10%, 15%, 20%, 25%, 30%, 40% or 50% or more. In some of any such embodiments, the transcribed RNA from the reference polynucleotide exhibits greater than at or about 10%, 15%, 20%, 25%, 30%, 40% or 50% or more RNA heterogeneity. In some of any such embodiments, the transcribed RNA messenger RNA (mRNA). In some of any such embodiments, the RNA homogeneity or heterogeneity or both is determined by agarose gel electrophoresis, chip-based capillary electrophoresis, analytical ultracentrifugation, field flow fractionation, or liquid chromatography.

In some of any such embodiments, the polynucleotide is codon-optimized for expression in a human cell.

In some of any such embodiments, said polynucleotide contains a nucleic acid encoding the $V_H$ containing the sequence set forth in SEQ ID NO: 111, 120, 102 or 129, and a nucleic acid encoding the $V_L$ containing the sequence set forth in SEQ ID NO: 114, 123, 105 or 131. In some of any such embodiments, said polynucleotide contains a nucleic acid encoding the $V_H$ containing the sequence set forth in SEQ ID NO: 111, and a nucleic acid encoding the $V_L$ containing the sequence set forth in SEQ ID NO: 114. In some of any such embodiments, said polynucleotide contains a nucleic acid encoding the $V_H$ containing the sequence set forth in SEQ ID NO: 120, and a nucleic acid encoding the $V_L$ containing the sequence set forth in SEQ ID NO: 123.

In some of any such embodiments, said polynucleotide contains a nucleic acid encoding the scFv containing the sequence set forth in SEQ ID NO: 117, 126, 108 or 133. In some of any such embodiments, said polynucleotide contains a nucleic acid encoding the scFv containing the sequence set forth in SEQ ID NO: 117. In some of any such embodiments, said polynucleotide contains a nucleic acid encoding the scFv containing the sequence set forth in SEQ ID NO: 126.

In some of any such embodiments, said polynucleotide contains a nucleic acid encoding the spacer containing the sequence set forth in SEQ ID NO:136. In some of any such embodiments, said polynucleotide contains a nucleic acid encoding the spacer containing the sequence set forth in SEQ ID NO:139. In some of any such embodiments, said polynucleotide contains a nucleic acid encoding the spacer containing the sequence set forth in SEQ ID NO:196.

In some of any such embodiments, said polynucleotide contains the sequence set forth in SEQ ID NO: 156, 157, 158, 159, 160 or 161 or a sequence that exhibits at least 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 156, 157, 158, 159, 160 or 161. In some of any such embodiments, said polynucleotide contains the sequence set forth in SEQ ID NO: 156 or a sequence that exhibits at least 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 156. In some of any such embodiments, said polynucleotide contains the sequence set forth in SEQ ID NO: 156. In some of any such embodiments, said polynucleotide contains the sequence set forth in SEQ ID NO: 157 or a sequence that exhibits at least 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 157. In some of any such embodiments, said polynucleotide contains the sequence set forth in SEQ ID NO: 157.

In some of any such embodiments, the polynucleotide further contains a CD33 signal sequence, a GM-CSF signal sequence, a CD8 signal sequence or an Ig kappa signal sequence. In some of any such embodiments, the polynucleotide further contains a CD33 signal sequence. In some of any such embodiments, the CD33 signal sequence is set forth in SEQ ID NO:190 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO:190.

Also provided herein is a vector, containing the polynucleotide of any of the embodiments provided herein. In some embodiments, the vector is a viral vector. In some embodiments, the viral vector is a retroviral vector or a lentiviral vector.

Also provided herein is a cell containing the anti-ROR1 chimeric antigen receptor of any of the embodiments provided herein. Also provided herein is a cell containing the polynucleotide of any of the embodiments provided herein, or the vector of any of the embodiments provided herein. Also provided herein is a cell containing the anti-ROR1 antibody or antigen-binding fragment thereof of the embodiments provided herein, the conjugate of any of the embodiments provided herein, the single chain cell surface protein of any of the embodiments provided herein, the anti-ROR1 chimeric antigen receptor of any of the embodiments provided herein, the polynucleotide of any of the embodiments provided herein, or the vector of any of the embodiments provided herein.

In some embodiments, the cell is a lymphocyte. In some embodiments, the cell is an NK cell or a T cell. In some of any such embodiments, the cell is a T cell and the T cell is a CD4+ or a CD8+ T cell. In some of any such embodiments, the cell is a primary cell obtained from a subject.

In some of any such embodiments, among a plurality of the cells, less than at or about 10%, at or about 9%, at or about 8%, at or about 7%, at or about 5%, at or about 4%, at or about 3%, at or about 2% or at or about 1% of the cells in the plurality contain an anti-ROR1 chimeric antigen receptor that exhibits tonic signaling or antigen independent activity or signaling.

Also provided herein is a composition containing the anti-ROR1 antibody or antigen-binding fragment thereof of any of the embodiments provided herein, the conjugate of any of the embodiments provided herein, the single chain cell surface protein of any of the embodiments provided herein or the anti-ROR1 chimeric antigen receptor of any of the embodiments provided herein.

Also provided herein is a composition containing the cell of any of the embodiments provided herein. In some of any such embodiments, the composition further contains a pharmaceutically acceptable excipient. In some of any such embodiments, the composition contains CD4+ and CD8+ T cells and the ratio of CD4+ to CD8+ T cells is from at or about 1:3 to 3:1. In some of any such embodiments, the composition contains CD4+ and CD8+ T cells and the ratio of CD4+ to CD8+ T cells is at or about 1:2 to 2:1. In some of any such embodiments, the composition contains CD4+ and CD8+ T cells and the ratio of CD4+ to CD8+ T cells is at or about 1:1.

In some of any such embodiments, among a plurality of the cells in the composition, less than at or about 10%, at or about 9%, at or about 8%, at or about 7%, at or about 5%, at or about 4%, at or about 3%, at or about 2% or at or about 1% of the cells in the plurality contain an anti-ROR1 chimeric antigen receptor that exhibits tonic signaling or antigen independent activity or signaling.

Also provided herein is a method of treatment, containing administering the composition of any of the embodiments provided herein to a subject having a disease or disorder associated with ROR1.

Also provided herein is a method of treatment, containing administering the anti-ROR1 antibody or antigen-binding fragment thereof of any of the embodiments provided herein, the conjugate of any of the embodiments provided herein, the single chain cell surface protein of any of the embodiments provided herein, the anti-ROR1 chimeric antigen receptor of any of the embodiments provided herein, the polynucleotide of any of the embodiments provided herein, the vector of any of the embodiments provided herein, or the cell of any of the embodiments provided herein to a subject having a disease or disorder associated with ROR1. Also provided herein is a composition of any of the embodiments provided herein for use in treating a disease or disorder associated with ROR1. Also provided herein is a use of a composition of any of the embodiments provided herein for the manufacture of a medicament for treating a disease or disorder associated with ROR1. Also provided herein is a use of a composition of any of the embodiments provided herein for the treatment of a disease or disorder associated with ROR1. Also provided herein is a method of treatment, containing administering the cells of any of the embodiments provided herein to a subject having a disease or disorder associated with ROR1.

Also provided herein is a method of treatment, containing administering the anti-ROR1 antibody or antigen-binding fragment thereof of any of the embodiments provided herein, the conjugate of any of the embodiments provided herein, the single chain cell surface protein of any of the embodiments provided herein, the anti-ROR1 chimeric antigen receptor of any of the embodiments provided herein, the polynucleotide of any of the embodiments provided herein, the vector of any of the embodiments provided herein, or the cell of any of the embodiments provided herein to a subject having a disease or disorder associated with ROR1. Also provided herein is a cell of any of the embodiments provided herein for use in treating a disease or disorder associated with ROR1. Also provided herein is a use of a cell of any of the embodiments provided herein for the manufacture of a medicament for treating a disease or disorder associated with ROR1. Also provided herein is a use of a cell of any of the embodiments provided herein for the treatment of a disease or disorder associated with ROR1.

In some of any of the provided embodiments, the disease or disorder associated with ROR1 is a cancer. In some of any of the provided embodiments, the cancer is a ROR1-expressing cancer. In some of any of the provided embodiments, the cancer is associated with a ROR1-expressing solid tumor or a ROR1-expressing hematologic malignancy.

In some of any of the provided embodiments, the cancer is associated with a ROR1-expressing solid tumor. In some of any of the provided embodiments, the cancer associated with a solid tumor is selected from the group consisting of neuroblastoma, renal cell carcinoma, colon cancer, colorectal cancer, breast cancer, epithelial squamous cell cancer, melanoma, myeloma, stomach cancer, brain cancer, lung cancer, pancreatic cancer, cervical cancer, ovarian cancer, liver cancer, bladder cancer, prostate cancer, testicular cancer, thyroid cancer, uterine cancer, adrenal cancer and head and neck cancer. In some of any of the provided embodiments, the lung cancer is a non-small cell lung cancer (NSCLC), lung adenocarcinoma, adenocarcinoma, squamous cell carcinoma, small cell carcinoma, and atypical carcinoid. In some of any of the provided embodiments, the lung cancer is a non-small cell lung cancer (NSCLC). In some of any of the provided embodiments, the breast cancer is a triple negative breast cancer (TNBC).

In some of any of the provided embodiments, the cancer is associated with a ROR1-expressing hematologic malignancy. In some of any of the provided embodiments, the hematologic malignancy is selected from the group consisting of B cell leukemia, lymphoma, B cell chronic lymphocytic leukemia (CLL), acute myeloid leukemia (AML), acute lymphocytic leukemia (ALL), Burkitt's Lymphoma or mantle cell lymphoma (MCL).

In some embodiments of the methods provided herein, the disease or disorder associated with ROR1 is a cancer. In some embodiments of the methods provided herein, the cancer is a ROR1-expressing cancer. In some embodiments of the methods provided herein, the cancer is associated with a ROR1-expressing solid tumor or a ROR1-expressing hematologic malignancy.

In some embodiments of the methods provided herein, the cancer is associated with a ROR1-expressing solid tumor. In some embodiments of the methods provided herein, the cancer associated with a solid tumor is selected from the group consisting of neuroblastoma, renal cell carcinoma, colon cancer, colorectal cancer, breast cancer, epithelial squamous cell cancer, melanoma, myeloma, stomach cancer, brain cancer, lung cancer, pancreatic cancer, cervical cancer, ovarian cancer, liver cancer, bladder cancer, prostate cancer, testicular cancer, thyroid cancer, uterine cancer, adrenal cancer and head and neck cancer. In some embodiments of the methods provided herein, the lung cancer is a non-small cell lung cancer (NSCLC), lung adenocarcinoma, adenocarcinoma, squamous cell carcinoma, small cell carcinoma, and atypical carcinoid. In some embodiments of the methods provided herein, the lung cancer is a non-small cell lung cancer (NSCLC). In some embodiments of the methods provided herein, the breast cancer is a triple negative breast cancer (TNBC).

In some embodiments of the methods provided herein, the cancer is associated with a ROR1-expressing hematologic malignancy. In some embodiments of the methods provided herein, the hematologic malignancy is selected from the group consisting of B cell leukemia, lymphoma, B cell chronic lymphocytic leukemia (CLL), acute myeloid leukemia (AML), acute lymphocytic leukemia (ALL), Burkitt's Lymphoma or mantle cell lymphoma (MCL).

In some embodiments of the cells or compositions for use provided herein, the disease or disorder associated with ROR1 is a cancer. In some embodiments of the cells or compositions for use provided herein, the cancer is a ROR1-expressing cancer. In some embodiments of the cells or compositions for use provided herein, the cancer is associated with a ROR1-expressing solid tumor or a ROR1-expressing hematologic malignancy.

In some embodiments of the cells or compositions for use provided herein, the cancer is associated with a ROR1-expressing solid tumor. In some embodiments of the cells or compositions for use provided herein, the cancer associated with a solid tumor is selected from the group consisting of neuroblastoma, renal cell carcinoma, colon cancer, colorectal cancer, breast cancer, epithelial squamous cell cancer, melanoma, myeloma, stomach cancer, brain cancer, lung cancer, pancreatic cancer, cervical cancer, ovarian cancer, liver cancer, bladder cancer, prostate cancer, testicular cancer, thyroid cancer, uterine cancer, adrenal cancer and head and neck cancer. In some embodiments of the cells or compositions for use provided herein, the lung cancer is a non-small cell lung cancer (NSCLC), lung adenocarcinoma, adenocarcinoma, squamous cell carcinoma, small cell carcinoma, and atypical carcinoid. In some embodiments of the cells or compositions for use provided herein, the lung cancer is a non-small cell lung cancer (NSCLC). In some embodiments of the cells or compositions for use provided herein, the breast cancer is a triple negative breast cancer (TNBC).

In some embodiments of the cells or compositions for use provided herein, the cancer is associated with a ROR1-expressing hematologic malignancy. In some embodiments of the cells or compositions for use provided herein, the hematologic malignancy is selected from the group consisting of B cell leukemia, lymphoma, B cell chronic lymphocytic leukemia (CLL), acute myeloid leukemia (AML), acute lymphocytic leukemia (ALL), Burkitt's Lymphoma or mantle cell lymphoma (MCL).

In some embodiments of the uses provided herein, the disease or disorder associated with ROR1 is a cancer. In some embodiments of the uses provided herein, the cancer is a ROR1-expressing cancer. In some embodiments of the uses provided herein, the cancer is associated with a ROR1-expressing solid tumor or a ROR1-expressing hematologic malignancy.

In some embodiments of the uses provided herein, the cancer is associated with a ROR1-expressing solid tumor. In some embodiments of the uses provided herein, the cancer associated with a solid tumor is selected from the group consisting of neuroblastoma, renal cell carcinoma, colon cancer, colorectal cancer, breast cancer, epithelial squamous cell cancer, melanoma, myeloma, stomach cancer, brain cancer, lung cancer, pancreatic cancer, cervical cancer, ovarian cancer, liver cancer, bladder cancer, prostate cancer, testicular cancer, thyroid cancer, uterine cancer, adrenal cancer and head and neck cancer. In some embodiments of the uses provided herein, the lung cancer is a non-small cell lung cancer (NSCLC). In some embodiments of the uses provided herein, the breast cancer is a triple negative breast cancer (TNBC).

In some embodiments of the uses provided herein, the cancer is associated with a ROR1-expressing hematologic malignancy. In some embodiments of the uses provided herein, the hematologic malignancy is selected from the group consisting of B cell leukemia, lymphoma, B cell chronic lymphocytic leukemia (CLL), acute myeloid leukemia (AML), acute lymphocytic leukemia (ALL), Burkitt's Lymphoma or mantle cell lymphoma (MCL).

In some of any such embodiments, the disease or disorder associated with ROR1 is associated with ROR1 expression. In some of any such embodiments, the disease or disorder associated with ROR1 is a B cell-related disorder. In some of any such embodiments, the disease or disorder associated with ROR1 is a cancer. In some of any such embodiments, the cancer is a ROR1-expressing cancer. In some of any such embodiments, the ROR1-expressing cancer is selected from the group consisting of B cell leukemia, lymphoma, B cell chronic lymphocytic leukemia (CLL), acute myeloid leukemia (AML), acute lymphocytic leukemia (ALL), Burkitt's Lymphoma, mantle cell lymphoma (MCL), non-small cell lung cancer (NSCLC), neuroblastoma, renal cell carcinoma, colon cancer, colorectal cancer, breast cancer, epithelial squamous cell cancer, melanoma, myeloma, stomach cancer, brain cancer, lung cancer, pancreatic cancer, cervical cancer, ovarian cancer, liver cancer, bladder cancer, prostate cancer, testicular cancer, thyroid cancer, uterine cancer, adrenal cancer and head and neck cancer.

Also provided herein is a kit containing the anti-ROR1 antibody or antigen-binding fragment thereof of any of the embodiments provided herein, the single chain cell surface protein of any of the embodiments provided herein, the conjugate of any of the embodiments provided herein, the anti-ROR1 chimeric antigen receptor of any of the embodiments provided herein, the cell of any of the embodiments provided herein, or the composition of any of the embodiments provided herein, and instructions for use. In some of any such embodiments, the instructions are for administering the anti-ROR1 antibody or antigen-binding fragment thereof, the single chain cell surface protein, the conjugate, the anti-ROR1 chimeric antigen receptor, the cell or the composition. In some of any such embodiments, the instructions are in accord with the method, the composition for use or the use of any of the embodiments provided herein.

Also provided herein is an article of manufacture containing the anti-ROR1 antibody or antigen-binding fragment thereof of any of the embodiments provided herein, the single chain cell surface protein of any of the embodiments provided herein, the conjugate of any of the embodiments provided herein, the anti-ROR1 chimeric antigen receptor of any of the embodiments provided herein, the cell of any of the embodiments provided herein, the composition of any of the embodiments provided herein, or the kit of any of the embodiments provided herein.

BRIEF DESCRIPTION OF THE DRAWINGS

FIGS. 5A-5D show the anti-tumor activity, as assessed by the changes in mean or individual tumor volume after administration of cells expressing one of 6 selected candidate anti-ROR1 CARs or the reference anti-ROR1 (R12) CAR, in a H1975 non-small cell lung cancer (NSCLC) mouse model. FIG. 5A (low dose) and FIG. 5B (high dose) depict mean tumor volume of all treated mice; in this depiction, tumor curves were terminated after the first mouse of a group succumbed to disease. Results from all individual mice are shown in FIG. 5C (low dose) or FIG. 5D (high dose). As a control, mice were administered cells not expressing a CAR (mock) or were untreated.

FIGS. 6A-6B depict the Kaplan-Meier survival curves after administration of a low dose (FIG. 6A) or a high dose (FIG. 6B) of cells expressing one of 6 selected candidate anti-ROR1 CARs or the reference anti-ROR1 (R12) CAR, in a H1975 non-small cell lung cancer (NSCLC) mouse model.

Figure 7A:
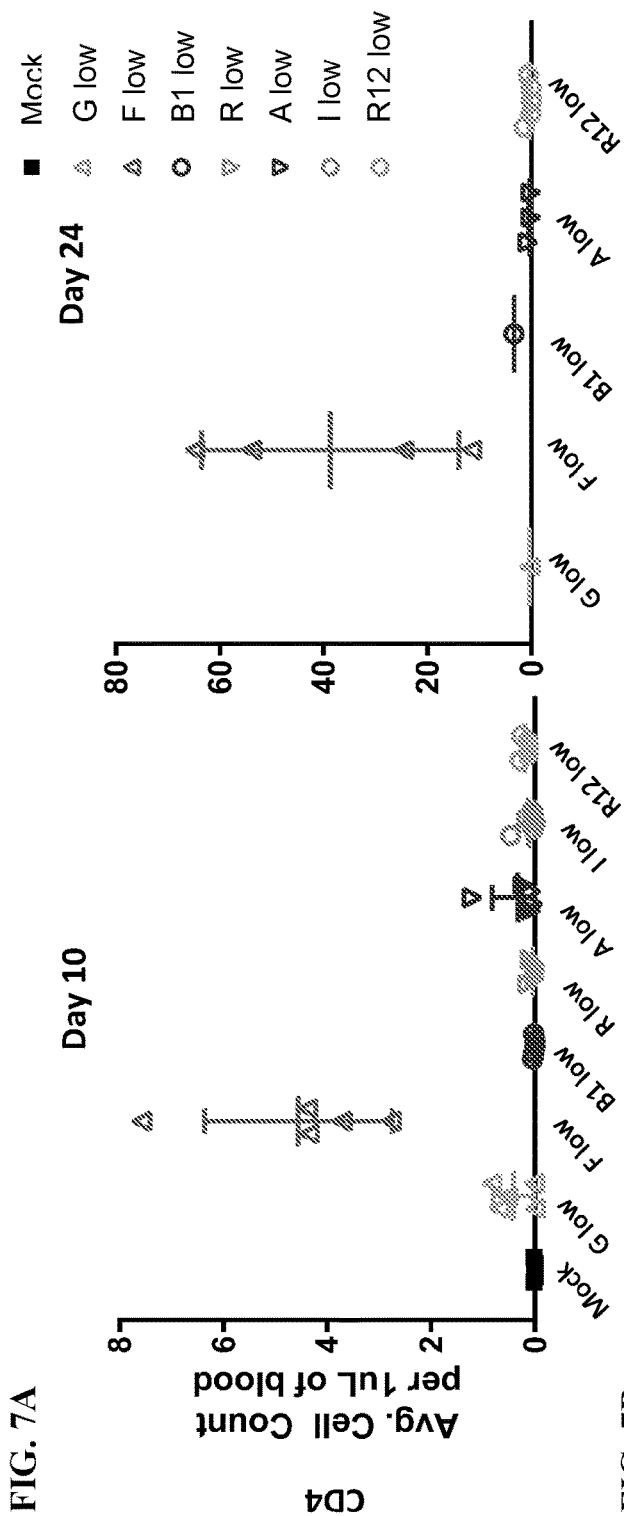
FIGS. 7A-7D show the average number of CD4+ and CD8+ CAR-expressing cells in the blood of each mouse determined at day 10 and day 24 after administration of cells expressing one of 6 selected candidate anti-ROR1 CARs or the reference anti-ROR1 (R12) CAR, at the low dose (FIGS. 7A and 7B) or high dose (FIGS. 7C and 7D).
Figure 7B:
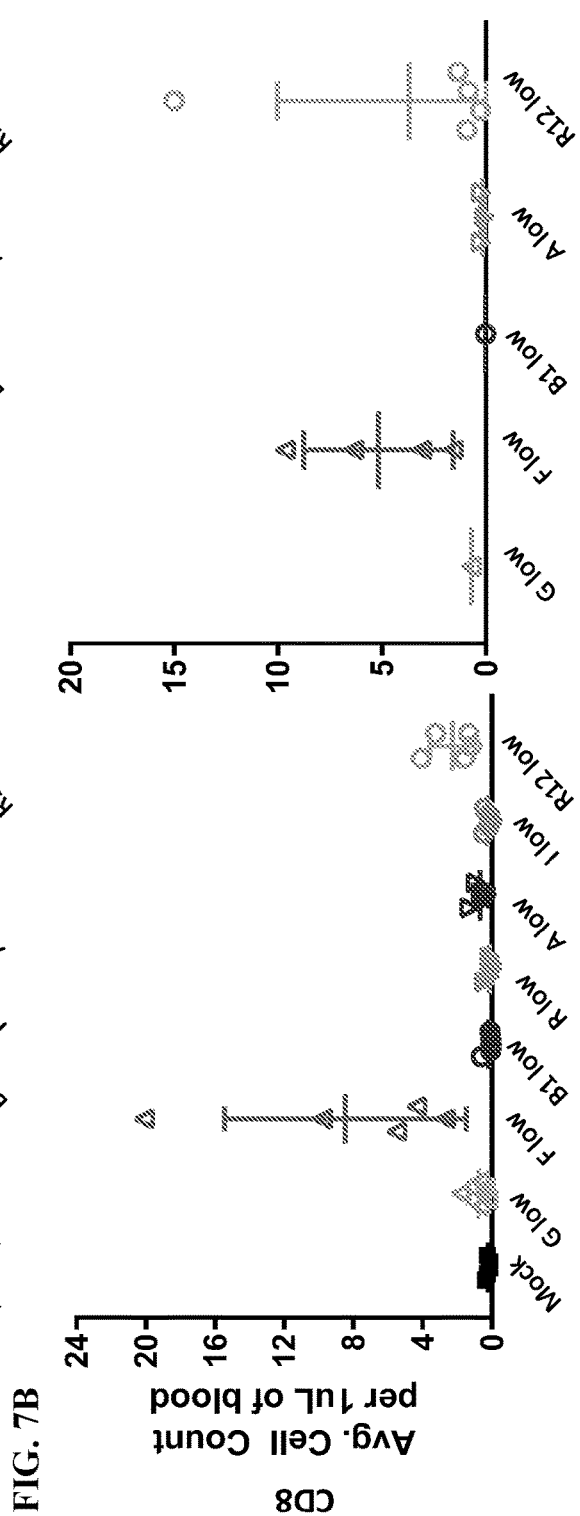
Figures 7C, 7D:
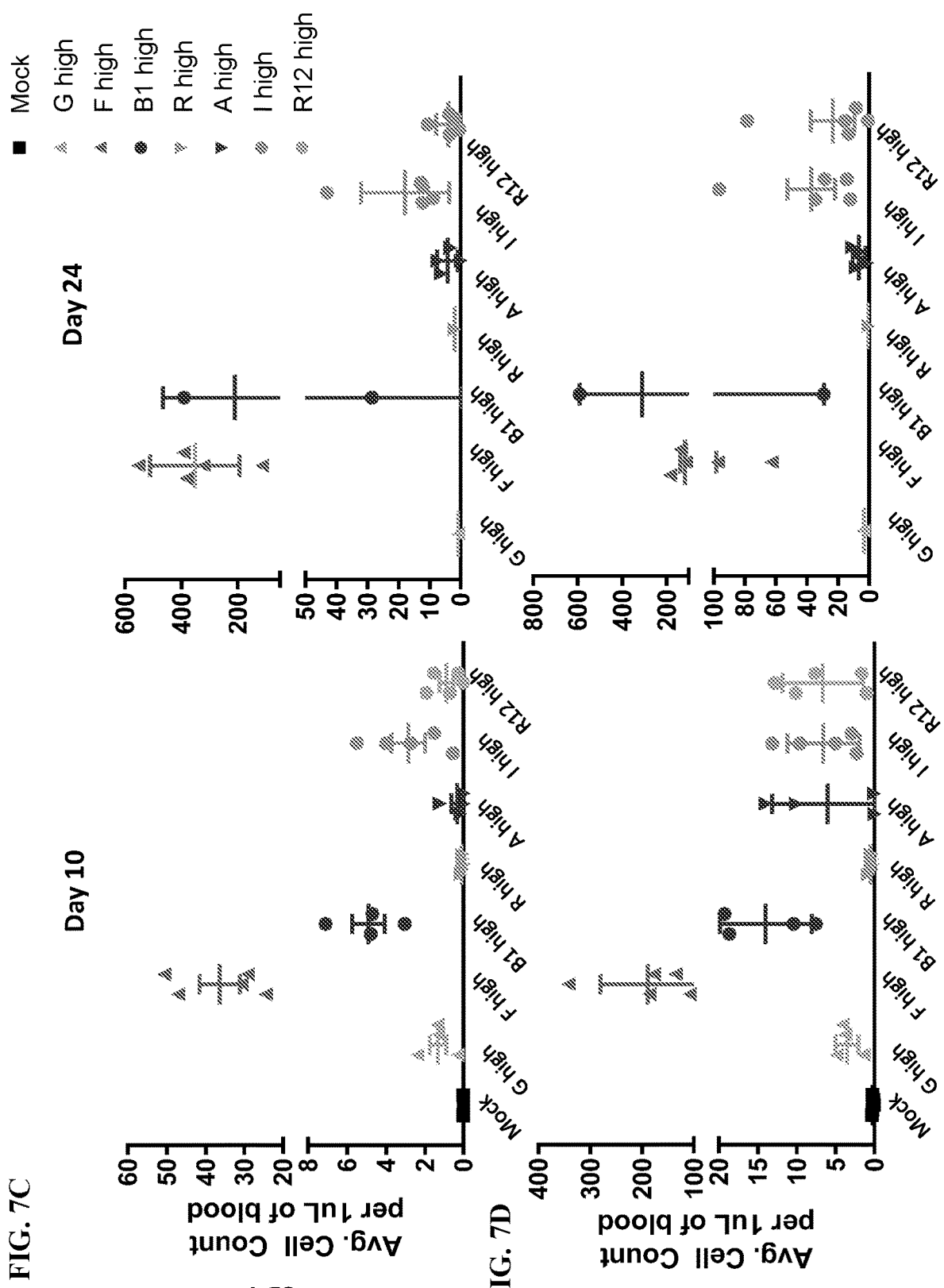
Figure 7E:
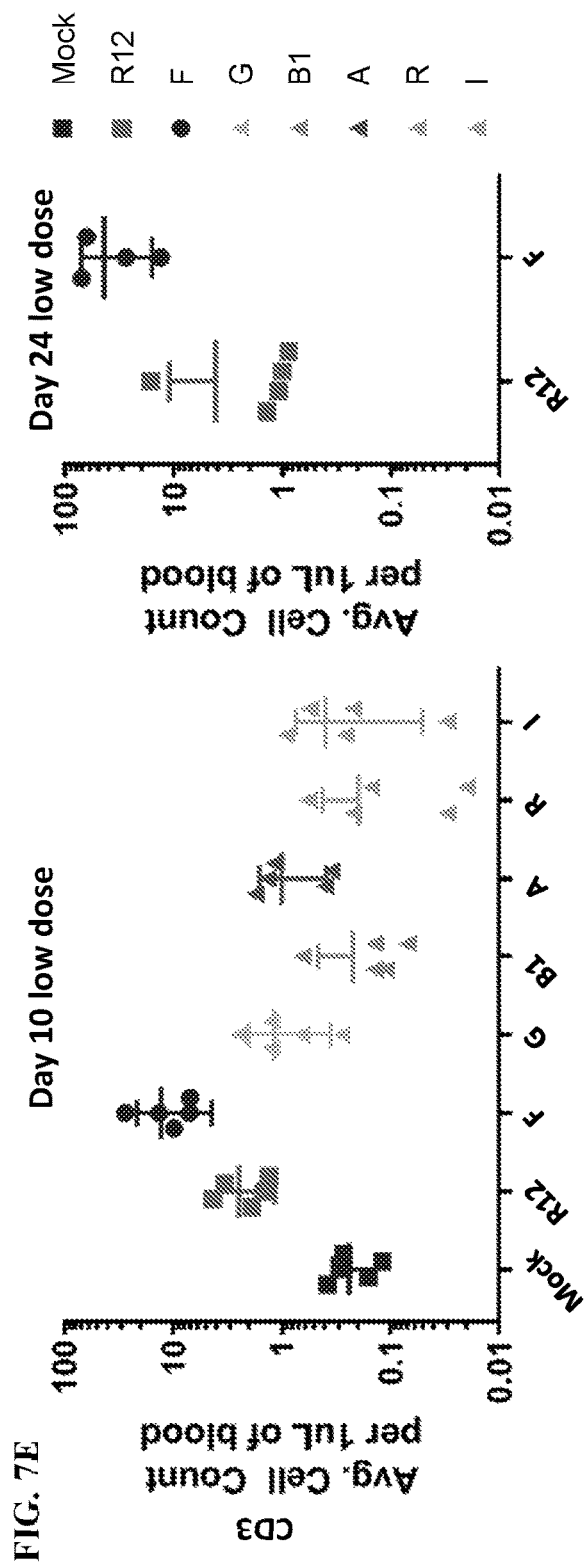
FIGS. 7E-7F show the average number of CD3+ CAR-expressing cells in the blood of each mouse determined at day 10 and day 24 after administration of cells expressing one of 6 selected candidate anti-ROR1 CARs or the reference anti-ROR1
Figure 7F:
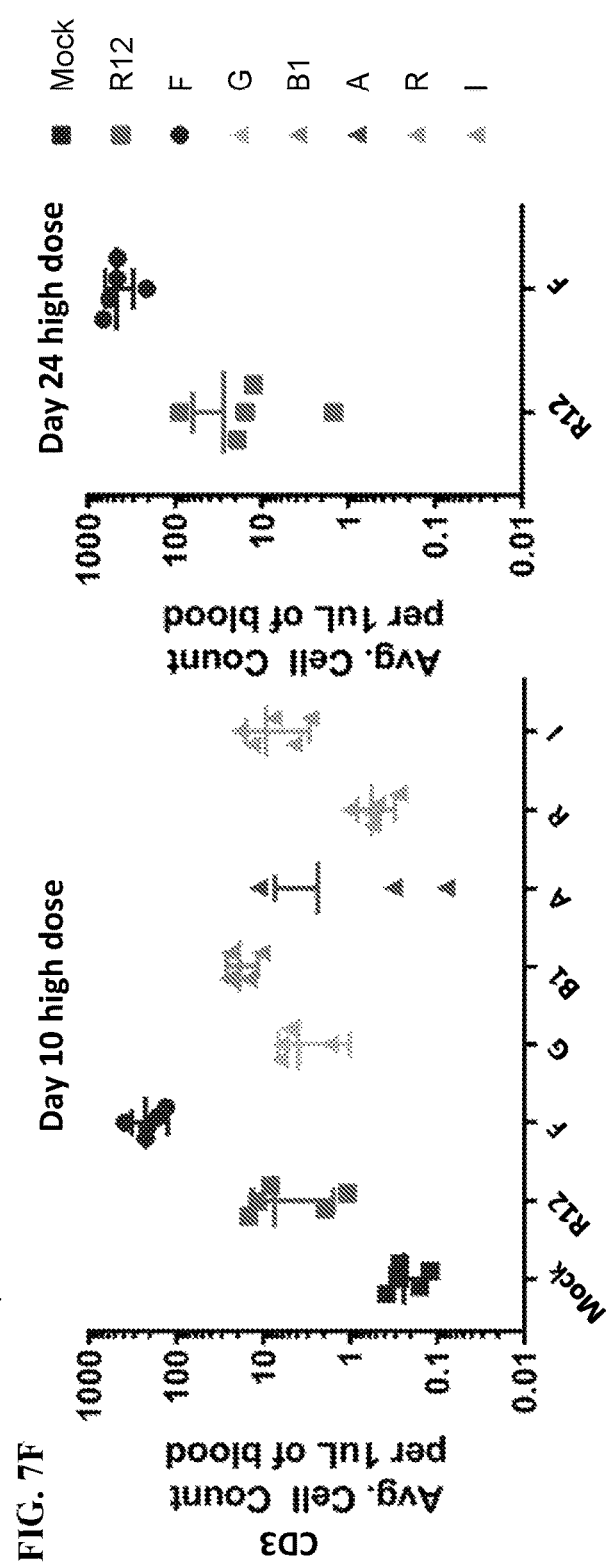

(R12) CAR, at the low dose (FIG. 7E) or high dose (FIG. 7F). Data are shown as individual values along with group means±standard deviation.

FIGS. 8A-8C depict the changes in the mean and individual tumor volume in H1975 non-small cell lung cancer (NSCLC) mice administered cells expressing anti-ROR1 CAR-F, CAR-A or the R12 reference CAR, at the low dose (mean: FIG. 8A; individual: FIG. 8C) or the high dose (mean: FIG. 8B; individual: FIG. 8C). As a control, mice were administered cells not expressing a CAR (mock) or were untreated.

Figures 9A, 9B:
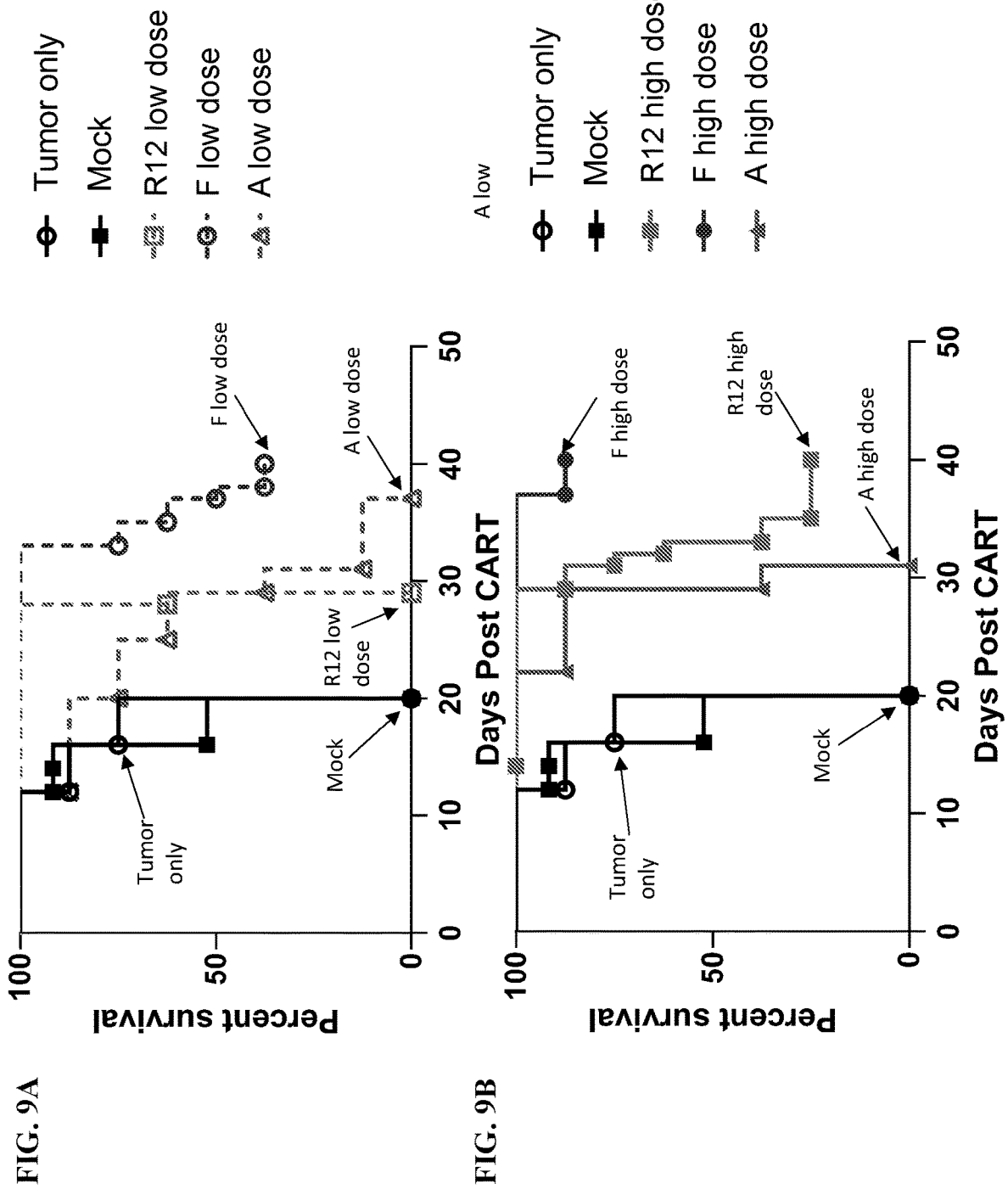

FIGS. 9A-9B depict the Kaplan-Meier survival curves after administration of a low dose (FIG. 9A) or a high dose (FIG. 9B) of mice administered cells expressing anti-ROR1 CAR-F, CAR-A or the R12 reference CAR. As a control, mice were administered cells not expressing a CAR (mock) or were untreated.

FIGS. 10A-10D depict the average CD4+ (FIGS. 10A and 10C) and CD8+ (FIGS. 10B and 10D) CAR+ T cell count per microliter of blood at days 7, 14 and 21 after administration of a low dose (FIGS. 10A and 10B) or a high dose (FIGS. 10C and 10D) cells expressing anti-ROR1 CAR-F, CAR-A or the R12 reference CAR.

Figure 11A:
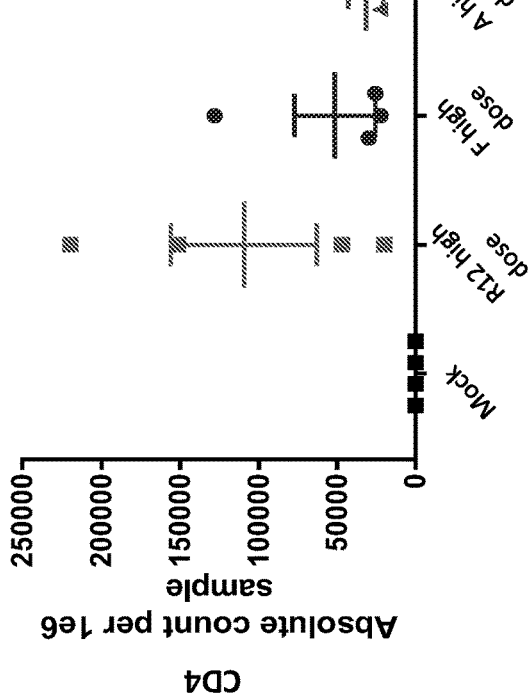
Figure 11B:
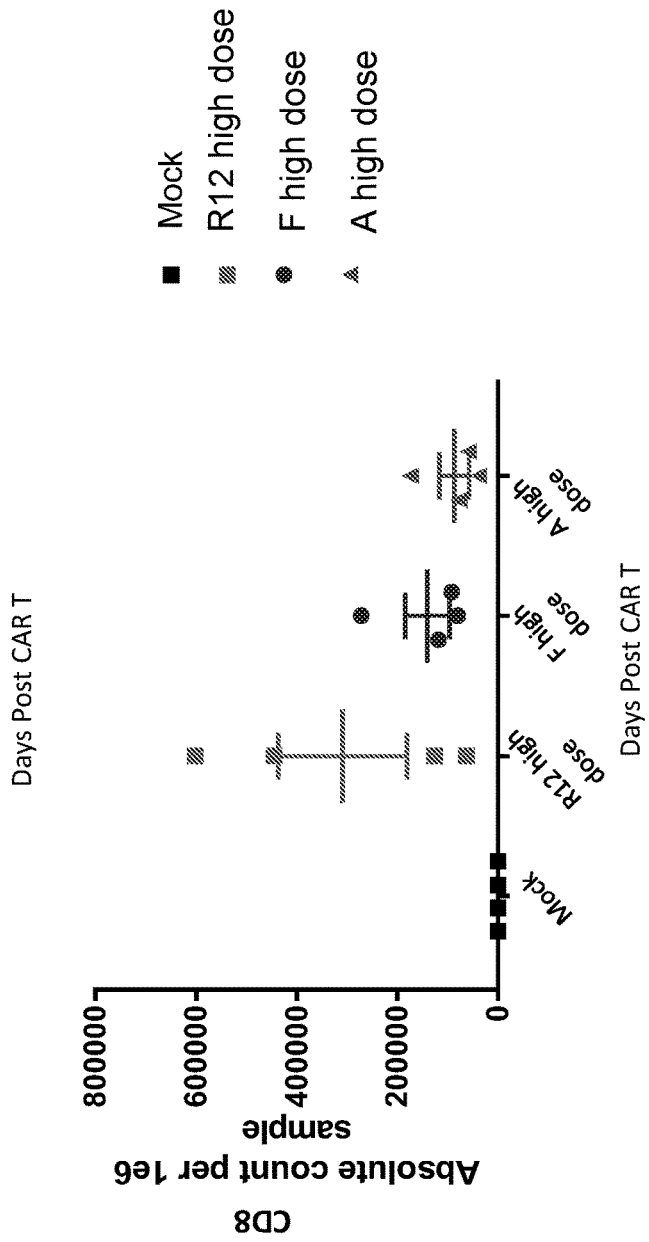

FIGS. 11A-11B depict the number of CD4+ (FIG. 11A) and CD8+ (FIG. 11B) CAR+ T cells present in the tumor at 14 days after administration of cells expressing anti-ROR1 CAR-F, CAR-A or the R12 reference CAR.

Figure 12A:
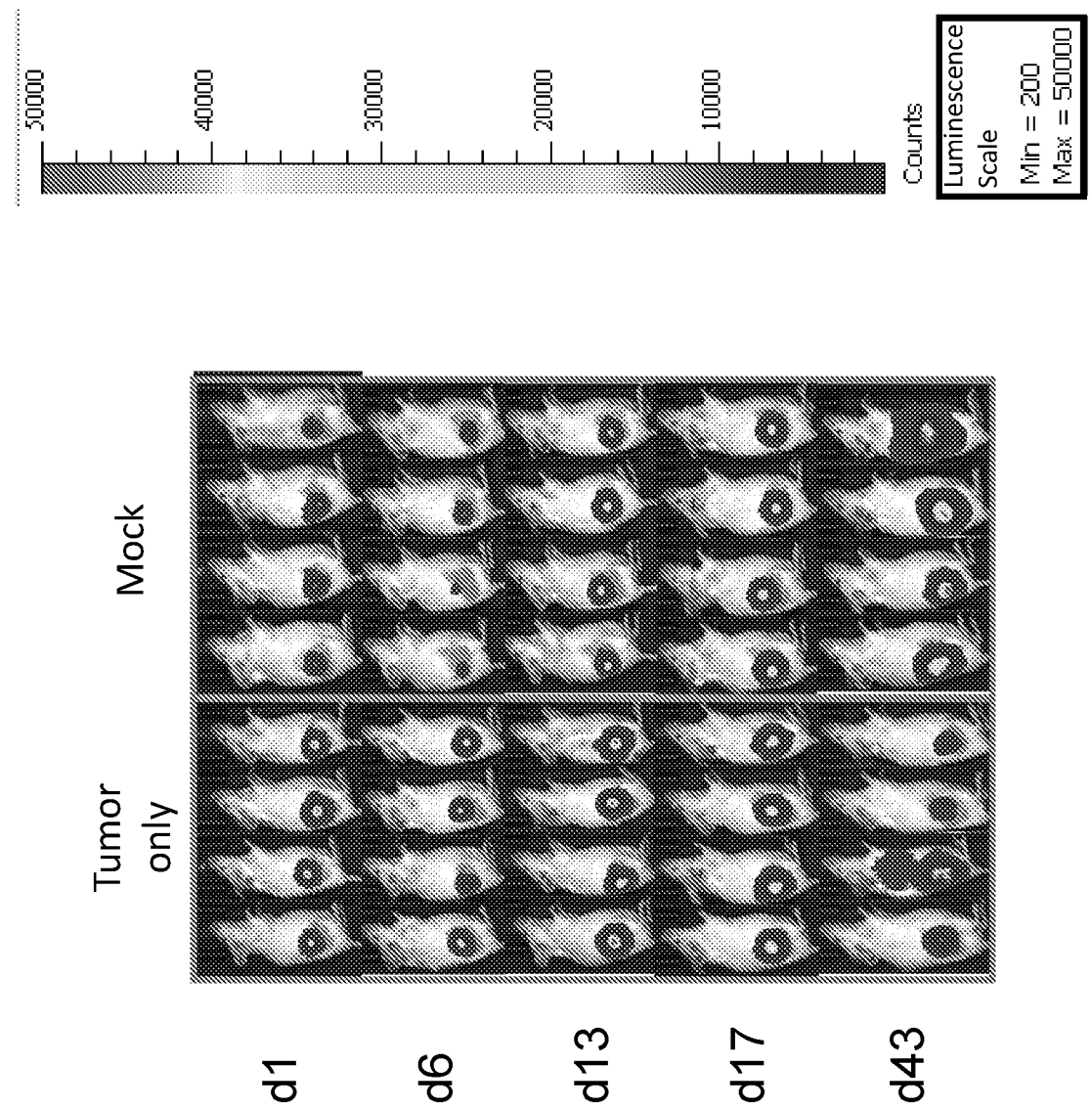
Figure 12B:
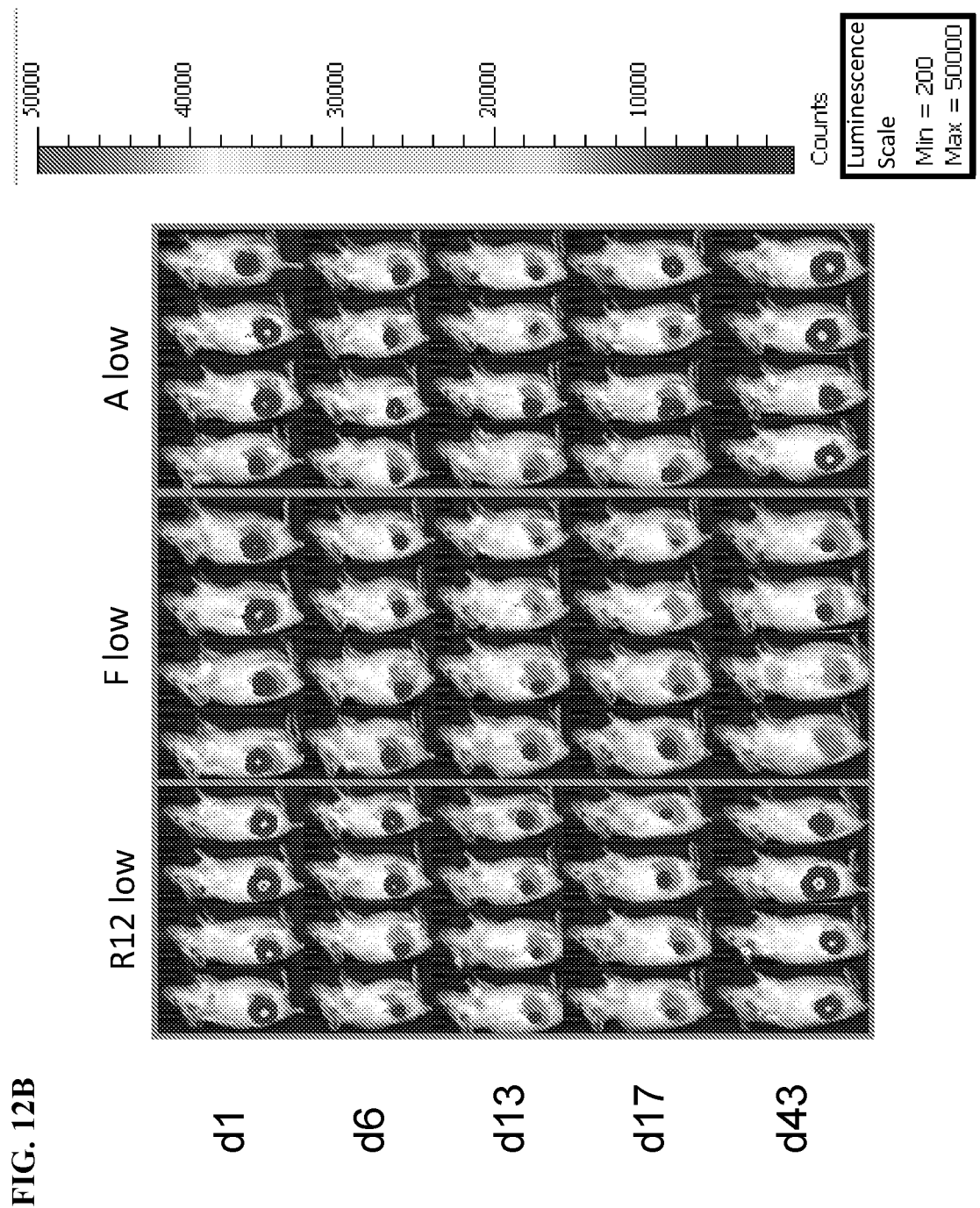
Figure 12C:
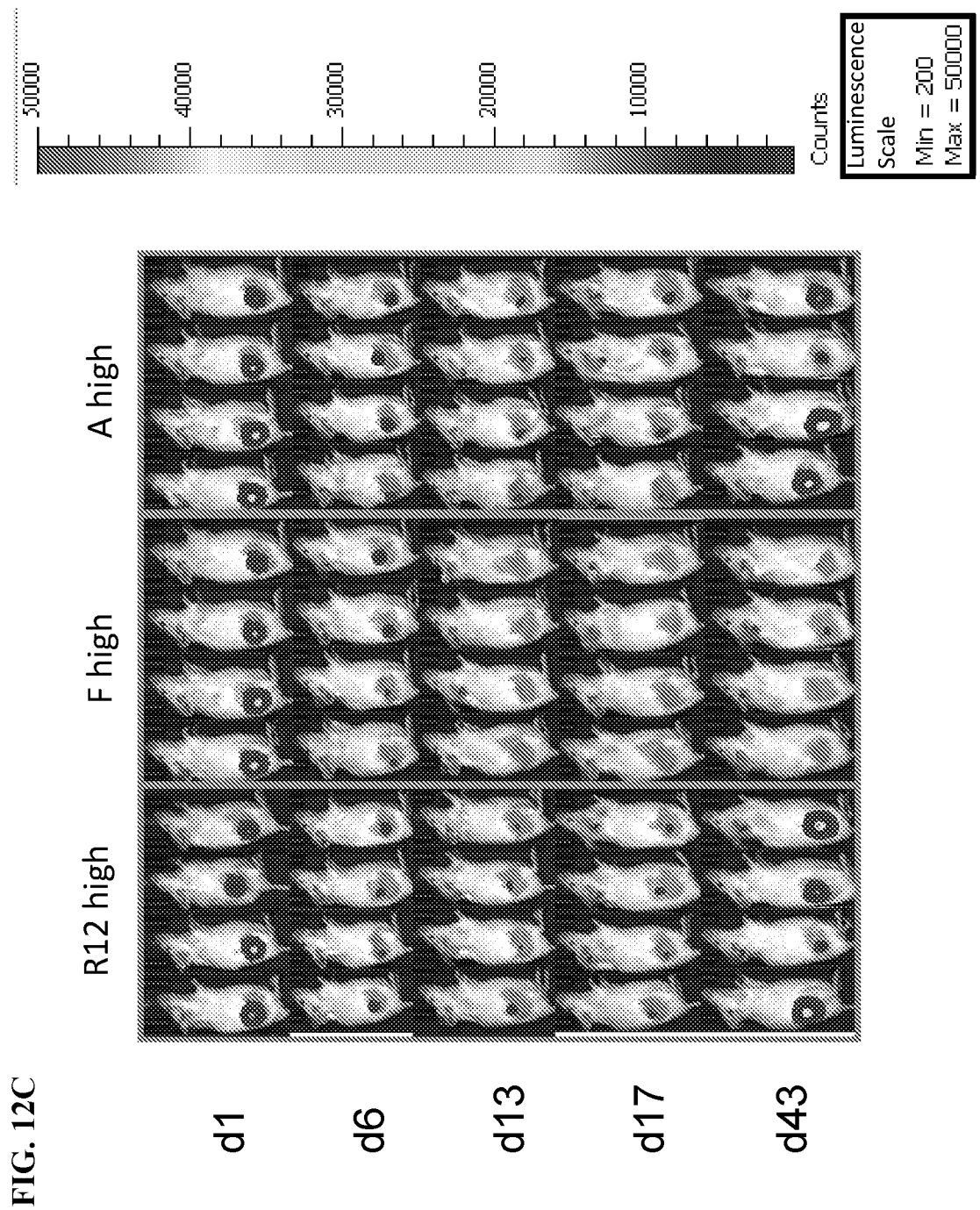

FIGS. 12A-12C depict bioluminescence images assessed up to approximately day 49 post administration of a low dose (FIG. 12B) or a high dose (FIG. 12C) of cells expressing anti-ROR1 CAR-F, CAR-A or the R12 reference CAR in MDA-MB-231 triple negative breast cancer mouse model. As a control, mice were administered cells not expressing a CAR (mock) or were untreated (FIG. 12A).

Figure 13A:
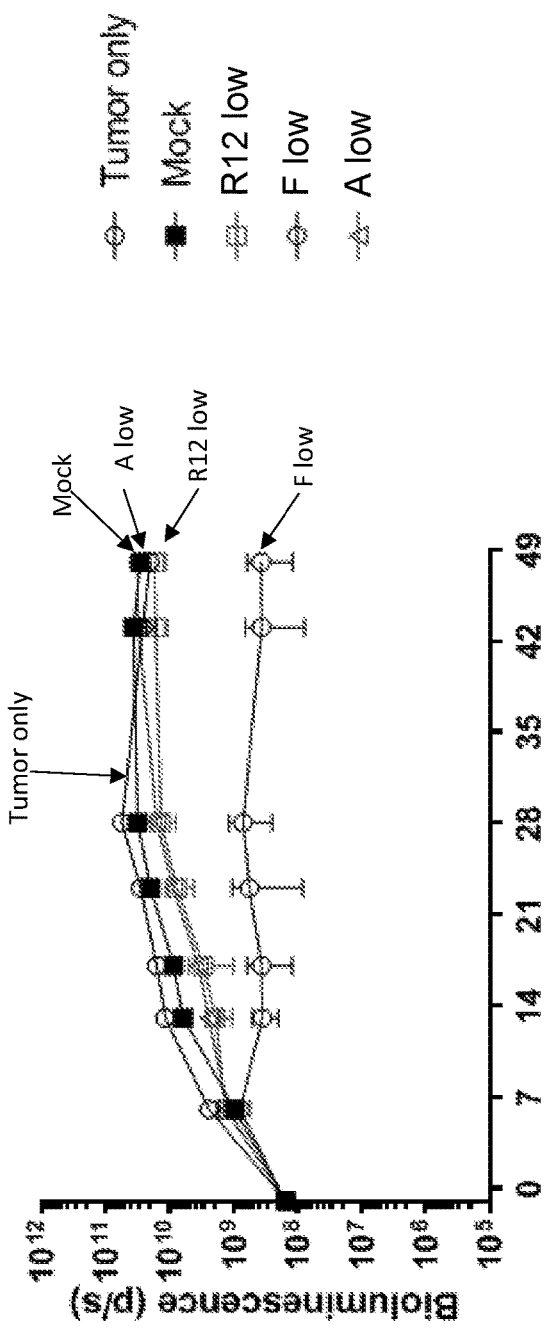
Figure 13B:
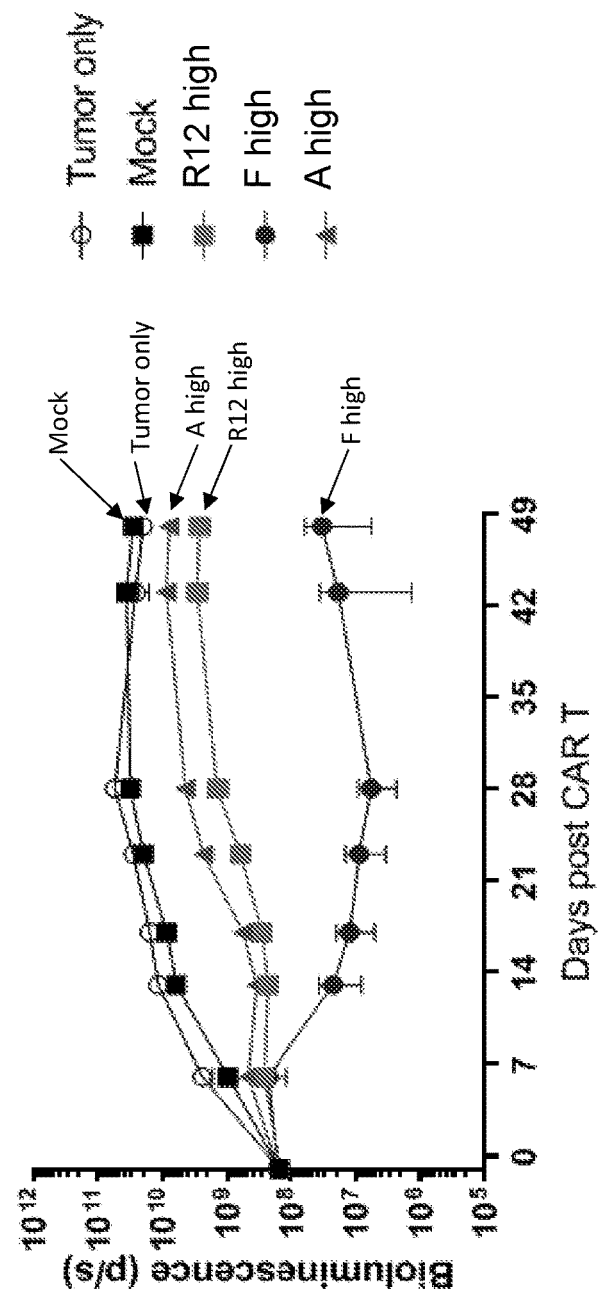

FIGS. 13A-13C depict the mean measured total flux (p/s) from the bioluminescence imaging, assessed up to approximately day 49 post administration of a low dose (FIG. 13A) or a high dose (FIG. 13B) of cells expressing anti-ROR1 CAR-F, CAR-A or the R12 reference CAR in MDA-MB-231 triple negative breast cancer mouse model, shown as group means±standard error. FIG. 13C depicts the measured total flux (p/s) of individual mice. As a control, mice were administered cells not expressing a CAR (mock) or were untreated.

Figure 14C:
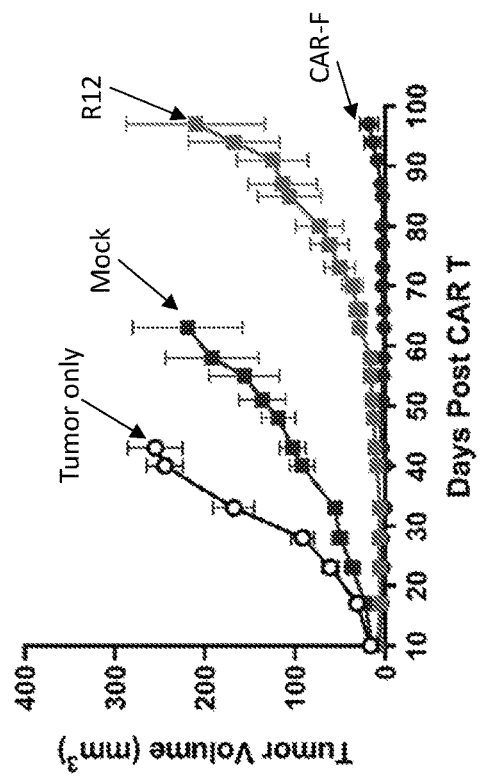
Figure 14D:
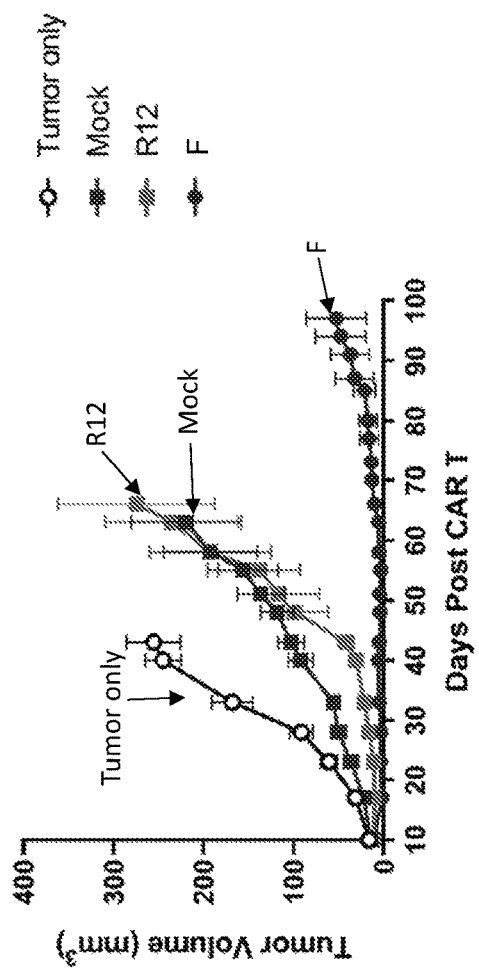

FIGS. 14A-14E depict the changes in the mean and individual tumor volume in MDA-MB-231 triple negative breast cancer model mice administered cells expressing anti-ROR1 CAR-F, CAR-A or the R12 reference CAR, at the low dose (mean: FIG. 14A) or the high dose (mean: FIG. 14B). The changes in the mean tumor volume following administration of T cells expressing anti-ROR1 CAR F and reference CAR R12, up to a further time point in the same study are depicted for the high dose (FIG. 14C) and low dose (FIG. 14D). Results of tumor volume for individual treated mice at the high dose or low dose for each treated condition are shown in FIG. 14E. Mean tumor volume is depicted as group means±standard error up to the last day that all mice in treatment groups survived. As a control, mice were administered cells not expressing a CAR (mock) or were untreated.

Figures 15A, 15B:
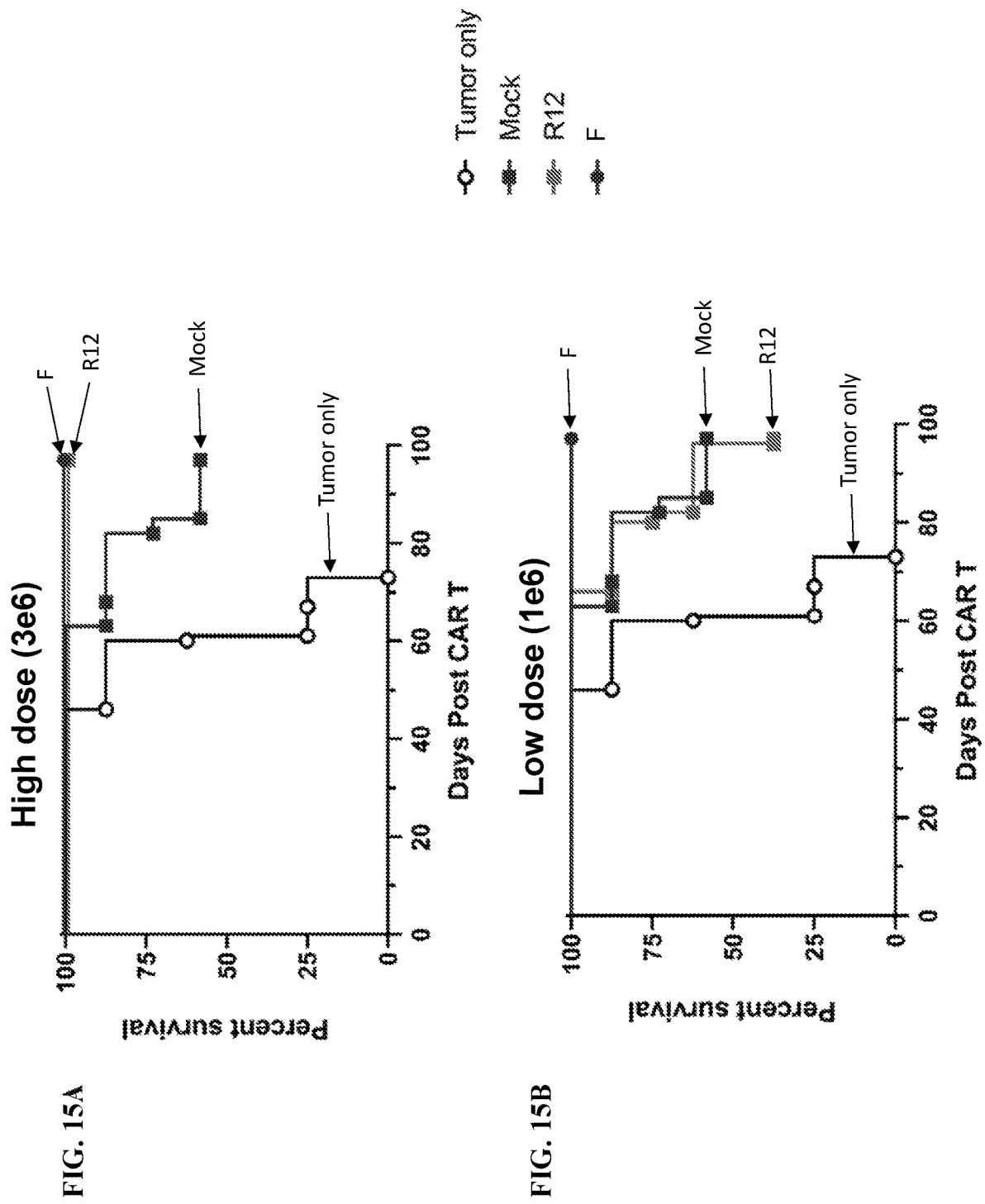

FIGS. 15A and 15B depict the Kaplan-Meier survival curve in MDA-MB-231 triple negative breast cancer model mice administered cells expressing anti-ROR1 CAR-F or the R12 reference CAR, at the low dose (FIG. 15B) or the high dose (FIG. 15A). As a control, mice were administered cells not expressing a CAR (mock) or were untreated.

Figures 16C, 16D:
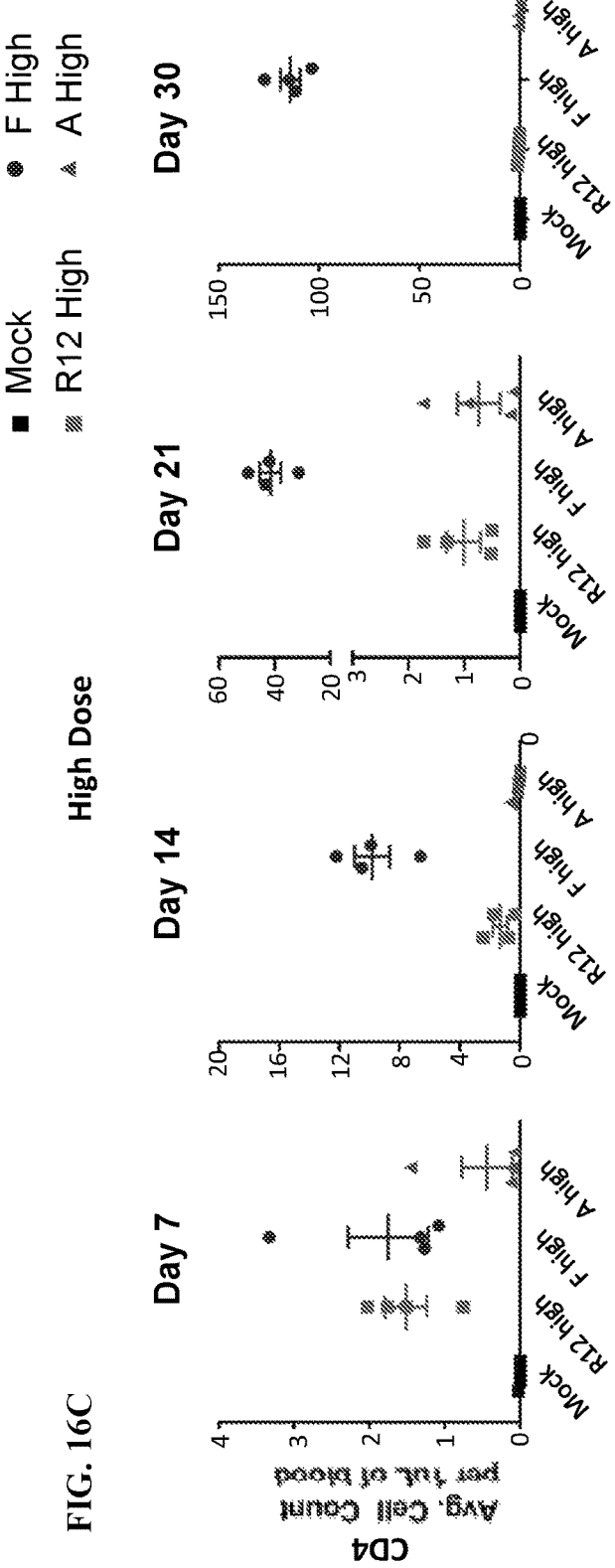
Figure 16E:
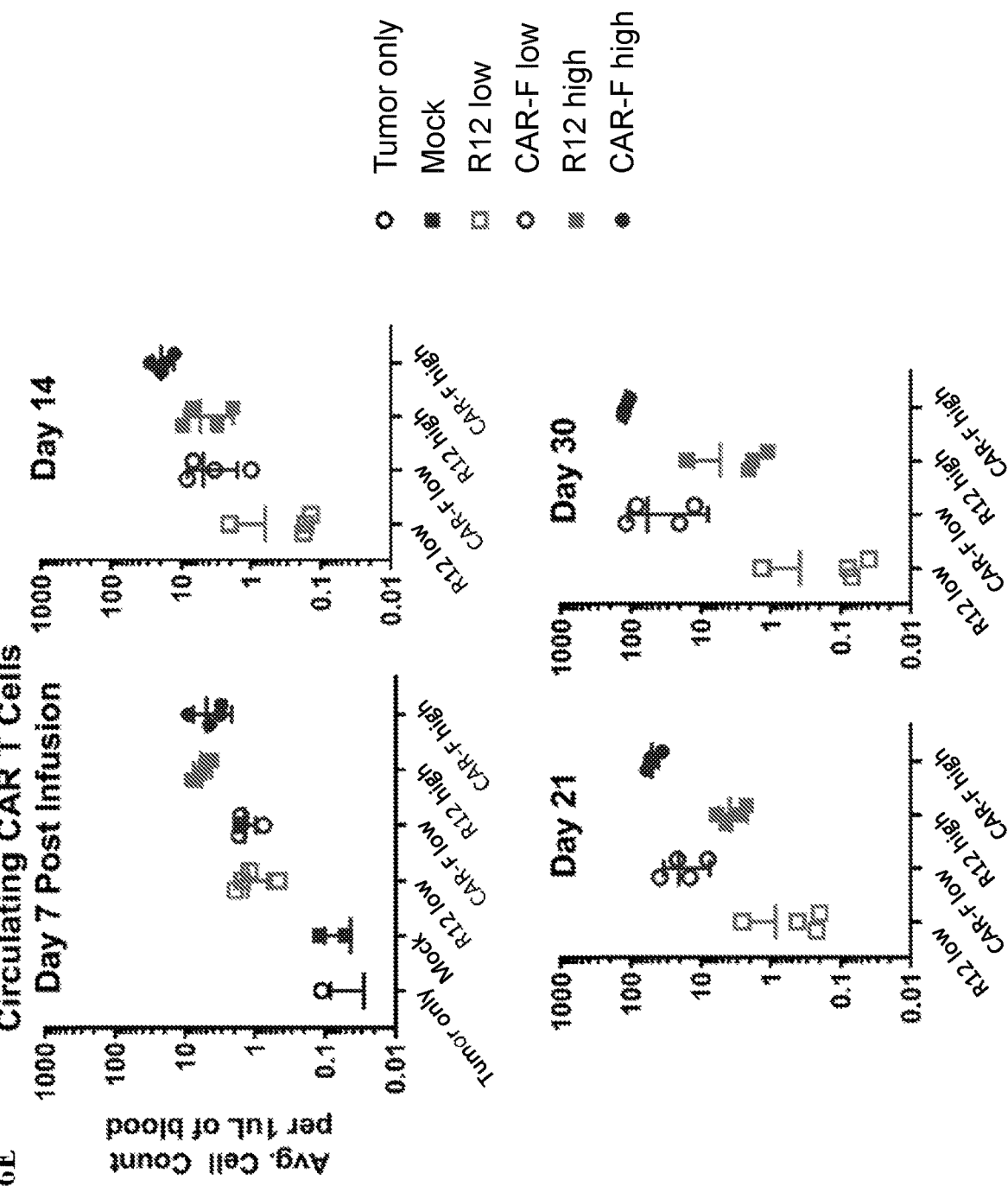

FIGS. 16A-16D show the average number of CD4+ (FIGS. 16A and 16C) and CD8+ (FIGS. 16B and 16D) CAR-expressing cells in the blood of the animal were determined at days 7, 14, 21 and 30 after administration after administration of cells expressing anti-ROR1 CAR-F, CAR-A or the R12 reference CAR, at the low dose (FIGS. 16A and 16B) or a high dose (FIGS. 16C and 16D). The average number of CD3+ CAR-expressing cells (CD45+ CD3+ CAR+) in the blood of each mouse administered cells expressing anti-ROR1 CAR-F or the R12 reference CAR also was determined at days 7, 14, 21 and 30 are shown in FIG. 16E. As shown, cells expressing anti-ROR1 CAR-F exhibited high expansion in the MDA-MB-231 mouse model, when administered at both high and low doses.

Figure 17:
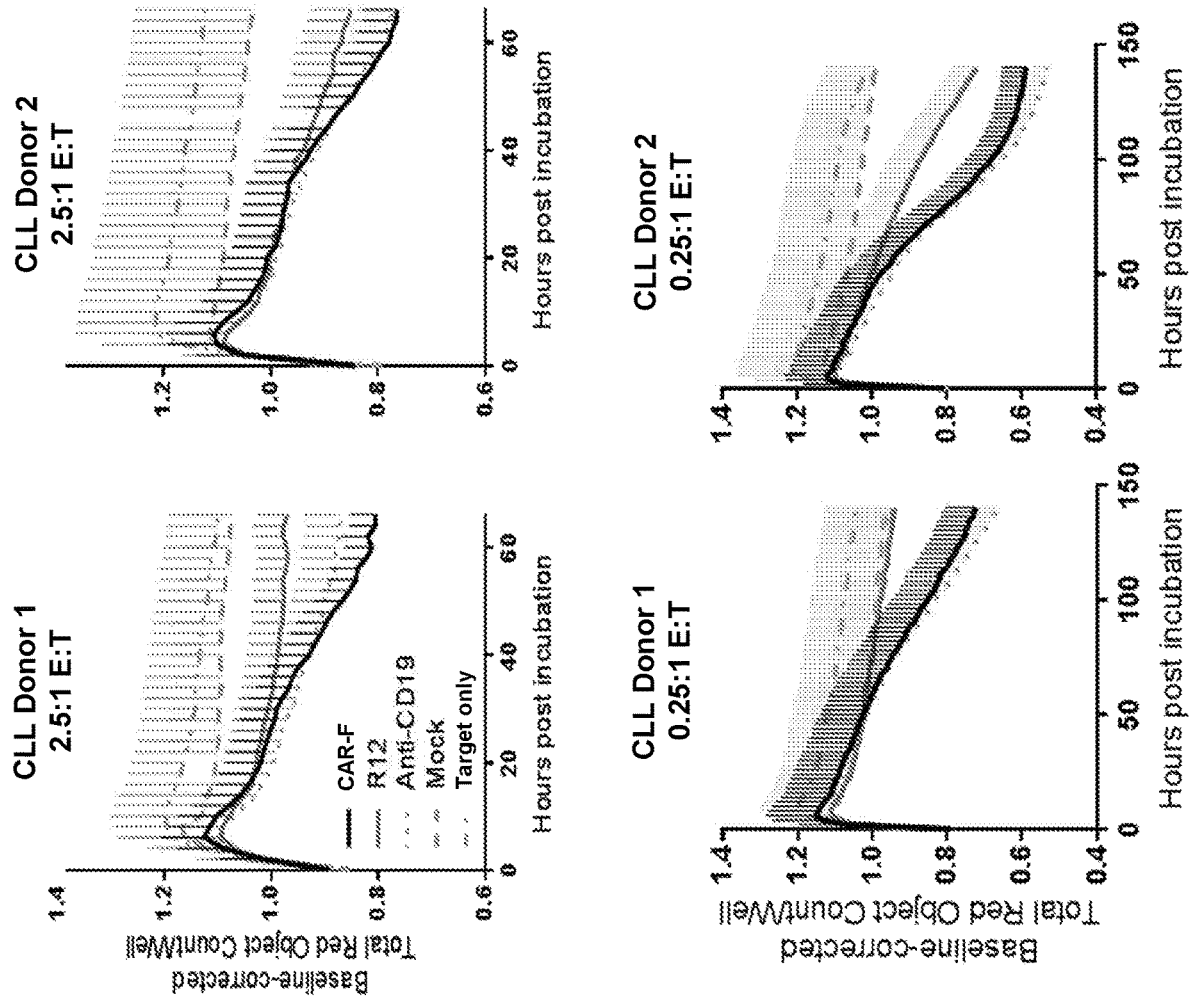

FIG. 17 depicts the loss of Rapid Red labeled target cells (CD4/CD8 T cell depleted leukapheresis samples) co-cultured for approximately 6 days with engineered cells expressing anti-ROR1 CAR-F, anti-CD19 CAR or the R12 reference CAR generated from with from two primary CLL donors, at two E:T ratios.

Figure 18A:
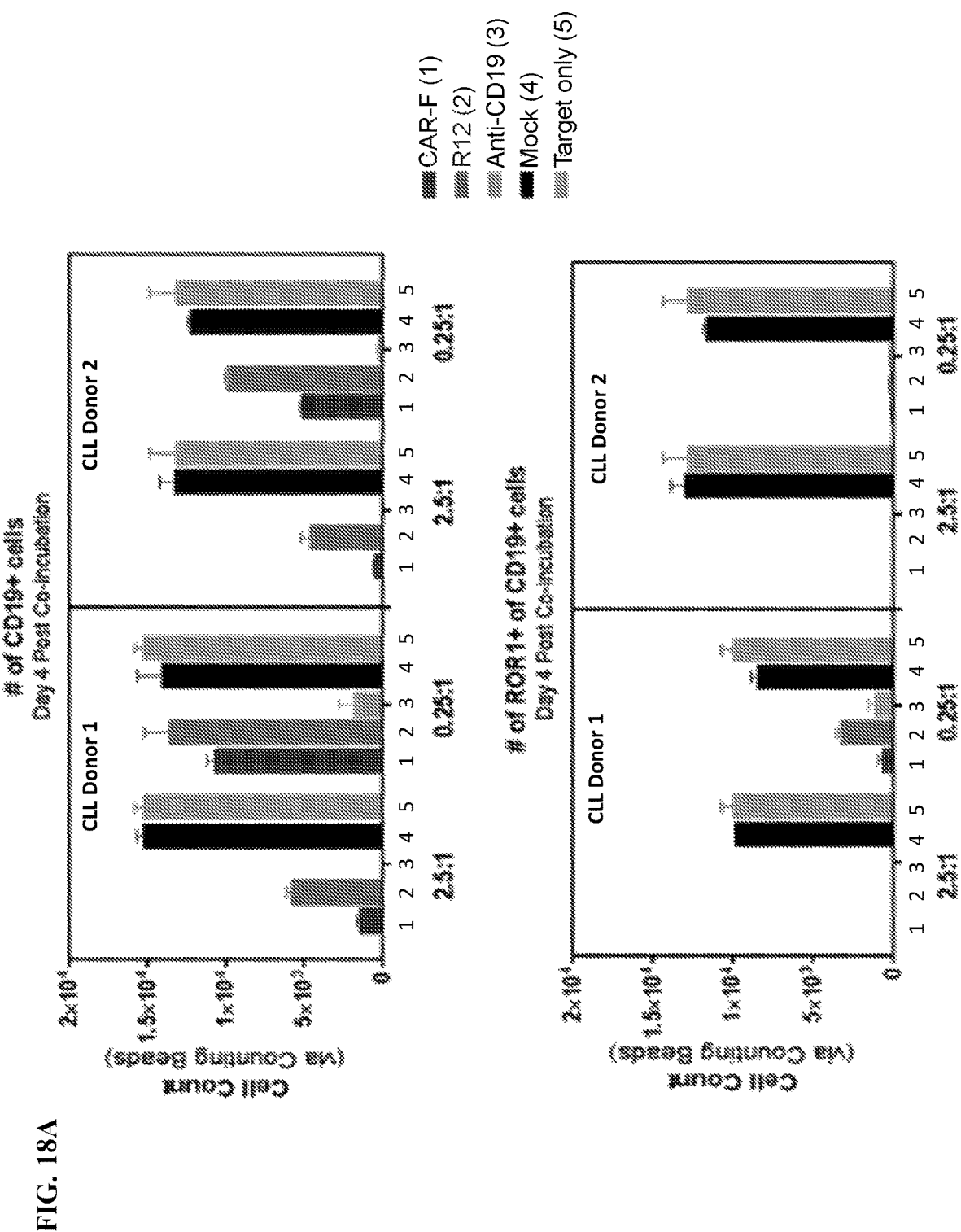
Figure 18B:
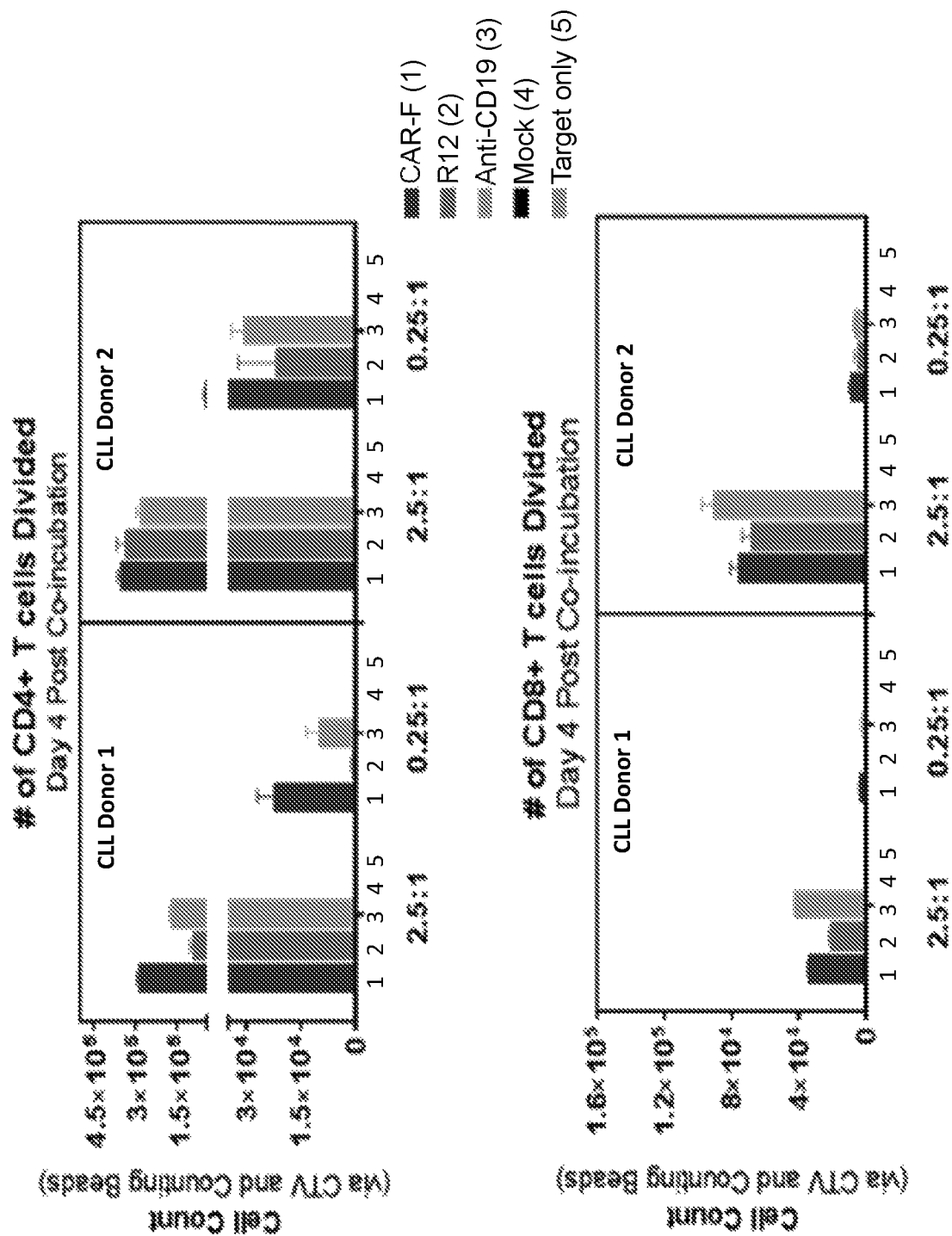
Figure 18C:
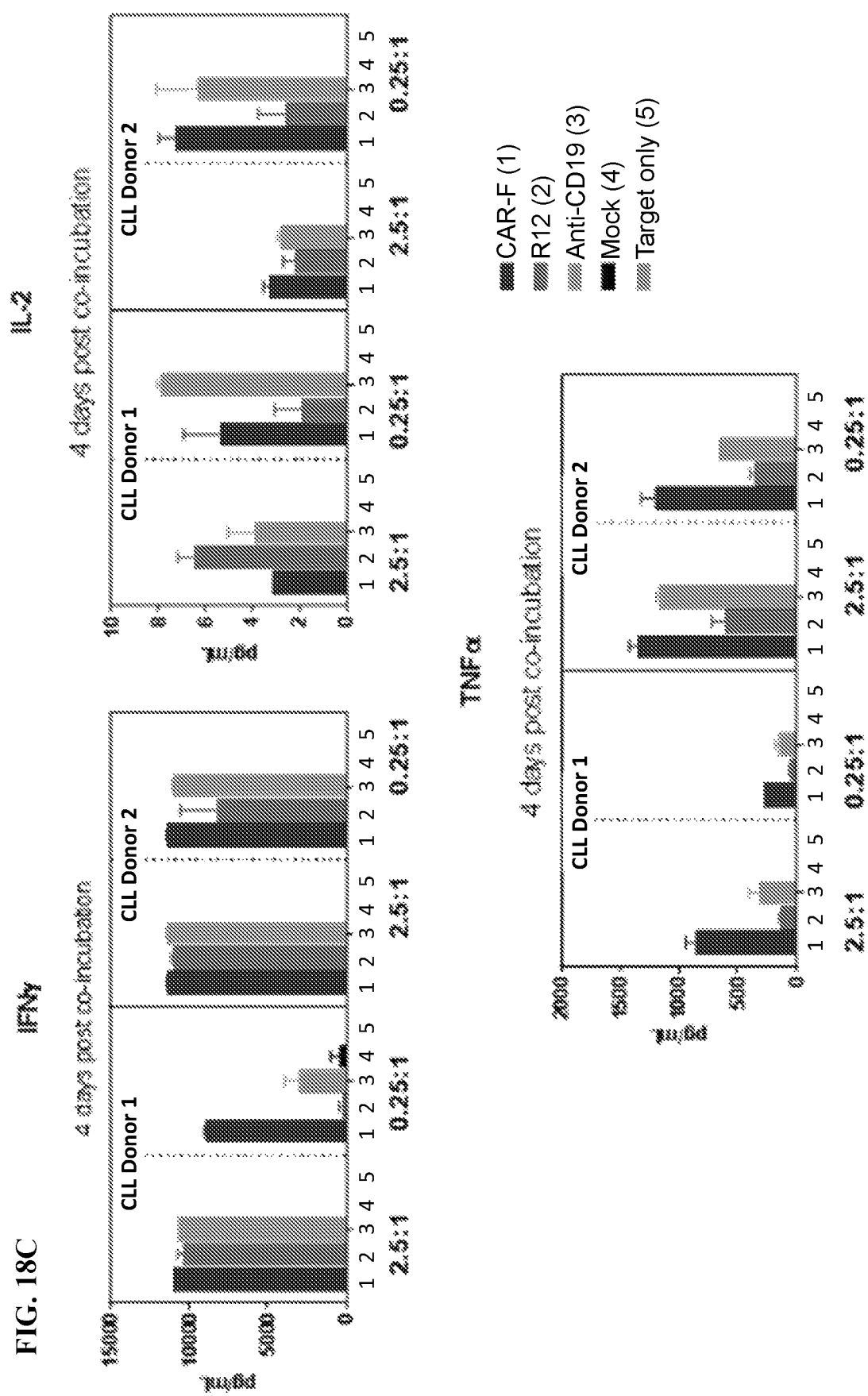

FIG. 18A shows the results of a cytotoxicity assay by flow cytometry, showing the loss of CD19+ target cells or CD19+ ROR1+ target cells (CD4/CD8 T cell depleted leukapheresis samples) co-cultured for approximately 4 days with engineered cells expressing anti-ROR1 CAR-F, anti-CD19 CAR or the R12 reference CAR generated from two primary CLL donors, at two E:T ratios. FIG. 18B depicts the proliferation of CAR-expressing cells (anti-ROR1 CAR-F, anti-CD19 CAR or the R12 reference CAR) labeled with CellTrace™ Violet (CTV) cell proliferation reagent, and co-cultured with target cells from the subjects with CLL at an E:T ratio of 2.5:1 and 0.25:1. FIG. 18C shows the production of IFN-γ, TNF-α and IL-2, as assessed from the supernatant of the co-culture on day 4. Mock treated cells or target cells only were compared as controls.

FIGS. 19A-19D depict the changes in the mean and individual tumor volume in a mouse model of mantel cell lymphoma (MCL), implanted with firefly luciferase and green fluorescent protein (FfLuc-GFP)-expressing human mantel cell lymphoma (MCL) JeKo-1 cells administered cells expressing anti-ROR1 CAR-F, anti-CD19 or the R12 reference CAR, at the high dose (mean: FIG. 19A; individual: FIG. 19C) or the low dose (mean: FIG. 19B; individual: FIG. 19D) or. As a control, mice were administered cells not expressing a CAR (mock) or were untreated.

FIGS. 20A-20B depict the Kaplan-Meier survival curve in a mouse model of MCL administered cells expressing anti-ROR1 CAR-F, anti-CD19 or the R12 reference CAR, at the high dose (FIG. 20A) or the low dose (FIG. 20B). As a control, mice were administered cells not expressing a CAR (mock) or were untreated.

FIG. 21 shows the average number of average number of CD3+ CAR-expressing cells in the blood of a mouse model of MCL, determined at days 7, 14, 21 and 28 after administration of engineered cells expressing anti-ROR1 CAR-F, anti-CD19 or the R12 reference CAR, at the low dose or a high dose.

Figure 22A:
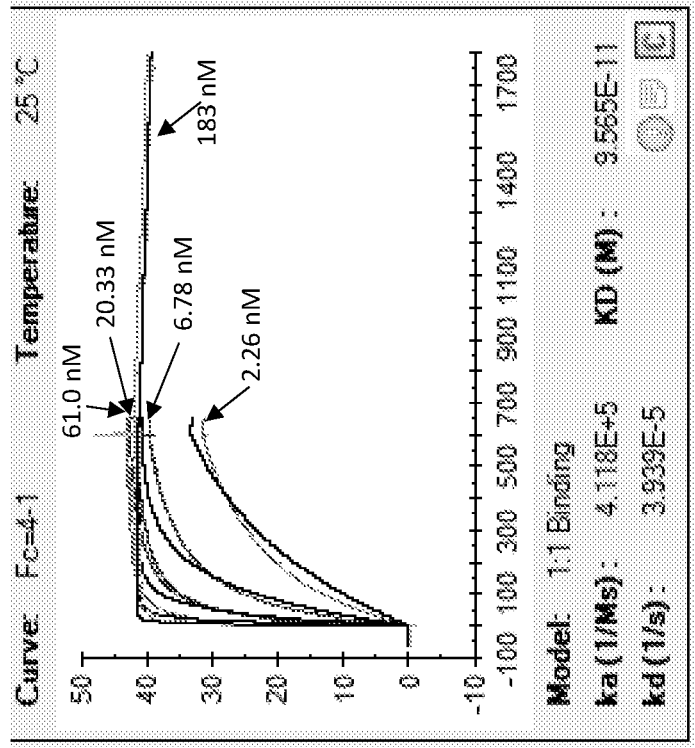
Figure 22B:
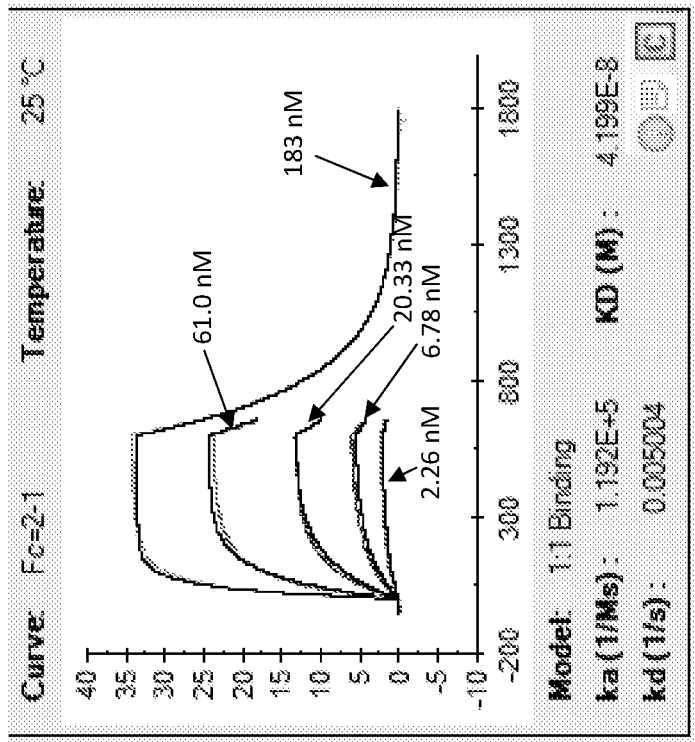
Figure 22C:
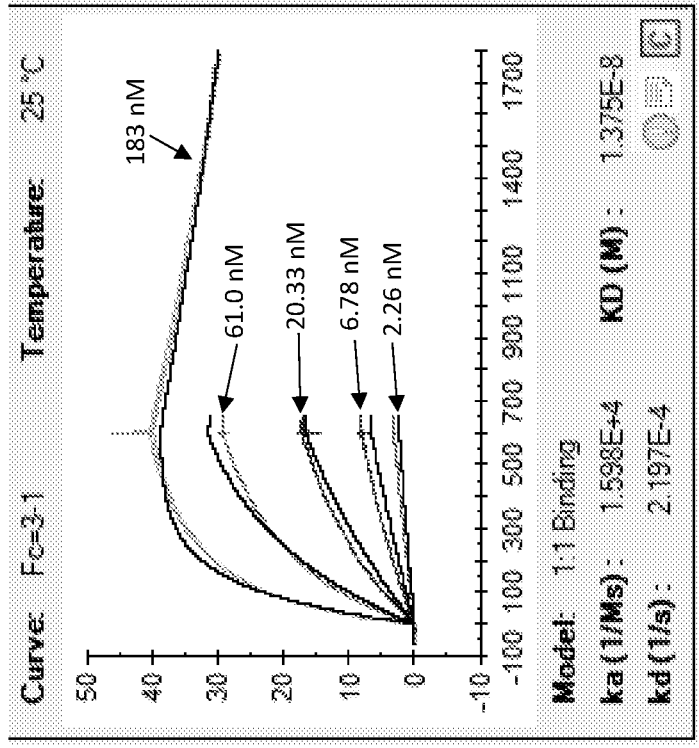
Figure 22D:
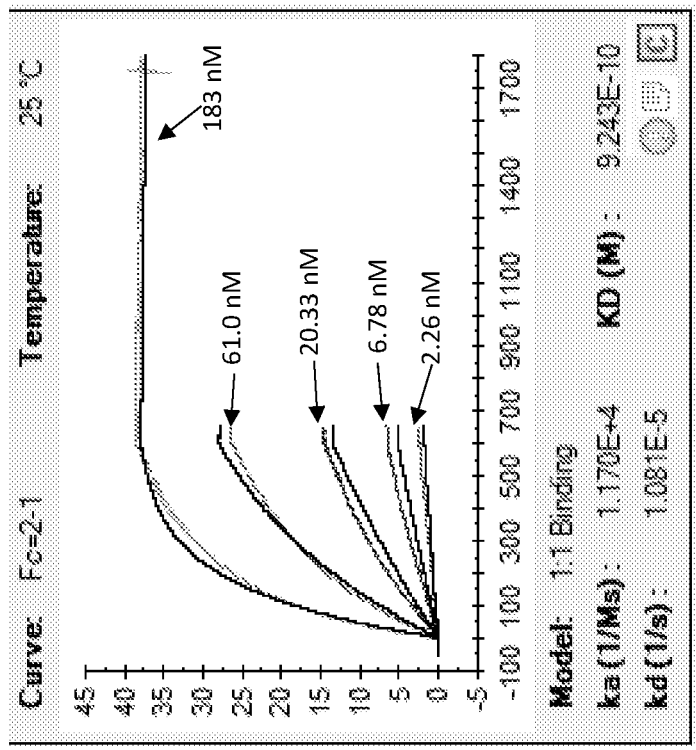
Figure 22E:
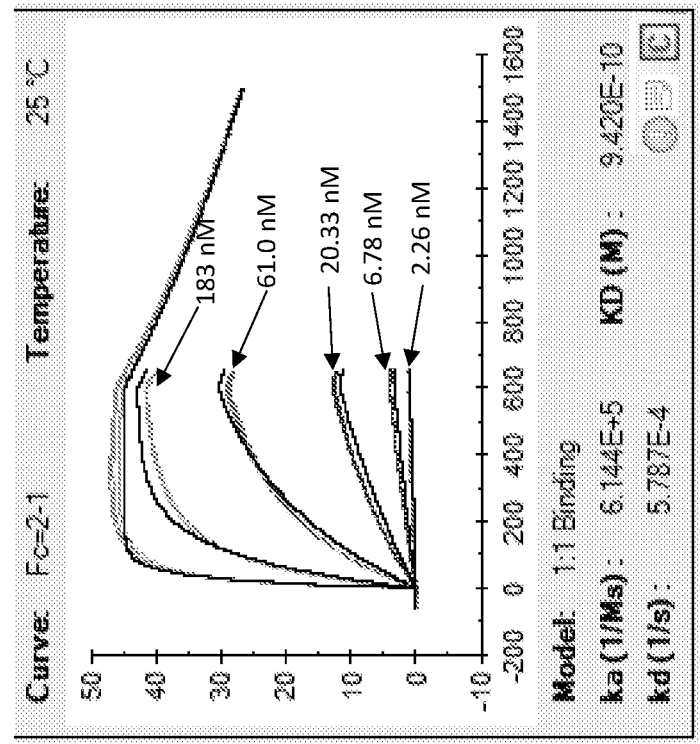

FIGS. 22A-22E depict binding of various recombinantly produced anti-ROR1 scFv-mFcs, including anti-ROR1 scFv ROR1-1 (SEQ ID NO: 118; FIG. 22A), ROR1-2 (SEQ ID NO: 127; FIG. 22B), ROR1-3 (SEQ ID NO: 109; FIG. 22C) and ROR1-4 (SEQ ID NO: 134; FIG. 22D), the scFv binding domains of CAR-A, CAR-F, CAR-G, CAR-I, CAR-R and CAR-B1, and the scFv antigen binding domain of the reference CAR R12 (SEQ ID NO: 142; FIG. 22E), to with a C-terminal 6xHis tag (ROR1 ECD 6xHis), assessed by surface plasmon resonance (SPR) using multi-cycle kinetics implemented by subsequent injections of recombinant human ROR1 at concentrations of 183, 61.0, 20.33, 6.78, and 2.26 nM.

Figure 23:
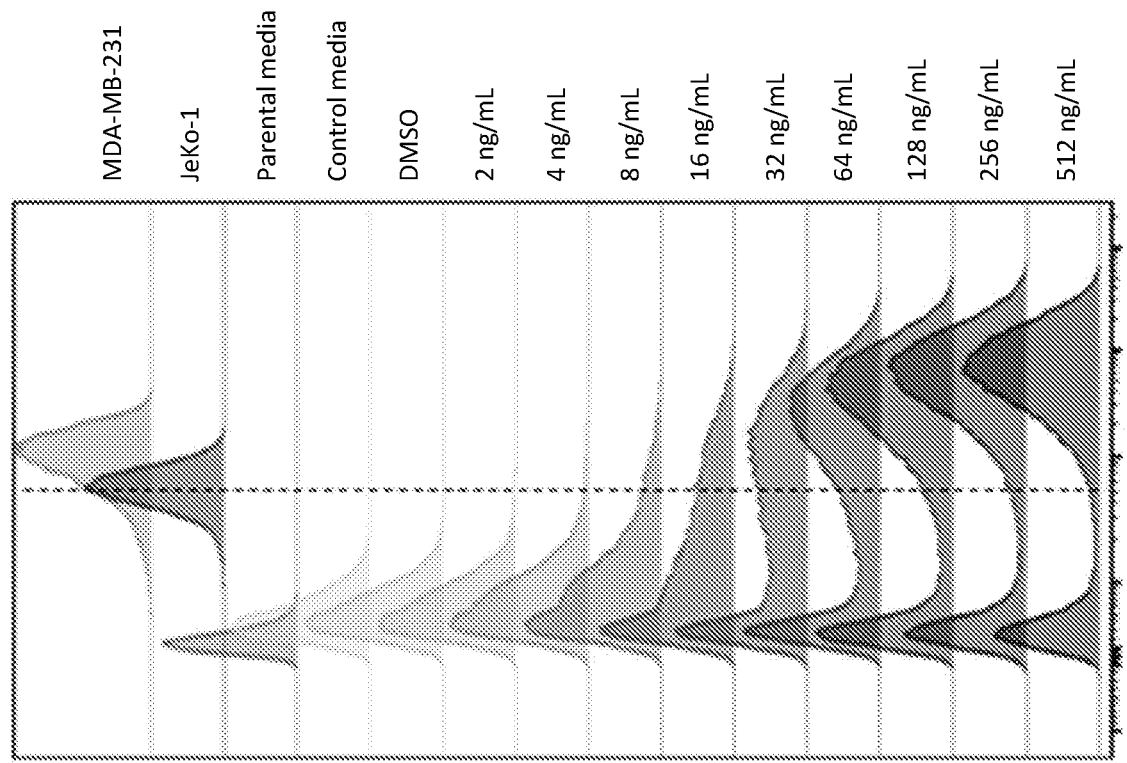

FIG. 23 depicts ROR1 expression in response to a 2-fold increasing dilution series of doxycycline from 512 ng/mL to 0 ng/mL in a K562-ROR1-TetOn cell line. The ROR1− parental K562 cells, two endogenously expressing ROR1+ cell lines, the MCL cell line JeKo-1 and the TNBC cell line MDA-MB-231 were used as controls.

Figure 24:
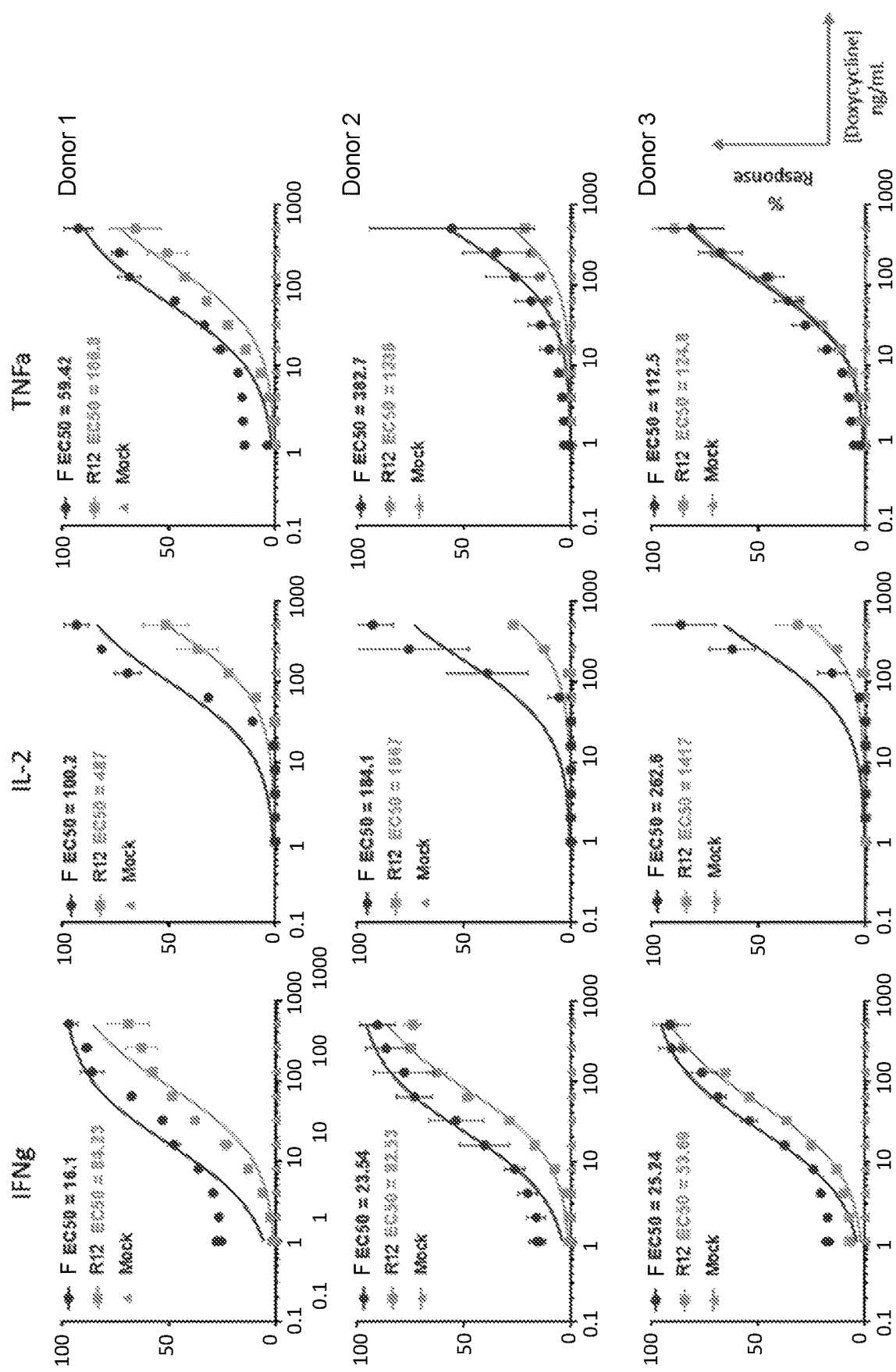

FIG. 24 depicts a dose response curve for production of IFNγ, IL-2 and TNFα assessed from supernatants of a 72 hour co-culture of engineered cells expressing anti-ROR1 CAR-F or the reference CAR R12, with K562-ROR1-TetOn at a 4:1 E:T ratio with the addition of increasing concentrations of doxycycline. Cells not expressing a CAR (mock) were used as a control.

Figure 25A:
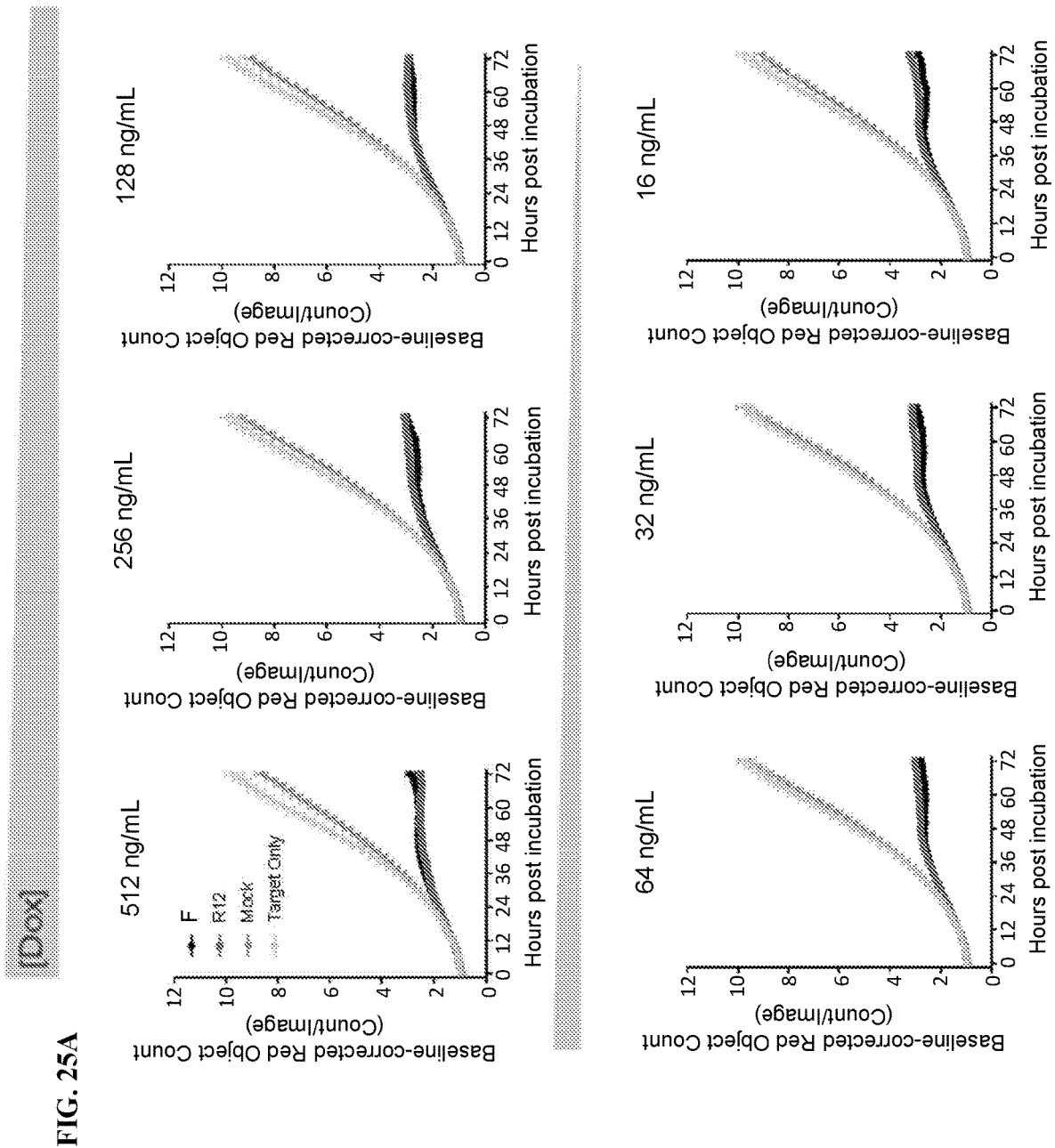
Figure 25B:
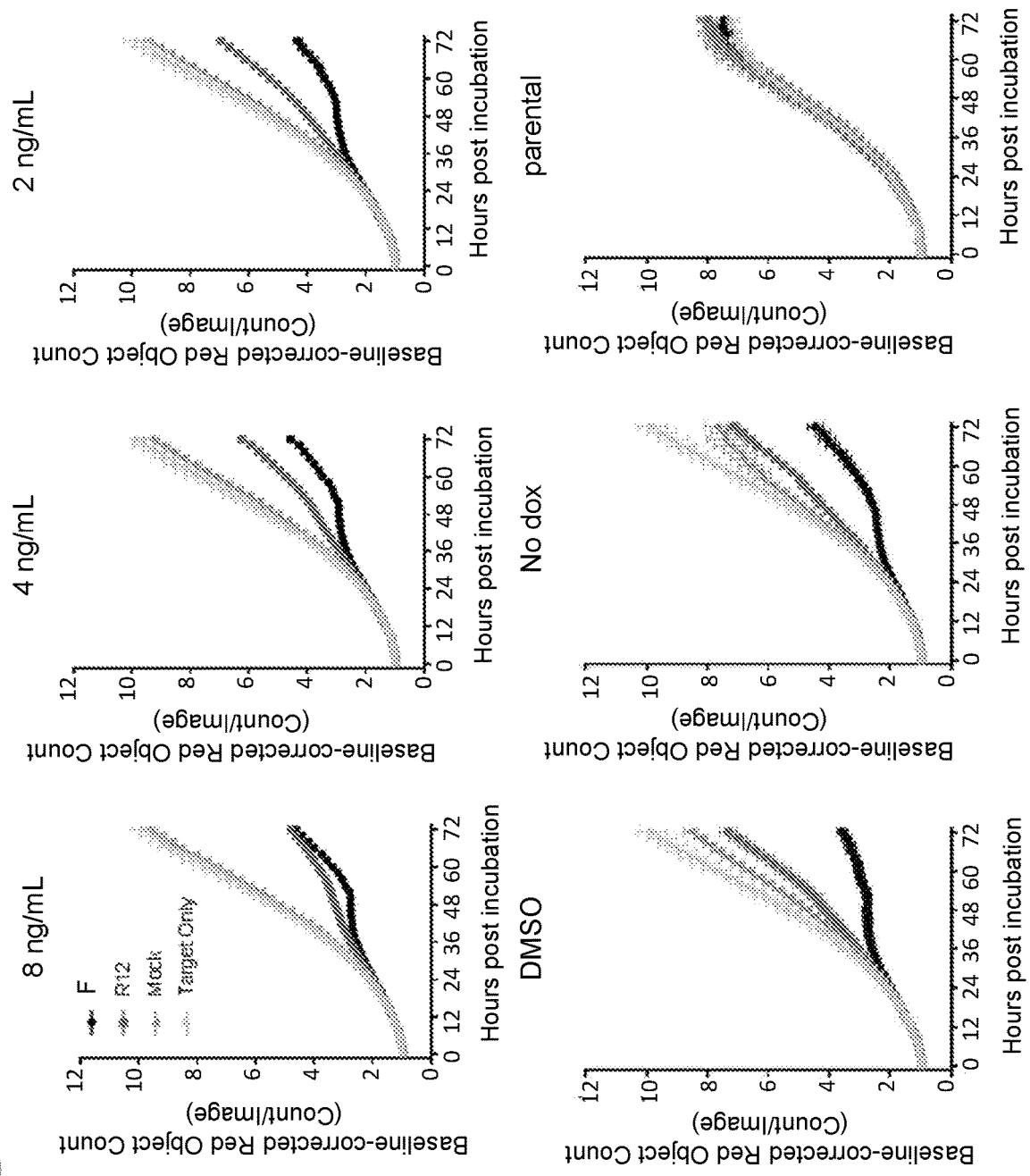

FIGS. 25A-25B depict results of a cytotoxicity assay, as determined by loss of red fluorescent signal from NucLight Red-labeled K562-ROR1-TetOn cells cultured in the presence of various concentrations (2 ng/mL-512 ng/mL) of doxycycline and of engineered cells expressing anti-ROR1 CAR-F or the reference CAR R12, at a 4:1 E:T ratio, for approximately 72 hours. DMSO, no doxycycline and untreated cells were used as controls.

Figure 26:
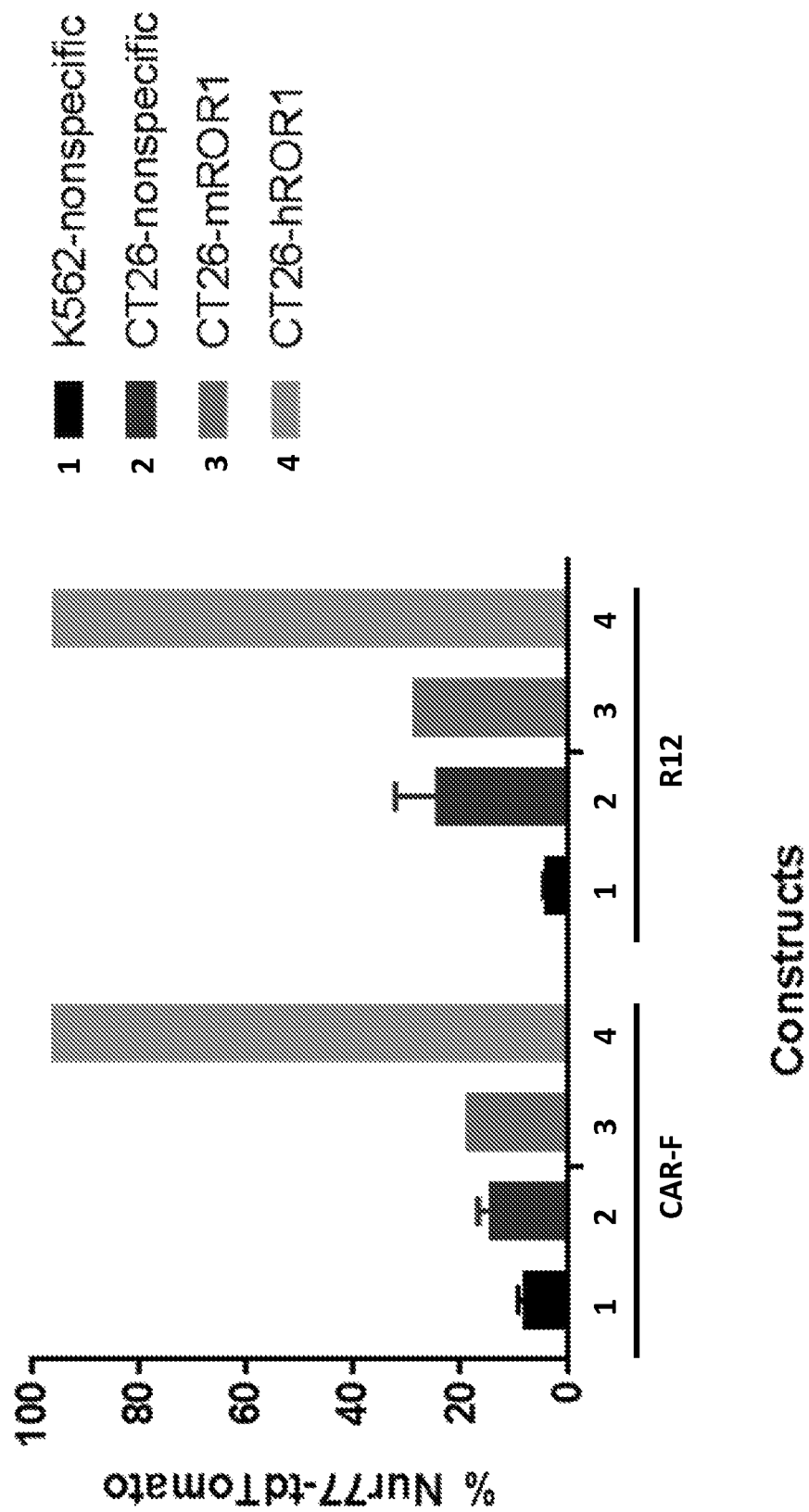

FIG. 26 shows assessment of ROR1 species cross reactivity in Jurkat Nur77 reporter cells expressing either the ROR1 CAR-F or the ROR1 R12 CAR co-cultured with CT26 cells engineered to express human ROR1 (hROR1) or murine ROR1 (mROR1). K562 cells and unmodified CT26 cells were used as non-specific controls.

DETAILED DESCRIPTION

Provided are receptor tyrosine kinase-like orphan receptor 1 (ROR1)-binding molecules, such as antibodies (including antigen-binding antibody fragments, such as single chain fragments, including single chain Fv fragments (scFvs)) and recombinant receptors, including chimeric receptors containing such antibodies or fragments and nucleic acids encoding such antibodies, fragments or recombinant receptors. In some aspects, provided are antibodies, fragments and chimeric antigen receptors (CARs) targeting or directed to ROR1 and ROR1-expressing cells and disease. It is observed that ROR1 is expressed in cells or tissues associated with certain diseases and conditions such as malignancies, e.g., on malignant plasma cells such as from relapsed or newly diagnosed myeloma patients, for example, with little expression on normal tissues. Among the provided embodiments are approaches useful in the treatment of diseases and conditions and/or for targeting such cell types, including nucleic acid molecules that encode ROR1-binding antibodies, fragments or receptors and the encoded antibodies or antigen-binding fragments and receptors. Also provided are compositions and articles of manufacture comprising the same. The receptors generally can contain antibodies (including antigen-binding antibody fragments, such as heavy chain variable ($V_H$) regions, single domain antibody fragments and single chain fragments, including scFvs) specific for ROR1, for example as the antigen-binding domain. Also provided are cells, such as engineered or recombinant cells, expressing such ROR1-binding receptors, e.g., anti-ROR1 CARs and/or containing nucleic acids encoding such receptors, and compositions and articles of manufacture and therapeutic doses containing such cells. Also provided are methods of making and using the antibodies and fragments as well as cells expressing or containing the antibodies and fragments, such as for production of the antibodies or fragments thereof. Also provided are compositions, including pharmaceutical compositions, containing such antibodies, antigen-binding fragments, receptors or cells, and conjugates comprising such antibodies or fragments. In some aspects, the provided compositions, antibodies, antigen-binding fragments, receptors or cells can be used in connection with a therapy or a method of treatment.

Therapies targeting ROR1, such as with anti-ROR1 antibodies or adoptive cell therapies (including those involving the administration of cells expressing chimeric receptors such as chimeric antigen receptors (CARs) and/or other recombinant antigen receptors, specific for ROR1, as well as other adoptive immune cell and adoptive T cell therapies) can be effective in the treatment of cancer and other diseases and disorders, for example, ROR1. In certain contexts, available approaches to adoptive cell therapy may not always be entirely satisfactory. In some aspects, the ability of the administered cells to recognize and bind to a target, e.g., target antigen such as ROR1, to traffic, localize to and successfully enter appropriate sites within the subject, tumors, and environments thereof, to become activated, expand, to exert various effector functions, including cytotoxic killing and secretion of various factors such as cytokines, to persist, including long-term, to differentiate, transition or engage in reprogramming into certain phenotypic states to provide effective and robust recall responses following clearance and re-exposure to target ligand or antigen, and avoid or reduce exhaustion, anergy, terminal differentiation, and/or differentiation into a suppressive state.

In some contexts, properties of particular target antigens that the antibodies or recombinant receptors containing antigen-binding domains specifically bind, recognize or target, can that affect the activity of the receptor. In some contexts, ROR1 is expressed by certain cancers and is an attractive therapeutic target for cell therapy. Improved strategies are needed for optimal responses to antibody or cell therapies, in particular, for recombinant receptors that specifically bind, recognize or target ROR1. Provided are embodiments that meet such needs.

In some aspects, the provided embodiments are based on observations that administration of engineered cells expressing the provided ROR1 binding molecules, such as chimeric antigen receptors (CARs), exhibit an improved antigen-specific activity, signaling and function, high anti-tumor activity, consistent antigen-dependent activity or signaling, greater or prolonged in vivo expansion, and improved persistence when administered, while exhibiting minimal antigen-independent activity or signaling or cross-reactivity to a different antigen. Such antibodies and recombinant receptors can be used to facilitate safe and effective treatment of particular diseases and disorders, such as those associated with expression of ROR1.

In some contexts, optimal response to therapy can depend on the ability of the antibody or antigen-binding fragment, or recombinant receptors that contain such antibody or antigen-binding fragment as antigen-binding domains, to recognize the target antigen. In some aspects, it is observed herein that the binding affinity, specificity or kinetics of binding to ROR1 of certain provided antibody or antigen-binding fragments, such as when present as the antigen-binding domain of a recombinant receptor (e.g. CAR), can be associated with an improved or greater response to the therapy. In some aspects, the provided embodiments are based on observations that provided binding molecules exhibit a lower binding affinity and/or a faster dissociation rate constant ($k_{off}$ or $k_d$; fast off-rate) to ROR1 compared to available antibodies, and also exhibit improved anti-tumor activity, greater or prolonged in vivo expansion, improved persistence, and/or reduced antigen-independent activity or signaling. In some aspects, engineered cells (e.g. T cells) expressing a recombinant receptor containing an antigen-binding domain (e.g., antibody or antigen-binding fragment thereof) with a lower binding affinity (e.g. higher equilibrium dissociation constant) may exhibit substantially improved in vivo expansion, increased persistence, greater or improved antigen-specific anti-tumor activity and prolonged survival, including against various different types of tumors.

In some aspects, engineered cells (e.g. T cells) expressing a recombinant receptor containing an antigen-binding domain (e.g., antibody or antigen-binding fragment thereof) with a faster dissociation rate constant ($k_{off}$ or $k_d$; fast off-rate) may exhibit substantially improved in vivo expansion, increased persistence, greater or improved antigen-specific anti-tumor activity and prolonged survival, including against various different types of tumors. In some aspects, engineered cells (e.g. T cells) expressing a recombinant receptor containing an antigen-binding domain (e.g., antibody or antigen-binding fragment thereof) with a lower binding affinity (e.g. higher equilibrium dissociation constant) and a faster dissociation rate constant ($k_{off}$ or $k_d$; fast off-rate) may exhibit substantially improved in vivo expansion, increased persistence, greater or improved antigen-specific anti-tumor activity and prolonged survival, including against various different types of tumors. Without wishing to be bound by theory, in some aspects, it is observed herein that the increased antigen-binding off-rate of the binding domain of an exemplary anti-ROR1 CAR for ROR1 binding potentially contributes to increased sensitivity of the CAR to low antigen levels.

In some contexts, optimal response to therapy such as cell therapy can depend on the ability of the engineered recombinant receptors such as CARs, to be consistently and reliably expressed on the surface of the cells and/or bind the target antigen. For example, in some cases, heterogeneity of the transcribed RNA from an introduced transgene (e.g., encoding the recombinant receptor) can affect the expression and/or activity of the recombinant receptor, in some cases when expressed in a cell, such as a human T cell, used in cell therapy.

In some contexts, the length and type of spacer in the recombinant receptor, such as a CAR, can affect the expression, activity and/or function of the receptor.

Also, in some contexts, certain recombinant receptors can exhibit antigen-independent activity or signaling (also known as "tonic signaling"), which could lead to undesirable effects, such as due to increased differentiation and/or exhaustion of T cells that express the recombinant receptor. In some aspects, such activities may limit the T cell's activity, effect or potency. In some cases, during engineering and ex vivo expansion of the cells for recombinant receptor expression, the cells may exhibit phenotypes indicative of exhaustion, due to tonic signaling through the recombinant receptor.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. ROR1-Binding Molecules

Provided in some aspects are ROR1-binding molecules, such as ROR1-binding polypeptides. Such binding molecules include antibodies (including antigen-binding fragments) that specifically bind to ROR1 proteins, such as a human ROR1 protein. Also among the binding molecules are polypeptides containing such antibodies, including single chain cell surface proteins, e.g., recombinant receptors such as chimeric antigen receptors (CARs), containing such antibodies. Provided in some aspects are ROR1-binding cell surface proteins, such as recombinant receptors or chimeric antigen receptors (CARs) that bind ROR1 molecules and polynucleotides encoding ROR1 binding cell surface proteins, such as recombinant receptors (e.g., CARs), and cells expressing such receptors. Also provided are polynucleotides containing nucleic acids sequences encoding all or a portion of such antibodies, antigen-binding fragments and binding molecules, such as those described in Section I.A or I.D. Exemplary of such polynucleotides include those described in Section I.E. In some aspects the polynucleotides can be introduced into a cell to generate an engineered cell that contains or expresses the provided binding molecules, e.g., ROR1-binding antibodies, antigen-binding domains and receptors, such as CARs.

A. ROR1-Targeting Antibodies

Provided are anti-ROR1 polypeptides, including antibodies and functional antigen-binding fragments. Among the ROR1-binding polypeptides are antibodies, such as single-chain antibodies (e.g., antigen binding antibody fragments), such as those containing a heavy chain variable ($V_H$) region and/or a light chain variable ($V_L$) region, or a portion thereof. In some embodiments, the antibodies or antigen-binding fragments include a $V_H$ and a $V_L$, such as single chain Fv fragments (scFvs). The antibodies include antibodies that specifically bind to ROR1, e.g., human ROR1. Among the provided anti-ROR1 antibodies are human antibodies, or antibodies that are modified from or variant of human antibodies. The antibodies include isolated antibodies. Also provided are ROR1-binding molecules containing such antibodies, such as single-chain proteins, fusion proteins, conjugates and/or recombinant receptors such as chimeric receptors, including antigen receptors. In some aspects, the ROR1-binding molecules include isolated molecules.

Also provided are ROR1-binding cell surface proteins, such as ROR1-binding recombinant receptors. The ROR1-binding cell surface proteins can contain the provided antibodies (e.g., antigen-binding antibody fragments) that specifically bind to ROR1, such as to ROR1 proteins, such as human ROR1 protein. In some aspects, the provided binding molecules bind to an extracellular portion of ROR1. In some examples, the recombinant receptors are chimeric antigen receptors, such as those containing anti-ROR1 antibodies or antigen-binding fragments thereof.

Also provided are polynucleotides containing nucleic acids sequences encoding all or a portion of such antibodies, antigen-binding fragments and binding molecules. The provided polynucleotides can be incorporated into constructs, such as deoxyribonucleic acid (DNA) or RNA constructs, such as those that can be introduced into cells for expression of the encoded ROR1-binding antibodies, antigen-binding fragments, conjugates or receptors, e.g., anti-ROR1 CARs. In some aspects, the encoded antibodies, antigen-binding fragments, conjugates and receptors, such as those containing ROR1-binding polypeptides, and compositions and articles of manufacture and uses of the same, also are provided.

The term "antibody" herein is used in the broadest sense and includes polyclonal and monoclonal antibodies, including intact antibodies and functional (antigen-binding) antibody fragments, including fragment antigen binding (Fab) fragments, F(ab')$_2$ fragments, Fab' fragments, Fv fragments, recombinant IgG (rIgG) fragments, heavy chain variable ($V_H$) regions capable of specifically binding the antigen, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific or trispecific, antibodies, diabodies, triabodies, and tetrabodies, tandem di-scFv, tandem tri-scFv. Unless otherwise stated, the term "antibody" should be understood to encompass functional antibody fragments thereof also referred to herein as "antigen-binding fragments." The term also encompasses intact or full-length antibodies, including antibodies of any class or sub-class, including IgG and sub-classes thereof, IgM, IgE, IgA, and IgD.

The terms "complementarity determining region," and "CDR," synonymous with "hypervariable region" or "HVR," are known to refer to non-contiguous sequences of amino acids within antibody variable regions, which confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4).

The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme); Al-Lazikani et al., (1997) JMB 273, 927-948 ("Chothia" numbering scheme); MacCallum et al., J. Mol. Biol. 262: 732-745 (1996), "Antibody-antigen interactions: Contact analysis and binding site topography," J. Mol. Biol. 262, 732-745." ("Contact" numbering scheme); Lefranc M P et al., "IMGT unique numbering for immunoglobulin and T cell receptor variable domains and Ig superfamily V-like domains," Dev Comp Immunol, 2003 January; 27(1):55-77 ("IMGT" numbering scheme); Honegger A and Plückthun A, "Yet another numbering scheme for immunoglobulin variable domains: an automatic modeling and analysis tool," J Mol Biol, 2001 Jun. 8; 309(3):657-70, ("Aho" numbering scheme); Martin et al., "Modeling antibody hypervariable loops: a combined algorithm," PNAS, 1989, 86(23):9268-9272, ("AbM" numbering scheme); and Ye et al., "IgBLAST: an immunoglobulin variable domain sequence analysis tool," Nucleic Acids Res. 2013 July; 41 (Web Server issue):W34-40, ("IgBLAST numbering scheme).

The boundaries of a given CDR or FR may vary depending on the scheme used for identification. For example, the Kabat scheme is based on structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme. The AbM scheme is a compromise between Kabat and Chothia definitions based on that used by Oxford Molecular's AbM antibody modeling software. The IgBLAST scheme is based on matching to germline V, D and J genes, and can be determined using National Center for Biotechnology Information (NCBI)'s IgBLAST tool.

Table 1, below, lists exemplary position boundaries of CDR-L1, CDR-L2, CDR-L3 and CDR-H1, CDR-H2, CDR-H3 as identified by Kabat, Chothia, AbM, and Contact schemes, respectively. For CDR-H1, residue numbering is listed using both the Kabat and Chothia numbering schemes. FRs are located between CDRs, for example, with FR-L1 located before CDR-L1, FR-L2 located between CDR-L1 and CDR-L2, FR-L3 located between CDR-L2 and CDR-L3 and so forth. It is noted that because the shown Kabat numbering scheme places insertions at H35A and H35B, the end of the Chothia CDR-H1 loop when numbered using the shown Kabat numbering convention varies between H32 and H34, depending on the length of the loop.

TABLE 1

Boundaries of CDRs according to various numbering schemes.

| CDR | Kabat | Chothia | AbM | Contact |
|---|---|---|---|---|
| CDR-L1 | L24--L34 | L24--L34 | L24--L34 | L30--L36 |
| CDR-L2 | L50--L56 | L50--L56 | L50--L56 | L46--L55 |
| CDR-L3 | L89--L97 | L89--L97 | L89--L97 | L89--L96 |
| CDR-H1 (Kabat Numbering[1]) | H31--H35B | H26--H32.34 | H26--H35B | H30--H35B |
| CDR-H1 (Chothia Numbering[2]) | H31--H35 | H26--H32 | H26--H35 | H30--H35 |
| CDR-H2 | H50--H65 | H52--H56 | H50--H58 | H47--H58 |
| CDR-H3 | H95--H102 | H95--H102 | H95--H102 | H93--H101 |

[1]Kabat et al. (1991), "Sequences of Proteins of Immunological Interest," 5th Ed. Public Health Service, National Institutes of Health, Bethesda, MD
[2]Al-Lazikani et al., (1997) JMB 273, 927-948

Thus, unless otherwise specified, a "CDR" or "complementary determining region," or individual specified CDRs (e.g., CDR-H1, CDR-H2, CDR-H3), of a given antibody or region thereof, such as a variable region thereof, should be understood to encompass a (or the specific) complementary determining region as defined by any of the aforementioned schemes, or other known schemes. For example, where it is stated that a particular CDR (e.g., a CDR-H3) contains the amino acid sequence of a corresponding CDR in a given $V_H$ or $V_L$ region amino acid sequence, it is understood that such a CDR has a sequence of the corresponding CDR (e.g., CDR-H3) within the variable region, as defined by any of the aforementioned schemes, or other known schemes. In some embodiments, specific CDR sequences are specified. Exemplary CDR sequences of provided antibodies are described using various numbering schemes (see e.g. Table 2), although it is understood that a provided antibody can include CDRs as described according to any of the other aforementioned numbering schemes or other known numbering schemes.

Likewise, unless otherwise specified, a FR or individual specified FR(s) (e.g., FR-H1, FR-H2, FR-H3, FR-H4), of a given antibody or region thereof, such as a variable region thereof, should be understood to encompass a (or the specific) framework region as defined by any of the known schemes. In some instances, the scheme for identification of a particular CDR, FR, or FRs or CDRs is specified, such as the CDR as defined by the Kabat, Chothia, AbM, IgBLAST, IMGT, or Contact method, or other known schemes. In other cases, the particular amino acid sequence of a CDR or FR is given.

The term "variable region" or "variable domain" refers to the domain of an antibody heavy or light chain that is involved in binding the antibody to antigen. The variable regions of the heavy chain and light chain ($V_H$ and $V_L$, respectively) of a native antibody generally have similar structures, with each domain comprising four conserved framework regions (FRs) and three CDRs. (See, e.g., Kindt et al. Kuby Immunology, 6th ed., W. H. Freeman and Co., page 91 (2007). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively. See, e.g., Portolano et al., J. Immunol. 150: 880-887 (1993); Clarkson et al., Nature 352:624-628 (1991).

Among the provided antibodies are antibody fragments. An "antibody fragment" or "antigen-binding fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; heavy chain variable ($V_H$) regions, single-chain antibody molecules such as scFvs and single-domain antibodies comprising only the $V_H$ region; and multispecific antibodies formed from antibody fragments. In some embodiments, the antibody is or comprises an antibody fragment comprising a variable heavy chain ($V_H$) and a variable light chain ($V_L$) region. In particular embodiments, the antibodies are single-chain antibody fragments comprising a heavy chain variable ($V_H$) region and/or a light chain variable ($V_L$) region, such as scFvs.

Single-domain antibodies (sdAbs) are antibody fragments comprising all or a portion of the heavy chain variable region or all or a portion of the light chain variable region of an antibody. In certain embodiments, a single-domain antibody is a human single-domain antibody.

Antibody fragments can be made by various techniques, including but not limited to proteolytic digestion of an intact antibody as well as production by recombinant host cells. In some embodiments, the antibodies are recombinantly-produced fragments, such as fragments comprising arrangements that do not occur naturally, such as those with two or more antibody regions or chains joined by synthetic linkers, e.g., peptide linkers, and/or that are may not be produced by enzyme digestion of a naturally-occurring intact antibody. In some aspects, the antibody fragments are scFvs.

A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody, refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity.

Among the provided anti-ROR1 antibodies are human antibodies. A "human antibody" is an antibody with an amino acid sequence corresponding to that of an antibody produced by a human or a human cell, or non-human source that utilizes human antibody repertoires or other human antibody-encoding sequences, including human antibody libraries. The term excludes humanized forms of non-human antibodies comprising non-human antigen-binding regions, such as those in which all or substantially all CDRs are non-human. The term includes antigen-binding fragments of human antibodies.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic animals, the endogenous immunoglobulin loci have generally been inactivated. Human antibodies also may be derived from human antibody libraries, including phage display and cell-free libraries, containing antibody-encoding sequences derived from a human repertoire.

Among the provided antibodies are monoclonal antibodies, including monoclonal antibody fragments. The term "monoclonal antibody" as used herein refers to an antibody obtained from or within a population of substantially homogeneous antibodies, i.e., the individual antibodies comprising the population are identical, except for possible variants containing naturally occurring mutations or arising during production of a monoclonal antibody preparation, such variants generally being present in minor amounts. In contrast to polyclonal antibody preparations, which typically include different antibodies directed against different epitopes, each monoclonal antibody of a monoclonal antibody preparation is directed against a single epitope on an antigen. The term is not to be construed as requiring production of the antibody by any particular method. A monoclonal antibody may be made by a variety of techniques, including but not limited to generation from a hybridoma, recombinant DNA methods, phage-display and other antibody display methods.

The terms "polypeptide" and "protein" are used interchangeably to refer to a polymer of amino acid residues, and are not limited to a minimum length. Polypeptides, including the provided antibodies and antibody chains and other peptides, e.g., linkers and ROR1-binding peptides, may include amino acid residues including natural and/or non-natural amino acid residues. The terms also include post-expression modifications of the polypeptide, for example, glycosylation, sialylation, acetylation, phosphorylation, and the like. In some aspects, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification.

1. Exemplary Antibodies

In some embodiments, the antibody, e.g., the anti-ROR1 antibody, e.g., antigen-binding antibody fragment, contains a heavy and/or light chain variable ($V_H$ or $V_L$) region sequence as described, or a sufficient antigen-binding portion thereof. In some embodiments, the antibody, e.g., the anti-ROR1 antibody, e.g., antigen-binding antibody fragment, contains a heavy chain variable region ($V_H$) sequence and/or a light chain variable region ($V_L$) sequence as described, or a sufficient antigen-binding portion thereof. In some embodiments, the antibody, e.g., the anti-ROR1 antibody, e.g., antigen-binding antibody fragment, is a single chain fragment, such as a single chain Fv (scFv) fragment. In some aspects, the scFv comprises a $V_H$ region and a $V_L$ region. In some embodiments, the antibody, e.g., the anti-ROR1 antibody, e.g., antigen-binding antibody fragment, is a single domain antibody (sdAb), such as an antibody that contains a $V_H$ region only.

In some embodiments, the anti-ROR1 antibody, e.g., antigen-binding antibody fragment, contains a $V_H$ region sequence or sufficient antigen-binding portion thereof that contains a heavy chain complementarity determining region 1 (CDR-H1), a heavy chain complementarity determining region 2 (CDR-H2) and/or a heavy chain complementarity determining region 3 (CDR-H3) as described. In some embodiments, the anti-ROR1 antibody, e.g., antigen-binding antibody fragment, contains a $V_H$ region sequence or sufficient antigen-binding portion thereof that contains a CDR-H1, a CDR-H2 and a CDR-H3 as described. In some embodiments, the anti-ROR1 antibody, e.g., antigen-binding antibody fragment, contains a $V_L$ region sequence or sufficient antigen-binding portion that contains a light chain complementarity determining region 1 (CDR-L1), a light chain complementarity determining region 2 (CDR-L2), and/or a light chain complementarity determining region 3 (CDR-L3) as described. In some embodiments, the anti-ROR1 antibody, e.g., antigen-binding antibody fragment, contains a $V_L$ region sequence or sufficient antigen-binding portion that contains a CDR-L1, a CDR-L2 and a CDR-L3 as described.

In some embodiments, the anti-ROR1 antibody, e.g., antigen-binding antibody fragment, contains a $V_H$ region sequence that contains a CDR-H1, a CDR-H2 and/or a CDR-H3 as described and contains a $V_L$ region sequence that contains a CDR-L1, a CDR-L2 and/or a CDR-L3 as described. In some embodiments, the anti-ROR1 antibody, e.g., antigen-binding antibody fragment, contains a $V_H$ region sequence that contains a CDR-H1, a CDR-H2 and a CDR-H3 as described and contains a $V_L$ region sequence that contains a CDR-L1, a CDR-L2 and a CDR-L3 as described. Also among the provided antibodies and fragment thereof are those having sequences at least at or about 85%, at or about 86%, at or about 87%, at or about 88%, at or about 89%, at or about 90%, at or about 91%, at or about 92%, at or about 93%, at or about 94%, at or about 95%, at or about 96%, at or about 97%, at or about 98%, or at or about 99% identical to such a sequence, e.g., any of the CDR-H1, CDR-H2, CDR-H3, CDR-L1, CDR-L2, CDR-L3, $V_H$, $V_L$, scFv sequences or other sequences of the antibodies of fragment thereof described herein. In some aspects, among the provided antibodies and fragment thereof are those having sequences at least at or about 85% sequence identity to any such sequences. In some aspects, among the provided antibodies and fragment thereof are those having sequences at least at or about 86% sequence identity to any such sequences. In some aspects, among the provided antibodies and fragment thereof are those having sequences at least at or about 87% sequence identity to any such sequences. In some aspects, among the provided antibodies and fragment thereof are those having sequences at least at or about 88% sequence identity to any such sequences. In some aspects, among the provided antibodies and fragment thereof are those having sequences at least at or about 89% sequence identity to any such sequences. In some aspects, among the provided antibodies and fragment thereof are those having sequences at least at or about 90% sequence identity to any such sequences. In some aspects, among the provided antibodies and fragment thereof are those having sequences at least at or about 91% sequence identity to any such sequences. In some aspects, among the provided antibodies and fragment thereof are those having sequences at least at or about 92% sequence identity to any such sequences. In some aspects, among the provided antibodies and fragment thereof are those having sequences at least at or about 93% sequence identity to any such sequences. In some aspects, among the provided antibodies and fragment thereof are those having sequences at least at or about 94% sequence identity to any such sequences. In some aspects, among the provided antibodies and fragment thereof are those having sequences at least at or about 95% sequence identity to any such sequences. In some aspects, among the provided antibodies and fragment thereof are those having sequences at least at or about 96% sequence identity to any such sequences. In some aspects, among the provided antibodies and fragment thereof are those having sequences at least at or about 97% sequence identity to any such sequences. In some aspects, among the provided antibodies and fragment thereof are those having sequences at least at or about 98% sequence identity to any such sequences. In some aspects, among the provided antibodies and fragment thereof are those having sequences at least at or about 99% sequence identity to any such sequences.

In some embodiments, the antibody is an sdAb comprising only a $V_H$ region sequence or a sufficient antigen-binding portion thereof, such as any of the $V_H$ sequences described herein (e.g., a CDR-H1, a CDR-H2, a CDR-H3 and/or a CDR-H4). In some embodiments, the antibodies or antigen-binding fragments include those that are single domain antibodies, containing a $V_H$ region that, without pairing with a $V_L$ region) and/or without any additional antibody domain or binding site, are capable of specifically binding to ROR1.

In some embodiments, the $V_H$ region of an antibody or antigen-binding fragment thereof comprises a CDR-H1, a CDR-H2 and/or a CDR-H3 according to Kabat numbering. In some embodiments, the $V_H$ region of an antibody or antigen-binding fragment thereof comprises a CDR-H1, a CDR-H2 and/or a CDR-H3 according to Chothia numbering. In some embodiments, the $V_H$ region of an antibody or antigen-binding fragment thereof comprises a CDR-H1, a CDR-H2 and/or a CDR-H3 according to AbM numbering. In some embodiments, the $V_H$ region of an antibody or antigen-binding fragment thereof comprises a CDR-H1, a CDR-H2 and/or a CDR-H3 according to IgBLAST numbering. In some embodiments, the $V_H$ region of an antibody or antigen-binding fragment thereof comprises a CDR-H1, a CDR-H2 and/or a CDR-H3 according to Kabat, Chothia, AbM, IMGT or IgBLAST numbering, or other numbering schemes.

In some embodiments of the antibody, antigen-binding fragment, receptor, e.g., CAR, conjugates or binding molecules provided herein, has a heavy chain variable ($V_H$)

region having the amino acid sequence set forth in SEQ ID NO: 112, 121, 103 or 130, or an amino acid sequence that has at least at or about 85%, 86%, 87%, 88%, 89%, 90%, 91%, 92%, 93%, 94%, 95%, 96%, 97%, 98%, or 99% sequence identity to the $V_H$ region amino acid sequence set forth in SEQ ID NO: 112, 121, 103 or 130, or contains a heavy chain complementarity determining region 1 (CDR-H1), a heavy chain complementarity determining region 2 (CDR-H2) and/or a heavy chain complementarity determining region 3 (CDR-H3) present in such a $V_H$ sequence, such as one that contains a CDR-H1, a CDR-H2, and a CDR-H3 present in such a $V_H$ sequence. In some embodiments of the antibody, antigen-binding fragment, receptor, e.g., CAR, conjugates or binding molecules provided herein, has a $V_H$ region having the amino acid sequence set forth in SEQ ID NO: 112 or 121, or an amino acid sequence that has at least at or about 85%, 86%, 87%, 88%, 89%, 90%, 91%, 92%, 93%, 94%, 95%, 96%, 97%, 98%, or 99% sequence identity to the $V_H$ region amino acid sequence set forth in SEQ ID NO: 112 or 121, or contains a CDR-H1, a CDR-H2 and/or a CDR-H3 present in such a $V_H$ sequence, such as one that contains a CDR-H1, a CDR-H2, and a CDR-H3 present in such a $V_H$ sequence.

In some embodiments of the antibody, antigen-binding fragment, receptor, e.g., CAR, conjugates or binding molecules provided herein, has a $V_H$ region having the amino acid sequence set forth in SEQ ID NO: 112, or an amino acid sequence that has at least at or about 85%, 86%, 87%, 88%, 89%, 90%, 91%, 92%, 93%, 94%, 95%, 96%, 97%, 98%, or 99% sequence identity to the $V_H$ region amino acid sequence set forth in SEQ ID NO: 112, or contains a CDR-H1, a CDR-H2 and/or a CDR-H3 present in such a $V_H$ sequence, such as one that contains a CDR-H1, a CDR-H2, and a CDR-H3 present in such a $V_H$ sequence. In some embodiments, the antibody, e.g., antigen-binding fragment thereof, has a $V_H$ region having the amino acid sequence set forth in SEQ ID NO: 121, or an amino acid sequence that has at least at or about 85%, 86%, 87%, 88%, 89%, 90%, 91%, 92%, 93%, 94%, 95%, 96%, 97%, 98%, or 99% sequence identity to the $V_H$ region amino acid sequence set forth in SEQ ID NO: 121, or contains a CDR-H1, a CDR-H2 and/or a CDR-H3 present in such a $V_H$ sequence, such as one that contains a CDR-H1, a CDR-H2, and a CDR-H3 present in such a $V_H$ sequence. In some embodiments of the antibody, antigen-binding fragment, receptor, e.g., CAR, conjugates or binding molecules provided herein, has a $V_H$ region having the amino acid sequence set forth in SEQ ID NO: 103, or an amino acid sequence that has at least at or about 85%, 86%, 87%, 88%, 89%, 90%, 91%, 92%, 93%, 94%, 95%, 96%, 97%, 98%, or 99% sequence identity to the $V_H$ region amino acid sequence set forth in SEQ ID NO: 103, or contains a CDR-H1, a CDR-H2 and/or a CDR-H3 present in such a $V_H$ sequence, such as one that contains a CDR-H1, a CDR-H2, and a CDR-H3 present in such a $V_H$ sequence. In some embodiments, the antibody, e.g., antigen-binding fragment thereof, has a $V_H$ region having the amino acid sequence set forth in SEQ ID NO: 130, or an amino acid sequence that has at least at or about 85%, 86%, 87%, 88%, 89%, 90%, 91%, 92%, 93%, 94%, 95%, 96%, 97%, 98%, or 99% sequence identity to the $V_H$ region amino acid sequence set forth in SEQ ID NO: 130, or contains a CDR-H1, a CDR-H2 and/or a CDR-H3 present in such a $V_H$ sequence, such as one that contains a CDR-H1, a CDR-H2, and a CDR-H3 present in such a $V_H$ sequence.

In some of any of the provided embodiments, the $V_H$ region comprises a CDR-H1 comprising the sequence set forth in SEQ ID NO: 67, 82 or 52. In some of any of the provided embodiments, the $V_H$ region comprises a CDR-H2 comprising the sequence set forth in SEQ ID NO: 71, 86, 56 or 97. In some of any of the provided embodiments, the $V_H$ region comprises a CDR-H3 comprising the sequence set forth in SEQ ID NO: 73, 88, 58 or 99.

In some of any of the provided embodiments, the $V_H$ region comprises a CDR-H1 comprising the sequence set forth in SEQ ID NO: 65, 80 or 50. In some of any of the provided embodiments, the $V_H$ region comprises a CDR-H2 comprising the sequence set forth in SEQ ID NO: 69, 84, 54 or 95. In some of any of the provided embodiments, the $V_H$ region comprises a CDR-H3 comprising the sequence set forth in SEQ ID NO: 73, 88, 58 or 99.

In some of any of the provided embodiments, the $V_H$ region comprises a CDR-H1 comprising the sequence set forth in SEQ ID NO: 66, 81 or 51. In some of any of the provided embodiments, the $V_H$ region comprises a CDR-H2 comprising the sequence set forth in SEQ ID NO: 70, 85, 55 or 96. In some of any of the provided embodiments, the $V_H$ region comprises a CDR-H3 comprising the sequence set forth in SEQ ID NO: 73, 88, 58 or 99.

In some of any of the provided embodiments, the $V_H$ region comprises a CDR-H1 comprising the sequence set forth in SEQ ID NO: 68, 83 or 53. In some of any of the provided embodiments, the $V_H$ region comprises a CDR-H2 comprising the sequence set forth in SEQ ID NO: 72, 87, 57 or 98. In some of any of the provided embodiments, the $V_H$ region comprises a CDR-H3 comprising the sequence set forth in SEQ ID NO: 74, 89, 59 or 100.

In some embodiments of the antibody, antigen-binding fragment, receptor, e.g., CAR, conjugates or binding molecules provided herein, the $V_H$ region comprises a CDR-H1 comprising the sequence set forth in SEQ ID NO: 67, 82 or 52, a CDR-H2 comprising the sequence set forth in SEQ ID NO: 71, 86, 56 or 97, and a CDR-H3 comprising the sequence set forth in SEQ ID NO: 73, 88, 58 or 99. In some embodiments of the antibody, antigen-binding fragment, receptor, e.g., CAR, conjugates or binding molecules provided herein, the $V_H$ region comprises a CDR-H1 comprising the sequence set forth in SEQ ID NO: 65, 80 or 50, a CDR-H2 comprising the sequence set forth in SEQ ID NO: 69, 84, 54 or 95, and a CDR-H3 comprising the sequence set forth in SEQ ID NO: 73, 88, 58 or 99. In some embodiments of the antibody, antigen-binding fragment, receptor, e.g., CAR, conjugates or binding molecules provided herein, the $V_H$ region comprises a CDR-H1 comprising the sequence set forth in SEQ ID NO: 66, 81 or 51, a CDR-H2 comprising the sequence set forth in SEQ ID NO: 70, 85, 55 or 96, and a CDR-H3 comprising the sequence set forth in SEQ ID NO: 73, 88, 58 or 99. In some embodiments of the antibody, antigen-binding fragment, receptor, e.g., CAR, conjugates or binding molecules provided herein, the $V_H$ region comprises a CDR-H1 comprising the sequence set forth in SEQ ID NO: 68, 83 or 53, a CDR-H2 comprising the sequence set forth in SEQ ID NO: 72, 87, 57 or 98, and a CDR-H3 comprising the sequence set forth in SEQ ID NO: 74, 89, 59 or 100.

In some embodiments of the antibody, antigen-binding fragment, receptor, e.g., CAR, conjugates or binding molecules provided herein, the $V_H$ region comprises a CDR-H1 comprising the sequence set forth in SEQ ID NO: 67 or 82, a CDR-H2 comprising the sequence set forth in SEQ ID NO: 71 or 86, and a CDR-H3 comprising the sequence set forth in SEQ ID NO: 73 or 88. In some embodiments of the antibody, antigen-binding fragment, receptor, e.g., CAR, conjugates or binding molecules provided herein, the $V_H$ region comprises a CDR-H1 comprising the sequence set forth in SEQ ID NO: 65 or 80, a CDR-H2 comprising the sequence set forth in SEQ ID NO: 69 or 84, and a CDR-H3 comprising the sequence set forth in SEQ ID NO: 73 or 88. In some embodiments of the antibody, antigen-binding fragment, receptor, e.g., CAR, conjugates or binding molecules provided herein, the $V_H$ region comprises a CDR-H1 comprising the sequence set forth in SEQ ID NO: 66 or 81, a CDR-H2 comprising the sequence set forth in SEQ ID NO: 70 or 85, and a CDR-H3 comprising the sequence set forth in SEQ ID NO: 73 or 88. In some embodiments of the antibody, antigen-binding fragment, receptor, e.g., CAR, conjugates or binding molecules provided herein, the $V_H$ region comprises a CDR-H1 comprising the sequence set forth in SEQ ID NO: 68 or 83, a CDR-H2 comprising the sequence set forth in SEQ ID NO: 72 or 87, and a CDR-H3 comprising the sequence set forth in SEQ ID NO: 74 or 89.

In some embodiments of the antibody, antigen-binding fragment, receptor, e.g., CAR, conjugates or binding molecules provided herein, the $V_H$ region comprises a CDR-H1, a CDR-H2 and a CDR-H3 comprising the sequence set forth in SEQ ID NOS:67, 71 and 73, respectively; SEQ ID NOS:82, 86 and 88; SEQ ID NOS:52, 56 and 58, respectively; or SEQ ID NOS:52, 97 and 99, respectively. In some embodiments of the antibody, antigen-binding fragment, receptor, e.g., CAR, conjugates or binding molecules provided herein, the $V_H$ region comprises a CDR-H1, a CDR-H2 and a CDR-H3 comprising the sequence set forth in SEQ ID NOS:65, 69 and 73, respectively; SEQ ID NOS:80, 84 and 88, respectively; SEQ ID NOS:50, 54 and 58, respectively; or SEQ ID NOS:50, 95 and 99, respectively. In some embodiments of the antibody, antigen-binding fragment, receptor, e.g., CAR, conjugates or binding molecules provided herein, the $V_H$ region comprises a CDR-H1, a CDR-H2 and a CDR-H3 comprising the sequence set forth in SEQ ID NOS:66, 70 and 73, respectively; SEQ ID NOS:81, 85 and 88, respectively; SEQ ID NOS:51, 55 and 58, respectively; or SEQ ID NOS:51, 96 and 99. In some embodiments of the antibody, antigen-binding fragment, receptor, e.g., CAR, conjugates or binding molecules provided herein, the $V_H$ region comprises a CDR-H1, a CDR-H2 and a CDR-H3 comprising the sequence set forth in SEQ ID NOS:68, 72 and 74, respectively; SEQ ID NOS:83, 87 and 89, respectively; SEQ ID NOS:53, 57 and 59, respectively; or SEQ ID NOS:53, 98 and 100, respectively.

In some embodiments of the antibody, antigen-binding fragment, receptor, e.g., CAR, conjugates or binding molecules provided herein, the $V_H$ region comprises a CDR-H1, a CDR-H2 and a CDR-H3 comprising the sequence set forth in SEQ ID NOS:67, 71 and 73, respectively. In some embodiments of the antibody, antigen-binding fragment, receptor, e.g., CAR, conjugates or binding molecules provided herein, the $V_H$ region comprises a CDR-H1, a CDR-H2 and a CDR-H3 comprising the sequence set forth in SEQ ID NOS:65, 69 and 73, respectively. In some embodiments of the antibody, antigen-binding fragment, receptor, e.g., CAR, conjugates or binding molecules provided herein, the $V_H$ region comprises a CDR-H1, a CDR-H2 and a CDR-H3 comprising the sequence set forth in SEQ ID NOS:66, 70 and 73, respectively. In some embodiments of the antibody, antigen-binding fragment, receptor, e.g., CAR, conjugates or binding molecules provided herein, the $V_H$ region comprises a CDR-H1, a CDR-H2 and a CDR-H3 comprising the sequence set forth in SEQ ID NOS:68, 72 and 74, respectively.

In some embodiments of the antibody, antigen-binding fragment, receptor, e.g., CAR, conjugates or binding molecules provided herein, the $V_H$ region comprises a CDR-H1, a CDR-H2 and a CDR-H3 comprising the sequence set forth in SEQ ID NOS:82, 86 and 88, respectively. In some embodiments of the antibody, antigen-binding fragment, receptor, e.g., CAR, conjugates or binding molecules provided herein, the $V_H$ region comprises a CDR-H1, a CDR-H2 and a CDR-H3 comprising the sequence set forth in SEQ ID NOS:80, 84 and 88, respectively. In some embodiments of the antibody, antigen-binding fragment, receptor, e.g., CAR, conjugates or binding molecules provided herein, the $V_H$ region comprises a CDR-H1, a CDR-H2 and a CDR-H3 comprising the sequence set forth in SEQ ID NOS:81, 85 and 88, respectively. In some embodiments of the antibody, antigen-binding fragment, receptor, e.g., CAR, conjugates or binding molecules provided herein, the $V_H$ region comprises a CDR-H1, a CDR-H2 and a CDR-H3 comprising the sequence set forth in SEQ ID NOS:83, 87 and 89, respectively.

In some embodiments of the antibody, antigen-binding fragment, receptor, e.g., CAR, conjugates or binding molecules provided herein, the $V_H$ region comprises a CDR-H1, a CDR-H2 and a CDR-H3, respectively, comprising the amino acid sequence of a CDR-H1, a CDR-H2 and a CDR-H3 contained within the $V_H$ region amino acid sequence set forth in any one of SEQ ID NOs: 112, 121, 103 or 130. In some embodiments of the antibody, antigen-binding fragment, receptor, e.g., CAR, conjugates or binding molecules provided herein, the $V_H$ region comprises a CDR-H1, a CDR-H2 and a CDR-H3 contained within SEQ ID NO:112 or 121.

In some embodiments of the antibody, antigen-binding fragment, receptor, e.g., CAR, conjugates or binding molecules provided herein, the $V_H$ region comprises a CDR-H1, a CDR-H2 and a CDR-H3 contained within SEQ ID NO:112. In some embodiments of the antibody, antigen-binding fragment, receptor, e.g., CAR, conjugates or binding molecules provided herein, the $V_H$ region comprises a CDR-H1, a CDR-H2 and a CDR-H3 contained within SEQ ID NO:121. In some embodiments of the antibody, antigen-binding fragment, receptor, e.g., CAR, conjugates or binding molecules provided herein, the $V_H$ region comprises a CDR-H1, a CDR-H2 and a CDR-H3 contained within SEQ ID NO:103. In some embodiments of the antibody, antigen-binding fragment, receptor, e.g., CAR, conjugates or binding molecules provided herein, the $V_H$ region comprises a CDR-H1, a CDR-H2 and a CDR-H3 contained within SEQ ID NO:130.

In some embodiments of the antibody, antigen-binding fragment, receptor, e.g., CAR, conjugates or binding molecules provided herein, the $V_H$ region comprises any of the CDR-H1, the CDR-H2 and the CDR-H3 as described and comprises a framework region 1 (FR1), a FR2, a FR3 and/or a FR4 having at least at or about 85%, 86%, 87%, 88%, 89%, 90%, 91%, 92%, 93%, 94%, 95%, 96%, 97%, 98% or 99%, respectively, to a FR1, a FR2, a FR3 and/or a FR4 contained within the $V_H$ region amino acid sequence set forth in any one of SEQ ID NOs: 112, 121, 103 or 130. In some of any embodiments, the $V_H$ region comprises a FR1, a FR2, a FR3 and/or a FR4 having at least at or about 85%, 86%, 87%, 88%, 89%, 90%, 91%, 92%, 93%, 94%, 95%, 96%, 97%, 98% or 99%, respectively, to a FR1, a FR2, a FR3 and/or a FR4 contained within the $V_H$ region amino acid sequence set forth in SEQ ID NO: 112. In some of any embodiments, the $V_H$ region comprises a FR1, a FR2, a FR3 and/or a FR4 having at least at or about 85%, 86%, 87%, 88%, 89%, 90%, 91%, 92%, 93%, 94%, 95%, 96%, 97%, 98% or 99%, respectively, to a FR1, a FR2, a FR3 and/or a FR4 contained within the $V_H$ region amino acid sequence set forth in SEQ ID NO: 121. In some of any embodiments, the $V_H$ region comprises a FR1, a FR2, a FR3 and/or a FR4 having at least at or about 85%, 86%, 87%, 88%, 89%, 90%, 91%, 92%, 93%, 94%, 95%, 96%, 97%, 98% or 99%, respectively, to a FR1, a FR2, a FR3 and/or a FR4 contained within the $V_H$ region amino acid sequence set forth in SEQ ID NO: 103. In some of any embodiments, the $V_H$ region comprises a FR1, a FR2, a FR3 and/or a FR4 having at least at or about 85%, 86%, 87%, 88%, 89%, 90%, 91%, 92%, 93%, 94%, 95%, 96%, 97%, 98% or 99%, respectively, to a FR1, a FR2, a FR3 and/or a FR4 contained within the $V_H$ region amino acid sequence set forth in SEQ ID NO: 130.

In some embodiments of the antibody, antigen-binding fragment, receptor, e.g., CAR, conjugates or binding molecules provided herein, the $V_H$ region is or comprises the amino acid sequence set forth in any one of SEQ ID NOs: 112, 121, 103 or 130. In some embodiments of the antibody, antigen-binding fragment, receptor, e.g., CAR, conjugates or binding molecules provided herein, the $V_H$ region is or comprises the amino acid sequence set forth in SEQ ID NO:112. In some embodiments of the antibody, antigen-binding fragment, receptor, e.g., CAR, conjugates or binding molecules provided herein, the $V_H$ region is or comprises the amino acid sequence set forth in SEQ ID NO:121. In some embodiments of the antibody, antigen-binding fragment, receptor, e.g., CAR, conjugates or binding molecules provided herein, the $V_H$ region is or comprises the amino acid sequence set forth in SEQ ID NO:103. In some embodiments of the antibody, antigen-binding fragment, receptor, e.g., CAR, conjugates or binding molecules provided herein, the $V_H$ region is or comprises the amino acid sequence set forth in SEQ ID NO:130.

In some embodiments of the antibody, antigen-binding fragment, receptor, e.g., CAR, conjugates or binding molecules provided herein, the $V_H$ region is or comprises the amino acid sequence encoded by SEQ ID NO: 110, 119, 101 or 128 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 110, 119, 101 or 128. In some embodiments of the antibody, antigen-binding fragment, receptor, e.g., CAR, conjugates or binding molecules provided herein, the $V_H$ region is or comprises the amino acid sequence encoded by SEQ ID NO: 111, 120, 102 or 129.

In some embodiments of the antibody, antigen-binding fragment, receptor, e.g., CAR, conjugates or binding molecules provided herein, the $V_H$ region is or comprises the amino acid sequence encoded by SEQ ID NO: 110 or 119 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 110 or 119. In some embodiments of the antibody, antigen-binding fragment, receptor, e.g., CAR, conjugates or binding molecules provided herein, the $V_H$ region is or comprises the amino acid sequence encoded by SEQ ID NO: 111 or 120.

In some embodiments of the antibody, antigen-binding fragment, receptor, e.g., CAR, conjugates or binding molecules provided herein, the $V_H$ region is or comprises the amino acid sequence encoded by SEQ ID NO: 110 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 110. In some embodiments of the antibody, antigen-binding fragment, receptor, e.g., CAR, conjugates or binding molecules provided herein, the $V_H$ region is or comprises the amino acid sequence encoded by SEQ ID NO: 111.

In some embodiments of the antibody, antigen-binding fragment, receptor, e.g., CAR, conjugates or binding molecules provided herein, the $V_H$ region is or comprises the amino acid sequence encoded by SEQ ID NO: 119 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 119. In some embodiments of the antibody, antigen-binding fragment, receptor, e.g., CAR, conjugates or binding molecules provided herein, the $V_H$ region is or comprises the amino acid sequence encoded by SEQ ID NO: 120.

In some embodiments of the antibody, antigen-binding fragment, receptor, e.g., CAR, conjugates or binding molecules provided herein, the $V_H$ region is or comprises the amino acid sequence encoded by SEQ ID NO: 101 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 101. In some embodiments of the antibody, antigen-binding fragment, receptor, e.g., CAR, conjugates or binding molecules provided herein, the $V_H$ region is or comprises the amino acid sequence encoded by SEQ ID NO: 102.

In some embodiments of the antibody, antigen-binding fragment, receptor, e.g., CAR, conjugates or binding molecules provided herein, the $V_H$ region is or comprises the amino acid sequence encoded by SEQ ID NO: 128 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 128. In some embodiments of the antibody, antigen-binding fragment, receptor, e.g., CAR, conjugates or binding molecules provided herein, the $V_H$ region is or comprises the amino acid sequence encoded by SEQ ID NO: 129. Also provided are polynucleotides that contain any of the nucleotide sequences described herein, e.g., encoding all of a portion of the provided binding molecules.

In some embodiments, the antibody or antibody fragment, in the provided CAR (e.g., an anti-ROR1 CAR), comprises a light chain or a sufficient antigen binding portion thereof. For example, in some embodiments, the antibody or antigen-binding fragment thereof contains a variable light chain ($V_L$) region, or a sufficient antigen-binding portion of a $V_L$ region. In some embodiments, the antibody or antigen-binding fragment thereof contains a $V_H$ region and a variable light chain ($V_L$) region, or a sufficient antigen-binding portion of a $V_H$ and $V_L$ region. In any such embodiments, a $V_H$ region sequence can be any of the $V_H$ region sequence described herein. In any such embodiments, a $V_L$ region sequence can be any of the $V_L$ region sequence described herein. In any such embodiments, any of the $V_H$ region sequence and any of the $V_L$ region sequence described herein can be used in combination. In some of any such embodiments, any one or more of the CDR-H1, the CDR-H2 and/or the CDR-H3 sequences described herein, and any one or more of the CDR-L1, the CDR-L2 and/or the CDR-L3 sequences described herein can be used in combination. In some such embodiments, the antibody is an antigen-binding fragment, such as a Fab or an scFv. In some embodiments, the antibody or antigen-binding fragment further comprises at least a portion of an immunoglobulin constant region or a variant thereof. In some such embodiments, the antibody is a full-length antibody that also contains a constant region.

In some embodiments, a binding molecule, such as a receptor, e.g., a CAR provided herein, contains an antibody such as an anti-ROR1 antibody, or antigen-binding fragment thereof that contains any of contains a $V_L$ region or a sufficient antigen binding portion thereof. For example, in some embodiments, the CAR contains an antibody or antigen-binding fragment thereof that contains a $V_H$ region and a $V_L$ region, or a sufficient antigen-binding portion of a $V_H$ and $V_L$ region. In any such embodiments, a $V_H$ region sequence can be any of the $V_H$ region sequence described herein. In any such embodiments, a $V_L$ region sequence can be any of the $V_L$ region sequence described herein. In any such embodiments, any of the $V_H$ region sequence and any of the $V_L$ region sequence described herein can be used in combination. In some of any such embodiments, any one or more of the CDR-H1, the CDR-H2 and/or the CDR-H3 sequences described herein, and any one or more of the CDR-L1, the CDR-L2 and/or the CDR-L3 sequences described herein can be used in combination. In some such embodiments, the antibody contained in the provided recombinant receptor is an antigen-binding fragment, such as a Fab or an scFv. In some such embodiments, the receptor, e.g., CAR, further contains a spacer, such as a portion of an immunoglobulin constant region or a variant thereof, for example, as described below in Section I.B.

In some embodiments, the $V_H$ region of an antibody or antigen-binding fragment thereof comprises a CDR-L1, a CDR-L2 and/or a CDR-L3 according to Kabat numbering. In some embodiments, the $V_H$ region of an antibody or antigen-binding fragment thereof comprises a CDR-L1, a CDR-L2 and/or a CDR-L3 according to Chothia numbering. In some embodiments, the $V_H$ region of an antibody or antigen-binding fragment thereof comprises a CDR-L1, a CDR-L2 and/or a CDR-L3 according to AbM numbering. In some embodiments, the $V_H$ region of an antibody or antigen-binding fragment thereof comprises a CDR-L1, a CDR-L2 and/or a CDR-L3 according to IMGT numbering. In some embodiments, the $V_H$ region of an antibody or antigen-binding fragment thereof comprises a CDR-L1, a CDR-L2 and/or a CDR-L3 according to IgBLAST numbering. In some embodiments, the $V_H$ region of an antibody or antigen-binding fragment thereof comprises a CDR-L1, a CDR-L2 and/or a CDR-L3 according to Kabat, Chothia, AbM, IMGT or IgBLAST numbering, or other numbering schemes.

In some embodiments of the antibody, antigen-binding fragment, receptor, e.g., CAR, conjugates or binding molecules provided herein, has a light chain variable ($V_L$) region having the amino acid sequence set forth in SEQ ID NO: 115, 124 or 106, or an amino acid sequence that has at least at or about 85%, 86%, 87%, 88%, 89%, 90%, 91%, 92%, 93%, 94%, 95%, 96%, 97%, 98%, or 99% sequence identity to the $V_L$ region amino acid sequence set forth in SEQ ID NO: 115, 124 or 106, or contains a light chain complementarity determining region 1 (CDR-L1), a light chain complementarity determining region 2 (CDR-L2) and/or a light chain complementarity determining region 3 (CDR-L3) present in such a $V_L$ sequence, such as one that contains a CDR-L1, a CDR-L2, and a CDR-L3 present in such a $V_L$ sequence. In some embodiments of the antibody, antigen-binding fragment, receptor, e.g., CAR, conjugates or binding molecules provided herein, has a $V_L$ region having the amino acid sequence set forth in SEQ ID NO:115 or 124, or an amino acid sequence that has at least at or about 85%, 86%, 87%, 88%, 89%, 90%, 91%, 92%, 93%, 94%, 95%, 96%, 97%, 98%, or 99% sequence identity to the $V_L$ region amino acid sequence set forth in SEQ ID NO: 115 or 124, or contains a CDR-L1, a CDR-L2 and/or a CDR-L3 present in such a $V_L$ sequence, such as one that contains a CDR-L1, a CDR-L2, and a CDR-L3 present in such a $V_L$ sequence.

In some embodiments of the antibody, antigen-binding fragment, receptor, e.g., CAR, conjugates or binding molecules provided herein, has a $V_L$ region having the amino acid sequence set forth in SEQ ID NO: 115, or an amino acid sequence that has at least at or about 85%, 86%, 87%, 88%, 89%, 90%, 91%, 92%, 93%, 94%, 95%, 96%, 97%, 98%, or 99% sequence identity to the $V_L$ region amino acid sequence set forth in SEQ ID NO: 115, or contains a CDR-L1, a CDR-L2 and/or a CDR-L3 present in such a $V_L$ sequence, such as one that contains a CDR-L1, a CDR-L2, and a CDR-L3 present in such a $V_L$ sequence. In some embodiments, the antibody, e.g., antigen-binding fragment thereof, has a $V_L$ region having the amino acid sequence set forth in SEQ ID NO: 124, or an amino acid sequence that has at least at or about 85%, 86%, 87%, 88%, 89%, 90%, 91%, 92%, 93%, 94%, 95%, 96%, 97%, 98%, or 99% sequence identity to the $V_L$ region amino acid sequence set forth in SEQ ID NO: 124, or contains a CDR-L1, a CDR-L2 and/or a CDR-L3 present in such a $V_L$ sequence, such as one that contains a CDR-L1, a CDR-L2, and a CDR-L3 present in such a $V_L$ sequence. In some embodiments, the antibody, e.g., antigen-binding fragment thereof, has a $V_L$ region having the amino acid sequence set forth in SEQ ID NO: 106, or an amino acid sequence that has at least at or about 85%, 86%, 87%, 88%, 89%, 90%, 91%, 92%, 93%, 94%, 95%, 96%, 97%, 98%, or 99% sequence identity to the $V_L$ region amino acid sequence set forth in SEQ ID NO: 106, or contains a CDR-L1, a CDR-L2 and/or a CDR-L3 present in such a $V_L$ sequence, such as one that contains a CDR-L1, a CDR-L2, and a CDR-L3 present in such a $V_L$ sequence.

In some of any of the provided embodiments, the $V_L$ region comprises a CDR-L1 comprising the sequence set forth in SEQ ID NO: 75, 90 or 60. In some of any of the provided embodiments, the $V_L$ region comprises a CDR-L2 comprising the sequence set forth in SEQ ID NO: 77, 92 or 62. In some of any of the provided embodiments, the $V_L$ region comprises a CDR-L3 comprising the sequence set forth in SEQ ID NO: 79, 94 or 64.

In some of any of the provided embodiments, the $V_L$ region comprises a CDR-L1 comprising the sequence set forth in SEQ ID NO: 76, 91 or 61. In some of any of the provided embodiments, the $V_L$ region comprises a CDR-L2 comprising the sequence set forth in SEQ ID NO: 78, 93 or 63. In some of any of the provided embodiments, the $V_L$ region comprises a CDR-L3 comprising the sequence set forth in SEQ ID NO: 79, 94 or 64.

In some embodiments of the antibody, antigen-binding fragment, receptor, e.g., CAR, conjugates or binding molecules provided herein, the $V_L$ region comprises a CDR-L1 comprising the sequence set forth in SEQ ID NO: 75, 90 or 60, a CDR-L2 comprising the sequence set forth in SEQ ID NO: 77, 92 or 62, and a CDR-L3 comprising the sequence set forth in SEQ ID NO: 79, 94 or 64. In some embodiments of the antibody, antigen-binding fragment, receptor, e.g., CAR, conjugates or binding molecules provided herein, the $V_L$ region comprises a CDR-L1 comprising the sequence set forth in SEQ ID NO: 76, 91 or 61, a CDR-L2 comprising the sequence set forth in SEQ ID NO: 78, 93 or 63; and a CDR-L3 comprising the sequence set forth in SEQ ID NO: 79, 94 or 64.

In some embodiments of the antibody, antigen-binding fragment, receptor, e.g., CAR, conjugates or binding molecules provided herein, the $V_L$ region comprises a CDR-L1 comprising the sequence set forth in SEQ ID NO: 75 or 90, a CDR-L2 comprising the sequence set forth in SEQ ID NO: 77 or 92; and a CDR-L3 comprising the sequence set forth in SEQ ID NO: 79 or 94. In some embodiments of the antibody, antigen-binding fragment, receptor, e.g., CAR, conjugates or binding molecules provided herein, the $V_L$ region comprises a CDR-L1 comprising the sequence set forth in SEQ ID NO: 76 or 91, a CDR-L2 comprising the sequence set forth in SEQ ID NO: 78 or 93; and a CDR-L3 comprising the sequence set forth in SEQ ID NO: 79 or 94.

In some embodiments of the antibody, antigen-binding fragment, receptor, e.g., CAR, conjugates or binding molecules provided herein, the $V_L$ region comprises a CDR-L1, a CDR-L2 and a CDR-L3 comprising the sequence set forth in SEQ ID NOS:75, 77 and 79, respectively; SEQ ID NOS:90, 92 and 94; SEQ ID NOS:60, 62 and 64, respectively; or SEQ ID NOS:60, 62 and 64, respectively. In some embodiments of the antibody, antigen-binding fragment, receptor, e.g., CAR, conjugates or binding molecules provided herein, the $V_L$ region comprises a CDR-L1, a CDR-L2 and a CDR-L3 comprising the sequence set forth in SEQ ID NOS:76, 78 and 79, respectively; SEQ ID NOS:91, 93 and 94, respectively; SEQ ID NOS:60, 63 and 64, respectively; or SEQ ID NOS:61, 63 and 64, respectively.

In some embodiments of the antibody, antigen-binding fragment, receptor, e.g., CAR, conjugates or binding molecules provided herein, the $V_L$ region comprises a CDR-L1, a CDR-L2 and a CDR-L3 comprising the sequence set forth in SEQ ID NOS:75, 77 and 79, respectively. In some embodiments of the antibody, antigen-binding fragment, receptor, e.g., CAR, conjugates or binding molecules provided herein, the $V_L$ region comprises a CDR-L1, a CDR-L2 and a CDR-L3 comprising the sequence set forth in SEQ ID NOS:76, 78 and 79, respectively.

In some embodiments of the antibody, antigen-binding fragment, receptor, e.g., CAR, conjugates or binding molecules provided herein, the $V_L$ region comprises a CDR-L1, a CDR-L2 and a CDR-L3 comprising the sequence set forth in SEQ ID NOS:90, 92 and 94, respectively. In some embodiments of the antibody, antigen-binding fragment, receptor, e.g., CAR, conjugates or binding molecules provided herein, the $V_L$ region comprises a CDR-L1, a CDR-L2 and a CDR-L3 comprising the sequence set forth in SEQ ID NOS:91, 93 and 94, respectively.

In some embodiments of the antibody, antigen-binding fragment, receptor, e.g., CAR, conjugates or binding molecules provided herein, the $V_L$ region comprises a CDR-L1, a CDR-L2 and a CDR-L3, respectively, comprising the amino acid sequence of a CDR-L1, a CDR-L2 and a CDR-L3 contained within the $V_L$ region amino acid sequence set forth in any one of SEQ ID NOs: 115, 124 or 106. In some embodiments of the antibody, antigen-binding fragment, receptor, e.g., CAR, conjugates or binding molecules provided herein, the $V_L$ region comprises a CDR-L1, a CDR-L2 and a CDR-L3 contained within SEQ ID NO: 115 or 124.

In some embodiments of the antibody, antigen-binding fragment, receptor, e.g., CAR, conjugates or binding molecules provided herein, the $V_L$ region comprises CDR-L1, a CDR-L2 and a CDR-L3 contained within SEQ ID NO: 115. In some embodiments of the antibody, antigen-binding fragment, receptor, e.g., CAR, conjugates or binding molecules provided herein, the $V_L$ region comprises CDR-L1, a CDR-L2 and a CDR-L3 contained within SEQ ID NO: 124. In some embodiments of the antibody, antigen-binding fragment, receptor, e.g., CAR, conjugates or binding molecules provided herein, the $V_L$ region comprises CDR-L1, a CDR-L2 and a CDR-L3 contained within SEQ ID NO: 106.

In some embodiments of the antibody, antigen-binding fragment, receptor, e.g., CAR, conjugates or binding molecules provided herein, the $V_L$ region comprises any of the CDR-L1, the CDR-L2 and the CDR-L3 as described and comprises a framework region 1 (FR1), a FR2, a FR3 and/or a FR4 having at least at or about 85%, 86%, 87%, 88%, 89%, 90%, 91%, 92%, 93%, 94%, 95%, 96%, 97%, 98% or 99%, respectively, to a FR1, a FR2, a FR3 and/or a FR4 contained within the $V_L$ region amino acid sequence set forth in any one of SEQ ID NOs: 115, 124 or 106. In some of any embodiments, the $V_L$ region comprises a FR1, a FR2, a FR3 and/or a FR4 having at least at or about 85%, 86%, 87%, 88%, 89%, 90%, 91%, 92%, 93%, 94%, 95%, 96%, 97%, 98% or 99%, respectively, to a FR1, a FR2, a FR3 and/or a FR4 contained within the $V_L$ region amino acid sequence set forth in SEQ ID NO: 115. In some of any embodiments, the $V_L$ region comprises a FR1, a FR2, a FR3 and/or a FR4 having at least at or about 85%, 86%, 87%, 88%, 89%, 90%, 91%, 92%, 93%, 94%, 95%, 96%, 97%, 98% or 99%, respectively, to a FR1, a FR2, a FR3 and/or a FR4 contained within the $V_L$ region amino acid sequence set forth in SEQ ID NO: 124. In some of any embodiments, the $V_L$ region comprises a FR1, a FR2, a FR3 and/or a FR4 having at least at or about 85%, 86%, 87%, 88%, 89%, 90%, 91%, 92%, 93%, 94%, 95%, 96%, 97%, 98% or 99%, respectively, to a FR1, a FR2, a FR3 and/or a FR4 contained within the $V_L$ region amino acid sequence set forth in SEQ ID NO: 106.

In some embodiments of the antibody, antigen-binding fragment, receptor, e.g., CAR, conjugates or binding molecules provided herein, the $V_L$ region is or comprises the amino acid sequence set forth in any one of SEQ ID NOs: 115, 124 or 106. In some embodiments of the antibody, antigen-binding fragment, receptor, e.g., CAR, conjugates or binding molecules provided herein, the $V_L$ region is or comprises the amino acid sequence set forth in SEQ ID NO: 115. In some embodiments of the antibody, antigen-binding fragment, receptor, e.g., CAR, conjugates or binding molecules provided herein, the $V_L$ region is or comprises the amino acid sequence set forth in SEQ ID NO: 124. In some embodiments of the antibody, antigen-binding fragment, receptor, e.g., CAR, conjugates or binding molecules provided herein, the $V_L$ region is or comprises the amino acid sequence set forth in SEQ ID NO: 106.

In some embodiments of the antibody, antigen-binding fragment, receptor, e.g., CAR, conjugates or binding molecules provided herein, the $V_L$ region is or comprises the amino acid sequence encoded by SEQ ID NO: 113, 122 or 104, or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 113, 122 or 104. In some embodiments of the antibody, antigen-binding fragment, receptor, e.g., CAR, conjugates or binding molecules provided herein, the $V_L$ region is or comprises the amino acid sequence encoded by SEQ ID NO: 114, 123, 105 or 131.

In some embodiments of the antibody, antigen-binding fragment, receptor, e.g., CAR, conjugates or binding molecules provided herein, the $V_L$ region is or comprises the amino acid sequence encoded by SEQ ID NO: 113 or 122, or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 113 or 122. In some embodiments of the antibody, antigen-binding fragment, receptor, e.g., CAR, conjugates or binding molecules provided herein, the $V_L$ region is or comprises the amino acid sequence encoded by SEQ ID NO: 114 or 123.

In some embodiments of the antibody, antigen-binding fragment, receptor, e.g., CAR, conjugates or binding molecules provided herein, the $V_L$ region is or comprises the amino acid sequence encoded by SEQ ID NO: 113, or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 113. In some embodiments of the antibody, antigen-binding fragment, receptor, e.g., CAR, conjugates or binding molecules provided herein, the $V_L$ region is or comprises the amino acid sequence encoded by SEQ ID NO: 114.

In some embodiments of the antibody, antigen-binding fragment, receptor, e.g., CAR, conjugates or binding molecules provided herein, the $V_L$ region is or comprises the amino acid sequence encoded by SEQ ID NO: 122, or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 122. In some embodiments of the antibody, antigen-binding fragment, receptor, e.g., CAR, conjugates or binding molecules provided herein, the $V_L$ region is or comprises the amino acid sequence encoded by SEQ ID NO: 123.

In some embodiments of the antibody, antigen-binding fragment, receptor, e.g., CAR, conjugates or binding molecules provided herein, the $V_L$ region is or comprises the amino acid sequence encoded by SEQ ID NO: 104, or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 104. In some embodiments of the antibody, antigen-binding fragment, receptor, e.g., CAR, conjugates or binding molecules provided herein, the $V_L$ region is or comprises the amino acid sequence encoded by SEQ ID NO: 105. In some embodiments of the antibody, antigen-binding fragment, receptor, e.g., CAR, conjugates or binding molecules provided herein, the $V_L$ region is or comprises the amino acid sequence encoded by SEQ ID NO: 131.

In some embodiments, the antibody or antigen binding fragment is an scFv comprising a heavy chain variable ($V_H$) region and a light chain variable ($V_L$) region. In some embodiments of the antibody, antigen-binding fragment, receptor, e.g., CAR, conjugates or binding molecules provided herein, the $V_H$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO: 112, 121, 103 or 130, and the $V_L$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO: 115, 124 or 106. In some embodiments of the antibody, antigen-binding fragment, receptor, e.g., CAR, conjugates or binding molecules provided herein, the $V_H$ region is or comprises an amino acid sequence having at least at or about 90%, 91%, 92%, 93%, 94%, 95%, 96%, 97%, 98% or 99% sequence identity to SEQ ID NO:112 or 121, and the $V_L$ region is or comprises an amino acid sequence having at least at or about 90%, 91%, 92%, 93%, 94%, 95%, 96%, 97%, 98%, or 99% sequence identity to SEQ ID NO:115 or 124.

In some embodiments of the antibody, antigen-binding fragment, receptor, e.g., CAR, conjugates or binding molecules provided herein, the $V_H$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:112, and the $V_L$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO: 115; the $V_H$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:121, and the $V_L$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:124; the $V_H$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:103, and the $V_L$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:106; or the $V_H$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:130, and the $V_L$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:106.

In some embodiments of the antibody, antigen-binding fragment, receptor, e.g., CAR, conjugates or binding molecules provided herein, the $V_H$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:112, and the $V_L$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO: 115. In some embodiments of the antibody, antigen-binding fragment, receptor, e.g., CAR, conjugates or binding molecules provided herein, the $V_H$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:121, and the $V_L$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:124. In some embodiments of the antibody, antigen-binding fragment, receptor, e.g., CAR, conjugates or binding molecules provided herein, the $V_H$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:103, and the $V_L$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:106. In some embodiments of the antibody, antigen-binding fragment, receptor, e.g., CAR, conjugates or binding molecules provided herein, the $V_H$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:130, and the $V_L$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:106.

In some embodiments of the antibody, antigen-binding fragment, receptor, e.g., CAR, conjugates or binding molecules provided herein, the $V_H$ region of the antibody or antigen-binding fragment thereof comprises a CDR-H1, a CDR-H2, a CDR-H3, respectively, comprising the amino acid sequences of CDR-H1, a CDR-H2 and a CDR-H3 contained within the $V_H$ region amino acid sequence selected from any one of SEQ ID NOs: 112, 121, 103 or 130; and comprises a CDR-L1, a CDR-L2, a CDR-L3, respectively, comprising the amino acid sequences of CDR-L1, a CDR-L2 and a CDR-L3, respectively contained within the $V_L$ region amino acid sequence selected from any one of SEQ ID NOs: 115, 124 or 106. In some of any such embodiments, the $V_H$ region comprises a CDR-H1, a CDR-H2 and a CDR-H3 contained within SEQ ID NO:112 or 121, and the $V_L$ region comprises a CDR-L1, a CDR-L2 and a CDR-L3 contained within SEQ ID NO:115 or 124.

In some of any such embodiments, the $V_H$ region comprises a CDR-H1, a CDR-H2 and a CDR-H3 contained within SEQ ID NO:112, and the $V_L$ region comprises a CDR-L1, a CDR-L2 and a CDR-L3 contained within SEQ ID NO:115. In some of any such embodiments, the $V_H$ region comprises a CDR-H1, a CDR-H2 and a CDR-H3 contained within SEQ ID NO:121, and the $V_L$ region comprises a CDR-L1, a CDR-L2 and a CDR-L3 contained within SEQ ID: NO 124. In some of any such embodiments, the $V_H$ region comprises a CDR-H1, a CDR-H2 and a CDR-H3 contained within SEQ ID NO:103, and the $V_L$ region comprises a CDR-L1, a CDR-L2 and a CDR-L3 contained within SEQ ID: NO 106. In some of any such embodiments, the $V_H$ region comprises a CDR-H1, a CDR-H2 and a CDR-H3 contained within SEQ ID NO:130, and the $V_L$ region comprises a CDR-L1, a CDR-L2 and a CDR-L3 contained within SEQ ID: NO 106.

In some embodiments of the antibody, antigen-binding fragment, receptor, e.g., CAR, conjugates or binding molecules provided herein, the $V_H$ region comprises a heavy chain complementarity determining region 1 (CDR-H1) comprising the sequence set forth in SEQ ID NO: 67, 82 or 52, a heavy chain complementarity determining region 2 (CDR-H2) comprising the sequence set forth in SEQ ID NO: 71, 86, 56 or 97, and a heavy chain complementarity determining region 3 (CDR-H3) comprising the sequence set forth in SEQ ID NO: 73, 88, 58 or 99, and the $V_L$ region comprises a light chain complementarity determining region 1 (CDR-L1) comprising the sequence set forth in SEQ ID NO: 75, 90 or 60, a light chain complementarity determining region 2 (CDR-L2) comprising the sequence set forth in SEQ ID NO: 77, 92 or 62; and a light chain complementarity determining region 3 (CDR-L3) comprising the sequence set forth in SEQ ID NO: 79, 94 or 64.

In some embodiments of the antibody, antigen-binding fragment, receptor, e.g., CAR, conjugates or binding molecules provided herein, the $V_H$ region comprises a CDR-H1 comprising the sequence set forth in SEQ ID NO: 65, 80 or 50, a CDR-H2 comprising the sequence set forth in SEQ ID NO: 69, 84, 54 or 95, and a CDR-H3 comprising the sequence set forth in SEQ ID NO: 73, 88, 58 or 99, and the $V_L$ region comprises a CDR-L1 comprising the sequence set forth in SEQ ID NO: 75, 90 or 60, a CDR-L2 comprising the sequence set forth in SEQ ID NO: 77, 92 or 62; and a CDR-L3 comprising the sequence set forth in SEQ ID NO: 79, 94 or 64; or In some embodiments of the antibody, antigen-binding fragment, receptor, e.g., CAR, conjugates or binding molecules provided herein, the $V_H$ region comprises a CDR-H1 comprising the sequence set forth in SEQ ID NO: 66, 81 or 51, a CDR-H2 comprising the sequence set forth in SEQ ID NO: 70, 85, 55 or 96, and a CDR-H3 comprising the sequence set forth in SEQ ID NO: 73, 88, 58 or 99, and the $V_L$ region comprises a CDR-L1 comprising the sequence set forth in SEQ ID NO: 75, 90 or 60, a CDR-L2 comprising the sequence set forth in SEQ ID NO: 77, 92 or 62; and a CDR-L3 comprising the sequence set forth in SEQ ID NO: 79, 94 or 64; or In some embodiments of the antibody, antigen-binding fragment, receptor, e.g., CAR, conjugates or binding molecules provided herein, the $V_H$ region comprises a CDR-H1 comprising the sequence set forth in SEQ ID NO: 68, 83 or 53, a CDR-H2 comprising the sequence set forth in SEQ ID NO: 72, 87, 57 or 98, and a CDR-H3 comprising the sequence set forth in SEQ ID NO: 74, 89, 59 or 100, and the $V_L$ region comprises a CDR-L1 comprising the sequence set forth in SEQ ID NO: 76, 91 or 61, a CDR-L2 comprising the sequence set forth in SEQ ID NO: 78, 93 or 63; and a CDR-L3 comprising the sequence set forth in SEQ ID NO: 79, 94 or 64.

In some embodiments of the antibody, antigen-binding fragment, receptor, e.g., CAR, conjugates or binding molecules provided herein, the $V_H$ region comprises a CDR-H1 comprising the sequence set forth in SEQ ID NO: 67 or 82, a CDR-H2 comprising the sequence set forth in SEQ ID NO: 71 or 86, and a CDR-H3 comprising the sequence set forth in SEQ ID NO: 73 or 88, and the $V_L$ region comprises a CDR-L1 comprising the sequence set forth in SEQ ID NO: 75 or 90, a CDR-L2 comprising the sequence set forth in SEQ ID NO: 77 or 92; and a CDR-L3 comprising the sequence set forth in SEQ ID NO: 79 or 94.

In some embodiments of the antibody, antigen-binding fragment, receptor, e.g., CAR, conjugates or binding molecules provided herein, the $V_H$ region comprises a CDR-H1 comprising the sequence set forth in SEQ ID NO: 65 or 80, a CDR-H2 comprising the sequence set forth in SEQ ID NO: 69 or 84, and a CDR-H3 comprising the sequence set forth in SEQ ID NO: 73 or 88, and the $V_L$ region comprises a CDR-L1 comprising the sequence set forth in SEQ ID NO: 75 or 90, a CDR-L2 comprising the sequence set forth in SEQ ID NO: 77 or 92; and a CDR-L3 comprising the sequence set forth in SEQ ID NO: 79 or 94.

In some embodiments of the antibody, antigen-binding fragment, receptor, e.g., CAR, conjugates or binding molecules provided herein, the $V_H$ region comprises a CDR-H1 comprising the sequence set forth in SEQ ID NO: 66 or 81, a CDR-H2 comprising the sequence set forth in SEQ ID NO: 70 or 85, and a CDR-H3 comprising the sequence set forth in SEQ ID NO: 73 or 88, and the $V_L$ region comprises a CDR-L1 comprising the sequence set forth in SEQ ID NO: 75 or 90, a CDR-L2 comprising the sequence set forth in SEQ ID NO: 77 or 92; and a CDR-L3 comprising the sequence set forth in SEQ ID NO: 79 or 94.

In some embodiments of the antibody, antigen-binding fragment, receptor, e.g., CAR, conjugates or binding molecules provided herein, the $V_H$ region comprises a CDR-H1 comprising the sequence set forth in SEQ ID NO: 68 or 83, a CDR-H2 comprising the sequence set forth in SEQ ID NO: 72 or 87, and a CDR-H3 comprising the sequence set forth in SEQ ID NO: 74 or 89, and the $V_L$ region comprises a CDR-L1 comprising the sequence set forth in SEQ ID NO: 76 or 91, a CDR-L2 comprising the sequence set forth in SEQ ID NO: 78 or 93; and a CDR-L3 comprising the sequence set forth in SEQ ID NO: 79 or 94.

In some embodiments of the antibody, antigen-binding fragment, receptor, e.g., CAR, conjugates or binding molecules provided herein, the $V_H$ region comprises a heavy chain complementarity determining region 1 (CDR-H1), a heavy chain complementarity determining region 2 (CDR-H2) and a heavy chain complementarity determining region 3 (CDR-H3) comprising the sequence set forth in SEQ ID NOS:67, 71 and 73, respectively, and the $V_L$ region comprises a light chain complementarity determining region 1 (CDR-L1), a light chain complementarity determining region 2 (CDR-L2) and a light chain complementarity determining region 3 (CDR-L3) comprising the sequence set forth in SEQ ID NOS:75, 77 and 79, respectively; the $V_H$ region comprises a CDR-H1, a CDR-H2 and a CDR-H3 comprising the sequence set forth in SEQ ID NOS:82, 86 and 88, respectively, and the $V_L$ region comprises a CDR-L1, a CDR-L2 and a CDR-L3 comprising the sequence set forth in SEQ ID NOS:90, 92 and 94, respectively; the $V_H$ region comprises a CDR-H1, a CDR-H2 and a CDR-H3 comprising the sequence set forth in SEQ ID NOS:52, 56 and 58, respectively, and the $V_L$ region comprises a CDR-L1, a CDR-L2 and a CDR-L3 comprising the sequence set forth in SEQ ID NOS:60, 62 and 64, respectively; or the $V_H$ region comprises a CDR-H1, a CDR-H2 and a CDR-H3 comprising the sequence set forth in SEQ ID NOS:52, 97 and 99, respectively, and the $V_L$ region comprises a CDR-L1, a CDR-L2 and a CDR-L3 comprising the sequence set forth in SEQ ID NOS:60, 62 and 64, respectively.

In some embodiments of the antibody, antigen-binding fragment, receptor, e.g., CAR, conjugates or binding molecules provided herein, the $V_H$ region comprises a CDR-H1, a CDR-H2 and a CDR-H3 comprising the sequence set forth in SEQ ID NOS:65, 69 and 73, respectively, and the $V_L$ region comprises a CDR-L1, a CDR-L2 and a CDR-L3 comprising the sequence set forth in SEQ ID NOS:75, 77 and 79, respectively; the $V_H$ region comprises a CDR-H1, a CDR-H2 and a CDR-H3 comprising the sequence set forth in SEQ ID NOS:80, 84 and 88, respectively, and the $V_L$ region comprises a CDR-L1, a CDR-L2 and a CDR-L3 comprising the sequence set forth in SEQ ID NOS:90, 92 and 94, respectively; the $V_H$ region comprises a CDR-H1, a CDR-H2 and a CDR-H3 comprising the sequence set forth in SEQ ID NOS:50, 54 and 58, respectively, and the $V_L$ region comprises a CDR-L1, a CDR-L2 and a CDR-L3 comprising the sequence set forth in SEQ ID NOS:60, 62 and 64, respectively; or the $V_H$ region comprises a CDR-H1, a CDR-H2 and a CDR-H3 comprising the sequence set forth in SEQ ID NOS:50, 95 and 99, respectively, and the $V_L$ region comprises a CDR-L1, a CDR-L2 and a CDR-L3 comprising the sequence set forth in SEQ ID NOS:60, 62 and 64, respectively;

In some embodiments of the antibody, antigen-binding fragment, receptor, e.g., CAR, conjugates or binding molecules provided herein, the $V_H$ region comprises a CDR-H1, a CDR-H2 and a CDR-H3 comprising the sequence set forth in SEQ ID NOS:66, 70 and 73, respectively, and the $V_L$ region comprises a CDR-L1, a CDR-L2 and a CDR-L3 comprising the sequence set forth in SEQ ID NOS:75, 77 and 79, respectively; the $V_H$ region comprises a CDR-H1, a CDR-H2 and a CDR-H3 comprising the sequence set forth in SEQ ID NOS:81, 85 and 88, respectively, and the $V_L$ region comprises a CDR-L1, a CDR-L2 and a CDR-L3 comprising the sequence set forth in SEQ ID NOS:90, 92 and 94, respectively; the $V_H$ region comprises a CDR-H1, a CDR-H2 and a CDR-H3 comprising the sequence set forth in SEQ ID NOS:51, 55 and 58, respectively, and the $V_L$ region comprises a CDR-L1, a CDR-L2 and a CDR-L3 comprising the sequence set forth in SEQ ID NOS:60, 62 and 64, respectively; or the $V_H$ region comprises a CDR-H1, a CDR-H2 and a CDR-H3 comprising the sequence set forth in SEQ ID NOS:51, 96 and 99, respectively, and the $V_L$ region comprises a CDR-L1, a CDR-L2 and a CDR-L3 comprising the sequence set forth in SEQ ID NOS:60, 62 and 64, respectively;

In some embodiments of the antibody, antigen-binding fragment, receptor, e.g., CAR, conjugates or binding molecules provided herein, the $V_H$ region comprises a CDR-H1, a CDR-H2 and a CDR-H3 comprising the sequence set forth in SEQ ID NOS:68, 72 and 74, respectively, and the $V_L$ region comprises a CDR-L1, a CDR-L2 and a CDR-L3 comprising the sequence set forth in SEQ ID NOS:76, 78 and 79, respectively; or the $V_H$ region comprises a CDR-H1, a CDR-H2 and a CDR-H3 comprising the sequence set forth in SEQ ID NOS:83, 87 and 89, respectively, and the $V_L$ region comprises a CDR-L1, a CDR-L2 and a CDR-L3 comprising the sequence set forth in SEQ ID NOS:91, 93 and 94, respectively; the $V_H$ region comprises a CDR-H1, a CDR-H2 and a CDR-H3 comprising the sequence set forth in SEQ ID NOS:53, 57 and 59, respectively, and the $V_L$ region comprises a CDR-L1, a CDR-L2 and a CDR-L3 comprising the sequence set forth in SEQ ID NOS:60, 63 and 64, respectively; or the $V_H$ region comprises a CDR-H1, a CDR-H2 and a CDR-H3 comprising the sequence set forth in SEQ ID NOS:53, 98 and 100, respectively, and the $V_L$ region comprises a CDR-L1, a CDR-L2 and a CDR-L3 comprising the sequence set forth in SEQ ID NOS:61, 63 and 64, respectively.

In some embodiments of the antibody, antigen-binding fragment, receptor, e.g., CAR, conjugates or binding molecules provided herein, the $V_H$ region comprises a CDR-H1, a CDR-H2 and a CDR-H3 comprising the sequence set forth in SEQ ID NOS:67, 71 and 73, respectively, and the $V_L$ region comprises a CDR-L1, a CDR-L2 and a CDR-L3 comprising the sequence set forth in SEQ ID NOS:75, 77 and 79, respectively.

In some embodiments of the antibody, antigen-binding fragment, receptor, e.g., CAR, conjugates or binding molecules provided herein, the $V_H$ region comprises a CDR-H1, a CDR-H2 and a CDR-H3 comprising the sequence set forth in SEQ ID NOS:65, 69 and 73, respectively, and the $V_L$ region comprises a CDR-L1, a CDR-L2 and a CDR-L3 comprising the sequence set forth in SEQ ID NOS:75, 77 and 79, respectively.

In some embodiments of the antibody, antigen-binding fragment, receptor, e.g., CAR, conjugates or binding molecules provided herein, the $V_H$ region comprises a CDR-H1, a CDR-H2 and a CDR-H3 comprising the sequence set forth in SEQ ID NOS:66, 70 and 73, respectively, and the $V_L$ region comprises a CDR-L1, a CDR-L2 and a CDR-L3 comprising the sequence set forth in SEQ ID NOS:75, 77 and 79, respectively.

In some embodiments of the antibody, antigen-binding fragment, receptor, e.g., CAR, conjugates or binding molecules provided herein, the $V_H$ region comprises a CDR-H1, a CDR-H2 and a CDR-H3 comprising the sequence set forth in SEQ ID NOS:68, 72 and 74, respectively, and the $V_L$ region comprises a CDR-L1, a CDR-L2 and a CDR-L3 comprising the sequence set forth in SEQ ID NOS:76, 78 and 79, respectively.

In some embodiments of the antibody, antigen-binding fragment, receptor, e.g., CAR, conjugates or binding molecules provided herein, the $V_H$ region comprises a CDR-H1, a CDR-H2 and a CDR-H3 comprising the sequence set forth in SEQ ID NOS:82, 86 and 88, respectively, and the $V_L$ region comprises a CDR-L1, a CDR-L2 and a CDR-L3 comprising the sequence set forth in SEQ ID NOS:90, 92 and 94, respectively.

In some embodiments of the antibody, antigen-binding fragment, receptor, e.g., CAR, conjugates or binding molecules provided herein, the $V_H$ region comprises a CDR-H1, a CDR-H2 and a CDR-H3 comprising the sequence set forth in SEQ ID NOS:80, 84 and 88, respectively, and the $V_L$ region comprises a CDR-L1, a CDR-L2 and a CDR-L3 comprising the sequence set forth in SEQ ID NOS:90, 92 and 94, respectively.

In some embodiments of the antibody, antigen-binding fragment, receptor, e.g., CAR, conjugates or binding molecules provided herein, the V$_H$ region comprises a CDR-H1, a CDR-H2 and a CDR-H3 comprising the sequence set forth in SEQ ID NOS:81, 85 and 88, respectively, and the V$_L$ region comprises a CDR-L1, a CDR-L2 and a CDR-L3 comprising the sequence set forth in SEQ ID NOS:90, 92 and 94, respectively.

In some embodiments of the antibody, antigen-binding fragment, receptor, e.g., CAR, conjugates or binding molecules provided herein, the V$_H$ region comprises a CDR-H1, a CDR-H2 and a CDR-H3 comprising the sequence set forth in SEQ ID NOS:83, 87 and 89, respectively, and the V$_L$ region comprises a CDR-L1, a CDR-L2 and a CDR-L3 comprising the sequence set forth in SEQ ID NOS:91, 93 and 94, respectively.

In some embodiments of the antibody, antigen-binding fragment, receptor, e.g., CAR, conjugates or binding molecules provided herein, the V$_H$ region comprises a CDR-H1, a CDR-H2 and a CDR-H3 comprising the sequence set forth in SEQ ID NOS:52, 56 and 58, respectively, and the V$_L$ region comprises a CDR-L1, a CDR-L2 and a CDR-L3 comprising the sequence set forth in SEQ ID NOS:60, 62 and 64, respectively.

In some embodiments of the antibody, antigen-binding fragment, receptor, e.g., CAR, conjugates or binding molecules provided herein, the V$_H$ region comprises a CDR-H1, a CDR-H2 and a CDR-H3 comprising the sequence set forth in SEQ ID NOS:50, 54 and 58, respectively, and the V$_L$ region comprises a CDR-L1, a CDR-L2 and a CDR-L3 comprising the sequence set forth in SEQ ID NOS:60, 62 and 64, respectively.

In some embodiments of the antibody, antigen-binding fragment, receptor, e.g., CAR, conjugates or binding molecules provided herein, the V$_H$ region comprises a CDR-H1, a CDR-H2 and a CDR-H3 comprising the sequence set forth in SEQ ID NOS:51, 55 and 58, respectively, and the V$_L$ region comprises a CDR-L1, a CDR-L2 and a CDR-L3 comprising the sequence set forth in SEQ ID NOS:60, 62 and 64, respectively.

In some embodiments of the antibody, antigen-binding fragment, receptor, e.g., CAR, conjugates or binding molecules provided herein, the V$_H$ region comprises a CDR-H1, a CDR-H2 and a CDR-H3 comprising the sequence set forth in SEQ ID NOS:53, 57 and 59, respectively, and the V$_L$ region comprises a CDR-L1, a CDR-L2 and a CDR-L3 comprising the sequence set forth in SEQ ID NOS:60, 63 and 64, respectively.

In some embodiments of the antibody, antigen-binding fragment, receptor, e.g., CAR, conjugates or binding molecules provided herein, the V$_H$ region comprises a CDR-H1, a CDR-H2 and a CDR-H3 comprising the sequence set forth in SEQ ID NOS:52, 97 and 99, respectively, and the V$_L$ region comprises a CDR-L1, a CDR-L2 and a CDR-L3 comprising the sequence set forth in SEQ ID NOS:60, 62 and 64, respectively.

In some embodiments of the antibody, antigen-binding fragment, receptor, e.g., CAR, conjugates or binding molecules provided herein, the V$_H$ region comprises a CDR-H1, a CDR-H2 and a CDR-H3 comprising the sequence set forth in SEQ ID NOS:50, 95 and 99, respectively, and the V$_L$ region comprises a CDR-L1, a CDR-L2 and a CDR-L3 comprising the sequence set forth in SEQ ID NOS:60, 62 and 64, respectively.

In some embodiments of the antibody, antigen-binding fragment, receptor, e.g., CAR, conjugates or binding molecules provided herein, the V$_H$ region comprises a CDR-H1, a CDR-H2 and a CDR-H3 comprising the sequence set forth in SEQ ID NOS:51, 96 and 99, respectively, and the V$_L$ region comprises a CDR-L1, a CDR-L2 and a CDR-L3 comprising the sequence set forth in SEQ ID NOS:60, 62 and 64, respectively.

In some embodiments of the antibody, antigen-binding fragment, receptor, e.g., CAR, conjugates or binding molecules provided herein, the V$_H$ region comprises a CDR-H1, a CDR-H2 and a CDR-H3 comprising the sequence set forth in SEQ ID NOS:53, 98 and 100, respectively, and the V$_L$ region comprises a CDR-L1, a CDR-L2 and a CDR-L3 comprising the sequence set forth in SEQ ID NOS:61, 63 and 64, respectively.

In some embodiments, the V$_H$ region of the antibody or antigen-binding fragment thereof, receptor, e.g., CAR, conjugates or binding molecules comprise the amino acid sequence of SEQ ID NOs: 112, 121, 103 or 130 and the V$_L$ regions of the antibody or antigen-binding fragment comprises the amino acid sequence 115, 124 or 106. In some embodiments, the V$_H$ and V$_L$ regions of the antibody or antigen-binding fragment thereof, receptor, e.g., CAR, conjugates or binding molecules comprise the amino acid sequences of SEQ ID NOs: 112 and 115, respectively; SEQ ID NOs: 121 and 124, respectively; SEQ ID NOs: 103 and 106, respectively; or SEQ ID NOs: 130 and 106, respectively, or any antibody or antigen-binding fragment thereof that has at least at or about 90% sequence identity to any of the above V$_H$ and V$_L$, such as at least at or about 90%, 91%, 92%, 93%, 94%, 95%, 96%, 97%, 98%, or 99% sequence identity thereto. For example, the V$_H$ and V$_L$ regions of the antibody or antigen-binding fragment thereof provided therein comprise the amino acid sequences selected from: SEQ ID NOs: 112 and 115; SEQ ID NOs: 121 and 124; SEQ ID NOs: 103 and 106; or SEQ ID NOs: 130 and 106, respectively.

In some embodiments of the antibody, antigen-binding fragment, receptor, e.g., CAR, conjugates or binding molecules provided herein, the V$_H$ region and the V$_L$ region are or comprise the sequence set forth in SEQ ID NOS: 112 and 115, respectively. In some embodiments of the antibody, antigen-binding fragment, receptor, e.g., CAR, conjugates or binding molecules provided herein, the V$_H$ region and the V$_L$ region are or comprise the sequence set forth in SEQ ID NOS: 121 and 124, respectively. In some embodiments of the antibody, antigen-binding fragment, receptor, e.g., CAR, conjugates or binding molecules provided herein, the V$_H$ region and the V$_L$ region are or comprise the sequence set forth in SEQ ID NOS: 103 and 106, respectively. In some embodiments of the antibody, antigen-binding fragment, receptor, e.g., CAR, conjugates or binding molecules provided herein, the V$_H$ region and the V$_L$ region are or comprise the sequence set forth in SEQ ID NOS: 130 and 106, respectively.

In some embodiments of the antibody, antigen-binding fragment, receptor, e.g., CAR, conjugates or binding molecules provided herein, the V$_H$ region is or comprises the amino acid sequence encoded by SEQ ID NO: 110, 119, 101 or 128 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 110, 119, 101 or 128, and the V$_L$ region is or comprises the amino acid sequence encoded by SEQ ID NO: 113, 122 or 104, or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 113, 122 or 104. In some embodiments of the antibody, antigen-binding fragment, receptor, e.g., CAR, conjugates or binding molecules provided herein, the $V_H$ region is or comprises the amino acid sequence encoded by SEQ ID NO: 111, 120, 102 or 129, and the $V_L$ region is or comprises the amino acid sequence encoded by SEQ ID NO: 114, 123, 105 or 131.

In some embodiments of the antibody, antigen-binding fragment, receptor, e.g., CAR, conjugates or binding molecules provided herein, the $V_H$ region is or comprises the amino acid sequence encoded by SEQ ID NO: 110 or 119 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 110 or 119, and the $V_L$ region is or comprises the amino acid sequence encoded by SEQ ID NO: 113 or 122, or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 113 or 122. In some embodiments of the antibody, antigen-binding fragment, receptor, e.g., CAR, conjugates or binding molecules provided herein, the $V_H$ region is or comprises the amino acid sequence encoded by SEQ ID NO: 111 or 120, and the $V_L$ region is or comprises the amino acid sequence encoded by SEQ ID NO: 114 or 123.

In some embodiments of the antibody, antigen-binding fragment, receptor, e.g., CAR, conjugates or binding molecules provided herein, the $V_H$ region is or comprises the amino acid sequence encoded by SEQ ID NO: 110 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 110, and the $V_L$ region is or comprises the amino acid sequence encoded by SEQ ID NO: 113, or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 113. In some embodiments of the antibody, antigen-binding fragment, receptor, e.g., CAR, conjugates or binding molecules provided herein, the $V_H$ region is or comprises the amino acid sequence encoded by SEQ ID NO: 111, and the $V_L$ region is or comprises the amino acid sequence encoded by SEQ ID NO: 114.

In some embodiments of the antibody, antigen-binding fragment, receptor, e.g., CAR, conjugates or binding molecules provided herein, the $V_H$ region is or comprises the amino acid sequence encoded by SEQ ID NO: 119 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 119, and the $V_L$ region is or comprises the amino acid sequence encoded by SEQ ID NO: 122, or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 122. In some embodiments of the antibody, antigen-binding fragment, receptor, e.g., CAR, conjugates or binding molecules provided herein, the $V_H$ region is or comprises the amino acid sequence encoded by SEQ ID NO: 120, and the $V_L$ region is or comprises the amino acid sequence encoded by SEQ ID NO: 123.

In some embodiments of the antibody, antigen-binding fragment, receptor, e.g., CAR, conjugates or binding molecules provided herein, the $V_H$ region is or comprises the amino acid sequence encoded by SEQ ID NO: 101 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 101, and the $V_L$ region is or comprises the amino acid sequence encoded by SEQ ID NO: 104, or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 104. In some embodiments of the antibody, antigen-binding fragment, receptor, e.g., CAR, conjugates or binding molecules provided herein, the $V_H$ region is or comprises the amino acid sequence encoded by SEQ ID NO: 102 and the $V_L$ region is or comprises the amino acid sequence encoded by SEQ ID NO: 105.

In some embodiments of the antibody, antigen-binding fragment, receptor, e.g., CAR, conjugates or binding molecules provided herein, the $V_H$ region is or comprises the amino acid sequence encoded by SEQ ID NO: 128 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 128 and the $V_L$ region is or comprises the amino acid sequence encoded by SEQ ID NO: 104, or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 104. In some embodiments of the antibody, antigen-binding fragment, receptor, e.g., CAR, conjugates or binding molecules provided herein, the $V_H$ region is or comprises the amino acid sequence encoded by SEQ ID NO: 129, and the $V_L$ region is or comprises the amino acid sequence encoded by SEQ ID NO: 131.

In some embodiments, the antibody or antigen-binding fragment thereof, in the provided CAR, is a single-chain antibody fragment, such as a single chain variable fragment (scFv) or a diabody or a single domain antibody (sdAb). In some embodiments, the antibody or antigen binding fragment is a multi-domain antibody, such as an scFv comprising a heavy chain variable ($V_H$) region and a light chain variable ($V_L$) region. In some embodiments, the single-chain antibody fragment (e.g., scFv) includes one or more linkers joining two antibody domains or regions, such as a heavy chain variable ($V_H$) region and a light chain variable ($V_L$) region. The linker typically is a peptide linker, e.g., a flexible and/or soluble peptide linker. Among the linkers are those rich in glycine and serine and/or in some cases threonine. In some embodiments, the linkers further include charged residues such as lysine and/or glutamate, which can improve solubility. In some embodiments, the linkers further include one or more proline.

Accordingly, the provided CARs contain anti-ROR1 antibodies that include single-chain antibody fragments, such as scFvs and diabodies, particularly human single-chain antibody fragments, typically comprising linker(s) joining two antibody domains or regions, such $V_H$ and $V_L$ regions. The linker typically is a peptide linker, e.g., a flexible and/or soluble peptide linker, such as one rich in glycine and serine.

In some aspects, the linkers rich in glycine and serine (and/or threonine) include at least 80%, 85%, 90%, 91%, 92%, 93%, 94%, 95%, 96%, 97%, 98%, or 99% such amino acid(s). In some embodiments, they include at least at or about 50%, 55%, 60%, 70%, or 75%, glycine, serine, and/or threonine. In some embodiments, the linker is comprised substantially entirely of glycine, serine, and/or threonine. The linkers generally are between about 5 and about 50 amino acids in length, typically between at or about 10 and at or about 30, e.g., 10, 11, 12, 13, 14, 15, 16, 17, 18, 19, 20, 21, 22, 23, 24, 25, 26, 27, 28, 29, or 30, and in some examples between 10 and 25 amino acids in length. Exemplary linkers include linkers having various numbers of repeats of the sequence GGGGS (4GS; SEQ ID NO: 39) or GGGS (3GS; SEQ ID NO: 40), such as between 2, 3, 4 and 5 repeats of such a sequence. Exemplary linkers include those having or consisting of an sequence set forth in SEQ ID NO: 41 (GGGGSGGGGSGGGGS). Exemplary linkers further include those having or consisting of the sequence set forth in SEQ ID NO: 24 (GSTSGSGKPGSGEGSTKG). Exemplary linkers further include those having or consisting of the sequence set forth in SEQ ID NO: 162 (SRGGGGSGGGGSGGGGSLEMA). An exemplary linker includes those having or consisting of the sequence set forth in SEQ ID NO; 163 (GSRGGGGSGGGGSGGGGSLEMA).

Accordingly, in some embodiments, the provided embodiments include single-chain antibody fragments, e.g., scFvs, comprising one or more of the aforementioned linkers, such as glycine/serine rich linkers, including linkers having repeats of GGGS (SEQ ID NO: 40) or GGGGS (SEQ ID NO: 39), such as the linker set forth in SEQ ID NO: 41, 162 or 163.

In some embodiments, the $V_H$ region may be amino terminal to the $V_L$ region. In some embodiments, the $V_H$ region may be carboxy terminal to the $V_L$ region. In particular embodiments, the fragment, e.g., scFv, may include a $V_H$ region or portion thereof, followed by the linker, followed by a $V_L$ region or portion thereof. In other embodiments, the fragment, e.g., the scFv, may include the $V_L$ region or portion thereof, followed by the linker, followed by the $V_H$ region or portion thereof.

In some embodiments of the antibody, antigen-binding fragment, receptor, e.g., CAR, conjugates or binding molecules provided herein, the scFv is or comprises the sequence set forth in SEQ ID NO: 118, 127, 109 or 134, or an amino acid sequence having at least at or about 85%, 86%, 87%, 88%, 89%, 90%, 91%, 92%, 93%, 94%, 95%, 96%, 97%, 98% or 99% sequence identity to SEQ ID NO: 118, 127, 109 or 134. In some embodiments of the antibody, antigen-binding fragment, receptor, e.g., CAR, conjugates or binding molecules provided herein, the scFv is or comprises the sequence set forth in SEQ ID NO: 118 or 127 or an amino acid sequence having at least at or about 85%, 86%, 87%, 88%, 89%, 90%, 91%, 92%, 93%, 94%, 95%, 96%, 97%, 98% or 99% sequence identity to SEQ ID NO: 118 or 127. In some of any of the provided embodiments, the scFv is or comprises the sequence set forth in SEQ ID NO: 118. In some of any of the provided embodiments, the scFv is or comprises the sequence set forth in SEQ ID NO: 127. In some of any of the provided embodiments, the scFv is or comprises the sequence set forth in SEQ ID NO: 109. In some of any of the provided embodiments, the scFv is or comprises the sequence set forth in SEQ ID NO: 134.

In some embodiments of the antibody, antigen-binding fragment, receptor, e.g., CAR, conjugates or binding molecules provided herein, the scFv is or comprises the amino acid sequence encoded by SEQ ID NO: 116, 125, 107 or 132 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 116, 125, 107 or 132. In some of any of the provided embodiments, the scFv is or comprises the amino acid sequence encoded by SEQ ID NO: 117, 126, 108 or 133.

In some of any of the provided embodiments, the scFv is or comprises the amino acid sequence encoded by SEQ ID NO: 116 or 125 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 116 or 125. In some embodiments, the scFv is or comprises the amino acid sequence encoded by SEQ ID NO: 117 or 126. In some embodiments, the scFv is or comprises the amino acid sequence encoded by SEQ ID NO: 117. In some embodiments, the scFv is or comprises the amino acid sequence encoded by SEQ ID NO: 126. In some embodiments, the scFv is or comprises the amino acid sequence encoded by SEQ ID NO: 108. In some embodiments, the scFv is or comprises the amino acid sequence encoded by SEQ ID NO: 133

Table 2 provides the SEQ ID NOS: of exemplary provided antibody fragments, such as scFvs. In some aspects, the exemplary provided antibody fragments can be comprised in the provided ROR1-binding receptors, such as anti-ROR1 chimeric antigen receptors (CARs). In some embodiments, the ROR1-binding antibody or fragment thereof, such as an scFv, comprises a $V_H$ region that comprises the CDR-H1, the CDR-H2 and the CDR-H3 sequence and a $V_L$ region that comprises the CDR-L1, the CDR-L2 and the CDR-L3 sequence set forth in the SEQ ID NOS: listed in each row of Table 2 below (by Kabat, Chothia, AbM and IgBLAST numbering schemes). In some embodiments, the ROR1-binding antibody or fragment thereof, such as an scFv, comprises a $V_H$ region sequence and a $V_L$ region sequence set forth in the SEQ ID NOS: listed in each row of Table 2 below, or an antibody comprising a $V_H$ region and a $V_L$ region amino acid sequence that has at least 90%, 91%, 92%, 93%, 94%, 95%, 96%, 97%, 98%, or 99% sequence identity to the $V_H$ region sequence and the $V_L$ region sequence set forth in the SEQ ID NOS: listed in each row of Table 2 below. In some embodiments, the ROR1-binding antibody or fragment thereof, such as an scFv, comprises a $V_H$ region sequence and a $V_L$ region sequence set forth in the SEQ ID NOS: listed in each row of Table 2 below. In some embodiments, the ROR1-binding antibody or fragment thereof comprises an scFv sequence set forth in the SEQ ID NOS: listed in each row of Table 2 below, or an antibody comprising an scFv amino acid sequence that has at least at or about 85%, 86%, 87%, 88%, 89%, 90%, 91%, 92%, 93%, 94%, 95%, 96%, 97%, 98%, or 99% sequence identity to the scFv sequence set forth in the SEQ ID NOS: listed in each row of Table 2 below. In some embodiments, the ROR1-binding antibody or fragment thereof comprises an scFv sequence set forth in the SEQ ID NOS: listed in each row of Table 2 below. In some embodiments, any of the antibody or antigen-binding fragment thereof, such as scFv, listed in each row of Table 2 can be comprised in a receptor, such as a chimeric antigen receptor (CAR), for example, as the extracellular antigen-binding domain In some embodiments, the provided antibody or antigen-binding fragment thereof comprises a $V_H$ region and a $V_L$ region, wherein the $V_H$ region of the antibody or antigen-binding fragment thereof can contain a combination of any of the CDR-H1, the CDR-H2 and the CDR-H3 amino acid sequences set forth in Table 2, and the $V_L$ region of the antibody or antigen-binding fragment thereof can contain a combination of any of the CDR-L1, the CDR-L2 and the CDR-L3 amino acid sequences set forth in Table 2. In some embodiments, the provided antibody or antigen-binding fragment thereof comprises a $V_H$ region and/or a $V_L$ region set forth in Table 2, in any combination, orientation or containing a different linker. In some aspects, the antibody or antigen-binding fragment thereof comprises a $V_H$ region described in Table 2. In some aspects, the antibody or antigen-binding fragment thereof comprises a $V_L$ region described in Table 2. In some embodiments, the provided antibody or antigen-binding fragment thereof is a single-domain antibody (sdAb), comprising a $V_H$ region set forth in Table 2, or a $V_L$ region set forth in Table 2. In some embodiments, the provided antibody or antigen-binding fragment thereof is a single-domain antibody (sdAb), comprising a $V_H$ region containing a CDR-H1, a CDR-H2 and/or a CDR-H3 set forth in Table 2, or a $V_L$ region containing a CDR-L1, a CDR-L2 and/or a CDR-L3 set forth in Table 2.

segment, and/or a portion having at least 95%, 96%, 97%, 98%, 99%, or 100% sequence identity to an amino acid sequence encoded by a germline nucleotide human heavy chain J segment; and contains a $V_L$ region that comprises a portion having at least 95%, 96%, 97%, 98%, 99%, or 100% sequence identity to an amino acid sequence encoded by a

TABLE 2

Sequence identifier (SEQ ID NO) for Exemplary scFvs

| scFv | CDR-H1 | CDR-H2 | CDR-H3 | CDR-L1 | CDR-L2 | CDR-L3 | $V_H$ | $V_L$ | Linker | Order | scFv |
|---|---|---|---|---|---|---|---|---|---|---|---|
| | Kabat | | | Kabat | | | | | | | |
| ROR1-1 | 67 | 71 | 73 | 75 | 77 | 79 | 112 | 115 | 41 | $V_H$-$V_L$ | 118 |
| ROR1-2 | 82 | 86 | 88 | 90 | 92 | 94 | 121 | 124 | 41 | $V_H$-$V_L$ | 127 |
| ROR1-3 | 52 | 56 | 58 | 60 | 62 | 64 | 103 | 106 | 41 | $V_H$-$V_L$ | 109 |
| ROR1-4 | 52 | 97 | 99 | 60 | 62 | 64 | 130 | 106 | 41 | $V_H$-$V_L$ | 134 |
| | Chothia | | | Chothia | | | | | | | |
| ROR1-1 | 65 | 69 | 73 | 75 | 77 | 79 | 112 | 115 | 41 | $V_H$-$V_L$ | 118 |
| ROR1-2 | 80 | 84 | 88 | 90 | 92 | 94 | 121 | 124 | 41 | $V_H$-$V_L$ | 127 |
| ROR1-3 | 50 | 54 | 58 | 60 | 62 | 64 | 103 | 106 | 41 | $V_H$-$V_L$ | 109 |
| ROR1-4 | 50 | 95 | 99 | 60 | 62 | 64 | 130 | 106 | 41 | $V_H$-$V_L$ | 134 |
| | AbM | | | AbM | | | | | | | |
| ROR1-1 | 66 | 70 | 73 | 75 | 77 | 79 | 112 | 115 | 41 | $V_H$-$V_L$ | 118 |
| ROR1-2 | 81 | 85 | 88 | 90 | 92 | 94 | 121 | 124 | 41 | $V_H$-$V_L$ | 127 |
| ROR1-3 | 51 | 55 | 58 | 60 | 62 | 64 | 103 | 106 | 41 | $V_H$-$V_L$ | 109 |
| ROR1-4 | 51 | 96 | 99 | 60 | 62 | 64 | 130 | 106 | 41 | $V_H$-$V_L$ | 134 |
| | IgBLAST | | | IgBLAST | | | | | | | |
| ROR1-1 | 68 | 72 | 74 | 76 | 78 | 79 | 112 | 115 | 41 | $V_H$-$V_L$ | 118 |
| ROR1-2 | 83 | 87 | 89 | 91 | 93 | 94 | 121 | 124 | 41 | $V_H$-$V_L$ | 127 |
| ROR1-3 | 53 | 57 | 59 | 61 | 63 | 64 | 103 | 106 | 41 | $V_H$-$V_L$ | 109 |
| ROR1-4 | 53 | 98 | 100 | 61 | 63 | 64 | 130 | 106 | 41 | $V_H$-$V_L$ | 134 |

Among the provided antibodies, e.g., antigen-binding fragments, are human antibodies. In some embodiments of a provided human anti-ROR1 antibody, e.g., antigen-binding fragments, the human antibody contains a $V_H$ region that comprises a portion having at least 95%, 96%, 97%, 98%, 99%, or 100% sequence identity to an amino acid sequence encoded by a germline nucleotide human heavy chain V segment, a portion having at least 95%, 96%, 97%, 98%, 99%, or 100% sequence identity to an amino acid sequence encoded by a germline nucleotide human heavy chain D segment, and/or a portion having at least 95%, 96%, 97%, 98%, 99%, or 100% sequence identity to an amino acid sequence encoded by a germline nucleotide human heavy chain J segment; and/or contains a $V_L$ region that comprises a portion having at least 95%, 96%, 97%, 98%, 99%, or 100% sequence identity to an amino acid sequence encoded by a germline nucleotide human kappa or lambda chain V segment, and/or a portion having at least 95%, 96%, 97%, 98%, 99%, or 100% sequence identity to an amino acid sequence encoded by a germline nucleotide human kappa or lambda chain J segment.

Among the provided antibodies, e.g., antigen-binding fragments, are human antibodies. In some embodiments of a provided human anti-ROR1 antibody, e.g., antigen-binding fragments, the human antibody contains a $V_H$ region that comprises a portion having at least 95%, 96%, 97%, 98%, 99%, or 100% sequence identity to an amino acid sequence encoded by a germline nucleotide human heavy chain V segment, a portion having at least 95%, 96%, 97%, 98%, 99%, or 100% sequence identity to an amino acid sequence encoded by a germline nucleotide human heavy chain D segment, and/or a portion having at least 95%, 96%, 97%, 98%, 99%, or 100% sequence identity to an amino acid sequence encoded by a germline nucleotide human heavy chain J segment; and contains a $V_L$ region that comprises a portion having at least 95%, 96%, 97%, 98%, 99%, or 100% sequence identity to an amino acid sequence encoded by a germline nucleotide human kappa or lambda chain V segment, and/or a portion having at least 95%, 96%, 97%, 98%, 99%, or 100% sequence identity to an amino acid sequence encoded by a germline nucleotide human kappa or lambda chain J segment. In some embodiments, the portion of the $V_H$ region corresponds to the CDR-H1, the CDR-H2 and/or the CDR-H3. In some embodiments, the portion of the $V_H$ region corresponds to the CDR-H1, the CDR-H2 and the CDR-H3. In some embodiments, the portion of the $V_H$ region corresponds to the framework region 1 (FR1), FR2, FR2 and/or FR4. In some embodiments, the portion of the $V_L$ region corresponds to the CDR-L1, the CDR-L2 and/or the CDR-L3. In some embodiments, the portion of the $V_L$ region corresponds to the CDR-L1, the CDR-L2 and the CDR-L3. In some embodiments, the portion of the $V_L$ region corresponds to the FR1, FR2, FR2 and/or FR4.

In some embodiments, the human antibody or antigen-binding fragment thereof, contains a CDR-H1 having at least 95%, 96%, 97%, 98%, 99%, or 100% sequence identity to an amino acid sequence of the corresponding CDR-H1 region within a sequence encoded by a germline nucleotide human heavy chain V segment. For example, the human antibody in some embodiments contains a CDR-H1 having a sequence that is 100% identical or with no more than one, two or three amino acid differences as compared to the corresponding CDR-H1 region within a sequence encoded by a germline nucleotide human heavy chain V segment.

In some embodiments, the human antibody or antigen-binding fragment thereof, contains a CDR-H2 having at least 95%, 96%, 97%, 98%, 99%, or 100% sequence identity to an amino acid sequence of the corresponding CDR-H2 region within a sequence encoded by a germline nucleotide human heavy chain V segment. For example, the human antibody in some embodiments contains a CDR-H2 having a sequence that is 100% identical or with no more than one, two or three amino acid difference as compared to the corresponding CDR-H2 region within a sequence encoded by a germline nucleotide human heavy chain V segment.

In some embodiments, the human antibody or antigen-binding fragment thereof, contains a CDR-H3 having at least 95%, 96%, 97%, 98%, 99%, or 100% sequence identity to an amino acid sequence of the corresponding CDR-H3 region within a sequence encoded by a germline nucleotide human heavy chain V segment, D segment and J segment. For example, the human antibody in some embodiments contains a CDR-H3 having a sequence that is 100% identical or with no more than one, two or three amino acid differences as compared to the corresponding CDR-H3 region within a sequence encoded by a germline nucleotide human heavy chain V segment, D segment and J segment.

In some embodiments, the human antibody or antigen-binding fragment thereof, contains a CDR-L1 having at least 95%, 96%, 97%, 98%, 99%, or 100% sequence identity to an amino acid sequence of the corresponding CDR-L1 region within a sequence encoded by a germline nucleotide human light chain V segment. For example, the human antibody in some embodiments contains a CDR-L1 having a sequence that is 100% identical or with no more than one, two or three amino acid differences as compared to the corresponding CDR-L1 region within a sequence encoded by a germline nucleotide human light chain V segment.

In some embodiments, the human antibody or antigen-binding fragment thereof, contains a CDR-L2 having at least 95%, 96%, 97%, 98%, 99%, or 100% sequence identity to an amino acid sequence of the corresponding CDR-L2 region within a sequence encoded by a germline nucleotide human light chain V segment. For example, the human antibody in some embodiments contains a CDR-L2 having a sequence that is 100% identical or with no more than one, two or three amino acid difference as compared to the corresponding CDR-L2 region within a sequence encoded by a germline nucleotide human light chain V segment.

In some embodiments, the human antibody or antigen-binding fragment thereof, contains a CDR-L3 having at least 95%, 96%, 97%, 98%, 99%, or 100% sequence identity to an amino acid sequence of the corresponding CDR-L3 region within a sequence encoded by a germline nucleotide human light chain V segment and J segment. For example, the human antibody in some embodiments contains a CDR-L3 having a sequence that is 100% identical or with no more than one, two or three amino acid differences as compared to the corresponding CDR-L3 region within a sequence encoded by a germline nucleotide human light chain V segment and J segment.

In some embodiments, the human antibody or antigen-binding fragment thereof, contains a framework region that contains human germline gene segment sequences. For example, in some embodiments, the human antibody contains a $V_H$ region in which the framework region, e.g. FR1, FR2, FR3 and FR4, has at least 95%, 96%, 97%, 98%, 99%, or 100% sequence identity to a framework region encoded by a human germline antibody segment, such as a V segment and/or J segment. In some embodiments, the human antibody contains a $V_L$ region in which the framework region e.g. FR1, FR2, FR3 and FR4, has at least 95%, 96%, 97%, 98%, 99%, or 100% sequence identity to a framework region encoded by a human germline antibody segment, such as a V segment and/or J segment. For example, in some embodiments, the framework region sequence contained within the $V_H$ region and/or $V_L$ region differs by no more than 10 amino acids, such as no more than 9, 8, 7, 6, 5, 4, 3, 2 or 1 amino acid, compared to the framework region sequence encoded by a human germline antibody segment.

The antibody or antigen-binding fragment thereof, may contain at least a portion of an immunoglobulin constant region, such as one or more constant region domain. In some embodiments, the constant regions include a light chain constant region and/or a heavy chain constant region 1 ($C_H1$). In some embodiments, the antibody includes at least a portion of a hinge region or a variant thereof. In some embodiments, the antibody includes a $C_H2$ and/or $C_H3$ domain, such as an Fc region. In some embodiments, the Fc region is an Fc region of a human IgG, such as an IgG1 or IgG4.

2. Exemplary Features

In some aspects, the provided antibodies have one or more specified functional features, such as binding properties, including binding to particular epitopes or exhibiting lower or reduced binding to a related but non-specific antigen. In some aspects, the provided antibodies can bind to an epitope that is similar to or overlaps with epitopes of other antibodies, such as reference antibodies, and/or exhibit particular binding affinities. In some aspects, the provided antibodies can bind to an epitope that is different from epitopes of other antibodies, e.g., binding a conformational epitope.

In some embodiments, the provided antibodies or antigen-binding fragment thereof specifically bind to a receptor tyrosine kinase-like orphan receptor 1 (ROR1) protein. In some of any of the embodiments provided herein, ROR1 refers to human ROR1. The observation that an antibody or other binding molecule binds to ROR1 or specifically binds to ROR1 does not necessarily mean that it binds to ROR1 from every species. For example, in some embodiments, features of binding to ROR1, such as the ability to specifically bind thereto and/or to compete for binding thereto with a reference antibody, and/or to bind with a particular affinity or compete to a particular degree, in some embodiments, refers to the ability with respect to a human ROR1 protein and the antibody may not have this feature with respect to a ROR1 of another species such as mouse. In some embodiments, the antibody binds to human ROR1 and binds to ROR1 of another species, such as *Rhesus macaque* or cynomolgus macaque. In some embodiments, the antibody or an antigen-binding fragment thereof binds to human ROR1 and does not bind to ROR1 of another species, such as mouse. In some embodiments, the antibody binds to human ROR1 and binds to ROR1 of another species, such as mouse.

In some embodiments, the antibodies, such as the anti-ROR1 antibodies, e.g., the human antibodies, specifically bind to a particular epitope or region of ROR1, such as generally an extracellular epitope or region. ROR1 is a type I membrane protein that contains an extracellular region containing an immunoglobulin (Ig) domain, a frizzled (Fz) domain and a kringle (Kr) domain followed by a transmembrane domain. With reference to human ROR1 set forth in SEQ ID NO:144 (GenBank No. AAA60275.1; sequence including the signal peptide set forth in SEQ ID NO:215, Uniprot No. Q01973), the extracellular region corresponds to amino acids 1-377, amino acids 13-118 correspond to the Ig domain, amino acids 136-270 correspond to the Fz domain and amino acids 283-362 correspond to the Kr domain (corresponding to amino acids 42-147 for the Ig domain, amino acids 165-299 for the Fz domain and amino acids 312-391 for the Kr domain with reference to amino acid sequence set forth in SEQ ID NO:215). In some embodiments, the antibodies, such as human antibodies, bind to an epitope comprising residues within the Ig domain, the Fz domain and/or the Kr domain. In some embodiments, the antibodies, such as human antibodies, bind to an epitope comprising residues with the Ig domain and/or Fz domain. In some embodiments, the antibodies, such as human antibodies, bind to an epitope comprising residues within both the Ig and Fz domains.

In some embodiments, the antibodies or antigen-binding fragment thereof bind, such as specifically bind, to human ROR1, such as to one or more epitopes or region of human ROR1, such as the human ROR1 set forth in SEQ ID NO:144 (GenBank No. AAA60275.1; sequence including the signal peptide set forth in SEQ ID NO:215, Uniprot No. Q01973), or an allelic variant or splice variant thereof. In some embodiments, the antibodies or antigen-binding fragment thereof specifically binds to one or more epitopes within a human ROR1 protein. In one embodiment, human ROR1 is a transcript variant or isoform that has the sequence of amino acids forth in SEQ ID NO:145 or 146. In some embodiments, human ROR1 protein comprises an amino acid sequence set forth in SEQ ID NO: 144, 145, 146 or 215. In some embodiments, the antibodies or antigen-binding fragment thereof bind to the extracellular region ROR1, such as to one or more extracellular epitopes present within the extracellular region of human ROR1, e.g., corresponding to residues 1-377 of the human ROR1 sequence set forth in SEQ ID NO:144 (corresponding to residues 30-406 of the human ROR1 sequence set forth in SEQ ID NO:215 that includes the signal peptide).

In some embodiments, the antibodies or antigen-binding fragment thereof bind one or more epitope of ROR1, such as a human ROR1. In some embodiments, the antibodies or antigen-binding fragment thereof bind a linear epitope of ROR1, such as a human ROR1. In some embodiments, the antibodies or antigen-binding fragment thereof bind one or more conformational epitopes of ROR1, such as a human ROR1.

In some embodiments, the antibodies or antigen-binding fragment thereof bind one or more epitopes of human ROR1, such as one or more epitopes comprising or consisting of an amino acid sequence selected from among any one of SEQ ID NOS: 199-214, or one or more epitopes present within an amino acid sequence selected from among any one of SEQ ID NOS: 199-214. In some embodiments, the antibodies or antigen-binding fragment thereof bind one or more epitopes of human ROR1, such as one or more epitopes that include the sequence FRSTIYGSRLRIRNL (set forth in SEQ ID NO:199). In some embedment's, the anti-ROR1 antibody or antigen-binding fragment thereof specifically binds to an epitope consisting of the sequence set forth in SEQ ID NO:199 or an epitope present within the sequence set forth in SEQ ID NO:199. In some embodiments, the antibodies or antigen-binding fragment thereof bind additional epitopes, such as one or more conformational epitopes. In some embodiments, the antibodies or antigen-binding fragment thereof bind additional epitopes, in addition to the sequence FRSTIYGSRLRIRNL (set forth in SEQ ID NO:199). Exemplary of one or more additional epitopes include, but are not limited to, one or more of the sequences set forth in SEQ ID NO:200-214 or one or more epitopes present within an amino acid sequence selected from among any one of SEQ ID NOS: 200-214.

In some embodiments, the antibody binds to non-human ROR1, such as *Rhesus macaques* (*Macaca mulatta*) ROR1 (set forth in SEQ ID NO:216, Uniprot No. F6RUP2) or cynomolgus macaques (*Macaca fasicularis*) ROR1 (set forth in SEQ ID NO:217, Uniprot No. A0A2K5WTX7; or SEQ ID NO:218, Uniprot No. A0A2K5WTX4). In some aspects, the extracellular domain of the non-human ROR1 is at least 99% identical to the human ROR1 sequence.

In some embodiments, the antibody binds to non-human ROR1, such as monkey, rabbit, rat, mouse, or other species of ROR1. In some embodiments, the antibody binds to mouse (*Mus musculus*) ROR1, such as to an epitope or region of mouse ROR1, such as the mouse ROR1 set forth in SEQ ID NO: 171 (GenBank No. NP_038873; sequence including the signal peptide set forth in SEQ ID NO:219, Uniprot No. Q9Z139). In some embodiments, the antibody binds to human ROR1 and binds to mouse ROR1. In some embodiments, the extent of binding of some of the provided anti-ROR1 antibodies or fragments thereof to a non-human ROR1, such as mouse ROR1, is at least at or about 75%, 80%, 90%, 95%, 100%, 110%, 120%, 130%, 140%, 150% or more of the binding of the antibody to human ROR1.

In some of any of the provided embodiments, the antibody or antigen-binding fragment thereof does not bind to, is not cross-reactive to, or binds at a lower extent, level or degree or affinity to a non-human ROR1, optionally a mouse ROR1. In some embodiments, the extent of binding of an anti-ROR1 antibody to an unrelated, non-ROR1 protein or to a non-human ROR1 protein, such as a mouse ROR1 protein, or other non-ROR1 protein, is less than at or about 50%, 40%, 30%, 20% or 10% of the binding of the antibody to human ROR1 as measured. In some embodiments, the antibodies or antigen-binding fragments thereof do not bind to mouse ROR1, such as the mouse ROR1 set forth in SEQ ID NO:171 or 219. In some embodiments, the antibodies or antigen-binding fragments do not bind to, is not cross-reactive to, or binds at a lower level or degree or affinity to a mouse ROR1. In some embodiments, the extent, level or degree or affinity of binding of the provided anti-ROR1 antibody or antigen-binding fragment thereof to a mouse ROR1 is at least at or about 75%, 80%, 90%, 95% or 99% less than the extent, level or degree or affinity of binding to a human ROR1.

In some of any of the provided embodiments, the antibody or antigen-binding fragment thereof does not bind to, is not cross-reactive to, or binds at a lower extent, level or degree or affinity to a receptor tyrosine kinase-like orphan receptor 2 (ROR2) protein, optionally a human ROR2 protein. In some embodiments, the extent of binding of some of the provided anti-ROR1 antibodies or fragments thereof to a non-ROR1 protein, such as a ROR2 protein, is at least at or about 75%, 80%, 90%, 95% or 99% less than the binding of the antibody to human ROR1. In some embodiments, the provided antibody or antigen-binding fragment thereof does not bind to, is not cross-reactive to, or binds at a lower level or degree or affinity to a ROR2 protein, optionally a human ROR2 protein. In some embodiments, among provided antibodies are antibodies in which binding to mouse ROR1 is less than or at or about 30%, 20% or 10%, such as less than at or about 10%, of the binding of the antibody to human ROR1. In some embodiments, among provided antibodies are antibodies in which binding to a ROR2, such as a human ROR2, is less than or at or about 30%, 20% or 10%, such as less than at or about 10%, of the binding of the antibody to human ROR1.

In some embodiments, the provided antibodies are capable of binding ROR1, such as human ROR1, with at least a certain affinity, as measured by any of a number of known methods. In some embodiments, the affinity is represented by an equilibrium dissociation constant ($K_D$). In some embodiments, the affinity is represented by $EC_{50}$.

A variety of assays are known for assessing binding affinity, equilibrium dissociation constant ($K_D$), equilibrium association constant ($K_A$), $EC_{50}$, on-rate (association rate constant; $k_{on}$ or $k_a$; units of 1/Ms or $M^{-1}s^{-1}$) and the off-rate (dissociation rate constant; $k_{off}$ or $k_d$; units of 1/s or $s^{-1}$) and/or determining whether a binding molecule (e.g., an antibody or fragment thereof) specifically binds to a particular ligand (e.g., an antigen, such as a ROR1 protein). One can determine the binding affinity of a binding molecule, e.g., an antibody or an antigen-binding fragment thereof, for an antigen, e.g., ROR1, such as human ROR1 or cynomolgus ROR1 or mouse ROR1, such as by using any of a number of binding assays that are well known. For example, in some embodiments, a BIAcore® instrument can be used to determine the binding kinetics and constants of a complex between two proteins (e.g., an antibody or fragment thereof, and an antigen, such as a ROR1 protein), using surface plasmon resonance (SPR) analysis (see, e.g., Scatchard et al., *Ann. N.Y. Acad. Sci.* 51:660, 1949; Wilson, *Science* 295:2103, 2002; Wolff et al., *Cancer Res.* 53:2560, 1993; and U.S. Pat. Nos. 5,283,173, 5,468,614, or the equivalent).

SPR measures changes in the concentration of molecules at a sensor surface as molecules bind to or dissociate from the surface. The change in the SPR signal is directly proportional to the change in mass concentration close to the surface, thereby allowing measurement of binding kinetics between two molecules. The dissociation rate constant ($k_{off}$ or $k_d$), the association rate constant ($k_{on}$ or $k_a$) and/or equilibrium dissociation constant ($K_D$) and/or equilibrium association constant ($K_A$) for the complex can be determined by monitoring changes in the refractive index with respect to time as buffer is passed over the chip. Other suitable assays for measuring the binding of one protein to another include, for example, immunoassays such as enzyme linked immunosorbent assays (ELISA) and radioimmunoassays (RIA), or determination of binding by monitoring the change in the spectroscopic or optical properties of the proteins through fluorescence, UV absorption, circular dichroism, or nuclear magnetic resonance (NMR). Other exemplary assays include, but are not limited to, Western blot, ELISA, analytical ultracentrifugation, spectroscopy, flow cytometry, sequencing, genetic reporter assays, flow cytometry, and other methods for detection of expressed nucleic acids or binding of proteins.

In some embodiments, the binding molecule, e.g., antibody or fragment thereof, binds, such as specifically binds, to an antigen, e.g., a ROR1 protein or an epitope therein, with an affinity or $K_A$ (i.e., an equilibrium association constant of a particular binding interaction with units of 1/M or $M^{-1}$; equal to the ratio of the on-rate [$k_{on}$ or $k_a$] to the off-rate [$k_{off}$ or $k_d$] for this association reaction, assuming bimolecular interaction) equal to or greater than $10^5$ $M^{-1}$. In some embodiments, the peptide binding molecule binds, such as specifically binds, to an epitope of an antigen, e.g., human ROR1, with an affinity or $K_A$ (i.e., an equilibrium association constant of a particular binding interaction with units of 1/M or $M^{-1}$) equal to or greater than $10^5$ $M^{-1}$ (which equals the ratio of the on-rate [$k_{on}$] to the off-rate [$k_{off}$] for this association reaction). In some embodiments, the binding molecule, e.g., antibody or antigen-binding fragment thereof, exhibits a binding affinity for a T cell epitope of the target polypeptide with an affinity or $K_A$ ranging from at or about $10^6$ $M^{-1}$ to at or about $10^{10}$ $M^{-1}$, such as from at or about $10^6$ $M^{-1}$ to at or about $10^9$ $M^{-1}$, or from at or about $10^6$ $M^{-1}$ to at or about $10^8$ $M^{-1}$. In some embodiments, binding affinity may be classified as high affinity or as low affinity. For example, in some cases, a binding molecule, e.g., antibody or antigen-binding fragment thereof, that exhibits high affinity binding to a particular epitope interacts with such epitope with a $K_A$ of at least at or about $10^7$ $M^{-1}$, at least at or about $10^8$ $M^{-1}$, at least at or about $10^9$ $M^{-1}$, at least at or about $10^{10}$ $M^{-1}$, at least at or about $10^{-11}$ $M^{-1}$, at least at or about $10^{12}$ $M^{-1}$, or at least at or about $10^{13}$ $M^{-1}$. In some cases, a binding molecule, e.g., antibody or antigen-binding fragment thereof, that exhibits low affinity binding exhibits a $K_A$ of up to $10^7$ $M^{-1}$, up to $10^6$ $M^{-1}$, up to $10^5$ $M^{-1}$.

Alternatively, affinity can be defined as an equilibrium dissociation constant ($K_D$) of a particular binding interaction with units of M (e.g., $10^{-5}$ M to $10^{-13}$ M). In some embodiments, the antibody or fragment thereof exhibits a binding affinity for the epitope with a $K_D$ (i.e., an equilibrium dissociation constant of a particular binding interaction with units of M; equal to the ratio of the off-rate [$k_{off}$ or $k_d$] to the on-rate [$k_{on}$ or $k_d$] for this association reaction, assuming bimolecular interaction) of equal to or less than $10^{-5}$ M. For example, the equilibrium dissociation constant $K_D$ can range from $10^{-5}$ M to $10^{-13}$ M, such as $10^{-7}$ M to $10^{-11}$ M, $10^{-7}$ M to $10^{-10}$ M, $10^{-7}$ M to $10^{-9}$ M, $10^{-8}$ M to $10^{-10}$ M, or $10^{-9}$ M to $10^{-10}$ M.

The on-rate (association rate constant; $k_{on}$ or $k_a$; units of 1/Ms or $M^{-1}$ $s^{-1}$) and the off-rate (dissociation rate constant; $k_{off}$ or $k_d$; units of 1/s or $s^{-1}$) can be determined using any of the known assay methods, for example, surface plasmon resonance (SPR), or other methods described herein for measuring the binding of one protein to another.

In some embodiments, the binding affinity ($EC_{50}$) and/or the equilibrium dissociation constant ($K_D$) of the antibody to ROR1, such as human ROR1, is from at or about 0.1 nM to at or about 500 nM, from at or about 0.1 nM to at or about 100 nM, from at or about 0.1 nM to at or about 50 nM, from at or about 0.1 nM to at or about 10 nM, from at or about 0.1 nM to at or about 1 nM, from at or about 1 nM to at or about 500 nM, from at or about 1 nM to at or about 100 nM, from at or about 1 nM to at or about 50 nM, from at or about 1 nM to at or about 10 nM, from at or about 10 nM to at or about 500 nM, from at or about 10 nM to at or about 100 nM, from at or about 10 nM to at or about 50 nM, from at or about 50 nM to at or about 500 nM, from at or about 50 nM to at or about 100 nM or from at or about 100 nM to at or about 500 nM. In certain embodiments, the binding affinity ($EC_{50}$) and/or the equilibrium dissociation constant ($K_D$) of the antibody to ROR1, such as human ROR1, is at or about or less than at or about 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM, or a range defined by any of the foregoing. In some embodiments, the antibodies bind to ROR1, such as human ROR1, with a sub-nanomolar binding affinity, for example, with a binding affinity less than at or about 1 nM, such as less than at or about 0.9 nM, 0.8 nM, 0.7 nM, 0.6 nM, 0.5 nM, 0.4 nM, 0.3 nM, 0.2 nM or 0.1 nM. In some embodiments, the binding affinity ($EC_{50}$) and/or the equilibrium dissociation constant, $K_D$, of the binding molecule, e.g., anti-ROR1 antibody or fragment thereof, to a ROR1 protein, such as a human ROR1 protein, is from at or about 0.01 nM to about 1 μM, 0.1 nM to 1 μM, 1 nM to 1 μM, 1 nM to 500 nM, 1 nM to 100 nM, 1 nM to 50 nM, 1 nM to 10 nM, 10 nM to 500 nM, 10 nM to 100 nM, 10 nM to 50 nM, 50 nM to 500 nM, 50 nM to 100 nM or 100 nM to 500 nM. In certain embodiments, the binding affinity ($EC_{50}$) and/or the equilibrium dissociation constant, $K_D$, of the binding molecule, e.g., anti-ROR1 antibody or fragment thereof, to a ROR1 protein, such as a human ROR1 protein, is at or about or less than at or about 1 µM, 500 nM, 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM or less, or a range defined by any of the foregoing.

In some embodiments, the $EC_{50}$ and/or the $K_D$ of the binding molecule, e.g., anti-ROR1 antibody or fragment thereof, to a ROR1 protein, is between at or about 10 nM and at or about 90 nM, between at or about 20 nM and at or about 80 nM, between at or about 30 nM and at or about 70 nM, between at or about 40 nM and at or about 60 nM, or between at or about 40 nM and at or about 50 nM. In certain embodiments, the $EC_{50}$ and/or the $K_D$ of the binding molecule, e.g., anti-ROR1 antibody or fragment thereof, to a ROR1 protein, such as a human ROR1 protein, is at or about 10 nM, 20 nM, 30 nM, 40 nM, 50 nM, 60 nM, 70 nM, 80 nM, 90 nM or 100 nM, or a range defined by any of the foregoing. In certain embodiments, the $EC_{50}$ and/or the $K_D$ of the binding molecule, e.g., anti-ROR1 antibody or fragment thereof, to a ROR1 protein, such as a human ROR1 protein, is at or about 10 nM, 20 nM, 30 nM, 40 nM, 50 nM, 60 nM, 70 nM, 80 nM, 90 nM or 100 nM, or a range defined by any of the foregoing. In certain embodiments, the $EC_{50}$ and/or the $K_D$ of the binding molecule, e.g., anti-ROR1 antibody or fragment thereof, to a ROR1 protein, such as a human ROR1 protein, is at or about 40 nM, 41 nM, 42 nM, 43 nM, 44 nM, or 45 nM, or a range defined by any of the foregoing.

In some embodiments, the $V_H$ region of the provided binding molecules comprises a CDR-H1, a CDR-H2 and a CDR-H3 contained within SEQ ID NO:112, and the $V_L$ region of the provided binding molecules comprises a CDR-L1, a CDR-L2 and a CDR-L3 contained within SEQ ID: NO 115 and the equilibrium dissociation constant ($K_D$) for human ROR1 is between at or about 30 nM and at or about 50 nM. In some embodiments, the $V_H$ region and the $V_L$ region of the provided binding molecules are or comprise the sequence set forth in SEQ ID NOS: 112 and 115, respectively, and the off-rate ($k_{off}$ or $k_d$) for human ROR1 is at or about 40 nM.

In some embodiments, the provided binding molecule, e.g., anti-ROR1 antibody or antigen-binding fragment thereof or receptors containing such antibody or antigen-binding fragments, has a fast off-rate (dissociation rate constant; $k_{off}$ or Ica; units of 1/s or $s^{-1}$). In some embodiments, the off-rate ($k_{off}$ or $k_d$) of the provided binding molecules is between at or about $1\times10^{-5}$ $s^{-1}$ and at or about $1\times10^{-2}$ $s^{-1}$, such as at or about $5\times10^{-5}$ $s^{-1}$ and at or about $9\times10^{-3}$ at or about $1\times10$ $s^{-1}$ and at or about $8\times10^{-3}$ $s^{-1}$, at or about $5\times10^{-4}$ $s^{-1}$ and at or about $7\times10^{-3}$ $s^{-1}$, at or about $1\times10^{-3}$ $s^{-1}$ and at or about $6\times10^{-3}$ $s^{-1}$, and at or about $4\times10^{-3}$ $s^{-1}$ and at or about $6\times10^{-3}$ $s^{-1}$. In some embodiments, the off-rate ($k_{off}$ or $k_d$) of the provided binding molecules is at least at or about $1\times10^{-5}$ $s^{-1}$, $5\times10^{-5}$ $s^{-1}$, $1\times10^{-4}$ $s^{-1}$, $5\times10^{-4}$ $s^{-1}$, $1\times10^{-3}$ $s^{-1}$, $5\times10^{-3}$ $s^{-1}$, or $1\times10^{-2}$ $s^{-1}$. In some embodiments, the off-rate ($k_{off}$ or $k_d$) of the provided binding molecules is at least at or about $6\times10^{-4}$ $s^{-1}$, $7\times10^{-4}$ $s^{-1}$, $8\times10^{-4}$ $s^{-1}$, $9\times10^{-4}$ $s^{-1}$, $1\times10^{-3}$ $s^{-1}$, $2\times10^{-3}$ $s^{-1}$, $3\times10^{-3}$ $s^{-1}$, $4\times10^{-3}$ $s^{-1}$, $5\times10^{-3}$ $s^{-1}$, $6\times10^{-3}$ $s^{-1}$, $7\times10^{-3}$ $s^{-1}$, $8\times10^{-3}$ $s^{-1}$, $9\times10^{-3}$ $s^{-1}$ or $1\times10^{-2}$ $s^{-1}$. In some embodiments, the off-rate ($k_{off}$ or $k_d$) of the provided binding molecules is at least at or about $4\times10^{-3}$ $s^{-1}$, $5\times10^{-3}$ $s^{-1}$ or $6\times10^{-3}$ $s^{-1}$, or a range defined by any of the foregoing. In some embodiments, the provided binding molecule, e.g., anti-ROR1 antibody or antigen-binding fragment thereof or receptors containing such antibody or antigen-binding fragments, has an off-rate that is at least at or about 2-fold, 3-fold, 4-fold, 5-fold, 6-fold, 7-fold, 8-fold, 9-fold or 10-fold faster than the off-rate of a reference anti-ROR1 antibody or an antigen-binding fragment thereof, or receptors containing such antibody or antigen-binding fragments, for example, anti-ROR1 antibody R12.

In some embodiments, the $V_H$ region of the provided binding molecules comprises a CDR-H1, a CDR-H2 and a CDR-H3 contained within SEQ ID NO:112, and the $V_L$ region of the provided binding molecules comprises a CDR-L1, a CDR-L2 and a CDR-L3 contained within SEQ ID: NO 115 and the off-rate ($k_{off}$ or $k_d$) for human ROR1 is between at or about $4\times10^{-3}$ $s^{-1}$ and at or about $6\times10^{-3}$ $s^{-1}$. In some embodiments, the $V_H$ region and the $V_L$ region of the provided binding molecules are or comprise the sequence set forth in SEQ ID NOS: 112 and 115, respectively, and the off-rate ($k_{off}$ or $k_d$) for human ROR1 is at or about $5\times10^{-3}$ $s^{-1}$.

In some embodiments, the binding affinity of a binding molecule, such as an anti-ROR1 antibody, for different antigens, e.g., ROR1 proteins from different species can be compared to determine the species cross-reactivity. For example, species cross-reactivity can be classified as high cross reactivity or low cross reactivity. In some embodiments, the equilibrium dissociation constant, $K_D$, for different antigens, e.g., ROR1 proteins from different species such as human, cynomolgus monkey or mouse, can be compared to determine species cross-reactivity. In some embodiments, the species cross-reactivity of an anti-ROR1 antibody can be high, e.g., the anti-ROR1 antibody binds to human ROR1 and a species variant ROR1 to a similar degree, e.g., the ratio of $K_D$ for human ROR1 and $K_D$ for the species variant ROR1 is or is about 1. In some embodiments, the species cross-reactivity of an anti-ROR1 antibody can be low, e.g., the anti-ROR1 antibody has a high affinity for human ROR1 but a low affinity for a species variant ROR1, or vice versa. For example, the ratio of $K_D$ for the species variant ROR1 and $K_D$ for the human ROR1 is more than 10, 15, 20, 25, 30, 40, 50, 60, 70, 80, 90, 100, 200, 500, 1000, 2000 or more, and the anti-ROR1 antibody has low species cross-reactivity. The degree of species cross-reactivity can be compared with the species cross-reactivity of a known antibody, such as a reference antibody.

In some embodiments, the provided antibodies or antigen binding fragments thereof bind to a similar degree to a human ROR1 protein and a non-human ROR1 protein. For example, in some embodiments, the provided antibodies or antigen binding fragments thereof bind to a human ROR1 protein, or an allelic variant or splice variant thereof, with a specific an equilibrium dissociation constant ($K_D$), and to a non-human ROR1, such as a cynomolgus monkey ROR1, with a Kr) that is similar, or about the same, or less than 2-fold different, or less than 5-fold different.

For example, in some embodiments, the provided antibodies or antigen binding fragments thereof bind to a human ROR1 with a $K_D$ of about or less than at or about 1 µM, 500 nM, 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM or less, and binds to a cynomolgus monkey ROR1 with a $K_D$ of about or less than at or about 1 µM, 500 nM, 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM or less. In some embodiments, the provided antibodies or antigen binding fragments thereof bind to a mouse ROR1 protein with a $K_D$ of about or less than at or about 1 µM, 500 nM, 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM or less. In some embodiments, the provided antibodies or antigen binding fragments thereof bind to a human ROR1, a cynomolgus monkey ROR1 and a mouse ROR1 with high affinity. In some embodiments, the provided antibodies or antigen binding fragments thereof bind to a human ROR1 and cynomolgus monkey ROR1 with a high affinity, and to a mouse ROR1 with low affinity. In some embodiments, the provided antibodies or antigen binding fragments thereof bind to a human ROR1 and ROR1 from other species, or other variants of the ROR1 protein, with high affinity.

In some embodiments, the total binding capacity ($R_{max}$), as measured using particular surface plasmon resonance (SPR) conditions, is used to determine the ability or capacity of binding of the provided antibody or antigen binding fragment thereof, to the antigen, e.g., a ROR1 protein, such as a human ROR1 protein. For SPR analysis, the "ligand" is the immobilized target molecule on the surface of the sensor, for example, a ROR1 protein, and the "analyte" is the tested molecule, e.g., antibody, for binding to the "ligand". For example, the "analyte" can be any of the provided antibodies or antigen binding fragments thereof, that binds to a ROR1 protein. For a particular ligand and analyte pair in SPR, the $R_{max}$ can be determined assuming a 1:1 binding stoichiometry model, for a particular condition. In some embodiments, binding capacity ($R_{max}$) can be determined using the following formula: $R_{max}$ (RU)=(analyte molecular weight)/(ligand molecular weight)×immobilized ligand level (RU). In particular aspects of SPR conditions, the $R_{max}$ of binding between any of the provided antibody or antigen binding fragment thereof and a ROR1 protein, such as a human ROR1 or a cynomolgus ROR1, is at least or at least about 50 resonance units (RU), such as about 25 RU, 20 RU, 15 RU, 10 RU, 5 RU or 1 RU.

In some embodiments, properties or features of the provided antibodies are described in relation to properties observed for another antibody, e.g., a reference antibody. In some embodiments, the reference antibody is a non-human anti-ROR1 antibody, such as a rabbit or chimeric or humanized anti-ROR1 antibody. In some aspects, the reference antibody is the chimeric rabbit/human IgG1 antibody designated R12 (see, e.g., Yang et al. (2011) PloS ONE, 6:e21018; U.S. Patent Application No. US 2013/0251642), and/or a fragment derived therefrom such as an scFv fragment thereof, and/or an antibody containing the $V_H$ and $V_L$ sequences of such an antibody and/or the heavy and light chain CDRs of such an antibody. A chimeric antigen receptor (CAR) containing an antigen-binding scFv fragment of R12 has been demonstrated to effectively promote antitumor reactivity in a CAR therapy (Hudecek et al. (2013) Clin. Cancer Res., 19:3153; International published PCT Appl. No. WO2014031687). In some embodiments, the reference antibody is an scFv that comprises the sequence of amino acids set forth in SEQ ID NO:142.

In some embodiments, the reference antibody is the mouse anti-human ROR1 antibody designated 2A2, and/or a fragment derived therefrom such as an scFv fragment thereof, and/or an antibody containing the $V_H$ and $V_L$ sequences of such an antibody and/or the heavy and light chain CDRs of such an antibody (see, e.g., Baskar et al. (2012) MAbs, 4:349-361; published U.S. Patent Appl. No. US2012/20058051). For example, in some embodiments, the reference antibody has a $V_H$ region containing the sequence set forth in SEQ ID NO: 172 and a $V_L$ containing the sequence set forth in SEQ ID NO: 173. In some embodiments, the reference antibody is an scFv form of antibody 2A2.

In some embodiments, the reference antibody is a human or humanized anti-ROR1 antibody. Exemplary humanized anti-ROR1 antibodies are described in International PCT Appl. No. WO2014/031174. In some embodiments, the reference antibody is a humanized variant of an antibody designated 99961. In some embodiments, the reference antibody has a $V_H$ region containing the sequence set forth in SEQ ID NO: 174, 175, 176 or 177 and a $V_L$ containing the sequence set forth in SEQ ID NO: 178, 179, 180 or 181.

In some embodiments, the provided antibody contains heavy and light chain CDRs that are distinct from the CDRs present in the reference antibody or antibodies. Among the provided antibodies are those that compete for binding with and/or bind to the same or overlapping epitopes of ROR1 as those bound by a reference antibody or antibody, such as R12, but nonetheless contain distinct CDRs, e.g., distinct heavy and/or light chain CDR1, CDR2, and CDR3.

In some embodiments, the antibody has an affinity that is about the same as or lower than that of the corresponding form of the reference antibody, e.g., $EC_{50}$ or $K_D$ that is no more than at or about 1.5-fold or no more than at or about 2-fold greater, no more than at or about 3-fold greater, and/or no more than at or about 10-fold greater, than the $EC_{50}$ or $K_D$ of the corresponding form of the reference antibody. In some embodiments, the antibody has an affinity that is about the same as or lower than that of the corresponding form of the reference antibody, e.g., $EC_{50}$ or $K_D$ that is at least at or about 1.5-fold greater, at least at or about 2-fold greater, at least at or about 3-fold greater, at least at or about 5-fold greater, at least at or about 10-fold greater, at least at or about 20-fold greater, at least at or about 25-fold greater, at least at or about 30-fold greater, at least at or about 40-fold greater, at least at or about 50-fold greater, or at least at or about 100-fold greater, than the $EC_{50}$ or $K_D$ of the corresponding form of the reference antibody. In some embodiments, the antibody has an affinity that is about the same as or lower than that of the corresponding form of the reference antibody, an affinity that is at or about 1.5-fold, 2-fold, 3-fold, 4-fold, 5-fold, 6-fold, 7-fold, 8-fold, 9-fold, 10-fold, 20-fold, 25-fold, 30-fold, 40-fold, 50-fold or 100-fold lower than the affinity of the reference antibody.

In some embodiments, the antibody has an affinity that is greater than that of the corresponding form of the reference antibody, e.g., $EC_{50}$ or $K_D$ that is lower than or lower than at or about 5-fold, 10-fold, 20-fold, 30-fold, 40-fold, 50-fold, 60-fold, 70-fold, 80-fold, 90-fold, 100-fold, 150-fold, 200-fold, 250-fold or lower than the $EC_{50}$ or $K_D$ of the corresponding form of the reference antibody.

In some embodiments, the antibodies display a binding preference for ROR1-expressing cells as compared to ROR1-negative cells, such as particular cells known and/or described herein to express ROR1 and known not to express ROR1, or expressing a related but different antigen, e.g., ROR2. In some embodiments, the binding preference is observed where a significantly greater degree of binding is measured to the ROR1-expressing, as compared to the non-expressing, cells or cells expressing a related but different antigen. In some embodiments, the fold change in degree of binding detected, for example, as measured by mean fluorescence intensity in a flow cytometry-based assay and/or dissociation constant or $EC_{50}$, to the ROR1-expressing cells as compared to the non-ROR1-expressing cells or cells expressing a related but different antigen, is at least at or about 1.5, 2, 3, 4, 5, 6, or more, and/or is about as great, about the same, at least as great or at least about as great, or greater, than the fold change observed for the corresponding form of the reference antibody. In some cases, the total degree of observed binding to ROR1 or to the ROR1-expressing cells is approximately the same, at least as great, or greater than that observed for the corresponding form of the reference antibody.

In some aspects, the affinity is at or about the same degree or substantially the same degree of affinity compared to the corresponding form of the reference antibody, such as rabbit ROR1 antibody. In some aspects, the affinity is at least at or about 80, 85, 90, 95, or 99% of or the same as that of the corresponding form of the reference antibody.

In some embodiments, the antibody specifically binds to an epitope that overlaps with the epitope of ROR1 bound by a reference antibody. In some aspects, among such antibodies are antibodies that bind to the same or a similar epitope as the reference antibody. In some embodiments, the antibodies bind to the same or a similar epitope or an epitope within the same region or containing residues within the same region of ROR1 as a reference antibody, such as anti-ROR1 antibody R12 or scFv fragment thereof (set forth in SEQ ID NO: 142; see e.g. Yang et al. (2011) PloS ONE, 6:e21018). In some embodiments, the antibody inhibits binding to and/or competes for binding to ROR1, such as human ROR1, with the reference antibody.

Competitive inhibition assays are known and include ELISA-based, flow cytometry-based assays, and RIA-based assays. In some aspects, competitive inhibition assays are carried out by incorporating an excess of an unlabeled form of one of the antibodies and assessing its ability to block binding of the other antibody, which is labeled with a detectable marker, such that degree of binding and reduction thereof can be assessed by detection of the label or marker. In some embodiments, addition of the provided antibody in excess, e.g., 1-, 2-, 5-, 10-, 50- or 100-fold excess, as compared to the amount or concentration of the reference antibody, inhibits binding to the antigen by the reference antibody (or vice versa). In some embodiments, the inhibition of binding is by at least 50%, and in some embodiments by at least 75%, 90% or 99%. In some aspects, the competitive inhibition is as measured in a competitive binding assay (see, e.g., Junghans et al., Cancer Res. 1990:50:1495-1502). Competition assays may be used to identify an antibody that competes with any of the antibodies described herein. Assays for mapping epitopes bound by the antibodies and reference antibodies also may be used and are known.

In some embodiments, where the reference antibody is present at a concentration of or of about 2 nM, the provided antibody inhibits binding of the reference antibody with an $IC_{50}$ of less than at or about 200 nM, 150 nM, 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, or 10 nM, or less than at or about 9 nM, 8 nM, 7 nM, 6 nM, or 5 nM. In some embodiments, where the provided antibody is present at a concentration of or about 2 nM, the reference antibody inhibits binding of the provided antibody with an $IC_{50}$ of less than at or about 200 nM, 150 nM, 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, or 10 nM, or less than at or about 9 nM, 8 nM, 7 nM, 6 nM, or 5 nM. In some embodiments, competitive inhibition of the reference antibody's binding by the provided antibody (or vice versa) is at or about at least at or about the same degree as the degree of competitive inhibition of the reference antibody's binding by the reference antibody itself, e.g., unlabeled reference antibody. In some embodiments, the provided antibody inhibits binding of the reference antibody, such as binding of R12 scFv, to human ROR1 by at least 70%, 75%, 80%, 85%, 90%, 91%, 92%, 93%, 94%, 95%, 96%, 97%, 98%, or 99%.

Anti-ROR1 antibodies provided herein may be identified, screened for, or characterized for their physical/chemical properties and/or biological activities by various known assays. In one aspect, the antibody is tested for its antigen binding activity, e.g., by known methods such as ELISA, Western blotting, and/or flow cytometric assays, including cell-based binding assays, for example, assessing binding of the antibody (e.g., conjugated to a fluorescent marker or tagged) to a cell expressing the target antigen, e.g., ROR1, in some cases compared to results using cells that do not express the target antigen, e.g., ROR1, or cells that express a different antigen, e.g., ROR2. Binding affinity may be measured as $K_D$, $K_A$ or $EC_{50}$.

3. Variants

In certain embodiments, the antibodies include one or more amino acid variations, e.g., substitutions, deletions, insertions, and/or mutations, compared to the sequence of an antibody described herein. Exemplary variants include those designed to improve the binding affinity and/or other biological properties of the antibody Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In certain embodiments, the antibodies include one or more amino acid substitutions, e.g., as compared to an antibody sequence described herein and/or compared to a sequence of a natural repertoire, e.g., human repertoire. Sites of interest for substitutional mutagenesis include the CDRs and FRs Amino acid substitutions may be introduced into an antibody of interest and the products screened for a desired activity, e.g., retained/improved antigen binding, decreased immunogenicity, improved half-life, and/or improved effector function, such as the ability to promote antibody-dependent cellular cytotoxicity (ADCC) or complement-dependent cytotoxicity (CDC).

In some embodiments, one or more residues within a CDR of a parent antibody (e.g. a humanized or human antibody) is/are substituted. In some embodiments, the substitution is made to revert a sequence or position in the sequence to a germline sequence, such as an antibody sequence found in the germline (e.g., human germline), for example, to reduce the likelihood of immunogenicity, e.g., upon administration to a human subject.

In some embodiments, alterations are made in CDR "hotspots," residues encoded by codons that undergo mutation at high frequency during the somatic maturation process (see, e.g., Chowdhury, Methods Mol. Biol. 207:179-196 (2008)), and/or residues that contact antigen, with the resulting variant $V_H$ or $V_L$ being tested for binding affinity. Affinity maturation by constructing and reselecting from secondary libraries has been described, e.g., in Hoogenboom et al. in Methods in Molecular Biology 178:1-37 (O'Brien et al., ed., Human Press, Totowa, NJ, (2001)). In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves CDR-directed approaches, in which several CDR residues (e.g., 4-6 residues at a time) are randomized. CDR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in CDRs. Such alterations may, for example, be outside of antigen contacting residues in the CDRs. In certain embodiments of the variant $V_H$ and $V_L$ sequences provided above, each CDR either is unaltered, or contains no more than one, two or three amino acid substitutions.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme or a polypeptide which increases the serum half-life of the antibody.

4. Modifications

In certain embodiments, the antibody is altered to increase or decrease the extent to which the antibody is glycosylated, for example, by removing or inserting one or more glycosylation sites by altering the amino acid sequence and/or by modifying the oligosaccharide(s) attached to the glycosylation sites, e.g., using certain cell lines.

In some embodiments, an N-linked glycosylation, which is a glycosylation site that occurs at asparagines in the consensus sequence -Asn-Xaa-Ser/Thr is removed or inserted. In some embodiments, one or more re replaced with another amino acid to remove the glycosylation site.

Exemplary modifications, variants, and cell lines are described, e.g., in Patent Publication Nos. US 2003/0157108, US 2004/0093621, US 2003/0157108; WO 2000/61739; WO 2001/29246; US 2003/0115614; WO 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336:1239-1249 (2004); Yamane-Ohnuki et al. Biotech. Bioeng. 87: 614 (2004). Ripka et al. Arch. Biochem. Biophys. 249:533-545 (1986); US Pat Appl No US 2003/0157108 A1, Presta, L; and WO 2004/056312 A1, Yamane-Ohnuki et al. Biotech. Bioeng. 87: 614 (2004); Kanda, Y. et al., Biotechnol. Bioeng., 94(4):680-688 (2006); and WO2003/085107); WO 2003/011878 (Jean-Mairet et al.); U.S. Pat. No. 6,602,684 (Umana et al.); and US 2005/0123546 (Umana et al.); WO 1997/30087 (Patel et al.); WO 1998/58964 (Raju, S.); and WO 1999/22764 (Raju, S.).

Among the modified antibodies are those having one or more amino acid modifications in the Fc region, such as those having a human Fc region sequence or other portion of a constant region (e.g., a human IgG1, IgG2, IgG3 or IgG4 Fc region) comprising an amino acid modification (e.g. a substitution) at one or more amino acid positions.

Such modifications can be made, e.g., to improve half-life, alter binding to one or more types of Fc receptors, and/or alter effector functions.

Also among the variants are cysteine engineered antibodies such as "thioMAbs" and other cysteine engineered variants, in which one or more residues of an antibody are substituted with cysteine residues, in order to generate reactive thiol groups at accessible sites, e.g., for use in conjugation of agents and linker-agents, to produce immunoconjugates. Cysteine engineered antibodies are described, e.g., in U.S. Pat. Nos. 7,855,275 and 7,521,541.

In some embodiments, the antibodies are modified to contain additional nonproteinaceous moieties, including water soluble polymers. Exemplary polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

B. Immunoconjugates

In some embodiments, the antibody is or is part of an immunoconjugate, in which the antibody is conjugated to one or more heterologous molecule(s), such as, but not limited to, a cytotoxic or an imaging agent. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins. In some embodiments, the antibody is conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

Among the immunoconjugates are antibody-drug conjugates (ADCs), in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA*

97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

Also among the immunoconjugates are those in which the antibody is conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

Also among the immunoconjugates are those in which the antibody is conjugated to a radioactive atom to form a radioconjugate. Exemplary radioactive isotopes include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu.

Conjugates of an antibody and cytotoxic agent may be made using any of a number of known protein coupling agents, e.g., linkers, (see Vitetta et al., *Science* 238:1098 (1987)), WO94/11026. The linker may be a "cleavable linker" facilitating release of a cytotoxic drug in the cell, such as acid-labile linkers, peptidase-sensitive linkers, photolabile linkers, dimethyl linkers, and disulfide-containing linkers (Chari et al., *Cancer Res.* 52:127-131 (1992); U.S. Pat. No. 5,208,020).

C. Multispecific Antibodies

In certain embodiments, the ROR1-binding molecules, e.g., antibodies or polypeptides such as chimeric receptors containing the same, are multispecific. Among the multispecific binding molecules are multispecific antibodies, including, e.g. bispecific. Multispecific binding partners, e.g., antibodies, have binding specificities for at least two different sites, which may be in the same or different antigens. In certain embodiments, one of the binding specificities is for ROR1 and the other is for another antigen. In certain embodiments, bispecific antibodies may bind to two different epitopes of ROR1. Bispecific antibodies may also be used to localize cytotoxic agents to cells which express ROR1. Bispecific antibodies can be prepared as full length antibodies or antibody fragments. Among the multispecific antibodies are multispecific single-chain antibodies, e.g., diabodies, triabodies, and tetrabodies, tandem di-scFvs, and tandem tri-scFvs. Also provided are multispecific chimeric receptors, such as multispecific CARs, containing the antibodies. Also provided are multispecific cells containing the antibodies or polypeptides including the same, such as cells containing a cell surface protein including the anti-ROR1 antibody and an additional cell surface protein, such as an additional chimeric receptor, which binds to a different antigen or a different epitope on ROR1.

Exemplary additional antigens include B cell specific antigens, other tumor-specific antigens, such as antigens expressed specifically on or associated with B cell leukemia, lymphoma, B cell chronic lymphocytic leukemia (CLL), acute myeloid leukemia (AML), acute lymphocytic leukemia (ALL), Burkitt's Lymphoma, mantle cell lymphoma (MCL), non-small cell lung cancer (NSCLC), neuroblastoma, renal cell carcinoma, colon cancer, colorectal cancer, breast cancer, epithelial squamous cell cancer, melanoma, myeloma, stomach cancer, brain cancer, lung cancer, pancreatic cancer, cervical cancer, ovarian cancer, liver cancer, bladder cancer, prostate cancer, testicular cancer, thyroid cancer, uterine cancer, adrenal cancer and/or head and neck cancer, and antigens expressed on T cells. Exemplary antigens include CD4, CD5, CD8, CD14, CD15, CD19, CD20, CD21, CD22, CD23, CD25, CD33, CD37, CD38, CD40, CD40L, CD46, CD52, CD54, CD74, CD80, CD126, CD138, B7, MUC-1, Ia, HM1.24, HLA-DR, tenascin, an angiogenesis factor, VEGF, PIGF, ED-B fibronectin, an oncogene, an oncogene product, CD66a-d, necrosis antigens, Ii, IL-2, T101, TAC, IL-6, TRAIL-R1 (DR4) and TRAIL-R2 (DR5).

D. Recombinant Receptors

Among the provided binding molecules, e.g., ROR1 binding molecules, are cell surface proteins, such as recombinant receptors, such as those that include one of the provided antibodies or antigen-binding fragments. Also provided are polynucleotides that encode all or a portion of such cell surface proteins, e.g., receptors. The receptors include antigen receptors and other chimeric receptors that specifically bind to ROR1, such as receptors containing the provided anti-ROR1 antibodies, e.g., antigen-binding fragments. Among the antigen receptors are functional non-TCR antigen receptors, such as chimeric antigen receptors (CARs). The ROR1-binding receptors generally contain antibodies (e.g., antigen-binding fragments), and/or other binding peptides that specifically bind to ROR1, such as to ROR1 proteins, such as a human ROR1 protein. Also provided are cells expressing the recombinant receptors, compositions containing such cells and uses thereof in adoptive cell therapy, such as treatment of diseases and disorders associated with ROR1 expression, compositions and articles of manufacture and uses of the same.

Among the provided polynucleotides are those that encode recombinant receptors, such as antigen receptors, that specifically bind ROR1. In some aspects, the encoded receptors, such as those containing ROR1-binding polypeptides, and compositions and articles of manufacture and uses of the same, also are provided. The provided polynucleotides can be incorporated into constructs, such as deoxyribonucleic acid (DNA) or RNA constructs, such as those that can be introduced into cells for expression of the encoded recombinant ROR1-binding receptors.

I. Exemplary Receptors

The provided ROR1-binding cell surface proteins, such as receptors, generally contain an extracellular antigen-binding domain and an intracellular signaling region. Among the provided receptors, e.g., recombinant receptors, are polypeptides containing the provided antibodies or antigen-binding fragment thereof, such as one or more of the provided anti-ROR1 antibody or fragment thereof. In some embodiments, the provided cell surface proteins specifically bind to ROR1, such as a human ROR1.

Among the antigen receptors are chimeric and/or functional non-TCR antigen receptors, such as chimeric antigen receptors (CARs). The chimeric receptors, such as CARs, generally include an extracellular antigen binding domain that includes, is, or is comprises an anti-ROR1 antibody, such as an anti-ROR1 antibody or fragment thereof described herein. In some embodiments, the chimeric receptors, e.g., CARs, include an intracellular signaling domain. In some embodiments, the chimeric receptors also include a spacer and/or a transmembrane domain. In some embodiments, the spacer is located between the extracellular antigen-binding domain and the transmembrane domain. In some embodiments, the CAR contains an extracellular antigen-binding domain, a spacer, a transmembrane region and an intracellular signaling region. Exemplary CARs provided herein include those containing an antigen-binding domain comprising an antibody or antigen-binding fragment thereof described herein, e.g., in Section I.A and/or in Table 2, or those described in Section I.D herein, in Table 3 and/or in Table E1. Also provided are CARs encoded by the polynucleotides described in Section I.E herein, in Table 3 and/or in Table E1.

In some cases, CARs are referred to as first, second, and/or third generation CARs. In some aspects, a first generation CAR is one that solely provides a CD3-chain induced signal upon antigen binding; in some aspects, a second-generation CARs is one that provides such a signal and costimulatory signal, such as one including an intracellular signaling domain from a costimulatory receptor such as CD28 or CD137; in some aspects, a third generation CAR in some aspects is one that includes multiple costimulatory domains of different costimulatory receptors.

In some embodiments, the CAR contains an extracellular antigen-binding domain, in some cases comprising an antibody, e.g., an antibody fragment that binds ROR1, a transmembrane domain that is or contains a transmembrane portion of CD28 or a functional variant thereof, and an intracellular signaling domain containing a signaling portion of CD28 or functional variant thereof and a signaling portion of CD3 zeta or functional variant thereof. In some embodiments, the CAR contains an extracellular antigen-binding domain, in some cases comprising an antibody, e.g., antibody fragment that binds ROR1, a transmembrane domain that is or contains a transmembrane portion of CD28 or a functional variant thereof, and an intracellular signaling domain containing a signaling portion of a 4-1BB or functional variant thereof and a signaling portion of CD3 zeta or functional variant thereof. In some such embodiments, the receptor further includes a spacer containing a portion of an Ig molecule, such as a human Ig molecule, such as an Ig hinge, e.g., an IgG4 hinge, such as a hinge-only spacer.

In some embodiments, the chimeric antigen receptor includes an extracellular portion containing the antibody or fragment thereof described herein. In some aspects, the chimeric antigen receptor includes an extracellular portion containing the antibody or fragment thereof described herein and an intracellular signaling domain. In some embodiments, the antibody or fragment thereof includes an scFv and the intracellular signaling region contains an ITAM. In some aspects, the intracellular signaling domain includes a signaling domain of a zeta chain of a CD3-zeta (CD3ζ) chain. In some embodiments, the chimeric antigen receptor includes a transmembrane domain linking the extracellular domain and the intracellular signaling domain.

Other exemplary antigen receptors, including CARs, and methods for engineering and introducing such receptors into cells, include those described, for example, in WO200014257, WO2013126726, WO2012/129514, WO2014031687, WO2013/166321, WO2013/071154, WO2013/123061 U.S. patent application publication numbers US2002131960, US2013287748, 0520130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., Cancer Discov. 2013 April; 3(4): 388-398; Davila et al. (2013) *PLoS ONE* 8(4): e61338; Turtle et al., *Curr. Opin. Immunol.*, 2012 October; 24(5): 633-39; Wu et al., *Cancer*, 2012 March 18(2): 160-75. In some aspects, the antigen receptors include a CAR as described in U.S. Pat. No. 7,446,190, and those described in WO/2014055668 A1. Exemplary of the CARs include CARs as disclosed in any of the aforementioned publications, such as WO2014031687, U.S. Pat. Nos. 8,339,645, 7,446,179, US 2013/0149337, U.S. Pat. Nos. 7,446,190, 8,389,282, e.g., and in which the antigen-binding portion, e.g., scFv, is replaced by an antibody, e.g., as provided herein.

Other ROR1-targeting CARs are described, for example, by Hudecek et al., *Clin Cancer Res,* 19(12), 3153-3164 (2013) and Baskar et al. *MAbs.* 4(3): 349-361 (2012). See also WO2014031687; US2012/20058051.

a. Extracellular Antigen-Binding Domain

Among the chimeric receptors are chimeric antigen receptors (CARs). The chimeric receptors, such as CARs, generally include an extracellular antigen binding domain that includes, is, or is comprised within, one or more of the provided anti-ROR1 antibodies or antigen-binding fragments. Thus, the chimeric receptors, e.g., CARs, typically include in their extracellular portions one or more ROR1-binding molecules, such as one or more antigen-binding fragment, domain, or portion, or one or more antibody variable domains and/or antibody molecules, such as those described herein. In some embodiments, the CAR includes a ROR1-binding portion or portions of the antibody molecule, such as a variable heavy ($V_H$) chain region and/or variable light ($V_L$) chain region of the antibody, e.g., an scFv. In some embodiments, the CAR includes a ROR1-binding portion or portions of the antibody molecule, such as a variable heavy ($V_H$) chain region and a variable light ($V_L$) chain region of the antibody, e.g., an scFv. In some aspects, the CAR includes one or more of any of the ROR1-binding antibodies or antigen-binding fragments thereof described herein, e.g., in Section I.A.

In some embodiments, Table 2 provides the SEQ ID NOS: of exemplary antigen-binding domains, such as antibodies or antigen-binding fragments, that can be comprised in the provided ROR1-binding receptors, such as anti-ROR1 chimeric antigen receptors (CARs). In some aspects, the CAR comprises an scFv described in Table 2, for example, as a part of the extracellular antigen-binding domain. In some aspects, the CAR comprises a $V_H$ region described in Table 2, for example, as a part of the extracellular antigen-binding domain. In some aspects, the CAR comprises a $V_L$ region described in Table 2, for example, as a part of the extracellular antigen-binding domain. In some embodiments, the ROR1-binding receptor contains a ROR1-binding antibody or fragment thereof, comprising a $V_H$ region that comprises a CDR-H1, a CDR-H2 and a CDR-H3 sequence and a $V_L$ region that comprises a CDR-L1, a CDR-L2 and a CDR-L3 sequence set forth in the SEQ ID NOS: listed in each row of Table 2. In some embodiments, the ROR1-binding receptor contains a ROR1-binding antibody or fragment thereof, comprising a $V_H$ region sequence and a $V_L$ region sequence set forth in the SEQ ID NOS: listed in each row of Table 2, or an antibody comprising a $V_H$ and $V_L$ region amino acid sequence that has at least 90%, 91%, 92%, 93%, 94%, 95%, 96%, 97%, 98%, or 99% sequence identity to the $V_H$ region sequence and the $V_L$ region sequence set forth in the SEQ ID NOS: listed in each row of Table 2. In some embodiments, the ROR1-binding receptor contains a ROR1-binding antibody or fragment thereof, comprising a $V_H$ region sequence and a $V_L$ region sequence set forth in the SEQ ID NOS: listed in each row of Table 2. In some embodiments, the ROR1-binding receptor contains a ROR1-binding antibody or fragment thereof, comprising an scFv sequence set forth in the SEQ ID NOS: listed in each row of Table 2, or an antibody comprising an scFv amino acid sequence that has at least 90%, 91%, 92%, 93%, 94%, 95%, 96%, 97%, 98%, or 99% sequence identity to the scFv sequence set forth in the SEQ ID NOS: listed in each row of Table 2. In some embodiments, the ROR1-binding receptor contains a ROR1-binding antibody or fragment thereof, comprising an scFv sequence set forth in the SEQ ID NOS: listed in each row of Table 2.

In some embodiments, the provided CARs can include an extracellular antigen-binding domain that contains all or a portion of an antibody, including polyclonal and monoclonal antibodies, including intact antibodies and functional (antigen-binding) antibody fragments, including fragment antigen binding (Fab) fragments, F(ab')2 fragments, Fab' fragments, Fv fragments, recombinant IgG (rIgG) fragments, heavy chain variable ($V_H$) regions capable of specifically binding the antigen, single chain antibody fragments, including single chain variable fragments (scFv), and single domain antibodies (e.g., sdAb, sdFv, nanobody) fragments. In some aspects, the antibody or fragment thereof contained in the CARs include genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific or trispecific, antibodies, diabodies, triabodies, and tetrabodies, tandem di-scFv, tandem tri-scFv.

b. Spacer

In some embodiments, the recombinant receptor such as the CAR, such as the antibody portion thereof, further includes a spacer (in some cases also called a spacer region), which may be or include at least a portion of an immunoglobulin constant region or variant or modified version thereof, such as a hinge region, e.g., an IgG4 hinge region, and/or a $C_H1/C_L$, $C_H2$ and/or $C_H3$ and/or Fc region. In some embodiments, the constant region or portion is of a human IgG, such as IgG4, IgG2 or IgG1. In some aspects, the portion of the constant region serves as a spacer between the antigen-recognition component, e.g., scFv, and transmembrane domain.

In some embodiments, the length of the spacer is adjusted to optimize the biophysical synapse distance between the CAR-expressing cell, such as a CAR-expressing cell, and the target of the CAR, such as a ROR1-expressing tumor cell. In some embodiments, the CAR is expressed by a T cell, and the length of the spacer is adjusted to a length that is compatible for T cell activation or to optimize CAR T-cell performance.

In some embodiments, the spacer can be of a length that provides for increased responsiveness of the cell following antigen binding, as compared to in the absence of the spacer or as compared to an alternative spacer of a different length (e.g. longer in length). In some examples, the spacer is at or about 12 amino acids in length or is no more than at or about 12 amino acids in length. In some examples, the spacer is at or about 15 amino acids in length or is no more than at or about 15 amino acids in length.

Exemplary spacers include those having at least at or about 10 to at or about 300 amino acids, at or about 10 to at or about 229 amino acids, at or about 10 to at or about 200 amino acids, at or about 10 to at or about 175 amino acids, at or about 10 to at or about 150 amino acids, at or about 10 to at or about 125 amino acids, at or about 10 to at or about 100 amino acids, at or about 10 to at or about 75 amino acids, at or about 10 to at or about 50 amino acids, at or about 10 to at or about 40 amino acids, at or about 10 to at or about 30 amino acids, at or about 10 to at or about 20 amino acids, or at or about 10 to at or about 15 amino acids in length, and including any integer between the endpoints of any of the listed ranges. Exemplary spacers include those having at least at or about at or about 50 to at or about 175 amino acids, at or about 50 to at or about 150 amino acids, at or about 10 to at or about 125 amino acids, at or about 50 to at or about 100 amino acids, at or about 100 to at or about 300 amino acids, at or about 100 to at or about 250 amino acids, at or about 125 to at or about 250 amino acids, or at or about 200 to at or about 250 amino acids, and including any integer between the endpoints of any of the listed ranges. In some embodiments, a spacer is at least at or about 12 amino acids, at least at or about 119 amino acids, at least at or about 125 amino acids, at least at or about 200 amino acids, or at least at or about 220 amino acids, or at least at or about 225 amino acids in length. In some embodiments, a spacer is at least at or about 13 amino acids, at least at or about 120 amino acids, at least at or about 125 amino acids, at least at or about 200 amino acids, or at least at or about 220 amino acids, or at least at or about 229 amino acids in length. In some embodiments, a spacer is at or about 11, 12, 13, 14, 15, 16, 17, 18, 19, 20, 21, 22, 23, 24, 25 amino acids or less in length. In some embodiments, the spacer is at least at or about 100 amino acids in length, such as at least at or about 110, 111, 112, 113, 114, 115, 116, 117, 118, 119, 120, 121, 122, 123, 124, 125, 130, 135, 140, 145, 150, 160, 170, 180, 190, 200, 210, 220, 230, 240, or 250 amino acids in length.

In some embodiments, the spacer is at least at or about 125 to at or about 300 amino acids, at or about 125 to at or about 250 amino acids, at or about 125 to at or about 230 amino acids, at or about 125 to at or about 200 amino acids, at or about 125 to at or about 180 amino acids, at or about 125 to at or about 150 amino acids, at or about 150 to at or about 300 amino acids, at or about 150 to at or about 250 amino acids, at or about 150 to at or about 230 amino acids, at or about 150 to at or about 200 amino acids, at or about 150 to at or about 180 amino acids, at or about 180 to at or about 300 amino acids, at or about 180 to at or about 250 amino acids, at or about 180 to at or about 230 amino acids, at or about 180 to at or about 200 amino acids, at or about 200 to at or about 300 amino acids, at or about 200 to at or about 250 amino acids, at or about 200 to at or about 230 amino acids, at or about 230 to at or about 300 amino acids, at or about 230 to at or about 250 amino acids in length or 250 to at or about 300 amino acids in length. In some embodiments, the spacer is at least at or about 129, 130, 140, 150, 160, 170, 180, 190, 200, 210, 220, 221, 222, 223, 224, 225, 226, 227, 228, 229 or 230 amino acids in length, or a length between any of the foregoing.

Exemplary spacers include an IgG hinge alone, an IgG hinge linked to one or more of a $C_H2$ and $C_H3$ domain, or IgG hinge linked to the $C_H3$ domain. In some embodiments, the spacer includes an IgG hinge alone. In some embodiments, the IgG hinge, $C_H2$ and/or $C_H3$ can be derived all or in part from IgG4 or IgG2, such as all or in part from human IgG4 or human IgG2. In some embodiments, the spacer can be a chimeric polypeptide containing one or more of a hinge, $C_H2$ and/or $C_H3$ sequence(s) derived from IgG4, IgG2, and/or IgG2 and IgG4. In some embodiments, the hinge region comprises all or a portion of an IgG4 hinge region. In some embodiments, the hinge region comprises all or a portion of an IgG4 hinge region and/or of an IgG2 hinge region, wherein the IgG4 hinge region is optionally a human IgG4 hinge region and the IgG2 hinge region is optionally a human IgG2 hinge region; the $C_H2$ region comprises all or a portion of an IgG4 $C_H2$ region and/or of an IgG2 $C_H2$ region, wherein the IgG4 $C_H2$ region is optionally a human IgG4 $C_H2$ region and the IgG2 $C_H2$ region is optionally a human IgG2 $C_H2$ region; and/or the $C_H3$ region comprises all or a portion of an IgG4 $C_H3$ region and/or of an IgG2 $C_H3$ region, wherein the IgG4 $C_H3$ region is optionally a human IgG4 $C_H3$ region and the IgG2 $C_H3$ region is optionally a human IgG2 $C_H3$ region. In some embodiments, the hinge, $C_H2$ and $C_H3$ comprises all or a portion of each of a hinge region, $C_H2$ and $C_H3$ from IgG4. In some embodiments, the hinge region is chimeric and comprises a hinge region from human IgG4 and human IgG2; the $C_H2$ region is chimeric and comprises a $C_H2$ region from human IgG4 and human IgG2; and/or the $C_H3$ region is chimeric and comprises a $C_H3$ region from human IgG4 and human IgG2. In some embodiments, the spacer comprises an IgG4/2 chimeric hinge or a modified IgG4 hinge comprising at least one amino acid replacement compared to human IgG4 hinge region; an human IgG2/4 chimeric $C_H2$ region; and a human IgG4 $C_H3$ region.

In some embodiments, the spacer comprises or consists of all or a portion of an immunoglobulin hinge or a modified version thereof. In some embodiments, the spacer is at or about 15 amino acids or less in length. In some embodiments, the spacer comprises or consists of all or a portion of an immunoglobulin hinge, optionally an IgG4 hinge, or a modified version thereof and/or comprises about 15 amino acids or less. In some embodiments, the spacer is at or about 13 amino acids in length and/or comprises or consists of all or a portion of an immunoglobulin hinge, optionally an IgG4, or a modified version thereof. In some embodiments, the spacer is at or about 12 amino acids in length and/or comprises or consists of all or a portion of an immunoglobulin hinge, optionally an IgG4, or a modified version thereof. In some embodiments, the spacer comprises or consists of the sequence of SEQ ID NO: 1, 26, 27, 28, 29, 31, 32, 33 or 135, or a variant of any of the foregoing having at least 85%, 86%, 87%, 88%, 89%, 90%, 91%, 92%, 93%, 94%, 95%, 96%, 97%, 98%, 99% or more sequence identity thereto. In some embodiments, the spacer comprises the formula $X_1PPX_2P$ (SEQ ID NO:25), where $X_1$ is glycine, cysteine or arginine and $X_2$ is cysteine or threonine. In some embodiments, the spacer does not comprise a CD28 extracellular region or a CD8 extracellular region. In certain cases, the spacer has a methionine residue at the C-terminus.

In some of any such embodiments, the spacer is or contains the sequence set forth in SEQ ID NO:1. In some of any such embodiments, the spacer is or contains the amino acid sequence encoded by SEQ ID NO: 2 or 30 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 2 or 30. In some of any such embodiments, the spacer is or contains the amino acid sequence encoded by SEQ ID NO: 30.

In some of any such embodiments, the spacer is or contains the sequence set forth in SEQ ID NO:135. In some of any such embodiments, the spacer is or contains the amino acid sequence encoded by SEQ ID NO: 192 or 136 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 192 or 136. In some of any such embodiments, the spacer is or contains the amino acid sequence encoded by SEQ ID NO: 136.

In some embodiments, the spacer is or comprises IgG hinge linked to the $C_H3$ domain, e.g., of a human immunoglobulin, such as IgG4 and/or IgG2. In some aspects, the spacer is at or about 111, 112, 113, 114, 115, 116, 117, 118, 119, 120, 121, 122, 123, 124 or 125 amino acids in length, or has a length between any of the foregoing. In some aspects, the spacer is at or about 119 or 120 amino acids in length. In some embodiments, the spacer comprises or consists of the sequence of SEQ ID NO: 3 or 138, or a variant of any of the foregoing having at least 85%, 86%, 87%, 88%, 89%, 90%, 91%, 92%, 93%, 94%, 95%, 96%, 97%, 98%, 99% or more sequence identity thereto.

In some of any such embodiments, the spacer is or contains an amino acid sequence having at least at or about 85%, 86%, 87%, 88%, 89%, 90%, 91%, 92%, 93%, 94%, 95%, 96%, 97%, 98% or 99% identity to SEQ ID NO: 138. In some of any such embodiments, the spacer is or contains the sequence set forth in SEQ ID NO:138. In some of any such embodiments, the spacer is or contains the amino acid sequence encoded by SEQ ID NO: 193 or 139 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 193 or 139. In some of any such embodiments, the spacer is or contains the amino acid sequence encoded by SEQ ID NO: 139.

In some of any such embodiments, the spacer is at or about 120 amino acids in length. In some of any such embodiments, the spacer is or contains an amino acid sequence having at least at or about 85%, 86%, 87%, 88%, 89%, 90%, 91%, 92%, 93%, 94%, 95%, 96%, 97%, 98% or 99% identity to SEQ ID NO: 3. In some of any such embodiments, the spacer is or contains the sequence set forth in SEQ ID NO:3. In some of any such embodiments, the spacer is or contains the amino acid sequence encoded by SEQ ID NO: 4 or 137 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 4 or 137. In some of any such embodiments, the spacer is or contains the amino acid sequence encoded by SEQ ID NO: 137.

In some embodiments, the spacer can be from all or in part from IgG4 and/or IgG2 and can contain mutations, such as one or more single amino acid mutations in one or more domains. In some examples, the amino acid modification is a substitution of a proline (P) for a serine (S) in the hinge region of an IgG4. In some embodiments, the amino acid modification is a substitution of a glutamine (Q) for an asparagine (N) to reduce glycosylation heterogeneity, such as an N177Q mutation at position 177, in the $C_H2$ region, of the full-length IgG4 Fc sequence set forth in SEQ ID NO: 48 or an N176Q at position 176, in the $C_H2$ region, of the full-length IgG2 Fc sequence set forth in SEQ ID NO:49. In some embodiments, the spacer is or comprises an IgG4/2 chimeric hinge or a modified IgG4 hinge; an IgG2/4 chimeric $C_H2$ region; and an IgG4 $C_H3$ region and optionally is about 228 or 229 amino acids in length; or a spacer set forth in SEQ ID NO: 37 or 194.

In some of any such embodiments, the spacer is or contains an amino acid sequence having at least at or about 85%, 86%, 87%, 88%, 89%, 90%, 91%, 92%, 93%, 94%, 95%, 96%, 97%, 98% or 99% identity to SEQ ID NO:194. In some of any such embodiments, the spacer is or contains the sequence set forth in SEQ ID NO: 194. In some of any such embodiments, the spacer is or contains the amino acid sequence encoded by SEQ ID NO: 195 or 196 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 195 or 196. In some of any such embodiments, the spacer is or contains the amino acid sequence encoded by SEQ ID NO: 196.

In some of any such embodiments, the spacer is or contains an amino acid sequence having at least at or about 85%, 86%, 87%, 88%, 89%, 90%, 91%, 92%, 93%, 94%, 95%, 96%, 97%, 98% or 99% identity to SEQ ID NO:37. In some of any such embodiments, the spacer is or contains the sequence set forth in SEQ ID NO: 37. In some of any such embodiments, the spacer is or contains the amino acid sequence encoded by SEQ ID NO: 38 or 140 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 38 or 140. In some of any such embodiments, the spacer is or contains the amino acid sequence encoded by SEQ ID NO: 140.

In some embodiments, the spacer is encoded by a polynucleotide that has been optimized for codon expression and/or to eliminate splice sites such as cryptic splice sites. In some embodiments, the coding sequence for the spacer comprises the nucleic acid sequence set forth in SEQ ID NO: 30. In some embodiments, the coding sequence for the spacer comprises the nucleic acid sequence set forth in SEQ ID NO: 136. In some embodiments, the coding sequence for the spacer comprises the nucleic acid sequence set forth in SEQ ID NO: 137. In some embodiments, the coding sequence for the spacer comprises the nucleic acid sequence set forth in SEQ ID NO: 139. In some embodiments, the coding sequence for the spacer comprises the nucleic acid sequence set forth in SEQ ID NO: 140. In some embodiments, the coding sequence for the spacer comprises the nucleic acid sequence set forth in SEQ ID NO: 196.

Additional exemplary spacers include, but are not limited to, those described in Hudecek et al. (2013) *Clin. Cancer Res.*, 19:3153, Hudecek et al. (2015) *Cancer Immunol. Res.*, 3(2):125-135, or WO2014031687. In some embodiments, the nucleotide sequence of the spacer is optimized to reduce RNA heterogeneity upon expression. In some embodiments, the nucleotide sequence of the spacer is optimized to reduce cryptic splice sites or reduce the likelihood of a splice event at a splice site.

In some embodiments, the spacer has the amino acid sequence set forth in SEQ ID NO:1, and is encoded by the polynucleotide sequence set forth in SEQ ID NO:2. In some embodiments, the spacer has the amino acid sequence set forth in SEQ ID NO:135, and is encoded by the polynucleotide sequence set forth in SEQ ID NO:192. In some embodiments, the spacer has the amino acid sequence set forth in SEQ ID NO:3, and is encoded by the polynucleotide sequence set forth in SEQ ID NO:4. In some embodiments, the spacer has the amino acid sequence set forth in SEQ ID NO:138, and is encoded by the polynucleotide sequence set forth in SEQ ID NO:193. In some embodiments, the spacer has the amino acid sequence set forth in SEQ ID NO:37, and is encoded by the polynucleotide sequence set forth in SEQ ID NO:38. In some embodiments, the spacer has the amino acid sequence set forth in SEQ ID NO:194, and is encoded by the polynucleotide sequence set forth in SEQ ID NO:195.

In some embodiments, the spacer is encoded by a polynucleotide that has been optionally optimized for codon usage and/or to reduce RNA heterogeneity, e.g., by removing cryptic splice sites. In some embodiments, the spacer has the amino acid sequence set forth in SEQ ID NO:1, and is encoded by the polynucleotide sequence set forth in SEQ ID NO:30. In some embodiments, the spacer has the amino acid sequence set forth in SEQ ID NO:135, and is encoded by the polynucleotide sequence set forth in SEQ ID NO:136. In some embodiments, the spacer has the amino acid sequence set forth in SEQ ID NO:3, and is encoded by the polynucleotide sequence set forth in SEQ ID NO:137. In some embodiments, the spacer has the amino acid sequence set forth in SEQ ID NO:138, and is encoded by the polynucleotide sequence set forth in SEQ ID NO:139. In some embodiments, the spacer has the amino acid sequence set forth in SEQ ID NO:37, and is encoded by the polynucleotide sequence set forth in SEQ ID NO:140. In some embodiments, the spacer has the amino acid sequence set forth in SEQ ID NO:194, and is encoded by the polynucleotide sequence set forth in SEQ ID NO:196. In some embodiments, the spacer has an amino acid sequence that exhibits at least at or about 85%, 86%, 87%, 88%, 89%, 90%, 91%, 92%, 93%, 94%, 95%, 96%, 97%, 98% or 99% sequence identity to SEQ ID NO:1, 3 or 37 and is encoded by a polynucleotide that has been optionally optimized for codon usage and/or to reduce RNA heterogeneity. In some embodiments, the spacer has an amino acid sequence that exhibits at least at or about 85%, 86%, 87%, 88%, 89%, 90%, 91%, 92%, 93%, 94%, 95%, 96%, 97%, 98% or 99% sequence identity to SEQ ID NO:135, 138 or 194 and is encoded by a polynucleotide that has been optionally optimized for codon usage and/or to reduce RNA heterogeneity.

c. Transmembrane Domain

The antigen-recognition component generally is linked to one or more intracellular signaling components, such as signaling components that mimic activation through an antigen receptor complex, such as a TCR complex, in the case of a CAR, and/or signal via another cell surface receptor. Thus, in some embodiments, a ROR1-binding molecule (e.g., antibody or antigen binding fragment thereof) is linked to one or more transmembrane domains such as those described herein and intracellular signaling domains comprising one or more intracellular components such as those described herein. In some embodiments, the transmembrane domain is fused to the extracellular domain. In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane domains include those derived from (i.e. comprise at least the transmembrane domain(s) of) the alpha, beta or zeta chain of the T-cell receptor, CD3 epsilon, CD4, CD5, CD8, CD9, CD16, CD22, CD28, CD33, CD37, CD45, CD64, CD80, CD86, CD134, CD137, and/or CD154. For example, the transmembrane domain can be a CD28 transmembrane domain that comprises the sequence of amino acids set forth in SEQ ID NO: 149, encoded by the nucleic acid sequence set forth in SEQ ID NO:147 or 148. For example, the transmembrane domain can be a CD28 transmembrane domain that comprises the sequence of amino acids set forth in SEQ ID NO: 8, encoded by the nucleic acid sequence set forth in SEQ ID NO:197 or 198. In some embodiments, the transmembrane domain of the receptor, e.g., the CAR is a transmembrane domain of human CD28 or variant thereof, e.g., a 27-amino acid transmembrane domain of a human CD28 (Accession No.: P10747.1), or a 28-amino acid sequence, or is a transmembrane domain that comprises the sequence of amino acids set forth in SEQ ID NO:8 or 149 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 8 or 149. In some embodiments, the transmembrane domain is encoded by a polynucleotide that has been optionally optimized for codon usage and/or to reduce RNA heterogeneity, e.g., by removing cryptic splice sites. In some embodiments, the transmembrane domain has the amino acid sequence set forth in SEQ ID NO:8 or 149, and is encoded by the polynucleotide sequence set forth in SEQ ID NO:147, 148, 197 or 198, or a polynucleotide sequence having at least 90% sequence identity thereto. In certain cases, the transmembrane domain has a methionine residue at the N-terminus.

In some of any such embodiments, the transmembrane domain is or contains SEQ ID NO: 8 or an amino acid sequence having at least at or about 90%, 91%, 92%, 93%, 94%, 95%, 96%, 97%, 98% or 99% sequence identity to SEQ ID NO: 8. In some of any such embodiments, the transmembrane domain is or contains the sequence set forth in SEQ ID NO: 8. In some of any such embodiments, the transmembrane domain is or contains the amino acid sequence encoded by SEQ ID NO: 197 or 198 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 197 or 198. In some of any such embodiments, the transmembrane domain is or contains the amino acid sequence encoded by SEQ ID NO: 198.

In some of any such embodiments, the transmembrane domain is or contains SEQ ID NO: 149 or an amino acid sequence having at least at or about 90%, 91%, 92%, 93%, 94%, 95%, 96%, 97%, 98% or 99% sequence identity to SEQ ID NO: 149. In some of any such embodiments, the transmembrane domain is or contains the sequence set forth in SEQ ID NO: 149. In some of any such embodiments, the transmembrane domain is or contains the amino acid sequence encoded by SEQ ID NO: 147 or 148 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 147 or 148. In some of any such embodiments, the transmembrane domain is or contains the amino acid sequence encoded by SEQ ID NO: 148.

Alternatively, the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s).

d. Intracellular Signaling Components

Among the intracellular signaling domains are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the intracellular signaling domain of the CAR.

The receptor, e.g., the CAR, generally includes an intracellular signaling region comprising at least one intracellular signaling component or components. In some embodiments, the receptor includes an intracellular component or signaling domain of a TCR complex, such as a TCR CD3 chain that mediates T-cell activation and cytotoxicity, e.g., CD3 zeta (CD3-ζ) chain. Thus, in some aspects, the ROR1-binding antibody is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor γ, CD8, CD4, CD25, or CD16. For example, in some aspects, the CAR includes a chimeric molecule between CD3-zeta (CD3-ζ) or Fc receptor γ and CD8, CD4, CD25 or CD16.

In some embodiments, upon ligation of the CAR, the cytoplasmic domain or intracellular signaling region of the CAR stimulates and/or activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling domain of an antigen receptor component or costimulatory molecule is used in place of an intact immunostimulatory chain, for example, if it transduces the effector function signal. In some embodiments, the intracellular signaling domain or domains include the cytoplasmic sequences of the T cell receptor (TCR), and in some aspects also those of co-receptors that in the natural context act in concert with such receptor to initiate signal transduction following antigen receptor engagement, and/or any derivative or variant of such molecules, and/or any synthetic sequence that has the same functional capability.

In the context of a natural TCR, full activation generally requires not only signaling through the TCR, but also a costimulatory signal. Thus, in some embodiments, to promote full activation, a component for generating secondary or co-stimulatory signal is also included in the CAR. In other embodiments, the CAR does not include a component for generating a costimulatory signal. In some aspects, an additional CAR is expressed in the same cell and provides the component for generating the secondary or costimulatory signal.

T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such classes of cytoplasmic signaling sequences.

In some aspects, the CAR includes a primary cytoplasmic signaling sequence that regulates primary stimulation and/or activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from TCR or CD3 zeta, FcR gamma, CD3 gamma, CD3 delta and CD3 epsilon. In some embodiments, the intracellular signaling region in the CAR contain(s) a cytoplasmic signaling domain, portion thereof, or sequence derived from CD3 zeta. In some embodiments the CD3 zeta comprises the sequence of amino acids set forth in SEQ ID NO:13, 14 or 15, encoded by the nucleic acid sequence set forth in SEQ ID NO: 150 or 182. In some embodiments, the CD3 zeta is encoded by a polynucleotide that has been optionally optimized for codon usage and/or to reduce RNA heterogeneity, e.g., by removing cryptic splice sites. In some embodiments, the CD3 zeta has the amino acid sequence set forth in SEQ ID NO:13, and is encoded by the polynucleotide sequence set forth in SEQ ID NO:150. In some embodiments, the intracellular signaling domain comprises a human CD3 zeta stimulatory signaling domain or functional variant thereof, such as an 112 AA cytoplasmic domain of isoform 3 of human CD3 (Accession No.: P20963.2) or a CD3 zeta signaling domain as described in U.S. Pat. Nos. 7,446,190 or 8,911,993. In some embodiments, the intracellular signaling domain comprises the sequence of amino acids set forth in SEQ ID NO: 13, 14 or 15 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 13, 14 or 15.

In some embodiments, the CAR includes a signaling domain (e.g., an intracellular or cytoplasmic signaling domain) and/or transmembrane portion of a costimulatory molecule, such as a T cell costimulatory molecule. Exemplary costimulatory molecules include CD28, 4-1BB, OX40, DAP10, and ICOS. For example, a costimulatory molecule can be derived from 4-1BB and can comprise the amino acid sequence set forth in SEQ ID NO: 12, encoded by the nucleotide sequence set forth in SEQ ID NO: 154 or 155. In some embodiments, the costimulatory molecule from 4-1BB is encoded by a polynucleotide that has been optionally optimized for codon usage and/or to reduce RNA heterogeneity, e.g., by removing cryptic splice sites. In some embodiments, the costimulatory molecule from 4-1BB has the amino acid sequence set forth in SEQ ID NO:12, and is encoded by the polynucleotide sequence set forth in SEQ ID NO:155. In some embodiments, the intracellular domain comprises an intracellular costimulatory signaling domain of 4-1BB or functional variant or portion thereof, such as a 42-amino acid cytoplasmic domain of a human 4-1BB (Accession No. Q07011.1) or functional variant or portion thereof, such as the sequence of amino acids set forth in SEQ ID NO: 12 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 12. In some embodiments, a costimulatory molecule can be derived from CD28 and can comprise the amino acid sequence set forth in SEQ ID NO: 10, encoded by the nucleotide sequence set forth in SEQ ID NO: 183. In some embodiments, the intracellular signaling domain comprises an intracellular costimulatory signaling domain of human CD28 or functional variant or portion thereof, such as a 41 amino acid domain thereof and/or such a domain with an LL to GG substitution at positions 186-187 of a native CD28 protein. In some embodiments, the intracellular signaling domain can comprise the sequence of amino acids set forth in SEQ ID NO: 10 or 11 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 10 or 11. In some aspects, the same CAR includes both the stimulatory or activating components (e.g., cytoplasmic signaling sequence) and costimulatory components.

In some aspects, the transmembrane domain contains a transmembrane portion of CD28. The extracellular domain and transmembrane can be linked directly or indirectly. In some embodiments, the extracellular domain and transmembrane are linked by a spacer, such as any described herein. In some embodiments, the chimeric antigen receptor contains an intracellular domain of a T cell costimulatory molecule, such as between the transmembrane domain and intracellular signaling domain. In some aspects, the T cell costimulatory molecule is CD28 or 4-1BB.

In some embodiments, the stimulatory or activating components are included within one CAR, whereas the costimulatory component is provided by another CAR recognizing another antigen. In some embodiments, the CARs include activating or stimulatory CARs, and costimulatory CARs, both expressed on the same cell (see WO 2014/055668). In some aspects, the ROR1-targeting CAR is the stimulatory or activating CAR; in other aspects, it is the costimulatory CAR. In some embodiments, the cells further include inhibitory CARs (iCARs, see Fedorov et al., Sci. Transl. Medicine, 5(215) (December, 2013), such as a CAR recognizing an antigen other than ROR1, whereby a stimulatory or an activating signal delivered through the ROR1-targeting CAR is diminished or inhibited by binding of the inhibitory CAR to its ligand, e.g., to reduce off-target effects.

In some embodiments, the two receptors induce, respectively, an activating and an inhibitory signal to the cell, such that ligation of one of the receptor to its antigen activates the cell or induces a response, but ligation of the second inhibitory receptor to its antigen induces a signal that suppresses or dampens that response. Examples are combinations of activating CARs and inhibitory CARs (iCARs). Such a strategy may be used, for example, to reduce the likelihood of off-target effects in the context in which the activating CAR binds an antigen expressed in a disease or condition but which is also expressed on normal cells, and the inhibitory receptor binds to a separate antigen which is expressed on the normal cells but not cells of the disease or condition.

In some aspects, the chimeric receptor is or includes an inhibitory CAR (e.g. iCAR) and includes intracellular components that dampen or suppress an immune response, such as an ITAM- and/or co stimulatory-promoted response in the cell. Exemplary of such intracellular signaling components are those found on immune checkpoint molecules, including PD-1, CTLA4, LAG3, BTLA, OX2R, TIM-3, TIGIT, LAIR-1, PGE2 receptors, EP2/4 Adenosine receptors including A2AR. In some aspects, the engineered cell includes an inhibitory CAR including a signaling domain of or derived from such an inhibitory molecule, such that it serves to dampen the response of the cell, for example, that induced by an activating and/or costimulatory CAR.

In certain embodiments, the intracellular signaling region comprises a CD28 transmembrane and signaling domain linked to a CD3 (e.g., CD3-zeta) intracellular domain. In some embodiments, the intracellular signaling domain comprises a chimeric CD28 and 4-1BB (CD137; TNFRSF9) co-stimulatory domains, linked to a CD3 zeta intracellular domain.

In some embodiments, the CAR encompasses one or more, e.g., two or more, costimulatory domains and a stimulatory or an activation domain, e.g., primary activation domain, in the cytoplasmic portion. Exemplary CARs include intracellular components of CD3-zeta, CD28, and 4-1BB.

In some embodiments, provided embodiments of anti-ROR1 CAR contains an extracellular antigen-binding domain containing any of the anti-ROR1 antibody or antigen-binding fragments described herein, such as in Section I.A.1 and/or Table 2; a spacer comprising an IgG4/2 chimeric hinge or a modified IgG4 hinge, such as one that is about 12 amino acids in length, or a spacer set forth in SEQ ID NO:1, such as encoded by the nucleotide sequence set forth in SEQ ID NOS: 2 or 30; a transmembrane domain, such as a transmembrane domain from a human CD28; and an intracellular signaling region comprising a cytoplasmic signaling domain of a CD3-zeta (CD3ζ) chain and a costimulatory signaling region. In some embodiments, provided embodiments of anti-ROR1 CAR contains an extracellular antigen-binding domain containing any of the anti-ROR1 antibody or antigen-binding fragments described herein, such as in Section I.A.1 and/or Table 2; a spacer comprising an IgG4/2 chimeric hinge or a modified IgG4 hinge, such as one that is about 13 amino acids in length, or a spacer set forth in SEQ ID NO:135, such as encoded by the nucleotide sequence set forth in SEQ ID NOS: 136 or 192; a transmembrane domain, such as a transmembrane domain from a human CD28; and an intracellular signaling region comprising a cytoplasmic signaling domain of a CD3-zeta (CD3ζ) chain and a costimulatory signaling region.

In some embodiments, provided embodiments of anti-ROR1 CAR contains an extracellular antigen-binding domain containing any of the anti-ROR1 antibody or antigen-binding fragments described herein, such as in Section I.A.1 and/or Table 2; a spacer comprising a modified IgG4 hinge-$C_H3$, such as one that is about 119 amino acids in length, or a spacer set forth in SEQ ID NO:3, such as encoded by the nucleotide sequence set forth in SEQ ID NO:4 or 137; a transmembrane domain, such as a transmembrane domain from a human CD28; and an intracellular signaling region comprising a cytoplasmic signaling domain of a CD3-zeta (CD3ζ) chain and a costimulatory signaling region. In some embodiments, provided embodiments of anti-ROR1 CAR contains an extracellular antigen-binding domain containing any of the anti-ROR1 antibody or antigen-binding fragments described herein, such as in Section I.A.1 and/or Table 2; a spacer comprising a modified IgG4 hinge-$C_H3$, such as one that is about 120 amino acids in length, or a spacer set forth in SEQ ID NO:138, such as encoded by the nucleotide sequence set forth in SEQ ID NO:193 or 139; a transmembrane domain, such as a transmembrane domain from a human CD28; and an intracellular signaling region comprising a cytoplasmic signaling domain of a CD3-zeta (CD3ζ) chain and a costimulatory signaling region.

In some of any such embodiments, the transmembrane domain is or comprises the sequence set forth in SEQ ID NO:8. In some of any such embodiments, the transmembrane domain is or comprises the sequence set forth in SEQ ID NO:149. In some of any such embodiments, the costimulatory signaling region is an intracellular signaling domain of human CD28, human 4-1BB or human ICOS or a signaling portion thereof. In particular embodiments, the intracellular signaling domain is an intracellular signaling domain of human 4-1BB. In some of any such embodiments, the intracellular signaling domain is or comprises the sequence set forth in SEQ ID NO:12. In some of any such embodiments, the cytoplasmic signaling domain is a human CD3-zeta cytoplasmic signaling domain, such as set forth in SEQ ID NO:13. In some of any such embodiments, the intracellular signaling region comprises the sequences set forth in SEQ ID NO:13 and SEQ ID NO:12. In some of any such embodiments, those described in Section I.D herein, in Table 3 and/or in Table E1. Also provided are CARs encoded by the polynucleotides described in Section I.E herein, in Table 3 and/or in Table E1. Also provided are polynucleotides that contain any of the nucleotide sequences described herein, e.g., encoding all or a portion of the provided binding molecules. In certain cases, the transmembrane domain has a methionine residue at the N-terminus. In certain cases, the spacer has a methionine residue at the C-terminus.

In some of any of the provided embodiments, the anti-ROR1 chimeric antigen receptor is or comprises the sequence set forth in SEQ ID NO: 184, 185, 186, 187, 188 or 189 or a sequence that exhibits at least 85%, 86%, 87%, 88%, 89%, 90%, 91%, 92%, 93%, 94%, 95%, 96%, 97%, 98%, or 99% sequence identity to the sequence set forth in SEQ ID NO: 184, 185, 186, 187, 188 or 189. In some of any embodiments, the anti-ROR1 CARs has the amino acid sequence set forth in SEQ ID NO:184, or an amino acid sequence that is at least at or about 85%, at or about 86%, at or about 87%, at or about 88%, at or about 89%, at or about 90%, at or about 91%, at or about 92%, at or about 93%, at or about 94%, at or about 95%, at or about 96%, at or about 97%, at or about 98% or at or about 99% sequence identity to the amino acid sequence set forth in SEQ ID NO:184. In some of any embodiments, the anti-ROR1 CARs has the amino acid sequence set forth in SEQ ID NO:185, or an amino acid sequence that is at least at or about 85%, at or about 86%, at or about 87%, at or about 88%, at or about 89%, at or about 90%, at or about 91%, at or about 92%, at or about 93%, at or about 94%, at or about 95%, at or about 96%, at or about 97%, at or about 98% or at or about 99% sequence identity to the amino acid sequence set forth in SEQ ID NO:185. In some of any embodiments, the anti-ROR1 CARs has the amino acid sequence set forth in SEQ ID NO:186, or an amino acid sequence that is at least at or about 85%, at or about 86%, at or about 87%, at or about 88%, at or about 89%, at or about 90%, at or about 91%, at or about 92%, at or about 93%, at or about 94%, at or about 95%, at or about 96%, at or about 97%, at or about 98% or at or about 99% sequence identity to the amino acid sequence set forth in SEQ ID NO:186. In some of any embodiments, the anti-ROR1 CARs has the amino acid sequence set forth in SEQ ID NO:187, or an amino acid sequence that is at least at or about 85%, at or about 86%, at or about 87%, at or about 88%, at or about 89%, at or about 90%, at or about 91%, at or about 92%, at or about 93%, at or about 94%, at or about 95%, at or about 96%, at or about 97%, at or about 98% or at or about 99% sequence identity to the amino acid sequence set forth in SEQ ID NO:187. In some of any embodiments, the anti-ROR1 CARs has the amino acid sequence set forth in SEQ ID NO:188, or an amino acid sequence that is at least at or about 85%, at or about 86%, at or about 87%, at or about 88%, at or about 89%, at or about 90%, at or about 91%, at or about 92%, at or about 93%, at or about 94%, at or about 95%, at or about 96%, at or about 97%, at or about 98% or at or about 99% sequence identity to the amino acid sequence set forth in SEQ ID NO:188. In some of any embodiments, the anti-ROR1 CARs has the amino acid sequence set forth in SEQ ID NO:189, or an amino acid sequence that is at least at or about 85%, at or about 86%, at or about 87%, at or about 88%, at or about 89%, at or about 90%, at or about 91%, at or about 92%, at or about 93%, at or about 94%, at or about 95%, at or about 96%, at or about 97%, at or about 98% or at or about 99% sequence identity to the amino acid sequence set forth in SEQ ID NO:189.

In some of any of the provided embodiments, the anti-ROR1 chimeric antigen receptor is encoded by the sequence set forth in SEQ ID NO: 156, 157, 158, 159, 160 or 161 or a sequence that exhibits at least 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 156, 157, 158, 159, 160 or 161. In some of any embodiments, the anti-ROR1 CARs is encoded by the nucleotide sequence set forth in SEQ ID NO:156, or a nucleotide sequence that is at least at or about 85%, at or about 86%, at or about 87%, at or about 88%, at or about 89%, at or about 90%, at or about 91%, at or about 92%, at or about 93%, at or about 94%, at or about 95%, at or about 96%, at or about 97%, at or about 98% or at or about 99% sequence identity to the nucleotide sequence set forth in SEQ ID NO:156. In some of any embodiments, the anti-ROR1 CARs is encoded by the nucleotide sequence set forth in SEQ ID NO:157, or a nucleotide sequence that is at least at or about 85%, at or about 86%, at or about 87%, at or about 88%, at or about 89%, at or about 90%, at or about 91%, at or about 92%, at or about 93%, at or about 94%, at or about 95%, at or about 96%, at or about 97%, at or about 98% or at or about 99% sequence identity to the nucleotide sequence set forth in SEQ ID NO:157. In some of any embodiments, the anti-ROR1 CARs is encoded by the nucleotide sequence set forth in SEQ ID NO:158, or a nucleotide sequence that is at least at or about 85%, at or about 86%, at or about 87%, at or about 88%, at or about 89%, at or about 90%, at or about 91%, at or about 92%, at or about 93%, at or about 94%, at or about 95%, at or about 96%, at or about 97%, at or about 98% or at or about 99% sequence identity to the nucleotide sequence set forth in SEQ ID NO:158. In some of any embodiments, the anti-ROR1 CARs is encoded by the nucleotide sequence set forth in SEQ ID NO:159, or a nucleotide sequence that is at least at or about 85%, at or about 86%, at or about 87%, at or about 88%, at or about 89%, at or about 90%, at or about 91%, at or about 92%, at or about 93%, at or about 94%, at or about 95%, at or about 96%, at or about 97%, at or about 98% or at or about 99% sequence identity to the nucleotide sequence set forth in SEQ ID NO:159. In some of any embodiments, the anti-ROR1 CARs is encoded by the nucleotide sequence set forth in SEQ ID NO:160, or a nucleotide sequence that is at least at or about 85%, at or about 86%, at or about 87%, at or about 88%, at or about 89%, at or about 90%, at or about 91%, at or about 92%, at or about 93%, at or about 94%, at or about 95%, at or about 96%, at or about 97%, at or about 98% or at or about 99% sequence identity to the nucleotide sequence set forth in SEQ ID NO:160. In some of any embodiments, the anti-ROR1 CARs is encoded by the nucleotide sequence set forth in SEQ ID NO:161, or a nucleotide sequence that is at least at or about 85%, at or about 86%, at or about 87%, at or about 88%, at or about 89%, at or about 90%, at or about 91%, at or about 92%, at or about 93%, at or about 94%, at or about 95%, at or about 96%, at or about 97%, at or about 98% or at or about 99% sequence identity to the nucleotide sequence set forth in SEQ ID NO:161.

2. Exemplary Features

In some of any of the provided embodiments, the provided recombinant receptors, e.g., CARs, containing an ROR1-binding antibody or fragment thereof, binds, such as specifically binds to ROR1, such as ROR1 on the surface of a cancer cell or a tumor cell. In any of the embodiments, an antibody or antigen binding fragment, in the provided CARs, specifically binds ROR1, such as a human ROR1. Exemplary ROR1-binding recombinant receptors, e.g., CARs, can exhibit any binding affinity, binding specificity and/or other features of antigen recognition, such as species cross-reactivity, as described herein, such as in Section I.A.2. In some embodiments, a CAR containing an extracellular antigen binding domain comprising the antibodies or fragments thereof exhibit similar or substantially the same binding properties and features as the antibody or fragment thereof. In some cases, the CAR containing an extracellular antigen binding domain comprising the antibodies or fragment thereof exhibit different binding properties and features as the antibody or fragment thereof.

In some embodiments, the provided CARs specifically bind to a receptor tyrosine kinase-like orphan receptor 1 (ROR1) protein. In some of any of the embodiments herein, ROR1 refers to human ROR1. The observation that an antibody or other binding molecule, e.g., CAR, binds to ROR1 or specifically binds to ROR1 does not necessarily mean that it binds to ROR1 from every species. For example, in some embodiments, features of binding to ROR1, such as the ability to specifically bind thereto and/or to compete for binding thereto with a reference receptor, e.g., reference CAR, containing a reference antibody, and/or to bind with a particular affinity or compete to a particular degree, in some embodiments, refers to the ability with respect to a human ROR1 protein and the antibody may not have this feature with respect to a ROR1 of another species such as mouse. In some embodiments, the CAR binds to human ROR1 and binds to ROR1 of another species, such as *Rhesus macaque* or macaque. In some embodiments, the CAR or an antigen-binding fragment thereof binds to human ROR1 and does not bind to ROR1 of another species, such as mouse. In some embodiments, the CAR binds to human ROR1 and binds to ROR1 of another species, such as mouse.

In some embodiments, the CARs bind, such as specifically bind, to human ROR1, such as to an epitope or region of human ROR1, such as the human ROR1 set forth in SEQ ID NO:144 (GenBank No. AAA60275.1; sequence including the signal peptide set forth in SEQ ID NO:215, Uniprot No. Q01973), or an allelic variant or splice variant thereof. In one embodiment, human ROR1 is a transcript variant or isoform that has the sequence of amino acids forth in SEQ ID NO:145 or 146. In some embodiments, human ROR1 protein comprises an amino acid sequence set forth in SEQ ID NO: 144, 145, 146 or 215. In some embodiments, the CARs bind to the extracellular region ROR1, such as to one or more extracellular epitopes present within the extracellular region of human ROR1, e.g., corresponding to residues 1-377 of the human ROR1 sequence set forth in SEQ ID NO:144 (corresponding to residues 30-406 of the human ROR1 sequence set forth in SEQ ID NO:215 that includes the signal peptide).

In some embodiments, the CAR binds a linear epitope of ROR1, such as a human ROR1. In some embodiments, the one or more epitopes comprises a conformational epitope. In some embodiments, the antibodies or antigen-binding fragment thereof bind one or more conformational epitopes of ROR1, such as a human ROR1. In some embodiments, the antibodies or antigen-binding fragment thereof bind one or more epitopes of human ROR1, such as one or more epitopes that include the sequence FRSTIYGSRLRIRNL (set forth in SEQ ID NO:199) or the sequence set forth in any one of SEQ ID NO:200-214 or in Table E2 herein. In some embodiments, the antibodies or antigen-binding fragment thereof bind one or more epitopes of human ROR1, such as one or more epitopes that include the sequence FRSTIYGSRLRIRNL (set forth in SEQ ID NO:199). In some embodiments, the antibodies or antigen-binding fragment thereof bind additional epitopes, such as one or more conformational epitopes, in addition to the sequence FRSTIYGSRLRIRNL (set forth in SEQ ID NO:199). Exemplary of one or more additional epitopes include, but are not limited to, one or more of the sequence set forth in any one of SEQ ID NO:200-214 or in Table E2 herein.

In some embodiments, the antibody binds to non-human ROR1, such as *Rhesus macaques* (*Macaca mulatta*) ROR1 (set forth in SEQ ID NO:216, Uniprot No. F6RUP2) or cynomolgus macaques (*Macaca fasicularis*) ROR1 (set forth in SEQ ID NO:217, Uniprot No. A0A2K5WTX7; or SEQ ID NO:218, Uniprot No. A0A2K5WTX4). In some aspects, the extracellular domain of the non-human ROR1 is at least 99% identical to the human ROR1 sequence.

In some embodiments, the CAR binds to non-human ROR1, such as monkey, rabbit, rat, mouse, or other species of ROR1. In some embodiments, the CAR binds to mouse (*Mus musculus*) ROR1, such as to an epitope or region of mouse ROR1, such as the mouse ROR1 set forth in SEQ ID NO: 171 (GenBank No. NP_038873; sequence including the signal peptide set forth in SEQ ID NO:219, Uniprot No. Q9Z139). In some embodiments, the CAR binds to human ROR1 and binds to mouse ROR1. In some embodiments, the extent of binding of some of the provided anti-ROR1 antibodies or fragments thereof to a non-human ROR1, such as mouse ROR1, is at least at or about 75%, 80%, 90%, 95%, 100%, 110%, 120%, 130%, 140%, 150% or more of the binding of the CAR to human ROR1. In some embodiments, the antibodies do not bind to mouse ROR1, such as the mouse ROR1 set forth in SEQ ID NO:171.

In some of any of the provided embodiments, the extent of binding of the CAR, e.g., containing a ROR1-binding antibody or antigen-binding fragment thereof does not bind to, is not cross-reactive to, or binds at a lower extent, level or degree or affinity to a non-human ROR1, optionally a mouse ROR1. In some embodiments, the extent of binding of an anti-ROR1 antibody to an unrelated, non-ROR1 protein or to a non-human ROR1 protein, such as a mouse ROR1 protein, or other non-ROR1 protein, is less than at or about 50%, 40%, 30%, 20% or 10% of the binding of the CAR to human ROR1 as measured. In some embodiments, the antibodies or antigen-binding fragments thereof do not bind to mouse ROR1, such as the mouse ROR1 set forth in SEQ ID NO:171 or 219.

In some of any of the provided embodiments, the CAR or antigen-binding fragment thereof does not bind to, is not cross-reactive to, or binds at a lower extent, level or degree or affinity to a receptor tyrosine kinase-like orphan receptor 2 (ROR2) protein, optionally a human ROR2 protein. In some embodiments, the extent of binding of some of the provided CAR, e.g., containing a ROR1-binding antibody or fragment thereof to a non-ROR1 protein, such as a ROR2 protein, is at least at or about 75%, 80%, 90%, 95% or 99% less than the binding of the CAR to human ROR1. In some embodiments, the provided antibody or antigen-binding fragment thereof does not bind to, is not cross-reactive to, or binds at a lower level or degree or affinity to a ROR2 protein, optionally a human ROR2 protein. In some embodiments, among provided CAR, e.g., containing a ROR1-binding antibody or fragment thereof, are CARs in which binding to mouse ROR1 is less than or at or about 30%, 20% or 10%, such as less than at or about 10%, of the binding of the CAR to human ROR1. In some embodiments, among provided CAR, e.g., containing a ROR1-binding antibody or fragment thereof, are CARs in which binding to a ROR2, such as a human ROR2, is less than or at or about 30%, 20% or 10%, such as less than at or about 10%, of the binding of the CAR to human ROR1. In some embodiments, the provided CARs exhibit the same, substantially the same or lower level or degree or affinity of binding to a ROR2 protein compared to a reference ROR1-specific chimeric antigen receptor, optionally under the same or substantially the same conditions or assay. In some aspects, binding affinity and/or specificity to a particular antigen (e.g., human ROR1) can be assessed using any methods for assessing binding, such as any described in Section I.A.2 herein.

In some embodiments, the provided CARs are capable of binding ROR1, such as human ROR1, with at least a certain affinity, as measured by any of a number of known methods. In some embodiments, the affinity is represented by an equilibrium dissociation constant ($K_D$). In some embodiments, the affinity is represented by $EC_{50}$.

In some embodiments, the binding molecule, e.g., CAR, binds, such as specifically binds, to an antigen, e.g., a ROR1 protein or an epitope therein, with an affinity or $K_A$ (i.e., an equilibrium association constant of a particular binding interaction with units of 1/M or $M^{-1}$; equal to the ratio of the on-rate [$k_{on}$ or $k_a$] to the off-rate [$k_{off}$ or $k_d$] for this association reaction, assuming bimolecular interaction), the binding affinity ($EC_{50}$) and/or the equilibrium dissociation constant ($K_D$; i.e., an equilibrium dissociation constant of a particular binding interaction with units of M; equal to the ratio of the off-rate [$k_{off}$ or $k_d$] to the on-rate [$k_{on}$ or $k_a$] for this association reaction, assuming bimolecular interaction), or an off-rate (dissociation rate constant; $k_{off}$ or $k_d$) as described herein, e.g., in Section I.A.2 herein. For example, the equilibrium dissociation constant $K_D$ can range from $10^{-5}$ M to $10^{-13}$ M, such as $10^{-7}$ M to $10^{-11}$ M, $10^{-7}$ M to $10^{-10}$ M, $10^{-7}$ M to $10^{-9}$ M, $10^{-8}$ M to $10^{-10}$ M, or $10^{-9}$ M to $10^{-10}$ M.

In certain embodiments, the binding affinity ($EC_{50}$) and/or the equilibrium dissociation constant, $K_D$, of the binding molecule, e.g., anti-ROR1 CAR, to a ROR1 protein, such as a human ROR1 protein, is at or about or less than at or about 1 µM, 500 nM, 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM or less, or a range defined by any of the foregoing. In some embodiments, the $EC_{50}$ and/or the $K_D$ of the binding molecule, e.g., anti-ROR1 CAR, to a ROR1 protein, is between at or about 10 nM and at or about 90 nM, between at or about 20 nM and at or about 80 nM, between at or about 30 nM and at or about 70 nM, between at or about 40 nM and at or about 60 nM, or between at or about 40 nM and at or about 50 nM. In certain embodiments, the $EC_{50}$ and/or the $K_D$ of the binding molecule, e.g., anti-ROR1 CAR, to a ROR1 protein, such as a human ROR1 protein, is at or about 10 nM, 20 nM, 30 nM, 40 nM, 50 nM, 60 nM, 70 nM, 80 nM, 90 nM or 100 nM, or a range defined by any of the foregoing. In certain embodiments, the $EC_{50}$ and/or the $K_D$ of the binding molecule, e.g., anti-ROR1 CAR, to a ROR1 protein, such as a human ROR1 protein, is at or about 10 nM, 20 nM, 30 nM, 40 nM, 50 nM, 60 nM, 70 nM, 80 nM, 90 nM or 100 nM, or a range defined by any of the foregoing. In certain embodiments, the $EC_{50}$ and/or the $K_D$ of the binding molecule, e.g., anti-ROR1 CAR, to a ROR1 protein, such as a human ROR1 protein, is at or about 40 nM, 41 nM, 42 nM, 43 nM, 44 nM, or 45 nM, or a range defined by any of the foregoing.

In some embodiments, the provided binding molecule, e.g., anti-ROR1 CAR, has a fast off-rate (dissociation rate constant; $k_{off}$ or $k_d$; units of 1/s or $s^{-1}$). In some embodiments, the off-rate ($k_{off}$ or $k_d$) of the provided binding molecules is between at or about $1 \times 10^{-5}$ $s^{-1}$ and at or about $1 \times 10^{-2}$ $s^{-1}$, such as at or about $5 \times 10^{-5}$ $s^{-1}$ and at or about $9 \times 10^{-3}$ $s^{-1}$, at or about $1 \times 10$ $s^{-1}$ and at or about $8 \times 10^{-3}$ $s^{-1}$, at or about $5 \times 10^{-4}$ $s^{-1}$ and at or about $7 \times 10^{-3}$ $s^{-1}$, at or about $1 \times 10^{-3}$ $s^{-1}$ and at or about $6 \times 10^{-3}$ $s^{-1}$, and at or about $4 \times 10^{-3}$ $s^{-1}$ and at or about $6 \times 10^{-3}$ $s^{-1}$. In some embodiments, the off-rate ($k_{off}$ or $k_d$) of the provided binding molecules is at least at or about $1 \times 10^{-5}$ $s^{-1}$, $5 \times 10^{-5}$ $s^{-1}$, $1 \times 10^{-4}$ $s^{-1}$, $5 \times 10^{-4}$ $s^{-1}$, $1 \times 10^{-3}$ $s^{-1}$, $5 \times 10^{-3}$ $s^{-1}$, or $1 \times 10^{-2}$ $s^{-1}$. In some embodiments, the off-rate ($k_{off}$ or $k_d$) of the provided binding molecules is at least at or about $6 \times 10^{-4}$ s$^{-1}$, $7 \times 10^{-4}$ s$^{-1}$, $8 \times 10^{-4}$ s$^{-1}$, $9 \times 10^{-4}$ s$^{-1}$, $1 \times 10^{-3}$ s$^{-1}$, $2 \times 10^{-3}$ s$^{-1}$, $3 \times 10^{-3}$ s$^{-1}$, $4 \times 10^{-3}$ s$^{-1}$, $5 \times 10^{-3}$ s$^{-1}$, $6 \times 10^{-3}$ s$^{-1}$, $7 \times 10^{-3}$ s$^{-1}$, $8 \times 10^{-3}$ s$^{-1}$, $9 \times 10^{-3}$ s$^{-1}$ or $1 \times 10^{-2}$ s$^{-1}$. In some embodiments, the off-rate ($k_{off}$ or $k_d$) of the provided binding molecules is at least at or about $4 \times 10^{-3}$ s$^{-1}$, $5 \times 10^{-3}$ s or $6 \times 10^{-3}$ s$^{-1}$, or a range defined by any of the foregoing. In some embodiments, the provided binding molecule, e.g., anti-ROR1 CAR, has an off-rate that is at least at or about 2-fold, 3-fold, 4-fold, 5-fold, 6-fold, 7-fold, 8-fold, 9-fold or 10-fold faster than the off-rate of a reference anti-ROR1 CAR, for example, anti-ROR1 CAR R12.

In some embodiments, the binding affinity of a binding molecule, such as an anti-ROR1 CAR, for different antigens, e.g., ROR1 proteins from different species can be compared to determine the species cross-reactivity. For example, species cross-reactivity can be classified as high cross reactivity or low cross reactivity. In some embodiments, the equilibrium dissociation constant, $K_D$, for different antigens, e.g., ROR1 proteins from different species such as human, cynomolgus monkey or mouse, can be compared to determine species cross-reactivity. In some embodiments, the species cross-reactivity of an anti-ROR1 CAR can be high, e.g., the anti-ROR1 CAR binds to human ROR1 and a species variant ROR1 to a similar degree, e.g., the ratio of $K_D$ for human ROR1 and $K_D$ for the species variant ROR1 is or is about 1. In some embodiments, the species cross-reactivity of an anti-ROR1 CAR can be low, e.g., the anti-ROR1 CAR has a high affinity for human ROR1 but a low affinity for a species variant ROR1, or vice versa. For example, the ratio of $K_D$ for the species variant ROR1 and $K_D$ for the human ROR1 is more than 10, 15, 20, 25, 30, 40, 50, 60, 70, 80, 90, 100, 200, 500, 1000, 2000 or more, and the anti-ROR1 CAR has low species cross-reactivity. The degree of species cross-reactivity can be compared with the species cross-reactivity of a known CAR, such as a reference CAR.

In some embodiments, properties or features of the provided CARs are described in relation to properties observed for another CAR, e.g., a reference CAR. In some embodiments, the reference CAR contains, as an extracellular antigen-binding domain, a reference antibody described herein or fragment thereof, such as, the chimeric rabbit/human IgG1 antibody designated R12 (see, e.g., Yang et al. (2011) PloS ONE, 6:e21018; U.S. Patent Application No. US 2013/0251642); mouse anti-human ROR1 antibody designated 2A2 (see, e.g., Baskar et al. (2012) MAbs, 4:349-361; published U.S. Patent Appl. No. US2012/20058051); humanized anti-ROR1 antibodies described in International PCT Appl. No. WO2014/031174; humanized variant of an antibody designated 99961.

In some embodiments, the CAR has an affinity that is about the same as or lower than that of the corresponding form of the reference CAR, e.g., $EC_{50}$ or $K_D$ that is no more than at or about 1.5-fold or no more than at or about 2-fold greater, no more than at or about 3-fold greater, and/or no more than at or about 10-fold greater, than the $EC_{50}$ or $K_D$ of the corresponding form of the reference CAR. In some embodiments, the CAR has an affinity that is about the same as or lower than that of the corresponding form of the reference CAR, e.g., $EC_{50}$ or $K_D$ that is at least at or about 1.5-fold greater, at least at or about 2-fold greater, at least at or about 3-fold greater, at least at or about 5-fold greater, at least at or about 10-fold greater, at least at or about 20-fold greater, at least at or about 25-fold greater, at least at or about 30-fold greater, at least at or about 40-fold greater, at least at or about 50-fold greater, or at least at or about 100-fold greater, than the $EC_{50}$ or $K_D$ of the corresponding form of the reference CAR. In some embodiments, the CAR has an affinity that is about the same as or lower than that of the corresponding form of the reference CAR, an affinity that is at or about 1.5-fold, 2-fold, 3-fold, 4-fold, 5-fold, 6-fold, 7-fold, 8-fold, 9-fold, 10-fold, 20-fold, 25-fold, 30-fold, 40-fold, 50-fold or 100-fold lower than the affinity of the reference CAR.

In some embodiments, the CAR has an affinity that is greater than that of the corresponding form of the reference CAR, e.g., $EC_{50}$ or $K_D$ that is lower than or lower than at or about 5-fold, 10-fold, 20-fold, 30-fold, 40-fold, 50-fold, 60-fold, 70-fold, 80-fold, 90-fold, 100-fold, 150-fold, 200-fold, 250-fold or lower than the $EC_{50}$ or $K_D$ of the corresponding form of the reference CAR.

In some embodiments, the CAR specifically binds to an epitope that overlaps with the epitope of ROR1 bound by a reference CAR. In some aspects, among such CARs are CARs that bind to the same or a similar epitope as the reference CAR. In some embodiments, the CARs bind to the same or a similar epitope or an epitope within the same region or containing residues within the same region of ROR1 as a reference CAR, such as anti-ROR1 CAR R12 or scFv fragment thereof (set forth in SEQ ID NO: 142; see e.g. Yang et al. (2011) PloS ONE, 6:e21018). In some embodiments, the CAR inhibits binding to and/or competes for binding to ROR1, such as human ROR1, with the reference CAR.

Among the provided CARs are CARs that exhibit antigen-dependent activity or signaling, i.e. signaling activity that is measurably absent or at background levels in the absence of antigen, e.g. ROR1, and/or in the presence of non-specific antigen. Thus, in some aspects, provided CARs do not exhibit, or exhibit no more than background or a tolerable or low level of, tonic signaling or antigen-independent activity or signaling in the absence of antigen, e.g. ROR1, being present. In some embodiments, the provided anti-ROR1 CAR-expressing cells exhibit biological activity or function, including cytotoxic activity, cytokine production, and ability to proliferate. In some embodiments, the provided CARs receptor exhibits the same, substantially the same or higher antigen-specific signaling and/or antigen dependent activity or signaling compared to a reference ROR1-specific chimeric antigen receptor, optionally under the same or substantially the same conditions or assay.

In some embodiments, the provided CARs exhibit absent, reduced or lower levels of activity or signaling in the absence of antigen, e.g., ROR1. In some embodiments, the provided CARs exhibit reduced, lower or is nearly absent of or completely absent of tonic signaling or antigen-independent signaling or activity, e.g., signaling or activity in the absence of antigen, such that the signaling or activity is less than or at or about 30%, 20% or 10%, such as less than at or about 10%, of the signaling or activity of the CAR in the presence of human ROR1. In some embodiments, the provided CARs exhibit the same, substantially the same or lower tonic signaling and/or antigen independent activity or signaling compared to a reference ROR1-specific chimeric antigen receptor (CAR), optionally under the same or substantially the same conditions or assay. In some aspects, among a plurality or population of cells that are engineered to express the CARs, less than at or about 10%, at or about 9%, at or about 8%, at or about 7%, at or about 5%, at or about 4%, at or about 3%, at or about 2% or at or about 1% of the cells in the plurality comprise a chimeric antigen receptor that exhibits tonic signaling and/or antigen independent activity or signaling. In some embodiments, reference ROR1-specific CARs include those that have an antigen-binding domain that comprises any reference anti-ROR1 antibodies described herein, such as those described in Section I.A.2 herein, for example, R12, A2A or 99961, or an antigen-binding fragment thereof.

In some embodiments, the provided CARs exhibit absent, reduced or lower levels of activity or signaling when exposed to a non-specific antigen, such as a different but related protein, such as ROR2. In some embodiments, the provided CARs exhibit the same, substantially the same or lower level or degree or affinity of binding to a ROR2 protein compared to a reference ROR1-specific chimeric antigen receptor, optionally under the same or substantially the same conditions or assay. In some embodiments, the provided CARs exhibit reduced signaling or activity in the presence of a ROR2, such as a human ROR2, such that the signaling or activity is less than or at or about 30%, 20% or 10%, such as less than at or about 10%, of the signaling or activity of the CAR in the presence of human ROR1.

In some embodiments, engineered cells expressing the provided anti-ROR1 CARs exhibit improved biological activity or functional activity, such as anti-tumor activity, tumor growth inhibition, tumor volume reduction, persistence, expansion, or prolonged survival of the subject, when administered to a subject for adoptive cell therapy. In some embodiments, engineered cells expressing the provided CARs exhibit improved biological activity or functional activity, such as anti-tumor activity, tumor growth inhibition, tumor volume reduction, persistence, expansion, or prolonged survival of the subject, compared to engineered cells expressing a reference ROR1-specific chimeric antigen receptor, optionally under the same or substantially the same conditions or assay. In some embodiments, biological activity or functional activity of a chimeric receptor, such as cytotoxic activity, can be measured using any of a number of known methods. The activity can be assessed or determined either in vitro or in vivo. In some embodiments, activity can be assessed once the cells are administered to the subject (e.g., human) Parameters to assess include specific binding of an engineered or natural T cell or other immune cell to antigen, e.g., in vivo, e.g., by imaging, or ex vivo, e.g., by ELISA or flow cytometry. In certain embodiments, the ability of the engineered cells to destroy target cells can be measured using any suitable known methods, such as cytotoxicity assays described in, for example, Kochenderfer et al., J. Immunotherapy, 32(7): 689-702 (2009), and Herman et al. J. Immunological Methods, 285 (1): 25-40 (2004). In certain embodiments, the biological activity of the cells also can be measured by assaying expression and/or secretion of certain cytokines, such as interleukin-2 (IL-2), interferon-gamma (IFNγ), interleukin-4 (IL-4), TNF-alpha (TNFα), interleukin-6 (IL-6), interleukin-10 (IL-10), interleukin-12 (IL-12), granulocyte-macrophage colony-stimulating factor (GM-CSF), CD107a, and/or TGF-beta (TGFβ). Assays to measure cytokines are well known, and include but are not limited to, ELISA, intracellular cytokine staining, cytometric bead array, RT-PCR, ELISPOT, flow cytometry and bio-assays in which cells responsive to the relevant cytokine are tested for responsiveness (e.g. proliferation) in the presence of a test sample. In some aspects the biological activity can be measured using an animal model of the disease or condition, such as a tumor xenograft model, and assessing the reduction in tumor burden or load and/or survival. In some aspects the biological activity is measured by assessing clinical outcome, such as reduction in tumor burden or load.

In some embodiments, administration of engineered cells expressing the provided anti-ROR1 CARs exhibit substantially improved tumor growth inhibition, in vivo persistence and/or prolonged survival of the subject with a tumor, compared to administration of engineered cells expressing reference CAR, such as anti-ROR1 R12. In some aspects, such improvement is observed in subjects having various types of ROR1-expressing cancers, including, but not limited to, lung cancer, breast cancer, chronic lymphocytic leukemia (CLL), ovarian cancer or mantle cell lymphoma (MCL).

In some embodiments, engineered cells expressing the provided anti-ROR1 CARs exhibit improved persistence and expansion when administered to a subject for adoptive cell therapy. In some embodiments, engineered cells expressing the provided CARs exhibit the same, substantially the same or higher persistence and expansion compared to engineered cells expressing a reference ROR1-specific chimeric antigen receptor, optionally under the same or substantially the same conditions or assay. In some aspects, the proliferation, expansion and/or persistence of an engineered cell expressing any of the provided receptors, e.g., CARs, can be assessed by determining the exposure, number, concentration, persistence and proliferation of the engineered cells, e.g., cells administered for adoptive cell therapy. In some embodiments, the exposure, number or level of engineered T cells, e.g., T cells administered for the T cell based therapy, or subset thereof, such as $CD3^+$ cells, $CD4^+$ cells, $CD8^+$ cells, $CD3^+$ $CAR^+$ cells, $CD4^+$ $CAR^+$ cells or $CD8^+$ $CAR^+$ cells can be assessed, e.g., from a subject, such as a human subject or an animal subject, that had been administered engineered cells. In some aspects, the exposure, number, concentration, persistence and proliferation relate to pharmacokinetic parameters. In some cases, pharmacokinetics can be assessed by measuring such parameters as the maximum (peak) plasma concentration ($C_{max}$), the peak time (i.e. when maximum plasma concentration ($C_{max}$) occurs; $T_{max}$), the minimum plasma concentration (i.e. the minimum plasma concentration between doses of a therapeutic agent, e.g., $CAR^+$ T cells; $C_{min}$), the elimination half-life ($T_{1/2}$) and area under the curve (i.e. the area under the curve generated by plotting time versus plasma concentration of the therapeutic agent $CAR^+$ T cells; AUC), following administration. The concentration of a particular therapeutic agent, e.g., $CAR^+$ T cells, in the plasma following administration can be measured using any known methods suitable for assessing concentrations of the therapeutic agents, e.g., $CAR^+$ T cells, in samples of blood, or any methods described herein. For example, nucleic acid-based methods, such as quantitative PCR (qPCR) or flow cytometry-based methods, or other assays, such as an immunoassay, ELISA, or chromatography/mass spectrometry-based assays can be used.

In some aspects, a reporter cell line can be employed to monitor antigen-independent activity and/or tonic signaling through anti-ROR1 CAR-expressing cells. In some embodiments, a T cell line, such as a Jurkat cell line, contains a reporter molecule, such as a fluorescent protein or other detectable molecule, such as a red fluorescent protein, expressed under the control of the endogenous Nur77 transcriptional regulatory elements. In some embodiments, the Nur77 reporter expression is cell intrinsic and dependent upon signaling through a recombinant reporter containing a primary activation signal in a T cell, a signaling domain of a T cell receptor (TCR) component, and/or a signaling domain comprising an immunoreceptor tyrosine-based activation motif (ITAM), such as a CD3 chain. Nur77 expression is generally not affected by other signaling pathways such as cytokine signaling or toll-like receptor (TLR) signaling, which may act in a cell extrinsic manner and may not depend on signaling through the recombinant receptor. Thus, only cells that express the exogenous recombinant receptor, e.g., anti-ROR1 CAR, containing the appropriate signaling regions is capable of expressing Nur77 upon stimulation (e.g., binding of the specific antigen). In some cases, Nur77 expression also can show a dose-dependent response to the amount of stimulation (e.g., antigen).

In some cases, to assess the specificity, cross-reactivity and/or antigen dependency of a particular activity, signaling or function of the receptor, e.g., CAR, any of the described assays for assessing activity, signaling or biological function of the receptors can be assessed in the presence and absence of the specific target antigen, e.g., human ROR1, or in the presence of the specific target antigen, e.g., human ROR1, and in the presence of a different, non-specific antigen, e.g., human ROR2 or a non-human ROR1, such as a mouse ROR1.

In some of any embodiments, the provided anti-ROR1 CAR exhibits the same, substantially the same or lower level or degree of signaling or activity in the presence of a ROR2 protein, e.g., a human ROR2, compared to the level or degree of signaling or activity in the presence of a ROR1 protein, e.g., a human ROR1, e.g., under the same or substantially the same conditions or assay. For example, in some aspects, the provided anti-ROR1 CAR exhibits a level or degree of signaling or activity in the presence of a human ROR2 that is at least at or about 75%, 80%, 90%, 95% or 99% less than the level or degree of signaling or activity in the presence of a human ROR1, e.g., under the same or substantially the same conditions or assay.

In some of any embodiments, the provided anti-ROR1 CAR exhibits the same, substantially the same or lower level or degree of signaling or activity in the presence of a ROR2 protein, e.g., a human ROR2, compared to a reference ROR1-specific CAR, e.g., under the same or substantially the same conditions or assay. In some of any embodiments, the provided anti-ROR1 CAR exhibits the same, substantially the same or lower level or degree of signaling or activity in the presence of a ROR2 protein, e.g., a human ROR2, compared to a reference ROR1-specific CAR, e.g., under the same or substantially the same conditions or assay. In some of any embodiments, the provided anti-ROR1 CAR exhibits the same, substantially the same or higher antigen-specific signaling and/or antigen dependent activity or signaling compared to a reference ROR1-specific CAR, e.g., under the same or substantially the same conditions or assay.

In some of any embodiments, the provided anti-ROR1 CAR exhibits the same, substantially the same or lower tonic signaling and/or antigen independent activity or signaling compared to a reference ROR1-specific CAR, e.g., under the same or substantially the same conditions or assay. For example, in some embodiments, the provided anti-ROR1 CAR exhibits a level or degree of tonic signaling and/or antigen independent activity or signaling that is at least at or about 75%, 80%, 90%, 95% or 99% less than the level or degree of tonic signaling and/or antigen independent activity of a reference ROR1-specific CAR, e.g., under the same or substantially the same conditions or assay.

In some embodiments, the provided anti-ROR1 CARs exhibit improved expression on the surface of cells, such as compared to an alternative CAR that has an identical amino acid sequence but that is encoded by non-splice site eliminated and/or a codon-optimized nucleotide sequence. In some embodiments, the expression of the recombinant receptor on the surface of the cell can be assessed. Approaches for determining expression of the recombinant receptor on the surface of the cell may include use of chimeric antigen receptor (CAR)-specific antibodies (e.g., Brentjens et al., Sci. Transl. Med. 2013 March; 5(177): 177ra38), Protein L (Zheng et al., J. Transl. Med. 2012 February; 10:29), epitope tags, and monoclonal antibodies that specifically bind to a CAR polypeptide (see WO2014190273). In some embodiments, the expression of the recombinant receptor on the surface of the cell, e.g., primary T cell, can be assessed, for example, by flow cytometry, using binding molecules that can bind to the recombinant receptor or a portion thereof that can be detected. In some embodiments, the binding molecules used for detecting expression of the recombinant receptor an anti-idiotypic antibody, e.g., an anti-idiotypic agonist antibody specific for a binding domain, e.g., scFv, or a portion thereof. In some embodiments, the binding molecule is or comprises an isolated or purified antigen, e.g., recombinantly expressed antigen.

E. Polynucleotides Encoding Binding Molecules

Also provided are polynucleotides encoding the binding molecules, such as anti-ROR1 antibodies, antigen-binding fragments thereof, recombinant receptors (e.g., chimeric antigen receptors) and/or portions, e.g., chains or fragments, thereof. Among the provided polynucleotides are those encoding the anti-ROR1 antibodies (e.g., antigen-binding fragment) or chimeric antigen receptors described herein. The polynucleotides may include those encompassing natural and/or non-naturally occurring nucleotides and bases, e.g., including those with backbone modifications. The terms "nucleic acid molecule", "nucleic acid", "sequence of nucleotides", and "polynucleotide" may be used interchangeably, and refer to a polymer of nucleotides. Such polymers of nucleotides may contain natural and/or non-natural nucleotides, and include, but are not limited to, DNA, RNA, and PNA. "Nucleic acid sequence" refers to the linear sequence of nucleotides that comprise the nucleic acid molecule or polynucleotide.

Provided are polynucleotides that contain a nucleic acid encoding any of the anti-ROR1 antibody or antigen-binding domain thereof described herein, or any portion, fragment, chain or domain thereof. In some embodiments, the antibody or antigen-binding fragment thereof contain multiple domains or chains (e.g., heavy chain and a light chain), and all of the antibody or antigen-binding fragment thereof is encoded in one polynucleotide. Also provided are polynucleotides that contain a nucleic acid encoding any of the single chain cell surface proteins described herein. Also provided are polynucleotides that contain a nucleic acid encoding any of the conjugate described herein. Also provided are polynucleotides that contain a nucleic acid encoding any of the anti-ROR1 chimeric antigen receptors described herein. In some embodiments, the binding molecule, such as the antibody or antigen-binding fragment thereof or recombinant receptors, contain multiple domains or chains (e.g., a heavy chain and a light chain), and all of the binding molecule is encoded in more than one polynucleotide, such as two or more polynucleotides. In some embodiments, the polynucleotides are comprised in a vector.

In some aspects, provided are polynucleotides that contain nucleic acid sequences encoding any of the binding molecules provided herein, for example, in Section I.A and I.D. In some embodiments, provided are polynucleotides that contain nucleic acid sequences encoding a portion, fragment, chain or domain of any of the binding molecules provided herein, for example, in Section I.A and I.D.

In some cases, the polynucleotide encoding the ROR1-binding molecules, such as an antibody or antigen-binding fragment thereof or a recombinant receptor (e.g., CAR) contains a signal sequence that encodes a signal peptide, in some cases encoded upstream of the nucleic acid sequences encoding the ROR1-binding molecules, such as an antibody or antigen-binding fragment thereof or a recombinant receptor (e.g., CAR), or joined at the 5' terminus of the nucleic acid sequences encoding the antigen-binding domain. In some cases, the polynucleotide containing nucleic acid sequences encoding the ROR1-binding molecules, such as an antibody or antigen-binding fragment thereof or a recombinant receptor (e.g., CAR), contains a signal sequence that encodes a signal peptide. In some aspects, the signal sequence may encode a signal peptide derived from a native polypeptide. In other aspects, the signal sequence may encode a heterologous or non-native signal peptide. In some aspects, non-limiting exemplary signal peptide include a signal peptide of the IgG kappa chain set forth in SEQ ID NO: 43 or encoded by the nucleotide sequence set forth in SEQ ID NO:44. In some aspects, a non-limiting exemplary signal peptide includes a signal peptide of a GMCSFR alpha chain set forth in SEQ ID NO:45 and encoded by the nucleotide sequence set forth in SEQ ID NO:46. In some aspects, a non-limiting exemplary signal peptide includes a signal peptide of a CD8 alpha signal peptide set forth in SEQ ID NO:47. In some aspects, a non-limiting exemplary signal peptide includes a signal peptide of a CD33 signal peptide set forth in SEQ ID NO:42 and encoded by the nucleotide sequence set forth in SEQ ID NO:190. In some cases, the polynucleotide encoding the ROR1-binding molecules, such as an antibody or antigen-binding fragment thereof or a recombinant receptor (e.g., CAR) can contain nucleic acid sequence encoding additional molecules, such as a surrogate marker or other markers, or can contain additional components, such as promoters, regulatory elements and/or multicistronic elements. In some embodiments, the nucleic acid sequence encoding the ROR1-binding molecules, such as an antibody or antigen-binding fragment thereof or a recombinant receptor (e.g., CAR) can be operably linked to any of the additional components.

In some embodiments, provided are polynucleotides contain nucleic acid sequences encoding a variable heavy chain domain ($V_H$) of an antibody or an antigen-binding fragment thereof, or a recombinant receptor containing an antibody or an antigen-binding fragment thereof. In some embodiments, provided are polynucleotides contain nucleic acid sequences encoding a variable light chain domain ($V_L$) of an antibody or an antigen-binding fragment thereof, or a recombinant receptor containing an antibody or an antigen-binding fragment thereof. In some embodiments, provided are polynucleotides that contain nucleic acid sequences encoding a variable heavy chain domain ($V_H$) and a variable light chain domain ($V_L$) of an antibody or an antigen-binding fragment thereof, or a recombinant receptor containing an antibody or an antigen-binding fragment thereof.

In some of any embodiments, said polynucleotide contains a nucleic acid encoding the $V_H$ comprising the sequence set forth in SEQ ID NO: 110, 119, 101 or 128 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 110, 119, 101 or 128. In some of any embodiments, said polynucleotide contains a nucleic acid encoding the $V_L$ comprising the sequence set forth in SEQ ID NO: 113, 122 or 104, or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 113, 122 or 104.

In some of any embodiments, said polynucleotide contains a nucleic acid encoding the $V_H$ comprising the sequence set forth in SEQ ID NO: 110, 119, 101 or 128 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 110, 119, 101 or 128, and a nucleic acid encoding the $V_L$ comprising the sequence set forth in SEQ ID NO: 113, 122 or 104, or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 113, 122 or 104.

In some of any embodiments, said polynucleotide contains a nucleic acid encoding the $V_H$ comprising the sequence set forth in SEQ ID NO: 110 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 110. In some embodiments, said polynucleotide contains a nucleic acid encoding the $V_L$ comprising the sequence set forth in SEQ ID NO: 113, or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 113. In some of any embodiments, said polynucleotide contains a nucleic acid encoding the $V_H$ comprising the sequence set forth in SEQ ID NO: 119 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 119. In some embodiments, said polynucleotide contains a nucleic acid encoding the $V_L$ comprising the sequence set forth in SEQ ID NO: 122, or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 122.

In some of any embodiments, said polynucleotide contains a nucleic acid encoding the $V_H$ comprising the sequence set forth in SEQ ID NO: 101 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 101. In some embodiments, said polynucleotide contains a nucleic acid encoding the $V_L$ comprising the sequence set forth in SEQ ID NO: 104, or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 104. In some of any embodiments, said polynucleotide contains a nucleic acid encoding the $V_H$ comprising the sequence set forth in SEQ ID NO: 128 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 128. In some embodiments, said polynucleotide contains a nucleic acid encoding the $V_L$ comprising the sequence set forth in SEQ ID NO: 104, or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 104.

In some of any embodiments, said polynucleotide contains a nucleic acid encoding the $V_H$ comprising the sequence set forth in SEQ ID NO: 110 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO:

110, and a nucleic acid encoding the $V_L$ comprising the sequence set forth in SEQ ID NO: 113, or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 113. In some of any embodiments, said polynucleotide contains a nucleic acid encoding the $V_H$ comprising the sequence set forth in SEQ ID NO: 119 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 119, and a nucleic acid encoding the $V_L$ comprising the sequence set forth in SEQ ID NO: 122, or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 122.

In some of any embodiments, said polynucleotide contains a nucleic acid encoding the $V_H$ comprising the sequence set forth in SEQ ID NO: 101 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 101, and a nucleic acid encoding the $V_L$ comprising the sequence set forth in SEQ ID NO: 104, or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 104. In some of any embodiments, said polynucleotide contains a nucleic acid encoding the $V_H$ comprising the sequence set forth in SEQ ID NO: 128 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 128, and a nucleic acid encoding the $V_L$ comprising the sequence set forth in SEQ ID NO: 104, or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 104.

In some of any embodiments, said polynucleotide contains a nucleic acid encoding the scFv comprising the sequence set forth in SEQ ID NO: 116, 125, 107 or 132 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 116, 125, 107 or 132. In some of any embodiments, said polynucleotide contains a nucleic acid encoding the scFv comprising the sequence set forth in SEQ ID NO: 116 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 116. In some of any embodiments, said polynucleotide contains a nucleic acid encoding the scFv comprising the sequence set forth in SEQ ID NO: 125 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 125. In some of any embodiments, said polynucleotide contains a nucleic acid encoding the scFv comprising the sequence set forth in SEQ ID NO: 107 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 107. In some of any embodiments, said polynucleotide contains a nucleic acid encoding the scFv comprising the sequence set forth in SEQ ID NO: 132 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 132.

In some of any embodiments, said polynucleotide contains a nucleic acid encoding the spacer comprising the sequence set forth in SEQ ID NO: 30 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 30. In some of any embodiments, said polynucleotide contains a nucleic acid encoding the spacer comprising the sequence set forth in SEQ ID NO: 192 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 192. In some of any embodiments, said polynucleotide contains a nucleic acid encoding the spacer comprising the sequence set forth in SEQ ID NO: 193 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 193. In some of any embodiments, said polynucleotide contains a nucleic acid encoding the spacer comprising the sequence set forth in SEQ ID NO: 195 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 195.

Also provided are polynucleotides that have been optimized for codon usage and/or to eliminate splice sites, such as cryptic splice sites. In some embodiments, the polynucleotides are modified to optimize codon usage. In some embodiments, the polynucleotides are codon optimized for expression in a human cell such as a human T cell such as a primary human T cell. In some embodiments, the polynucleotides, such as those encoding any of the antibodies, receptors (such as antigen receptors such as chimeric antigen receptors) and/or ROR1-specific binding proteins provided herein, are or have been modified to reduce heterogeneity or contain one or more nucleic acid sequences observed herein (such as by the optimization methods) to result in improved features of the polypeptides, such as the CARs, as compared to those containing distinct, reference, sequences or that have not been optimized. In some embodiments, the polynucleotide is optimized by splice site elimination. Among such features include improvements in RNA heterogeneity, such as that resulting from the presence of one or more splice sites, such as one or more cryptic splice sites, and/or improved expression and/or surface expression of the encoded protein, such as increased levels, uniformity, or consistency of expression among cells or different therapeutic cell compositions engineered to express the polypeptides. In some embodiments, the polynucleotides can be codon optimized for expression in human cells.

Genomic nucleic acid sequences generally, in nature, in a mammalian cell, undergo processing co-transcriptionally or immediately following transcription, wherein a nascent precursor messenger ribonucleic acid (pre-mRNA), transcribed from a genomic deoxyribonucleic acid (DNA) sequence, is in some cases edited by way of splicing, to remove introns, followed by ligation of the exons in eukaryotic cells. Consensus sequences for splice sites are known, but in some aspects, specific nucleotide information defining a splice site may be complex and may not be readily apparent based on available methods. Cryptic splice sites are splice sites that are not predicted based on the standard consensus sequences and are variably activated. Hence, variable splicing of pre-mRNA at cryptic splice sites leads to heterogeneity in the transcribed mRNA products upon expression in eukaryotic cells.

Polynucleotides generated for the expression of transgenes are typically constructed from nucleic acid sequences, such as complementary DNA (cDNA), or portions thereof, that do not contain introns. Thus, splicing of such sequences is not expected to occur. However, the presence of cryptic splice sites within the cDNA sequence can lead to unintended or undesired splicing reactions and heterogeneity in the transcribed mRNA. Such heterogeneity results in translation of unintended protein products, such as truncated protein products with variable amino acid sequences that exhibit modified expression and/or activity.

In some embodiments, eliminating splice sites, such as cryptic splice sites, can improve or optimize expression of a transgene product, such as a polypeptide translated from the transgene, such as an anti-ROR1 CAR polypeptide. Splicing at cryptic splice sites of an encoded transgene, such as an encoded ROR1 CAR molecule, can lead to reduced protein expression, e.g., expression on cell surfaces, and/or reduced function, e.g., reduced intracellular signaling. Provided herein are polynucleotides, encoding anti-ROR1 CAR proteins that have been optimized to reduce or eliminate cryptic splice sites. Also provided herein are polynucleotides encoding anti-ROR1 CAR proteins that have been optimized for codon expression and/or in which one or more sequence, such as one identified by the methods or observations herein regarding splice sites, is present, and/or in which an identified splice site, such as any of the identified splice sites herein, is not present. Among the provided polynucleotides are those exhibiting below a certain degree of RNA heterogeneity or splice forms when expressed under certain conditions and/or introduced into a specified cell type, such as a human T cell, such as a primary human T cell, and cells and compositions and articles of manufacture containing such polypeptides and/or exhibiting such properties. In some embodiments, the RNA heterogeneity of transcribed RNA is reduced by greater than or greater than about 10%, 15%, 20%, 25%, 30%, 40%, 50% or more compared to a polynucleotide that has not been modified to remove cryptic splice sites and/or by codon optimization. In some embodiments, the provided polynucleotides encoding an anti-ROR1 CAR exhibit RNA homogeneity of transcribed RNA that is at least 70%, 75%, 80%, 85%, 90%, or 95% or greater.

RNA heterogeneity can be determined by any of a number of methods provided herein or described or known. In some embodiments, RNA heterogeneity of a transcribed nucleic acid is determined by amplifying the transcribed nucleic acid, such as by reverse transcriptase polymerase chain reaction (RT-PCR) followed by detecting one or more differences, such as differences in size, in the one or more amplified products. In some embodiments, the RNA heterogeneity is determined based on the number of differently sized amplified products, or the proportion of various differently sized amplified products. In some embodiments, RNA, such as total RNA or cytoplasmic polyadenylated RNA, is harvested from cells, expressing the transgene to be optimized, and amplified by reverse transcriptase polymerase chain reaction (RT-PCR) using a primer specific to the 5' untranslated region (5' UTR), in some cases corresponding to a portion of the promoter sequence in the expression vector, located upstream of the transgene in the transcribed RNA, and a primer specific to the 3' untranslated region (3' UTR), located downstream of the expressed transgene in the transcribed RNA sequence or a primer specific to a sequence within the transgene. In particular embodiments, at least one primer complementary to a sequence in the 5' untranslated region (UTR) and at least one primer complementary to a sequence in the 3' untranslated region (UTR) are employed to amplify the transgene. One can resolve RNA, such as messenger RNA, and analyze the heterogeneity thereof by several methods. Non-limiting, exemplary methods include agarose gel electrophoresis, chip-based capillary electrophoresis, analytical centrifugation, field flow fractionation, and chromatography, such as size exclusion chromatography or liquid chromatography.

In some embodiments, a provided polynucleotide encoding an anti-ROR1 CAR provided herein, or a construct provided herein, includes modifications to remove one or more splice donor and/or acceptor site that may contribute to splice events and/or reduced expression and/or increased RNA heterogeneity. In some embodiments, provided polynucleotides are modified in one or more polynucleotides in the spacer region to eliminate or reduce splice events.

In some of any embodiments, said polynucleotide contains a nucleic acid encoding the $V_H$ comprising the sequence set forth in SEQ ID NO: 111, 120, 102 or 129, and a nucleic acid encoding the $V_L$ comprising the sequence set forth in SEQ ID NO: 114, 123, 105 or 131. In some of any embodiments, said polynucleotide contains a nucleic acid encoding the $V_H$ comprising the sequence set forth in SEQ ID NO: 111, and a nucleic acid encoding the $V_L$ comprising the sequence set forth in SEQ ID NO: 114. In some of any embodiments, said polynucleotide contains a nucleic acid encoding the $V_H$ comprising the sequence set forth in SEQ ID NO: 120, and a nucleic acid encoding the $V_L$ comprising the sequence set forth in SEQ ID NO: 123. In some of any embodiments, said polynucleotide contains a nucleic acid encoding the $V_H$ comprising the sequence set forth in SEQ ID NO: 102, and a nucleic acid encoding the $V_L$ comprising the sequence set forth in SEQ ID NO: 105. In some of any embodiments, said polynucleotide contains a nucleic acid encoding the $V_H$ comprising the sequence set forth in SEQ ID NO: 129, and a nucleic acid encoding the $V_L$ comprising the sequence set forth in SEQ ID NO: 131.

In some of any embodiments, said polynucleotide contains a nucleic acid encoding the scFv comprising the sequence set forth in SEQ ID NO: 117, 126, 108 or 133. In some of any embodiments, said polynucleotide contains a nucleic acid encoding the scFv comprising the sequence set forth in SEQ ID NO: 117. In some of any embodiments, said polynucleotide contains a nucleic acid encoding the scFv comprising the sequence set forth in SEQ ID NO: 126. In some of any embodiments, said polynucleotide contains a nucleic acid encoding the scFv comprising the sequence set forth in SEQ ID NO: 108. In some of any embodiments, said polynucleotide contains a nucleic acid encoding the scFv comprising the sequence set forth in SEQ ID NO: 133.

In some of any embodiments, said polynucleotide contains a nucleic acid encoding the spacer comprising the sequence set forth in SEQ ID NO:136. In some of any embodiments, said polynucleotide contains a nucleic acid encoding the spacer comprising the sequence set forth in SEQ ID NO:139. In some of any embodiments, said polynucleotide contains a nucleic acid encoding the spacer comprising the sequence set forth in SEQ ID NO:196.

Provided in are exemplary chimeric antigen receptors (CARs) specific for ROR1, and polynucleotides containing nucleic acid sequences encoding all or a portion, fragment, domain or chain of any of the exemplary CARs described herein. In some embodiments, the exemplary CARs contain one of the ROR1-binding antibody fragment, such as those described in Section I.A and/or Table 2. In some embodiments, the exemplary CARs are among those described in each row of Table E1 and/or Table 3. Also provided herein are polynucleotides encoding the CARs. In some embodiments, the CAR can be encoded by more than one different polynucleotides, such as two or more polynucleotides. In some of any such embodiments, two or more polynucleotides can each contain nucleic acids encoding a portion, fragment, domain or chain of the CAR.

Also provided herein are exemplary modified polynucleotides, including polynucleotides that were modified for codon optimization (O) and/or splice site elimination (SSE). Examples of the SEQ ID NOS: for such polynucleotides are set forth in Table 3, wherein exemplary nucleotide (nt) sequences for the components of the exemplary CAR constructs prior to splice site elimination and codon optimization (N/O), nucleic acid (nt) sequences for the components of the CAR constructs following splice site elimination and optimization (O/SSE), and the corresponding amino acid (aa) sequences encoded by the nucleic acid sequences are provided. The components include the anti-ROR1 scFv, spacer, transmembrane (tm) domain, 4-1BB costimulatory signaling region sequence (costim), CD3ζ signaling domain (CD3ζ). The full sequences of the exemplary CARs following splice site elimination and optimization (CAR) are also provided. In some cases, the polynucleotide also includes the CD33 signal sequence (ss), a T2A ribosomal skip element (T2A) and truncated EGF receptor (EGFRt) sequence. Polynucleotide sequences of exemplary CAR are set forth in SEQ ID NOs: 156-161, encoding the amino acid sequences set forth in SEQ ID NOs: 184-189.

In some of any embodiments, said polynucleotide contains the sequence set forth in SEQ ID NO: 156, 157, 158, 159, 160 or 161 or a sequence that exhibits at least 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 156, 157, 158, 159, 160 or 161. In some of any embodiments, said polynucleotide contains the sequence set forth in SEQ ID NO: 156 or a sequence that exhibits at least 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 156. In some of any embodiments, said polynucleotide contains the sequence set forth in SEQ ID NO: 156. In some of any embodiments, said polynucleotide contains the sequence set forth in SEQ ID NO: 157 or a sequence that exhibits at least 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 157. In some of any embodiments, said polynucleotide contains the sequence set forth in SEQ ID NO: 157. In some of any embodiments, said polynucleotide contains the sequence set forth in SEQ ID NO: 158 or a sequence that exhibits at least 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 158. In some of any embodiments, said polynucleotide contains the sequence set forth in SEQ ID NO: 158. In some of any embodiments, said polynucleotide contains the sequence set forth in SEQ ID NO: 159 or a sequence that exhibits at least 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 159. In some of any embodiments, said polynucleotide contains the sequence set forth in SEQ ID NO: 159. In some of any embodiments, said polynucleotide contains the sequence set forth in SEQ ID NO: 160 or a sequence that exhibits at least 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 160. In some of any embodiments, said polynucleotide contains the sequence set forth in SEQ ID NO: 160. In some of any embodiments, said polynucleotide contains the sequence set forth in SEQ ID NO: 161 or a sequence that exhibits at least 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 161. In some of any embodiments, said polynucleotide contains the sequence set forth in SEQ ID NO: 161.

In some of any embodiments, said polynucleotide contains a nucleic acid encoding the sequence set forth in SEQ ID NO: 184, 185, 186, 187, 188 or 189 or a sequence that encodes a polypeptide sequence that exhibits at least 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 184, 185, 186, 187, 188 or 189. In some of any embodiments, said polynucleotide contains a nucleic acid encoding the sequence set forth in SEQ ID NO: 184 or a sequence that encodes a polypeptide sequence that exhibits at least 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 184. In some of any embodiments, said polynucleotide contains a nucleic acid encoding the sequence set forth in SEQ ID NO: 184. In some of any embodiments, said polynucleotide contains a nucleic acid encoding the sequence set forth in SEQ ID NO: 185 or a sequence that encodes a polypeptide sequence that exhibits at least 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 185. In some of any embodiments, said polynucleotide contains a nucleic acid encoding the sequence set forth in SEQ ID NO: 185. In some of any embodiments, said polynucleotide contains a nucleic acid encoding the sequence set forth in SEQ ID NO: 186 or a sequence that encodes a polypeptide sequence that exhibits at least 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 186. In some of any embodiments, said polynucleotide contains a nucleic acid encoding the sequence set forth in SEQ ID NO: 186. In some of any embodiments, said polynucleotide contains a nucleic acid encoding the sequence set forth in SEQ ID NO: 187 or a sequence that encodes a polypeptide sequence that exhibits at least 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 187. In some of any embodiments, said polynucleotide contains a nucleic acid encoding the sequence set forth in SEQ ID NO: 187. In some of any embodiments, said polynucleotide contains a nucleic acid encoding the sequence set forth in SEQ ID NO: 188 or a sequence that encodes a polypeptide sequence that exhibits at least 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 188. In some of any embodiments, said polynucleotide contains a nucleic acid encoding the sequence set forth in SEQ ID NO: 188. In some of any embodiments, said polynucleotide contains a nucleic acid encoding the sequence set forth in SEQ ID NO: 189 or a sequence that encodes a polypeptide sequence that exhibits at least 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 189. In some of any embodiments, said polynucleotide contains a nucleic acid encoding the sequence set forth in SEQ ID NO: 189.

and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. Among the methods include off-the-shelf methods. In some aspects, such as for off-the-

TABLE 3

Exemplary ROR1-binding CAR components (SEQ ID NOS:)

Nucleotides (nt)

| | | scFv | | spacer | | TM | | 4-1BB | | CD3ξ | | CAR |
|---|---|---|---|---|---|---|---|---|---|---|---|---|
| CAR # | scFv# | N/O | O/SSE | N/O | O/SSE | N/O | O/SSE | N/O | O/SSE | N/O | O/SSE | O/SSE |
| F | ROR1-1 | 116 | 117 | 192 | 136 | 197 | 198 | 154 | 155 | 182 | 150 | 156 |
| A | ROR1-2 | 125 | 126 | 192 | 136 | 197 | 198 | 154 | 155 | 182 | 150 | 157 |
| G | ROR1-1 | 116 | 117 | 193 | 139 | 197 | 198 | 154 | 155 | 182 | 150 | 158 |
| I | ROR1-3 | 107 | 108 | 193 | 139 | 197 | 198 | 154 | 155 | 182 | 150 | 159 |
| R | ROR1-2 | 125 | 126 | 193 | 139 | 197 | 198 | 154 | 155 | 182 | 150 | 160 |
| B1 | ROR1-4 | 132 | 133 | 193 | 139 | 197 | 198 | 154 | 155 | 182 | 150 | 161 |

Amino acids (aa)

| CAR # | scFv# | scFv | spacer | TM | 4-1BB | CD3z | CAR |
|---|---|---|---|---|---|---|---|
| F | ROR1-1 | 118 | 135 | 8 | 12 | 13 | 184 |
| A | ROR1-2 | 127 | 135 | 8 | 12 | 13 | 185 |
| G | ROR1-1 | 118 | 138 | 8 | 12 | 13 | 186 |
| I | ROR1-3 | 109 | 138 | 8 | 12 | 13 | 187 |
| R | ROR1-2 | 127 | 138 | 8 | 12 | 13 | 188 |
| B1 | ROR1-4 | 134 | 138 | 8 | 12 | 13 | 189 |

II. Engineered Cells

Also provided are cells such as engineered cells that contain a recombinant receptor (e.g., a chimeric antigen receptor) such as one that contains an extracellular domain including an anti-ROR1 antibody or fragment as described herein. Also provided are populations of such cells, compositions containing such cells and/or enriched for such cells, such as in which cells expressing the ROR1-binding molecule make up at least 50, 60, 70, 80, 90, 91, 92, 93, 94, 95, 96, 97, 98, 99, or more percent of the total cells in the composition or cells of a certain type such as T cells or CD8+ or CD4+ cells. Among the compositions are pharmaceutical compositions and formulations for administration, such as for adoptive cell therapy. Also provided are therapeutic methods for administering the cells and compositions to subjects, e.g., patients.

Thus also provided are genetically engineered cells expressing the recombinant receptors containing the antibodies, e.g., cells containing the CARs. The cells generally are eukaryotic cells, such as mammalian cells, and typically are human cells. In some embodiments, the cells are derived from the blood, bone marrow, lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). The cells typically are primary cells, such as those isolated directly from a subject and/or isolated from a subject and frozen. In some embodiments, the cells include one or more subsets of T cells or other cell types, such as whole T cell populations, CD4+ cells, CD8+ cells, shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, as described herein, and re-introducing them into the same patient, before or after cryopreservation.

Among the sub-types and subpopulations of T cells and/or of CD4+ and/or of CD8+ T cells are naïve T ($T_N$) cells, effector T cells ($T_{EFF}$), memory T cells and sub-types thereof, such as stem cell memory T ($T_{SCM}$), central memory T ($T_{CM}$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

In some embodiments, the cells include one or more polynucleotides introduced via genetic engineering, and thereby express recombinant or genetically engineered products of such polynucleotides. In some embodiments, the polynucleotides are heterologous, i.e., normally not present in a cell or sample obtained from the cell, such as one obtained from another organism or cell, which for example, is not ordinarily found in the cell being engineered and/or an organism from which such cell is derived. In some embodiments, the polynucleotides are not naturally occurring, such as a polynucleotide not found in nature, including one comprising chimeric combinations of polynucleotides encoding various domains from multiple different cell types. In some embodiments, the cells (e.g., engineered cells) comprise a vector (e.g., a viral vector, expression vector, etc.) as described herein such as a vector comprising a nucleic acid encoding a recombinant receptor described herein.

A. Vectors and Methods for Genetic Engineering

Also provided are nucleic acids, e.g., polynucleotides, encoding the antibodies and/or portions, e.g., chains, thereof. Among the provided nucleic acids are those encoding the anti-ROR1 antibodies (e.g., antigen-binding fragment) described herein. Also provided are nucleic acids, e.g., polynucleotides, encoding one or more antibodies and/or portions thereof, e.g., those encoding one or more of the anti-ROR1 antibodies (e.g., antigen-binding fragment) described herein and/or other antibodies and/or portions thereof, e.g., antibodies and/or portions thereof that binds other target antigens. Also provided are methods, nucleic acids, compositions, and kits, for expressing the binding molecules (e.g., anti-ROR1 binding molecules), including recombinant receptors (e.g., CARs) comprising the binding molecules, and for producing the genetically engineered cells expressing such binding molecules. In some embodiments, one or more binding molecules, including recombinant receptors (e.g., CARs) can be genetically engineered into cells or plurality of cells. The genetic engineering generally involves introduction of a nucleic acid encoding the recombinant or engineered component into the cell, such as by retroviral transduction, transfection, or transformation.

The nucleic acids may include those encompassing natural and/or non-naturally occurring nucleotides and bases, e.g., including those with backbone modifications. The terms "nucleic acid molecule", "nucleic acid" and "polynucleotide" may be used interchangeably, and refer to a polymer of nucleotides. Such polymers of nucleotides may contain natural and/or non-natural nucleotides, and include, but are not limited to, DNA, RNA, and PNA. "Nucleic acid sequence" refers to the linear sequence of nucleotides that comprise the nucleic acid molecule or polynucleotide. In some aspects, the nucleic acid sequence encoding at least a portion of the antibody or antigen-binding fragment thereof, such as an scFv, conjugates, receptors (e.g., CARs) provided herein can be optimized, for example, codon-optimized for expression in a human cell and/or optimized to reduce or eliminate cryptic splice sites.

In some embodiments, the polynucleotides also include one or more additional sequences, such as those encoding one or more additional molecules, such as a marker, or promoters, regulatory elements and/or multicistronic elements. In some embodiments, the provided polynucleotides include any of the polynucleotides described herein, e.g., in Section I.E.

Also provided are vectors containing the nucleic acids, e.g., polynucleotides, and host cells containing the vectors, e.g., for producing the antibodies or antigen-binding fragments thereof. Also provided are methods for producing the antibodies or antigen-binding fragments thereof. The nucleic acid may encode an amino acid sequence comprising the $V_L$ region and/or an amino acid sequence comprising the $V_H$ region of the antibody (e.g., the light and/or heavy chains of the antibody). The nucleic acid may encode one or more amino acid sequence comprising the $V_L$ region and/or an amino acid sequence comprising the $V_H$ region of the antibody (e.g., the light and/or heavy chains of the antibody). In some embodiments, the nucleic acid, e.g., polynucleotide encodes one or more $V_H$ region and/or one or more $V_L$ region of the antibody, in any order or orientation. In some embodiments, the nucleic acid, e.g., polynucleotide encodes a $V_H$ region and a $V_L$ region, and the coding sequence for the $V_H$ region is upstream of the coding sequence for the $V_L$ region. In some embodiments, the nucleic acid, e.g., polynucleotide encodes a $V_H$ region and a $V_L$ region, and the coding sequence for the $V_L$ region is upstream of the coding sequence for the $V_H$ region.

Also provided are vectors containing the nucleic acids, e.g., polynucleotides, and engineered cells containing the vectors, e.g., engineered immune cells expressing the binding molecules such as recombinant receptors. Also provided are methods for engineering cells, such as immune cells, to express the anti-ROR1 binding molecule, such as a recombinant receptor, e.g., a chimeric antigen receptor (CAR). The nucleic acid may encode an amino acid sequence comprising the $V_L$ region and/or an amino acid sequence comprising the $V_H$ region of the antibody (e.g., the light and/or heavy chains of the antibody) as the extracellular antigen-binding domain; a transmembrane domain and intracellular domains, such as a CD3 zeta and a costimulatory signaling domain In a further embodiment, one or more vectors (e.g., expression vectors) comprising such polynucleotides are provided. In a further embodiment, a host cell comprising such polynucleotides is provided. In one such embodiment, a host cell comprises (e.g., has been transformed with) a vector comprising a nucleic acid that encodes an amino acid sequence comprising the $V_H$ region of the antibody. In another such embodiment, a host cell comprises (e.g., has been transformed with) (1) a vector comprising a nucleic acid that encodes an amino acid sequence comprising the $V_L$ region of the antibody and an amino acid sequence comprising the $V_H$ region of the antibody, or (2) a first vector comprising a nucleic acid that encodes an amino acid sequence comprising the $V_L$ region of the antibody and a second vector comprising a nucleic acid that encodes an amino acid sequence comprising the $V_H$ region of the antibody. In some embodiments, a host cell comprises (e.g., has been transformed with) one or more vectors comprising one or more nucleic acid that encodes one or more an amino acid sequence comprising one or more antibodies and/or portions thereof, e.g., antigen-binding fragments thereof. In some embodiments, one or more such host cells are provided. In some embodiments, a composition containing one or more such host cells are provided. In some embodiments, the one or more host cells can express different antibodies, or the same antibody. In some embodiments, each of the host cells can express more than one antibody.

Also provided are methods of making the anti-ROR1 chimeric antigen receptors. For recombinant production of the chimeric receptors, a nucleic acid sequence encoding a chimeric receptor antibody, e.g., as described herein, may be isolated and inserted into one or more vectors for further cloning and/or expression in a host cell. Such nucleic acid sequences may be readily isolated and sequenced using conventional procedures (e.g., by using oligonucleotide probes that are capable of binding specifically to genes encoding the heavy and light chains of the antibody). In some embodiments, a method of making the anti-ROR1 chimeric antigen receptor is provided, wherein the method comprises culturing a host cell comprising a nucleic acid sequence encoding the antibody, as provided above, under conditions suitable for expression of the receptor.

Also provided are methods of making the anti-ROR1 antibodies (including antigen-binding fragments). For recombinant production of the anti-ROR1 antibody, a nucleic acid sequence or a polynucleotide encoding an antibody, e.g., as described above, may be isolated and inserted into one or more vectors for further cloning and/or expression in a host cell. Such nucleic acid sequences may be readily isolated and sequenced using conventional procedures (e.g., by using oligonucleotide probes that are capable of binding specifically to genes encoding the heavy and light chains of the antibody). In some embodiments, a method of making the anti-ROR1 antibody is provided, wherein the method comprises culturing a host cell comprising a nucleic acid sequence encoding the antibody, as provided above, under conditions suitable for expression of the antibody, and optionally recovering the antibody from the host cell (or host cell culture medium).

In addition to prokaryotes, eukaryotic microbes such as filamentous fungi or yeast are suitable cloning or expression hosts for antibody-encoding vectors, including fungi and yeast strains whose glycosylation pathways have been modified to mimic or approximate those in human cells, resulting in the production of an antibody with a partially or fully human glycosylation pattern. See Gerngross, Nat. Biotech. 22:1409-1414 (2004), and Li et al., Nat. Biotech. 24:210-215 (2006).

Exemplary eukaryotic cells that may be used to express polypeptides include, but are not limited to, COS cells, including COS 7 cells; 293 cells, including 293-6E cells; CHO cells, including CHO-S, DG44. Lec13 CHO cells, and FUT8 CHO cells; PER.C6® cells; and NSO cells. In some embodiments, the antibody heavy chains and/or light chains (e.g., $V_H$ region and/or $V_L$ region) may be expressed in yeast. See, e.g., U.S. Publication No. US 2006/0270045 A1. In some embodiments, a particular eukaryotic host cell is selected based on its ability to make desired post-translational modifications to the heavy chains and/or light chains (e.g., $V_H$ region and/or $V_L$ region). For example, in some embodiments, CHO cells produce polypeptides that have a higher level of sialylation than the same polypeptide produced in 293 cells.

In some embodiments, the antibody or antigen-binding fragment provided herein is produced in a cell-free system. Exemplary cell-free systems are described, e.g., in Sitaraman et al., Methods Mol. Biol. 498: 229-44 (2009); Spirin, Trends Biotechnol. 22: 538-45 (2004); Endo et al., Biotechnol. Adv. 21: 695-713 (2003).

The provided embodiments further include vectors and host cells and other expression systems for expressing and producing the antibodies and other antigen-binding proteins, including eukaryotic and prokaryotic host cells, including bacteria, filamentous fungi, and yeast, as well as mammalian cells such as human cells, as well as cell-free expression systems.

In some embodiments, gene transfer is accomplished by first stimulating the cell, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications.

In some contexts, overexpression of a stimulatory factor (for example, a lymphokine or a cytokine) may be toxic to a subject. Thus, in some contexts, the engineered cells include gene segments that cause the cells to be susceptible to negative selection in vivo, such as upon administration in adoptive immunotherapy. For example in some aspects, the cells are engineered so that they can be eliminated as a result of a change in the in vivo condition of the patient to which they are administered. The negative selectable phenotype may result from the insertion of a gene that confers sensitivity to an administered agent, for example, a compound. Negative selectable genes include the Herpes simplex virus type I thymidine kinase (HSV-I TK) gene (Wigler et al., Cell 2:223, 1977) which confers ganciclovir sensitivity; the cellular hypoxanthine phosphoribosyltransferase (HPRT) gene, the cellular adenine phosphoribosyltransferase (APRT) gene, bacterial cytosine deaminase, (Mullen et al., Proc. Natl. Acad. Sci. USA. 89:33 (1992)).

In some aspects, the cells further are engineered to promote expression of cytokines or other factors. Various methods for the introduction of genetically engineered components, e.g., antigen receptors, e.g., CARs, are well known and may be used with the provided methods and compositions. Exemplary methods include those for transfer of polynucleotides encoding the receptors, including via viral, e.g., retroviral or lentiviral, transduction, transposons, and electroporation.

In some embodiments, recombinant polynucleotides are transferred into cells using recombinant infectious virus particles, such as, e.g., vectors derived from simian virus 40 (SV40), adenoviruses, adeno-associated virus (AAV). In some embodiments, recombinant polynucleotides are transferred into T cells using recombinant lentiviral vectors, such as HIV-1 lentivirus-based vectors (lentivectors; see, e.g., Amado et al., Science. 1999 Jul. 30; 285(5428):674-676), or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 Nov. 29(11): 550-557).

In some embodiments, the retroviral vector or lentiviral vector has a long terminal repeat sequence (LTR). In some embodiments the vector is derived from the Moloney murine leukemia virus (MoMLV), myeloproliferative sarcoma virus (MPSV), murine embryonic stem cell virus (MESV), murine stem cell virus (MSCV), spleen focus forming virus (SFFV), human immunodeficiency virus type 1 (HIV-1) or human immunodeficiency virus type 2 (HIV-2/SIV). In some embodiments, the vectors are self-inactivating (SIN). In some embodiments, the vectors are conditionally replicating (mobilizable) vectors. Most lentiviral vectors are derived from human, feline or simian lentiviruses. Most retroviral vectors are derived from murine retroviruses. In some embodiments, the lentiviruses or retroviruses include those derived from any avian or mammalian cell source. The lentiviruses or retroviruses typically are amphotropic, meaning that they are capable of infecting host cells of several species, including humans. In one embodiment, the gene to be expressed replaces the retroviral gag, pol and/or env sequences. Methods of lentiviral transduction are known. Exemplary methods are described in, e.g., Wang et al. (2012) J. Immunother. 35(9): 689-701; Cooper et al. (2003) Blood. 101:1637-1644; Verhoeyen et al. (2009) Methods Mol Biol. 506: 97-114; and Cavalieri et al. (2003) Blood. 102(2): 497-505. A number of illustrative retroviral systems have also been described (e.g., Amado et al., (1999) Science 285(5428):674-676, U.S. Pat. Nos. 5,219,740; 6,207,453; 5,219,740; Miller and Rosman (1989) BioTechniques 7:980-990; Miller (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109).

In some embodiments, recombinant polynucleotides are transferred into T cells via electroporation (see, e.g., Chicaybam et al, (2013) PLoS ONE 8(3): e60298 and Van Tedeloo et al. (2000) Gene Therapy 7(16): 1431-1437). In some embodiments, recombinant polynucleotides are transferred into T cells via transposition (see, e.g., Manuri et al. (2010) Hum Gene Ther 21(4): 427-437; Sharma et al. (2013) Molec Ther Nucl Acids 2, e74; and Huang et al. (2009) Methods Mol Biol 506: 115-126). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston (1990) Nature 346: 776-777); and strontium phosphate DNA co-precipitation (Brash et al., (1987) Mol. Cell Biol. 7: 2031-2034). Other approaches and vectors for transfer of the polynucleotides encoding the recombinant products are those described, e.g., in WO2014055668, and U.S. Pat. No. 7,446,190.

Among additional polynucleotides, e.g., genes for introduction are those to improve the outcome of therapy, such as by promoting viability and/or function of transferred cells; genes to provide a genetic marker for selection and/or evaluation of the cells, such as to assess in vivo survival or localization; genes to improve safety, for example, by making the cell susceptible to negative selection in vivo as described by Lupton S. D. et al., Mol. and Cell Biol., 11:6 (1991); and Riddell et al., Human Gene Therapy 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. See, e.g., Riddell et al., U.S. Pat. No. 6,040,177, at columns 14-17.

In some embodiments the vector or construct can contain a promoter and/or enhancer or regulatory elements to regulate expression of the encoded recombinant receptor. In some examples the promoter and/or enhancer or regulatory elements can be condition-dependent promoters, enhancers, and/or regulatory elements. In some examples these elements drive expression of the transgene. In some examples, the CAR transgene can be operatively linked to a promoter, such as an EF1alpha promoter with an HTLV1 enhancer (SEQ ID NO:164). In some examples, the CAR transgene is operatively linked to a Woodchuck Hepatitis Virus (WHP) Posttranscriptional Regulatory Element (WPRE; SEQ ID NO: 165), located downstream of the transgene.

In some embodiments, the vector or construct can contain a single promoter that drives the expression of one or more nucleic acid molecules. In some embodiments, such nucleic acid molecules, e.g., transcripts, can be multicistronic (bicistronic or tricistronic, see e.g., U.S. Pat. No. 6,060,273). For example, in some embodiments, transcription units can be engineered as a bicistronic unit containing an IRES (internal ribosome entry site), which allows coexpression of gene products (e.g., encoding a first and second chimeric receptor) by a message from a single promoter. For example, in some embodiments, the vector or construct can contain a nucleic acid encoding an anti-ROR1 receptor (e.g., an anti-ROR1 CAR) provided herein and a nucleic acid encoding a different molecule, separated by an IRES, under the regulation of a single promoter.

Alternatively, in some cases, a single promoter may direct expression of an RNA that contains, in a single open reading frame (ORF), two or three genes (e.g. encoding a first and second binding molecules, e.g., antibody recombinant receptor) separated from one another by sequences encoding a self-cleavage peptide (e.g., 2A cleavage sequences) or a protease recognition site (e.g., furin). The ORF thus encodes a single polypeptide, which, either during (in the case of T2A) or after translation, is cleaved into the individual proteins. In some cases, the peptide, such as T2A, can cause the ribosome to skip (ribosome skipping) synthesis of a peptide bond at the C-terminus of a 2A element, leading to separation between the end of the 2A sequence and the next peptide downstream (see, for example, de Felipe. Genetic Vaccines and Ther. 2:13 (2004) and deFelipe et al. Traffic 5:616-626 (2004)). Many 2A elements are known. Examples of 2A sequences that can be used in the methods and polynucleotides disclosed herein, without limitation, 2A sequences from the foot-and-mouth disease virus (F2A, e.g., SEQ ID NO:21 or 168), equine rhinitis A virus (E2A, e.g., SEQ ID NO: 20 or 167), Thosea asigna virus (T2A, e.g., SEQ ID NO: 6, 17 or 166), and porcine teschovirus-1 (P2A, e.g., SEQ ID NO: 18 or 19) as described in U.S. Patent Publication No. 20070116690. In some embodiments, the one or more different or separate promoters drive the expression of one or more nucleic acid molecules encoding the one or more binding molecules, e.g., recombinant receptors.

Any of the recombinant receptors provided herein, e.g., anti-ROR1 recombinant receptors and/or the additional recombinant receptors, can be encoded by polynucleotides containing one or more nucleic acid molecules encoding the receptors, in any combinations or arrangements. For example, one, two, three or more polynucleotides can encode one, two, three or more different receptors or domains. In some embodiments, one vector or construct contains nucleic acid molecules encoding one or more recombinant receptor(s), and a separate vector or construct contains nucleic acid molecules encoding an additional binding molecule, e.g., antibody and/or recombinant receptor, such as an anti-ROR1 receptor (e.g., anti-ROR1 CAR).

In some embodiments, the nucleic acid molecules can also encode one or more surrogate marker(s), such as fluorescent protein (e.g., green fluorescent protein (GFP)) or a cell surface marker (e.g., a truncated surface marker such as truncated EGFR (tEGFR), which may be used to confirm transduction or engineering of the cell to express the receptor. For example, in some aspects, extrinsic marker genes are utilized in connection with engineered cell therapies to permit detection or selection of cells and, in some cases, also to promote cell suicide by ADCC. Exemplary marker genes include truncated epidermal growth factor receptor (EGFRt), which can be co-expressed with a transgene of interest (e.g., a CAR or TCR) in transduced cells (see, e.g., U.S. Pat. No. 8,802,374). EGFRt contains an epitope recognized by the antibody cetuximab (Erbitux®). For this reason, Erbitux® can be used to identify or select cells that have been engineered with the EGFRt construct, including in cells also co-engineered with another recombinant receptor, such as a chimeric antigen receptor (CAR).

In some embodiments, the nucleic acid encoding the binding molecules further contain contains a nucleic acid sequence encoding one or more marker(s). In some embodiments, the one or more marker(s) is a transduction marker, surrogate marker and/or a selection marker.

In some embodiments, the marker is a transduction marker or a surrogate marker. A transduction marker or a surrogate marker can be used to detect cells that have been introduced with the polynucleotide, e.g., a polynucleotide encoding a recombinant receptor. In some embodiments, the transduction marker can indicate or confirm modification of a cell. In some embodiments, the surrogate marker is a protein that is made to be co-expressed on the cell surface with the recombinant receptor, e.g. CAR. In particular embodiments, such a surrogate marker is a surface protein that has been modified to have little or no activity. In certain embodiments, the surrogate marker is encoded on the same polynucleotide that encodes the recombinant receptor. In some embodiments, the nucleic acid sequence encoding the recombinant receptor is operably linked to a nucleic acid sequence encoding a marker, optionally separated by an internal ribosome entry site (IRES), or a nucleic acid encoding a self-cleaving peptide or a peptide that causes ribosome skipping, such as a 2A sequence, such as a T2A, a P2A, an E2A or an F2A. Extrinsic marker genes may in some cases be utilized in connection with engineered cell to permit detection or selection of cells and, in some cases, also to promote cell suicide.

Exemplary surrogate markers can include truncated forms of cell surface polypeptides, such as truncated forms that are non-functional and to not transduce or are not capable of transducing a signal or a signal ordinarily transduced by the full-length form of the cell surface polypeptide, and/or do not or are not capable of internalizing Exemplary truncated cell surface polypeptides including truncated forms of growth factors or other receptors such as a truncated human epidermal growth factor receptor 2 (tHER2), a truncated epidermal growth factor receptor (tEGFR, exemplary tEGFR sequence set forth in SEQ ID NO:7, 16 or 153) or a prostate-specific membrane antigen (PSMA) or modified form thereof. tEGFR may contain an epitope recognized by the antibody cetuximab (Erbitux®) or other therapeutic anti-EGFR antibody or binding molecule, which can be used to identify or select cells that have been engineered with the tEGFR construct and an encoded exogenous protein, and/or to eliminate or separate cells expressing the encoded exogenous protein. See U.S. Pat. No. 8,802,374 and Liu et al., Nature Biotech. 2016 April; 34(4): 430-434). In some aspects, the marker, e.g. surrogate marker, includes all or part (e.g., truncated form) of CD34, a NGFR, a CD19 or a truncated CD19, e.g., a truncated non-human CD19, or epidermal growth factor receptor (e.g., tEGFR).

In some embodiments, the marker is or comprises a fluorescent protein, such as green fluorescent protein (GFP), enhanced green fluorescent protein (EGFP), such as superfold GFP (sfGFP), red fluorescent protein (RFP), such as tdTomato, mCherry, mStrawberry, AsRed2, DsRed or DsRed2, cyan fluorescent protein (CFP), blue green fluorescent protein (BFP), enhanced blue fluorescent protein (EBFP), and yellow fluorescent protein (YFP), and variants thereof, including species variants, monomeric variants, and codon-optimized and/or enhanced variants of the fluorescent proteins. In some embodiments, the marker is or comprises an enzyme, such as a luciferase, the lacZ gene from *E. coli*, alkaline phosphatase, secreted embryonic alkaline phosphatase (SEAP), chloramphenicol acetyl transferase (CAT). Exemplary light-emitting reporter genes include luciferase (luc), β-galactosidase, chloramphenicol acetyltransferase (CAT), β-glucuronidase (GUS) or variants thereof.

In some embodiments, the marker is a selection marker. In some embodiments, the selection marker is or comprises a polypeptide that confers resistance to exogenous agents or drugs. In some embodiments, the selection marker is an antibiotic resistance gene. In some embodiments, the selection marker is an antibiotic resistance gene confers antibiotic resistance to a mammalian cell. In some embodiments, the selection marker is or comprises a Puromycin resistance gene, a Hygromycin resistance gene, a Blasticidin resistance gene, a Neomycin resistance gene, a Geneticin resistance gene or a Zeocin resistance gene or a modified form thereof.

In some embodiments, the nucleic acid encoding the marker is operably linked to a polynucleotide encoding for a linker sequence, such as a cleavable linker sequence, e.g., a T2A. For example, a marker, and optionally a linker sequence, can be any as disclosed in PCT Pub. No. WO2014031687. For example, the marker can be a truncated EGFR (tEGFR) that is, optionally, linked to a linker sequence, such as a T2A cleavable linker sequence. An exemplary polypeptide for a truncated EGFR (e.g. tEGFR) comprises the sequence of amino acids set forth in SEQ ID NO: 7, 16 or 153 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 7, 16 or 153.

In some embodiments, the marker is a molecule, e.g., cell surface protein, not naturally found on T cells or not naturally found on the surface of T cells, or a portion thereof.

In some embodiments, the molecule is a non-self molecule, e.g., non-self protein, i.e., one that is not recognized as "self" by the immune system of the host into which the cells will be adoptively transferred.

In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells upon adoptive transfer and encounter with ligand.

Also provided are compositions containing one or more of the nucleic acid molecules, vectors or constructs, such as any described above. In some embodiments, the nucleic acid molecules, vectors, constructs or compositions can be used to engineer cells, such as T cells, to express any of the binding molecules, e.g., antibody or recombinant receptor, and/or the additional binding molecules.

B. Preparation of Cells for Engineering

In some embodiments, preparation of the engineered cells includes one or more culture and/or preparation steps. The cells for introduction of the recombinant receptor (e.g., CAR) may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g., transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, or pig.

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contain cells other than red blood cells and platelets.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, Ca++/Mg++ free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a Percoll or Ficoll gradient.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

For example, in some aspects, specific subpopulations of T cells, such as cells positive or expressing high levels of one or more surface markers, e.g., CD28+, CD62L+, CCR7+, CD27+, CD127+, CD4+, CD8+, CD45RA+, and/or CD45RO+ T cells, are isolated by positive or negative selection techniques.

For example, CD3+, CD28+ T cells can be positively selected using anti-CD3/anti-CD28 conjugated magnetic beads (e.g., DYNABEADS® M-450 CD3/CD28 T Cell Expander, MACSiBeads™, etc.).

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed (marker+) at a relatively higher level (marker$^{high}$) on the positively or negatively selected cells, respectively.

In some embodiments, T cells are separated from a PBMC sample by negative selection of markers expressed on non-T cells, such as B cells, monocytes, or other white blood cells, such as CD14. In some aspects, a CD4+ or CD8+ selection step is used to separate CD4+ helper and CD8+ cytotoxic T cells. Such CD4+ and CD8+ populations can be further sorted into sub-populations by positive or negative selection for markers expressed or expressed to a relatively higher degree on one or more naive, memory, and/or effector T cell subpopulations.

In some embodiments, CD8+ cells are further enriched for or depleted of naive, central memory, effector memory, and/or central memory stem cells, such as by positive or negative selection based on surface antigens associated with the respective subpopulation. In some embodiments, enrichment for central memory T ($T_{CM}$) cells is carried out to increase certain features, such as to improve long-term survival, expansion, and/or engraftment following administration, which in some aspects is particularly robust in such sub-populations (see Terakura et al. (2012) Blood. 1:72-82; Wang et al. (2012) J Immunother. 35(9):689-701). In some embodiments, combining TCM-enriched CD8+ T cells and CD4+ T cells further enhances response.

In embodiments, memory T cells are present in both CD62L+ and CD62L− subsets of CD8+ peripheral blood lymphocytes. PBMC can be enriched for or depleted of CD62L-CD8+ and/or CD62L+CD8+ fractions, such as using anti-CD8 and anti-CD62L antibodies.

In some embodiments, the enrichment for central memory T ($T_{CM}$) cells is based on positive or high surface expression of CD45RO, CD62L, CCR7, CD28, CD3, and/or CD 127; in some aspects, it is based on negative selection for cells expressing or highly expressing CD45RA and/or granzyme B. In some aspects, isolation of a CD8+ population enriched for TCM cells is carried out by depletion of cells expressing CD4, CD14, CD45RA, and positive selection or enrichment for cells expressing CD62L. In one aspect, enrichment for central memory T ($T_{CM}$) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the CD8+ cell population or subpopulation, also is used to generate the CD4+ cell population or sub-population, such that both the positive and negative fractions from the CD4-based separation are retained and used in subsequent steps of the methods, optionally following one or more further positive or negative selection steps.

In a particular example, a sample of PBMCs or other white blood cell sample is subjected to selection of CD4+ cells, where both the negative and positive fractions are retained. The negative fraction then is subjected to negative selection based on expression of CD14 and CD45RA, and positive selection based on a marker characteristic of central memory T cells, such as CD62L or CCR7, where the positive and negative selections are carried out in either order.

CD4+ T helper cells are sorted into naïve, central memory, and effector cells by identifying cell populations that have cell surface antigens. CD4+ lymphocytes can be obtained by standard methods. In some embodiments, naive CD4+ T lymphocytes are CD45RO−, CD45RA+, CD62L+, CD4+ T cells. In some embodiments, central memory CD4$^+$ cells are CD62L+ and CD45RO+. In some embodiments, effector CD4+ cells are CD62L− and CD45RO−.

In one example, to enrich for CD4+ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinity magnetic) separation techniques (reviewed in Methods in Molecular Medicine, vol. 58: Metastasis Research Protocols, Vol. 2: Cell Behavior In vitro and In vivo, p 17-25 Edited by: S. A. Brooks and U. Schumacher© Humana Press Inc., Totowa, NJ).

In some aspects, the sample or composition of cells to be separated is incubated with small, magnetizable or magnetically responsive material, such as magnetically responsive particles or microparticles, such as paramagnetic beads (e.g., such as Dynabeads® or MACS® beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084, are other examples.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, magnetizable particles or antibodies conjugated to cleavable linkers, etc. In some embodiments, the magnetizable particles are biodegradable.

In some embodiments, the affinity-based selection is via magnetic-activated cell sorting (MACS®) (Miltenyi Biotec, Auburn, CA). Magnetic Activated Cell Sorting (MACS®) systems are capable of high-purity selection of cells having magnetized particles attached thereto. In certain embodiments, MACS® operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in WO2009/072003 or US 20110003380.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some aspects, the separation and/or other steps is carried out using CliniMACS® system (Miltenyi Biotec), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS® system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy® system (Miltenyi Biotec). The CliniMACS Prodigy® system in some aspects is equipped with a cell processing unity that permits automated washing and fractionation of cells by centrifugation. The CliniMACS Prodigy® system can also include an onboard camera and image recognition software that determines the optimal cell fractionation endpoint by discerning the macroscopic layers of the source cell product. For example, peripheral blood may be automatically separated into erythrocytes, white blood cells and plasma layers. The CliniMACS Prodigy® system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope (see, e.g., Klebanoff et al. (2012) J Immunother. 35(9): 651-660, Terakura et al. (2012) Blood. 1:72-82, and Wang et al. (2012) J Immunother. 35(9):689-701).

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) Lab Chip 10, 1567-1573; and Godin et al. (2008) J Biophoton. 1(5):355-376. In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are then frozen to −80° C. at a rate of 1° C. per minute and stored in the vapor phase of a liquid nitrogen storage tank.

In some embodiments, the provided methods include cultivation, incubation, culture, and/or genetic engineering steps. For example, in some embodiments, provided are methods for incubating and/or engineering the depleted cell populations and culture-initiating compositions.

Thus, in some embodiments, the cell populations are incubated in a culture-initiating composition. The incubation and/or engineering may be carried out in a culture vessel, such as a unit, chamber, well, column, tube, tubing set, valve, vial, culture dish, bag, or other container for culture or cultivating cells.

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of stimulating or activating an intracellular signaling domain of a TCR complex. In some aspects, the agent turns on or initiates TCR/CD3 intracellular signaling cascade in a T cell. Such agents can include antibodies, such as those specific for a TCR component and/or costimulatory receptor, e.g., anti-CD3, anti-CD28, for example, bound to solid support such as a bead, and/or one or more cytokines. Optionally, the expansion method may further comprise the step of adding anti-CD3 and/or anti-CD28 antibody to the culture medium (e.g., at a concentration of at least about 0.5 ng/mL). In some embodiments, the stimulating agents include IL-2 and/or IL-15, for example, an IL-2 concentration of at least about 10 units/mL.

In some aspects, incubation is carried out in accordance with techniques such as those described in U.S. Pat. No. 6,040,177 to Riddell et al., Klebanoff et al. (2012) J Immunother. 35(9): 651-660, Terakura et al. (2012) Blood. 1:72-82, and/or Wang et al. (2012) J Immunother. 35(9):689-701.

In some embodiments, the T cells are expanded by adding to the culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In embodiments, antigen-specific T cells, such as antigen-specific CD4+ and/or CD8+ T cells, are obtained by stimulating naive or antigen specific T lymphocytes with antigen. For example, antigen-specific T cell lines or clones can be generated to cytomegalovirus antigens by isolating T cells from infected subjects and stimulating the cells in vitro with the same antigen.

C. Engineered Cells, Vectors and Compositions for Multi-Targeting

Also provided are cells such as engineered cells that can bind to and/or target multiple antigens. In some embodiments, improved selectivity and specificity is achieved through strategies targeting multiple antigens. Such strategies generally involve multiple antigen-binding domains, which typically are present on distinct genetically engineered antigen receptors and specifically bind to distinct antigens. In some embodiments, the cells are engineered with the ability to bind more than one antigen. For example, in some embodiments, the cells are engineered to express multispecific binding molecules. In some embodiments, the cells express multiple binding molecules, e.g., recombinant receptors, each of which can target one antigen or multiple antigens, e.g., one receptor that targets ROR1, such as any described herein, and another receptor that targets another antigen, e.g., tumor antigen. In some aspects, a plurality of genetically engineered antigen receptors are introduced into the cell, which specifically bind to different antigens, each expressed in or on the disease or condition to be targeted with the cells or tissues or cells thereof. Such features can in some aspects address or reduce the likelihood of off-target effects or increase efficacy. For example, where a single antigen expressed in a disease or condition is also expressed on or in non-diseased or normal cells, such multi-targeting approaches can provide selectivity for desired cell types by requiring binding via multiple antigen receptors in order to activate the cell or induce a particular effector function. In some embodiments, a plurality of cells can be engineered to express one or more different binding molecules, e.g., recombinant receptors, each of which can target one antigen or multiple antigens.

Also provided are multispecific cells containing any of the binding molecules described herein, such as cells containing a cell surface protein including the anti-ROR1 antibody or an antigen-binding fragment thereof and an additional cell surface protein, such as an additional chimeric receptor, which binds to a different antigen or a different epitope on ROR1. In some embodiments, provided are compositions of cells that express recombinant receptors, wherein one or more of the binding molecules, multispecific binding molecules and/or recombinant receptors bind and/or target ROR1. Also provided are compositions of cells containing a plurality of cells that express one or more different binding molecules, e.g., recombinant receptors that can target one or multiple antigens. In some embodiments, the multispecific binding molecules and/or recombinant receptors target one or more different epitopes on ROR1.

In some embodiments, provided are composition of cells, wherein each type of cell expresses one or more binding molecules, e.g., recombinant receptors. In some embodiments, the cell comprises (e.g., has been transformed with) one or more vectors comprising one or more nucleic acid that encodes one or more an amino acid sequence comprising one or more antibodies and/or portions thereof, e.g., antigen-binding fragments thereof. In some embodiments, one or more such cells are provided. In some embodiments, a composition containing one or more such cells is provided. In some embodiments, the one or more cells can express different antibodies, or the same antibody. In some embodiments, each of the cells expresses one or more antibodies, such as more than one antibody. In some embodiments, each of the cells expresses a multispecific binding molecule, e.g., a multispecific receptor, e.g., CAR.

In some embodiments, the cells include multi-targeting strategies that target ROR1 and a second or additional antigen associated with a particular disease or condition. In some embodiments, the second or additional antigen is targeted by a multispecific binding molecule and/or multiple binding molecules and/or a plurality of cells, e.g., one or more cells, each engineered to express one or more recombinant receptors. In some embodiments, a recombinant receptor targeting a second or additional antigen is expressed on the same cell as a ROR1 binding molecule, or on a different cell.

In some embodiments, among the second or additional antigens for multi-targeting strategies includes those in which at least one of the antigens is a universal tumor antigen, or a family member thereof. In some embodiments, the second or additional antigen is an antigen expressed on a tumor. In some embodiments, the ROR1-binding molecules provided herein target an antigen on the same tumor type as the second or additional antigen. In some embodiments, the second or additional antigen may also be a universal tumor antigen or may be a tumor antigen specific to a tumor type. In some embodiments, the cell further comprises an additional genetically engineered antigen receptor that recognizes a second or additional antigen expressed on a disease or condition to be treated and induces a stimulatory or activating signal.

Exemplary antigens include CD4, CD5, CD8, CD14, CD15, CD19, CD20, CD21, CD22, CD23, CD25, CD33, CD37, CD38, CD40, CD40L, CD46, CD52, CD54, CD74, CD80, CD126, CD138, B7, MUC-1, Ia, HM1.24, HLA-DR, tenascin, an angiogenesis factor, VEGF, PIGF, ED-B fibronectin, an oncogene, an oncogene product, CD66a-d, necrosis antigens, Ii, IL-2, T101, TAC, IL-6, TRAIL-R1 (DR4), TRAIL-R2 (DR5), B cell maturation antigen (BCMA), Her2, L1-CAM, mesothelin, CEA, hepatitis B surface antigen, anti-folate receptor, CD24, CD30, CD44, EGFR, EGP-2, EGP-4, EPHa2, ErbB2, ErbB3, ErbB4, erbB dimers, EGFR vIII, FBP, FCRL5, FCRH5, fetal acetylcholine receptor, GD2, GD3, HMW-MAA, IL-22R-alpha, IL-13R-alpha2, kdr, kappa light chain, Lewis Y, L1-cell adhesion molecule (L1-CAM), Melanoma-associated antigen (MAGE)-A1, MAGE-A3, MAGE-A6, Preferentially expressed antigen of melanoma (PRAME), survivin, EGP2, EGP40, TAG72, B7-H6, IL-13 receptor a2 (IL-13Ra2), CA9, CD171, G250/CAIX, HLA-AI MAGE A1, HLA-A2 NY-ESO-1, PSCA, folate receptor-a, CD44v6, CD44v7/8, avb6 integrin, 8H9, NCAM, VEGF receptors, 5T4, Foetal AchR, NKG2D ligands, dual antigen, an antigen associated with a universal tag, a cancer-testes antigen, MUC1, MUC16, NY-ESO-1, MART-1, gp100, oncofetal antigen, VEGF-R2, carcinoembryonic antigen (CEA), prostate specific antigen, PSMA, Her2/neu, estrogen receptor, progesterone receptor, ephrinB2, CD123, c-Met, GD-2, 0-acetylated GD2 (OGD2), CE7, Wilms Tumor 1 (WT-1), a cyclin, cyclin A2, CCL-1, hTERT, MDM2, CYP1B, WT1, livin, AFP, p53, cyclin (Dl), CS-1, BCMA, BAFF-R, TACI, CD56, TIM-3, CD123, L1-cell adhesion molecule, MAGE-A1, MAGE A3, a cyclin, such as cyclin A1 (CCNA1) and/or a pathogen-specific antigen, biotinylated molecules, molecules expressed by HIV, HCV, HBV and/or other pathogens, and/or in some aspects, neoepitopes or neoantigens thereof. In some embodiments, the antigen is associated with or is a universal tag.

In some embodiments, the plurality of antigens, e.g., the first antigen, e.g., ROR1, and the second or additional antigens, are expressed on the cell, tissue, or disease or condition being targeted, such as on the cancer cell. In some aspects, the cell, tissue, disease or condition is or is associated with a cancer or a tumor. One or more of the plurality of antigens generally also is expressed on a cell which it is not desired to target with the cell therapy, such as a normal or non-diseased cell or tissue, and/or the engineered cells themselves. In such embodiments, by requiring ligation of multiple receptors to achieve a response of the cell, specificity and/or efficacy is/are achieved.

In some embodiments, the cells and methods include multi-targeting strategies, such as expression of two or more genetically engineered receptors on the cell, each recognizing a different antigen and typically each including a different intracellular signaling component. Such multi-targeting strategies are described, for example, in WO 2014055668 (describing combinations of activating and costimulatory CARs, e.g., targeting two different antigens present individually on off-target, e.g., normal cells, but present together only on cells of the disease or condition to be treated) and Fedorov et al., *Sci. Transl. Medicine,* 5(215) (December, 2013) (describing cells expressing an activating and an inhibitory CAR, such as those in which the activating CAR binds to one antigen expressed on both normal or non-diseased cells and cells of the disease or condition to be treated, and the inhibitory CAR binds to another antigen expressed only on the normal cells or cells which it is not desired to treat).

In some embodiments, a plurality of cells, each engineered to express one or more recombinant receptors, are provided. For example, in some embodiments, one cell is engineered to express a binding molecule that binds and/or targets ROR1, and another cell is engineered to express a binding molecule that binds and/or targets an additional or second antigen. In some embodiments, the cells can each express a multispecific binding molecule, e.g., a multispecific recombinant receptor, where one or more of the target antigen is ROR1. In some of such embodiments, the plurality of cells can be administered together or separately. In some embodiments, some of the plurality of cells are administered simultaneously or concurrently with other cells, e.g., administered on the same day, and/or sequentially with or intermittently with, in any order, another engineered cell in the plurality. For example, in some embodiments, an engineered cell expressing a ROR1-binding molecule, e.g., CAR, is administered simultaneously with or sequentially with, in any order, another engineered cell expressing a binding molecule that binds a different target antigen or a different epitope on ROR1. In some embodiments, the plurality of cells can be in the same composition or in different compositions. Exemplary compositions of the cells include compositions described in Section III below.

III. Pharmaceutical Compositions

Also provided are compositions including the ROR1-binding molecules, immunoconjugates, recombinant receptors, and engineered cells, including pharmaceutical compositions and formulations. Also provided are compositions comprising engineered cells that express the ROR1-binding molecules provided herein, such as recombinant receptors (e.g., CARs), including pharmaceutical compositions and formulations.

Provided are pharmaceutical formulations comprising a ROR1-binding molecule (e.g., antibody), an immunoconjugate, a recombinant receptor (e.g., chimeric antigen receptor), engineered cells expressing said molecules (e.g., antibody or recombinant receptor), a plurality of engineered cells expressing said molecules (e.g., recombinant receptor) and/or additional agents for combination treatment or therapy. The pharmaceutical compositions and formulations generally include one or more optional pharmaceutically acceptable carrier or excipient. In some embodiments, the composition includes at least one additional therapeutic agent.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell, binding molecule, and/or antibody, and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

Formulations of the antibodies described herein can include lyophilized formulations and aqueous solutions.

The formulation or composition may also contain more than one active ingredient useful for the particular indication, disease, or condition being treated with the binding molecules or cells, preferably those with activities complementary to the binding molecule or cell, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In some embodiments, the cells or antibodies are administered in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

Active ingredients may be entrapped in microcapsules, in colloidal drug delivery systems (for example, liposomes, albumin microspheres, microemulsions, nano-particles and nanocapsules) or in macroemulsions. In certain embodiments, the pharmaceutical composition is formulated as an inclusion complex, such as cyclodextrin inclusion complex, or as a liposome. Liposomes can serve to target the host cells (e.g., T-cells or NK cells) to a particular tissue. Many methods are available for preparing liposomes, such as those described in, for example, Szoka et al., Ann. Rev. Biophys. Bioeng., 9: 467 (1980), and U.S. Pat. Nos. 4,235,871, 4,501,728, 4,837,028, and 5,019,369.

The pharmaceutical composition in some aspects can employ time-released, delayed release, and sustained release delivery systems such that the delivery of the composition occurs prior to, and with sufficient time to cause, sensitization of the site to be treated. Many types of release delivery systems are available and known. Such systems can avoid repeated administrations of the composition, thereby increasing convenience to the subject and the physician.

The pharmaceutical composition in some embodiments contains the binding molecules and/or cells in amounts effective to treat or prevent the disease or condition, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

In certain embodiments, in the context of genetically engineered cells containing the binding molecules, a subject is administered the range of at or about one million to at or about 100 billion cells, such as, e.g., at or about 1 million to at or about 50 billion cells (e.g., at or about 5 million cells, at or about 25 million cells, at or about 500 million cells, at or about 1 billion cells, at or about 5 billion cells, at or about 20 billion cells, at or about 30 billion cells, at or about 40 billion cells, or a range defined by any two of the foregoing values), such as at or about 10 million to at or about 100 billion cells (e.g., at or about 20 million cells, at or about 30 million cells, at or about 40 million cells, at or about 60 million cells, at or about 70 million cells, at or about 80 million cells, at or about 90 million cells, at or about 10 billion cells, at or about 25 billion cells, at or about 50 billion cells, at or about 75 billion cells, at or about 90 billion cells, or a range defined by any two of the foregoing values), and in some cases at or about 100 million cells to at or about 50 billion cells (e.g., at or about 120 million cells, at or about 250 million cells, at or about 350 million cells, at or about 450 million cells, at or about 650 million cells, at or about 800 million cells, at or about 900 million cells, at or about 3 billion cells, at or about 30 billion cells, at or about 45 billion cells) or any value in between these ranges, and/or such a number of cells per kilogram of body weight of the subject.

The may be administered using standard administration techniques, formulations, and/or devices. Provided are formulations and devices, such as syringes and vials, for storage and administration of the compositions. Administration of the cells can be autologous or heterologous. For example, immune cells, immunoresponsive cells or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition (e.g., a pharmaceutical composition containing a genetically modified immune cell such as a T cell), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the cell populations are administered parenterally. The term "parenteral," as used herein, includes intravenous, intramuscular, subcutaneous, rectal, vaginal, intracranial, intrathoracic, and intraperitoneal administration. In some embodiments, the cell populations are administered to a subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the binding molecule in a solvent, such as in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin.

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

Also provided are pharmaceutical compositions for combination therapy. Any of the additional agents for combination therapy described herein, such as agents described in Section IV.B, can be prepared and administered as one or more pharmaceutical compositions, with the ROR1-binding molecule (e.g., antibody), immunoconjugate, recombinant receptor (e.g., chimeric antigen receptor) and/or engineered cells expressing said molecules (e.g., recombinant receptor) described herein. The combination therapy can be administered in one or more pharmaceutical compositions, e.g., where the binding molecules, recombinant receptors and/or cells are in the same pharmaceutical composition as the additional agent, or in separate pharmaceutical compositions. For example, in some embodiments, the additional agent is an additional engineered cell, e.g., cell engineered to express a different recombinant receptor that targets a different antigen or a different epitope on ROR1, and is administered in the same composition or in a separate composition. In some embodiments, each of the pharmaceutical composition is formulated in a suitable formulation according to the particular binding molecule, recombinant receptor, cell, e.g., engineered cell, and/or additional agent, and the particular dosage regimen and/or method of delivery.

IV. Methods and Uses

Also provided methods, such as methods of treatment, of using and uses of the ROR1-binding molecules, immunoconjugates, recombinant receptors, engineered cells, and pharmaceutical compositions and formulations thereof, such as in the treatment of diseases, conditions, and disorders in which ROR1 is expressed, and/or detection, diagnostic, and prognostic methods. Also provided are methods of combination therapy and/or treatment.

A. Therapeutic and Prophylactic Methods and Uses

Also provided are methods of administering and uses, such as therapeutic and prophylactic uses, of the ROR1-binding molecules, including the anti-ROR1 antibodies, e.g., antibody fragments and proteins containing the same such as the recombinant receptors (e.g., CARs), engineered cells expressing the recombinant receptors (e.g., CARs), plurality of engineered cells expressing the receptors, and/or compositions comprising the same. Such methods and uses include therapeutic methods and uses, for example, involving administration of the molecules (e.g., ROR1-binding molecules, recombinant receptors), cells (e.g., engineered cells), or compositions containing the same, to a subject having a disease, condition, or disorder associated with ROR1 such as a disease, condition, or disorder associated with ROR1 expression, and/or in which cells or tissues express, e.g., specifically express ROR1. In some embodiments, the molecule, cell, and/or composition is administered in an effective amount to effect treatment of the disease or disorder. Provided herein are uses of the binding molecules (e.g., anti-ROR1 antibodies or antigen-binding fragments thereof), recombinant receptors (e.g., CARs), and cells (e.g., engineered cells) in such methods and treatments, and in the preparation of a medicament in order to carry out such therapeutic methods. Uses include uses of the binding molecules, CARs, antibodies, and cells in such methods and treatments, and in the preparation of a medicament in order to carry out such therapeutic methods. In some embodiments, the methods are carried out by administering the binding molecules or cells, or compositions comprising the same, to the subject having, having had, or suspected of having the disease or condition. In some embodiments, the methods thereby treat the disease or condition or disorder in the subject. Also provided herein are of use of any of the compositions, such as pharmaceutical compositions provided herein, for the treatment of a disease or disorder associated with ROR1, for example, a ROR1-expressing cancer.

As used herein, "treatment" (and grammatical variations thereof such as "treat" or "treating") refers to complete or partial amelioration or reduction of a disease or condition or disorder, or a symptom, adverse effect or outcome, or phenotype associated therewith. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. The terms do not imply complete curing of a disease or complete elimination of any symptom or effect(s) on all symptoms or outcomes.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. In some embodiments, the provided molecules and compositions are used to delay development of a disease or to slow the progression of a disease.

As used herein, to "suppress" a function or activity is to reduce the function or activity when compared to otherwise same conditions except for a condition or parameter of interest, or alternatively, as compared to another condition. For example, an antibody or composition or cell which suppresses tumor growth reduces the rate of growth of the tumor compared to the rate of growth of the tumor in the absence of the antibody or composition or cell.

An "effective amount" of an agent, e.g., a pharmaceutical formulation, binding molecule, antibody, or cells, or composition, in the context of administration, refers to an amount effective, at dosages/amounts and for periods of time necessary, to achieve a desired result, such as a therapeutic or prophylactic result.

A "therapeutically effective amount" of an agent, e.g., a pharmaceutical formulation, antibody, or cells, refers to an amount effective, at dosages and for periods of time necessary, to achieve a desired therapeutic result, such as for treatment of a disease, condition, or disorder, and/or pharmacokinetic or pharmacodynamic effect of the treatment. The therapeutically effective amount may vary according to factors such as the disease state, age, sex, and weight of the subject, and the populations of cells administered. In some embodiments, the provided methods involve administering the molecules, cells, and/or compositions at effective amounts, e.g., therapeutically effective amounts.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

As used herein, a "subject" is a mammal, such as a human or other animal, and typically is human.

Among the diseases to be treated are any ROR1-associated disease or condition or disease or condition in which ROR1 is specifically expressed. In certain diseases and conditions, ROR1 is expressed on malignant cells and cancers. In some embodiments, the disease or condition is a ROR1-expressing cancer. Among the ROR1-associated diseases or conditions that can be treated include, but are not limited to, B cell leukemia, lymphoma, B cell chronic lymphocytic leukemia (CLL), acute myeloid leukemia (AML), acute lymphocytic leukemia (ALL), Burkitt's Lymphoma, mantle cell lymphoma (MCL), non-small cell lung cancer (NSCLC), neuroblastoma, renal cell carcinoma, colon cancer, colorectal cancer, breast cancer, epithelial squamous cell cancer, melanoma, myeloma, stomach cancer, brain cancer, lung cancer, pancreatic cancer, cervical cancer, ovarian cancer, liver cancer, bladder cancer, prostate cancer, testicular cancer, thyroid cancer, uterine cancer, adrenal cancer and head and neck cancer. In some embodiments, the disease or condition to be treated is selected from a CLL, a MCL, an ovarian cancer, a lung cancer, a pancreatic cancer or a breast cancer. In some embodiments, the disease or condition to be treated is a CLL. In some embodiments, the disease or condition to be treated is a MCL. In some embodiments, the disease or condition to be treated is an ovarian cancer. In some embodiments, the disease or condition to be treated is a lung cancer. In some embodiments, the disease or condition to be treated is a pancreatic cancer. In some embodiments, the disease or condition to be treated is a breast cancer. In some embodiments, the disease or condition to be treated is a lung cancer, and the lung cancer is selected from among lung adenocarcinoma, adenocarcinoma, squamous cell carcinoma, small cell carcinoma, non-small cell lung cancer (NSCLC) and atypical carcinoid. In some embodiments, the disease or condition to be treated is a lung cancer, and the lung cancer is anon-small cell lung cancer (NSCLC). In some embodiments, the disease or condition to be treated is a breast cancer, and the breast cancer is a triple-negative breast cancer.

In some aspects, in certain diseases and conditions, ROR1 is expressed on malignant cells and cancers, including cancers associated with a solid tumor or a hematologic malignancy. In some embodiments, the disease or condition is a ROR1-expressing cancer. In some embodiments among the disease or disorder to be treated is a cancer, such as a ROR1-expressing cancer. In some embodiments, the cancer is associated with a solid tumor or a hematologic malignancy.

In some embodiments, the cancer is associated with a ROR1-expressing solid tumor. In some embodiments, the disease or disorder to be treated is a cancer associated with a solid tumor, such as neuroblastoma, renal cell carcinoma, colon cancer, colorectal cancer, breast cancer, epithelial squamous cell cancer, melanoma, myeloma, stomach cancer, brain cancer, lung cancer, pancreatic cancer, cervical cancer, ovarian cancer, liver cancer, bladder cancer, prostate cancer, testicular cancer, thyroid cancer, uterine cancer, adrenal cancer and head and neck cancer. In some embodiments, the lung cancer is a non-small cell lung cancer (NSCLC). In some embodiments, the breast cancer is a triple negative breast cancer (TNBC). In some aspects, triple negative breast cancer refers to a breast cancer that is negative for expression of estrogen receptors, progesterone receptors and human epidermal growth factor receptor 2 (HER2) overexpression.

In some embodiments, the cancer is associated with a ROR1-expressing hematologic malignancy. In some embodiments, the disease or disorder associated with ROR1 is a B cell-related disorder. In some embodiments, the disease or disorder to be treated is a cancer associated with a hematologic malignancy, such as B cell leukemia, lymphoma, B cell chronic lymphocytic leukemia (CLL), acute myeloid leukemia (AML), acute lymphocytic leukemia (ALL), Burkitt's Lymphoma or mantle cell lymphoma (MCL).

In some embodiments, the methods include administering engineered cells (e.g. T cells) expressing a provided binding molecule to a subject having a ROR1-associated disease or condition, such as a ROR1-expressing cancer. In particular embodiments, the engineered cells (e.g. T cells) express a recombinant receptor, such as a CAR, containing as an antigen-binding domain a provided antibody or antigen-binding fragment thereof (e.g. scFv). In some embodiments, the engineered cells are autologous to the subject being treated. In some embodiments, the engineered cells are allogeneic to the subject being treated, in which case the cells are obtained from the diseased subject and engineered with the recombinant receptor (e.g. CAR) prior to administration of the engineered cells.

In some contexts, engineering primary T cells obtained from subjects with diseases or disorders such as chronic lymphocytic leukemia (CLL) to express recombinant receptors has been reported to result in engineered T cells with impaired function, compared to primary T cells from subjects with other hematologic malignancies (see, e.g., Gorgun et al., J Clin Invest. 2005 July; 115(7):1797-805; Ramsay et al., J Clin Invest. 2008 July; 118(7):2427-37; Riches et al., Discov Med. 2013 December; 16(90):295-302). In some cases, as described herein, the provided recombinant receptors can be expressed from primary T cells obtained from subjects with CLL, without observed impairment in function. In some aspects, engineered cells expressing provided binding molecules, e.g., recombinant receptors targeting ROR1, can be successfully generated using cells from subjects with diseases or disorders such as CLL.

In some embodiments, the methods may identify a subject who has, is suspected to have, or is at risk for developing a ROR1-associated disease or disorder. Hence, provided are methods for identifying subjects with diseases or disorders associated with elevated ROR1 expression and selecting them for treatment with a provided ROR1 binding molecule, including any of the anti-ROR1 antibodies, e.g., antibody fragments and proteins containing the same such as the chimeric receptors, and/or engineered cells expressing the recombinant receptors.

For example, a subject may be screened for the presence of a disease or disorder associated with elevated ROR1 expression, such as a ROR1-expressing cancer. In some embodiments, the methods include screening for or detecting the presence of a ROR1-associated disease, e.g. a tumor. Thus, in some aspects, a sample may be obtained from a patient suspected of having a disease or disorder associated with elevated ROR1 expression and assayed for the expression level of ROR1. In some aspects, a subject who tests positive for a ROR1-associated disease or disorder may be selected for treatment by the present methods, and may be administered a therapeutically effective amount of an anti-ROR1 antibody, a ROR1-targeting CAR, cells containing a CAR or a pharmaceutical composition thereof as described herein. In some embodiments, the methods can be used to monitor the size or density of a ROR1-expressing tissue, e.g. tumor, over time, e.g., before, during, or after treatment by the methods.

In some embodiments, the subject has persistent or relapsed disease, e.g., following treatment with another ROR1-specific antibody and/or cells expressing a ROR1-targeting chimeric receptor and/or other therapy, including chemotherapy, radiation, and/or hematopoietic stem cell transplantation (HSCT), e.g., allogenic HSCT. In some embodiments, the administration effectively treats the subject despite the subject having become resistant to another ROR1-targeted therapy. In some embodiments, the subject has not relapsed but is determined to be at risk for relapse, such as at a high risk of relapse, and thus the compound or composition is administered prophylactically, e.g., to reduce the likelihood of or prevent relapse.

In some embodiments, the treatment does not induce an immune response by the subject to the therapy, and/or does not induce such a response to a degree that prevents effective treatment of the disease or condition. In some aspects, the degree of immunogenicity and/or graft versus host response is less than that observed with a different but comparable treatment. For example, in the case of adoptive cell therapy using cells expressing CARs including the provided anti-ROR1 antibodies, the degree of immunogenicity in some embodiments is reduced compared to CARs including a different antibody that binds to a similar, e.g., overlapping epitope and/or that competes for binding to ROR1 with the provided antibody, such as a mouse or rabbit or humanized antibody.

In some embodiments, the methods include adoptive cell therapy, whereby genetically engineered cells expressing the provided ROR1-targeting receptors (e.g., containing ROR1-targeting antibody or fragment thereof) are administered to subjects. Such administration can promote activation of the cells (e.g., T cell activation) in a ROR1-targeting manner, such that the cells of the disease or disorder are targeted for destruction.

Thus, the provided methods and uses include methods and uses for adoptive cell therapy. In some embodiments, the methods include administration of the cells or a composition containing the cells to a subject, tissue, or cell, such as one having, at risk for, or suspected of having the disease, condition or disorder. In some embodiments, the cells, populations, and compositions are administered to a subject having the particular disease or condition to be treated, e.g., via adoptive cell therapy, such as adoptive T cell therapy. In some embodiments, the cells or compositions are administered to the subject, such as a subject having or at risk for the disease or condition. In some aspects, the methods thereby treat, e.g., ameliorate one or more symptom of the disease or condition, such as by lessening tumor burden in a ROR1-expressing cancer.

Methods for administration of cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338.

In some embodiments, the cell therapy, e.g., adoptive cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

In some embodiments, the subject, to whom the cells, cell populations, or compositions are administered is a primate, such as a human. In some embodiments, the primate is a monkey or an ape. The subject can be male or female and can be any suitable age, including infant, juvenile, adolescent, adult, and geriatric subjects. In some embodiments, the subject is a non-primate mammal, such as a rodent. In some examples, the patient or subject is a validated animal model for disease, adoptive cell therapy, and/or for assessing toxic outcomes such as cytokine release syndrome (CRS).

The ROR1-binding molecules, such as antibodies and chimeric receptors containing the antibodies and cells expressing the same, can be administered by any suitable means, for example, by injection, e.g., intravenous or subcutaneous injections, intraocular injection, periocular injection, subretinal injection, intravitreal injection, trans-septal injection, subscleral injection, intrachoroidal injection, intracameral injection, subconjectval injection, subconjunctival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, intracranial, intrathoracic, or subcutaneous administration. Dosing and administration may depend in part on whether the administration is brief or chronic. Various dosing schedules include but are not limited to single or multiple administrations over various time-points, bolus administration, and pulse infusion.

For the prevention or treatment of disease, the appropriate dosage of the binding molecule or cell may depend on the type of disease to be treated, the type of binding molecule, the severity and course of the disease, whether the binding molecule is administered for preventive or therapeutic purposes, previous therapy, the patient's clinical history and response to the binding molecule, and the discretion of the attending physician. The compositions and molecules and cells are in some embodiments suitably administered to the patient at one time or over a series of treatments.

Depending on the type and severity of the disease, dosages of antibodies may include at or about 1 µg/kg to at or about 15 mg/kg (e.g. at or about 0.1 mg/kg at or about 10 mg/kg), at or about 1 µg/kg to at or about 100 mg/kg or more, at or about 0.05 mg/kg to at or about 10 mg/kg, at or about 0.5 mg/kg, at or about 2.0 mg/kg, at or about 4.0 mg/kg or at or about 10 mg/kg. Multiple doses may be administered intermittently, e.g. every week or every three weeks. An initial higher loading dose, followed by one or more lower doses may be administered.

In certain embodiments, the cells, or individual populations of sub-types of cells, are administered to the subject at a range of at or about 0.1 million to at or about 100 billion cells and/or that amount of cells per kilogram of body weight of the subject, such as, e.g., at or about 0.1 million to at or about 50 billion cells (e.g., at or about 5 million cells, at or about 25 million cells, at or about 500 million cells, at or about 1 billion cells, at or about 5 billion cells, at or about 20 billion cells, at or about 30 billion cells, at or about 40 billion cells, or a range defined by any two of the foregoing values), at or about 1 million to at or about 50 billion cells (e.g., at or about 5 million cells, at or about 25 million cells, at or about 500 million cells, at or about 1 billion cells, at or about 5 billion cells, at or about 20 billion cells, at or about 30 billion cells, at or about 40 billion cells, or a range defined by any two of the foregoing values), such as at or about 10 million to at or about 100 billion cells (e.g., at or about 20 million cells, at or about 30 million cells, at or about 40 million cells, at or about 60 million cells, at or about 70 million cells, at or about 80 million cells, at or about 90 million cells, at or about 10 billion cells, at or about 25 billion cells, at or about 50 billion cells, at or about 75 billion cells, at or about 90 billion cells, or a range defined by any two of the foregoing values), and in some cases at or about 100 million cells to at or about 50 billion cells (e.g., at or about 120 million cells, at or about 250 million cells, at or about 350 million cells, at or about 650 million cells, at or about 800 million cells, at or about 900 million cells, at or about 3 billion cells, at or about 30 billion cells, at or about 45 billion cells) or any value in between these ranges and/or per kilogram of body weight of the subject. Dosages may vary depending on attributes particular to the disease or disorder and/or patient and/or other treatments. In some embodiments, such values refer to numbers of recombinant receptor-expressing cells; in other embodiments, they refer to number of T cells or PBMCs or total cells administered.

In some embodiments, for example, where the subject is a human, the dose includes fewer than about $5 \times 10^8$ total recombinant receptor (e.g., CAR)-expressing cells, T cells, or peripheral blood mononuclear cells (PBMCs), e.g., in the range of at or about $1 \times 10^6$ to at or about $5 \times 10^8$ such cells, such as at or about $2 \times 10^6$, $5 \times 10^6$, $1 \times 10^7$, $5 \times 10^7$, $1 \times 10^8$, $1.5 \times 10^8$, or $5 \times 10^8$ total such cells, or the range between any two of the foregoing values. In some embodiments, for example, where the subject is a human, the dose includes more than at or about $1 \times 10^6$ total recombinant receptor (e.g., CAR)-expressing cells, T cells, or peripheral blood mononuclear cells (PBMCs) and fewer than at or about $2 \times 10^9$ total recombinant receptor (e.g., CAR)-expressing cells, T cells, or peripheral blood mononuclear cells (PBMCs), e.g., in the range of at or about $2.5 \times 10^7$ to at or about $1.2 \times 10^9$ such cells, such as at or about $2.5 \times 10^7$, $5 \times 10^7$, $1 \times 10^8$, $1.5 \times 10^8$, $8 \times 10^8$, or $1.2 \times 10^9$ total such cells, or the range between any two of the foregoing values.

In some embodiments, the dose of genetically engineered cells comprises from at least or at least about or is $1 \times 10^5$ to at or about $5 \times 10^8$ total CAR-expressing (CAR$^+$) T cells, from at or about $1 \times 10^5$ to at or about $2.5 \times 10^8$ total CAR$^+$ T cells, from at or about $1 \times 10^5$ to at or about $1 \times 10^8$ total CAR$^+$ T cells, from at or about $1 \times 10^5$ to at or about $5 \times 10^7$ total CAR$^+$ T cells, from at or about $1 \times 10^5$ to at or about $2.5 \times 10^7$ total CAR$^+$ T cells, from at or about $1 \times 10^5$ to at or about $1 \times 10^7$ total CAR$^+$ T cells, from at or about $1 \times 10^5$ to at or about $5 \times 10^6$ total CAR$^+$ T cells, from at or about $1 \times 10^5$ to at or about $2.5 \times 10^6$ total CAR$^+$ T cells, from at or about $1 \times 10^5$ to at or about $1 \times 10^6$ total CAR$^+$ T cells, from at or about $1 \times 10^6$ to at or about $5 \times 10^8$ total CAR$^+$ T cells, from at or about $1 \times 10^6$ to at or about $2.5 \times 10^8$ total CAR$^+$ T cells, from at or about $1 \times 10^6$ to at or about $1 \times 10^8$ total CAR$^+$ T cells, from at or about $1 \times 10^6$ to at or about $5 \times 10^7$ total CAR$^+$ T cells, from at or about $1 \times 10^6$ to at or about $2.5 \times 10^7$ total CAR+ T cells, from at or about $1 \times 10^6$ to at or about $1 \times 10^7$ total CAR$^+$ T cells, from at or about $1 \times 10^6$ to at or about $5 \times 10^6$ total CAR$^+$ T cells, from at or about $1 \times 10^6$ to at or about $2.5 \times 10^6$ total CAR$^+$ T cells, from at or about $2.5 \times 10^6$ to at or about $5 \times 10^8$ total CAR$^+$ T cells, from at or about $2.5 \times 10^6$ to at or about $2.5 \times 10^8$ total CAR$^+$ T cells, from at or about $2.5 \times 10^6$ to at or about $1 \times 10^8$ total CAR$^+$ T cells, from at or about $2.5 \times 10^6$ to at or about $5 \times 10^7$ total CAR$^+$ T cells, from at or about $2.5 \times 10^6$ to at or about $2.5 \times 10^7$ total CAR$^+$ T cells, from at or about $2.5 \times 10^6$ to at or about $1 \times 10^7$ total CAR$^+$ T cells, from at or about $2.5 \times 10^6$ to at or about $5 \times 10^6$ total CAR$^+$ T cells, from at or about $5 \times 10^6$ to at or about $5 \times 10^8$ total CAR$^+$ T cells, from at or about $5 \times 10^6$ to at or about $2.5 \times 10^8$ total CAR$^+$ T cells, from at or about $5 \times 10^6$ to at or about $1 \times 10^8$ total CAR$^+$ T cells, from at or about $5 \times 10^6$ to at or about $5 \times 10^7$ total CAR$^+$ T cells, from at or about $5 \times 10^6$ to at or about $2.5 \times 10^7$ total CAR$^+$ T cells, from at or about $5 \times 10^6$ to at or about $1 \times 10^7$ total CAR$^+$ T cells, from at or about $1 \times 10^7$ to at or about $5 \times 10^8$ total CAR$^+$ T cells, from at or about $1 \times 10^7$ to at or about $2.5 \times 10^8$ total CAR$^+$ T cells, from at or about $1 \times 10^7$ to at or about $1 \times 10^8$ total CAR$^+$ T cells, from at or about $1 \times 10^7$ to at or about $5 \times 10^7$ total CAR$^+$ T cells, from at or about $1 \times 10^7$ to at or about $2.5 \times 10^7$ total CAR$^+$ T cells, from at or about $2.5 \times 10^7$ to at or about $5 \times 10^8$ total CAR$^+$ T cells, from at or about $2.5 \times 10^7$ to at or about $2.5 \times 10^8$ total CAR$^+$ T cells, from at or about $2.5 \times 10^7$ to at or about $1 \times 10^8$ total CAR$^+$ T cells, from at or about $2.5 \times 10^7$ to at or about $5 \times 10^7$ total CAR$^+$ T cells, from at or about $5 \times 10^7$ to at or about $5 \times 10^8$ total CAR$^+$ T cells, from at or about $5 \times 10^7$ to at or about $2.5 \times 10^8$ total CAR$^+$ T cells, from at or about $5 \times 10^7$ to at or about $1 \times 10^8$ total CAR$^+$ T cells, from at or about $5 \times 10^7$ to at or about $1 \times 10^8$ total CAR$^+$ T cells, from at or about $1 \times 10^8$ to at or about $2.5 \times 10^8$ total CAR$^+$ T cells, from at or about or $2.5 \times 10^8$ to at or about $5 \times 10^7$ total CAR$^+$ T cells. In some embodiments, the dose of genetically engineered cells comprises from or from about $2.5 \times 10^7$ to at or about $1.5 \times 10^8$ total CAR$^+$ T cells, such as from or from about $5 \times 10^7$ to or to about $1 \times 10^8$ total CAR$^+$ T cells.

In some embodiments, the dose of genetically engineered cells comprises at least at or about $1 \times 10^5$ CAR$^+$ cells, at least at or about $2.5 \times 10^5$ CAR$^+$ cells, at least at or about $5 \times 10^5$ CAR$^+$ cells, at least at or about $1 \times 10^6$ CAR$^+$ cells, at least at or about $2.5 \times 10^6$ CAR$^+$ cells, at least at or about $5 \times 10^6$ CAR$^+$ cells, at least at or about $1 \times 10^7$ CAR$^+$ cells, at least at or about $2.5 \times 10^7$ CAR$^+$ cells, at least at or about $5 \times 10^7$ CAR$^+$ cells, at least at or about $1 \times 10^8$ CAR$^+$ cells, at least at or about $1.5 \times 10^8$ CAR$^+$ cells, at least at or about $2.5 \times 10^8$ CAR$^+$ cells, or at least at or about $5 \times 10^8$ CAR$^+$ cells.

In some embodiments, the cell therapy comprises administration of a dose comprising a number of cell from or from about $1 \times 10^5$ to or to about $5 \times 10^7$ total recombinant receptor-expressing cells, total T cells, or total peripheral blood mononuclear cells (PBMCs), from or from about $5 \times 10^5$ to or to about $1 \times 10^7$ total recombinant receptor-expressing cells, total T cells, or total peripheral blood mononuclear cells (PBMCs) or from or from about $1 \times 10^6$ to or to about $1 \times 10^7$ total recombinant receptor-expressing cells, total T cells, or total peripheral blood mononuclear cells (PBMCs), each inclusive. In some embodiments, the cell therapy comprises administration of a dose of cells comprising a number of cells at least or at least about $1 \times 10^5$ total recombinant receptor-expressing cells, total T cells, or total peripheral blood mononuclear cells (PBMCs), such at least or at least $1 \times 10^6$, at least or at least about $1 \times 10^7$, at least or at least about $1 \times 10^8$ of such cells. In some embodiments, the number is with reference to the total number of CD3$^+$ or CD8$^+$, in some cases also recombinant receptor-expressing (e.g. CAR$^+$) cells. In some embodiments, the cell therapy comprises administration of a dose comprising a number of cell from or from about $1 \times 10^5$ to or to about $5 \times 10^8$ CD3$^+$ or CD8$^+$ total T cells or CD3$^+$ or CD8$^+$ recombinant receptor-expressing cells, from or from about $5 \times 10^5$ to or to about $1 \times 10^7$ CD3$^+$ or CD8$^+$ total T cells or CD3$^+$ or CD8$^+$ recombinant receptor-expressing cells, or from or from about $1 \times 10^6$ to or to about $1 \times 10^7$ CD3$^+$ or CD8$^+$ total T cells or CD3$^+$ or CD8$^+$ recombinant receptor-expressing cells, each inclusive. In some embodiments, the cell therapy comprises administration of a dose comprising a number of cell from or from about $1 \times 10^5$ to or to about $5 \times 10^8$ total CD3$^+$/CAR$^+$ or CD8$^+$/CAR$^+$ cells, from or from about $5 \times 10^5$ to or to about $1 \times 10^7$ total CD3$^+$/CAR$^+$ or CD8$^+$/CAR$^+$ cells, or from or from about $1 \times 10^6$ to or to about $1 \times 10^7$ total CD3$^+$/CAR$^+$ or CD8$^+$/CAR$^+$ cells, each inclusive.

In some embodiments, the T cells of the dose include CD4+ T cells, CD8+ T cells or CD4+ and CD8+ T cells.

In some embodiments, for example, where the subject is human, the CD8$^+$ T cells of the dose, including in a dose including CD4$^+$ and CD8$^+$ T cells, includes between at or about $1 \times 10^6$ and at or about $5 \times 10^8$ total recombinant receptor (e.g., CAR)-expressing CD8$^+$ cells, e.g., in the range of from at or about $5 \times 10^6$ to at or about $1 \times 10^8$ such cells, such as $1 \times 10^7$, $2.5 \times 10^7$, $5 \times 10^7$, $7.5 \times 10^7$, $1 \times 10^8$, $1.5 \times 10^8$, or $5 \times 10^8$ total such cells, or the range between any two of the foregoing values. In some embodiments, the patient is administered multiple doses, and each of the doses or the total dose can be within any of the foregoing values. In some embodiments, the dose of cells comprises the administration of from or from about $1 \times 10^7$ to or to about $0.75 \times 10^8$ total recombinant receptor-expressing CD8$^+$ T cells, from or from about $1 \times 10^7$ to or to about $5 \times 10^7$ total recombinant receptor-expressing CD8+ T cells, from or from about 1×10$^7$ to or to about 0.25×10$^8$ total recombinant receptor-expressing CD8+ T cells, each inclusive. In some embodiments, the dose of cells comprises the administration of at or about 1×10$^7$, 2.5×10$^7$, 5×10$^7$, 7.5×10$^7$, 1×10$^8$, 1.5×10$^8$, 2.5×10$^8$, or 5×10$^8$ total recombinant receptor-expressing CD8+ T cells.

In some embodiments, the dose of cells, e.g., recombinant receptor-expressing T cells, is administered to the subject as a single dose or is administered only one time within a period of two weeks, one month, three months, six months, 1 year or more.

In some embodiments, the cells or antibodies are administered as part of a combination treatment, such as simultaneously with or sequentially with, in any order, another therapeutic intervention, such as another antibody or engineered cell or receptor or agent, such as a cytotoxic or therapeutic agent.

The cells or antibodies in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells or antibodies are administered prior to the one or more additional therapeutic agents. In some embodiments, the cells or antibodies are administered after to the one or more additional therapeutic agents.

Once the cells are administered to a mammal (e.g., a human), the biological activity of the engineered cell populations and/or antibodies in some aspects is measured by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable known methods, such as cytotoxicity assays described in, for example, Kochenderfer et al., J. Immunotherapy, 32(7): 689-702 (2009), and Herman et al. J. Immunological Methods, 285(1): 25-40 (2004). In certain embodiments, the biological activity of the cells also can be measured by assaying expression and/or secretion of certain cytokines, such as CD 107a, IFNγ, IL-2, and TNF. In some aspects the biological activity is measured by assessing clinical outcome, such as reduction in tumor burden or load.

In certain embodiments, engineered cells are modified in any number of ways, such that their therapeutic or prophylactic efficacy is increased. For example, the engineered CAR or TCR expressed by the population in some embodiments are conjugated either directly or indirectly through a linker to a targeting moiety. The practice of conjugating compounds, e.g., the CAR or TCR, to targeting moieties is known. See, for instance, Wadwa et al., J. Drug Targeting 3: 1 1 1 (1995), and U.S. Pat. No. 5,087,616.

B. Combination Therapy

Also provided are methods of combination therapy that includes administering and uses, such as therapeutic and prophylactic uses, of the ROR1-binding molecules, including the anti-ROR1 antibodies, e.g., antibody fragments, conjugates, and proteins containing the same, such as the recombinant receptors (e.g., CARs), engineered cells expressing the recombinant receptors (e.g., CARs), plurality of engineered cells expressing the receptors, and/or compositions comprising the same.

In some embodiments, the ROR1-binding molecule (e.g., antibody), immunoconjugate, recombinant receptor (e.g., chimeric antigen receptor) and/or engineered cells expressing said molecules (e.g., recombinant receptor) described herein are administered as part of a combination treatment or combination therapy, such as simultaneously with, sequentially with or intermittently with, in any order, one or more additional therapeutic intervention. In some embodiments, the one or more additional therapeutic intervention includes, for example, an antibody, an engineered cell, a receptor and/or an agent, such as a cell expressing a recombinant receptor, and/or cytotoxic or therapeutic agent, e.g., a chemotherapeutic agent. In some embodiments, the combination therapy includes administration of one or more additional agents, therapies and/or treatments, e.g., any of the additional agents, therapy and/or treatments described herein. In some embodiments, the combination therapy includes administration of one or more additional agents for treatment or therapy, such as an immunomodulatory agent, immune checkpoint inhibitor, adenosine pathway or adenosine receptor antagonist or agonist and kinase inhibitors. In some embodiments, the combination treatment or combination therapy includes an additional treatment, such as a surgical treatment, transplant, and/or radiation therapy. Also provided are methods of combination treatment or combination therapy that includes administering the binding molecules (e.g., ROR1-binding molecules), recombinant receptors, cells and/or compositions described herein and one or more additional therapeutic interventions.

In some embodiments, the additional agent for combination treatment or combination therapy enhances, boosts and/or promotes the efficacy and/or safety of the therapeutic effect of binding molecules, recombinant receptors, cells and/or compositions. In some embodiments, the additional agent enhances or improves the efficacy, survival or persistence of the administered cells, e.g., cells expressing the binding molecule or a recombinant receptor. In some embodiments, the additional agent is selected from among a protein phosphatase inhibitor, a kinase inhibitor, a cytokine, an immunomodulator, or an agent that decreases the level or activity of a regulatory T (Treg) cell. In some embodiments, the additional agent enhances safety, by virtue of reducing or ameliorating adverse effects of the administered binding molecules, recombinant receptors, cells and/or compositions. In some embodiments, the additional agent can treat the same disease, condition or a comorbidity. In some embodiments, the additional agent can ameliorate, reduce or eliminate one or more toxicities, adverse effects or side effects that are associated with administration of the binding molecules, recombinant receptors, cells and/or compositions, e.g., CAR-expressing cells.

In some embodiments, the additional therapy, treatment or agent includes chemotherapy, radiation therapy, surgery, transplantation, adoptive cell therapy, antibodies, cytotoxic agents, chemotherapeutic agents, cytokines, growth inhibitory agents, anti-hormonal agents, kinase inhibitors, anti-angiogenic agents, cardioprotectants, immunostimulatory agents, immunosuppressive agents, immune checkpoint inhibitors, antibiotics, angiogenesis inhibitors, metabolic modulators or other therapeutic agents or any combination thereof. In some embodiments, the additional agent is a protein, a peptide, a nucleic acid, a small molecule agent, a cell, a toxin, a lipid, a carbohydrate or combinations thereof, or any other type of therapeutic agent, e.g. radiation. In some embodiments, the additional therapy, agent or treatment includes surgery, chemotherapy, radiation therapy, transplantation, administration of cells expressing a recombinant receptor, e.g., CAR, kinase inhibitor, immune checkpoint inhibitor, mTOR pathway inhibitor, immunosuppressive agents, immunomodulators, antibodies, immunoablative agents, antibodies and/or antigen binding fragments thereof, antibody conjugates, other antibody therapies, cytotoxins, steroids, cytokines, peptide vaccines, hormone therapy, antimetabolites, metabolic modulators, drugs that inhibit either the calcium dependent phosphatase calcineurin or the p70S6 kinase FK506) or inhibit the p70S6 kinase, alkylating agents, anthracyclines, vinca alkaloids, proteasome inhibitors, GITR agonists, protein tyrosine phosphatase inhibitors, protein kinase inhibitors, an oncolytic virus, and/or other types of immunotherapy. In some embodiments, the additional agent or treatment is bone marrow transplantation, T cell ablative therapy using chemotherapy agents such as, fludarabine, external-beam radiation therapy (XRT), cyclophosphamide, and/or antibody therapy.

In some embodiments, the cells, binding molecules (e.g., ROR1-binding molecules), recombinant receptors and/or compositions, e.g., CAR-expressing cells, are administered in combination with other engineered cells, e.g., other CAR-expressing cells. In some embodiments, the additional agent is a kinase inhibitor, e.g., an inhibitor of Bruton's tyrosine kinase (Btk), e.g., ibrutinib. In some embodiments, the additional agent is an adenosine pathway or adenosine receptor antagonist or agonist. In some embodiments, the additional agent is an immunomodulator such as thalidomide or a thalidomide derivative (e.g., lenalidomide). In some embodiments, the additional therapy, agent or treatment is a cytotoxic or chemotherapy agent, a biologic therapy (e.g., antibody, e.g., monoclonal antibody, or cellular therapy), or an inhibitor (e.g., kinase inhibitor).

In some embodiments, a chemotherapeutic agent (sometimes referred to as a cytotoxic agent) is administered to the subject to disrupt a lesion. In certain embodiments, the lesion is tumor. In particular embodiments, the lesion is cancerous. In particular embodiments, the chemotherapeutic agent is any agent known to those of skill in the art to be effective for the treatment, prevention or amelioration of hyperproliferative disorders such as cancer. Chemotherapeutic agents include, but are not limited to, small molecules, synthetic drugs, peptides, polypeptides, proteins, nucleic acids (e.g., DNA and RNA polynucleotides including, but not limited to, antisense nucleotide sequences, triple helices and nucleotide sequences encoding biologically active proteins, polypeptides or peptides), antibodies, synthetic or natural inorganic molecules, mimetic agents, and synthetic or natural organic molecules. In particular embodiments, chemotherapeutic drugs include alkylating agents, anthracyclines, cytoskeletal disruptors (taxanes), epothilones, histone deacetylase inhibitors, topoisomerase inhibitors, topoisomerase II inhibitors, kinase inhibitors, nucleotide analogs and precursor analogs, peptide antibiotics, platinum-based agents, and vinca alkaloids and derivatives.

In certain embodiments, a lesion is disrupted by administering a chemotherapeutic agent to modulate genetically engineered cells in vivo. Chemotherapeutic agents may include, but are not limited to, abarelix, aldesleukin, alemtuzumab, alitretinoin, allopurinol, altretamine, amifostine, anastrozole, arsenic trioxide, asparaginase, BCG live, bevaceizumab, bexarotene, bleomycin, bortezomib, busulfan, calusterone, camptothecin, capecitabine, carboplatin, carmustine, celecoxib, cetuximab, chlorambucil, cinacalcet, cisplatin, cladribine, cyclophosphamide, cytarabine, dacarbazine, dactinomycin, darbepoetin alfa, daunorubicin, denileukin diftitox, dexrazoxane, docetaxel, doxorubicin, dromostanolone, Elliott's B solution, epirubicin, epoetin alfa, estramustine, etoposide, exemestane, filgrastim, floxuridine, fludarabine, fluorouracil, fulvestrant, gemcitabine, gemtuzumab ozogamicin, gefitinib, goserelin, hydroxyurea, ibritumomab tiuxetan, idarubicin, ifosfamide, imatinib, interferon alfa-2a, interferon alfa-2b, irinotecan, letrozole, leucovorin, levamisole, lomustine, meclorethamine, megestrol, melphalan, mercaptopurine, mesna, methotrexate, methoxsalen, methylprednisolone, mitomycin C, mitotane, mitoxantrone, nandrolone, nofetumomab, oblimersen, oprelvekin, oxaliplatin, paclitaxel, pamidronate, pegademase, pegaspargase, pegfilgrastim, pemetrexed, pentostatin, pipobroman, plicamycin, polifeprosan, porfimer, procarbazine, quinacrine, rasburicase, rituximab, sargramostim, streptozocin, talc, tamoxifen, tarceva, temozolomide, teniposide, testolactone, thioguanine, thiotepa, topotecan, toremifene, tositumomab, trastuzumab, tretinoin, uracil mustard, valrubicin, vinblastine, vincristine, vinorelbine, and zoledronate.

In some embodiments, exemplary chemotherapeutic agents include an anthracycline (e.g., doxorubicin, such as liposomal doxorubicin); a vinca alkaloid (e.g., vinblastine, vincristine, vindesine, vinorelbine); an alkylating agent (e.g., cyclophosphamide, decarbazine, melphalan, ifosfamide, temozolomide); an immune cell antibody (e.g., alemtuzumab, gemtuzumab, rituximab, tositumomab); an antimetabolite (including, e.g., folic acid antagonists, pyrimidine analogs, purine analogs and adenosine deaminase inhibitors such as fludarabine); a TNFR glucocorticoid induced TNFR related protein (GITR) agonist; a proteasome inhibitor (e.g., aclacinomycin A, gliotoxin or bortezomib); an immunomodulatory such as thalidomide or a thalidomide derivative (e.g., lenalidomide).

In some embodiments, the additional therapy or treatment is cell therapy, e.g., adoptive cell therapy. In some embodiments, the additional therapy includes administration of engineered cells, e.g., additional CAR-expressing cell. In some embodiments, the additional engineered cell is a CAR-expressing cell that expresses the same or different recombinant receptor as the engineered cells provided herein, e.g., anti-ROR1 CAR-expressing cells. In some embodiments, the recombinant receptor, e.g., CAR, expressed on the additional engineered cell, recognizes a different antigen and/or epitope. In some embodiments, the recombinant receptor, e.g., CAR, expressed on the additional engineered cell, recognizes a different epitope of the same antigen as the recombinant receptors described herein, e.g., ROR1. In some embodiments, the recombinant receptor, e.g., CAR, expressed on the additional engineered cell, recognizes a different antigen, e.g., a different tumor antigen or combination of antigens. For example, in some embodiments, the recombinant receptor, e.g., CAR, expressed on the additional engineered cell, targets cancer cells that express early lineage markers, e.g., cancer stem cells, while other CAR-expressing cells target cancer cells that express later lineage markers. In such embodiments, the additional engineered cell is administered prior to, concurrently with, or after administration (e.g., infusion) of the CAR-expressing cells described herein. In some embodiments, the additional engineered cell expresses allogeneic CAR.

In some embodiments, the configurations of one or more of the CAR molecules comprise a primary intracellular signaling domain and two or more, e.g., 2, 3, 4, or 5 or more, costimulatory signaling domains. In some embodiments, the one or more of the CAR molecules may have the same or a different primary intracellular signaling domain, the same or different costimulatory signaling domains, or the same number or a different number of costimulatory signaling domains. In some embodiments, the one or more of the CAR molecules can be configured as a split CAR, in which one of the CAR molecules comprises an antigen binding domain and a costimulatory domain (e.g., 4-1BB), while the other CAR molecule comprises an antigen binding domain and a primary intracellular signaling domain (e.g., CD3 zeta).

In some embodiments, the additional agent is any of the multispecific binding molecules and/or cells engineered to express one or more of the binding molecules described herein and/or cells engineered to express additional binding molecules, e.g., recombinant receptors, e.g., CAR, that target a different antigen. In some embodiments, the additional agent includes any of the cells or plurality of cells described herein, e.g., in Section I.C. In some embodiments, the additional agent is a cell engineered to express a recombinant receptor, e.g., CAR, targeting a different epitope and/or antigen, e.g., a different antigen associated with a disease or condition. In some embodiments, the additional agent is a cell engineered to express a recombinant receptor, e.g., CAR, targeting a second or additional antigen expressed in the disease or disorder, e.g., a cancer or a tumor.

In some embodiments, the additional agent is an immunomodulatory agent. In some embodiments, the combination therapy includes an immunomodulatory agent that can stimulate, amplify and/or otherwise enhance an anti-tumor immune response, e.g., anti-tumor immune response from the administered engineered cells, such as by inhibiting immunosuppressive signaling or enhancing immunostimulant signaling. In some embodiments, the immunomodulatory agent is a peptide, protein or is a small molecule. In some embodiments, the protein can be a fusion protein or a recombinant protein. In some embodiments, the immunomodulatory agent binds to an immunologic target, such as a cell surface receptor expressed on immune cells, such a T cells, B cells or antigen-presenting cells. For example, in some embodiments, the immunomodulatory agent is an antibody or antigen-binding antibody fragment, a fusion protein, a small molecule or a polypeptide. In some embodiments, the binding molecules, recombinant receptors, cells and/or compositions are administered in combination with an additional agent that is an antibody or an antigen-binding fragment thereof, such as a monoclonal antibody.

In some embodiments, the immunomodulatory agent blocks, inhibits or counteracts a component of the immune checkpoint pathway. The immune system has multiple inhibitory pathways that are involved in maintaining self-tolerance and for modulating immune responses. Tumors can use certain immune-checkpoint pathways as a major mechanism of immune resistance, particularly against T cells that are specific for tumor antigens (Pardoll (2012) Nature Reviews Cancer 12:252-264), e.g., engineered cells such as CAR-expressing cells. Because many such immune checkpoints are initiated by ligand-receptor interactions, they can be readily blocked by antibodies against the ligands and/or their receptors.

Therefore, therapy with antagonistic molecules blocking an immune checkpoint pathway, such as small molecules, nucleic acid inhibitors (e.g., RNAi) or antibody molecules, are becoming promising avenues of immunotherapy for cancer and other diseases. In contrast to the majority of anti-cancer agents, checkpoint inhibitors do not necessarily target tumor cells directly, but rather target lymphocyte receptors or their ligands in order to enhance the endogenous antitumor activity of the immune system.

As used herein, the term "immune checkpoint inhibitor" refers to molecules that totally or partially reduce, inhibit, interfere with or modulate one or more checkpoint proteins. Checkpoint proteins regulate T-cell activation or function. These proteins are responsible for co-stimulatory or inhibitory interactions of T-cell responses Immune checkpoint proteins regulate and maintain self-tolerance and the duration and amplitude of physiological immune responses. In some embodiments, the subject can be administered an additional agent that can enhance or boost the immune response, e.g., immune response effected by the binding molecules (e.g., ROR1-binding molecules), recombinant receptors, cells and/or compositions provided herein, against a disease or condition, e.g., a cancer, such as any described herein.

Immune checkpoint inhibitors include any agent that blocks or inhibits in a statistically significant manner, the inhibitory pathways of the immune system. Such inhibitors may include small molecule inhibitors or may include antibodies, or antigen binding fragments thereof, that bind to and block or inhibit immune checkpoint receptors, ligands and/or receptor-ligand interaction. In some embodiments, modulation, enhancement and/or stimulation of particular receptors can overcome immune checkpoint pathway components. Illustrative immune checkpoint molecules that may be targeted for blocking, inhibition, modulation, enhancement and/or stimulation include, but are not limited to, PD-1 (CD279), PD-L1 (CD274, B7-H1), PDL2 (CD273, B7-DC), CTLA-4, LAG-3 (CD223), TIM-3, 4-1BB (CD137), 4-1BBL (CD137L), GITR (TNFRSF18, AITR), CD40, OX40 (CD134, TNFRSF4), CXCR2, tumor associated antigens (TAA), B7-H3, B7-H4, BTLA, HVEM, GAL9, B7H3, B7H4, VISTA, KIR, 2B4 (belongs to the CD2 family of molecules and is expressed on all NK, γδ, and memory CD8+ (αβ) T cells), CD160 (also referred to as BY55), CGEN-15049, CEACAM (e.g., CEACAM-1, CEACAM-3 and/or CEACAM-5), TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and a transforming growth factor receptor (TGFR; e.g., TGFR beta) Immune checkpoint inhibitors include antibodies, or antigen binding fragments thereof, or other binding proteins that bind to and block or inhibit and/or enhance or stimulate the activity of one or more of any of the said molecules.

Exemplary immune checkpoint inhibitors include Tremelimumab (CTLA-4 blocking antibody, also known as ticilimumab, CP-675,206), anti-OX40, PD-L1 monoclonal antibody (Anti-B7-H1; MEDI4736), MK-3475 (PD-1 blocker), nivolumab (anti-PD-1 antibody), CT-011 (anti-PD-1 antibody), BY55 monoclonal antibody, AMP224 (anti-PD-L1 antibody), BMS-936559 (anti-PD-L1 antibody), MPLDL3280A (anti-PD-L1 antibody), MSB0010718C (anti-PD-L1 antibody) and ipilimumab (anti-CTLA-4 antibody, also known as Yervoy®, MDX-010 and MDX-101). Exemplary of immunomodulatory antibodies include, but are not limited to, Daclizumab (Zenapax), Bevacizumab (Avastin Basiliximab, Ipilimumab, Nivolumab, pembrolizumab, MPDL3280A, Pidilizumab (CT-011), MK-3475, BMS-936559, MPDL3280A (Atezolizumab), tremelimumab, IMP321, BMS-986016, LAG525, urelumab, PF-05082566, TRX518, MK-4166, dacetuzumab (SGN-40), lucatumumab (HCD122), SEA-CD40, CP-870, CP-893, MEDI6469, MEDI6383, MOXR0916, AMP-224, MSB0010718C (Avelumab), MEDI4736, PDR001, rHIgM12B7, Ulocuplumab, BKT140, Varlilumab (CDX-1127), ARGX-110, MGA271, lirilumab (BMS-986015, IPH2101), IPH2201, ARGX-115, Emactuzumab, CC-90002 and MNRP1685A or an antibody-binding fragment thereof. Other exemplary immunomodulators include, e.g., afutuzumab (available from Roche®); pegfilgrastim (Neulasta®); lenalidomide (CC-5013, Revlimid®); thalidomide (Thalomid®), actimid (CC4047); and IRX-2 (mixture of human cytokines including interleukin 2, and interferon gamma, CAS 951209-71-5, available from IRX Therapeutics).

Programmed cell death 1 (PD-1) is an immune checkpoint protein that is expressed in B cells, NK cells, and T cells (Shinohara et al., 1995, Genomics 23:704-6; Blank et al., 2007, Cancer Immunol Immunother 56:739-45; Finger et al., 1997, Gene 197:177-87; Pardoll (2012) Nature Reviews Cancer 12:252-264). The major role of PD-1 is to limit the activity of T cells in peripheral tissues during inflammation in response to infection, as well as to limit autoimmunity. PD-1 expression is induced in activated T cells and binding of PD-1 to one of its endogenous ligands acts to inhibit T-cell activation by inhibiting stimulatory kinases. PD-1 also acts to inhibit the TCR "stop signal". PD-1 is highly expressed on Treg cells and may increase their proliferation in the presence of ligand (Pardoll (2012) Nature Reviews Cancer 12:252-264). Anti-PD 1 antibodies have been used for treatment of melanoma, non-small-cell lung cancer, bladder cancer, prostate cancer, colorectal cancer, head and neck cancer, triple-negative breast cancer, leukemia, lymphoma and renal cell cancer (Topalian et al., 2012, N Engl J Med 366:2443-54; Lipson et al., 2013, Clin Cancer Res 19:462-8; Berger et al., 2008, Clin Cancer Res 14:3044-51; Gildener-Leapman et al., 2013, Oral Oncol 49:1089-96; Menzies & Long, 2013, Ther Adv Med Oncol 5:278-85). Exemplary anti-PD-1 antibodies include nivolumab (Opdivo by BMS), pembrolizumab (Keytruda by Merck), pidilizumab (CT-011 by Cure Tech), lambrolizumab (MK-3475 by Merck), and AMP-224 (Merck), nivolumab (also referred to as Opdivo, BMS-936558 or MDX1106; Bristol-Myers Squibb) is a fully human IgG4 monoclonal antibody which specifically blocks PD-1. Nivolumab (clone 5C4) and other human monoclonal antibodies that specifically bind to PD-1 are described in U.S. Pat. No. 8,008,449 and WO2006/121168. Pidilizumab (CT-011; Cure Tech) is a humanized IgG1k monoclonal antibody that binds to PD-1. Pidilizumab and other humanized anti-PD-1 monoclonal antibodies are described in WO2009/101611. Pembrolizumab (formerly known as lambrolizumab, and also referred to as Keytruda, MK03475; Merck) is a humanized IgG4 monoclonal antibody that binds to PD-1. Pembrolizumab and other humanized anti-PD-1 antibodies are described in U.S. Pat. No. 8,354,509 and WO2009/114335. Other anti-PD-1 antibodies include AMP 514 (Amplimmune), among others, e.g., anti-PD-1 antibodies described in U.S. Pat. No. 8,609,089, US 2010028330, US 20120114649 and/or US 20150210769. AMP-224 (B7-DCIg; Amplimmune; e.g., described in WO2010/027827 and WO2011/066342), is a PD-L2 Fc fusion soluble receptor that blocks the interaction between PD-1 and B7-H1.

PD-L1 (also known as CD274 and B7-H1) and PD-L2 (also known as CD273 and B7-DC) are ligands for PD-1, found on activated T cells, B cells, myeloid cells, macrophages, and some types of tumor cells. Anti-tumor therapies have focused on anti-PD-L1 antibodies. The complex of PD-1 and PD-L1 inhibits proliferation of CD8+ T cells and reduces the immune response (Topalian et al., 2012, N Engl J Med 366:2443-54; Brahmer et al., 2012, N Eng J Med 366:2455-65). Anti-PD-L1 antibodies have been used for treatment of non-small cell lung cancer, melanoma, colorectal cancer, renal-cell cancer, pancreatic cancer, gastric cancer, ovarian cancer, breast cancer, and hematologic malignancies (Brahmer et al., 2012, N Eng J Med 366:2455-65; Ott et al., 2013, Clin Cancer Res 19:5300-9; Radvanyi et al., 2013, Clin Cancer Res 19:5541; Menzies & Long, 2013, Ther Adv Med Oncol 5:278-85; Berger et al., 2008, Clin Cancer Res 14:13044-51). Exemplary anti-PD-L1 antibodies include MDX-1105 (Medarex), MEDI4736 (Medimmune) MPDL3280A (Genentech), BMS-935559 (Bristol-Myers Squibb) and MSB0010718C. MEDI4736 (Medimmune) is a human monoclonal antibody that binds to PD-L1, and inhibits interaction of the ligand with PD-1. MDPL3280A (Genentech/Roche) is a human Fc optimized IgG1 monoclonal antibody that binds to PD-L1. MDPL3280A and other human monoclonal antibodies to PD-L1 are described in U.S. Pat. No. 7,943,743 and U.S Publication No. 20120039906. Other anti-PD-L1 binding agents include YW243.55.570 (see WO2010/077634) and MDX-1105 (also referred to as BMS-936559, and, e.g., anti-PD-L1 binding agents described in WO2007/005874).

Cytotoxic T-lymphocyte-associated antigen (CTLA-4), also known as CD152, is a co-inhibitory molecule that functions to regulate T-cell activation. CTLA-4 is a member of the immunoglobulin superfamily that is expressed exclusively on T-cells. CTLA-4 acts to inhibit T-cell activation and is reported to inhibit helper T-cell activity and enhance regulatory T-cell immunosuppressive activity. Although the precise mechanism of action of CTLA-4 remains under investigation, it has been suggested that it inhibits T cell activation by outcompeting CD28 in binding to CD80 and CD86, as well as actively delivering inhibitor signals to the T cell (Pardoll (2012) Nature Reviews Cancer 12:252-264). Anti-CTLA-4 antibodies have been used in clinical trials for the treatment of melanoma, prostate cancer, small cell lung cancer, non-small cell lung cancer (Robert & Ghiringhelli, 2009, Oncologist 14:848-61; Ott et al., 2013, Clin Cancer Res 19:5300; Weber, 2007, Oncologist 12:864-72; Wada et al., 2013, J Transl Med 11:89). A significant feature of anti-CTLA-4 is the kinetics of anti-tumor effect, with a lag period of up to 6 months after initial treatment required for physiologic response. In some cases, tumors may actually increase in size after treatment initiation, before a reduction is seen (Pardoll (2012) Nature Reviews Cancer 12:252-264). Exemplary anti-CTLA-4 antibodies include ipilimumab (Bristol-Myers Squibb) and tremelimumab (Pfizer). Ipilimumab has recently received FDA approval for treatment of metastatic melanoma (Wada et al., 2013, J Transl Med 11:89).

Lymphocyte activation gene-3 (LAG-3), also known as CD223, is another immune checkpoint protein. LAG-3 has been associated with the inhibition of lymphocyte activity and in some cases the induction of lymphocyte anergy. LAG-3 is expressed on various cells in the immune system including B cells, NK cells, and dendritic cells. LAG-3 is a natural ligand for the MHC class II receptor, which is substantially expressed on melanoma-infiltrating T cells including those endowed with potent immune-suppressive activity. Exemplary anti-LAG-3 antibodies include BMS-986016 (Bristol-Myers Squib), which is a monoclonal antibody that targets LAG-3. IMP701 (Immutep) is an antagonist LAG-3 antibody and IMP731 (Immutep and GlaxoSmithKline) is a depleting LAG-3 antibody. Other LAG-3 inhibitors include IMP321 (Immutep), which is a recombinant fusion protein of a soluble portion of LAG-3 and Ig that binds to MHC class II molecules and activates antigen presenting cells (APC). Other antibodies are described, e.g., in WO2010/019570 and US 2015/0259420

T-cell immunoglobulin domain and mucin domain-3 (TIM-3), initially identified on activated Th1 cells, has been shown to be a negative regulator of the immune response.

Blockade of TIM-3 promotes T-cell mediated anti-tumor immunity and has anti-tumor activity in a range of mouse tumor models. Combinations of TIM-3 blockade with other immunotherapeutic agents such as TSR-042, anti-CD137 antibodies and others, can be additive or synergistic in increasing anti-tumor effects. TIM-3 expression has been associated with a number of different tumor types including melanoma, NSCLC and renal cancer, and additionally, expression of intratumoral TIM-3 has been shown to correlate with poor prognosis across a range of tumor types including NSCLC, cervical, and gastric cancers. Blockade of TIM-3 is also of interest in promoting increased immunity to a number of chronic viral diseases. TIM-3 has also been shown to interact with a number of ligands including galectin-9, phosphatidylserine and HMGB1, although which of these, if any, are relevant in regulation of anti-tumor responses is not clear at present. In some embodiments, antibodies, antibody fragments, small molecules, or peptide inhibitors that target TIM-3 can bind to the IgV domain of TIM-3 to inhibit interaction with its ligands. Exemplary antibodies and peptides that inhibit TIM-3 are described in US 2015/0218274, WO2013/006490 and US 2010/0247521. Other anti-TIM-3 antibodies include humanized versions of RMT3-23 (Ngiow et al., 2011, Cancer Res, 71:3540-3551), and clone 8B.2C12 (Monney et al., 2002, Nature, 415:536-541). Bi-specific antibodies that inhibit TIM-3 and PD-1 are described in US 2013/0156774.

In some embodiments, the additional agent is a CEACAM inhibitor (e.g., CEACAM-1, CEACAM-3, and/or CEACAM-5 inhibitor). In some embodiments, the inhibitor of CEACAM is an anti-CEACAM antibody molecule. Exemplary anti-CEACAM-1 antibodies are described in WO 2010/125571, WO 2013/082366 WO 2014/059251 and WO 2014/022332, e.g., a monoclonal antibody 34B1, 26H7, and 5F4; or a recombinant form thereof, as described in, e.g., US 2004/0047858, U.S. Pat. No. 7,132,255 and WO 99/052552. In some embodiments, the anti-CEACAM antibody binds to CEACAM-5 as described in, e.g., Zheng et al. PLoS One. (2011) 6(6): e21146, or cross-reacts with CEACAM-1 and CEACAM-5 as described in, e.g., WO 2013/054331 and US 2014/0271618.

4-1BB, also known as CD137, is transmembrane glycoprotein belonging to the TNFR superfamily. 4-1BB receptors are present on activated T cells and B cells and monocytes. An exemplary anti-4-1BB antibody is urelumab (BMS-663513), which has potential immunostimulatory and antineoplastic activities.

Tumor necrosis factor receptor superfamily, member 4 (TNFRSF4), also known as OX40 and CD134, is another member of the TNFR superfamily. OX40 is not constitutively expressed on resting naive T cells and acts as a secondary co-stimulatory immune checkpoint molecule. Exemplary anti-OX40 antibodies are MEDI6469 and MOXR0916 (RG7888, Genentech).

In some embodiments, the additional agent includes a molecule that decreases the regulatory T cell (Treg) population. Methods that decrease the number of (e.g., deplete) Treg cells are known and include, e.g., CD25 depletion, cyclophosphamide administration, and modulating Glucocorticoid-induced TNFR family related gene (GITR) function. GITR is a member of the TNFR superfamily that is upregulated on activated T cells, which enhances the immune system. Reducing the number of Treg cells in a subject prior to apheresis or prior to administration of engineered cells, e.g., CAR-expressing cells, can reduce the number of unwanted immune cells (e.g., Tregs) in the tumor microenvironment and reduces the subject's risk of relapse.

In some embodiments, the additional agent includes a molecule targeting GITR and/or modulating GITR functions, such as a GITR agonist and/or a GITR antibody that depletes regulatory T cells (Tregs). In some embodiments, the additional agent includes cyclophosphamide. In some embodiments, the GITR binding molecule and/or molecule modulating GITR function (e.g., GITR agonist and/or Treg depleting GITR antibodies) is administered prior to the engineered cells, e.g., CAR-expressing cells. For example, in some embodiments, the GITR agonist can be administered prior to apheresis of the cells. In some embodiments, cyclophosphamide is administered to the subject prior to administration (e.g., infusion or re-infusion) of the engineered cells, e.g., CAR-expressing cells or prior to apheresis of the cells. In some embodiments, cyclophosphamide and an anti-GITR antibody are administered to the subject prior to administration (e.g., infusion or re-infusion) of the engineered cells, e.g., CAR-expressing cells or prior to apheresis of the cells.

In some embodiments, the additional agent is a GITR agonist. Exemplary GITR agonists include, e.g., GITR fusion proteins and anti-GITR antibodies (e.g., bivalent anti-GITR antibodies) such as, e.g., a GITR fusion protein described in U.S. Pat. No. 6,111,090, European Patent No. 090505B 1, U.S. Pat. No. 8,586,023, PCT Publication Nos.: WO 2010/003118 and 2011/090754, or an anti-GITR antibody described, e.g., in U.S. Pat. No. 7,025,962, European Patent No. 1947183B 1, U.S. Pat. Nos. 7,812,135, 8,388,967, 8,591,886, European Patent No. EP 1866339, WO 2011/028683, WO 2013/039954, WO2005/007190, WO 2007/133822, WO2005/055808, WO 99/40196, WO 2001/03720, WO99/20758, WO2006/083289, WO 2005/115451, U.S. Pat. No. 7,618,632, and WO 2011/051726. An exemplary anti-GITR antibody is TRX518.

In some embodiments, the additional agent enhances tumor infiltration or transmigration of the administered cells, e.g., CAR-expressing cells. For example, in some embodiments, the additional agent stimulates CD40, such as CD40L, e.g., recombinant human CD40L. Cluster of differentiation 40 (CD40) is also a member of the TNFR superfamily. CD40 is a costimulatory protein found on antigen-presenting cells and mediates a broad variety of immune and inflammatory responses. CD40 is also expressed on some malignancies, where it promotes proliferation. Exemplary anti-CD40 antibodies are dacetuzumab (SGN-40), lucatumumab (Novartis, antagonist), SEA-CD40 (Seattle Genetics), and CP-870,893. In some embodiments, the additional agent that enhances tumor infiltration includes tyrosine kinase inhibitor sunitnib, heparanase, and/or chemokine receptors such as CCR2, CCR4, and CCR7.

In some embodiments, the additional agent is a structural or functional analog or derivative of thalidomide and/or an inhibitor of E3 ubiquitin ligase. In some embodiments, the immunomodulatory agent binds to cereblon (CRBN). In some embodiments, the immunomodulatory agent binds to the CRBN E3 ubiquitin-ligase complex. In some embodiments, the immunomodulatory agent binds to CRBN and the CRBN E3 ubiquitin-ligase complex. In some embodiments, the immunomodulatory agent up-regulates the protein or gene expression of CRBN. In some aspects, CRBN is the substrate adaptor for the $CRL4^{CRBN}$ E3 ubiquitin ligase, and modulates the specificity of the enzyme. In some embodiments, binding to CRB or the CRBN E3 ubiquitin ligase complex inhibits E3 ubiquitin ligase activity. In some embodiments, the immunomodulatory agent induces the ubiquitination of KZF1 (Ikaros) and IKZF3 (Aiolos) and/or induces degradation of IKZF1 (Ikaros) and IKZF3 (Aiolos).

In some embodiments, the immunomodulatory agent induces the ubiquitination of casein kinase 1A1 (CK1α) by the CRL4$^{CRBN}$ E3 ubiquitin ligase. In some embodiments, the ubiquitination of CK1α results in CK1α degradation.

In some embodiments, the additional agent is an inhibitor of the Ikaros (IKZF1) transcription factor. In some embodiments, the additional agent enhances ubiquitination of Ikaros. In some embodiments, the additional agent enhances the degradation of Ikaros. In some embodiments, the additional agent down-regulates the protein or gene expression of Ikaros. In some embodiments, administration of the additional agent causes a decrease in Ikaros protein levels.

In some embodiments, the additional agent is an inhibitor of the Aiolos (IKZF3) transcription factor. In some embodiments, the additional agent enhances ubiquitination of Aiolos. In some embodiments, the additional agent enhances the degradation of Aiolos. In some embodiments, the additional agent down-regulates the protein or gene expression of Aiolos. In some embodiments, administration of the additional agent causes a decrease in Aiolos protein levels.

In some embodiments, the additional agent is an inhibitor of both the Ikaros (IKZF1) and Aiolos (IKZF3) transcription factors. In some embodiments, the additional agent enhances ubiquitination of both Ikaros and Aiolos. In some embodiments, the additional agent enhances the degradation of both Ikaros and Aiolos. In some embodiments, the additional agent enhances ubiquitination and degradation of both Ikaros and Aiolos. In some embodiments, administration of the additional agent causes both Aiolos protein levels and Ikaros protein levels to decrease.

In some embodiments, the additional agent is a selective cytokine inhibitory drug (SelCID). In some embodiments, the additional agent inhibits the activity of phosphodiesterase-4 (PDE4). In some embodiments, the additional agent suppresses the enzymatic activity of the CDC125 phosphatases. In some embodiments, the additional agent alters the intracellular trafficking of CDC125 phosphatases.

In some embodiments, the additional agent is thalidomide (2-(2,6-dioxopiperidin-3-yl)-1H-isoindole-1,3(2H)-dione) or an analog or derivative of thalidomide. In certain embodiments, a thalidomide derivative includes structural variants of thalidomide that have a similar biological activity. Exemplary thalidomide derivatives include, but are not limited to lenalidomide (REVLIMMUNOMODULATORY COMPOUND™; Celgene Corporation), pomalidomide (also known as ACTIMMUNOMODULATORY COMPOUND™ or POMALYST™ (Celgene Corporation)), CC-1088, CDC-501, and CDC-801, and the compounds disclosed in U.S. Pat. Nos. 5,712,291; 7,320,991; and 8,716,315; U.S. Appl. No. 2016/0313300; and PCT Pub. Nos. WO 2002/068414 and WO 2008/154252.

In some embodiments, the additional agent is 1-oxo- and 1,3 dioxo-2-(2,6-dioxopiperldin-3-yl) isoindolines substituted with amino in the benzo ring as described in U.S. Pat. No. 5,635,517 which is incorporated herein by reference.

In some embodiments, the additional agent is a compound of the following formula:

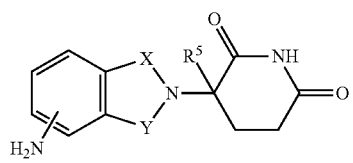

wherein one of X and Y is —C(O)— and the other of X and Y is —C(O)— or —CH$_2$—, and R$^5$ is hydrogen or lower alkyl, or a pharmaceutically acceptable salt thereof. In some embodiments, X is —C(O)— and Y is —CH$_2$—. In some embodiments, both X and Y are —C(O)—. In some embodiments, R$^5$ is hydrogen. In other embodiments, R$^5$ is methyl.

In some embodiments, the additional agent is a compound that belongs to a class of substituted 2-(2, 6-dioxopiperidin-3-yl)phthalate immunomodulatory compounds and substituted 2-(2,6-dioxopiperldin-3-yl)-1-oxoisoindoles, such as those described in U.S. Pat. Nos. 6,281,230; 6,316,471; 6,335,349; and 6,476,052, and International Patent Application No. PCT/US97/13375 (International Publication No. WO 98/03502), each of which is incorporated herein by reference.

In some embodiments, the additional agent is a compound of the following formula:

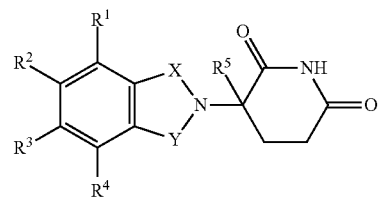

wherein
one of X and Y is —C(O)— and the other of X and Y is —C(O)— or —CH$_2$—;
(1) each of R$^1$, R$^2$, R$^3$, and R$^4$ are independently halo, alkyl of 1 to 4 carbon atoms, or alkoxy or 1 to 4 carbon atoms, or
(2) one of R$^1$, R$^3$, R$^4$, and R$^5$ is —NHR$^a$ and the remaining of R$^1$, R$^2$, R$^3$, and R$^4$ is are hydrogen, wherein R$^a$ is hydrogen or alkyl of 1 to 8 carbon atoms;
R$^5$ is hydrogen or alkyl of 1 to 8 carbon atoms, benzyl, or halo;
provided that R$^5$ is other than hydrogen if X and Y are —C(O)— and (i) each of R$^1$, R$^2$, R$^3$, and R$^4$ is fluoro; or (ii) one of R$^1$, R$^2$, R$^3$, and R$^4$ is amino;
or a pharmaceutically acceptable salt thereof.

In some embodiments, the additional agent is a compound that belongs to a class of isoindole-immunomodulatory compounds disclosed in U.S. Pat. No. 7,091,353, U.S. Patent Publication No. 2003/0045552, and International Application No. PCT/US01/50401 (International Publication No. WO02/059106), each of which are incorporated herein by reference. For example, in some embodiments, the additional agent is [2-(2,6-dioxo-piperidin-3-yl)-1,3-dioxo-2,3-dihydro-1H-isoindol-4-ylmethyl]-amide; (2-(2,6-dioxo-piperidin-3-yl)-1,3-dioxo-2,3-dihydro-1H-isoindol-4-ylmethyl)-carbamic acid tert-butyl ester; 4-(aminomethyl)-2-(2, 6-dioxo(3-piperidyl))-isoindoline-1,3-dione; N-(2-(2,6-dioxo-piperidin-3-yl)-1,3-dioxo-2,3-dihydro-1H-isoindol-4-ylmethyl)-acetamide; N-{(2-(2,6-dioxo(3-piperidyl)-1,3-dioxoisoindolin-4-yl)methyl}cyclopropyl-carboxamide; 2-chloro-N-{(2-(2,6-dioxo(3-piperidyl))-1,3-dioxoisoindo-lin-4-yl)methyl}acetamide; N-(2-(2,6-dioxo(3-piperidyl))-1,3-dioxoisoindolin-4-yl)-3-pyridylcarboxamide; 3-{1-oxo-4-(benzylamino)isoindolin-2-yl}piperidine-2,6-dione; 2-(2, 6-dioxo(3-piperidyl))-4-(benzylamino)isoindoline-1,3-dione; N-{(2-(2,6-dioxo(3-piperidyl))-1,3-dioxoisoindolin-4-yl)methyl}propanamide; N-{(2-(2,6-dioxo(3-piperidyl))-1,3-dioxoisoindolin-4-yl)methyl}-3-pyridylcarboxamide; N-{(2-(2,6-dioxo(3-piperidyl))-1,3-dioxoisoindolin-4-yl)

methyl}heptanamide; N-{(2-(2,6-dioxo(3-piperidyl))-1,3-dioxoisoindolin-4-yl)methyl}-2-furylcarboxamide; {N-(2-(2,6-dioxo(3-piperidyl))-1,3-dioxoisoindolin-4-yl)carbamoyl}methyl acetate; N-(2-(2,6-dioxo(3-piperidyl))-1,3-dioxoisoindolin-4-yl)pentanamide; N-(2-(2,6-dioxo(3-piperidyl))-1,3-dioxoisoindolin-4-yl)-2-thienylcarboxamide; N-{[2-(2,6-dioxo(3-piperidyl))-1,3-dioxoisoindolin-4-yl]methyl}(butylamino)carboxamide; N-{[2-(2,6-dioxo(3-piperidyl))-1,3-dioxoisoindolin-4-yl]methyl}(octylamino)carboxamide; or N-{[2-(2,6-dioxo(3-piperidyl))-1,3-dioxoisoindolin-4-yl]methyl}(benzylamino)carboxamide.

In some embodiments, the additional agent is a compound that belongs to a class of isoindole-immunomodulatory compounds disclosed in U.S. Patent Application Publication Nos. 2002/0045643, International Publication No. WO 98/54170, and U.S. Pat. No. 6,395,754, each of which is incorporated herein by reference. In some embodiments, the additional agent is a tetra substituted 2-(2,6-dioxopiperdin-3-yl)-1-oxoisoindolines described in U.S. Pat. No. 5,798,368, which is incorporated herein by reference. In some embodiments, the additional agent is 1-oxo and 1,3-dioxo-2-(2,6-dioxopiperidin-3-yl) isoindolines disclosed in U.S. Pat. No. 6,403,613, which is incorporated herein by reference. In some embodiments the additional agent is a 1-oxo or 1,3-dioxoisoindoline substituted in the 4- or 5-position of the indoline ring as described in U.S. Pat. Nos. 6,380,239 and 7,244,759, both of which are incorporated herein by reference.

In some embodiments, the additional agent is 2-(4-amino-1-oxo-1,3-dihydro-isoindol-2-yl)-4-carbamoyl-butyric acid or 4-(4-amino-1-oxo-1,3-dihydro-isoindol-2-yl)-4-carbamoyl-butyric acid. In some embodiments, the immunomodulatory compound is 4-carbamoyl-4-{4-[(furan-2-yl-methyl)-amino]-1,3-dioxo-1,3-dihydro-isoindol-2-yl}-butyric acid, 4-carbamoyl-2-{4-[(furan-2-yl-methyl)-amino]-1,3-dioxo-1,3-dihydro-isoindol-2-yl}-butyric acid, 2-{4-[(furan-2-yl-methyl)-amino]-1,3-dioxo-1,3-dihydro-isoindol-2-yl}-4-phenylcarbamoyl-butyric acid, or 2-{4-[(furan-2-yl-methyl)-amino]-1,3-dioxo-1,3-dihydro-isoindol-2-yl}-pentanedioic acid.

In some embodiments, the additional agent is a isoindoline-1-one or isoindoline-1,3-dione substituted in the 2-position with 2,6-dioxo-3-hydroxypiperidin-5-yl as described in U.S. Pat. No. 6,458,810, which is incorporated herein by reference. In some embodiments, the immunomodulatory compound is 3-(5-amino-2-methyl-4-oxo-4H-quinazolin-3-yl)-piperidine-2,6-dione, or an enantiomer or a mixture of enantiomers thereof; or a pharmaceutically acceptable salt, solvate, hydrate, co-crystal, clathrate, or polymorph thereof. In some embodiments, the immunomodulatory compound is 3-[4-(4-morpholin-4-ylmethyl-benzyloxy)-1-oxo-1,3-dihydro-isoindol-2-yl]-piperidine-2,6-dione.

In some embodiments, the additional agent is as described in Oshima, K. et al., Nihon Rinsho., 72(6):1130-5 (2014); Millrine, D. et al., Trends Mol Med., 23(4):348-364 (2017); and Collins, et al., Biochem J., 474(7):1127-1147 (2017).

In some embodiments, the additional agent includes thalidomide drugs or analogs thereof and/or derivatives thereof, such as lenalidomide, pomalidomide or apremilast. See, e.g., Bertilaccio et at, Blood (2013) 122:4171, Otahal et al., Oncoimmunology (2016) 5(4):e1115940; Fecteau et al., Blood (2014) 124(10):1637-1644 and Kuramitsu et al., Cancer Gene Therapy (2015) 22:487-495). Lenalidomide ((RS)-3-(4-Amino-1-oxo-1,3-dihydro-2H-isoindol-2-yl)piperidine-2,6-dione; also known as Revlimid) is a synthetic derivative of thalidomide, and has multiple immunomodulatory effects, including enforcement of immune synapse formation between T cell and antigen presenting cells (APCs). In some embodiments, the additional agent is lenalidomide, pomalidomide, avadomide, a stereoisomer of lenalidomide, pomalidomide, avadomide or a pharmaceutically acceptable salt, solvate, hydrate, co-crystal, clathrate, or polymorph thereof. In some embodiments, the immunomodulatory compound is lenalidomide, a stereoisomer of lenalidomide or a pharmaceutically acceptable salt, solvate, hydrate, co-crystal, clathrate, or polymorph thereof. In some embodiments, the immunomodulatory compound is lenalidomide, or ((RS)-3-(4-Amino-1-oxo-1,3-dihydro-2H-isoindol-2-yl)piperidine-2,6-dione).

In certain embodiments, the lesion is disrupted by administering the thalidomide derivative lenalidomide, ((RS)-3-(4-Amino-1-oxo-1,3-dihydro-2H-isoindol-2-yl)piperidine-2,6-dione) to the subject. Lenalidomide is FDA approved for the treatment of multiple myeloma, myelodysplastic syndrome associated with deletion 5q, and most recently in relapsed/refractory mantle-cell lymphoma (MCL). Lenalidomide generally is a synthetic derivative of thalidomide, and is currently understood to have multiple immunomodulatory effects, including enforcement of immune synapse formation between T cell and antigen presenting cells (APCs). For example, in some cases, lenalidomide modulates T cell responses and results in increased interleukin (IL)-2 production in $CD4^+$ and $CD8^+$ T cells, induces the shift of T helper (Th) responses from Th2 to Th1, inhibits expansion of regulatory subset of T cells (Tregs), and improves functioning of immunological synapses in follicular lymphoma and chronic lymphocytic leukemia (CLL) (Otahal et al., Oncoimmunology (2016) 5(4):e1115940). Lenalidomide also has direct tumoricidal activity in patients with multiple myeloma (MM) and directly and indirectly modulates survival of CLL tumor cells by affecting supportive cells, such as nurse-like cells found in the microenvironment of lymphoid tissues. Lenalidomide also can enhance T-cell proliferation and interferon-γ production in response to activation of T cells via CD3 ligation or dendritic cell-mediated activation. In addition, lenalidomide is thought to decrease proliferation of pro-inflammatory cytokines including TNF-α, IL-1, IL-6, and IL-12 and enhance antibody-dependent cellular cytotoxicity (ADCC) via increased NK cell activation. Lenalidomide can also induce malignant B cells to express higher levels of immunostimulatory molecules such as CD80, CD86, HLA-DR, CD95, and CD40 (Fecteau et al., Blood (2014) 124(10):1637-1644). Cereblon, an E3 ubiquitin ligase, was identified as the primary target for thalidomide-induced teratogenesis (Ito et al., T., (2010) Science 327: 1345-1350). Lenalidomide also targets cereblon and it has been shown that this leads to the reduction of c-Myc and IRF4 expression while also increasing expression of p21 that leads to G1 cell-cycle arrest (Lopez-Girona et al., (2012) Leukemia 26: 2326-2335).

In some embodiments, the additional agent is a B-cell inhibitor. In some embodiments, the additional agent is one or more B-cell inhibitors selected from among inhibitors of CD10, CD19, CD20, CD22, CD34, CD123, CD79a, CD79b, CD179b, FLT-3, or ROR1, or a combination thereof. In some embodiments, the B-cell inhibitor is an antibody (e.g., a mono- or bispecific antibody) or an antigen binding fragment thereof. In some embodiments, the additional agent is an engineered cell expressing recombinant receptors that target B-cell targets, e.g., CD10, CD19, CD20, CD22, CD34, CD123, CD79a, CD79b, CD179b, FLT-3, or ROR1.

In some embodiments, the additional agent is a CD20 inhibitor, e.g., an anti-CD20 antibody (e.g., an anti-CD20 mono- or bi-specific antibody) or a fragment thereof. Exemplary anti-CD20 antibodies include but are not limited to rituximab, ofatumumab, ocrelizumab (also known as GA101 or R05072759), veltuzumab, obinutuzumab, TRU-015 (Trubion Pharmaceuticals), ocaratuzumab (also known as AME-133v or ocaratuzumab), and Pro131921 (Genentech). See, e.g., Lim et al. Haematologica. (2010) 95(1):135-43. In some embodiments, the anti-CD20 antibody comprises rituximab. Rituximab is a chimeric mouse/human monoclonal antibody IgG1 kappa that binds to CD20 and causes cytolysis of a CD20 expressing cell. In some embodiments, the additional agent includes rituximab. In some embodiments, the CD20 inhibitor is a small molecule.

In some embodiments, the additional agent is a CD22 inhibitor, e.g., an anti-CD22 antibody (e.g., an anti-CD22 mono- or bi-specific antibody) or a fragment thereof. Exemplary anti-CD22 antibodies include epratuzumab and RFB4. In some embodiments, the CD22 inhibitor is a small molecule. In some embodiments, the antibody is a monospecific antibody, optionally conjugated to a second agent such as a chemotherapeutic agent. For instance, in some embodiments, the antibody is an anti-CD22 monoclonal antibody-MMAE conjugate (e.g., DCDT2980S). In some embodiments, the antibody is an scFv of an anti-CD22 antibody, e.g., an scFv of antibody RFB4. In some embodiments, the scFv is fused to all of or a fragment of *Pseudomonas* exotoxin-A (e.g., BL22). In some embodiments, the scFv is fused to all of or a fragment of (e.g., a 38 kDa fragment of) *Pseudomonas* exotoxin-A (e.g., moxetumomab pasudotox). In some embodiments, the anti-CD22 antibody is an anti-CD19/CD22 bispecific antibody, optionally conjugated to a toxin. For instance, in some embodiments, the anti-CD22 antibody comprises an anti-CD19/CD22 bispecific portion, (e.g., two scFv ligands, recognizing human CD19 and CD22) optionally linked to all of or a portion of diphtheria toxin (DT), e.g., first 389 amino acids of diphtheria toxin (DT), DT 390, e.g., a ligand-directed toxin such as DT2219ARL). In some embodiments, the bispecific portion (e.g., anti-CD 19/anti-CD22) is linked to a toxin such as deglycosylated ricin A chain (e.g., Combotox).

In some embodiments, the immunomodulatory agent is a cytokine. In some embodiments, the immunomodulatory agent is a cytokine or is an agent that induces increased expression of a cytokine in the tumor microenvironment. Cytokines have important functions related to T cell expansion, differentiation, survival, and homeostasis. Cytokines that can be administered to the subject receiving the binding molecules (e.g., ROR1-binding molecules), recombinant receptors, cells and/or compositions provided herein include one or more of IL-2, IL-4, IL-7, IL-9, IL-15, IL-18, and IL-21. In some embodiments, the cytokine administered is IL-7, IL-15, or IL-21, or a combination thereof. In some embodiments, administration of the cytokine to the subject that has sub-optimal response to the administration of the engineered cells, e.g., CAR-expressing cells improves efficacy and/or anti-tumor activity of the administered cells, e.g., CAR-expressing cells.

By "cytokine" is meant a generic term for proteins released by one cell population that act on another cell as intercellular mediators. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines. For example, the immunomodulatory agent is a cytokine and the cytokine is IL-4, TNF-α, GM-CSF or IL-2.

In some embodiments, the additional agent includes an interleukin-15 (IL-15) polypeptide, an interleukin-15 receptor alpha (IL-15Ra) polypeptide, or combination thereof, e.g., hetIL-15 (Admune Therapeutics, LLC). hetIL-15 is a heterodimeric non-covalent complex of IL-15 and IL-15Rα. hetIL-15 is described in, e.g., U.S. Pat. No. 8,124,084, U.S. 2012/0177598, U.S. 2009/0082299, U.S. 2012/0141413, and U.S. 2011/0081311. In some embodiments, the immunomodulatory agent can contain one or more cytokines. For example, the interleukin can include leukocyte interleukin injection (Multikine), which is a combination of natural cytokines. In some embodiments, the immunomodulatory agent is a Toll-like receptor (TLR) agonist, an adjuvant or a cytokine.

In some embodiments, the additional agent is an agent that ameliorates or neutralizes one or more toxicities or side effects associated with the cell therapy. In some embodiments, the additional agent is selected from among a steroid (e.g., corticosteroid), an inhibitor of TNFα, and an inhibitor of IL-6. An example of a TNFα inhibitor is an anti-TNFα antibody molecule such as, infliximab, adalimumab, certolizumab pegol, and golimumab. Another example of a TNFα inhibitor is a fusion protein such as entanercept. Small molecule inhibitors of TNFα include, but are not limited to, xanthine derivatives (e.g. pentoxifylline) and bupropion. An example of an IL-6 inhibitor is an anti-IL-6 antibody molecule such as tocilizumab, sarilumab, elsilimomab, CNTO 328, ALD518/BMS-945429, CNTO 136, CPSI-2364, CDP6038, VX30, ARGX-109, FE301, and FM101. In some embodiments, the anti-IL-6 antibody molecule is tocilizumab. In some embodiments, the additional agent is an IL-1R inhibitor, such as anakinra In some embodiments, the additional agent is a modulator of adenosine levels and/or an adenosine pathway component. Adenosine can function as an immunomodulatory agent in the body. For example, adenosine and some adenosine analogs that non-selectively activate adenosine receptor subtypes decrease neutrophil production of inflammatory oxidative products (Cronstein et al., Ann. N.Y. Acad. Sci. 451:291, 1985; Roberts et al., Biochem. J., 227:669, 1985; Schrier et al., J. Immunol. 137:3284, 1986; Cronstein et al., Clinical Immunol. Immunopath. 42:76, 1987). In some cases, concentration of extracellular adenosine or adenosine analogs can increase in specific environments, e.g., tumor microenvironment (TME). In some cases, adenosine or adenosine analog signaling depends on hypoxia or factors involved in hypoxia or its regulation, e.g., hypoxia inducible factor (HIF). In some embodiments, increase in adenosine signaling can increase in intracellular cAMP and cAMP-dependent protein kinase that results in inhibition of proinflammatory cytokine production, and can lead to the synthesis of immunosuppressive molecules and development of Tregs (Sitkovsky et al., Cancer Immunol Res (2014) 2(7): 598-605). In some embodiments, the additional agent can reduce or reverse immunosuppressive effects of adenosine, adenosine analogs and/or adenosine signaling. In some embodiments, the additional agent can reduce or reverse hypoxia-driven A2-adenosinergic T cell immunosuppression. In some embodiments, the additional agent is selected from among antagonists of adenosine receptors, extracellular adenosine-degrading agents, inhibitors of adenosine generation by CD39/CD73 ectoenzymes, and inhibitors of hypoxia-HIF-1a signaling. In some embodiments, the additional agent is an adenosine receptor antagonist or agonist.

Inhibition or reduction of extracellular adenosine or the adenosine receptor by virtue of an inhibitor of extracellular adenosine (such as an agent that prevents the formation of, degrades, renders inactive, and/or decreases extracellular adenosine), and/or an adenosine receptor inhibitor (such as an adenosine receptor antagonist) can enhance immune response, such as a macrophage, neutrophil, granulocyte, dendritic cell, T- and/or B cell-mediated response. In addition, inhibitors of the Gs protein mediated cAMP dependent intracellular pathway and inhibitors of the adenosine receptor-triggered Gi protein mediated intracellular pathways, can also increase acute and chronic inflammation.

In some embodiments, the additional agent is an adenosine receptor antagonist or agonist, e.g., an antagonist or agonist of one or more of the adenosine receptors A2a, A2b, A1, and A3. A1 and A3 inhibit, and A2a and A2b stimulate, respectively, adenylate cyclase activity. Certain adenosine receptors, such as A2a, A2b, and A3, can suppress or reduce the immune response during inflammation. Thus, antagonizing immunosuppressive adenosine receptors can augment, boost or enhance immune response, e.g., immune response from administered cells, e.g., CAR-expressing T cells. In some embodiments, the additional agent inhibits the production of extracellular adenosine and adenosine-triggered signaling through adenosine receptors. For example, enhancement of an immune response, local tissue inflammation, and targeted tissue destruction can be enhanced by inhibiting or reducing the adenosine-producing local tissue hypoxia; by degrading (or rendering inactive) accumulated extracellular adenosine; by preventing or decreasing expression of adenosine receptors on immune cells; and/or by inhibiting/antagonizing signaling by adenosine ligands through adenosine receptors.

An antagonist is any substance that tends to nullify the action of another, as an agent that binds to a cell receptor without eliciting a biological response. In some embodiments, the antagonist is a chemical compound that is an antagonist for an adenosine receptor, such as the A2a, A2b, or A3 receptor. In some embodiments, the antagonist is a peptide, or a peptidomimetic, that binds the adenosine receptor but does not trigger a Gi protein dependent intracellular pathway. Exemplary antagonists are described in U.S. Pat. Nos. 5,565,566; 5,545,627; 5,981,524; 5,861,405; 6,066,642; 6,326,390; 5,670,501; 6,117,998; 6,232,297; 5,786,360; 5,424,297; 6,313,131, 5,504,090; and 6,322,771.

In some embodiments, the additional agent is an A2 receptor (A2R) antagonist, such as an A2a antagonist. Exemplary A2R antagonists include KW6002 (istradefyline), SCH58261, caffeine, paraxanthine, 3,7-dimethyl-1-propargylxanthine (DMPX), 8-(m-chlorostyryl) caffeine (CSC), MSX-2, MSX-3, MSX-4, CGS-15943, ZM-241385, SCH-442416, preladenant, vipadenant (BII014), V2006, ST-1535, SYN-115, PSB-1115, ZM241365, FSPTP, and an inhibitory nucleic acid targeting A2R expression, e.g., siRNA or shRNA, or any antibodies or antigen-binding fragment thereof that targets an A2R. In some embodiments, the additional agent is an A2R antagonist described in, e.g., Ohta et al., Proc Natl Acad Sci USA (2006) 103:13132-13137; Jin et al., Cancer Res. (2010) 70(6):2245-2255; Leone et al., Computational and Structural Biotechnology Journal (2015) 13:265-272; Beavis et al., Proc Natl Acad Sci USA (2013) 110:14711-14716; and Pinna, A., Expert Opin Investig Drugs (2009) 18:1619-1631; Sitkovsky et al., Cancer Immunol Res (2014) 2(7):598-605; U.S. Pat. Nos. 8,080, 554; 8,716,301; US 20140056922; WO2008/147482; U.S. Pat. No. 8,883,500; US 20140377240; WO02/055083; U.S. Pat. Nos. 7,141,575; 7,405,219; 8,883,500; 8,450,329 and 8,987,279).

In some embodiments, the antagonist is an antisense molecule, inhibitory nucleic acid molecule (e.g., small inhibitory RNA (siRNA)) or catalytic nucleic acid molecule (e.g. a ribozyme) that specifically binds mRNA encoding an adenosine receptor. In some embodiments, the antisense molecule, inhibitory nucleic acid molecule or catalytic nucleic acid molecule binds nucleic acids encoding A2a, A2b, or A3. In some embodiments, an antisense molecule, inhibitory nucleic acid molecule or catalytic nucleic acid targets biochemical pathways downstream of the adenosine receptor. For example, the antisense molecule or catalytic nucleic acid can inhibit an enzyme involved in the Gs protein- or Gi protein-dependent intracellular pathway. In some embodiments, the additional agent includes dominant negative mutant form of an adenosine receptor, such as A2a, A2b, or A3.

In some embodiments, the additional agent that inhibits extracellular adenosine includes agents that render extracellular adenosine non-functional (or decrease such function), such as a substance that modifies the structure of adenosine to inhibit the ability of adenosine to signal through adenosine receptors. In some embodiments, the additional agent is an extracellular adenosine-generating or adenosine-degrading enzyme, a modified form thereof or a modulator thereof. For example, in some embodiments, the additional agent is an enzyme (e.g. adenosine deaminase) or another catalytic molecule that selectively binds and destroys the adenosine, thereby abolishing or significantly decreasing the ability of endogenously formed adenosine to signal through adenosine receptors and terminate inflammation.

In some embodiments, the additional agent is an adenosine deaminase (ADA) or a modified form thereof, e.g., recombinant ADA and/or polyethylene glycol-modified ADA (ADA-PEG), which can inhibit local tissue accumulation of extracellular adenosine. ADA-PEG has been used in treatment of patients with ADA SCID (Hershfield (1995) Hum Mutat. 5:107). In some embodiments, an agent that inhibits extracellular adenosine includes agents that prevent or decrease formation of extracellular adenosine, and/or prevent or decrease the accumulation of extracellular adenosine, thereby abolishing, or substantially decreasing, the immunosuppressive effects of adenosine. In some embodiments, the additional agent specifically inhibits enzymes and proteins that are involved in regulation of synthesis and/or secretion of pro-inflammatory molecules, including modulators of nuclear transcription factors. Suppression of adenosine receptor expression or expression of the Gs protein- or Gi protein-dependent intracellular pathway, or the cAMP dependent intracellular pathway, can result in an increase/enhancement of immune response.

In some embodiments, the additional agent can target ectoenzymes that generate or produce extracellular adenosine. In some embodiments, the additional agent targets CD39 and CD73 ectoenzymes, which function in tandem to generate extracellular adenosine. CD39 (also called ectonucleoside triphosphate diphosphohydrolase) converts extracellular ATP (or ADP) to 5'AMP. Subsequently, CD73 (also called 5'nucleotidase) converts 5'AMP to adenosine. The activity of CD39 is reversible by the actions of NDP kinase and adenylate kinase, whereas the activity of CD73 is irreversible. CD39 and CD73 are expressed on tumor stromal cells, including endothelial cells and Tregs, and also on many cancer cells. For example, the expression of CD39 and CD73 on endothelial cells is increased under the hypoxic conditions of the tumor microenvironment. Tumor hypoxia can result from inadequate blood supply and disorganized tumor vasculature, impairing delivery of oxygen (Carroll and Ashcroft (2005), Expert. Rev. Mol. Med. 7(6): 1-16). Hypoxia also inhibits adenylate kinase (AK), which converts adenosine to AMP, leading to very high extracellular adenosine concentration. Thus, adenosine is released at high concentrations in response to hypoxia, which is a condition that frequently occurs the tumor microenvironment (TME), in or around solid tumors. In some embodiments, the additional agent is one or more of anti-CD39 antibody or antigen binding fragment thereof, anti-CD73 antibody or antigen binding fragment thereof, e.g., MEDI9447 or TY/23, α-β-methylene-adenosine diphosphate (ADP), ARL 67156, POM-3, IPH52 (see, e.g., Allard et al. Clin Cancer Res (2013) 19(20):5626-5635; Hausler et al., Am J Transl Res (2014) 6(2):129-139; Zhang, B., Cancer Res. (2010) 70(16):6407-6411).

In some embodiments, the additional agent is an inhibitor of hypoxia inducible factor 1 alpha (HIF-1a) signaling. Exemplary inhibitors of HIF-la include digoxin, acriflavine, sirtuin-7 and ganetespib.

In some embodiments, the additional agent includes a protein tyrosine phosphatase inhibitor, e.g., a protein tyrosine phosphatase inhibitor described herein. In some embodiments, the protein tyrosine phosphatase inhibitor is an SHP-1 inhibitor, e.g., an SHP-1 inhibitor described herein, such as, e.g., sodium stibogluconate. In some embodiments, the protein tyrosine phosphatase inhibitor is an SHP-2 inhibitor, e.g., an SHP-2 inhibitor described herein.

In some embodiments, the additional agent is a kinase inhibitor. Kinase inhibitors, such as a CDK4 kinase inhibitor, a BTK kinase inhibitor, a MNK kinase inhibitor, or a DGK kinase inhibitor, can regulate the constitutively active survival pathways that exist in tumor cells and/or modulate the function of immune cells. In some embodiments, the kinase inhibitor is a Bruton's tyrosine kinase (BTK) inhibitor, e.g., ibrutinib. In some embodiments, the kinase inhibitor is a phosphatidylinositol-4,5-bisphosphate 3-kinase (PI3K) inhibitor. In some embodiments, the kinase inhibitor is a CDK4 inhibitor, e.g., a CDK4/6 inhibitor. In some embodiments, the kinase inhibitor is an mTOR inhibitor, such as, e.g., rapamycin, a rapamycin analog, OSI-027. The mTOR inhibitor can be, e.g., an mTORC1 inhibitor and/or an mTORC2 inhibitor, e.g., an mTORC1 inhibitor and/or mTORC2 inhibitor. In some embodiments, the kinase inhibitor is an MNK inhibitor, or a dual PI3K/mTOR inhibitor. In some embodiments, other exemplary kinase inhibitors include the AKT inhibitor perifosine, the mTOR inhibitor temsirolimus, the Src kinase inhibitors dasatinib and fostamatinib, the JAK2 inhibitors pacritinib and ruxolitinib, the PKCβ inhibitors enzastaurin and bryostatin, and the AAK inhibitor alisertib.

In some embodiments, the kinase inhibitor is a BTK inhibitor selected from ibrutinib (PCI-32765); GDC-0834; RN-486; CGI-560; CGI-1764; HM-71224; CC-292; ONO-4059; CNX-774; and LFM-A13. In some embodiments, the BTK inhibitor does not reduce or inhibit the kinase activity of interleukin-2-inducible kinase (ITK), and is selected from GDC-0834; RN-486; CGI-560; CGI-1764; HM-71224; CC-292; ONO-4059; CNX-774; and LFM-A13.

In some embodiments, the kinase inhibitor is a BTK inhibitor, e.g., ibrutinib (1-[(3R)-3-[4-Amino-3-(4-phenoxyphenyl)-1H-pyrazolo[3,4-d]pyrimidin-1-yl]piperidin-1-yl] prop-2-en-1-one; also known as PCI-32765). In some embodiments, the kinase inhibitor is a BTK inhibitor, e.g., ibrutinib (PCI-32765). In some embodiments, 1, 2, 3, 4, 5, 6, 7, 8, 9, 10, 11, 12 or more cycles of ibrutinib are administered. In some embodiments, the BTK inhibitor is a BTK inhibitor described in International Application WO 2015/079417.

In some embodiments, the kinase inhibitor is a PI3K inhibitor. PI3K is central to the PI3K/Akt/mTOR pathway involved in cell cycle regulation and lymphoma survival. Exemplary PI3K inhibitor includes idelalisib (PI3Kδ inhibitor). In some embodiments, the additional agent is idelalisib and rituximab.

In some embodiments, the additional agent is an inhibitor of mammalian target of rapamycin (mTOR). In some embodiments, the kinase inhibitor is an mTOR inhibitor selected from temsirolimus; ridaforolimus (also known as AP23573 and MK8669); everolimus (RAD001); rapamycin (AY22989); simapimod; AZD8055; PF04691502; SF1126; and XL765. In some embodiments, the additional agent is an inhibitor of mitogen-activated protein kinase (MAPK), such as vemurafenib, dabrafenib, and trametinib.

In some embodiments, the additional agent is an agent that regulates pro- or anti-apoptotic proteins. In some embodiments, the additional agent includes a B-cell lymphoma 2 (BCL-2) inhibitor (e.g., venetoclax, also called ABT-199 or GDC-0199; or ABT-737). Venetoclax is a small molecule (4-(4-{[2-(4-Chlorophenyl)-4,4-dimethyl-1-cyclohexen-1-yl]methyl}-1-piperazinyl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide) that inhibits the anti-apoptotic protein, BCL-2. Other agents that modulate pro- or anti-apoptotic protein include BCL-2 inhibitor ABT-737, navitoclax (ABT-263); Mcl-1 siRNA or Mcl-1 inhibitor retinoid N-(4-hydroxyphenyl) retinamide (4-HPR) for maximal efficacy. In some embodiments, the additional agent provides a pro-apoptotic stimuli, such as recombinant tumor necrosis factor-related apoptosis-inducing ligand (TRAIL), which can activate the apoptosis pathway by binding to TRAIL death receptors DR-4 and DR-5 on tumor cell surface, or TRAIL-R2 agonistic antibodies.

In some embodiments, the additional agent includes an indoleamine 2,3-dioxygenase (IDO) inhibitor. IDO is an enzyme that catalyzes the degradation of the amino acid, L-tryptophan, to kynurenine. Many cancers overexpress IDO, e.g., prostatic, colorectal, pancreatic, cervical, gastric, ovarian, head, and lung cancer. Plasmacytoid dendritic cells (pDCs), macrophages, and dendritic cells (DCs) can express IDO. In some aspects, a decrease in L-tryptophan (e.g., catalyzed by IDO) results in an immunosuppressive milieu by inducing T-cell anergy and apoptosis. Thus, in some aspects, an IDO inhibitor can enhance the efficacy of the binding molecules (e.g., ROR1-binding molecules), recombinant receptors, cells and/or compositions described herein, e.g., by decreasing the suppression or death of the administered CAR-expressing cell. Exemplary inhibitors of IDO include but are not limited to 1-methyl-tryptophan, indoximod, and INCB024360 (epacadostat).

In some embodiments, the additional agent includes a cytotoxic agent, e.g., CPX-351 (Celator Pharmaceuticals), cytarabine, daunorubicin, vosaroxin (Sunesis Pharmaceuticals), sapacitabine (Cyclacel Pharmaceuticals), idarubicin, or mitoxantrone. In some embodiments, the additional agent includes a hypomethylating agent, e.g., a DNA methyltransferase inhibitor, e.g., azacitidine or decitabine.

In another embodiment, the additional therapy is a transplantation, e.g., allogeneic stem cell transplant.

In some embodiments, the additional therapy is a lymphodepleting therapy. In some embodiments, lymphodepletion is performed on a subject, e.g., prior to administering engineered cells, e.g., CAR-expressing cells. In some embodiments, the lymphodepletion comprises administering one or more of melphalan, Cytoxan, cyclophosphamide, and fludarabine. In some embodiments, a lymphodepleting chemotherapy is administered to the subject prior to, concurrently with, or after administration (e.g., infusion) of engineered cells, e.g., CAR-expressing cells. In an example, the lymphodepleting chemotherapy is administered to the subject prior to administration of engineered cells, e.g., CAR-expressing cells.

In some embodiments, the additional agent is an oncolytic virus. In some embodiments, oncolytic viruses are capable of selectively replicating in and triggering the death of or slowing the growth of a cancer cell. In some cases, oncolytic viruses have no effect or a minimal effect on non-cancer cells. An oncolytic virus includes but is not limited to an oncolytic adenovirus, oncolytic Herpes Simplex Viruses, oncolytic retrovirus, oncolytic parvovirus, oncolytic vaccinia virus, oncolytic Sinbis virus, oncolytic influenza virus, or oncolytic RNA virus (e.g., oncolytic reovirus, oncolytic Newcastle Disease Virus (NDV), oncolytic measles virus, or oncolytic vesicular stomatitis virus (VSV)).

Other exemplary combination therapy, treatment and/or agents include anti-allergenic agents, anti-emetics, analgesics and adjunct therapies. In some embodiments, the additional agent includes cytoprotective agents, such as neuroprotectants, free-radical scavengers, cardioprotectors, anthracycline extravasation neutralizers and nutrients.

In some embodiments, an antibody used as an additional agent is conjugated or otherwise bound to a therapeutic agent, e.g., a chemotherapeutic agent (e.g., Cytoxan, fludarabine, histone deacetylase inhibitor, demethylating agent, peptide vaccine, anti-tumor antibiotic, tyrosine kinase inhibitor, alkylating agent, anti-microtubule or anti-mitotic agent), anti-allergic agent, anti-nausea agent (or anti-emetic), pain reliever, or cytoprotective agent described herein. In some embodiments, the additional agent is an antibody-drug conjugate.

In some embodiments, the additional agent can modulate, inhibit or stimulate particular factors at the DNA, RNA or protein levels, to enhance or boost the efficacy of the binding molecules (e.g., ROR1-binding molecules), recombinant receptors, cells and/or compositions provided herein. In some embodiments, the additional agent can modulate the factors at the nucleic acid level, e.g., DNA or RNA, within the administered cells, e.g., cells engineered to express recombinant receptors, e.g., CAR. In some embodiments, an inhibitory nucleic acid, e.g., an inhibitory nucleic acid, e.g., a dsRNA, e.g., an siRNA or shRNA, or a clustered regularly interspaced short palindromic repeats (CRISPR), a transcription-activator like effector nuclease (TALEN), or a zinc finger endonuclease (ZFN), can be used to inhibit expression of an inhibitory molecule in the engineered cell, e.g., CAR-expressing cell. In some embodiments the inhibitor is an shRNA. In some embodiments, the inhibitory molecule is inhibited within the engineered cell, e.g., CAR-expressing cell. In some embodiments, a nucleic acid molecule that encodes a dsRNA molecule that inhibits expression of the molecule that modulates or regulates, e.g., inhibits, T-cell function is operably linked to a promoter, e.g., a HI- or a U6-derived promoter such that the dsRNA molecule that inhibits expression of the inhibitory molecule is expressed within the engineered cell, e.g., CAR-expressing cell. See, e.g., Brummelkamp T R, et al. (2002) Science 296: 550-553; Miyagishi M, et al. (2002) Nat. Biotechnol. 19: 497-500.

In some embodiments, the additional agent is capable of disrupting the gene encoding an inhibitory molecule, such as any immune checkpoint inhibitors described herein. In some embodiments, disruption is by deletion, e.g., deletion of an entire gene, exon, or region, and/or replacement with an exogenous sequence, and/or by mutation, e.g., frameshift or missense mutation, within the gene, typically within an exon of the gene. In some embodiments, the disruption results in a premature stop codon being incorporated into the gene, such that the inhibitory molecule is not expressed or is not expressed in a form that is capable of being expressed on the cells surface and/or capable of mediating cell signaling. The disruption is generally carried out at the DNA level. The disruption generally is permanent, irreversible, or not transient.

In some aspects, the disruption is carried out by gene editing, such as using a DNA binding protein or DNA-binding nucleic acid, which specifically binds to or hybridizes to the gene at a region targeted for disruption. In some aspects, the protein or nucleic acid is coupled to or complexed with a nuclease, such as in a chimeric or fusion protein. For example, in some embodiments, the disruption is effected using a fusion comprising a DNA-targeting protein and a nuclease, such as a Zinc Finger Nuclease (ZFN) or TAL-effector nuclease (TALEN), or an RNA-guided nuclease such as a clustered regularly interspersed short palindromic nucleic acid (CRISPR)-Cas system, such as CRISPR-Cas9 system, specific for the gene being disrupted. In some embodiments, methods of producing or generating genetically engineered cells, e.g., CAR-expressing cells, include introducing into a population of cells nucleic acid molecules encoding a genetically engineered antigen receptor (e.g. CAR) and nucleic acid molecules encoding an agent targeting an inhibitory molecule that is a gene editing nuclease, such as a fusion of a DNA-targeting protein and a nuclease such as a ZFN or a TALEN, or an RNA-guided nuclease such as of the CRISPR-Cas9 system, specific for an inhibitory molecule.

Any of the additional agents described herein can be prepared and administered as combination therapy with the ROR1-binding molecule (e.g., antibody), immunoconjugate, recombinant receptor (e.g., chimeric antigen receptor) and/or engineered cells expressing said molecules (e.g., recombinant receptor) described herein, such as in pharmaceutical compositions comprising one or more agents of the combination therapy and a pharmaceutically acceptable carrier, such as any described herein. In some embodiments, the ROR1-binding molecule (e.g., antibody), immunoconjugate, recombinant receptor (e.g., chimeric antigen receptor), engineered cells expressing said molecules (e.g., recombinant receptor), plurality of engineered cells expressing said molecules (e.g., recombinant receptor) can be administered simultaneously, concurrently or sequentially, in any order with the additional agents, therapy or treatment, wherein such administration provides therapeutically effective levels each of the agents in the body of the subject. The agents can be co-administered with the binding molecules (e.g., ROR1-binding molecules), recombinant receptors, cells and/or compositions described herein, for example, as part of the same pharmaceutical composition or using the same method of delivery. In some embodiments, the additional agent is incubated with the engineered cell, e.g., CAR-expressing cells, prior to administration of the cells.

In some examples, the one or more additional agents are administered subsequent to or prior to the administration of the binding molecules (e.g., ROR1-binding molecules), recombinant receptors, cells and/or compositions described herein, separated by a selected time period. In some examples, the time period is 1 day, 2 days, 3 days, 4 days, 5 days, 6 days, 1 week, 2 weeks, 3 weeks, 1 month, 2 months, or 3 months. In some examples, the one or more additional agents are administered multiple times and/or the binding molecules (e.g., ROR1-binding molecules), recombinant receptors, cells and/or compositions described herein, is administered multiple times. For example, in some embodiments, the additional agent is administered prior to the binding molecules (e.g., ROR1-binding molecules), recombinant receptors, cells and/or compositions described herein, e.g., two weeks, 12 days, 10 days, 8 days, one week, 6 days, 5 days, 4 days, 3 days, 2 days or 1 day before the administration. For example, in some embodiments, the additional agent is administered after the binding molecules (e.g., ROR1-binding molecules), recombinant receptors, cells and/or compositions described herein, e.g., two weeks, 12 days, 10 days, 8 days, one week, 6 days, 5 days, 4 days, 3 days, 2 days or 1 day after the administration.

The dose of the additional agent can be any therapeutically effective amount, e.g., any dose amount described herein, and the appropriate dosage of the additional agent may depend on the type of disease to be treated, the type, dose and/or frequency of the binding molecule, recombinant receptor, cell and/or composition administered, the severity and course of the disease, whether the binding molecule, recombinant receptor, cell and/or composition is administered for preventive or therapeutic purposes, previous therapy, the patient's clinical history and response to the binding molecule, recombinant receptor, cell and/or composition, and the discretion of the attending physician. The binding molecule, recombinant receptor, cell and/or composition and/or the additional agent and/or therapy can be administered to the patient at one time, repeated or administered over a series of treatments.

C. Diagnostic and Detection Methods

Also provided are methods involving use of the provided binding molecules, e.g., antibodies or antigen-binding fragments thereof, in detection of ROR1, for example, in diagnostic and/or prognostic methods in association with a ROR1-expressing disease or condition. The methods in some embodiments include incubating a biological sample with the antibody or antigen-binding fragment thereof and/or administering the antibody or antigen-binding fragment thereof to a subject. In certain embodiments, a biological sample includes a cell or tissue, such as tumor or cancer tissue. In certain embodiments, the contacting is under conditions permissive for binding of the anti-ROR1 antibody to ROR1, and detecting whether a complex is formed between the anti-ROR1 antibody and ROR1. Such a method may be an in vitro or in vivo method. In one embodiment, an anti-ROR1 antibody (e.g., antigen-binding fragment) is used to select subjects eligible for therapy with an anti-ROR1 antibody (e.g., antigen-binding fragment) or recombinant receptor, e.g. where ROR1 is a biomarker for selection of patients.

In some embodiments, a sample, such as a cell, tissue sample, lysate, composition, or other sample derived therefrom is contacted with the anti-ROR1 antibody (e.g., antigen-binding fragment) and binding or formation of a complex between the antibody and the sample (e.g., ROR1 in the sample) is determined or detected. When binding in the test sample is demonstrated or detected as compared to a reference cell of the same tissue type, it may indicate the presence of an associated disease or condition. In some embodiments, the sample is from human tissues.

Various known methods for detecting specific antibody-antigen binding can be used. Exemplary immunoassays include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radio-immunoassay (RIA). An indicator moiety, or label group, can be attached to the subject antibodies and is selected so as to meet the needs of various uses of the method which are often dictated by the availability of assay equipment and compatible immunoassay procedures. Exemplary labels include radionuclides (e.g. $^{125}$I, $^{131}$I, $^{35}$S, $^{3}$H, or $^{32}$P), enzymes (e.g., alkaline phosphatase, horseradish peroxidase, luciferase, or β-galactosidase), fluorescent moieties or proteins (e.g., fluorescein, rhodamine, phycoerythrin, GFP, or BFP), or luminescent moieties (e.g., Qdot™ nanoparticles supplied by the Quantum Dot Corporation, Palo Alto, CA). General techniques to be used in performing the various immunoassays noted above are known to those of ordinary skill in the art.

For purposes of diagnosis, the antibodies (e.g., antigen-binding fragments) can be labeled with a detectable moiety including but not limited to radioisotopes, fluorescent labels, and various enzyme-substrate labels know in the art. Methods of conjugating labels to an antibody are known.

In some embodiments, antibodies (e.g., antigen-binding fragments) need not be labeled, and the presence thereof can be detected using a labeled antibody which binds to the antibodies.

The provided antibodies (e.g., antigen-binding fragments) in some embodiments can be employed in any known assay method, such as competitive binding assays, direct and indirect sandwich assays, and immunoprecipitation assays. Zola, Monoclonal Antibodies: A Manual of Techniques, pp. 147-158 (CRC Press, Inc. 1987).

The antibodies (e.g., antigen-binding fragments) and polypeptides can also be used for in vivo diagnostic assays, such as in vivo imaging. Generally, the antibody is labeled with a radionuclide (such as $^{111}$In, $^{99}$Tc, $^{14}$C, $^{131}$I, $^{125}$I, or $^{3}$H) so that the cells or tissue of interest can be localized in vivo following administration to a subject.

The antibody (e.g., antigen-binding fragment) may also be used as staining reagent in pathology, e.g., using known techniques.

V. Articles of Manufacture or Kits

Also provided are articles of manufacture or kit containing the provided binding molecules (e.g., antibodies), recombinant receptors (e.g., CARs), genetically engineered cells, and/or compositions comprising the same. The articles of manufacture may include a container and a label or package insert on or associated with the container. Suitable containers include, for example, bottles, vials, syringes, test tubes, IV solution bags, etc. The containers may be formed from a variety of materials such as glass or plastic. In some embodiments, the container has a sterile access port. Exemplary containers include an intravenous solution bags, vials, including those with stoppers pierceable by a needle for injection. The article of manufacture or kit may further include a package insert indicating that the compositions can be used to treat a particular condition such as a condition described herein (e.g., ROR1-expressing cancer). Alternatively, or additionally, the article of manufacture or kit may further include another or the same container comprising a pharmaceutically-acceptable buffer. It may further include other materials such as other buffers, diluents, filters, needles, and/or syringes.

The label or package insert may indicate that the composition is used for treating the ROR1-expressing or ROR1-associated disease, disorder or condition in an individual. The label or a package insert, which is on or associated with the container, may indicate directions for reconstitution and/or use of the formulation. The label or package insert may further indicate that the formulation is useful or intended for subcutaneous, intravenous, or other modes of administration for treating or preventing a ROR1-expressing or ROR1-associated disease, disorder or condition in an individual. In some aspects, the label or package insert can include instructions for use, for example instructions for administering the antibody or antigen-binding fragment thereof, the single chain cell surface protein, the conjugate, the chimeric antigen receptor, the cell or the composition, in some aspects in accord with any of the methods or uses described herein.

The container in some embodiments holds a composition which is by itself or combined with another composition effective for treating, preventing and/or diagnosing the condition. The article of manufacture or kit may include (a) a first container with a composition contained therein (i.e., first medicament), wherein the composition includes the antibody (e.g., anti-ROR1 antibody) or antigen-binding fragment thereof or recombinant receptor (e.g., CAR); and (b) a second container with a composition contained therein (i.e., second medicament), wherein the composition includes a further agent, such as a cytotoxic or otherwise therapeutic agent, and which article or kit further comprises instructions on the label or package insert for treating the subject with the second medicament, in an effective amount.

VI. Definitions

As used herein, reference to a "corresponding form" of an antibody means that when comparing a property or activity of two antibodies, the property is compared using the same form of the antibody. For example, if it is stated that an antibody has greater activity compared to the activity of the corresponding form of a first antibody, that means that a particular form, such as an scFv of that antibody, has greater activity compared to the scFv form of the first antibody.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, MD, 1991.

The terms "full length antibody," "intact antibody," and "whole antibody" are used herein interchangeably to refer to an antibody having a structure substantially similar to a native antibody structure or having heavy chains that contain an Fc region as defined herein.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., J. Chromatogr. B 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-ROR1 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

As used herein, "percent (%) amino acid sequence identity" and "percent identity" and "sequence identity" when used with respect to an amino acid sequence (reference polypeptide sequence) is defined as the percentage of amino acid residues in a candidate sequence (e.g., the subject antibody or fragment) that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software.

Those skilled in the art can determine appropriate parameters for aligning sequences, including any algorithms needed to achieve maximal alignment over the full length of the sequences being compared.

An amino acid substitution may include replacement of one amino acid in a polypeptide with another amino acid. The substitution may be a conservative amino acid substitution or a non-conservative amino acid substitution. Amino acid substitutions may be introduced into a binding molecule, e.g., antibody, of interest and the products screened for a desired activity, e.g., retained/improved antigen binding, decreased immunogenicity, or improved ADCC or CDC.

Amino acids generally can be grouped according to the following common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

In some embodiments, conservative substitutions can involve the exchange of a member of one of these classes for another member of the same class. In some embodiments, non-conservative amino acid substitutions can involve exchanging a member of one of these classes for another class.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "package insert" is used to refer to instructions customarily included in commercial packages of therapeutic products, that contain information about the indications, usage, dosage, administration, combination therapy, contraindications and/or warnings concerning the use of such therapeutic products.

As used herein, the singular forms "a," "an," and "the" include plural referents unless the context clearly dictates otherwise. For example, "a" or "an" means "at least one" or "one or more." It is understood that aspects, embodiments, and variations described herein include "comprising," "consisting," and/or "consisting essentially of" aspects, embodiments and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

As used herein, a "composition" refers to any mixture of two or more products, substances, or compounds, including cells. It may be a solution, a suspension, liquid, powder, a paste, aqueous, non-aqueous or any combination thereof.

As used herein, a statement that a cell or population of cells is "positive" for a particular marker refers to the detectable presence on or in the cell of a particular marker, typically a surface marker. When referring to a surface marker, the term refers to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker.

As used herein, a statement that a cell or population of cells is "negative" for a particular marker refers to the absence of substantial detectable presence on or in the cell of a particular marker, typically a surface marker. When referring to a surface marker, the term refers to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

VII. Exemplary Embodiments

Among the provided embodiments are:
1. An anti-ROR1 antibody or antigen-binding fragment thereof, comprising: a heavy chain variable ($V_H$) region, and a light chain variable ($V_L$) region, wherein the $V_H$ region comprises a heavy chain complementarity determining region 1 (CDR-H1) comprising the sequence set forth in SEQ ID NO: 67, 82 or 52, a heavy chain complementarity determining region 2 (CDR-H2) comprising the sequence set forth in SEQ ID NO: 71, 86, 56 or 97, and a heavy chain complementarity determining region 3 (CDR-H3) comprising the sequence set forth in SEQ ID NO: 73, 88, 58 or 99, and the V_L region comprises a light chain complementarity determining region 1 (CDR-L1) comprising the sequence set forth in SEQ ID NO: 75, 90 or 60, a light chain complementarity determining region 2 (CDR-L2) comprising the sequence set forth in SEQ ID NO: 77, 92 or 62; and a light chain complementarity determining region 3 (CDR-L3) comprising the sequence set forth in SEQ ID NO: 79, 94 or 64.

2. An anti-ROR1 antibody or antigen-binding fragment thereof, comprising: a heavy chain variable (V_H) region, and a light chain variable (V_L) region, wherein the V_H region comprises a heavy chain complementarity determining region 1 (CDR-H1), a heavy chain complementarity determining region 2 (CDR-H2) and a heavy chain complementarity determining region 3 (CDR-H3) comprising the sequence set forth in SEQ ID NOS:67, 71 and 73, respectively, and the V_L region comprises a light chain complementarity determining region 1 (CDR-L1), a light chain complementarity determining region 2 (CDR-L2) and a light chain complementarity determining region 3 (CDR-L3) comprising the sequence set forth in SEQ ID NOS:75, 77 and 79, respectively;

the V_H region comprises a CDR-H1, a CDR-H2 and a CDR-H3 comprising the sequence set forth in SEQ ID NOS:82, 86 and 88, respectively, and the V_L region comprises a CDR-L1, a CDR-L2 and a CDR-L3 comprising the sequence set forth in SEQ ID NOS:90, 92 and 94, respectively;

the V_H region comprises a CDR-H1, a CDR-H2 and a CDR-H3 comprising the sequence set forth in SEQ ID NOS:52, 56 and 58, respectively, and the V_L region comprises a CDR-L1, a CDR-L2 and a CDR-L3 comprising the sequence set forth in SEQ ID NOS:60, 62 and 64, respectively; or the V_H region comprises a CDR-H1, a CDR-H2 and a CDR-H3 comprising the sequence set forth in SEQ ID NOS:52, 97 and 99, respectively, and the V_L region comprises a CDR-L1, a CDR-L2 and a CDR-L3 comprising the sequence set forth in SEQ ID NOS:60, 62 and 64, respectively.

3. The anti-ROR1 antibody or antigen-binding fragment thereof of embodiment 1 or embodiment 2, wherein the V_H region comprises a CDR-H1, a CDR-H2 and a CDR-H3 comprising the sequence set forth in SEQ ID NOS:67, 71 and 73, respectively, and the V_L region comprises a CDR-L1, a CDR-L2 and a CDR-L3 comprising the sequence set forth in SEQ ID NOS:75, 77 and 79, respectively.

4. The anti-ROR1 antibody or antigen-binding fragment thereof of embodiment 1 or embodiment 2, wherein the V_H region comprises a CDR-H1, a CDR-H2 and a CDR-H3 comprising the sequence set forth in SEQ ID NOS:82, 86 and 88, respectively, and the V_L region comprises a CDR-L1, a CDR-L2 and a CDR-L3 comprising the sequence set forth in SEQ ID NOS:90, 92 and 94, respectively.

5. An anti-ROR1 antibody or antigen-binding fragment thereof, comprising: a heavy chain variable (V_H) region and a light chain variable (V_L) region, wherein:

the V_H region comprises a heavy chain complementarity determining region 1 (CDR-H1), a heavy chain complementarity determining region 2 (CDR-H2) and a heavy chain complementarity determining region 3 (CDR-H3) contained within SEQ ID NO: 112, 121, 103 or 130, and the V_L region comprises a light chain complementarity determining region 1 (CDR-L1), a light chain complementarity determining region 2 (CDR-L2) and a light chain complementarity determining region 3 (CDR-L3) contained within SEQ ID NO: 115, 124 or 106.

6. An anti-ROR1 antibody or antigen-binding fragment thereof, comprising: a heavy chain variable (V_H) region and a light chain variable (V_L) region, wherein:

the V_H region comprises a heavy chain complementarity determining region 1 (CDR-H1), a heavy chain complementarity determining region 2 (CDR-H2) and a heavy chain complementarity determining region 3 (CDR-H3) contained within SEQ ID NO:112, and the V_L region comprises a light chain complementarity determining region 1 (CDR-L1), a light chain complementarity determining region 2 (CDR-L2) and a light chain complementarity determining region 3 (CDR-L3) contained within SEQ ID NO:115;

the V_H region comprises a CDR-H1, a CDR-H2 and a CDR-H3 contained within SEQ ID NO:121, and the V_L region comprises a CDR-L1, a CDR-L2 and a CDR-L3 contained within SEQ ID: NO 124;

the V_H region comprises a CDR-H1, a CDR-H2 and a CDR-H3 contained within SEQ ID NO:103, and the V_L region comprises a CDR-L1, a CDR-L2 and a CDR-L3 contained within SEQ ID: NO 106; or the V_H region comprises a CDR-H1, a CDR-H2 and a CDR-H3 contained within SEQ ID NO:130, and the V_L region comprises a CDR-L1, a CDR-L2 and a CDR-L3 contained within SEQ ID: NO 106.

7. The anti-ROR1 antibody or antigen-binding fragment thereof of embodiment 5 or embodiment 6, wherein the V_H region comprises a CDR-H1, a CDR-H2 and a CDR-H3 contained within SEQ ID NO:112, and the V_L region comprises a CDR-L1, a CDR-L2 and a CDR-L3 contained within SEQ ID: NO 115.

8. The anti-ROR1 antibody or antigen-binding fragment thereof of embodiment 5 or embodiment 6, wherein the V_H region comprises a CDR-H1, a CDR-H2 and a CDR-H3 contained within SEQ ID NO:121, and the V_L region comprises a CDR-L1, a CDR-L2 and a CDR-L3 contained within SEQ ID: NO 124.

9. The anti-ROR1 antibody or antigen-binding fragment thereof of any of embodiments 1, 2, 5 and 6, wherein:

the V_H region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO: 112, 121, 103 or 130, and the V_L region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO: 115, 124 or 106.

10. The anti-ROR1 antibody or antigen-binding fragment thereof of any of embodiments 1, 2, and 5-7, wherein:

the V_H region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:112, and the V_L region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO: 115;

the V_H region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:121, and the V_L region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:124;

the $V_H$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:103, and the $V_L$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:106; or the $V_H$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:130, and the $V_L$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:106.

11. The anti-ROR1 antibody or antigen-binding fragment thereof of any of embodiments 1-10, wherein the $V_H$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:112, and the $V_L$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO: 115.

12. The anti-ROR1 antibody or antigen-binding fragment thereof of any of embodiments 1-10, wherein the $V_H$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:121, and the $V_L$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:124.

13. An anti-ROR1 antibody or antigen-binding fragment thereof, comprising: a heavy chain variable ($V_H$) region and a light chain variable ($V_L$) region, wherein:

the $V_H$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO: 112, 121, 103 or 130, and the $V_L$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO: 115, 124 or 106.

14. An anti-ROR1 antibody or antigen-binding fragment thereof, comprising: a heavy chain variable ($V_H$) region and a light chain variable ($V_L$) region, wherein:

the $V_H$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:112, and the $V_L$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO: 115;

the $V_H$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:121, and the $V_L$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:124;

the $V_H$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:103, and the $V_L$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:106; or the $V_H$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:130, and the $V_L$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:106.

15. The anti-ROR1 antibody or antigen-binding fragment thereof of embodiment 13 or embodiment 14, wherein the $V_H$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:112, and the $V_L$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO: 115.

16. The anti-ROR1 antibody or antigen-binding fragment thereof of embodiment 13 or embodiment 14, wherein the $V_H$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:121, and the $V_L$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:124.

17. The anti-ROR1 antibody or antigen-binding fragment thereof of any of embodiments 1, 2, 5, 6, 9, 10, 13 and 14, wherein:

the $V_H$ region is or comprises the sequence set forth in SEQ ID NO: 112, 121, 103 or 130, and the $V_L$ region is or comprises the sequence set forth in SEQ ID NO: 115, 124 or 106.

18. The anti-ROR1 antibody or antigen-binding fragment thereof of any of embodiments 1, 2, 5, 6, 9, 10, 13, 14 and 17, wherein:

the $V_H$ region and the $V_L$ region are or comprise the sequence set forth in SEQ ID NOS: 112 and 115, respectively;

the $V_H$ region and the $V_L$ region are or comprise the sequence set forth in SEQ ID NOS: 121 and 124, respectively;

the $V_H$ region and the $V_L$ region are or comprise the sequence set forth in SEQ ID NOS: 103 and 106, respectively; or the $V_H$ region and the $V_L$ region are or comprise the sequence set forth in SEQ ID NOS: 130 and 106, respectively.

19. An anti-ROR1 antibody or antigen-binding fragment thereof, comprising: a heavy chain variable ($V_H$) region and a light chain variable ($V_L$) region, wherein:

the $V_H$ region is or comprises the sequence set forth in SEQ ID NO: 112, 121, 103 or 130, and the V$_L$ region is or comprises the sequence set forth in SEQ ID NO: 115, 124 or 106.

20. An anti-ROR1 antibody or antigen-binding fragment thereof, comprising: a heavy chain variable (V$_H$) region and a light chain variable (V$_L$) region, wherein:
the V$_H$ region and the V$_L$ region are or comprise the sequence set forth in SEQ ID NOS: 112 and 115, respectively;
the V$_H$ region and the V$_L$ region are or comprise the sequence set forth in SEQ ID NOS: 121 and 124, respectively;
the V$_H$ region and the V$_L$ region are or comprise the sequence set forth in SEQ ID NOS: 103 and 106, respectively; or
the V$_H$ region and the V$_L$ region are or comprise the sequence set forth in SEQ ID NOS: 130 and 106, respectively.

21. The anti-ROR1 antibody or antigen-binding fragment thereof of any of embodiments 1-20, wherein the V$_H$ region and the V$_L$ region are or comprise the sequence set forth in SEQ ID NOS: 112 and 115, respectively.

22. The anti-ROR1 antibody or antigen-binding fragment thereof of any of embodiments 1-20, wherein the V$_H$ region and the V$_L$ region are or comprise the sequence set forth in SEQ ID NOS:121 and 124, respectively.

23. The anti-ROR1 antibody or antigen-binding fragment thereof of any of embodiments 1, 2, 5, 6, 9, 10, 13, 14 and 17-20, wherein the V$_H$ region is or comprises the amino acid sequence encoded by SEQ ID NO: 110, 119, 101 or 128 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 110, 119, 101 or 128, and the V$_L$ region is or comprises the amino acid sequence encoded by SEQ ID NO: 113, 122 or 104, or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 113, 122 or 104.

24. The anti-ROR1 antibody or antigen-binding fragment thereof of any of embodiments 1, 2, 5, 6, 9, 10, 13, 14, 17-20 and 23, wherein the V$_H$ region is or comprises the amino acid sequence encoded by SEQ ID NO: 111, 120, 102 or 129, and the V$_L$ region is or comprises the amino acid sequence encoded by SEQ ID NO: 114, 123, 105 or 131.

25. The anti-ROR1 antibody or antigen-binding fragment thereof of any of embodiments 1-24, wherein the V$_H$ region is or comprises the amino acid sequence encoded by SEQ ID NO: 110 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 110, and the V$_L$ region is or comprises the amino acid sequence encoded by SEQ ID NO: 113, or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 113.

26. The anti-ROR1 antibody or antigen-binding fragment thereof of any of embodiments 1-25, wherein the V$_H$ region is or comprises the amino acid sequence encoded by SEQ ID NO: 111, and the V$_L$ region is or comprises the amino acid sequence encoded by SEQ ID NO: 114.

27. The anti-ROR1 antibody or antigen-binding fragment thereof of any of embodiments 1-24, wherein the V$_H$ region is or comprises the amino acid sequence encoded by SEQ ID NO: 119 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 119, and the V$_L$ region is or comprises the amino acid sequence encoded by SEQ ID NO: 122, or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 122.

28. The anti-ROR1 antibody or antigen-binding fragment thereof of any of embodiments 1-25, wherein the V$_H$ region is or comprises the amino acid sequence encoded by SEQ ID NO: 120, and the V$_L$ region is or comprises the amino acid sequence encoded by SEQ ID NO: 123.

29. The anti-ROR1 antibody or antigen-binding fragment thereof of any of embodiments 1-28, wherein said anti-ROR1 antibody or antigen-binding fragment thereof is isolated.

30. The anti-ROR1 antibody or antigen-binding fragment thereof of any of embodiments 1-29, wherein said anti-ROR1 antibody or antigen-binding fragment thereof is recombinant.

31. The anti-ROR1 antibody or antigen-binding fragment thereof of any of embodiments 1-30, wherein at least a portion of the V$_H$ region and the V$_L$ region is human or is from a human protein.

32. The anti-ROR1 antibody or antigen-binding fragment thereof of any of embodiments 1-31, wherein the antigen-binding fragment thereof comprises a single chain fragment, optionally a single chain Fv (scFv).

33. The anti-ROR1 antibody or antigen-binding fragment thereof of any of embodiments 1-32, wherein the V$_H$ region is amino-terminal to the V$_L$ region.

34. The anti-ROR1 antibody or antigen-binding fragment thereof of any of embodiments 1-32, wherein the V$_H$ region is carboxy-terminal to the V$_L$ region.

35. The anti-ROR1 antibody or antigen-binding fragment thereof of any of embodiments 1-34, when the V$_H$ region and the V$_L$ region are joined by a flexible linker.

36. The anti-ROR1 antibody or antigen-binding fragment thereof of embodiment 35, wherein the flexible linker comprises the sequence set forth in SEQ ID NO:41.

37. The anti-ROR1 antibody or antigen-binding fragment thereof of any of embodiments 32, 33, 35 and 36, wherein the scFv is or comprises the sequence set forth in SEQ ID NO: 118, 127, 109 or 134, or an amino acid sequence having at least at or about 85%, 86%, 87%, 88%, 89%, 90%, 91%, 92%, 93%, 94%, 95%, 96%, 97%, 98% or 99% sequence identity to SEQ ID NO: 118, 127, 109 or 134.

38. The anti-ROR1 antibody or antigen-binding fragment thereof of any of embodiments 32, 33 and 35-37, wherein the scFv is or comprises the sequence set forth in SEQ ID NO: 118.

39. The anti-ROR1 antibody or antigen-binding fragment thereof of any of embodiments 32, 33 and 35-37, wherein the scFv is or comprises the sequence set forth in SEQ ID NO: 127.

40. The anti-ROR1 antibody or antigen-binding fragment thereof of any of embodiments 32, 33 and 35-37, wherein the scFv is or comprises the amino acid sequence encoded by SEQ ID NO: 116, 125, 107 or 132 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 116, 125, 107 or 132.

41. The anti-ROR1 antibody or antigen-binding fragment thereof of any of embodiments 32, 33, 35-37 and 40, wherein the scFv is or comprises the amino acid sequence encoded by SEQ ID NO: 117, 126, 108 or 133.

42. The anti-ROR1 antibody or antigen-binding fragment thereof of any of embodiments 32-41, wherein the scFv is or comprises the amino acid sequence encoded by SEQ ID NO: 116 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 116.

43. The anti-ROR1 antibody or antigen-binding fragment thereof of any of embodiments 32-42, wherein the scFv is or comprises the amino acid sequence encoded by SEQ ID NO: 117.

44. The anti-ROR1 antibody or antigen-binding fragment thereof of any of embodiments 32-41, wherein the scFv is or comprises the amino acid sequence encoded by SEQ ID NO: 125 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 125.

45. The anti-ROR1 antibody or antigen-binding fragment thereof of any of embodiments 32-41 and 43, wherein the scFv is or comprises the amino acid sequence encoded by SEQ ID NO: 126.

46. The anti-ROR1 antibody or antigen-binding fragment thereof of any of embodiments 1-45, wherein the anti-ROR1 antibody or fragment further comprises at least a portion of an immunoglobulin constant region or a variant thereof.

47. The anti-ROR1 antibody or antigen-binding fragment thereof of embodiment 46, wherein the portion of an immunoglobulin constant region comprises at least a portion of a hinge region or a variant thereof.

48. The anti-ROR1 antibody or antigen-binding fragment thereof of embodiment 46 or embodiment 47, wherein the at least a portion of an immunoglobulin constant region or a variant thereof comprises at least a portion of a CH2 region and/or a CH3 region or a variant thereof.

49. The anti-ROR1 antibody or antigen-binding fragment thereof of any of embodiments 46-48, wherein the at least a portion of an immunoglobulin constant region or a variant thereof is human or from a human protein or a variant thereof.

50. The anti-ROR1 antibody or antigen-binding fragment thereof of any of embodiments 1-49, wherein said anti-ROR1 antibody or antigen-binding fragment thereof specifically binds to a Receptor tyrosine kinase-like orphan receptor 1 (ROR1) protein, optionally a human ROR1.

51. The anti-ROR1 antibody or antigen-binding fragment thereof of embodiment 50, wherein the human ROR1 protein comprises an amino acid sequence set forth in SEQ ID NO: 144, 145 or 146.

52. The anti-ROR1 antibody or antigen-binding fragment thereof of any of embodiments 1-51, wherein said anti-ROR1 antibody or antigen-binding fragment thereof does not bind to, is not cross-reactive to, or binds at a lower level or degree or affinity to a Receptor tyrosine kinase-like orphan receptor 2 (ROR2) protein, optionally a human ROR2.

53. The anti-ROR1 antibody or antigen-binding fragment thereof of any of embodiments 1-52, wherein the extent, level or degree or affinity of binding of said anti-ROR1 antibody or antigen-binding fragment thereof to a human ROR2 is at least at or about 75%, 80%, 90%, 95% or 99% less than the extent, level or degree or affinity of binding to a human ROR1.

54. A single chain cell-surface protein, comprising the anti-ROR1 antibody or antigen-binding fragment thereof of any of embodiments 1-53 and 244-265.

55. A conjugate, comprising the anti-ROR1 antibody or antigen-binding fragment thereof of any of embodiments 1-53 and 244-265 and a heterologous molecule or moiety.

56. The conjugate of embodiment 55, wherein the heterologous molecule or moiety is a therapeutic moiety.

57. An anti-ROR1 chimeric antigen receptor (CAR) comprising an extracellular antigen-binding domain comprising the anti-ROR1 antibody or antigen-binding fragment thereof of any of embodiments 1-53 and 244-265 and an intracellular signaling region.

58. An anti-ROR1 chimeric antigen receptor (CAR) comprising:
an extracellular antigen-binding domain comprising a heavy chain variable ($V_H$) region, and a light chain variable ($V_L$) region, and an intracellular signaling region, wherein the $V_H$ region comprises a heavy chain complementarity determining region 1 (CDR-H1) comprising the sequence set forth in SEQ ID NO: 67, 82 or 52, a heavy chain complementarity determining region 2 (CDR-H2) comprising the sequence set forth in SEQ ID NO: 71, 86, 56 or 97, and a heavy chain complementarity determining region 3 (CDR-H3) comprising the sequence set forth in SEQ ID NO: 73, 88, 58 or 99, and the $V_L$ region comprises a light chain complementarity determining region 1 (CDR-L1) comprising the sequence set forth in SEQ ID NO: 75, 90 or 60, a light chain complementarity determining region 2 (CDR-L2) comprising the sequence set forth in SEQ ID NO: 77, 92 or 62; and a light chain complementarity determining region 3 (CDR-L3) comprising the sequence set forth in SEQ ID NO: 79, 94 or 64.

59. An anti-ROR1 chimeric antigen receptor (CAR) comprising:
an extracellular antigen-binding domain comprising a heavy chain variable ($V_H$) region, and a light chain variable ($V_L$) region, and an intracellular signaling region, wherein the $V_H$ region comprises a heavy chain complementarity determining region 1 (CDR-H1), a heavy chain complementarity determining region 2 (CDR-H2) and a heavy chain complementarity determining region 3 (CDR-H3) comprising the sequence set forth in SEQ ID NOS:67, 71 and 73, respectively, and the $V_L$ region comprises a light chain complementarity determining region 1 (CDR-L1), a light chain complementarity determining region 2 (CDR-L2) and a light chain complementarity determining region 3 (CDR-L3) comprising the sequence set forth in SEQ ID NOS:75, 77 and 79, respectively;
the $V_H$ region comprises a CDR-H1, a CDR-H2 and a CDR-H3 comprising the sequence set forth in SEQ ID NOS:82, 86 and 88, respectively, and the $V_L$ region comprises a CDR-L1, a CDR-L2 and a CDR-L3 comprising the sequence set forth in SEQ ID NOS:90, 92 and 94, respectively;

the $V_H$ region comprises a CDR-H1, a CDR-H2 and a CDR-H3 comprising the sequence set forth in SEQ ID NOS:52, 56 and 58, respectively, and the $V_L$ region comprises a CDR-L1, a CDR-L2 and a CDR-L3 comprising the sequence set forth in SEQ ID NOS:60, 62 and 64, respectively; or the $V_H$ region comprises a CDR-H1, a CDR-H2 and a CDR-H3 comprising the sequence set forth in SEQ ID NOS:52, 97 and 99, respectively, and the $V_L$ region comprises a CDR-L1, a CDR-L2 and a CDR-L3 comprising the sequence set forth in SEQ ID NOS:60, 62 and 64, respectively.

60. The anti-ROR1 chimeric antigen receptor of embodiment 58 or embodiment 59, wherein the $V_H$ region comprises a CDR-H1, a CDR-H2 and a CDR-H3 comprising the sequence set forth in SEQ ID NOS:67, 71 and 73, respectively, and the $V_L$ region comprises a CDR-L1, a CDR-L2 and a CDR-L3 comprising the sequence set forth in SEQ ID NOS:75, 77 and 79, respectively.

61. The anti-ROR1 chimeric antigen receptor of embodiment 58 or embodiment 59, wherein the $V_H$ region comprises a CDR-H1, a CDR-H2 and a CDR-H3 comprising the sequence set forth in SEQ ID NOS:82, 86 and 88, respectively, and the $V_L$ region comprises a CDR-L1, a CDR-L2 and a CDR-L3 comprising the sequence set forth in SEQ ID NOS:90, 92 and 94, respectively.

62. An anti-ROR1 chimeric antigen receptor (CAR) comprising:

an extracellular antigen-binding domain comprising a heavy chain variable ($V_H$) region and a light chain variable ($V_L$) region, and an intracellular signaling region, wherein:

the $V_H$ region comprises a heavy chain complementarity determining region 1 (CDR-H1), a heavy chain complementarity determining region 2 (CDR-H2) and a heavy chain complementarity determining region 3 (CDR-H3) contained within SEQ ID NO: 112, 121, 103 or 130, and the $V_L$ region comprises a light chain complementarity determining region 1 (CDR-L1), a light chain complementarity determining region 2 (CDR-L2) and a light chain complementarity determining region 3 (CDR-L3) contained within SEQ ID NO: 115, 124 or 106.

63. An anti-ROR1 chimeric antigen receptor (CAR) comprising:

an extracellular antigen-binding domain comprising a heavy chain variable ($V_H$) region and a light chain variable ($V_L$) region, and an intracellular signaling region, wherein:

the $V_H$ region comprises a heavy chain complementarity determining region 1 (CDR-H1), a heavy chain complementarity determining region 2 (CDR-H2) and a heavy chain complementarity determining region 3 (CDR-H3) contained within SEQ ID NO:112, and the $V_L$ region comprises a light chain complementarity determining region 1 (CDR-L1), a light chain complementarity determining region 2 (CDR-L2) and a light chain complementarity determining region 3 (CDR-L3) contained within SEQ ID NO:115;

the $V_H$ region comprises a CDR-H1, a CDR-H2 and a CDR-H3 contained within SEQ ID NO:121, and the $V_L$ region comprises a CDR-L1, a CDR-L2 and a CDR-L3 contained within SEQ ID: NO 124;

the $V_H$ region comprises a CDR-H1, a CDR-H2 and a CDR-H3 contained within SEQ ID NO:103, and the $V_L$ region comprises a CDR-L1, a CDR-L2 and a CDR-L3 contained within SEQ ID: NO 106; or the $V_H$ region comprises a CDR-H1, a CDR-H2 and a CDR-H3 contained within SEQ ID NO:130, and the $V_L$ region comprises a CDR-L1, a CDR-L2 and a CDR-L3 contained within SEQ ID: NO 106.

64. The anti-ROR1 chimeric antigen receptor of embodiment 62 or embodiment 63, wherein the $V_H$ region comprises a CDR-H1, a CDR-H2 and a CDR-H3 contained within SEQ ID NO:112, and the $V_L$ region comprises a CDR-L1, a CDR-L2 and a CDR-L3 contained within SEQ ID: NO 115.

65. The anti-ROR1 chimeric antigen receptor of embodiment 62 or embodiment 63, wherein the $V_H$ region comprises a CDR-H1, a CDR-H2 and a CDR-H3 contained within SEQ ID NO:121, and the $V_L$ region comprises a CDR-L1, a CDR-L2 and a CDR-L3 contained within SEQ ID: NO 124.

66. The anti-ROR1 chimeric antigen receptor of any of embodiments 58, 59, 62 and 63, wherein:

the $V_H$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO: 112, 121, 103 or 130, and the $V_L$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO: 115, 124 or 106.

67. The anti-ROR1 chimeric antigen receptor of any of embodiments 58, 59, and 62-64, wherein:

the $V_H$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:112, and the $V_L$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO: 115;

the $V_H$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:121, and the $V_L$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:124;

the $V_H$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:103, and the $V_L$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:106; or the $V_H$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:130, and the $V_L$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:106.

68. The anti-ROR1 chimeric antigen receptor of any of embodiments 58-67, wherein the $V_H$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:112, and the $V_L$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO: 115.

69. The anti-ROR1 chimeric antigen receptor of any of embodiments 58-67, wherein the $V_H$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:121, and the $V_L$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:124.

70. An anti-ROR1 chimeric antigen receptor (CAR) comprising:
an extracellular antigen-binding domain comprising a heavy chain variable ($V_H$) region and a light chain variable ($V_L$) region, and an intracellular signaling region, wherein:
the $V_H$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO: 112, 121, 103 or 130, and
the $V_L$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO: 115, 124 or 106.

71. An anti-ROR1 chimeric antigen receptor (CAR) comprising:
an extracellular antigen-binding domain comprising a heavy chain variable ($V_H$) region and a light chain variable ($V_L$) region, and an intracellular signaling region, wherein:
the $V_H$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:112, and the $V_L$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO: 115;
the $V_H$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:121, and the $V_L$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:124;
the $V_H$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:103, and the $V_L$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:106; or
the $V_H$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:130, and the $V_L$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:106.

72. The anti-ROR1 chimeric antigen receptor of embodiment 70 or embodiment 71, wherein the $V_H$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:112, and the $V_L$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO: 115.

73. The anti-ROR1 chimeric antigen receptor of embodiment 70 or embodiment 71, wherein the $V_H$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:121, and the $V_L$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:124.

74. The anti-ROR1 chimeric antigen receptor of any of embodiments 58, 59, 62, 63, 66, 67, 70 and 71, wherein:
the $V_H$ region is or comprises the sequence set forth in SEQ ID NO: 112, 121, 103 or 130, and
the $V_L$ region is or comprises the sequence set forth in SEQ ID NO: 115, 124 or 106.

75. The anti-ROR1 chimeric antigen receptor of any of embodiments 58, 59, 62, 63, 66, 67, 70, 71 and 74, wherein:
the $V_H$ region and the $V_L$ region are or comprise the sequence set forth in SEQ ID NOS: 112 and 115, respectively;
the $V_H$ region and the $V_L$ region are or comprise the sequence set forth in SEQ ID NOS: 121 and 124, respectively;
the $V_H$ region and the $V_L$ region are or comprise the sequence set forth in SEQ ID NOS: 103 and 106, respectively; or
the $V_H$ region and the $V_L$ region are or comprise the sequence set forth in SEQ ID NOS: 130 and 106, respectively.

76. An anti-ROR1 chimeric antigen receptor (CAR) comprising:
an extracellular antigen-binding domain comprising a heavy chain variable ($V_H$) region and a light chain variable ($V_L$) region, and an intracellular signaling region, wherein:
the $V_H$ region is or comprises the sequence set forth in SEQ ID NO: 112, 121, 103 or 130, and
the $V_L$ region is or comprises the sequence set forth in SEQ ID NO: 115, 124 or 106.

77. An anti-ROR1 chimeric antigen receptor (CAR) comprising:
an extracellular antigen-binding domain comprising a heavy chain variable ($V_H$) region and a light chain variable ($V_L$) region, and an intracellular signaling region, wherein:
the $V_H$ region and the $V_L$ region are or comprise the sequence set forth in SEQ ID NOS: 112 and 115, respectively;

the V_H region and the V_L region are or comprise the sequence set forth in SEQ ID NOS: 121 and 124, respectively;

the V_H region and the V_L region are or comprise the sequence set forth in SEQ ID NOS: 103 and 106, respectively; or the V_H region and the V_L region are or comprise the sequence set forth in SEQ ID NOS: 130 and 106, respectively.

78. The anti-ROR1 chimeric antigen receptor of any of embodiments 58-77, wherein the V_H region and the V_L region are or comprise the sequence set forth in SEQ ID NOS: 112 and 115, respectively.

79. The anti-ROR1 chimeric antigen receptor of any of embodiments 58-77, wherein the V_H region and the V_L region are or comprise the sequence set forth in SEQ ID NOS:121 and 124, respectively.

80. The anti-ROR1 chimeric antigen receptor of any of embodiments 58, 59, 62, 63, 66, 67, 70, 71 and 74-77, wherein the V_H region is or comprises the amino acid sequence encoded by SEQ ID NO: 110, 119, 101 or 128 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 110, 119, 101 or 128, and the V_L region is or comprises the amino acid sequence encoded by SEQ ID NO: 113, 122 or 104, or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 113, 122 or 104.

81. The anti-ROR1 chimeric antigen receptor of any of embodiments 58, 59, 62, 63, 66, 67, 70, 71, 74-77 and 80, wherein the V_H region is or comprises the amino acid sequence encoded by SEQ ID NO: 111, 120, 102 or 129, and the V_L region is or comprises the amino acid sequence encoded by SEQ ID NO: 114, 123, 105 or 131.

82. The anti-ROR1 chimeric antigen receptor of any of embodiments 58-81, wherein the V_H region is or comprises the amino acid sequence encoded by SEQ ID NO: 110 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 110, and the V_L region is or comprises the amino acid sequence encoded by SEQ ID NO: 113, or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 113.

83. The anti-ROR1 chimeric antigen receptor of any of embodiments 58-82, wherein the V_H region is or comprises the amino acid sequence encoded by SEQ ID NO: 111, and the V_L region is or comprises the amino acid sequence encoded by SEQ ID NO: 114.

84. The anti-ROR1 chimeric antigen receptor of any of embodiments 58-81, wherein the V_H region is or comprises the amino acid sequence encoded by SEQ ID NO: 119 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 119, and the V_L region is or comprises the amino acid sequence encoded by SEQ ID NO: 122, or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 122.

85. The anti-ROR1 chimeric antigen receptor of any of embodiments 58-82, wherein the V_H region is or comprises the amino acid sequence encoded by SEQ ID NO: 120, and the V_L region is or comprises the amino acid sequence encoded by SEQ ID NO: 123.

86. The anti-ROR1 chimeric antigen receptor of any of embodiments 58-85, wherein said anti-ROR1 antibody or antigen-binding fragment thereof is isolated.

87. The anti-ROR1 chimeric antigen receptor of any of embodiments 58-86, wherein said anti-ROR1 antibody or antigen-binding fragment thereof is recombinant.

88. The anti-ROR1 chimeric antigen receptor of any of embodiments 58-87, wherein at least a portion of the V_H region and the V_L region is human or is from a human protein.

89. The anti-ROR1 chimeric antigen receptor of any of embodiments 58-88, wherein the antigen-binding fragment thereof comprises a single chain fragment, optionally a single chain Fv (scFv).

90. The anti-ROR1 chimeric antigen receptor of any of embodiments 58-89, wherein the V_H region is amino-terminal to the V_L region.

91. The anti-ROR1 chimeric antigen receptor of any of embodiments 58-89, wherein the V_H region is carboxy-terminal to the V_L region.

92. The anti-ROR1 chimeric antigen receptor of any of embodiments 58-91, when the V_H region and the V_L region are joined by a flexible linker.

93. The anti-ROR1 chimeric antigen receptor of embodiment 92, wherein the flexible linker comprises the sequence set forth in SEQ ID NO:41.

94. The anti-ROR1 chimeric antigen receptor of any of embodiments 89, 90, 92 and 93, wherein the scFv is or comprises the sequence set forth in SEQ ID NO: 118, 127, 109 or 134, or an amino acid sequence having at least at or about 85%, 86%, 87%, 88%, 89%, 90%, 91%, 92%, 93%, 94%, 95%, 96%, 97%, 98% or 99% sequence identity to SEQ ID NO: 118, 127, 109 or 134.

95. The anti-ROR1 chimeric antigen receptor of any of embodiments 89, 90 and 92-94, wherein the scFv is or comprises the sequence set forth in SEQ ID NO: 118.

96. The anti-ROR1 chimeric antigen receptor of any of embodiments 89, 90 and 92-94, wherein the scFv is or comprises the sequence set forth in SEQ ID NO: 127.

97. The anti-ROR1 chimeric antigen receptor of any of embodiments 89, 90 and 92-94, wherein the scFv is or comprises the amino acid sequence encoded by SEQ ID NO: 116, 125, 107 or 132 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 116, 125, 107 or 132.

98. The anti-ROR1 chimeric antigen receptor of any of embodiments 89, 90, 92-94 and 40, wherein the scFv is or comprises the amino acid sequence encoded by SEQ ID NO: 117, 126, 108 or 133.

99. The anti-ROR1 chimeric antigen receptor of any of embodiments 89-98, wherein the scFv is or comprises the amino acid sequence encoded by SEQ ID NO: 116 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 116.

100. The anti-ROR1 chimeric antigen receptor of any of embodiments 89-99, wherein the scFv is or comprises the amino acid sequence encoded by SEQ ID NO: 117.
101. The anti-ROR1 chimeric antigen receptor of any of embodiments 89-98, wherein the scFv is or comprises the amino acid sequence encoded by SEQ ID NO: 125 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 125.
102. The anti-ROR1 chimeric antigen receptor of any of embodiments 89-98 and 100, wherein the scFv is or comprises the amino acid sequence encoded by SEQ ID NO: 126.
103. The anti-ROR1 chimeric antigen receptor of any of embodiments 58-102, further comprising a spacer.
104. The anti-ROR1 chimeric antigen receptor of embodiment 103, wherein the spacer comprises at least a portion of an immunoglobulin or a variant thereof.
105. The anti-ROR1 chimeric antigen receptor of embodiment 103 or embodiment 104, wherein the spacer comprises at least a portion of a hinge region of an immunoglobulin or a variant thereof.
106. The anti-ROR1 chimeric antigen receptor of any of embodiments 103-105, wherein the spacer is less than at or about 15 amino acids in length.
107. The anti-ROR1 chimeric antigen receptor of any of embodiments 103-106, wherein the spacer is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:1, 26, 27, 29, 31, 32, 33 or 135.
108. The anti-ROR1 chimeric antigen receptor of any of embodiments 105-107, wherein the at least a portion of a hinge region comprises all or a portion of an IgG4 hinge region, optionally a human IgG4 hinge region, or a variant thereof.
109. The anti-ROR1 chimeric antigen receptor of any of embodiments 105-107, wherein the at least a portion of a hinge region comprises all or a portion of an IgG2 hinge region, optionally a human IgG2 hinge region, or a variant thereof.
110. The anti-ROR1 chimeric antigen receptor of any of embodiments 103-109, wherein the spacer is or comprises the sequence set forth in SEQ ID NO: 135.
111. The anti-ROR1 chimeric antigen receptor of any of embodiments 103-110, wherein the spacer is or comprises the amino acid sequence encoded by SEQ ID NO: 192 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 192.
112. The anti-ROR1 chimeric antigen receptor of any of embodiments 103-111, wherein the spacer is or comprises the amino acid sequence encoded by SEQ ID NO: 136.
113. The anti-ROR1 chimeric antigen receptor of any of embodiments 103-112, wherein the spacer comprises at least a portion of a CH3 region of an immunoglobulin or a variant thereof.
114. The anti-ROR1 chimeric antigen receptor of any of embodiments 103-113, wherein the at least a portion of a CH3 region comprises all or a portion of an IgG4 CH3 and/or an IgG2 CH3, wherein the IgG4 CH3 is optionally a human IgG4 CH3 and the IgG2 CH3 is optionally a human IgG2 CH3.
115. The anti-ROR1 chimeric antigen receptor of any of embodiments 103-114, wherein the spacer comprises at least a portion of a hinge region and at least a portion of a CH3 region of an immunoglobulin or a variant thereof.
116. The anti-ROR1 chimeric antigen receptor of any of embodiments 103-115, wherein the spacer is at or about 111, 112, 113, 114, 115, 116, 117, 118, 119, 120, 121, 122, 123, 124 or 125 amino acids in length, or has a length between any of the foregoing.
117. The anti-ROR1 chimeric antigen receptor of any of embodiments 103-116, wherein the spacer is at or about 120 amino acids in length.
118. The anti-ROR1 chimeric antigen receptor of any of embodiments 103-117, wherein the spacer is or comprises an amino acid sequence having at least at or about 85%, 86%, 87%, 88%, 89%, 90%, 91%, 92%, 93%, 94%, 95%, 96%, 97%, 98% or 99% identity to SEQ ID NO: 138.
119. The anti-ROR1 chimeric antigen receptor of any of embodiments 103-118, wherein the spacer is or comprises the sequence set forth in SEQ ID NO:138.
120. The anti-ROR1 chimeric antigen receptor of any of embodiments 103-119, wherein the spacer is or comprises the amino acid sequence encoded by SEQ ID NO: 193 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 193.
121. The anti-ROR1 chimeric antigen receptor of any of embodiments 103-120, wherein the spacer is or comprises the amino acid sequence encoded by SEQ ID NO: 139.
122. The anti-ROR1 chimeric antigen receptor of any of embodiments 103-121, wherein the spacer comprises at least a portion of a CH2 of an immunoglobulin or a variant thereof.
123. The anti-ROR1 chimeric antigen receptor of any of embodiments 103-122, wherein the at least a portion of a CH2 region comprises all or a portion of an IgG4 CH2 and/or an IgG2 CH2, wherein the IgG4 CH2 is optionally a human IgG4 CH2 and the IgG2 CH2 is optionally a human IgG2 CH2.
124. The anti-ROR1 chimeric antigen receptor of any of embodiments 103-123, wherein the spacer comprises at least a portion of a hinge region, at least a portion of a CH2 and at least a portion of a CH3 region of an immunoglobulin or a variant thereof.
125. The anti-ROR1 chimeric antigen receptor of any of embodiments 103-124, wherein the spacer is at or about 130, 140, 150, 160, 170, 180, 190, 200, 210, 220, 221, 222, 223, 224, 225, 226, 227, 228, 229 or 230 amino acids in length, or has a length between any of the foregoing.
126. The anti-ROR1 chimeric antigen receptor of any of embodiments 103-125, wherein one or more of the hinge region, the CH2 region and the CH3 region comprises all or a portion of a CH2 region and all or a portion of a CH3 region from human IgG4.
127. The anti-ROR1 chimeric antigen receptor of any of embodiments 103-125, wherein one or more of the hinge region, the CH2 region and the CH3 region is chimeric and comprises a hinge, a CH2 region and a CH3 region from human IgG4 and human IgG2.
128. The anti-ROR1 chimeric antigen receptor of any of embodiments 103-125, wherein the spacer comprises a IgG4/2 chimeric hinge region or a modified IgG4 hinge region comprising at least one amino acid replacement compared to a human IgG4 hinge; an IgG2/4 chimeric CH2 region; and an IgG4 CH3 region.

129. The anti-ROR1 chimeric antigen receptor of any of embodiments 103-125, wherein the spacer is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:194.

130. The anti-ROR1 chimeric antigen receptor of any of embodiments 103-129, wherein the spacer is or comprises the sequence set forth in SEQ ID NO: 194.

131. The anti-ROR1 chimeric antigen receptor of any of embodiments 103-130, wherein the spacer is or comprises the amino acid sequence encoded by SEQ ID NO: 195 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 195.

132. The anti-ROR1 chimeric antigen receptor of any of embodiments 103-131, wherein the spacer is or comprises the amino acid sequence encoded by SEQ ID NO: 196.

133. The anti-ROR1 chimeric antigen receptor of any of embodiments 58-132, wherein the intracellular signaling region comprises an intracellular signaling domain.

134. The anti-ROR1 chimeric antigen receptor of embodiment 133, wherein the intracellular signaling domain is capable of inducing a primary activation signal in a T cell, is a T cell receptor (TCR) component and/or comprises an immunoreceptor tyrosine-based activation motif (ITAM).

135. The anti-ROR1 chimeric antigen receptor of embodiment 133 or embodiment 134, wherein the intracellular signaling domain is or comprises a cytoplasmic signaling domain of a CD3-zeta (CD3ζ) chain or a functional variant or signaling portion thereof.

136. The anti-ROR1 chimeric antigen receptor of any of embodiments 133-135, wherein the intracellular signaling domain is human or is from a human protein.

137. The anti-ROR1 chimeric antigen receptor of any of embodiments 133-136, wherein the intracellular signaling domain is or comprises the sequence set forth in SEQ ID NO:13, 14 or 15, or an amino acid sequence having at least at or about 90%, 91%, 92%, 93%, 94%, 95%, 96%, 97%, 98% or 99% sequence identity to SEQ ID NO:13, 14 or 15.

138. The anti-ROR1 chimeric antigen receptor of any of embodiments 133-137, wherein the intracellular signaling domain is or comprises the sequence set forth in SEQ ID NO:13.

139. The anti-ROR1 chimeric antigen receptor of any of embodiments 133-138, wherein the intracellular signaling region further comprises a costimulatory signaling region.

140. The anti-ROR1 chimeric antigen receptor of embodiment 139, wherein the costimulatory signaling region comprises an intracellular signaling domain of a T cell costimulatory molecule or a signaling portion thereof.

141. The anti-ROR1 chimeric antigen receptor of embodiment 139 or embodiment 140, wherein the costimulatory signaling region comprises an intracellular signaling domain of CD28, 4-1BB, or ICOS, or a signaling portion thereof.

142. The anti-ROR1 chimeric antigen receptor of any of embodiments 140-141, wherein the costimulatory signaling region is human or is from a human protein.

143. The anti-ROR1 chimeric antigen receptor of any of embodiments 140-142, wherein the costimulatory signaling region comprises an intracellular signaling domain of CD28.

144. The anti-ROR1 chimeric antigen receptor of any of embodiments 140-143, wherein the costimulatory signaling region is or comprises the sequence set forth in SEQ ID NO:10 or an amino acid sequence having at least at or about 90%, 91%, 92%, 93%, 94%, 95%, 96%, 97%, 98% or 99% sequence identity to SEQ ID NO:10.

145. The anti-ROR1 chimeric antigen receptor of any of embodiments 140-144, wherein the costimulatory signaling region comprises an intracellular signaling domain of 4-1BB.

146. The anti-ROR1 chimeric antigen receptor of any of embodiments 140-142 and 145, wherein the costimulatory signaling region is or comprises the sequence set forth in SEQ ID NO:12 or an amino acid sequence having at least at or about 90%, 91%, 92%, 93%, 94%, 95%, 96%, 97%, 98% or 99% sequence identity to SEQ ID NO: 12.

147. The anti-ROR1 chimeric antigen receptor of any of embodiments 58-146, further comprising a transmembrane region.

148. The anti-ROR1 chimeric antigen receptor of any of embodiments 140-147, wherein the costimulatory signaling region is between the transmembrane region and the intracellular signaling domain 149. The anti-ROR1 chimeric antigen receptor of embodiment 147 or embodiment 148, wherein the transmembrane region is or comprises a transmembrane domain from CD4, CD28, or CD8.

150. The anti-ROR1 chimeric antigen receptor of any of embodiments 147-149, wherein the transmembrane region is or comprises a transmembrane domain derived from CD28.

151. The anti-ROR1 chimeric antigen receptor of any of embodiments 147-150, wherein the transmembrane region is human or is from a human protein.

152. The anti-ROR1 chimeric antigen receptor of any of embodiments 147-151, wherein the transmembrane domain is or comprises SEQ ID NO: 8 or an amino acid sequence having at least at or about 90%, 91%, 92%, 93%, 94%, 95%, 96%, 97%, 98% or 99% sequence identity to SEQ ID NO: 8.

153. The anti-ROR1 chimeric antigen receptor of any of embodiments 147-152, wherein the encoded chimeric antigen receptor comprises from its N to C terminus in order: the extracellular antigen-binding domain, the spacer, the transmembrane region and the intracellular signaling region.

154. The anti-ROR1 chimeric antigen receptor of any of embodiments 58-153, wherein the encoded chimeric antigen receptor comprises, from its N to C terminus in order: an extracellular antigen-binding domain comprising an scFv, a spacer comprising a modified IgG4 hinge, optionally comprising the sequence set forth in SEQ ID NO:135; a transmembrane domain, optionally a transmembrane domain from a human CD28; and an intracellular signaling region comprising a cytoplasmic signaling domain of a CD3-zeta (CD3ζ) chain and an intracellular signaling domain of a costimulatory signaling region, optionally comprising an intracellular signaling domain of 4-1BB.

155. The anti-ROR1 chimeric antigen receptor of any of embodiments 58-153, wherein the encoded chimeric antigen receptor comprises, from its N to C terminus in order: an extracellular antigen-binding domain comprising an scFv, a spacer comprising a modified IgG4 hinge-CH3, optionally comprising the sequence set forth in SEQ ID NO: 138; a transmembrane domain, optionally a transmembrane domain from a human CD28; and an intracellular signaling region comprising a cytoplasmic signaling domain of a CD3-zeta (CD3ζ) chain and an intracellular signaling domain of a costimulatory signaling region, optionally comprising an intracellular signaling domain of 4-1BB.

156. The anti-ROR1 chimeric antigen receptor of any of embodiments 58-155, wherein the anti-ROR1 chimeric antigen receptor is or comprises the sequence set forth in SEQ ID NO: 184, 185, 186, 187, 188 or 189 or a sequence that exhibits at least 85%, 86%, 87%, 88%, 89%, 90%, 91%, 92%, 93%, 94%, 95%, 96%, 97%, 98%, or 99% sequence identity to the sequence set forth in SEQ ID NO: 184, 185, 186, 187, 188 or 189.

157. The anti-ROR1 chimeric antigen receptor of any of embodiments 58-156, wherein the anti-ROR1 chimeric antigen receptor is or comprises the sequence set forth in SEQ ID NO: 184 or a sequence that exhibits at least 85%, 86%, 87%, 88%, 89%, 90%, 91%, 92%, 93%, 94%, 95%, 96%, 97%, 98%, or 99% sequence identity to the sequence set forth in SEQ ID NO: 184.

158. The anti-ROR1 chimeric antigen receptor of any of embodiments 58-157, wherein the anti-ROR1 chimeric antigen receptor is or comprises the sequence set forth in SEQ ID NO: 184.

159. The anti-ROR1 chimeric antigen receptor of any of embodiments 58-156, wherein the anti-ROR1 chimeric antigen receptor is or comprises the sequence set forth in SEQ ID NO: 185 or a sequence that exhibits at least 85%, 86%, 87%, 88%, 89%, 90%, 91%, 92%, 93%, 94%, 95%, 96%, 97%, 98%, or 99% sequence identity to the sequence set forth in SEQ ID NO:185.

160. The anti-ROR1 chimeric antigen receptor of any of embodiments 58-156 and 159, wherein the anti-ROR1 chimeric antigen receptor is or comprises the sequence set forth in SEQ ID NO: 185.

161. The anti-ROR1 chimeric antigen receptor of any of embodiments 58-156, wherein the anti-ROR1 chimeric antigen receptor is encoded by the sequence set forth in SEQ ID NO: 156, 157, 158, 159, 160 or 161 or a sequence that exhibits at least 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 156, 157, 158, 159, 160 or 161.

162. The anti-ROR1 chimeric antigen receptor of any of embodiments 58-158 and 161, wherein the anti-ROR1 chimeric antigen receptor is encoded by the sequence set forth in SEQ ID NO: 156 or a sequence that exhibits at least 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 156.

163. The anti-ROR1 chimeric antigen receptor of any of embodiments 58-158, 161 and 162, wherein the anti-ROR1 chimeric antigen receptor is encoded by the sequence set forth in SEQ ID NO: 156.

164. The anti-ROR1 chimeric antigen receptor of any of embodiments 58-156 and 159-161, wherein the anti-ROR1 chimeric antigen receptor is encoded by the sequence set forth in SEQ ID NO: 157 or a sequence that exhibits at least 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 157.

165. The anti-ROR1 chimeric antigen receptor of any of embodiments 58-156, 159-161 and 164, wherein the anti-ROR1 chimeric antigen receptor is encoded by the sequence set forth in SEQ ID NO: 157.

166. The anti-ROR1 chimeric antigen receptor of any of embodiments 58-165, wherein said anti-ROR1 chimeric antigen receptor specifically binds to a receptor tyrosine kinase-like orphan receptor 1 (ROR1) protein, optionally a human ROR1.

167. The anti-ROR1 chimeric antigen receptor of embodiment 166, wherein the human ROR1 protein comprises an amino acid sequence set forth in SEQ ID NO: 144, 145 or 146.

168. The anti-ROR1 chimeric antigen receptor of any of embodiments 58-167, wherein said anti-ROR1 chimeric antigen receptor does not bind to, is not cross-reactive to, or binds at a lower level or degree or affinity to a receptor tyrosine kinase-like orphan receptor 2 (ROR2) protein, optionally a human ROR2.

169. The anti-ROR1 chimeric antigen receptor of any of embodiments 58-168, wherein the extent, level or degree or affinity of binding of said anti-ROR1 chimeric antigen receptor to a human ROR2 is at least at or about 75%, 80%, 90%, 95% or 99% less than the extent, level or degree or affinity of binding to a human ROR1, optionally under the same or substantially the same conditions or assay.

170. The anti-ROR1 chimeric antigen receptor of any of embodiments 58-169, wherein said anti-ROR1 chimeric antigen receptor exhibits the same, substantially the same or lower level or degree of signaling or activity in the presence of a ROR2 protein, optionally a human ROR2, compared to the level or degree of signaling or activity in the presence of a ROR1 protein, optionally a human ROR1, optionally under the same or substantially the same conditions or assay.

171. The anti-ROR1 chimeric antigen receptor of any of embodiments 58-170, wherein said anti-ROR1 chimeric antigen receptor exhibits a level or degree of signaling or activity in the presence of a human ROR2 that is at least at or about 75%, 80%, 90%, 95% or 99% less than the level or degree of signaling or activity in the presence of a human ROR1, optionally under the same or substantially the same conditions or assay.

172. The anti-ROR1 chimeric antigen receptor of any of embodiments 58-171, wherein said anti-ROR1 chimeric antigen receptor exhibits the same, substantially the same or lower level or degree of signaling or activity in the presence of a ROR2 protein, optionally a human ROR2, compared to a reference ROR1-specific chimeric antigen receptor, optionally under the same or substantially the same conditions or assay.

173. The anti-ROR1 chimeric antigen receptor of any of embodiments 58-172, wherein said anti-ROR1 chimeric antigen receptor exhibits the same, substantially the same or lower level or degree of signaling or activity in the presence of a ROR2 protein, optionally a human ROR2, compared to a reference ROR1-specific chimeric antigen receptor, optionally under the same or substantially the same conditions or assay.

174. The anti-ROR1 chimeric antigen receptor of any of embodiments 58-173, wherein said anti-ROR1 chimeric antigen receptor exhibits the same, substantially the same or higher antigen-specific signaling and/or antigen dependent activity or signaling compared to a reference ROR1-specific chimeric antigen receptor, optionally under the same or substantially the same conditions or assay.

175. The anti-ROR1 chimeric antigen receptor of any of embodiments 58-174, wherein said anti-ROR1 chimeric antigen receptor exhibits the same, substantially the same or lower tonic signaling and/or antigen independent activity or signaling compared to a reference ROR1-specific chimeric antigen receptor, optionally under the same or substantially the same conditions or assay.

176. The anti-ROR1 chimeric antigen receptor of any of embodiments 58-175, wherein said anti-ROR1 chimeric antigen receptor exhibits a level or degree of tonic signaling and/or antigen independent activity or signaling that is at least at or about 75%, 80%, 90%, 95% or 99% less than the level or degree of tonic signaling and/or antigen independent activity of a reference ROR1-specific chimeric antigen receptor, optionally under the same or substantially the same conditions or assay.

177. The anti-ROR1 chimeric antigen receptor of any of embodiments 172-176, wherein the reference ROR1-specific chimeric antigen receptor comprises the anti-ROR1 antibody R12 or the anti-ROR1 antibody 2A2 or an antigen-binding fragment thereof, optionally an scFv from R12 or 2A2.

178. A polynucleotide comprising a nucleic acid encoding the anti-ROR1 antibody or antigen-binding domain thereof of any of embodiments 1-53 and 244-265, the single chain cell surface protein of embodiment 54, the conjugate of embodiment 55 or embodiment 56 or the anti-ROR1 chimeric antigen receptor of any of embodiments 57-177 and 266-297.

179. The polynucleotide of embodiment 178, wherein said polynucleotide comprises a nucleic acid encoding the $V_H$ comprising the sequence set forth in SEQ ID NO: 110, 119, 101 or 128 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 110, 119, 101 or 128, and a nucleic acid encoding the $V_L$ comprising the sequence set forth in SEQ ID NO: 113, 122 or 104, or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 113, 122 or 104.

180. The polynucleotide of embodiment 178 or embodiment 179, wherein said polynucleotide comprises a nucleic acid encoding the $V_H$ comprising the sequence set forth in SEQ ID NO: 110 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 110, and a nucleic acid encoding the $V_L$ comprising the sequence set forth in SEQ ID NO: 113, or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 113.

181. The polynucleotide of embodiment 178 or embodiment 179, wherein said polynucleotide comprises a nucleic acid encoding the $V_H$ comprising the sequence set forth in SEQ ID NO: 119 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 119, and a nucleic acid encoding the $V_L$ comprising the sequence set forth in SEQ ID NO: 122, or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 122.

182. The polynucleotide of any of embodiments 178-180, wherein said polynucleotide comprises a nucleic acid encoding the scFv comprising the sequence set forth in SEQ ID NO: 116, 125, 107 or 132 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 116, 125, 107 or 132.

183. The polynucleotide of any of embodiments 178-180 and 182, wherein said polynucleotide comprises a nucleic acid encoding the scFv comprising the sequence set forth in SEQ ID NO: 116 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 116.

184. The polynucleotide of any of embodiments 178-180 and 182, wherein said polynucleotide comprises a nucleic acid encoding the scFv comprising the sequence set forth in SEQ ID NO: 125 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 125.

185. The polynucleotide of any of embodiments 178-184, wherein said polynucleotide comprises a nucleic acid encoding the spacer comprising the sequence set forth in SEQ ID NO: 192 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 192.

186. The polynucleotide of any of embodiments 178-184, wherein said polynucleotide comprises a nucleic acid encoding the spacer comprising the sequence set forth in SEQ ID NO: 193 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 193.

187. The polynucleotide of any of embodiments 178-184, wherein said polynucleotide comprises a nucleic acid encoding the spacer comprising the sequence set forth in SEQ ID NO: 195 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 195.

188. The polynucleotide of embodiment 187, wherein the nucleic acid encoding the anti-ROR1 antibody or antigen-binding domain thereof, the single chain cell surface protein, the conjugate or the anti-ROR1 chimeric antigen receptor comprises at least one modified splice donor and/or splice acceptor site, said modified splice donor and/or acceptor site comprising one or more nucleotide modifications corresponding to a reference splice donor site and/or reference splice acceptor site.

189. The polynucleotide of embodiment 188, wherein the one or more nucleotide modifications comprise a nucleic acid substitution.

190. The polynucleotide of embodiment 188 or embodiment 189, wherein the reference splice donor and/or reference splice acceptor sites are canonical, non-canonical, or cryptic splice sites.

191. The polynucleotide of any of embodiment 188-190, wherein:
the reference splice donor and/or reference splice acceptor site(s) has a splice site prediction score of at least at or about 0.4, 0.5, 0.6, 0.70, 0.75, 0.80, 0.85, 0.90, 0.95, 0.99 or 1.0; and/or
the reference splice donor and/or reference splice acceptor site(s) is/are predicted to be involved in a splice event with a probability of at least at or about 40%, 50%, 60%, 70%, 75%, 80%, 85%, 90%, 95%, 99% or 100%.

192. The polynucleotide of any of embodiment 188-191, wherein:
the reference splice donor and/or reference splice acceptor site(s) has a splice site prediction score of at least at or about 0.70, 0.75, 0.80, 0.85, 0.90, 0.95, 0.99 or 1.0; and/or
the reference splice donor and/or reference splice acceptor site(s) is/are predicted to be involved in a splice event with a probability of at least at or about 70%, 75%, 80%, 85%, 90%, 95%, 99% or 100%.

193. The polynucleotide of any of embodiments 188-192, wherein at least one of the one or more nucleotide modifications are within 1, 2, 3, 4, 5, 6, 7, 8, 9 or 10 residues of the splice site junction of the reference splice acceptor and/or reference splice donor site.

194. The polynucleotide of any of embodiments 188-193, wherein the one or more nucleotide modifications is silent and/or results in a degenerate codon and/or does not change the amino acid sequence of the encoded protein.

195. The polynucleotide of any of embodiments 188-194, wherein upon expression of the polynucleotide in a cell, the transcribed RNA, optionally messenger RNA (mRNA), from the polynucleotide, exhibits at least at or about 70%, at or about 75%, at or about 80%, at or about 85%, at or about 90%, or at or about 95% RNA homogeneity.

196. The polynucleotide of any of embodiments 188-195, wherein, upon expression in a cell, the transcribed RNA, optionally messenger RNA (mRNA), from the polynucleotide exhibits reduced heterogeneity compared to the heterogeneity of the mRNA transcribed from a reference polynucleotide, said reference polynucleotide encoding the same amino acid sequence as the polynucleotide, wherein the reference polynucleotide differs by the presence of one or more splice donor site and/or one or more splice acceptor site in the nucleic acid encoding the spacer and/or comprises one or more nucleotide modifications compared to the polynucleotide.

197. The polynucleotide of embodiment 196, wherein the RNA heterogeneity is reduced by greater than at or about 10%, 15%, 20%, 25%, 30%, 40% or 50% or more.

198. The polynucleotide of embodiment 196 or embodiment 197, wherein the transcribed RNA, optionally messenger RNA (mRNA), from the reference polynucleotide exhibits greater than at or about 10%, 15%, 20%, 25%, 30%, 40% or 50% or more RNA heterogeneity.

199. The polynucleotide of any of embodiments 188-198, wherein the RNA homogeneity and/or heterogeneity is determined by agarose gel electrophoresis, chip-based capillary electrophoresis, analytical ultracentrifugation, field flow fractionation, or liquid chromatography.

200. The polynucleotide of any of embodiments 188-199, wherein the polynucleotide is codon-optimized for expression in a human cell.

201. The polynucleotide of any of embodiments 178, 179, 182, 185, 186 and 188-200, wherein said polynucleotide comprises a nucleic acid encoding the $V_H$ comprising the sequence set forth in SEQ ID NO: 111, 120, 102 or 129, and a nucleic acid encoding the $V_L$ comprising the sequence set forth in SEQ ID NO: 114, 123, 105 or 131.

202. The polynucleotide of any of embodiments 178-180, 182, 183, 185, 186 and 198-201, wherein said polynucleotide comprises a nucleic acid encoding the $V_H$ comprising the sequence set forth in SEQ ID NO: 111, and a nucleic acid encoding the $V_L$ comprising the sequence set forth in SEQ ID NO: 114.

203. The polynucleotide of any of embodiments 178, 179, 181, 182, 184-186 and 198-201, wherein said polynucleotide comprises a nucleic acid encoding the $V_H$ comprising the sequence set forth in SEQ ID NO: 120, and a nucleic acid encoding the $V_L$ comprising the sequence set forth in SEQ ID NO: 123.

204. The polynucleotide of any of embodiments 178, 179, 182, 185, 186 and 188-201, wherein said polynucleotide comprises a nucleic acid encoding the scFv comprising the sequence set forth in SEQ ID NO: 117, 126, 108 or 133.

205. The polynucleotide of any of embodiments 178-180, 182, 183, 185, 186, 198-201 and 204, wherein said polynucleotide comprises a nucleic acid encoding the scFv comprising the sequence set forth in SEQ ID NO: 117.

206. The polynucleotide of any of embodiments 178, 179, 181, 182, 184-186, 198-201 and 204, wherein said polynucleotide comprises a nucleic acid encoding the scFv comprising the sequence set forth in SEQ ID NO: 126.

207. The polynucleotide of any of embodiments 178-185 and 188-206, wherein said polynucleotide comprises a nucleic acid encoding the spacer comprising the sequence set forth in SEQ ID NO:136.

208. The polynucleotide of any of embodiments 178-184, 186 and 188-206 wherein said polynucleotide comprises a nucleic acid encoding the spacer comprising the sequence set forth in SEQ ID NO:139.

209. The polynucleotide of any of embodiments 178-184 and 187-206 wherein said polynucleotide comprises a nucleic acid encoding the spacer comprising the sequence set forth in SEQ ID NO:196.

210. The polynucleotide of any of embodiments 178-186 and 188-209, wherein said polynucleotide comprises the sequence set forth in SEQ ID NO: 156, 157, 158, 159, 160 or 161 or a sequence that exhibits at least 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 156, 157, 158, 159, 160 or 161.

211. The polynucleotide of any of embodiments 178-186 and 188-210, wherein said polynucleotide comprises the sequence set forth in SEQ ID NO: 156 or a sequence that exhibits at least 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 156.
212. The polynucleotide of any of embodiments 178-186 and 188-211, wherein said polynucleotide comprises the sequence set forth in SEQ ID NO: 156.
213. The polynucleotide of any of embodiments 178-186 and 188-210, wherein said polynucleotide comprises the sequence set forth in SEQ ID NO: 157 or a sequence that exhibits at least 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth in SEQ ID NO: 157.
214. The polynucleotide of any of embodiments 178-186, 188-210 and 213, wherein said polynucleotide comprises the sequence set forth in SEQ ID NO: 157.
215. The polynucleotide of any of embodiments 178-214, further comprising a CD33 signal sequence, a GM-CSF signal sequence, a CD8 signal sequence or an Ig kappa signal sequence.
216. The polynucleotide of any of embodiments 178-214, further comprising a CD33 signal sequence.
217. The polynucleotide of embodiment 215 or embodiment 216, wherein the CD33 signal sequence is set forth in SEQ ID NO:190 or a nucleic acid sequence having at least at or about 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO:190.
218. A vector, comprising the polynucleotide of any of embodiments 178-217.
219. The vector of embodiment 218, wherein the vector is a viral vector.
220. The vector of embodiment 219, wherein the viral vector is a retroviral vector or a lentiviral vector.
221. A cell comprising the anti-ROR1 antibody or antigen-binding fragment thereof of any of embodiments 1-53 and 244-265, the conjugate of embodiment 55 or embodiment 56, the single chain cell surface protein of embodiment 54, the anti-ROR1 chimeric antigen receptor of any of embodiments 57-177 and 266-297, the polynucleotide of any of embodiments 178-217, or the vector of any of 218-220.
222. The cell of embodiment 221, that is a lymphocyte.
223. The cell of embodiment 222, that is an NK cell or a T cell.
224. The cell of embodiment 222 or embodiment 223, wherein the cell is a T cell and the T cell is a CD4+ or a CD8+ T cell.
225. The cell of any of embodiments 221-224, wherein the cell is a primary cell obtained from a subject.
226. The cell of any of embodiments 221-225, wherein, among a plurality of the cells, less than at or about 10%, at or about 9%, at or about 8%, at or about 7%, at or about 5%, at or about 4%, at or about 3%, at or about 2% or at or about 1% of the cells in the plurality comprise an anti-ROR1 chimeric antigen receptor that exhibits tonic signaling and/or antigen independent activity or signaling.
227. A composition comprising the anti-ROR1 antibody or antigen-binding fragment thereof of any of embodiments 1-53 and 244-265, the conjugate of embodiment 55 or embodiment 56, the single chain cell surface protein of embodiment 54 or the anti-ROR1 chimeric antigen receptor of any of embodiments 57-177 and 266-297.
228. A composition comprising the cell of any of embodiments 221-226.
229. The composition of embodiment 227 or embodiment 228, further comprising a pharmaceutically acceptable excipient.
230. The composition of embodiment 228 or embodiment 229, wherein the composition comprises CD4+ and CD8+ T cells and the ratio of CD4+ to CD8+ T cells is from at or about 1:3 to 3:1, optionally at or about 1:2 to 2:1, optionally at or about 1:1.
231. The composition of any of embodiments 227-230, wherein, among a plurality of the cells, less than at or about 10%, at or about 9%, at or about 8%, at or about 7%, at or about 5%, at or about 4%, at or about 3%, at or about 2% or at or about 1% of the cells in the plurality comprise an anti-ROR1 chimeric antigen receptor that exhibits tonic signaling and/or antigen independent activity or signaling.
232. A method of treatment, comprising administering the composition of any of embodiments 227-231 to a subject having a disease or disorder associated with ROR1.
233. A method of treatment, comprising administering the anti-ROR1 antibody or antigen-binding fragment thereof of any of embodiments 1-53 and 244-265, the conjugate of embodiment 55 or embodiment 56, the single chain cell surface protein of embodiment 54, the anti-ROR1 chimeric antigen receptor of any of embodiments 57-177 and 266-297, the polynucleotide of any of embodiments 178-217, the vector of any of 218-220 or the cell of any of embodiments 221-226 to a subject having a disease or disorder associated with ROR1.
234. A composition of any of embodiments 227-231 for use in treating a disease or disorder associated with ROR1.
235. Use of a composition of any of embodiments 227-231 for the manufacture of a medicament for treating a disease or disorder associated with ROR1.
236. Use of a composition of any of embodiments 227-231 for the treatment of a disease or disorder associated with ROR1.
237. The method, the composition for use or the use of any of embodiments 232-236 and 298-311, wherein the disease or disorder associated with ROR1 is associated with ROR1 expression.
238. The method, the composition for use or the use of any of embodiments 232-237 and 298-311, wherein the disease or disorder associated with ROR1 is a B cell-related disorder.
239. The method, the composition for use or the use of any of embodiments 232-238 and 298-311, wherein the disease or disorder associated with ROR1 is a cancer.
240. The method, the composition for use or the use of embodiment 239, wherein the cancer is a ROR1-expressing cancer.
241. The method, the composition for use or the use of embodiment 240, wherein the ROR1-expressing cancer is selected from the group consisting of B cell leukemia, lymphoma, B cell chronic lymphocytic leukemia (CLL), acute myeloid leukemia (AML), acute lymphocytic leukemia (ALL), Burkitt's Lymphoma, mantle cell lymphoma (MCL), non-small cell lung cancer (NSCLC), neuroblastoma, renal cell carcinoma, colon cancer, colorectal cancer, breast cancer, epithelial squamous cell cancer, melanoma, myeloma, stomach cancer, brain cancer, lung cancer, pancreatic cancer, cervical cancer, ovarian cancer, liver cancer, bladder cancer, prostate cancer, testicular cancer, thyroid cancer, uterine cancer, adrenal cancer and head and neck cancer.

242. A kit comprising the anti-ROR1 antibody or antigen-binding fragment thereof of any of embodiments 1-53 and 244-265, the single chain cell surface protein of embodiment 54, the conjugate of embodiment 55 or embodiment 56, the anti-ROR1 chimeric antigen receptor of any of embodiments 57-177 and 266-297, the cell of embodiment 221-226 or the composition of any of embodiments 227-231, and instructions for use, optionally wherein the instructions are for administering the anti-ROR1 antibody or antigen-binding fragment thereof, the single chain cell surface protein, the conjugate, the anti-ROR1 chimeric antigen receptor, the cell or the composition, optionally in accord with the method, the composition for use or the use of any of embodiments 234-241 and 298-311.

243. An article of manufacture comprising the anti-ROR1 antibody or antigen-binding fragment thereof of any of embodiments 1-53 and 244-265, the single chain cell surface protein of embodiment 54, the conjugate of embodiment 55 or embodiment 56, the anti-ROR1 chimeric antigen receptor of any of embodiments 57-177 and 266-297, the cell of embodiment 221-226, the composition of any of embodiments 227-231 or the kit of embodiment 242.

244. The anti-ROR1 antibody or antigen-binding fragment thereof of any of embodiments 1-53, wherein the $V_H$ region comprises a CDR-H1, a CDR-H2 and a CDR-H3 comprising the sequence set forth in SEQ ID NOS:52, 56 and 58, respectively, and the $V_L$ region comprises a CDR-L1, a CDR-L2 and a CDR-L3 comprising the sequence set forth in SEQ ID NOS:60, 62 and 64, respectively.

245. The anti-ROR1 antibody or antigen-binding fragment thereof of any of embodiments 1-53, wherein the $V_H$ region comprises a CDR-H1, a CDR-H2 and a CDR-H3 comprising the sequence set forth in SEQ ID NOS:52, 97 and 99, respectively, and the $V_L$ region comprises a CDR-L1, a CDR-L2 and a CDR-L3 comprising the sequence set forth in SEQ ID NOS:60, 62 and 64, respectively.

246. The anti-ROR1 antibody or antigen-binding fragment thereof of any of embodiments 1-53, wherein the $V_H$ region comprises a CDR-H1, a CDR-H2 and a CDR-H3 contained within SEQ ID NO:103, and the $V_L$ region comprises a CDR-L1, a CDR-L2 and a CDR-L3 contained within SEQ ID: NO 106.

247. The anti-ROR1 antibody or antigen-binding fragment thereof of any of embodiments 1-53, wherein the $V_H$ region comprises a CDR-H1, a CDR-H2 and a CDR-H3 contained within SEQ ID NO:130, and the $V_L$ region comprises a CDR-L1, a CDR-L2 and a CDR-L3 contained within SEQ ID: NO 106.

248. The anti-ROR1 antibody or antigen-binding fragment thereof of any of embodiments 1-53, wherein the $V_H$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:103, and the $V_L$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:106.

249. The anti-ROR1 antibody or antigen-binding fragment thereof of any of embodiments 1-53, wherein the $V_H$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:130, and the $V_L$ region is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:106.

250. The anti-ROR1 antibody or antigen-binding fragment thereof of any of embodiments 1-53, wherein the $V_H$ region and the $V_L$ region are or comprise the sequence set forth in SEQ ID NOS: 103 and 106, respectively.

251. The anti-ROR1 antibody or antigen-binding fragment thereof of any of embodiments 1-53, wherein the $V_H$ region and the $V_L$ region are or comprise the sequence set forth in SEQ ID NOS:130 and 106, respectively.

252. The anti-ROR1 antibody or antigen-binding fragment thereof of any of embodiments 1-53 and 244-251, wherein the antibody is a full length antibody.

253. The anti-ROR1 antibody or antigen-binding fragment thereof of any of embodiments 1-53 and 244-251, wherein the antibody is an antigen-binding fragment.

254. The anti-ROR1 antibody or antigen-binding fragment thereof of any of embodiments 1-53 and 244-253, wherein said anti-ROR1 antibody or antigen-binding fragment thereof is recombinant.

255. The anti-ROR1 antibody or antigen-binding fragment thereof of any of embodiments 1-53 and 244-254, wherein the $V_H$ region and the $V_L$ region is human or is from a human protein.

256. The anti-ROR1 antibody or antigen-binding fragment thereof of any of embodiments 1-53 and 244-255, wherein the scFv is or comprises the sequence set forth in SEQ ID NO: 109.

257. The anti-ROR1 antibody or antigen-binding fragment thereof of any of embodiments 1-53 and 244-255, wherein the scFv is or comprises the sequence set forth in SEQ ID NO: 134.

258. The anti-ROR1 antibody or antigen-binding fragment thereof of any of embodiments 1-53 and 244-257, wherein said anti-ROR1 antibody or antigen-binding fragment thereof specifically binds to an epitope consisting of the sequence set forth in SEQ ID NO:199 or an epitope present within the sequence set forth in SEQ ID NO:199.

259. The anti-ROR1 antibody or antigen-binding fragment thereof of any of embodiments 1-53 and 244-257, wherein the antibody or antigen-binding fragment thereof further binds to one or more epitopes consisting of a sequence selected from among any one of SEQ ID NOS: 200-214 or an epitope present within a sequence selected from among any one of SEQ ID NOS: 200-214.

260. The anti-ROR1 antibody or antigen-binding fragment thereof of any of embodiments 1-53 and 244-259, wherein the antibody or antigen-binding fragment thereof binds to human ROR1 protein with an equilibrium dissociation constant ($K_D$) of from about $1\times10^{-11}$ M to about $1\times10^{-7}$ M.

261. The anti-ROR1 antibody or antigen-binding fragment thereof of any of embodiments 1-53 and 244-260, wherein the antibody or antigen-binding fragment thereof binds to human ROR1 protein with an equilibrium dissociation constant ($K_D$) of from about $1\times10^{-8}$ M to about $1\times10^{-7}$ M.

262. The anti-ROR1 antibody or antigen-binding fragment thereof of any of embodiments 1-53 and 244-260, wherein the antibody or antigen-binding fragment thereof binds to human ROR1 protein with an equilibrium dissociation constant ($K_D$) of from about $5 \times 10^{-11}$ M to about $1 \times 10^{10}$ M.

263. The anti-ROR1 antibody or antigen-binding fragment thereof of any of embodiments 1-53 and 244-262, wherein the antibody or antigen-binding fragment thereof binds to human ROR1 protein with a dissociation rate constant ($k_d$ or $k_{off}$) of from about $1 \times 10^{-5}$ 1/s to about $1 \times 10^{-2}$ 1/s.

264. The anti-ROR1 antibody or antigen-binding fragment thereof of any of embodiments 1-53 and 244-263, wherein the antibody or antigen-binding fragment thereof binds to human ROR1 protein with a dissociation rate constant ($k_d$ or $k_{off}$) of from about $1 \times 10^{-3}$ 1/s to about $1 \times 10^{-2}$ 1/s.

265. The anti-ROR1 antibody or antigen-binding fragment thereof of any of embodiments 1-53 and 244-263, wherein the antibody or antigen-binding fragment thereof binds to human ROR1 protein with a dissociation rate constant ($k_d$ or $k_{off}$) of from about $1 \times 10^{-5}$ 1/s to about $1 \times 10^{-4}$ 1/s.

266. The anti-ROR1 chimeric antigen receptor of any of embodiments 57-177, wherein the at least a portion of a hinge region comprises all or a portion of an IgG4 hinge region, optionally a human IgG4 hinge region, or a variant thereof.

267. The anti-ROR1 chimeric antigen receptor of any of embodiments 57-177, wherein the at least a portion of a hinge region comprises all or a portion of an IgG2 hinge region, optionally a human IgG2 hinge region, or a variant thereof.

268. The anti-ROR1 chimeric antigen receptor of any of embodiments 57-177, wherein the spacer is or comprises the sequence set forth in SEQ ID NO: 1.

269. The anti-ROR1 chimeric antigen receptor of any of embodiments 57-177, wherein the spacer is or comprises the sequence set forth in SEQ ID NO: 135.

270. The anti-ROR1 chimeric antigen receptor of any of embodiments 57-177, wherein the spacer comprises at least a portion of a hinge region and at least a portion of a CH3 region of an immunoglobulin or a variant thereof.

271. The anti-ROR1 chimeric antigen receptor of any of embodiments 57-177 and 270, wherein the at least a portion of a CH3 region comprises all or a portion of an IgG4 CH3 and/or an IgG2 CH3, wherein the IgG4 CH3 is optionally a human IgG4 CH3 and the IgG2 CH3 is optionally a human IgG2 CH3.

272. The anti-ROR1 chimeric antigen receptor of any of embodiments 57-177, 270 and 271, wherein the spacer is at or about 111, 112, 113, 114, 115, 116, 117, 118, 119, 120, 121, 122, 123, 124 or 125 amino acids in length, or has a length between any of the foregoing.

273. The anti-ROR1 chimeric antigen receptor of any of embodiments 57-177 and 270-272, wherein the spacer is at or about 120 amino acids in length.

274. The anti-ROR1 chimeric antigen receptor of any of embodiments 57-177 and 270-273, wherein the spacer is or comprises an amino acid sequence having at least at or about 85%, 86%, 87%, 88%, 89%, 90%, 91%, 92%, 93%, 94%, 95%, 96%, 97%, 98% or 99% identity to SEQ ID NO: 3 or 138.

275. The anti-ROR1 chimeric antigen receptor of any of embodiments 57-177 and 270-274, wherein the spacer is or comprises the sequence set forth in SEQ ID NO: 3 or 138.

276. The anti-ROR1 chimeric antigen receptor of any of embodiments 57-177, wherein the spacer comprises at least a portion of a hinge region, at least a portion of a CH2 and at least a portion of a CH3 region of an immunoglobulin or a variant thereof.

277. The anti-ROR1 chimeric antigen receptor of any of embodiments 57-177 and 276, wherein the at least a portion of a CH2 region comprises all or a portion of an IgG4 CH2 and/or an IgG2 CH2, wherein the IgG4 CH2 is optionally a human IgG4 CH2 and the IgG2 CH2 is optionally a human IgG2 CH2.

278. The anti-ROR1 chimeric antigen receptor of any of embodiments 57-177, 276 and 277, wherein the spacer is at or about 130, 140, 150, 160, 170, 180, 190, 200, 210, 220, 221, 222, 223, 224, 225, 226, 227, 228, 229 or 230 amino acids in length, or has a length between any of the foregoing.

279. The anti-ROR1 chimeric antigen receptor of any of embodiments 57-177 and 276-278, wherein:
one or more of the hinge region, the CH2 region and the CH3 region comprises all or a portion of a CH2 region and all or a portion of a CH3 region from human IgG4; or
one or more of the hinge region, the CH2 region and the CH3 region is chimeric and comprises a hinge, a CH2 region and a CH3 region from human IgG4 and human IgG2; or the spacer comprises a IgG4/2 chimeric hinge region or a modified IgG4 hinge region comprising at least one amino acid replacement compared to a human IgG4 hinge; an IgG2/4 chimeric CH2 region; and an IgG4 CH3 region.

280. The anti-ROR1 chimeric antigen receptor of any of embodiments 57-177 and 276-279, wherein the spacer is or comprises an amino acid sequence having at least at or about 85%, 86%, 87%, 88%, 89%, 90%, 91%, 92%, 93%, 94%, 95%, 96%, 97%, 98% or 99% identity to SEQ ID NO:37 or 194.

281. The anti-ROR1 chimeric antigen receptor of any of embodiments 57-177 and 276-280, wherein the spacer is or comprises the sequence set forth in SEQ ID NO: 37 or 194.

282. The anti-ROR1 chimeric antigen receptor of any of embodiments 57-177 and 266-281, wherein the transmembrane region is or comprises a transmembrane domain from CD4, CD28, or CD8.

283. The anti-ROR1 chimeric antigen receptor of any of embodiments 57-177 and 266-282, wherein the transmembrane region is or comprises a transmembrane domain from CD28, optionally a human CD28.

284. The anti-ROR1 chimeric antigen receptor of any of embodiments 57-177 and 266-283, wherein the transmembrane domain is or comprises SEQ ID NO: 8 or 149 or an amino acid sequence having at least at or about 90%, 91%, 92%, 93%, 94%, 95%, 96%, 97%, 98% or 99% sequence identity to SEQ ID NO: 8 or 149.

285. The anti-ROR1 chimeric antigen receptor of any of embodiments 57-177 and 266-284, wherein the intracellular signaling region further comprises a costimulatory signaling region.

286. The anti-ROR1 chimeric antigen receptor of any of embodiments 57-177 and 266-285, wherein the anti-ROR1 chimeric antigen receptor is or comprises the sequence set forth in SEQ ID NO: 184, 185, 186, 187, 188 or 189 or a sequence that exhibits at least 85%, 86%, 87%, 88%, 89%, 90%, 91%, 92%, 93%, 94%, 95%, 96%, 97%, 98%, or 99% sequence identity to the sequence set forth in SEQ ID NO: 184, 185, 186, 187, 188 or 189.

287. The anti-ROR1 chimeric antigen receptor of any of embodiments 57-177 and 266-286, wherein the anti-ROR1 chimeric antigen receptor is or comprises the sequence set forth in SEQ ID NO: 184 or a sequence that exhibits at least 85%, 86%, 87%, 88%, 89%, 90%, 91%, 92%, 93%, 94%, 95%, 96%, 97%, 98%, or 99% sequence identity to the sequence set forth in SEQ ID NO: 184.

288. The anti-ROR1 chimeric antigen receptor of any of embodiments 57-177 and 266-286, wherein the anti-ROR1 chimeric antigen receptor is or comprises the sequence set forth in SEQ ID NO: 184.

289. The anti-ROR1 chimeric antigen receptor of any of embodiments 57-177 and 266-286, wherein the anti-ROR1 chimeric antigen receptor is or comprises the sequence set forth in SEQ ID NO: 185 or a sequence that exhibits at least 85%, 86%, 87%, 88%, 89%, 90%, 91%, 92%, 93%, 94%, 95%, 96%, 97%, 98%, or 99% sequence identity to the sequence set forth in SEQ ID NO:185.

290. The anti-ROR1 chimeric antigen receptor of any of embodiments 57-177 and 266-286, wherein the anti-ROR1 chimeric antigen receptor is or comprises the sequence set forth in SEQ ID NO: 185.

291. The anti-ROR1 chimeric antigen receptor of any of embodiments 57-177 and 266-286, wherein the anti-ROR1 chimeric antigen receptor is or comprises the sequence set forth in SEQ ID NO: 186 or a sequence that exhibits at least 85%, 86%, 87%, 88%, 89%, 90%, 91%, 92%, 93%, 94%, 95%, 96%, 97%, 98%, or 99% sequence identity to the sequence set forth in SEQ ID NO: 186.

292. The anti-ROR1 chimeric antigen receptor of any of embodiments 57-177 and 266-286, wherein the anti-ROR1 chimeric antigen receptor is or comprises the sequence set forth in SEQ ID NO: 186.

293. The anti-ROR1 chimeric antigen receptor of any of embodiments 57-177 and 266-286, wherein the anti-ROR1 chimeric antigen receptor is or comprises the sequence set forth in SEQ ID NO: 187 or a sequence that exhibits at least 85%, 86%, 87%, 88%, 89%, 90%, 91%, 92%, 93%, 94%, 95%, 96%, 97%, 98%, or 99% sequence identity to the sequence set forth in SEQ ID NO:187.

294. The anti-ROR1 chimeric antigen receptor of any of embodiments 57-177 and 266-286, wherein the anti-ROR1 chimeric antigen receptor is or comprises the sequence set forth in SEQ ID NO: 187.

295. The anti-ROR1 chimeric antigen receptor of any of embodiments 57-177 and 266-286, wherein the anti-ROR1 chimeric antigen receptor is or comprises the sequence set forth in SEQ ID NO: 188 or a sequence that exhibits at least 85%, 86%, 87%, 88%, 89%, 90%, 91%, 92%, 93%, 94%, 95%, 96%, 97%, 98%, or 99% sequence identity to the sequence set forth in SEQ ID NO: 188.

296. The anti-ROR1 chimeric antigen receptor of any of embodiments 57-177 and 266-286, wherein the anti-ROR1 chimeric antigen receptor is or comprises the sequence set forth in SEQ ID NO: 188.

297. The anti-ROR1 chimeric antigen receptor of any of embodiments 57-177 and 266-286, wherein the anti-ROR1 chimeric antigen receptor is or comprises the sequence set forth in SEQ ID NO: 189 or a sequence that exhibits at least 85%, 86%, 87%, 88%, 89%, 90%, 91%, 92%, 93%, 94%, 95%, 96%, 97%, 98%, or 99% sequence identity to the sequence set forth in SEQ ID NO:189.

298. A method of treatment, comprising administering the cell of any of embodiments 221-226 or the composition of any of embodiments 227-231 to a subject having a disease or disorder associated with ROR1.

299. The cell of any of embodiments 221-226 or the composition of any of embodiments 227-231 for use in treating a disease or disorder associated with ROR1.

300. Use of the cell of any of embodiments 221-226 or the composition of any of embodiments 227-231 for the manufacture of a medicament for treating a disease or disorder associated with ROR1.

301. Use of the cell of any of embodiments 221-226 or the composition of any of embodiments 227-231 for the treatment of a disease or disorder associated with ROR1.

302. The method, the cell, composition, antibody or antigen-binding fragment thereof, single chain cell surface protein, conjugate, chimeric antigen receptor, polynucleotide or vector for use or the use of any of embodiments 232-241 and 298-302, wherein the disease or disorder associated with ROR1 is a cancer.

303. The method, the cell, composition, antibody or antigen-binding fragment thereof, single chain cell surface protein, conjugate, chimeric antigen receptor, polynucleotide or vector for use or the use of embodiment 302, wherein the cancer is a ROR1-expressing cancer.

304. The method, the cell, composition, antibody or antigen-binding fragment thereof, single chain cell surface protein, conjugate, chimeric antigen receptor, polynucleotide or vector for use or the use of any of embodiments 232-241 and 298-303, wherein the cancer is associated with a ROR1-expressing solid tumor or a ROR1-expressing hematologic malignancy.

305. The method, the cell, composition, antibody or antigen-binding fragment thereof, single chain cell surface protein, conjugate, chimeric antigen receptor, polynucleotide or vector for use or the use of any of embodiments 232-241 and 298-304, wherein the cancer is associated with a ROR1-expressing solid tumor.

306. The method, the cell, composition, antibody or antigen-binding fragment thereof, single chain cell surface protein, conjugate, chimeric antigen receptor, polynucleotide or vector for use or the use of embodiment 304 or embodiment 305, wherein the cancer associated with a solid tumor is selected from the group consisting of neuroblastoma, renal cell carcinoma, colon cancer, colorectal cancer, breast cancer, epithelial squamous cell cancer, melanoma, myeloma, stomach cancer, brain cancer, lung cancer, pancreatic cancer, cervical cancer, ovarian cancer, liver cancer, bladder cancer, prostate cancer, testicular cancer, thyroid cancer, uterine cancer, adrenal cancer and head and neck cancer.

307. The method, the cell, composition, antibody or antigen-binding fragment thereof, single chain cell surface protein, conjugate, chimeric antigen receptor, polynucleotide or vector for use or the use of embodiment 306, wherein the lung cancer is a non-small cell lung cancer (NSCLC), lung adenocarcinoma, adenocarcinoma, squamous cell carcinoma, small cell carcinoma, and atypical carcinoid.

308. The method, the cell, composition, antibody or antigen-binding fragment thereof, single chain cell surface protein, conjugate, chimeric antigen receptor, polynucleotide or vector for use or the use of embodiment 307, wherein the lung cancer is a NSCLC.

309. The method, the cell, composition, antibody or antigen-binding fragment thereof, single chain cell surface protein, conjugate, chimeric antigen receptor, polynucleotide or vector for use or the use of embodiment 306, wherein the breast cancer is a triple negative breast cancer (TNBC).

310. The method, the cell, composition, antibody or antigen-binding fragment thereof, single chain cell surface protein, conjugate, chimeric antigen receptor, polynucleotide or vector for use or the use of any of embodiments 232-241 and 298-304, wherein the cancer is associated with a ROR1-expressing hematologic malignancy.

311. The method, the cell, composition, antibody or antigen-binding fragment thereof, single chain cell surface protein, conjugate, chimeric antigen receptor, polynucleotide or vector for use or the use of embodiment 310, wherein the hematologic malignancy is selected from the group consisting of B cell leukemia, lymphoma, B cell chronic lymphocytic leukemia (CLL), acute myeloid leukemia (AML), acute lymphocytic leukemia (ALL), Burkitt's Lymphoma or mantle cell lymphoma (MCL).

VIII. Examples

The following examples are included for illustrative purposes only and are not intended to limit the scope of the invention.

Example 1: Generation and Assessment of Anti-ROR1 Antibodies

Exemplary anti-receptor tyrosine kinase-like orphan receptor 1 (ROR1) antibodies that specifically bind to ROR1-expressing cells were generated by immunization of genetically engineered mice and assessed.

A. Antibody Generation

Mice that were genetically modified to produce antibodies containing fully human antibody variable regions (Trianni, Inc., San Francisco, CA) were immunized with recombinant extracellular domain (ECD) of human ROR1 fused to a histidine tag. The spleen, lymph nodes and bone marrow were harvested, and ROR1 specific memory B cells and plasma cells were enriched by immunoaffinity-based selection.

Cell populations from the enriched fractions were subject to high-throughput single-cell paired sequencing of antibody variable heavy ($V_H$) chain and variable light ($V_L$) chain. High throughput single cell antibody sequencing was performed as generally described in WO2012/048340, WO2012/048341, WO2016/044227 and WO2016/176322. The sequencing methods employed single-cell droplets, with droplet and molecular barcodes, to identify individual pairs of antibody $V_H$ and $V_L$ sequences at a single-cell level, for each of a large number of single cells present in a population of cells. Antibody $V_H/V_L$ pair sequences were selected for synthesis and polynucleotides encoding each of the paired candidates were synthesized as a single chain Fv fragment (scFv), in either a $V_H$ and $V_L$ chain orientation ($V_H$-$V_L$) or a $V_L$-$V_H$ orientation.

B. Anti-ROR1 Chimeric Antigen Receptor (CAR) Generation

The synthesized scFv-encoding sequences were cloned into an exemplary polynucleotide construct to generate candidate polynucleotides encoding chimeric antigen receptors (CARs) containing the candidate scFvs as the antigen-binding domains. Specifically, the polynucleotide CAR constructs contained nucleic acid sequences encoding a signal peptide; a candidate anti-ROR1 scFv; a spacer from among three exemplary spacers: a spacer containing a modified IgG4/IgG2-hinge $C_H2$-CH3 (SEQ ID NO:194), a spacer containing a modified IgG4 hinge-$C_H3$ (SEQ ID NO:138), or a spacer containing a modified IgG4 hinge region (SEQ ID NO:135); a human CD28 transmembrane domain; a human 4-1BB intracellular signaling region; and a human CD3-zeta intracellular signaling region. The constructs also contained a downstream T2A ribosomal skip elements (SEQ ID NO: 6) between the CAR-encoding sequences and sequences encoding a green fluorescent protein for use as a transduction marker. Polynucleotides encoding the CARs were cloned into a lentiviral expression vector for transduction of T cells.

C. Assessment of Candidate Anti-ROR1 CARs

Approximately 400 candidate anti-ROR1 CAR-encoding constructs were generated as described above and viral preparations containing constructs encoding the various candidate anti-ROR1 CARs were individually introduced into a Jurkat T cell line containing a Nur77 knock-in reporter (see e.g. WO 2019/089982). The Nur77 knock-in cell line contained nucleic acid sequences encoding a reporter molecule (e.g., a red fluorescent protein) knocked-in at the endogenous Nur77 locus, which is an immediate-early response gene induced by stimulation of signal from the T cell receptor and/or via molecules containing immunoreceptor tyrosine-based activation motif (ITAM). The Jurkat reporter cells were assessed for cell surface expression of the CAR, antigen-dependent and antigen-independent signaling and cross-reactivity to a related but distinct antigen ROR2.

After transduction, the reporter cells were evaluated for the expression of red fluorescent protein after co-culture with target cells, including K562 human myelogenous leukemia cells (ROR1 negative), K562 cells transduced to express a high level of ROR1, K562 cells transduced to express a low level of ROR1, and K562 cells expressing the non-specific antigen ROR2. To further assess antigen-independent activity, transduced reporter cells were cultured alone in the absence of antigen-expressing target cells. The transduced reporter cells were also assessed for GFP expression (transduction marker), and for binding of soluble recombinant ROR1-Fc (soluble human ROR1 fused to an Fc region of an IgG).

Jurkat reporter cells transduced with candidate anti-ROR1 CARs exhibited varying levels of antigen-specific activity, as indicated by reporter expression after co-culture with ROR1-expressing target cells expressing high or low levels of ROR1; varying levels of antigen-independent (tonic) signaling, as indicated by reporter expression after co-culture with K562 cells not expressing ROR1 or after culture without antigen-expressing target cells; varying levels of non-specific activity, as indicated by reporter expression after co-culture with cells expressing the non-specific antigen ROR2; and varying levels of binding by soluble ROR1-Fc. Candidate CARs that exhibited high ROR1 antigen-dependent activity, low tonic signaling, high ROR1-Fc binding and low ROR2 cross-reactivity were selected for assessment in primary human T cells.

Example 2: Assessment of CAR Expression and Function in Primary T Cells

The expression and function of selected anti-ROR1 CARs, described in Example 1, were assessed in primary human T cells.

CD4+ and CD8+ T cells were isolated by immunoaffinity-based enrichment from leukapheresis samples of one of three human donors. Isolated CD4+ and CD8+ T cells were mixed at approximately 1:1 ratio, stimulated and transduced with lentiviral preparations encoding one of the anti-ROR1 CARs selected as described in Example 1 (designated individually one of A-Z and A1-M1) and cultivated under conditions for expansion. The three human donors varied in the percentage of T cell subsets present in the leukapheresis sample (e.g. less than 15% naive T cells, about 40-60% naive T cells or about 20% effector memory RA T cells ($T_{EMRA}$)), representing variability in T cell subsets among disease subjects. As controls, primary T cells also were similarly stimulated and transduced with lentiviral preparations encoding an anti-CD19 CAR, a reference anti-ROR1 CAR (a rabbit-derived reference antibody R12, scFv set forth in SEQ ID NO:143) or one of two anti-ROR1 CARs obtained from a different source (designated N1, O1).

The CAR-expressing primary T cells were stimulated with plate-bound ROR1-Fc, and after 24 hours were assessed by flow cytometry for intracellular levels of IFN-γ, TNF-α and IL-2 by intracellular cytokine staining (ICS). The percentage of cells producing IFN-γ, TNF-α and IL-2, and the level of production per cell (as determined by the mean fluorescence intensity (MFI)) were determined. After stimulation, the CAR-expressing primary T cells were also stained for cell surface expression of T cell activation markers (e.g., CD25), costimulatory markers, markers indicative of certain T cell subtypes, such as memory cell subtypes, other T cell markers, e.g., CD4 and CD8, ROR1-Fc binding, and assessed for expression of the GFP transduction marker.

CAR-expressing primary T cells also were stimulated by co-culture with ROR1-expressing triple-negative human breast cancer cell line (MDA-MB-231 (ATCC® HTB-26™), at an effector:target (E:T) ratio of 1:4, and assessed for cytotoxicity and cytokine production. The MDA-MB-231 cell line was labeled with NucLight Red (NLR) to permit tracking of target cells by microscopy. Cytolytic activity was assessed by measuring the loss of viable target cells over a period of between 0 and 72 hours, as determined by changes in red fluorescent signal. The production of cytokines IFN-γ, TNF-α and IL-2 in the supernatant was also assessed.

Figure 1:
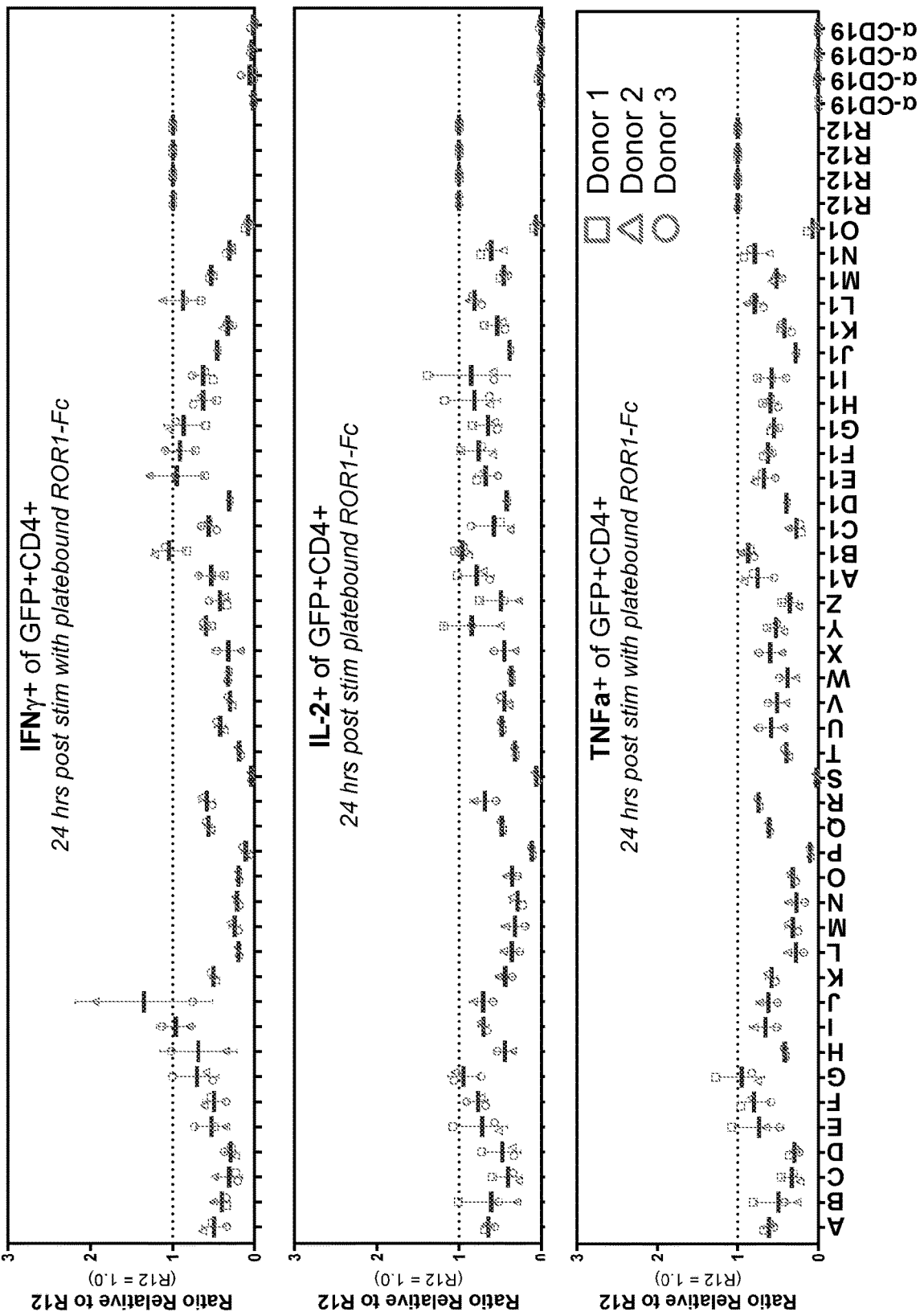
FIG. 1 depicts the relative intracellular TFN-γ, TNF-α or IL-2 expression levels by ICS in GFP+ CD4+ T cells compared to the levels of each cytokine in cells expressing the reference anti-ROR1 (R12) CAR, after 24 hours stimulation with plate-bound recombinant ROR1-Fc, in primary T cells expressing select candidate anti-ROR1 CAR-expressing T cells from a screen as described in Example 1.
Figure 2:
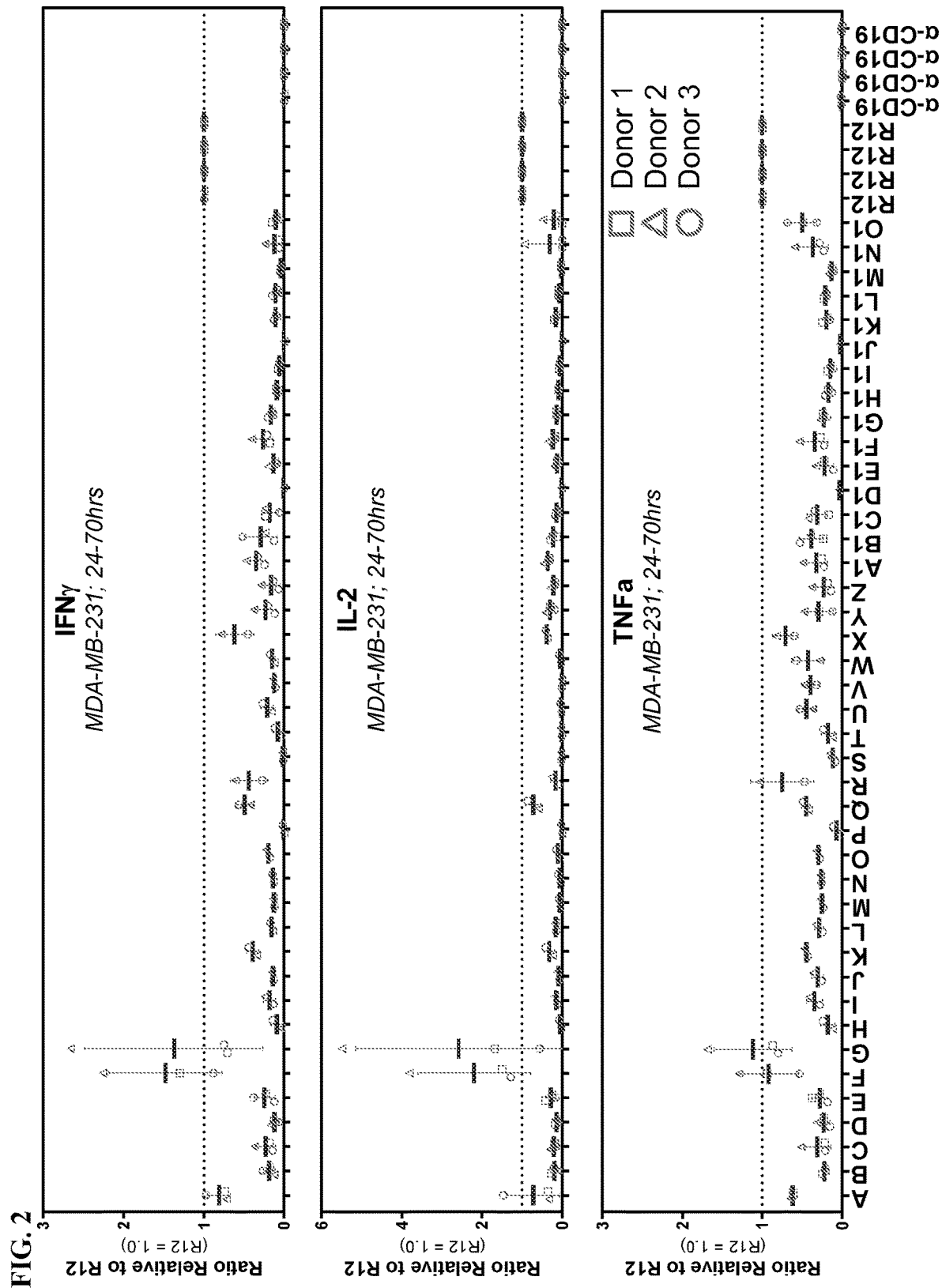
FIG. 2 shows the relative intracellular TFN-γ, TNF-α or IL-2 expression levels by ICS in primary T cells expressing select candidate anti-ROR1 CAR-expressing T cells from a screen as described in Example 1, compared to the levels of each cytokine in cells expressing the reference anti-ROR1 (R12) CAR, after 24-70 hour co-culture with MDA-MB-231 target cells expressing ROR1.

As shown in FIG. 1, certain candidate anti-ROR1 CAR-expressing T cells exhibited comparable or greater relative intracellular TFN-γ, TNF-α or IL-2 expression levels by ICS in GFP+ CD4+ T cells compared to the levels of each cytokine in cells expressing the reference anti-ROR1 (R12) CAR, after 24 hours stimulation with plate-bound recombinant ROR1-Fc. In the co-culture assay with MDA-MB-231 target cells expressing ROR1, certain selected candidates also exhibited comparable or greater IFN-γ, TNF-α or IL-2 secretion compared to cytokine secretion in cells expressing the reference anti-ROR1 (R12) CAR, as shown in FIG. 2. Fewer anti-ROR1 candidates exhibited comparable or greater cytokine secretion compared to reference anti-ROR1 (R12) CAR in the co-culture assay, compared to the number of anti-ROR1 candidates that showed comparable or greater cytokine expression levels by ICS.

These results showed varied responses by primary human T cells engineered to express the candidate anti-ROR1 CARs after stimulation by recombinant antigen or antigen-expressing target cells.

Example 3: Polynucleotide Optimization of Selected Anti-ROR1 Chimeric Antigen Receptors (CARs)

Among the candidate anti-ROR1 CARs, six (6) candidate CARs were further selected based on results of assessment of functional activity in engineered primary human T cells from the 3 different donors as described in Example 2. The constructs encoding the selected candidate CARs were subject to codon-optimization (CO) and assessed for potential splice sites and modified in a conservative manner, such as by not altering the encoded amino acid sequence, including elimination of potential predicted splice sites (SSE) in the polynucleotide construct encoding the CAR. The constructs were further modified to replace the GFP transduction marker with a truncated receptor as a surrogate transduction marker for CAR expression.

Table E1 lists sequence identifiers (SEQ ID NO:) corresponding to amino acid (aa) sequences of the of the antigen-binding domains of the selected candidate CARs, including amino acid sequences of the corresponding variable heavy ($V_H$) chain and variable light ($V_L$) chain, and complementarity determining regions (CDRs, by Kabat numbering) of each chain. The sequence identifier (SEQ ID NO:) of the $V_H$ and $V_L$ chain of the reference R12 CAR also is set forth in Table E1. The exemplary CARs contained an scFv having the $V_H$-$V_L$ orientation.

TABLE E1

Sequence identifier (SEQ ID NO:) for Exemplary Candidate CARs

| | | Nucleic Acid (codon optimized and splice site eliminated) | | | | Amino Acid (CDR Kabat numbering) | | | | | | | | |
|---|---|---|---|---|---|---|---|---|---|---|---|---|---|---|
| CAR | scFv # | $V_H$ | $V_L$ | scFv | spacer | $V_H$ | CDR-H1 | CDR-H2 | CDR-H3 | VL | CDR-L1 | CDR-L2 | CDR-L3 | scFv | spacer |
| A | ROR1-2 | 120 | 123 | 126 | 136 | 121 | 82 | 86 | 88 | 124 | 90 | 92 | 94 | 127 | 135 |
| F | ROR1-1 | 111 | 114 | 117 | 136 | 112 | 67 | 71 | 73 | 115 | 75 | 77 | 79 | 118 | 135 |
| G | ROR1-1 | 111 | 114 | 117 | 139 | 112 | 67 | 71 | 73 | 115 | 75 | 77 | 79 | 118 | 138 |
| I | ROR1-3 | 102 | 105 | 108 | 139 | 103 | 52 | 56 | 58 | 106 | 60 | 62 | 64 | 109 | 138 |
| R | ROR1-2 | 120 | 123 | 126 | 139 | 121 | 82 | 86 | 88 | 124 | 90 | 92 | 94 | 127 | 138 |
| B1 | ROR1-4 | 129 | 131 | 133 | 139 | 130 | 52 | 97 | 99 | 106 | 60 | 62 | 64 | 134 | 138 |
| R12 | | | | | | | | | | | | | | 142 | |

To assess activity of CARs encoded by the polynucleotides, CD4+ and CD8+ T cells isolated by immunoaffinity-based enrichment from leukapheresis samples from two (2) human donor subjects were stimulated and transduced with lentiviral preparations encoding one of the 6 candidate CARs or the reference anti-ROR1 (R12) CAR as a control.

The cells expressing the candidate CARs were co-cultured with a ROR1-expressing human non-small cell lung cancer cell line H1975 (ATCC® CRL-5908™) labeled with NucLight Red (NLR), and cytotoxicity and cytokine production was assessed. Cytolytic activity was assessed by measuring the loss of viable target cells over a period of between 0 and 70 hours, as determined by changes in red fluorescent signal. The production of cytokines TNF-α, TNF-α and IL-2 in the supernatant was also assessed after 70 hours of co-culture. As controls, cultures of target cells only and co-cultures of mock cells (not expressing a CAR) with the target cells were assessed.

Figures 3A, 3B:
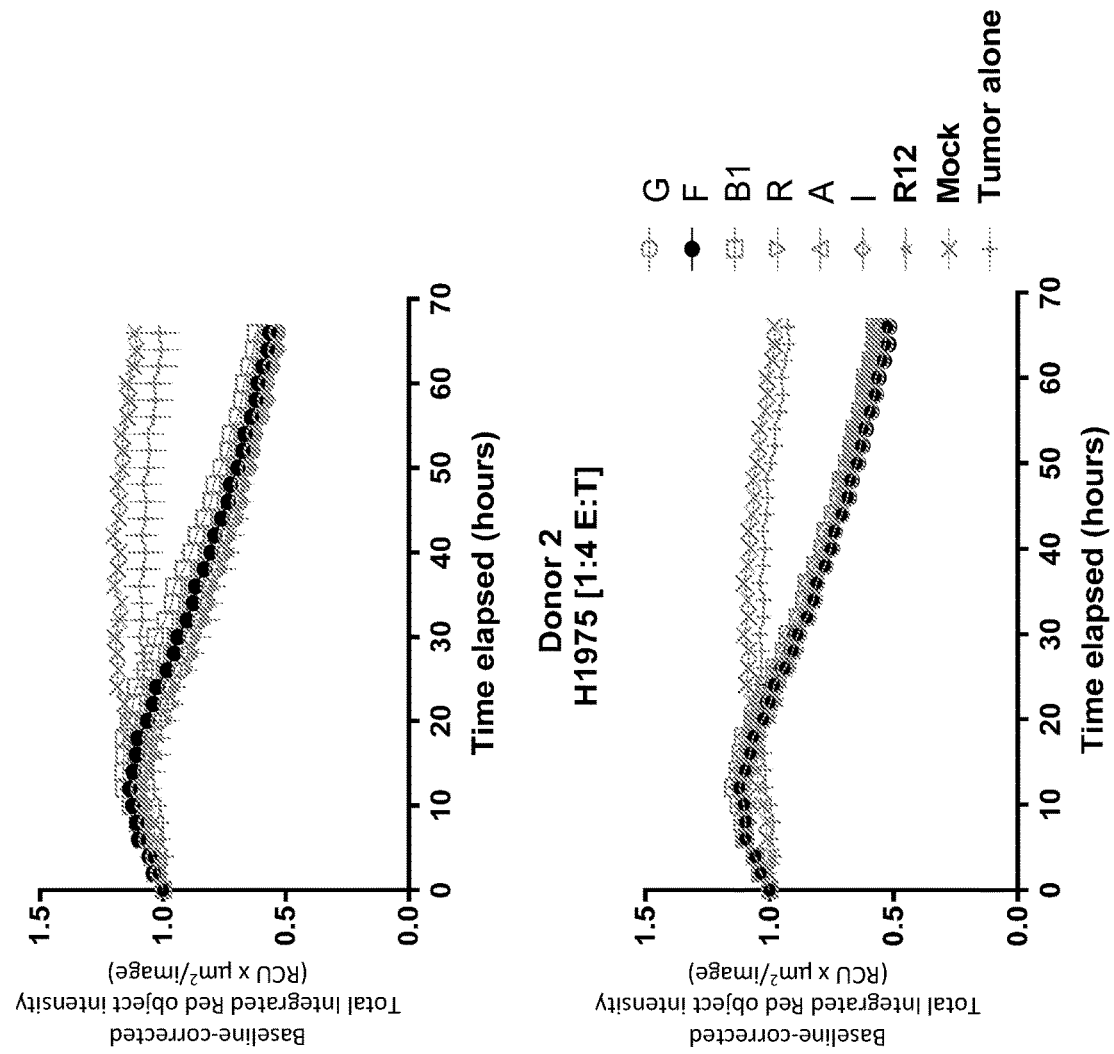
FIGS. 3A-3B depict the results from an in vitro cytotoxicity assay, after co-culture of NucLight Red (NLR)-labeled H1975 target cells and primary T cells expressing one of 6 selected candidate anti-ROR1 CARs, as assessed by measuring the loss of red fluorescent signal over a period of between 0 and 70 hours. As controls, cultures of target cells only and co-cultures of mock cells (not expressing a CAR) with the target cells were assessed.
Figure 4A:
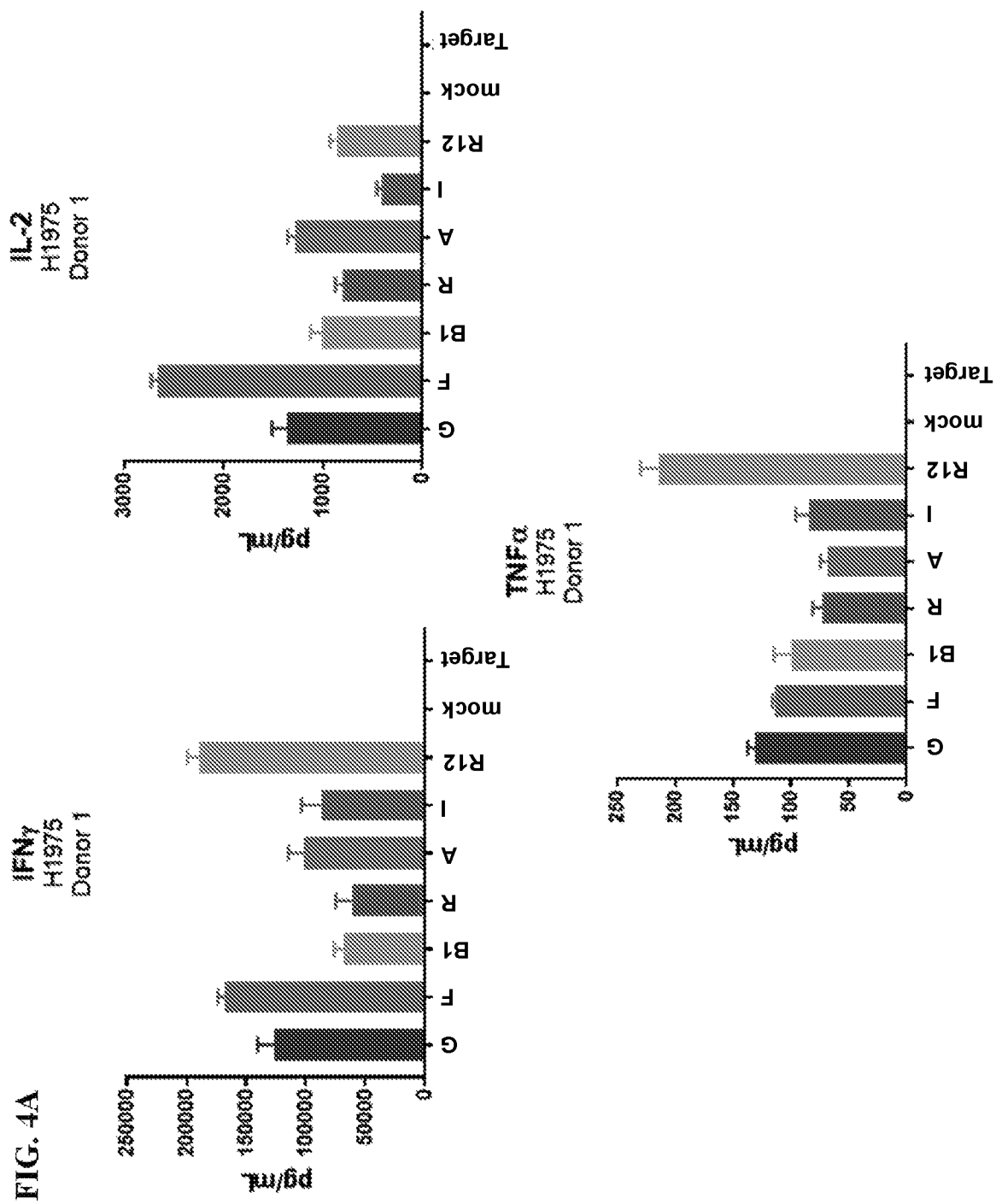
FIGS. 4A-4C show the production of IFN-γ, TNF-α or IL-2 after 70 hours of co-culture of primary T cells expressing one of 6 selected candidate anti-ROR1 CARs from two separate donors, with H1975 (FIGS. 4A and 4B), or the production of IL-2 after co-culture with MDA-MB-231, A549 or BT-549 (FIG. 4C) target cells. As controls, cultures of target cells only and co-cultures of mock cells (not expressing a CAR) with the target cells were assessed.
Figure 4B:
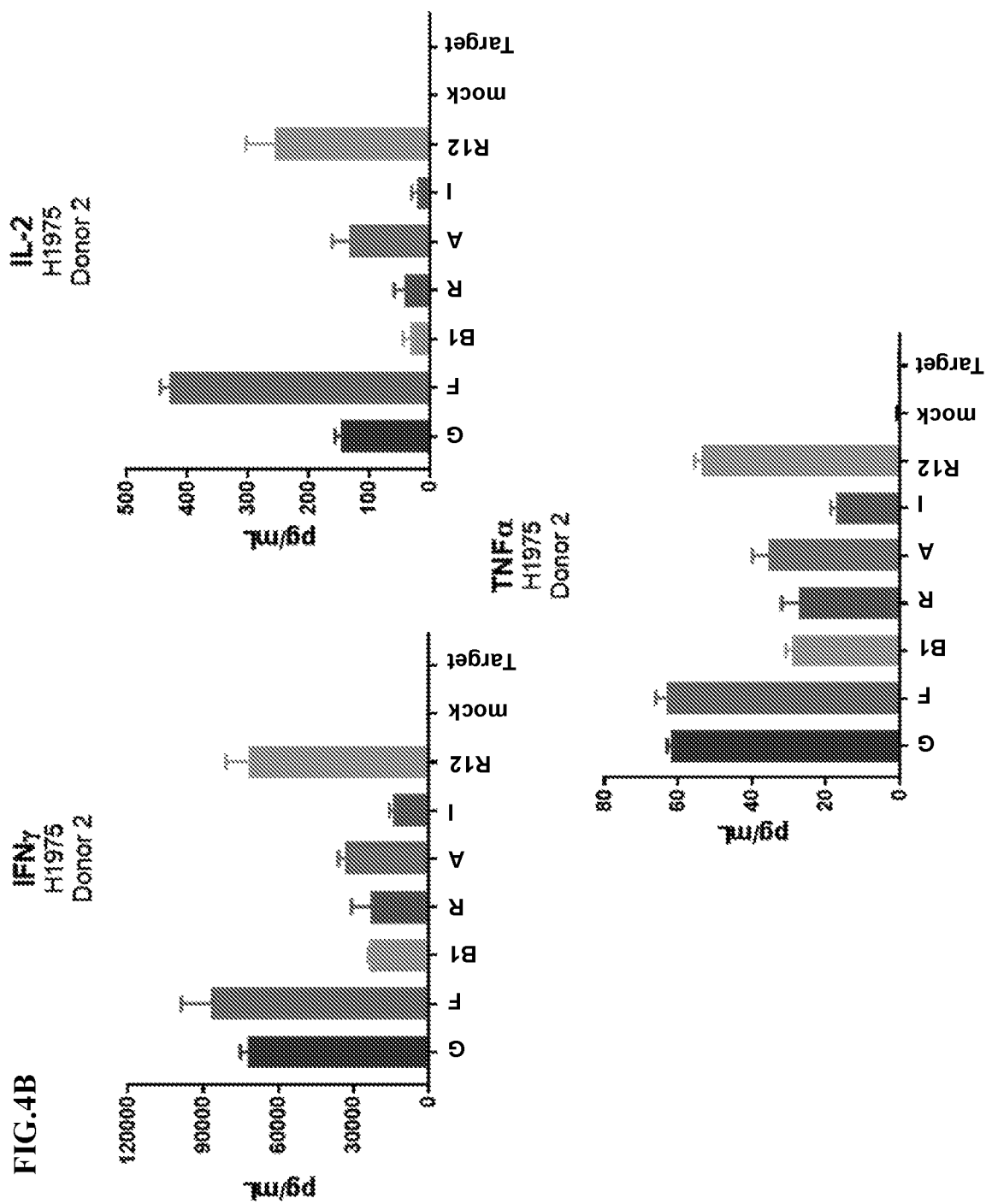

As shown in FIGS. 3A-3B, all of the candidate anti-ROR1 CARs tested showed similar in vitro cytotoxic activity against the H1975 target cells. As shown in FIGS. 4A-4B, all of the candidate anti-ROR1 CARs tested produced IFN-γ, TNF-α and IL-2 at various levels after in vitro co-culture with H1975 target cells. The results showed that after codon optimization and splice site elimination, all test constructs demonstrated cytotoxicity in co-culture with the H1975 (NSCLC) cell line. Among the tested CARs in this assay, cells expressing anti-ROR1 CAR-A, anti-ROR1 CAR-F and anti-ROR1 CAR-G generally exhibited among the highest cytokine production, which, for the various cytokines assessed, was similar to or greater than cytokine production of the cytokines from cells expressing the reference anti-ROR1 (R12) CAR. In particular, cells expressing anti-ROR1 CAR-F exhibited the highest IL-2 production compared to other candidate anti-ROR1 CARs and the reference anti-ROR1 (R12) CAR. The results were consistent with robust in vitro functional activity of the candidate CARs in co-culture with H1975 target cells.

Figure 4C:
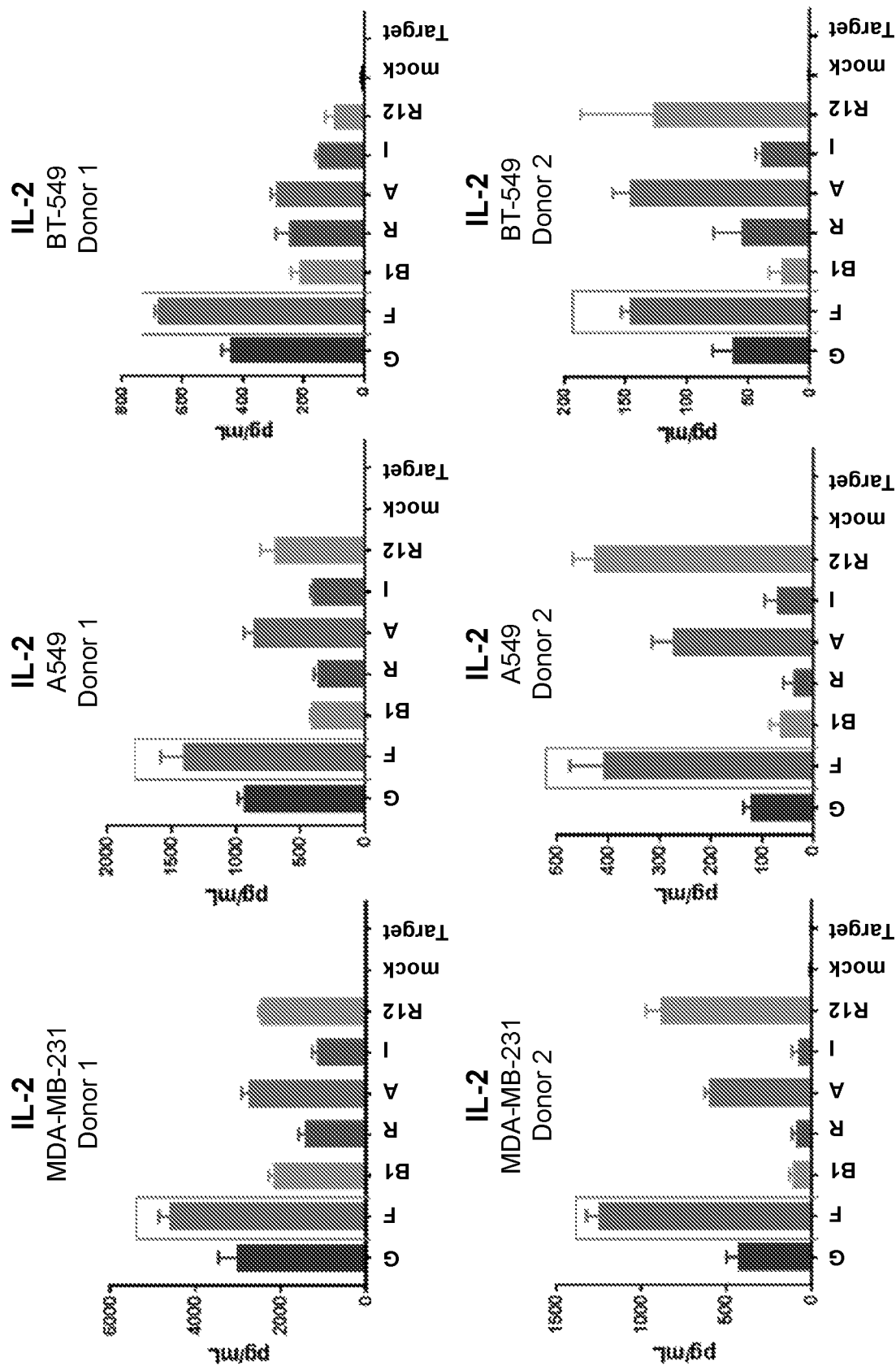

The production of cytokines IL-2 in the supernatant was also assessed after co-culture with other ROR1 expressing target cell lines, including MDA-MB-231 human triple negative breast cancer cells, A549 human epithelial lung carcinoma cells and BT-549 human epithelial breast ductal carcinoma cells, at an E:T ratio of 1:4. As shown in FIG. 4C, all of the candidate anti-ROR1 CARs tested produced IL-2 at various levels after in vitro co-culture with MDA-MB-231, A549 and BT-549 target cells. The results showed that cells expressing anti-ROR1 CAR-F exhibited the highest IL-2 production compared to other candidate anti-ROR1 CARs and the reference anti-ROR1 (R12) CAR, when co-cultured with all of the various target cells.

Example 4: Anti-Tumor Effect of Anti-ROR1 CAR-Expressing T Cells after Adoptive Transfer In Vivo in an Animal Model The anti-tumor effects of exemplary engineered anti-ROR1 CAR-expressing primary human T cells were assessed by monitoring tumors following adoptive transfer of cells in tumor-bearing animal models, including a H1975 human non-small cell lung cancer xenograft model and a MDA-MB-231 human triple negative breast cancer xenograft model. The mice were administered a preparation of engineered primary human T cells generated from one of the human donors, expressing one of anti-ROR1 CARs-A, -F, -G, -I, -R and -B1 as listed in Table E1 or a reference anti-ROR1 (R12) CAR, and that had been assessed in the in vitro assays described in Example 3.

A. H1975 Non-Small Cell Lung Cancer Model

1. Study 1

Eighty (80) NOD.Cg.Prkdc$^{scid}$IL2rg$^{tm/Wjl}$SzJ (NSG) mice were each injected subcutaneously with approximately $5 \times 10^6$ H1975 Non-Small Cell Lung Cancer cells. On day 16 following tumor engraftment, five (5) mice in each group received a single intravenous (i.v.) injection of engineered primary human T cells expressing one of anti-ROR1 CAR-A, -F, -G, -I, -R and -B1 or the reference anti-ROR1 (R12) CAR, at a dose of $1 \times 10^6$ cells (low dose) or $3 \times 10^6$ cells (high dose). As a control, mice were administered $3 \times 10^6$ cells not expressing a CAR (mock) or were untreated. Survival, tumor volume and number of circulating CAR$^+$ cells in the blood were assessed over approximately 65 days.

Figure 5C:
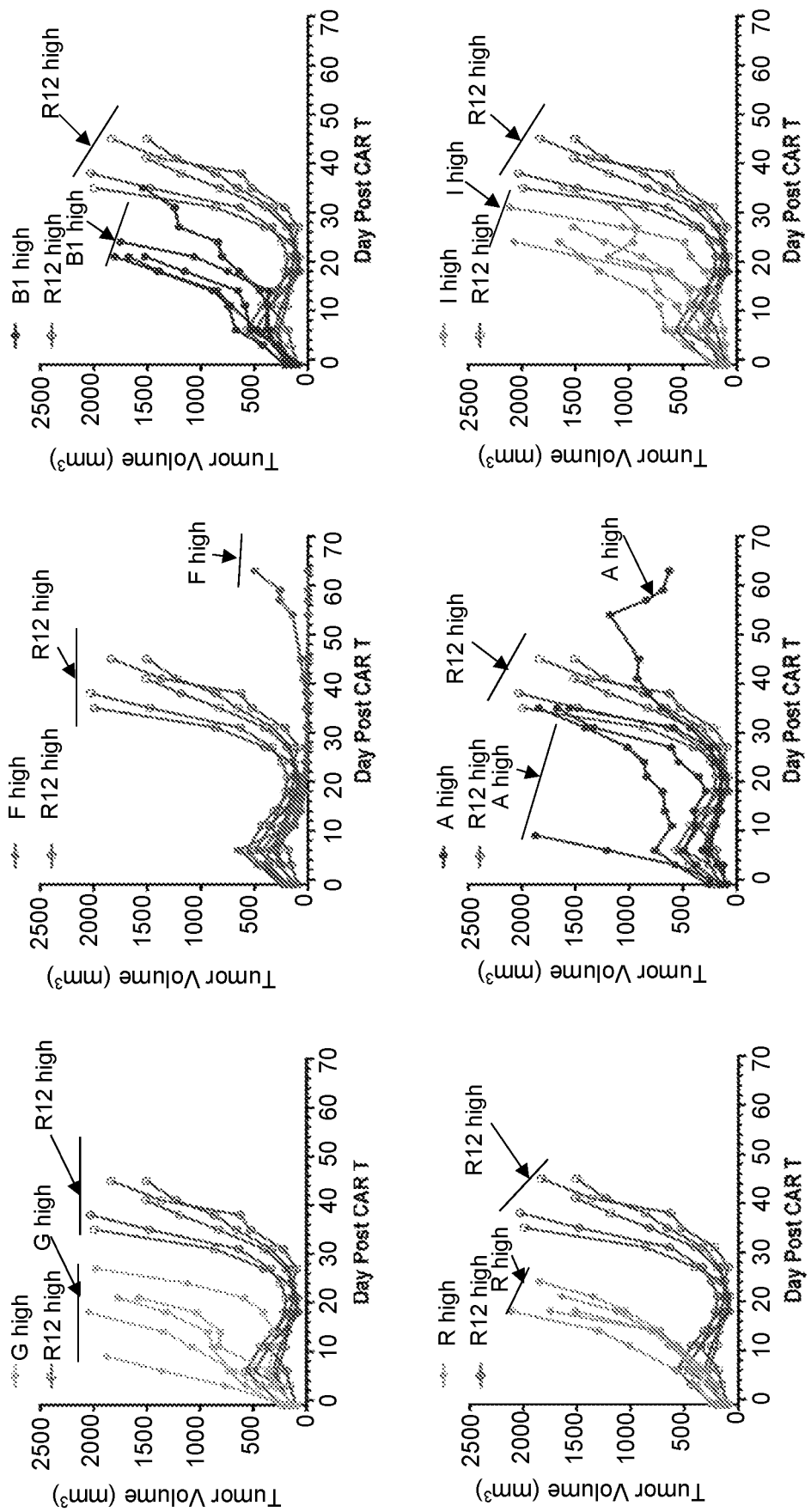
Figure 5D:
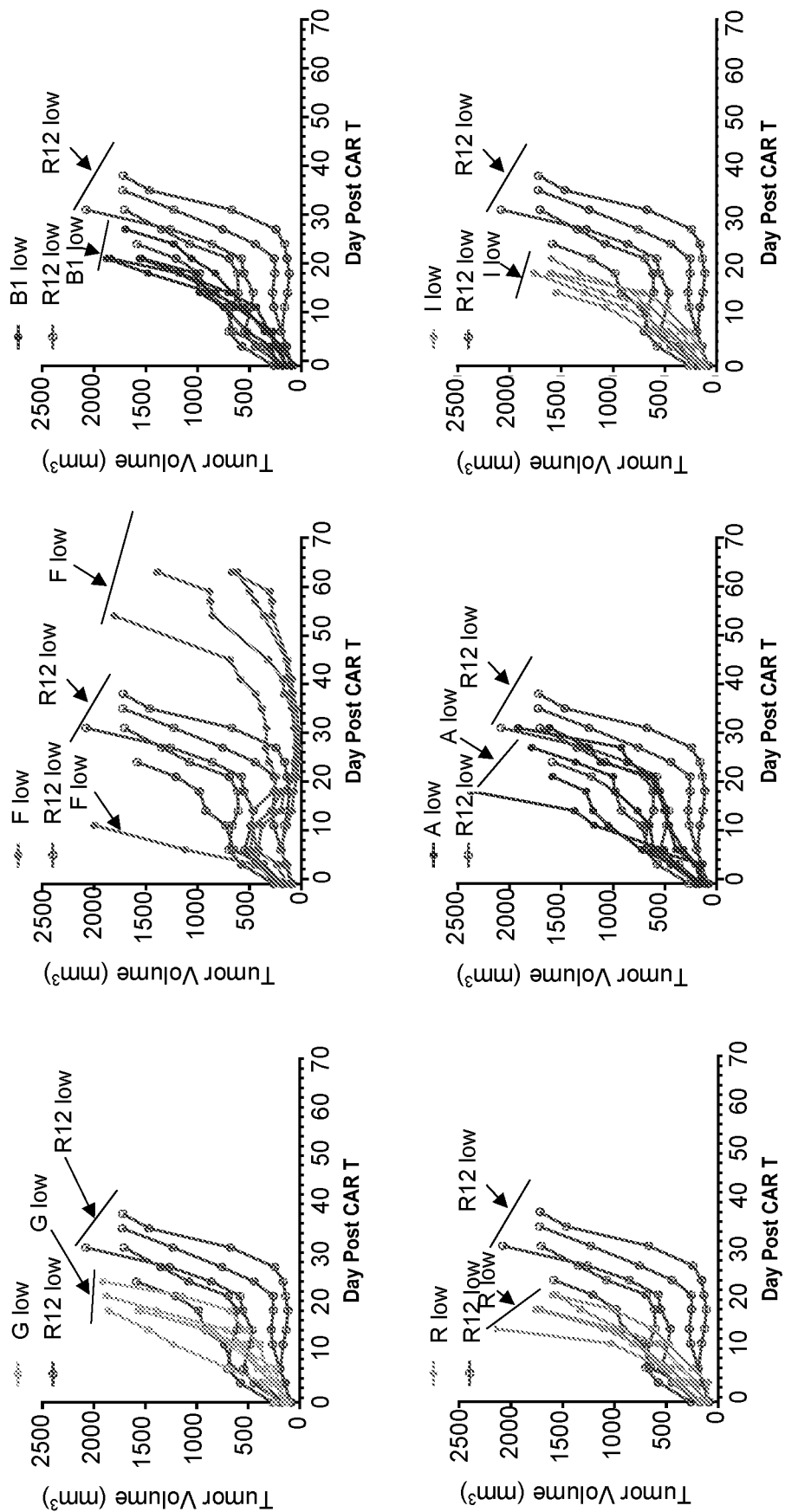

Anti-tumor activity of the adoptively transferred anti-ROR1 CAR+ T cells was monitored by determining the tumor volume every 3 to 6 days post administration. FIG. 5A (low dose) and FIG. 5B (high dose) depict mean tumor volume of all treated mice; in this depiction, tumor curves were terminated after the first mouse of a group succumbed to disease. Results from all individual mice are shown in FIG. 5C (low dose) or FIG. 5D (high dose). As shown in FIGS. 5A-5D, primary human T cells expressing the candidate anti-ROR1 CARs showed varying levels of anti-tumor activity in the H1975 mouse model. Primary human T cells expressing anti-ROR1 CAR-F exhibited the highest anti-tumor activity after a high dose administration, as shown by reduction in tumor volume, of tested anti-ROR1 CARs, including the anti-ROR (R12) reference CAR. Specifically, administration of anti-ROR1 CAR-F expressing cells resulted in mean tumor regression (below baseline) up to 52 days, compared to 6 days for the reference R12 CAR-expressing cells. 80% of H1975 tumor-bearing mice (4 of 5) treated with the high dose of anti-ROR1 CAR-F expressing cells exhibited complete and durable tumor clearance, whereas no animals treated with the high dose of the reference R12 CAR-expressing cells exhibited complete tumor clearance. At the low dose, 3 of 5 animals administered anti-ROR1 CAR-F expressing cells exhibited tumor regression below baseline up to 17 days, whereas only 1 of 5 animals administered R12 CAR-expressing cells exhibited tumor regression below baseline.

Survival of mice treated as described above was assessed. Kaplan-Meier survival curves of each of the groups are shown in FIGS. 6A-6B. As shown, administration of primary human T cells expressing the candidate CARs showed varying effects on survival of the treated mice. In this model, mice administered primary human T cells expressing anti-ROR1 CAR-F or anti-ROR1 CAR-A exhibited survival that was similar to or longer than survival of the reference anti-ROR1 (R12) CAR at one or both of the tested doses. Mice administered cells expressing anti-ROR1 CAR-F exhibited the longest survival with over 100% of mice surviving at 65 days following the initiation of administration of CAR-expressing cells at the highest dose in this model.

The average number of CD4+ and CD8+ CAR-expressing cells in the blood of each mouse was determined at day 10 and day 24 after administration of CAR-expressing T cells, at the low dose (FIGS. 7A and 7B) or high dose (FIGS. 7C and 7D). The average number of CD3+ CAR-expressing cells (CD45+ CD3+ CAR+) in the blood of each mouse also was determined at day 10 and day 24 after administration of CAR-expressing T cells, at the low dose (FIG. 7E) or high dose (FIG. 7F). As shown in FIGS. 7A-7F, a higher average CAR+ T cell number was observed in mice administered a higher dose of CAR+ T cells. T cells expressing anti-ROR1 CAR-F exhibited robust expansion following administration at both the low and high doses in this model. At 10 days post-infusion, the mean count of CAR-F expressing cells was 226.5 and 13.1 cells/μl of blood for the high and low doses, respectively, compared to the mean count of R12 expressing cells of 7.6 and 2.5 cells/μl of blood for the high and low doses, respectively. At 24 days post-infusion, the mean count of CAR-F expressing cells was 471.8 and 44.0 cells/0 of blood at the high and low doses, respectively, compared to the count of R12 expressing cells of 27.6 and 4.2 cells/0 of blood for the high and low doses, respectively.

2. Study 2

In a different study using the same H1975 mouse model, sixty-four (64) mice with engrafted H1975 tumors were staged based on measurement of tumor volume and administered a single intravenous (i.v.) injection of engineered primary human T cells expressing anti-ROR1 CAR-F, anti-ROR1 CAR-A, or reference anti-ROR1 (R12) CAR, at a dose of $1\times10^6$ cells (low dose) or $3\times10^6$ cells (high dose), eight (8) mice in each group. As a control, mice were administered $3\times10^6$ cells not expressing a CAR (mock) or were untreated. Tumor volume was measured up to approximately 70 days, and circulating CAR+ T cell number and survival were measured up to approximately 40 days.

The changes in the mean tumor volume in mice that were administered anti-ROR1 CAR-F, CAR-A or the R12 reference CAR at the low or the high dose are shown in FIGS. 8A and 8B, respectively. The changes in the mean tumor volume in individual mice are shown in FIG. 8C. Administration of anti-ROR1 CAR-F expressing cells resulted in mean tumor regression (below baseline) at 15 days, compared to administration of reference R12 CAR-expressing cells, which did not exhibit mean tumor regression below baseline (FIG. 8B). 25% of H1975 tumor-bearing mice (2 of 8) treated with the high dose of anti-ROR1 CAR-F expressing cells exhibited complete and durable tumor clearance, whereas 12.5% of mice (1 of 8) treated with 3 the high dose of the reference R12 CAR-expressing cells exhibited complete tumor clearance.

Mice were monitored for tumor growth and body condition at least twice weekly for 69 days post CAR T cell transfer and were euthanized when tumor volume exceeded 1500 mm³, when experiencing tumor ulceration, when displaying signs of severe xenogeneic graft versus host disease (xGvHD), or when otherwise moribund. The survival of mice in each group are shown in FIGS. 9A-9B. Median survival in untreated H1975 xenograft mice were left or administered mock treated cells was 20 days. Median survival of animals administered the high or low dose of R12 CAR T cells, was 33 and 29 days, respectively. Median survival in mice administered the anti-ROR1 CAR-F survived to 37.5 days for the low dose, and median survival was undetermined at the high dose, with 62.5% (5 of 8) animals remaining alive at study end.

Figure 10A:
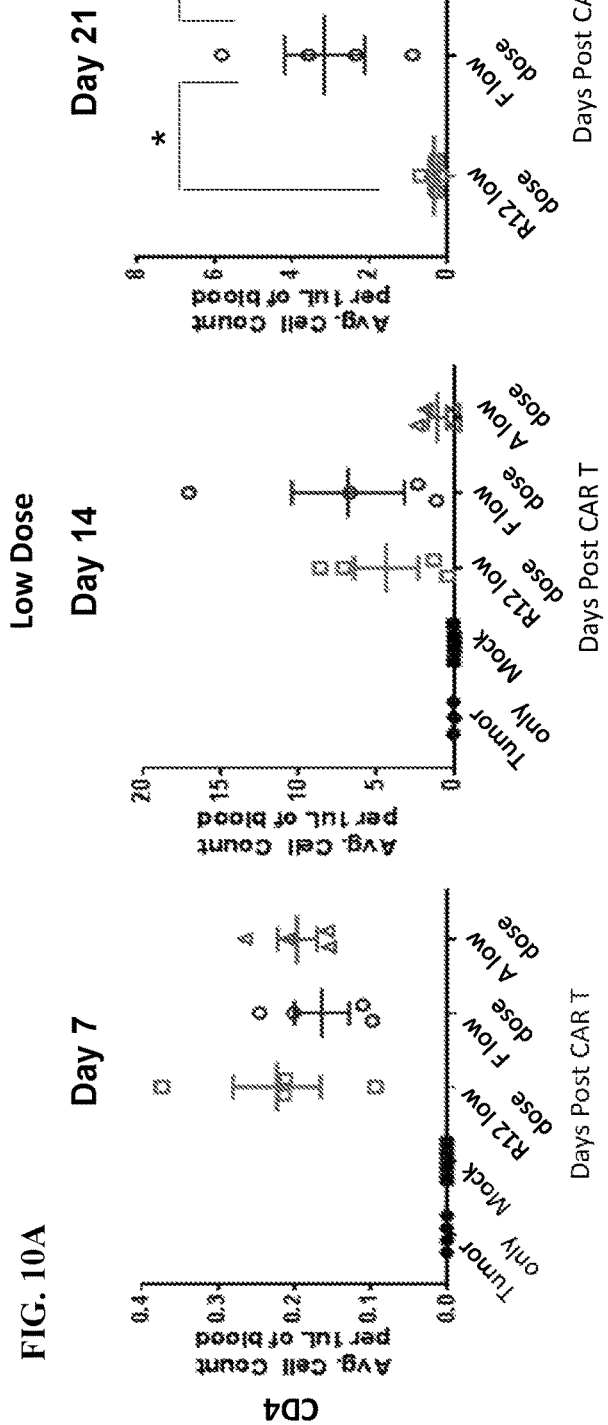
Figure 10B:
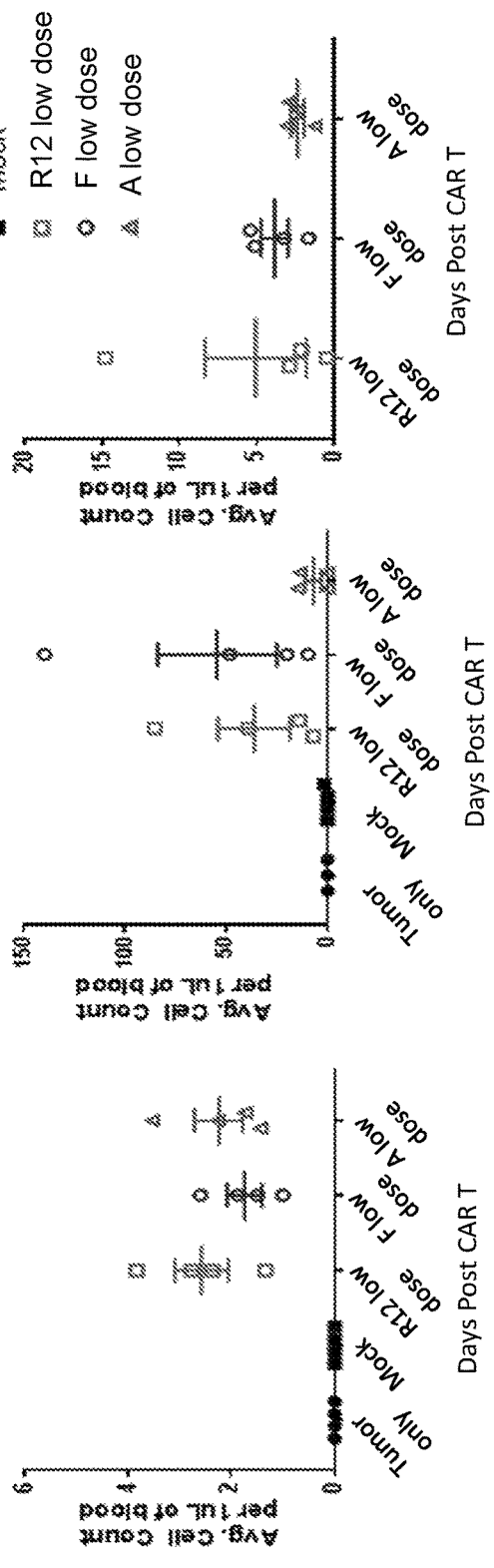
Figure 10C:
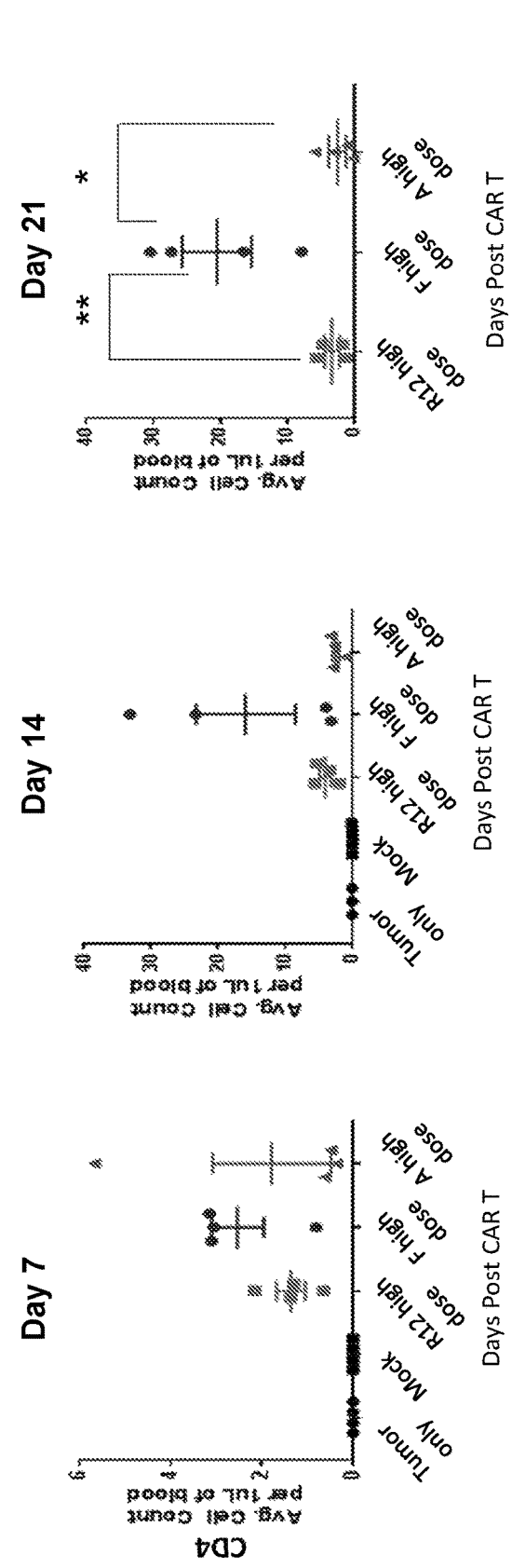
Figure 10D:
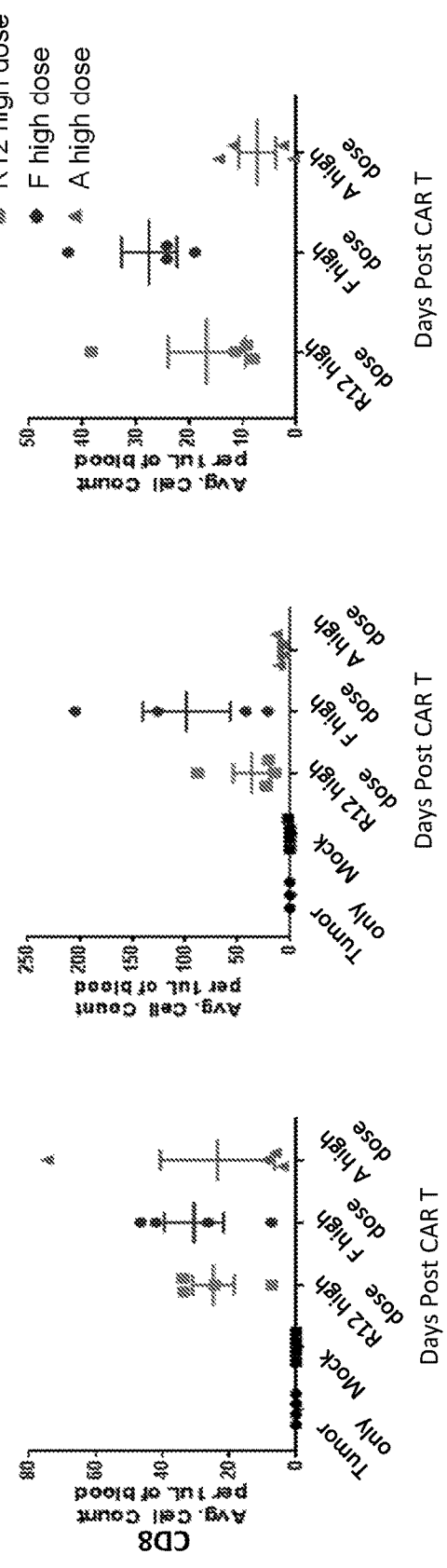

The average CD4+ and CD8+ CAR+ T cell count per microliter of blood at days 7, 14 and 21 after administration are shown in FIGS. 10A-10D. Consistent with the results in the study described above, the mean count of CAR-F expressing cells was highest compared to the meant count of the other CAR-expressing cells, particularly at day 21 and/or among CD4+ T cells (FIG. 10A and FIG. 10C), or at the high dose (FIG. 10C and FIG. 10D). At 7, 14, and 21 days post-administration of the high dose, the anti-ROR1 CAR-F expressing T cells showed mean counts of 37.6, 105.6, and 46.6 cells/μl of blood, respectively, whereas the reference R12-expressing cells showed mean counts of 28.9, 39.8, and 20.3 cells/0 of blood. At days 7, 14, and 21 post-administration of the lower dose, the anti-ROR1 CAR-F expressing cells showed mean counts of 2.2, 55.4, and 6.9 cells/μl of blood, respectively, whereas the reference R12-expressing cells showed mean counts of 3.1, 40.8, and 5.5 cells/μl of blood, respectively.

FIGS. 11A and 11B depict the number of CD4+ and CD8+ CAR+ T cells present in the tumor at 14 days after administration. The number of CAR+ cells in the tumor at day 14 were similar between the CARs tested.

3. Summary

As shown, mice with H1975 lung adenocarcinoma xenograft tumors administered anti-ROR1 CAR-F-expressing cells exhibited higher anti-tumor activity, as indicated by tumor volume reduction, longer survival, and increased number of circulating CAR+ T cells compared to mice administered the reference anti-ROR1 R12 CAR. The anti-tumor activity, survival and CAR+ T cell number was similar in mice administered anti-ROR1 CAR-A-expressing cells compared to anti-ROR1 R12 CAR-expressing cells.

B. MDA-MB-231 Triple Negative Breast Cancer Model

Sixty-four (64) NOD.Cg.Prkdc$^{scid}$IL2rg$^{tm1Wjl}$/SzJ (NSG) mice were each injected subcutaneously with $1\times10^6$ MDA-MB-231 cells expressing firefly luciferase. On day 7 following tumor engraftment, eight (8) mice in each group received a single intravenous (i.v.) injection of engineered primary human T cells expressing anti-ROR1 CAR-A, anti-ROR1 CAR-F, or reference anti-ROR1 (R12) CAR, at a dose of $1\times10^6$ cells (low dose) or $3\times10^6$ cells (high dose). As a control, mice were administered $3\times10^6$ T cells not expressing a CAR (mock) or were untreated. Bioluminescence imaging of tumor burden and flow cytometric analysis of the number of circulating CAR+ cells in the blood were assessed over approximately 100 days.

Anti-tumor activity of the adoptively transferred CAR-expressing T cells was monitored by bioluminescence imaging every 4 to 7 days post CAR-T cell administration. For bioluminescence imaging, mice received intraperitoneal (i.p.) injections of luciferin substrate (PerkinElmer, Waltham, MA) resuspended in PBS (approximately 150 mg/kg body weight). Mice were anesthetized and imaged essentially as described in WO2015/095895. The total flux (photon/s) was determined at each time point.

The results for bioluminescence images from treated mice and the mean measured total flux (p/s) are shown in FIGS. 12B and 13A, respectively, following administration of the low dose of CAR-expressing cells; or in FIGS. 12C and 13B, respectively, following administration of the high dose of CAR-expressing cells. FIG. 12A depicts bioluminescence images of untreated mice or mice administered mock T cells. FIG. 13C depicts the measured total flux (p/s) of individual mice.

The changes in the mean tumor volume at the low dose or high dose are shown in FIGS. 14A and 14B, respectively. As shown, mice administered cells expressing anti-ROR1 CAR-F, at both the low and high doses, were observed to generally have a lower degree of bioluminescence signal, indicating a reduction in tumor growth over time and/or a lower degree of tumor growth in the treated animals, compared to mice administered cells expressing the reference anti-ROR1 (R12) CAR. Mice administered cells expressing anti-ROR1 CAR-A, at both the low and high doses, were observed to generally have similar bioluminescence signal compared to mice administered cells expressing the reference anti-ROR1 (R12) CAR.

The changes in the mean tumor volume following administration of T cells expressing anti-ROR1 CAR F and reference CAR R12, up to a further time point in the same study are shown for the high dose and low dose in FIGS. 14C and 14D, respectively. Results of tumor volume for individual treated mice at the high dose or low dose for each treated condition are shown in FIG. 14E. Administration of anti-ROR1 CAR-F expressing cells resulted in mean tumor regression (below baseline, as measured by BLI) for at least 35 days, when BLI measurements terminated. The reference R12 CAR did not exhibit mean tumor regression below baseline, at either the high dose (FIGS. 14C and 14E) or the low dose (FIGS. 14D and 14E). By subcutaneous tumor volume, 50% of mice (4 of 8) administered anti-ROR1 CAR-F expressing cells at the high dose exhibited complete and durable tumor clearance, whereas only 12.5% of mice (1 of 8) treated with the high dose of R12 CAR-expressing cells exhibited complete tumor clearance (FIGS. 14C and 14E). At the low dose, 25% (2 of 8) of animals treated with anti-ROR1 CAR-F expressing cells exhibited complete tumor clearance, whereas no animals treated with reference R12 CAR-expressing cells at the low dose resulted in complete tumor clearance (FIGS. 14D and 14E).

Mice were monitored for tumor growth and body condition at least twice weekly for 97 days post CAR T cell transfer and were euthanized when tumor volume exceeded 1500 mm$^3$, when experiencing tumor ulceration, when showing signs of severe xGvHD (e.g., severe dermatitis and/or 20% weight loss attributed to xGvHD), or when otherwise moribund. Survival of mice treated as described above was assessed. Kaplan-Meier survival curves of each of the groups are shown in FIGS. 15A-15B. Median survival for untreated mice was 61 days. At the high dose, median survival was undetermined for mice administered the anti-ROR1 CAR-F expressing cells, R12 reference CAR expressing cells or mock treated cells, as 62.5% (5 of 8) of animals administered mock treated cells survived at study end, and there were no deaths in either groups administered CAR T cells (FIG. 15A). At the low dose, median survival for the mice administered the R12 CAR-expressing cells at the low dose was 96 days, with only 3 of 8 animals remaining alive at study end, whereas 100% survival (8 of 8) was observed in mice administered CAR-F expressing cells (FIG. 15B).

The average number of CD4+ and CD8+ CAR-expressing cells in the blood of the animal were determined at days 7, 14, 21 and 30 after administration of CAR-expressing T cells at the low dose (FIGS. 16A-16B) or high dose (FIGS. 16C-16D). The average number of CD3+ CAR-expressing cells (CD45+ CD3+ CAR+) in the blood of each mouse administered cells expressing anti-ROR1 CAR-F or the R12 reference CAR also was determined at days 7, 14, 21 and 30 are shown in FIG. 16E. At the high dose, the mean count of CAR-F expressing T cells was 5.0, 19.4, 50.7 and 119.2 cells/µl of blood for days 7, 14, 21, and 30, respectively, compared to the mean count of R12 expressing T cells of 6.0, 5.4, 3.9, and 5.4 cells/µl of blood. Administration of the low dose also showed a similar expansion, with the mean count of CAR-F expressing cells of 1.4, 4.9, 20.9 and 58.5 cells/µl of blood for days 7, 14, 21, and 30, respectively, compared to the mean count of R12 expressing cells of 1.3, 0.6, 0.9, and 0.4 cells/µl of blood. As shown, cells expressing anti-ROR1 CAR-F exhibited high expansion in the MDA-MB-231 mouse model, when administered at both high and low doses. In particular, anti-ROR1 CAR F-expressing cells exhibited substantially high expansion starting at day 14 continuing to day 30 after administration.

C. Conclusion

The results supported high anti-tumor activity and T cell expansion, and extended survival of mice administered anti-ROR1 CAR-F, using two different in vivo mouse tumor models, including the triple negative breast cancer xenograft tumor model. By most measurements, the anti-ROR1 CAR-F-expressing cells showed improvements compared to the anti-ROR1 reference R12 CAR.

Example 5: Anti-ROR1 CAR-Expressing T Cells Generated from Human Subjects with Chronic Lymphocytic Leukemia (CLL)

Engineered anti-ROR CAR-expressing primary T cells were generated from human subjects with chronic lymphocytic leukemia (CLL) and assessed for cytotoxicity and cytokine production in vitro.

A. Generation of Anti-ROR1 CAR-Expressing Cells from Subjects with CLL

Primary T cells from human subject with Chronic Lymphocytic Leukemia (CLL) were engineered to express the exemplary anti-ROR1 CAR, anti-ROR1 CAR-F, described in Example 3 above.

CD4+ and CD8+ T cells were isolated by immunoaffinity-based enrichment from leukapheresis samples of one of two human donors with CLL. Isolated CD4+ and CD8+ T cells were mixed at approximately 1:1 ratio, stimulated and transduced with lentiviral preparations encoding anti-ROR1 CAR-F as described in Example 3, an anti-CD19 CAR as a control or a reference anti-ROR1 CAR (R12), and cultivated under conditions for expansion. CD4- and CD8-depleted leukapheresis samples were assessed for CD19 and ROR1 expression levels and used as target cell population in the assays. For one of the subjects with CLL (CLL donor 1), ROR1 expression level was low, nearly as low as a K562 human chronic myelogenous leukemia (CML) cell line engineered to express ROR1 in response to the tetracycline derivative doxycycline, without addition of doxycycline (see Example 9).

B. Cytolytic Activity and Cytokine Production

Cytolytic activity of the primary T cells from subjects with CLL expressing the exemplary anti-ROR1 CAR F were assessed.

In one experiment, target cells obtained from the subjects (CD4- and CD8-depleted leukapheresis samples) were labeled with Rapid Red cell labeling reagent to permit tracking of target cells by microscopy, and incubated with the CAR-expressing cells at an E:T ratio of 2.5:1 and 0.25:1, or cultured with mock cells or cultured alone as controls. Cytolytic activity was assessed by measuring the loss of red fluorescent signal over a period of between 0 and 60 hours, compared to controls.

As shown in FIG. 17, for both donors and both E:T ratios, red fluorescent signal from the labeled target cells were lost more rapidly when co-cultured with CAR-expressing cells, compared to the expected loss from normal cell division observed in the target cells alone or co-culture with mock transduced cells. A greater loss of target cells was observed following co-culture of the target cells with anti-ROR1 CAR-F-expressing cells compared to anti-ROR1 R12-expressing cells, and was comparable to the loss of target cells following co-culture with anti-CD19 CAR-expressing cells.

In a different experiment, the loss of ROR1 expressing target cells was assessed by flow cytometry. For this, engineered CAR-expressing cells were labeled with CellTrace™ Violet (CTV) cell proliferation reagent, and co-cultured with target cells from the subjects with CLL at an E:T ratio of 2.5:1 and 0.25:1. On day 4, supernatants were collected to evaluate cytokine production (IFN-γ, TNF-α and IL-2) and the cells were collected to assess CTV levels by flow cytometry.

As shown in FIG. 18A, the number of ROR1+ target cells co-cultured with anti-ROR1 CAR F expressing cells generated from subjects with CLL were reduced substantially compared to target cells cultured alone or target cells co-cultured with mock transduced T cells. The reduction was greater than the reduction observed with a co-culture with R12-expressing cells, at both E:T ratios for both donors. As shown in FIGS. 18B-18C, anti-ROR1 CAR F expressing cells generated from subjects with CLL divided (FIG. 18B) and produced IFN-γ, TNF-α and IL-2 (FIG. 18C) in a co-culture with target cells from the same subject. Proliferation and cytokine production was similar to or higher than from R12-expressing cells tested in the same condition.

The results were consistent with an observation that engineered T cells expressing the exemplary anti-ROR1 CAR F were successfully generated from primary T cells from human subjects that has CLL. The cells were viable, exhibited cytolytic activity, produced cytokines and proliferated when incubated with ROR1-expressing target cells from the same subject, in some cases even when the target cells expressed low levels of ROR1. The results supported that cells expressing the exemplary anti-ROR1 CAR F can be generated with cells from subjects with CLL, previously reported as having difficulties in generating engineered CAR-expressing cells (see, e.g., Gorgun et al., J Clin Invest. 2005 July; 115(7):1797-805; Ramsay et al., J Clin Invest. 2008 July; 118(7):2427-37; Riches et al., Discov Med. 2013 December; 16(90):295-302). The results also showed that the exemplary anti-ROR1 CAR expressing cells are effective in killing target cells that express even low levels of ROR1, demonstrating a high sensitivity. By most measurements, the anti-ROR1 CAR-F-expressing cells showed improvements compared to cells expressing the anti-ROR1 reference R12 CAR.

Example 6: Anti-Tumor Effect of Anti-ROR1 CAR-Expressing T Cells after Adoptive Transfer In Vivo in an Animal Model of a B Cell Malignancy The anti-tumor effects of exemplary engineered anti-ROR1 CAR-expressing (CAR+) primary human T cells were assessed by monitoring tumors following adoptive transfer of cells in an animal model of a disseminated human B cell malignancy. The mice were administered a preparation of engineered primary human T cells generated from human donors, expressing an exemplary anti-ROR1 CAR-F, compared to a reference anti-ROR1 (R12) CAR or an anti-CD19 CAR, as described in Example 3 above.

NOD.Cg.Prkdc$^{scid}$IL2rg$^{tm1Wjl}$/SzJ (NSG) mice were injected intravenously with $1.0 \times 10^6$ firefly luciferase and green fluorescent protein (FfLuc-GFP)-expressing human mantel cell lymphoma (MCL) JeKo-1 cells on day 0. Tumor burden was assessed by bioluminescent imaging (BLI), by detecting bioluminescence minutes after mice were injected intraperitoneally with 3 mg of D-Luciferin. On day 6, mice were randomized into groups to balance tumor burden. On day 7, mice were administered engineered primary human T cells generated from a human donor expressing the exemplary anti-ROR1 CAR-F or the reference anti-ROR1 (R12) CAR, at a dose of $1 \times 10^6$ cells (low dose) or $3 \times 10^6$ cells (high dose) per mouse. As controls, mice either did not receive any T cells or received $3 \times 10^6$ cells mock-treated T cells from the same donor. Mice were monitored for tumor burden and survival for 139 days post administration. The number of circulating CAR+ T cells was monitored for 28 days post administration.

FIG. 19A (high dose) and FIG. 19B (low dose) depict mean tumor volume of all treated mice. Results from all individual mice are shown in FIG. 19C (high dose) or FIG. 19D (low dose). As shown in FIGS. 19A and 19C, JeKo-1 MCL xenograft mice administered $3 \times 10^6$ (high dose) anti-ROR1 CAR-F expressing cells or the anti-CD19 CAR+ cells resulted in mean tumor regression (below the baseline) for at least 111 days (the last day of BLI measurement). In comparison, mice administered the R12 CAR+ cells exhibited mean tumor regression for only up to 27 days. As shown in FIGS. 19B and 19D, at the lower dose of $1 \times 10^6$ cells, administration of cells expressing CAR-F resulted in mean tumor regression for the entire course of the study (up to 111 days). In comparison, mice administered the anti-CD19 CAR+ cells exhibited mean tumor regression for up to 36 days, and no mean tumor regression was observed for mice administered the R12 reference anti-ROR1 CAR.

Mice were monitored for body condition at least twice weekly for 139 days post CAR T cell administration and were euthanized when moribund or exhibiting signs of severe xenogeneic graft versus host disease (xGvHD). Kaplan-Meier survival curves of each of the groups are shown in FIG. 20A (high dose) and FIG. 20B (low dose). Untreated JeKo-1 xenograft mice had a median survival of 26.5 days. Animals administered $3 \times 10^6$ mock-treated cells had a median survival of 56 days. Median survival was unable to be determined for all animals treated with either dose of anti-ROR1 CAR-F expressing T cells, as 75% (6 of 8) of animals administered either the high dose ($3 \times 10^6$ cells; FIG. 20A) or the low dose ($1 \times 10^6$ cells; FIG. 20B) remained alive at the end of the study. Notably, the deaths observed in the mice administered the anti-ROR1 CAR-F were associated with xGvHD rather than lymphoma burden. Median survival was 70 and 106 days for animals administered R12 CAR+ T cells at the low and high doses, respectively. Median survival was unable to be determined for mice receiving anti-CD19 CAR+ T cells at the low dose (7 of 8 animals survived to study end) and the median survival was 139 days at the high dose (4 of 8 animals survived). The deaths in this group was also primarily associated with xGvHD rather than lymphoma burden.

The average number of CAR+ T cells in the peripheral blood of each mouse was assessed by flow cytometry at days 7, 14, 21 and 28 after CAR+ T cell administration. As shown in FIG. 21, Anti-ROR1 CAR-F expressing cells showed the greatest concentration of circulating CAR+ T cells in the peripheral blood at day 21 or day 28 after administration at both dose levels examined. At the high dose, the anti-CD19 CAR+ T cells demonstrated substantially greater expansion (172.5 cells/μl blood) at day 14 post-administration than either the anti-ROR1 CAR-F (77.0 cells/μl blood) or R12 CAR (25.0 cells/μl blood) expressing cells. However, by day 21, anti-ROR1 CAR-F expressing cells had substantially increased in counts (140.9 cells/μl blood) compared to both R12 CAR+ (0.3 cells/μl blood) and the anti-CD19 CAR+ (17.2 cells/μl blood) cells at the low dose. Similar increased expansion was observed at the high dose anti-ROR1 CAR-F expressing cells, with 392.7 cells/μl blood compared to 10.2 and 66.8 cells/μl blood in the R12 CAR+ and anti-CD19 CAR+ cells, respectively. This improvement in expansion was also observed at day 28 post-administration of the cells.

The results supported high anti-tumor activity, improved T cell expansion, and prolonged survival of mice administered the exemplary anti-ROR1 CAR-F in the mouse xenograft model with MCL. By most measurements, the anti-ROR1 CAR-F-expressing cells showed substantial improvements compared to the anti-ROR1 reference R12 CAR, and showed similar or improved activity against MCL compared to cells expressing an anti-CD19 CAR.

Example 7: Epitope Mapping

Epitopes recognized by the exemplary anti-ROR1 antigen-binding domain contained in the exemplary anti-ROR1 CAR-F and CAR-G (scFv sequence set forth in SEQ ID NO:118), were assessed using full discontinuous epitope mapping by Chemical Linkage of Peptides onto Scaffolds (CLIPS; Pepscan Presto BV, Lelystad, The Netherlands; see, e.g., Timmerman et al., (2007) J. Mol. Recognit. 20: 283-329). Mapping was carried out using anti-ROR1 scFv clones in which the scFv was fused with a human Fc (scFv-hFc; IgG1) or a mouse Fc (scFv-mFc).

The exemplary anti-ROR1 scFv-mFc and scFv-hFc were expressed and purified from transiently transfected HEK293 cells, and assessed by sodium dodecyl sulfate polyacrylamide gel electrophoresis (SDS-PAGE) and analytical size exclusion chromatography (SEC). The extracellular domain of ROR1 (ROR1 ECD) was recombinantly expressed and purified from transiently transfected HEK293 cells, and assessed by SDS-PAGE and SEC. The results showed a highly pure composition of anti-ROR1 scFv-hFc, scFv-mFc and ROR1-ECD (>99% pure, <1 high molecular weight multimers for scFv-hFc and ROR1-ECD; >97% pure, <3% high molecular weight multimers for scFv-mFc).

Linear and structured synthetic peptide libraries of various length were generated from human ROR1 (e.g., set forth in SEQ ID NO:144-146), each offset by one amino acid residue. The structured peptide library was prepared to fix peptides of different lengths into defined 3D structures, including any single loop, double loop, α-helical and β-turn segment of ROR1. The libraries were arranged into combinatory maps to yield combinations of loops and linear peptides representing conformational and/or discontinuous epitope of ROR1 in a non-biased manner An ELISA based heat map was generated on the individual and combined linear and structured peptides of ROR1 with the binders. Iterative double alanine substitution of all residues within peptides that showed positive binding were performed (for wild type alanine residues, glycine was substituted) Amino acids that resulted in a 70% or greater reduction in binding when substituted with alanine were determined to be core components of the epitope.

Analysis of epitope mapping showed that an scFv-hFC of the exemplary anti-ROR1 antigen-binding domain contained in the exemplary anti-ROR1 CAR-F and CAR-G (scFv sequence set forth in SEQ ID NO:118) bound to a discontinuous, conformation dependent epitope primarily centered around amino acids FRSTIYGSRLRIRNL (set forth in SEQ ID NO:199; corresponding to residues 78-92 of the human ROR1 sequence set forth in SEQ ID NO:144) Table E2 sets forth the epitopes identified from the epitope mapping. Most of the binding observed was to combinations with parts of FRSTIYGSRLRIRNL (SEQ ID NO:199), consistent with some cooperativity between different regions of the epitope.

TABLE E2

Binding epitopes of exemplary anti-ROR1 antigen-binding domain

| Amino acid residue (with reference to SEQ ID NO: 144) | Sequence | SEQ ID NO: |
|---|---|---|
| 5-17 | LSVSAELVPTSSW | 200 |
| 49-62 | HCKVSGNPPPTIRW | 201 |
| 62-87 | WFKNDAPVVQEPRRLSFRSTIYGSRL* | 202 |
| 111-119 | VSSTGVLFV | 203 |
| 117-129 | LFVKFGPPPTASP | 204 |
| 133-143 | DEYEEDGFCQP | 205 |
| 142-155 | QPYRGIACARFIGN* | 206 |
| 191-204 | SQFAIPSLCHYAFP | 207 |
| 202-213 | AFPYCDETSSVP | 208 |
| 228-247 | NVLCQTEYIFARSNPMILMR* | 209 |
| 248-259 | LKLPNCEDLPQP | 210 |
| 259-273 | PESPEAANCIRIGIP | 211 |
| 290-303 | VDYRGTVSVTKSGR | 212 |
| 310-323 | SQYPHTHTFTALRF | 213 |
| 366-380 | DSKEKNKMEILYILV | 214 |

Core residues, determined by ≥70% reduction in binding upon double alanine substitution, are underlined and in bold.
*likely contains multiple smaller parts of the epitope.

Example 8: Affinity and Binding Kinetics of Anti-ROR1 Antigen-Binding Domains

The binding affinity and kinetics of the exemplary anti-ROR1 antigen-binding domains to the antigen ROR1 was assessed by surface plasmon resonance (SPR).
A. Binding Affinity and Kinetics Equilibrium dissociation constant ($K_D$), the association rate constant ($k_a$ or $k_{on}$), and dissociation rate constant ($k_d$ or $k_{off}$) of the interaction between recombinant human ROR1 and the binding domain of exemplary ROR1 CARs was determined by surface plasmon resonance (SPR) using the Biacore™ T200 instrument and Biacore™ T200 Evaluation software v3. Specifically, the scFv binding domain of CARs as described in Example 3 and Table E1 above, including scFv ROR1-1, ROR1-2, ROR1-3 and ROR1-4 (set forth in SEQ ID NOS: 118, 127, 109 and 134, respectively; the scFv binding domains of CAR-A, CAR-F, CAR-G, CAR-I, CAR-R and CAR-B1) and the antigen binding domain of the reference CAR R12 (SEQ ID NO: 142), were assessed.

Recombinantly generated anti-ROR1 scFv binding domains and ROR1 extracellular domain with a C-terminal 6×His tag (ROR1 ECD 6×His) were used for binding affinity and kinetics analyses. The binding domains were constructed as a fusion of the scFv with the Fc portion of murine immunoglobulin heavy chain IgG2a (scFv-mFc). The murine IgG2a domain contained 4 point mutations to diminish both Fc receptor and complement binding. Active concentration of ROR1 ECD 6×His was determined by a calibration-free concentration analysis (CFCA) assay.

For SPR, an anti-mouse IgG capture surface chip (Mouse Antibody Capture Kit type 2, catalog number 29215281 and Series S Sensor Chip CM5, catalog number 29104988, GE Healthcare Bio-Sciences) was used to capture the anti-ROR1 scFv-mFc binding domains on a flow cell while another flow cell was left blank for reference. Multi-cycle kinetics were implemented by subsequent injections of recombinant human ROR1 at concentrations of 183, 61.0, 20.33, 6.78, and 2.26 nM with variable dissociation over both the active and reference flow cells.

ROR1 ECD was injected over the scFv-mFc bound chip at multiple concentrations using multicycle kinetics. A monovalent 1:1 model was used to analyze the sensograms and to calculate affinity and kinetic measurements of the interaction.

FIGS. 22A-22E depict the doubled-reference sensograms for anti-ROR1 scFv ROR1-1 (SEQ ID NO: 118; FIG. 22A), ROR1-2 (SEQ ID NO: 127; FIG. 22B), ROR1-3 (SEQ ID NO: 109; FIG. 22C) and ROR1-4 (SEQ ID NO: 134; FIG. 22D) and the scFv antigen binding domain of the reference CAR R12 (SEQ ID NO: 142; FIG. 22E). The affinity (equilibrium dissociation constant, $K_D$) of the interaction between the anti-ROR1 scFv binding domains and ROR1 are set forth in Table E3. The affinity (equilibrium dissociation constant, $K_D$) of the interaction between the anti-ROR1 scFv ROR1-1 (binding domain of CAR-F) and ROR1 was measured to be 42 nM, and the kinetic association rate constant ($k_a$ or $k_{on}$; on-rate) and dissociation rate constant ($k_d$ or $k_{off}$; off-rate) of the interaction were observed to be $k_a=1.2\times10^5$ 1/Ms and $k_d=5.0\times10^3$ 1/s, respectively. The anti-ROR1 scFv ROR1-1 (binding domain of CAR-F) exhibited substantially higher $K_D$ (lower affinity) and faster off rate ($k_d$ or $k_{off}$) compared to the reference R12 scFv binding domain The anti-ROR1 scFv ROR1-2 (binding domain of CAR-A) exhibited substantially lower $K_D$ (higher affinity) and slower off rate ($k_d$ or $k_{off}$) compared to the reference R12 scFv binding domain

TABLE E3

Affinity and binding kinetics of exemplary anti-ROR1 binding domains.

|  | scFv # | | | | |
| --- | --- | --- | --- | --- | --- |
|  | R12 | ROR1-1 | ROR1-2 | ROR1-3 | ROR1-4 |
| SEQ ID NO: | 142 | 118 | 127 | 134 | 109 |
| CAR | R12 | CAR-F, CAR-G | CAR-A, CAR-R | CAR-B1 | CAR-I |
| $K_D$ (M) | 9.420E−10 | 4.20E−08 | 9.57E−11 | 1.38E−08 | 9.24E−10 |
| $k_a$ or $k_{on}$ (1/Ms) | 6.14E+05 | 1.19E+05 | 4.12E+05 | 1.60E+04 | 1.17E+04 |
| $k_d$ or $k_{off}$ (1/s) | 5.79E−04 | 5.00E−03 | 3.94E−05 | 2.20E−04 | 1.08E−05 |

B. Epitope Binning

SPR was used in epitope binning analysis to compare the epitope binding regions recognized by the exemplary ROR1 binding domains compared to the epitope of the anti-ROR1 reference R12 binding domain. Reference R12 scFv binding domain was immobilized on the surface, ROR1 ECD 6×His was introduced and bound to the R12 binding domain, and recombinant scFv binding domains of exemplary anti-ROR1 CARs, including scFv ROR1-1, ROR1-2, ROR1-3 and ROR1-4 (set forth in SEQ ID NOS: 118, 127, 109 and 134, respectively; the scFv binding domains of CAR-A, CAR-F, CAR-G, CAR-I, CAR-R and CAR-B1) were injected to assess whether the recombinant scFv bound to similar regions of ROR1 as the R12 binding domain. The results showed that binding of the scFv R12 to the ROR1 ECD was competed for by the candidate anti-ROR1 scFv binding domains ROR1-1, ROR1-2, ROR1-3 and ROR1-4, consistent with an observation that the candidate scFv binding domains may bind to an overlapping epitope or region as that bound by the R12 binding domain Example 9: Antigen Sensitivity Assessment of Anti-ROR1 Antigen-Binding Domains The antigen sensitivity of T cells expressing the exemplary anti-ROR1 CAR-F and the reference anti-ROR1 CAR R12 were evaluated for ability to produce cytokines and cytotoxic activity after stimulation using a ROR1-expressing cell line with regulatable ROR1 expression levels.

K562 human myelogenous leukemia cell line was engineered to express ROR1 in response to the tetracycline derivative, doxycycline (TetOn). As compared to the endogenously ROR1 expressing cell lines, the K562-ROR1-TetOn engineered cell line expressed very low levels of ROR1 at baseline, even in the absence of doxycycline treatment.

$2\times10^{-4}$ K562-ROR1-TetOn or parental K562 target cells were transduced to stably express IncuCyte® NucLight Red. R10 culture media (RPMI 1640; 1×BME; 1×NEAA, 1×NaPyr; 10% heat inactivated FBS) were added to an optically clear 96-well flat-bottom plate. Thawed CAR-expressing T cells were re-suspended at a concentration of $1.6\times10^6$ CAR+ cells/mL in R10 media. CAR-T were then added to K562 target cells for a final CAR+ T cell count of $8\times10^{-4}$ cells per well resulting in a 4:1 E:T ratio. Doxycycline hydrochloride was diluted to the desired concentrations (2 ng/mL-512 ng/mL) using DMSO and added to the plated CAR-T/target cell mixtures in technical triplicates. Plates were incubated at 37° C./5% $CO_2$ for 72 hours with periodic measurement of NucLight Red fluorescence using the IncuCyte®.

As shown in FIG. 23, ROR1 expression on K562-ROR1-TetOn cells after incubation with doxycycline alone showed that ROR1 expression increased with increasing doxycycline concentration. After 72 hours of incubation, supernatants were collected from wells containing T cells expressing anti-ROR1 CAR-F or the reference R12 CAR that had been were mixed with K562-ROR1-TetOn target cells expressing increasing amounts of ROR1. As shown in FIG. 24, CAR-F expressing T cells resulted in equivalent or greater production of IFNγ, IL-2 and TNFα compared to R12 expressing cells, at all ROR1 expression levels tested. As shown in FIGS. 25A-25B, analysis of cytotoxic function, as determined by loss of red fluorescent signal over time, showed that CAR-F expressing cells responded to lower ROR1 levels more effectively compared to R12 expressing cells, indicating greater antigenic sensitivity without the loss of specificity as demonstrated by the lack of response to the parental cell line.

Example 10: Binding Specificity Assessment

Potential off-target binding and species cross-reactivity of the binding domain of the exemplary anti-ROR1 CAR-F was assessed by various methods.

A. Plasma Membrane Protein Array

Off-target binding was assessed based on a plasma membrane protein array. This chip-based platform contains over 4400 groups of cells genetically engineered to overexpress individual human extracellular membrane proteins that together represent over 75% of the human extracellular proteome. The panel also includes over 1000 tethered secreted protein targets. An scFv-Fc (scFv sequence set forth in SEQ ID NO:118) was generated and used for immunohistochemistry (IHC) against the cells in the array. Confirmation screening was performed. The scFv was determined to be highly selective for ROR1, with no additional specific interactions identified, including to ROR2. These results indicate low risk for off-target activity of the anti-ROR1 CAR-F expressing cells B. Species Cross-Reactivity Table E4 shows the extracellular domain (ECD) homology for ROR1 between human (*Homo sapiens*), Rhesus macaques (*Macaca mulatta*), cynomolgus macaques (*Macaca fasicularis*), and mice (*Mus musculus*). ROR1 is 100% conserved in the ECD between human and non-human primates.

TABLE E4

ROR1 ECD Homology Across Species

| | Macaca mulatta | Macaca fasicularis | Mus musculus |
|---|---|---|---|
| Homo sapiens | 100% | 100% | 98.7% |

Extracellular domain a.a. 30-406 of human ROR1
*Homo sapiens*: Uniprot Q01973 (set forth in SEQ ID NO: 214)
*Macaca mulatta*: Uniprot F6RUP2 (set forth in SEQ ID NO: 215)
*Macaca fasicularis*: Uniprot A0A2K5WTX7 (set forth in SEQ ID NO: 216), Uniprot A0A2K5WTX4 (set forth in SEQ ID NO: 217)
*Mus musculus*: Uniprot Q9Z139 (set forth in SEQ ID NO: 218)

Species cross-reactivity of anti-ROR1 CAR-F and R12 CAR was assessed by co-culturing an engineered Jurkat T cell line containing a Nur77-tdTomato reporter and expressing the anti-ROR1 CAR-F or the reference R12 CAR (as described above in Example 1.C), with CT26 murine fibroblasts engineered to express a mouse ROR1 (CT26-mROR1), CT26 cells engineered to express a human ROR1 (CT26-hROR1), or unmodified CT26 cells or unmodified K562 human myelogenous leukemia cells, and assessing expression of the reporter.

As shown in FIG. 26, although there is 98.7% homology between human and mouse ROR1, no cross-reactivity was observed for binding of the anti-ROR1 CAR-F or R12 CAR to mouse ROR1-expressing target cells.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

Sequences

| SEQ ID NO: | Sequence | Description |
|---|---|---|
| 1 | ESKYGPPCPPCP | Spacer (IgG4 hinge) (aa) |
| 2 | gaatctaagtacggaccgccctgccccccttgccct | Spacer (IgG4 hinge) (nt) |
| 3 | ESKYGPPCPPCPGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK | Hinge-$C_H3$ spacer (aa) |
| 4 | GAATCTAAGTACGGACCGCCTTGTCCTCCATGTCCTGGCCAGCCAAGAGAACCCCAGGTGTACACACTGCCTCCAAGCCAAGAGGAAATGACCAAGAACCAGGTGTCCCTGACCTGCCTGGTCAAGGGCTTCTACCCTTCCGATATCGCCGTGGAATGGGAGAGCAATGGCCAGCCTGAGAACAACTACAAGACCACACCTCCTGTGCTGGACAGCGACGGCTCATTCTTCCTGTACAGCCGGCTGACCGTGGACAAGAGCAGATGGCAAGAGGGCAACGTGTTCAGCTGCAGCGTGATGCACGAGGCCCTGCACAACCACTACACCCAGAAGTCTCTGAGCCTGAGCCTGGGCAAG | Hinge-$C_H3$ spacer (nt) |
| 5 | RWPESPKAQASSVPTAQPQAEGSLAKATTAPATTRNTGRGGEEKKKEKEKEEQEERETKTPECPSHTQPLGVYLLTPAVQDLWLRDKATFTCFVVGSDLKDAHLTWEVAGKVPTGGVEEGLLERHSNGSQSQHSRLTLPRSLWNAGTSVTCTLNHPSLPPQRLMALREPAAQAPVKLSLNLLASSDPPEAASWLLCEVSGFSPPNILLMWLEDQREVNTSGFAPARPPPQPGSTTFWAWSVLRVPAPPSPQPATYTCVVSHEDSRTLLNASRSLEVSYVTDH | IgD-hinge-Fc |
| 6 | LEGGGEGRGSLLTCGDVEENPGPR | T2A |
| 7 | MLLLVTSLLLCELPHPAFLLIPRKVCNGIGIGEFKDSLSINATNIKHFKNCTSISGDLHILPVAFRGDSFTHTPPLDPQELDILKTVKEITGFLLIQAWPENRTDLHAFENLEIIRGRTKQHGQFSLAVVSLNITSLGLRSLKEISDGDVIISGNKNLCYANTINWKKLFGTSGQKTKIISNRGENSCKATGQVCHALCSPEGCWGPEPRDCVSCRNVSRGRECVDKCNLLEGEPREFVENSECIQCHPECLPQAMNITCTGRGPDNCIQCAHYIDGPHCVKTCPAGVMGENNTLVWKYADAGHVCHLCHPNCTYGCTGPGLEGCPTNGPKIPSIATGMVGALLLLLVVALGIGLFM | tEGFR |
| 8 | FWVLVVVGGVLACYSLLVTVAFIIFWV | CD28 (amino acids 153-179 of Accession No. P10747) |

-continued

| SEQ ID NO: | Sequence | Description |
|---|---|---|
| 9 | IEVMYPPPYLDNEKSNGTIIHVKGKHLCPSPLFPGPSKPFWVLVVVGGVLACYSLLVTVAFIIFWV | CD28 (amino acids 114-179 of Accession No. P10747) |
| 10 | RSKRSRLLHSDYMNMTPRRPGPTRKHYQPYAPPRDFAAYRS | CD28 (amino acids 180-220 of P10747) |
| 11 | RSKRSRGGHSDYMNMTPRRPGPTRKHYQPYAPPRDFAAYRS | CD28 (LL to GG) |
| 12 | KRGRKKLLYIFKQPFMRPVQTTQEEDGCSCRFPEEEEGGCEL | 4-1 BB (amino acids 214-255 of Q07011.1) |
| 13 | RVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR | CD3 zeta |
| 14 | RVKFSRSAEPPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR | CD3 zeta |
| 15 | RVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR | CD3 zeta |
| 16 | RKVCNGIGIGEFKDSLSINATNIKHFKNCTSISGDLHILPVAFRGDSFTHTPPLDPQELDILKTVKEITGFLLIQAWPENRTDLHAFENLEIIRGRTKQHGQFSLAVVSLNITSLGLRSLKEISDGDVIISGNKNLCYANTINWKKLFGTSGQKTKIISNRGENSCKATGQVCHALCSPEGCWGPEPRDCVSCRNVSRGRECVDKCNLLEGEPREFVENSECIQCHPECLPQAMNITCTGRGPDNCIQCAHYIDGPHCVKTCPAGVMGENNTLVWKYADAGHVCHLCHPNCTYGCTGPGLEGCPTNGPKIPSIATGMVGALLLLLVVALGIGLFM | tEGFR |
| 17 | EGRGSLLTCGDVEENPGP | T2A |
| 18 | GSGATNFSLLKQAGDVEENPGP | P2A |
| 19 | ATNFSLLKQAGDVEENPGP | P2A |
| 20 | QCTNYALLKLAGDVESNPGP | E2A |
| 21 | VKQTLNFDLLKLAGDVESNPGP | F2A |
| 22 | PGGG-(SGGGG)5-P- wherein P is proline, G is glycine and S is serine | linker |
| 23 | GSADDAKKDAAKKDGKS | Linker |
| 24 | GSTSGSGKPGSGEGSTKG | Linker |
| 25 | $X_1$PP$X_2$P X1 is glycine, cysteine or arginine X2 is cysteine or threonine | Hinge |
| 26 | EPKSCDKTHTCPPCP | Hinge |
| 27 | ERKCCVECPPCP | Hinge |
| 28 | ELKTPLGDTHTCPRCPEPKSCDTPPPCPRCPEPKSCDTPPPCPRCPEPKSCDTPPPCPRCP | Hinge |
| 29 | ESKYGPPCPSCP | Hinge |
| 30 | gagtctaaatacggaccgccttgtcctccttgtccc | Spacer (IgG4hinge) (nt) O/SSE |
| 31 | YGPPCPPCP | Hinge |
| 32 | KYGPPCPPCP | Hinge |
| 33 | EVVVKYGPPCPPCP | Hinge |

| SEQ ID NO: | Sequence | Description |
|---|---|---|
| 34 | ESKYGPPCPPCPAPPVAGPSVFLFPPKPKDTLMISRTPEVTCVVVDVSQEDPEVQFNW YVDGVEVHNAKTKPREEQFQSTYRVVSVLTVLHQDWLNGKEYKCKVSNKGLPSSIEKT ISKAKGQPREPQVYTLPPSQEEMTKNQVSLTCLVKGFYPSDIAVEWESNGQPENNYKT TPPVLDSDGSFFLYSRLTVDKSRWQEGNVFSCSVMHEALHNHYTQKSLSLSLGK | Hinge-$C_H2$-$C_H3$ spacer aa |
| 35 | GAATCTAAGTACGGACCGCCTTGTCCTCCATGTCCTGCTCCTCCAGTTGCCGGACCTT CCGTGTTCCTGTTTCCTCCAAAGCCTAAGGACACCCTGATGATCAGCAGAACCCCTGA AGTGACCTGCGTGGTGGTGGACGTGTCCCAAGAGGATCCTGAGGTGCAGTTCAACTGG TATGTGGACGGCGTGGAAGTGCACAACGCCAAGACCAAGCCTAGAGAGGAACAGTTCC AGAGCACCTACAGAGTGGTGTCCGTGCTGACAGTGCTGCACCAGGATTGGCTGAACGG CAAAGAGTACAAGTGCAAGGTGTCCAACAAGGGCCTGCCTAGCAGCATCGAGAAAACC ATCAGCAAGGCCAAGGGCCAGCCAAGAGAACCCCAGGTGTACACTGCCTCCAAGCC AAGAGGAAATGACCAAGAACCAGGTGTCCCTGACCTGCCTGGTCAAGGGCTTCTACCC TTCCGATATCGCCGTGGAATGGGAGAGCAATGGCCAGCCTGAGAACAACTACAAGACC ACACCTCCTGTGCTGGACAGCGACGGCTCATTCTTCCTGTACAGCCGGCTGACCGTGG ACAAGAGCAGATGGCAAGAGGGCAACGTGTTCAGCTGCAGCGTGATGCACGAGGCCCT GCACAACCACTACACCCAGAAGTCTCTGAGCCTGAGCCTGGGCAAG | Hinge-$C_H2$-$C_H3$ spacer (nt |
| 36 | ESKYGPPCPPCPAPEFLGGPSVFLFPPKPKDTLMISRTPEVTCVVVDVSQEDPEVQFN WYVDGVEVHNAKTKPREEQFNSTYRVVSVLTVLHQDWLNGKEYKCKVSNKGLPSSIEK TISKAKGQPREPQVYTLPPSQEEMTKNQVSLTCLVKGFYPSDIAVEWESNGQPENNYK TTPPVLDSDGSFFLYSRLTVDKSRWQEGNVFSCSVMHEALHNHYTQKSLSLSLGK | Hinge-$C_H2$-$C_H3$ spacer (aa) |
| 37 | ESKYGPPCPPCPAPPVAGPSVFLFPPKPKDTLMISRTPEVTCVVVDVSQEDPEVQFNW YV DGVEVHNAKTKPREEQFQSTYRVVSVLTVLHQDWLNGKEYKCKVSNKGLPSSIEKTIS KA KGQPREPQVYTLPPSQEEMTKNQVSLTCLVKGFYPSDIAVEWESNGQPENNYKTTPPV LD SDGSFFLYSRLTVDKSRWQEGNVFSCSVMHEALHNHYTQKSLSLSLGK | IgG4/IgG2 hinge- IgG2/IgG4 $C_H2$-IgG4 $C_H3$ spacer (aa) |
| 38 | gaatctaagtacggaccgccctgccctccctgccctgctcctcctgtggctggaccaa gcgtgttcctgtttccacctaagcctaaagatacccctgatgatttcccgcacacctga agtgacttgcgtggtggtggacgtggagccaggaggatccgaagtgcagttcaactgg tacgtggacggcgtggaagtccacaatgctaagactaaaccccgagaggaacagtttc agtcaacttaccgggtcgtgagcgtgctgaccgtcctgcatcaggattggctgaacgg gaaggagtataagtgcaaagtgtctaataaggactgcctagctccatcgagaaaaca attagtaaggcaaaagggcagcctcgagaaccacaggtgtataccctgccccctagcc aggaggaaatgaccaagaaccaggtgtccctgacatgtctggtcaaaggcttctatcc aagtgacatcgccgtggagtgggaatcaaatgggcagcccgagaacaattacaagacc acaccacccgtgctggactctgatggaagtttctttctgtattccaggctgaccgtgg ataaatctcgctggcaggaggggcaacgtgttctcttgcagtgtcatgcacgaagccct gcacaatcattatacacagaagtcactgagcctgtccctgggcaaa | IgG4/IgG2 hinge- IgG2/IgG4 $C_H2$- IgG4 $C_H3$ spacer (nt) |
| 39 | GGGGS | 4GS linker (aa) |
| 40 | GGGS | 3GS linker (aa) |
| 41 | GGGGSGGGGSGGGGS | (4GS)$_3$ linker (aa) |
| 42 | MPLLLLLPLLWAGALA | CD33 Signal Peptide |
| 43 | MVLQTQVFISLLLWISGAYG | human IgG-kappa signal peptide (aa) |
| 44 | atggtgctgcagacccaggtgttcatcagcctgctgctgtggatctccggagcatacg ga | human IgG-kappa signal sequence (nt) |
| 45 | MLLLVTSLLLCELPHPAFLLIP | GMCSFR alpha chain signal peptide (aa) |
| 46 | atgcttctcctggtgacaagccttctgctctgtgagttaccacacccagcattcctcc tgatccca | GMCSFR alpha chain signal sequence (nt) |

| SEQ ID NO: | Sequence | Description |
|---|---|---|
| 47 | MALPVTALLLPLALLLHA | CD8 alpha signal peptide |
| 48 | ASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKCCVECPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDISVEWESNGQPENNYKTTPPMLDSDGSFFLYSKLTVDKSRWQQGNVFSCSVMHEALHNHYTQKSLSLSPGK | Human IgG2 Fc (Uniprot P01859) |
| 49 | ASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPSCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK | Human IgG4 Fc (Uniprot P01861) |
| 50 | GYTFTSY | CDR-H1 |
| 51 | GYTFTSYGIS | CDR-H1 |
| 52 | SYGIS | CDR-H1 |
| 53 | GYTFTSYG | CDR-H1 |
| 54 | SAYNGN | CDR-H2 |
| 55 | WISAYNGNTK | CDR-H2 |
| 56 | WISAYNGNTKYAQKLQG | CDR-H2 |
| 57 | ISAYNGNT | CDR-H2 |
| 58 | DEDILTGYNYYGMDV | CDR-H3 |
| 59 | ARDEDILTGYNYYGMDV | CDR-H3 |
| 60 | TLSSGHSSYAILA | CDR-L1 |
| 61 | SGHSSYA, | CDR-L1 |
| 62 | LNSDGSHSKGD | CDR-L2 |
| 63 | LNSDGSH | CDR-L2 |
| 64 | QTWGTGIRV | CDR-L3 |
| 65 | GGSISNY | CDR-H1 |
| 66 | GGSISNYYWS | CDR-H1 |
| 67 | NYYWS | CDR-H1 |
| 68 | GGSISNYY | CDR-H1 |
| 69 | YTSGS | CDR-H2 |
| 70 | RIYTSGSTN | CDR-H2 |
| 71 | RIYTSGSTNYNPSLKS | CDR-H2 |
| 72 | IYTSGST | CDR-H2 |
| 73 | YYDILTGFFDY | CDR-H3 |
| 74 | ARYYDILTGFFDY | CDR-H3 |
| 75 | RMSQDISSYLA | CDR-L1 |
| 76 | QDISSY | CDR-L1 |
| 77 | AASSLQS | CDR-L2 |

-continued

| SEQ ID NO: | Sequence | Description |
|---|---|---|
| 78 | AAS | CDR-L2 |
| 79 | QQYDSFPPT | CDR-L3 |
| 80 | GGSINSTTS | CDR-H1 |
| 81 | GGSINSTTSYWA | CDR-H1 |
| 82 | STTSYWA | CDR-H1 |
| 83 | GGSINSTTSY | CDR-H1 |
| 84 | FYSGK | CDR-H2 |
| 85 | TIFYSGKTY | CDR-H2 |
| 86 | TIFYSGKTYNNPSLKS | CDR-H2 |
| 87 | IFYSGKT | CDR-H2 |
| 88 | FDYGFHDAFDI | CDR-H3 |
| 89 | ARFDYGFHDAFDI | CDR-H3 |
| 90 | RASQSITSDYLS | CDR-L1 |
| 91 | QSITSDY | CDR-L1 |
| 92 | GASTRAT | CDR-L2 |
| 93 | GAS | CDR-L2 |
| 94 | QQDYNLTYT | CDR-L3 |
| 95 | SAYTGN | CDR-H2 |
| 96 | WISAYTGNTR | CDR-H2 |
| 97 | WISAYTGNTRYAQKLQG | CDR-H2 |
| 98 | ISAYTGNT | CDR-H2 |
| 99 | EEGATTDYDYYGMDV | CDR-H3 |
| 100 | AREEGATTDYDYYGMDV | CDR-H3 |
| 101 | CAGGTTCAGCTGGTGCAGTCTGGAGCTGAGGTGAAGAAGCCTGGGGCCTCAGTGAAGG TCTCCTGCAAGGCTTCTGGTTACACCTTTACCAGCTATGGTATCAGCTGGGTGCGACA GGCCCCTGGACAAGGGCTTGAGTGGATGGGATGGATCAGCGCTTACAATGGTAACACA AAGTATGCACAGAAGCTCCAGGGCAGAGTCACCATGACCACAGACACATCCACGAGCA CAGCCTACATGGAGCTGAGGAGCCTGAGATCTGACGACACGGCCGTGTATTACTGTGC GAGAGATGAGGATATTTTGACTGGTTACAACTACTACGGTATGGACGTCTGGGGCCAA GGGACCACGGTCACCGTCTCCTCA | $V_H$ (nt) |
| 102 | caggtgcagctggttcaatctggcgccgaagtgaagaaaccaggcgcctctgtgaagg tgtcctgcaaggccagcggctacacctttaccagctacggcatcagctgggtccgaca ggctcctggacaaggcttggaatggatgggctggatcagcgcctacaacggcaacacc aaatacgcccagaaactgcagggcagagtgaccatgaccaccgacaccagcacaagca ccgcctacatggaactgcggagcctgagatccgatgacaccgccgtgtactactgcgc cagagatgaggacatcctgaccggctacaactactacggcatggacgtgtgggggccag ggcacaacagtgacagtttcttct | $V_H$ (nt) O/SSE |
| 103 | QVQLVQSGAEVKKPGASVKVSCKASGYTFTSYGISWVRQAPGQGLEWMGWISAYNGNT KYAQKLQGRVTMTTDTSTSTAYMELRSLRSDDTAVYYCARDEDILTGYNYYGMDVWGQ GTTVTVSS | $V_H$ (aa) |
| 104 | CAGCTTGTGCTGACTCAATCGCCCTCTGCCTCTGCCTCCCTGGGAGCCTCGGTCAAGC TCACCTGCACTCTGAGCAGTGGGCACAGCAGCTACGCCATCGCATGGCATCAGCAGCA GCCAGAGAAGGGCCCTCGGTACTTGATGAAGCTTAACAGTGATGGCAGCCACAGCAAG GGGGACGGGATCCCTGATCGCTTCTCAGGCTCCAGCTCTGGGCTGAGCGCTACCTCA CCATCTCCAGCCTCCAGTCTGAGGATGAGGCTGACTATTACTGTCAGACCTGGGGCAC TGGCATTCGGGTGTTCGGTGGAGGAACCAAACTGACTGTCCTAGGC | $V_L$ (nt) |

-continued

| SEQ ID NO: | Sequence | Description |
|---|---|---|
| 105 | caactggtgctgacacagtctcctagcgcctctgcttctctgggagccagcgtgaagc tgacctgtacactgtctagcggccacagcagctacgccattgcttggcatcagcagca gcccgagaagggccctagatacctgatgaagctgaacagcgacggcagccactctaaa ggcgacggcatccccgatagattcagcggcagttctagcggagccgagcgctacctga caatcagctctctgcaatccgaggacgaggccgactactactgtcagacatggggcac cggcatcagagtgtttggcggaggcaccaagctgacagtgcttgga | $V_L$ (nt) O/SSE |
| 106 | QLVLTQSPSASASLGASVKLTCTLSSGHSSYAIAWHQQQPEKGPRYLMKLNSDGSHSK GDGIPDRFSGSSSGAERYLTISSLQSEDEADYYCQTWGTGIRVFGGGTKLTVLG | $V_L$ (aa) |
| 107 | CAGGTTCAGCTGGTGCAGTCTGGAGCTGAGGTGAAGAAGCCTGGGGCCTCAGTGAAGG TCTCCTGCAAGGCTTCTGGTTACACCTTTACCAGCTATGGTATCAGCTGGGTGCGACA GGCCCCTGGACAAGGGCTTGAGTGGATGGGATGGATCAGCGCTTACAATGGTAACACA AAGTATGCACAGAAGCTCCAGGGCAGAGTCACCATGACCACAGACACATCCACGAGCA CAGCCTACATGGAGCTGAGGAGCCTGAGATCTGACGACACGGCCGTGTATTACTGTGC GAGAGATGAGGATATTTTGACTGGTTACAACTACTACGGTATGGACGTCTGGGGCCAA GGGACCACGGTCACCGTCTCCTCAGGTGGTGGTGGTAGCGGCGGCGGCGGCTCTGGTG GTGGTGGATCCCAGCTTGTGCTGACTCAATCGCCCTCTGCCTCTGCCTCCCTGGGAGC CTCGGTCAAGCTCACCTGCACTCTGAGCAGTGGGCACAGCAGCTACGCCATCGCATGG CATCAGCAGCAGCCAGAGAAGGGCCCTCGGTACTTGATGAAGCTTAACAGTGATGGCA GCCACAGCAAGGGGGACGGGATCCCTGATCGCTTCTCAGGCTCCAGCTCTGGGGCTGA GCGCTACCTCACCATCTCCAGCCTCCAGTCTGAGGATGAGGCTGACTATTACTGTCAG ACCTGGGGCACTGGCATTCGGGTGTTCGGTGGAGGAACCAAACTGACTGTCCTAGGC | scFv ($V_H$-$V_L$) (nt) |
| 108 | caggtgcagctggttcaatctggcgccgaagtgaagaaaccaggcgcctctgtgaagg tgtcctgcaaggccagcggctacacctttaccagctacggcatcagctgggtccgaca ggctcctggacaagggcttggaatggatgggctggatcagcgcctacaacggcaacac aaatacgcccagaaactgcagggcagagtgaccatgaccaccgacacaagcaccagcaca ccgcctacatgcgagcctgagatccgatgacaccgccgtgtactactgcgc cagagatgaggacatcctgaccggctacaactactacggcatggacgtgtggggccag ggcacaacagtgacagttcttctggcggcggaggatctggcggaggtggaagcggag gcggtggatctcaactggtgctgacacagtctcctagcgcctctgcttctctgggagc cagcgtgaagctgacctgtacactgtctagcggccacagcagctacgccattgcttgg catcagcagcagcccgagaagggccctagatacctgatgaagctgaacagcgacggca gccactctaaaggcgacggcatccccgatagattcagcggcagttctagcggagccga gcgctacctgacaatcagctctctgcaatccgaggacgaggccgactactactgtcag acatggggcaccggcatcagagtgtttggcggaggcaccaagctgacagtgcttgga | scFv ($V_H$-$V_L$) (nt) O/SSE |
| 109 | QVQLVQSGAEVKKPGASVKVSCKASGYTFTSYGISWVRQAPGQGLEWMGWISAYNGNT KYAQKLQGRVTMTTDTSTSTAYMELRSLRSDDTAVYYCARDEDILTGYNYYGMDVWGQ GTTVTVSSGGGGSGGGGSGGGGSQLVLTQSPSASASLGASVKLTCTLSSGHSSYAIAW HQQQPEKGPRYLMKLNSDGSHSKGDGIPDRFSGSSSGAERYLTISSLQSEDEADYYCQ TWGTGIRVFGGGTKLTVLG | scFv ($V_H$-$V_L$) (aa) |
| 110 | CAGGTGCAGCTGCAGGAGTCGGGCCCAGGACTGGTGAAGCCTTCGGAGACCCTGTCCC TCACCTGCACTGTCTCTGGAGGCTCCATCAGTAATTACTACTGGAGCTGGATCCGGCA GCCCCCCGGGAAGGGACTGGAGTGGATTGGGCGTATCTATACCAGTGGGAGCACCAAC TACAACCCCTCCCTCAAGAGTCGAGTCACCATGTCAGTAGACACGTCCAAGAACCAGT TCTCCCTGAAGCTGAGTTCTTTGACCGCCGCGGACACGGCCATATATTACTGTGCGAG GTATTACGATATTTTGACTGGTTTCTTTGACTACTGGGGCCAGGGAACCCTGGTCACC GTCTCCTCA | $V_H$ (nt) |
| 111 | Caggttcagctgcaagagtctggccctggcctggtcaagcctagcgaaacactgagcc tgacctgtaccgtgtctggcggcagcatctccaactactactggtcctggatcagaca gcctgccggcaaaggcctggaatggatcggcagaatctacaccagcggcagcaccaac tacaaccccagcctgaagtccagagtgaccatgagcgtggacaccagcaagaaccagt tctccctgaagctgagcagcctgacagccgccgataccgccatctactactgtgcccg gtactacgatatcctgaccggcttcttcgactactggggccagggaacactggtcaca gtttctagc | $V_H$ (nt) O/SSE |
| 112 | QVQLQESGPGLVKPSETLSLTCTVSGGSISNYYWSWIRQPAGKGLEWIGRIYTSGSTN YNPSLKSRVTMSVDTSKNQFSLKLSSLTAADTAIYYCARYYDILTGFFDYWGQGTLVT VSS | $V_H$ (aa) |
| 113 | GTCATCTGGATGACCCAGTCTCCATCCTTACTCTCTGCATCTACAGGAGACAGTGTCA CCATCAGTTGTCGGATGAGTCAGGACATTAGCAGTTATTTAGCCTGGTATCAGCAAAA ACCAGGGAAAGCCCCTGAGCTCCTGATCTATGCTGCATCCAGTTTGCAAAGTGGGGTC CCATCAAGGTTCAGTGGCAGTGGATCTGGGACAGACTTCACTCTCACCATCAGTTCCC TGCAGTCTGAAGATTTTGCTACTTATTACTGTCAACAGTATGATAGTTTCCCTCCGAC GTTCGGCCAAGGGACCAAGGTGGAATTCAAACGG | $V_L$ (nt) |
| 114 | Gtgatttggatgacacagagccctagcctgctgagcgccagcacaggcgatagcgtga ccatcagctgcagaatgagccaggacatcagcagctacctggcttggtatcagcagaa | VL (nt) O/SSE |

| SEQ ID NO: | Sequence | Description |
|---|---|---|
| | gcctggcaaggcccctgaactgctgatctatgccgcttccagtctgcagagcggcgtg<br>ccatctagattttccggcagcggctctggcaccgacttcaccctgacaatcagctccc<br>tgcagtccgaggacttcgccacctactattgccagcagtacgacagcttccctccaac<br>ctttggccagggcaccaaggtggaattcaagcgc | |
| 115 | VIWMTQSPSLLSASTGDSVTISCRMSQDISSYLAWYQQKPGKAPELLIYAASSLQSGV<br>PSRFSGSGSGTDFTLTISSLQSEDFATYYCQQYDSFPPTFGQGTKVEFKR | $V_L$ (aa) |
| 116 | CAGGTGCAGCTGCAGGAGTCGGGCCCAGGACTGGTGAAGCCTTCGGAGACCCTGTCCC<br>TCACCTGCACTGTCTCTGGAGGCTCCATCAGTAATTACTACTGGAGCTGGATCCGGCA<br>GCCCGCCGGGAAGGGACTGGAGTGGATTGGGCGTATCTATACCAGTGGGAGCACCAAC<br>TACAACCCCTCCCTCAAGAGTCGAGTCACCATGTCAGTAGACACGTCCAAGAACCAGT<br>TCTCCCTGAAGCTGAGTTCTTTGACCGCCGCGGACACGGCCATATATTACTGTGCGAG<br>GTATTACGATATTTTGACTGGTTTCTTTGACTACTGGGGCCAGGGAACCCTGGTCACC<br>GTCTCCTCAGGTGGTGGTGGTAGCGGCGGCGGCGGCTCTGGTGGTGGTGGATCCGTCA<br>TCTGGATGACCCAGTCTCCATCCTTACTCTCTGCATCTACAGGAGACAGTGTCACCAT<br>CAGTTGTCGGATGAGTCAGGACATTAGCAGTTATTTAGCCTGGTATCAGCAAAAACCA<br>GGGAAAGCCCCTGAGCTCCTGATCTATGCTGCATCCAGTTTGCAAAGTGGGGTCCCAT<br>CAAGGTTCAGTGGCAGTGGATCTGGGACAGACTTCACTCTCACCATCAGTTCCCTGCA<br>GTCTGAAGATTTTGCTACTTATTACTGTCAACAGTATGATAGTTTCCCTCCGACGTTC<br>GGCCAAGGGACCAAGGTGGAATTCAAACGG | scFv ($V_H$-$V_L$) (nt) |
| 117 | caggttcagctgcaagagtctggccctggcctggtcaagcctagcgaaacactgagcc<br>tgacctgtaccgtgtctggcggcagcatctccaactactactggtcctggatcagaca<br>gcctgccggcaaaggcctggaatggatcggcagaatctacaccagcggcagcaccaac<br>tacaaccccagcctgaagtccagagtgaccatgagcgtggacaccagcaagaaccagt<br>tctccctgaagctgagcagcctgacagccgccgataccgccatctactactgtgcccg<br>gtactacgatatcctgaccggcttcttcgactactggggccagggaacactggtcaca<br>gtttctagcggaggcggaggatctggtggcggaggaagtggcggaggcggttctgtga<br>tttggatgacacagagccctagcctgctgagcgccagcacaggcgatagcgtgaccat<br>cagctgcagaatgagccaggacatcagcagctacctggcttggtatcagcagaagcct<br>ggcaaggcccctgaactgctgatctatgccgcttccagtctgcagagcggcgtgccat<br>ctagattttccggcagcggctctggcaccgacttcaccctgacaatcagctccctgca<br>gtccgaggacttcgccacctactattgccagcagtacgacagcttccctccaaccttt<br>ggccagggcaccaaggtggaattcaagcgc | scFV ($V_H$-$V_L$) (nt) O/SSE |
| 118 | QVQLQESGPGLVKPSETLSLTCTVSGGSISNYYWSWIRQPAGKGLEWIGRIYTSGSTN<br>YNPSLKSRVTMSVDTSKNQFSLKLSSLTAADTAIYYCARYYDILTGFFDYWGQGTLVT<br>VSSGGGGSGGGGSGGGGSVIWMTQSPSLLSASTGDSVTISCRMSQDISSYLAWYQQKP<br>GKAPELLIYAASSLQSGVPSRFSGSGSGTDFTLTISSLQSEDFATYYCQQYDSFPPTF<br>GQGTKVEFKR | sCFV ($V_H$-$V_L$) (aa) |
| 119 | CAGCTGCAGCTGCAGGAGTCGGGCCCAGGACTGGTGAAGCCTTCGGAGACCCTGTCCC<br>TCACCTGCACTGTCTCTGGTGGCTCCATCAACAGTACTACTTCCTACTGGGCCTGGAT<br>CCGCCAGCCCCCAGGGAAGGGGCTGGAGTGGATTGGGACTATCTTTTATAGTGGGAAA<br>ACCTACAACAACCCGTCCCTCAAGAGTCGAGTCACCATGTCCGTAGACACGTCCAAGA<br>ACCACTTCTCCCTGAAGGTGAACTCTGTGACCGCCGCAGACACGGCTGTGTATTACTG<br>TGCGAGGTTTGACTACGGTTTTCATGATGCTTTTGATATCTGGGGCCAGGGGACAATG<br>GTCACCGTCTCTTCA | $V_H$ (nt) |
| 120 | cagctccagctgcaagaatctggacctggcctggtcaagcccagcgagacactgtctc<br>tgacctgtacagtgtccggcggcagcatcaatagcaccacaagctactgggcctggat<br>cagacagcctcctggcaaaggcctggaatggatcggcaccatcttctacagcggcaag<br>acctacaacaaccccagcctgaagtccagagtgaccatgagcgtggacaccagcaaga<br>accacttcagcctgaaagtgaacagcgtgacagccgccgataccgccgtgtactactg<br>cgccagattcgactacggcttccacgacgccttcgacatctggggccagggcacaatg<br>gtcacagtttctagc | $V_H$ (nt) O/SSE |
| 121 | QLQLQESGPGLVKPSETLSLTCTVSGGSINSTTSYWAWIRQPPGKGLEWIGTIFYSGK<br>TYNNPSLKSRVTMSVDTSKNHFSLKVNSVTAADTAVYYCARFDYGFHDAFDIWGQGTM<br>VTVSS | $V_H$ (aa) |
| 122 | GAAATTGTAATGACACAGTCTCCAGCCACCCTGTCTTTGTCTCCAGGGGAAAGAGCCA<br>CCCTCTCCTGCAGGGCCAGTCAGAGTATTACCAGCGACTACTTATCCTGGTACCAACA<br>AAAACCTGGGCAGGCTCCCAGGCTCCTCATCTATGGTGCATCCACCAGGGCCACTGGC<br>ATCCCAGCCAGGTTCAGTGGCAGTGGGTCTGGGACAGACTTCACTCTCACCATCAGCA<br>GCCTGCAGCCTGAAGATTTTGTAGTTTATTACTGTCAGCAGGATTATAACTTGTACAC<br>TTTTGGCCAGGGGACCAAGCTGGAGATCAAACGG | $V_L$ (nt) |
| 123 | gagattgtgatgacacagagccccgccactctgagccttagtcctggcgaaagagcca<br>cactgagctgcagagccagccagagcattaccagcgattacctgagctggtatcagca<br>gaagcccggacaggctcccagactgctgatctatggcgcctctacaagagccaccggc<br>attcccgcccgcttttctggctctggaagcggcaccgacttcaccctgaccatatcta | $V_L$ (nt) O/SSE |

| SEQ ID NO: | Sequence | Description |
|---|---|---|
| | gcctgcagcctgaggacttcgtggtgtactattgccagcaggactacaacctgtacac cttcggccaggggaccaagctggaaatcaagaga | |
| 124 | EIVMTQSPATLSLSPGERATLSCRASQSITSDYLSWYQQKPGQAPRLLIYGASTRATG IPARFSGSGSGTDFTLTISSLQPEDFVVYYCQQDYNLYTFGQGTKLEIKR | $V_L$ (aa) |
| 125 | CAGCTGCAGCTGCAGGAGTCGGGCCCAGGACTGGTGAAGCCTTCGGAGACCCTGTCCC TCACCTGCACTGTCTCTGGTGGCTCCATCAACAGTACTACTTCCTACTGGGCCTGGAT CCGCCAGCCCCCAGGGAAGGGGCTGGAGTGGATTGGGACTATCTTTTATAGTGGGAAA ACCTACAACAACCCGTCCCTCAAGAGTCGAGTCACCATGTCCGTAGACACGTCCAAGA ACCACTTCTCCCTGAAGGTGAACTCTGTGACCGCCGCAGACACGGCTGTGTATTACTG TGCGAGGTTTGACTACGGTTTTCATGATGCTTTTGATATCTGGGGCCAGGGGACAATG GTCACCGTCTCTTCAGGTGGTGGTGGTAGCGGCGGCGGCGGCTCTGGTGGTGGTGGAT CCGAAATTGTAATGACACAGTCTCCAGCCACCCTGTCTTTGTCTCCAGGGGAAAGAGC CACCCTCTCCTGCAGGGCCAGTCAGAGTATTACCAGCGACTACTTATCCTGGTACCAA CAAAAACCTGGGCAGGCTCCCAGGCTCCTCATCTATGGTGCATCCACCAGGGCCACTG GCATCCCAGCCAGGTTCAGTGGCAGTGGGTCTGGGACAGACTTCACTCTCACCATCAG CAGCCTGCAGCCTGAAGATTTTGTAGTTTATTACTGTCAGCAGGATTATAACTTGTAC ACTTTTGGCCAGGGGACCAAGCTGGAGATCAAACGG | scFv ($V_H$-$V_L$) (nt) |
| 126 | Cagctccagctgcaagaatctggacctggcctggtcaagcccagcgagacactgtctc tgacctgtacagtgtccggcggcagcatcaatagcaccacaagctactgggcctggat cagacagcctcctggcaaaggcctggaatggatcggcaccatcttctacagcggcaag acctacaacaacccagcctgaagtccagagtgaccatgagcgtggacaccagcaaga accacttcagcctgaaagtgaacagcgtgacagccgccgataccgccgtgtactactg cgccagattcgactacggcttccacgacgccttcgacatctggggccagggcacaatg gtcacagtttctagcggaggcggaggatctggtggcggaggaagtggcggaggcggtt ctgagattgtgatgacacagagccccgccactctgagcctttagtcctggcgaaagagc cacactgagctgcagagccagcagagcatcaccagcgattacttacctggtaccaa cagaagcccggacaggctcccagactgctgatctatggcgcctctacaagagccaccg gcattccgcccgcttttctggctctggaagcggcaccgacttcaccctgaccatatc tagcctgcagcctgaggacttcgtggtgtactattgccagcaggactacaacctgtac accttcggccaggggaccaagctggaaatcaagaga | scFv ($V_H$-$V_L$) (nt) O/SSE |
| 127 | QLQLQESGPGLVKPSETLSLTCTVSGGSINSTTSYWAWIRQPPGKGLEWIGTIFYSGK TYNNPSLKSRVTMSVDTSKNHFSLKVNSVTAADTAVYYCARFDYGFHDAFDIWGQGTM VTVSSGGGGSGGGGSGGGGSEIVMTQSPATLSLSPGERATLSCRASQSITSDYLSWYQ QKPGQAPRLLIYGASTRATGIPARFSGSGSGTDFTLTISSLQPEDFVVYYCQQDYNLY TFGQGTKLEIKR | scFv ($V_H$-$V_L$) (aa) |
| 128 | CAGGTTCAGCTGCTGCAGTCTGGAGCTGAGGTGAAGAAGCCTGGGGCCTCAGTGAAGG TCTCCTGCAAGGCTTCTGGTTACACCTTTACCAGCTATGGTATCAGCTGGGTGCGACA GGCCCCTGGACAAGGGCTTGAGTGGATGGGATGGATCAGCGCTTACACTGGTAACACA AGGTATGCACAGAAGCTCCAGGGCAGAGTCACCATGACCACAGACACATCCACGAGCA CAGCCTACATGGAGCTGAGGAGCCTGAGATCTGACGACACGGCCGTGTATTACTGTGC GAGAGAAGAAGGAGCTACTACGGACTACGACTACTACGGTATGGACGTCTGGGGCCAA GGGACTGCGGTCACCGTCTCCTCA | $V_H$ (nt) |
| 129 | caggttcagctgcttcagtctggcgccgaagtgaagaaacctggcgcctctgtgaagg tgtcctgcaaggccagcggctacacctttaccagctacggcatcagctgggtccgaca ggctcctggacaaggcttggaatggatgggctggatcagcgcctacaccggcaatacc agatacgcccagaaactgcagggcagagtgaccatgaccaccgacaccagcacaagca ccgcctacatggaactgcggagcctgagatccgatgacaccgccgtgtactactgcgc cagagaagaaggcgccaccaccgactacgactactacggcatggatgtgtggggccag ggaacagccgtgacagtttcttct | $V_H$ (nt) O/SSE |
| 130 | QVQLLQSGAEVKKPGASVKVSCKASGYTFTSYGISWVRQAPGQGLEWMGWISAYTGNT RYAQKLQGRVTMTTDTSTSTAYMELRSLRSDDTAVYYCAREEGATTDYDYYGMDVWGQ GTAVTVSS | $V_H$ (aa) |
| 131 | caactggttctgacacagagcccaagcgcctctgcatctctgggagcttccgtgaagc tgacctgcacactgtctagcggccacagcagctatgccattgcctggcagcagcaaca gcccgagaagggccctagatacctgatgaagctgaacagcgacggcagccactctaaa ggcgacggcatccccgatagattcagcggcagttctagcggagccgagcgctacctga caatcagctctctgcaatccgaggacgaggccgattactactgtcagacatggggcac cggcatcagagtgtttggcggcggaacaaagctgaccgtgctgggc | $V_L$ (nt) O/SSE |
| 132 | CAGGTTCAGCTGCTGCAGTCTGGAGCTGAGGTGAAGAAGCCTGGGGCCTCAGTGAAGG TCTCCTGCAAGGCTTCTGGTTACACCTTTACCAGCTATGGTATCAGCTGGGTGCGACA GGCCCCTGGACAAGGGCTTGAGTGGATGGGATGGATCAGCGCTTACACTGGTAACACA AGGTATGCACAGAAGCTCCAGGGCAGAGTCACCATGACCACAGACACATCCACGAGCA CAGCCTACATGGAGCTGAGGAGCCTGAGATCTGACGACACGGCCGTGTATTACTGTGC GAGAGAAGAAGGAGCTACTACGGACTACGACTACTACGGTATGGACGTCTGGGGCCAA | scFv ($V_H$-$V_L$) (nt) |

| SEQ ID NO: | Sequence | Description |
|---|---|---|
| | GGGACTGCGGTCACCGTCTCCTCAGGTGGTGGTGGTAGCGGCGGCGGCGGCTCTGGTG<br>GTGGTGGATCCCAGCTTGTGCTGACTCAATCGCCCTCTGCCTCTGCCTCCCTGGGAGC<br>CTCGGTCAAGCTCACCTGCACTCTGAGCAGTGGGCACAGCAGCTACGCCATCGCATGG<br>CATCAGCAGCAGCCAGAGAAGGGCCCTCGGTACTTGATGAAGCTTAACAGTGATGGCA<br>GCCACAGCAAGGGGGACGGGATCCCTGATCGCTTCTCAGGCTCCAGCTCTGGGGCTGA<br>GCGCTACCTCACCATCTCCAGCCTCCAGTCTGAGGATGAGGCTGACTATTACTGTCAG<br>ACCTGGGGCACTGGCATTCGGGTGTTCGGTGGAGGAACCAAACTGACTGTCCTAGGC | |
| 133 | caggttcagctgcttcagtctggcgccgaagtgaagaaacctggcgcctctgtgaagg<br>tgtcctgcaaggccagcggctacacctttaccagctacggcatcagctgggtccgaca<br>ggctcctggacaaggcttggaatggatgggctggatcagcgcctacaccggcaatacc<br>agatacgcccagaaactgcagggcagagtgaccatgaccaccgacaccagcacaagca<br>ccgcctacatggaactgcggagcctgagatccgatgacaccgccgtgtactactgcgc<br>cagagaagaaggcgccaccaccgactacgactactacggcatggatgtgtggggccag<br>ggaacagccgtgacagtttcttctggtggcggaggatctggcggaggtggaagcggcg<br>gaggcggatctcaactggttctgacacagagcccaagcgctctgagcctctgggagc<br>ttccgtgaagctgacctgcacactgtctagcggccacagcagctatgccattgcctgg<br>catcagcaacagcccgagaagggccctagatacctgatgaagctgaacagcgacggca<br>gccactctaaaggcgacggcatccccgatagattcagcggcagttctagcggagccga<br>gcgctacctgacaatcagctctctgcaatccgaggacgaggccgattactactgtcag<br>acatggggcaccggcatcagagtgtttggcggcggaacaaagctgaccgtgctgggc | scFv (V$_H$-V$_L$) (nt) O/SSE |
| 134 | QVQLLQSGAEVKKPGASVKVSCKASGYTFTSYGISWVRQAPGQGLEWMGWISAYTGNT<br>RYAQKLQGRVTMTTDTSTSTAYMELRSLRSDDTAVYYCAREEGATTDYDYYGMDVWGQ<br>GTAVTVSSGGGGSGGGGSGGGGSQLVLTQSPSASASLGASVKLTCTLSSGHSSYAIAW<br>HQQQPEKGPRYLMKLNSDGSHSKGDGIPDRFSGSSSGAERYLTISSLQSEDEADYYCQ<br>TWGTGIRVFGGGTKLTVLG | scFv (V$_H$-V$_L$) (aa) |
| 135 | ESKYGPPCPPCPM | IgG4 hinge spacer (aa) |
| 136 | gagtctaaatacggaccgccttgtcctccttgtcccatg | IgG4 hinge spacer (nt) O/SSE |
| 137 | gagtctaaatacggaccgccttgtcctccttgtcccggccagccaagagagcccagg<br>tttacacactgcctccaagccaagaggaaatgaccaagaatcaggtgtccctgacatg<br>cctggtcaagggcttctacccctccgatatcgccgtggaatgggagagcaatggccag<br>cctgagaacaactacaagaccacacctcctgtgctggacagcgacggcagtttcttcc<br>tgtatagtagactcaccgtggataaatcaagatggcaagagggcaacgtgttcagctg<br>cagcgtgatgcacgaggccctgcacaaccactacacccagaaaagcctgagcctgtct<br>ctgggcaag | Hinge-C$_H$3 spacer (nt) O/SSE |
| 138 | ESKYGPPCPPCPGQPREPQVYTLPPSQEEMTKNQVSLTCLVKGFYPSDIAVEWESNGQ<br>PENNYKTTPPVLDSDGSFFLYSRLTVDKSRWQEGNVFSCSVMHEALHNHYTQKSLSLS<br>LGKM | Hinge-C$_H$3 spacer (aa) |
| 139 | gagtctaaatacggaccgccttgtcctccttgtcccggccagccaagagagcccagg<br>tttacacactgcctccaagccaagaggaaatgaccaagaatcaggtgtccctgacatg<br>cctggtcaagggcttctacccctccgatatcgccgtggaatgggagagcaatggccag<br>cctgagaacaactacaagaccacacctcctgtgctggacagcgacggcagtttcttcc<br>tgtatagtagactcaccgtggataaatcaagatggcaagagggcaacgtgttcagctg<br>cagcgtgatgcacgaggccctgcacaaccactacacccagaaaagcctgagcctgtct<br>ctgggcaagatg | Hinge-C$_H$3 spacer (nt) O/SSE |
| 140 | gagtctaaatacggaccgccttgtcctccttgtcccgctcctcctgttgccggacctt<br>ccgtgttcctgtttcctccaaagcctaaggacaccctgatgatcagcaggacccctga<br>agtgacctgcgtggtggtggatgtgtcccaagaggatcccgagtgcagttcaactgg<br>tatgtggacggcgtggaagtgcacaacgccaagaccaagcctagagaggaacagttcc<br>agagcacctacagagtggtgtccgtgctgacagtgctgcaccaggattggctgaacgg<br>caaagagtacaagtgcaaggtgtccaacaaggccctgcctagcagcatcgagaaaacc<br>atctccaaggccaagggccagccaagagagcccaggtttacacactgcctccaagcc<br>aagaggaaatgaccaagaatcaggtgtccctgacatgcctggtcaagggcttctaccc<br>ctccgatatcgccgtggaatgggagagcaatggccagcctgagaacaactacaagacc<br>acacctcctgtgctggacagcgacggcagtttcttcctgtatagtagactcaccgtgg<br>ataaatcaagatggcaagagggcaacgtgttcagctgcagcgtgatgcacgaggccct<br>gcacaaccactacacccagaaaagcctgagcctgtctctgggcaag | IgG4/IgG2 hinge-IgG2/IgG4 C$_H$2-IgG4 C$_H$3 spacer (nt) O/SSE |
| 141 | cttgaaggtggtggcgaaggcagaggcagcctgcttacatgcggagatgtggaagaga<br>accccggacctaga | T2A (nt) O/SSE |
| 142 | QEQLVESGGRLVTPGGSLTLSCKASGFDFSAYYMSWVRQAPGKGLEWIATIYPSSGKT<br>YYATWVNGRFTISSDNAQNTVDLQMNSLTAADRATYFCARDSYADDGALFNIWGPGTL | R12 V$_H$-V$_L$ scFv (aa) |

| SEQ ID NO: | Sequence | Description |
|---|---|---|
| | VTISSGGGGSGGGGSGGGGSELVLTQSPSVSAALGSPAKITCTLSSAHKTDTIDWYQQ<br>LQGEAPRYLMQVQSDGSYTKRPGVPDRFSGSSSGADRYLIIPSVQADDEADYYCGADY<br>IGGYVFGGGTQLTVTG | |
| 143 | caagaacagctggtggaatctggcggcagactggttacacctggcggaagcctgacac<br>tgagctgtaaagccagcggcttcgacttcagcgcctactacatgagctggtccgaca<br>ggcccctggcaaaggactggaatggatcgccacaatctaccccagctccggcaagacc<br>tactacgccacatgggcaacggccggttcaccatcagcagcgacaacgcccagaaca<br>ccgtggacctgcagatgaactctctgacagccgccgaccgggccaccttactttgtgc<br>cagagatagctacgccgacgacggcgccgttcaatatttgggacctggcacactc<br>gtgaccatctctagcggaggcggaggaagtggtggcggaggatcaggcggtggtggat<br>ctgaactggtgctgacacagagccctctgtgtctgctgctctgggaagcctgccaa<br>gatcacatgtaccctgagcagcgcccacaagaccgacaccatcgactggtatcagcag<br>ctgcagggcgaagccctagatacctgatgcaggttcagagcgacggcagctacacca<br>aaagacctggcgtgcccgatagattcagcggcagttcttctggcgccgatcgctacct<br>gatcatcccttctgtgcaagccgacgatgaggccgactattactgcggagccgattac<br>atcggctacgttttcggtggcggcacacagttgacagtgacaggcg | R12 V$_H$-V$_L$ scFv (nt) |
| 144 | QETELSVSAELVPTSSWNISSELNKDSYLTLDEPMNNITTSLGQTAELHCKVSGNPPP<br>TIRWFKNDAPVVQEPRRLSFRSTIYGSRLRIRNLDTTDTGYFQCVATNGKEVVSSTGV<br>LFVKFGPPPTASPGYSDEYEEDGFCQPYRGIACARFIGNRTVYMESLHMQGEIENQIT<br>AAFTMIGTSSHLSDKCSQFAIPSLCHYAFPYCDETSSVPKPRDLCRDECEILENVLCQ<br>TEYIFARSNPMILMRLKLPNCEDLPQPESPEAANCIRIGIPMADPINKNHKCYNSTGV<br>DYRGTVSVTKSGRQCQPWNSQYPHTHTFTALRFPELNGGHSYCRNPGNQKEAPWCFTL<br>DENFKSDLCDIPACDSKDSKEKNKMEILYILVPSVAIPLAIALLFFFICVCRNNQKSS<br>SAPVQRQPKHVRGQNVEMSMLNAYKPKSKAKELPLSAVRFMEELGECAFGKIYKGHLY<br>LPGMDHAQLVAIKTLKDYNNPQQWTEFQQEASLMAELHHPNIVCLLGAVTQEQPVCML<br>FEYINQGDLHEFLIMRSPHSDVGCSSDEDGTVKSSLDHGDFLHIAIQIAAGMEYLSSH<br>FFVHKDLAARNILIGEQLHVKISDLGLSREIYSADYYRVQSKSLLPIRWMPPEAIMYG<br>KFSSDSDIWSFGVVLWEIFSFGLQPYYGFSNQEVIEMVRKRQLLPCSEDCPPRMYSLM<br>TECWNEIPSRRPRFKDIHVRLRSWEGLSSHTSSTTPSGGNATTQTTSLSASPVSNLSN<br>PRYPNYMFPSQGITPQGQIAGFIGPPIPQNQRFIPINGYPIPPGYAAFPAAHYQPTGP<br>PRVIQHCPPPKSRSPSSASGSTSTGHVTSLPSSGSNQEANIPLLPHMSIPNHPGGMGI<br>TVFGNKSQKPYKIDSKQASLLGDANIHGHTESMISAEL | human ROR1 (aa)<br>GenBank: AAA60275.1 |
| 145 | QETELSVSAELVPTSSWNISSELNKDSYLTLDEPMNNITTSLGQTAELHCKVSGNPPP<br>TIRWFKNDAPVVQEPRRLSFRSTIYGSRLRIRNLDTTDTGYFQCVATNGKEVVSSTGV<br>LFVKFGPPPTASPGYSDEYEEDGFCQPYRGIACARFIGNRTVYMESLHMQGEIENQIT<br>AAFTMIGTSSHLSDKCSQFAIPSLCHYAFPYCDETSSVPKPRDLCRDECEILENVLCQ<br>TEYIFARSNPMILMRLKLPNCEDLPQPESPEAANCIRIGIPMADPINKNHKCYNSTGV<br>DYRGTVSVTKSGRQCQPWNSQYPHTHTFTALRFPELNGGHSYCRNPGNQKEAPWCFTL<br>DENFKSDLCDIPACDSKDSKEKNKMEILYILVPSVAIPLAIALLFFFICVCRNNQKSS<br>SAPVQRQPKHVRGQNVEMSMLNAYKPKSKAKELPLSAVRFMEELGECAFGKIYKGHLY<br>LPGMDHAQLVAIKTLKDYNNPQQWTEFQQEASLMAELHHPNIVCLLGAVTQEQPVC | human ROR1 isoform 2 (aa) |
| 146 | QETELSVSAELVPTSSWNISSELNKDSYLTLDEPMNNITTSLGQTAELHCKVSGNPPP<br>TIRWFKNDAPVVQEPRRLSFRSTIYGSRLRIRNLDTTDTGYFQCVATNGKEVVSSTGV<br>LFVKFGPPPTASPGYSDEYEEDGFCQPYRGIACARFIGNRTVYMESLHMQGEIENQIT<br>AAFTMIGTSSHLSDKCSQFAIPSLCHYAFPYCDETSSVPKPRDLCRDECEILENVLCQ<br>TEYIFARSNPMILMRLKLPNCEDLPQPESPEAANCIRIGIPMADPINKNHKCYNSTGV<br>DYRGTVSVTKSGRQCQPWNSQYPHTHTFTALRFPELNGGHSYCRNPGNQKEAPWCFTL<br>DENFKSDLCDIPACGK | human ROR1 isoform 3 (aa) |
| 147 | atgttttgggtgctggtcgtggtcggaggggtgctggcctgttacagcctgctggtga<br>cagtcgctttcatcatcttctgggtg | CD28 transmembrane domain (nt) |
| 148 | atgttctgggtgctcgtggtcgttggcggagtgctggcctgttacagcctgctggtta<br>ccgtggccttcatcatcttttgggtc | CD28 transmembrane domain (nt) (O/SSE) |
| 149 | MFWVLVVVGGVLACYSLLVTVAFIIFWV | CD28 transmembrane domain (aa) |
| 150 | agagtgaagttcagcagatccgccgacgctccagcctatcagcagggccaaaaccagc<br>tgtacaacgagctgaacctggggaagagaagagtacgacgtgctggataagcggag<br>aggcagagatcctgaaatgggcggcaagcccagacgaagaatcctcaagagggcctg<br>tataatgagctgcagaaagacaagatggccgaggcctacagcgagatcggaatgaagg<br>gcgagcgcagaagaggcaagggacacgatggactgtaccagggcctgagcaccgccac<br>caaggatacctatgacgcactgcacatgcaggccctgccacctaga | CD3-zeta derived intracellular signaling domain (nt) (O/SSE) |

| SEQ ID NO: | Sequence | Description |
|---|---|---|
| 151 | atgcttctcctggtgacaagccttctgctctgtgagttaccacacccagcattcctcc<br>tgatcccacgcaaagtgtgtaacggaataggtattggtgaatttaaagactcactctc<br>cataaatgctacgaatattaaacacttcaaaaactgcacctccatcagtggcgatctc<br>cacatcctgccggtggcatttaggggtgactccttcacacatactcctcctctggatc<br>cacaggaactggatatactgaaaaccgtaaaggaaatcacagggttttgctgattca<br>ggcttggcctgaaaacaggacggacctccatgcctttgagaacctagaaatcatacgc<br>ggcaggaccaagcaacatggtcagttttctcttgcagtcgtcagcctgaacataacat<br>cctgggattacgctccctcaaggagataagtgatggagatgtgataatttcaggaaa<br>caaaaatttgtgctatgcaaatacaataaaactggaaaaaactgtttgggacctccgt<br>cagaaaaccaaaattataagcaacagaggtgaaaacagctgcaaggccacaggccagg<br>tctgccatgccttgtgctcccccgagggctgctggggcccggagcccagggactgcgt<br>ctcttgccggaatgtcagccgaggcagggaatgcgtggacaactccactcctggag<br>ggtgagccaagggagtttgtggagaactctgagtgcatacagtgccacccagagtgcc<br>tgcctcaggccatgaacatcacctgcacaggacgggaccagacaactgtatccagtg<br>tgcccactacattgacggccccactgcgtcaagacctgcccggcaggagtcatggga<br>gaaaacaacaccctggtctggaagtacgcagacgccggcgtgatgccacctgtgcc<br>atccaaactgcacctacggatgcactgggccaggtcttgaaggctgtccaacgaatgg<br>gcctaagatcccgtccatcgccactgggatggtggggcctcctcttgctgctggtg<br>gtggccctggggatcggcctcttcatgtga | truncated EGFR (tEGFR) sequence (nt) |
| 152 | atgctgctcctcgtgacaagcctgctcctgtgtgaactccctcatccagcttttctgc<br>tcattcctcggaaagtgtgcaacggcatcggcatcggagagttcaaggacagcctgag<br>catcaatgccaccaacatcaagcacttcaagaattgcaccagcatcagcggcgacctg<br>cacattctgcctgtggccttagaggcgacagcttcaccacacacctccactgaatc<br>cccaagagctggatatcctgaaaaccgtgaaagagattaccggattcctcctgatcca<br>agcctggccagagaacagaaccgatctgcacgccttcgagaacctcgagatcatcaga<br>ggccggaccaaacagcacggccagtttagcctggctgtggtgtctctgaacatcacca<br>gtctgggcctgagaagcctgaaagaaatctccgacggcgacgtgatcatctccggaaa<br>caagaacctgtgctacgccaacaccatcaactggaagaagctgttcggcacctccggc<br>cagaaaacaaagatcatctctaaccggggcgagaacagctgcaaggccaccggacaag<br>tttgtcacgccctgtgtagccctgaaggctgttggggacccgaacctagagactgtgt<br>gtcctgccgaatgtgtcccggggcagagaatgtgtggataagtgcaacctgctggaa<br>ggcgagccccgagtttgtggaaaacagcgagtgcatccagtgccacccgagtgtc<br>tgccccaggccatgaacattacatgcaccggcagaggccccgacaactgtattcagtg<br>cgcccactacatcgacggccctcactgcgtgaaaacatgtccagctggcgtgatggga<br>gagaacaacaccctcgtgtggaagtatgccgacgccgacatgtgtgccacctgtgtc<br>accctaattgcacctacggctgtaccggacctggcctggaaggatgccctacaaacgg<br>ccctaagatccccagcattgccaccggaatggttggagccctgctgcttctgttggtg<br>gtggccctcggaatcggcctgttcatgtga | truncated EGFR (tEGFR) sequence (nt) (O/SSE) |
| 153 | MLLLVTSLLLCELPHPAFLLIPRKVCNGIGIGEFKDSLSINATNIKHFKNCTSISGDL<br>HILPVAFRGDSFTHTPPLDPQELDILKTVKEITGFLLIQAWPENRTDLHAFENLEIIR<br>GRTKQHGQFSLAVVSLNITSLGLRSLKEISDGDVIISGNKNLCYANTINWKKLFGTSG<br>QKTKIISNRGENSCKATGQVCHALCSPEGCWGPEPRDCVSCRNVSRGRECVDKCNLLE<br>GEPREFVENSECIQCHPECLPQAMNITCTGRGPDNCIQCAHYIDGPHCVKTCPAGVMG<br>ENNTLVWKYADAGHVCHLCHPNCTYGCTGPGLEGCPTNGPKIPSIATGMVGALLLLLV<br>VALGIGLFM | truncated EGFR (tEGFR) sequence (aa) |
| 154 | aagcgggggagaaagaaactgctgtatattttcaaacagccctttatgagacctgtgc<br>agactacccaggaggaagacggatgcagctgtaggtttccgaggaagaggaaggagg<br>ctgtgagctg | 4-1BB intracellular co-signaling sequence (nt) |
| 155 | aagcggggcagaaagaagctgctctacatcttcaagcagcccttcatgcggcccgtgc<br>agaccacacaagaggaagatggctgctcctgcagattccccgaggaagaagaaggcgg<br>ctgcgagctg | 4-1BB intracellular co-signaling sequence (nt)- (O/SSE) |
| 156 | caggttcagctgcaagagtctggccctggcctggtcaagcctagcgaaacactgagcc<br>tgacctgtaccgtgtctggcggcagcatctccaactactactggtcctggatcagaca<br>gcctgccggcaaaggcctggaatggattcggcagaatctcaccagcggcagcaccaac<br>tacaaccccagcctgaagtccagagtgaccatgagcgtggacacagcagaaccagt<br>tctccctgaagctgagcagcctgacagccgccgataccgccatctactactgtgcccg<br>gtactacgatatcctgaccggcttcttcgactactggggccagggaaacactggtcaca<br>gtttctagcggaggcggaggatctggtggcggaggaagtggcggaggcggttctgtga<br>tttggatgacacagagccctagcctgctgagcgccagcacaggcgatagcgtgaccat<br>cagctgcagaagcagcaggacatcagcagtcacctggcttggtatcagcagaagcct<br>ggcaaggcccctgaactgctgatctatgccgcttccagtctgcagagcggcgtgccat<br>ctagattttccggcagcggctctggcaccgacttcacccctgacaatcagctccctgca<br>gtccgaggacttcgccacctactattgccagcagtacgacagcttccctccaaccttt<br>ggccagggcaccaaggtggaattcaagcgcgagtctaaatacggaccgccttgtcctc<br>cttgtcccatgttctgggtgctcgtggtcgttggcggagtgctggcctgttacagcct | anti-ROR1 CAR (nt) |

| SEQ ID NO: | Sequence | Description |
|---|---|---|
| | gctggttaccgtggccttcatcatctttttgggtcaagcggggcagaaagaagctgctc<br>tacatcttcaagcagcccttcatgcggcccgtgcagaccacacaagaggaagatggct<br>gctcctgcagattccccgaggaagaagaaggcggctgcgagctgagagtgaagttcag<br>cagatccgccgacgctccagcctatcagcagggccaaaaccagctgtacaacgagctg<br>aacctggggagaagagaagagtacgacgtgctggataagcggagaggcagagatcctg<br>aaatgggcggcaagcccagacggaagaatcctcaagagggcctgtataatgagctgca<br>gaaagacaagatggccgaggcctacagcgagatcggaatgaagggcgagcgcagaaga<br>ggcaagggacacgatggactgtaccagggcctgagcaccgccaccaaggatacctatg<br>acgcactgcacatgcaggccctgccacctaga | |
| 157 | cagctccagctgcaagaatctggacctggcctggtcaagcccagcgagacactgtctc<br>tgacctgtacagtgtccggcggcagcatcaatagcaccacaagctactgggcctggat<br>cagacagcctcctggcaaaggcctggaatggatcggcaccatcttctacagcggcaag<br>acctacaacaacccagcctgaagtccagagtgaccatgagcgtggacaccagcaaga<br>accacttcagcctgaaagtgaacagcgtgacagccgccgataccgccgtgtactactg<br>cgccagattcgactacggcttccacgacgccttcgacatctgggggcagggcacaatg<br>gtcacagtttctagcggaggcggaggatctggtggcggaggaagtggcggaggcggtt<br>ctgagattgtgatgacacagagccccgccactctgagcctagtcctggcgaaagagc<br>cacactgagctgcagagccagcagagcatcaccagcgattacctgagctggtatcag<br>cagaagcccggacaggctcccagactgctgatctatggcgcctctacaagagccaccg<br>gcattcccgcccgcttttctggctctggaagcggcaccgacttcaccctgaccatatc<br>tagcctgcagcctgaggacttcgtggtgtactattgccagcaggactacaacctgtac<br>accttcggccaggggaccaagctggaaatcaagagagagtctaaatacgaccgcctt<br>gtcctccttgtcccatgttctgggtgctcgtggtcgttggcggagtgctggcctgtta<br>cagcctgctggttaccgtggccttcatcatctttttgggtcaagcggggcagaaagaag<br>ctgctctacatcttcaagcagcccttcatgcggcccgtgcagaccacacaagaggaa<br>atggctgctcctgcagattccccgaggaagaagaaggcggctgcgagctgagagtgaa<br>gttcagcagatccgccgacgctccagcctatcagcagggccaaaaccagctgtacaac<br>gagctgaacctggggagaagagaagagtacgacgtgctggataagcggagaggcagag<br>atcctgaaatgggcggcaagcccagacggaagaatcctcaagagggcctgtataatga<br>gctgcagaaagacaagatggccgaggcctacagcgagatcggaatgaagggcgagcgc<br>agaagaggcaagggacacgatggactgtaccagggcctgagcaccgccaccaaggata<br>cctatgacgcactgcacatgcaggccctgccacctaga | anti-ROR1 CAR (nt) |
| 158 | caggttcagctgcaagagtctggccctggcctggtcaagcctagcgaaacactgagcc<br>tgacctgtaccgtgtctggcggcagcatctccaactactactggtcctggatcagaca<br>gcctgccggcaaaggcctggaatggatcggcagaatctacaccagcggcagcaccaac<br>tacaacccagcctgaagtccagagtgaccatgagcgtggacaccagcaagaaccagt<br>ctcccctgaagctgagcagcctgacagccgccgataccgccatctactactgtgcccg<br>gtactacgatatcctgaccggcttcttcgactactggggccagggaacactggtcaca<br>gttctagcggaggcggaggatctggtggcggaggaagtggcggaggcggttctgtga<br>tttggatgacacagagccctagcctgctgagcgccagcacaggcgatagcgtgaccat<br>cagctgcagaatgagccaggacatcagcagctacctggcttggtatcagcagaagcct<br>ggcaaggcccctgaactgctgatctatgccgcttccagtctgcagagcggcgtgccat<br>ctagattttccggcagcggctctggcaccgacttcacccctgacaatcagctccctgca<br>gtccgaggacttcgccacctactattgccagcagtacgacgcttccctccaacctt<br>ggccagggcaccaaggtggaattcaagcgcgagtctaaatacggaccgccttgtcctc<br>cttgtcccggccagccaagagagccccaggttacacactgcctccaagccaagagga<br>aatgaccaagaatcaggtgtccctgacatgcctggtcaaggcttctaccccctccgat<br>atcgccgtggaatgggagagcaatggccagcctgagaacaactacaagaccacacctc<br>ctgtgctggacagcgacggcagttttcttcctgtatagtagactcaccgtggataaatc<br>aagatggcaagagggcaacgtgttcagctgcagcgtgatgcacgaggccctgcacaac<br>cactacacccagaaaagcctgagcctgtctctgggcaagatgttctgggtgctcgtgg<br>tcgttggcggagtgctggcctgttacagcctgctggttaccgtggccttcatcatctt<br>ttgggtcaagcggggcagaaagaagctgctctacatcttcaagcagcccttcatgcgg<br>cccgtgcagaccacacaagaggaagatggctgctcctgcagattccccgaggaagaag<br>aaggcggctgcgagctgagagtgaagttcagcagatccgccgacgctccagcctatca<br>gcagggccaaaaccagctgtacaacgagctgaacctggggagaagagaagagtacgac<br>gtgctggataagcggagaggcagagatcctgaaatgggcggcaagcccagacggaaga<br>atcctcaagagggcctgtataatgagctgcagaaagacaagatggccgaggcctacag<br>cgagatcggaatgaagggcgagcgcagaagaggcaagggacacgatggactgtaccag<br>ggcctgagcaccgccaccaaggatacctatgacgcactgcacatgcaggccctgccac<br>ctaga | anti-ROR1 CAR (nt) |
| 159 | caggtgcagctggttcaatctggcgccgaagtgaagaaaccaggcgcctctgtgaagg<br>tgtcctgcaaggccagcggctacacctttaccagctacgcatcagctgggtccgaca<br>ggctcctggacaaggcttggaatggatgggctggatcagcgcctacaacggcaacacc<br>aaatacgccaaactgcagggcagagtgaccatgaccaccgacaccagcacaagca<br>ccgcctacatggaactgcggagcctgagatccgatgacaccgccgtgtactactgcgc<br>cagagatgaggacatcctgaccggctacaactactacggcatggacgtgtggggccag<br>ggcacaacagtgacagtttcttctggcggcggaggatctggcggaggtggaagcggag<br>gcggtggatctcaactggtgctgacacagtctcctagcgcctctgcttctctgggagc<br>cagcgtgaagctgacctgtacactgtctagcggccacagcagctacgccattgcttgg | anti-ROR1 CAR (nt) |

| SEQ ID NO: | Sequence | Description |
|---|---|---|
| | catcagcagcagcccgagaagggccctagatacctgatgaagctgaacagcgacggca gccactctaaaggcgacggcatccccgatagattcagcggcagttctagcggagccga gcgctacctgacaatcagctctctgcaatccgaggacgaggccgactactactgtcag acatggggcaccggcatcagagtgtttggcggaggcaccaagctgacagtgcttggag agtctaaatacggaccgccttgtcctccttgtcccggccagccaagagagcccaggt ttacacactgcctccaagccaagaggaaatgaccaagaatcaggtgtccctgacatgc ctggtcaagggcttctacccctccgatatcgccgtggaatgggagagcaatggccagc ctgagaacaactacaagaccacacctcctgtgctggacagcgacggcagtttcttcct gtatagtagactcaccgtggataaatcaagatggcaagagggcaacgtgttcagctgc agcgtgatgcacgaggccctgcacaaccactacacccagaaaagcctgagcctgtctc tgggcaagatgttctgggtgctcgtggtcgttggcggagtgctggcctgttacagcct gctggttaccgtggccttcatcatcttttgggtcaagcggggcagaaagaagctgctc tacatcttcaagcagcccttcatgcggcccgtgcagaccacacaagaggaagatggct gctcctgcagattccccgaggaagaagaaggcggctgcgagctgagagtgaagttcag cagatccgccgacgctccagctatcagcagggccaaaaccagctgtacaacgagctg aacctggggagaagagaagagtacgacgtgctggataagcggagaggcagagatccgg aaatgggcggcaagcccagacggaagaatcctcaagagggcctgtataatgagctgca gaaagacaagatggccgaggcctacagcgagatcggaatgaagggcgagcgcagaaga ggcaaggacacgatggactgtaccagggcctgagcaccgccaccaaggatacctatg acgcactgcacatgcaggccctgccacctaga | |
| 160 | cagctccagctgcaagaatctggacctggcctggtcaagcccagcgagacactgtctc tgacctgtacagtgtccggcggcagcatcaatagcaccacaagctactgggcctggat cagacagcctcctggcaaaggcctggaatggatcggcaccatcttctacagcggcaag acctacaacaaccccagcctgaagtccagagtgaccatgagcgtggacaccagcaaga accacttcagcctgaaagtgaacagcgtgacagccgccgataccgccgtgtactactg cgccagattcgactacggcttccacgacgccttcgacatctggggccagggcacaatg gtcacagtttctagcggaggcggaggatctggtggcggaggtggcggaggcggtt ctgagattgtgatgacacagagccccgccactctgagccttagtcctggcgaaagagc cacactgagctgcagagccagccagagcatcaccagcgattacctgagctggtatcag cagaagcccggacaggctcccagactgctgatctatggcgcctctacaagagccaccg gcattcccgcccgcttttctggctctggaagcggcaccgacttcaccctgaccatatc tagcctgcagcctgaggacttcgtggtgtactattgccagcaggactacaacctgtac accttcggccagggggaccaagctggaaatcaagagagtctaaatacggaccgcctt gtcctccttgtcccggccagccaagagagcccaggtttacacactgcctccaagcca agaggaaatgaccaagaatcaggtgtccctgacatgcctggtcaagggcttctacccc tccgatatcgccgtggaatgggagagcaatggccagcctgagaacaactacaagacca cacctcctgtgctggacagcgacggcagtttcttcctgtatagtagactcaccgtgga taaatcaagatggcaagagggcaacgtgttcagctgcagcgtgatgcacgaggccctg cacaaccactacacccagaaaagcctgagcctgtctctgggcaagatgttctgggtgc tcgtggtcgttggcggagtgctggcctgttacagcctgctggttaccgtggccttcat catcttttgggtcaagcggggcagaaagaagctgctctacatcttcaagcagcccttc atgcggcccgtgcagaccacacaagaggaagatggctgctcctgcagattccccgagg aagaagaaggcggctgcgagctgagagtgaagttcagcagatccgccgacgctccagc ctatcagcagggccaaaaccagctgtacaacgagctgaacctggggagaagagaagag tacgacgtgctggataagcggagaggcagagatcctgaaatgggcggcaagcccagac ggaagaatcctcaagagggcctgtataatgagctgcagaaagacaagatggccgaggc ctacagcgagatcggaatgaagggcgagcgcagaagaggcaagggacacgatggactg taccagggcctgagcaccgccaccaaggatacctatgacgcactgcacatgcaggccc tgccacctaga | anti-ROR1 CAR (nt) |
| 161 | caggttcagctgcttcagtctggcgccgaagtgaagaaacctggcgcctctgtgaagg tgtcctgcaaggccagcggctacaccttaccagctacggcatcagctgggtccgaca ggctcctggacaaggcttggaatggatgggctggatcagcgcctacacccggcaatac agatacgcccagaaactgcagggcagagtgaccatgaccaccgacaccagcacaagca ccgcctacatggaactgcggagcctgagatccgatgacaccgccgtgtactactgcgc cagagaagaaggcgccaccaccgactacgactactacggcatggatgtgtggggccag ggaacagccgtgacagtttcttctggtggcggaggatctggtggcggaggtgaagcggcg gaggcggatctcaactggttctgacacagagcccaagcgcctctgcatctctgggagc ttccgtgaagctgacctgcacactgtctagcggccacagcagctatgccattgcctgg catcagcaacagcccgagaagggccctagatacctgatgaagctgaacagcgacggca gccactctaaaggcgacggcatccccgatagattcagcggcagttctagcggagccga gcgctacctgacaatcagctctctgcaatccgaggacgaggccgactactactgtcag acatggggcaccggcatcagagtgtttggcggcggaacaaagctgaccgtgctgggcg agtctaaatacggaccgccttgtcctccttgtcccggccagccaagagagcccaggt ttacacactgcctccaagccaagaggaaatgaccaagaatcaggtgtccctgacatgc ctggtcaagggcttctacccctccgatatcgccgtggaatgggagagcaatggccagc ctgagaacaactacaagaccacacctcctgtgctggacagcgacggcagtttcttcct gtatagtagactcaccgtggataaatcaagatggcaagagggcaacgtgttcagctgc agcgtgatgcacgaggccctgcacaaccactacacccagaaaagcctgagcctgtctc tgggcaagatgttctgggtgctcgtggtcgttggcggagtgctggcctgttacagcct gctggttaccgtggccttcatcatcttttgggtcaagcggggcagaaagaagctgctc tacatcttcaagcagcccttcatgcggcccgtgcagaccacacaagaggaagatggct | anti-ROR1 CAR (nt) |

| SEQ ID NO: | Sequence | Description |
|---|---|---|
| | gctcctgcagattccccgaggaagaagaaggcggctgcgagctgagagtgaagttcag cagatccgccgacgctccagcctatcagcagggccaaaaccagctgtacaacgagctg aacctggggagaagagaagagtacgacgtgctggataagcggagaggcagagatcctg aaatgggcggcaagcccagacggaagaatcctcaagagggcctgtataatgagctgca gaaagacaagatggccgaggcctacagcgagatcggaatgaagggcgagcgcagaaga ggcaagggacacgatggactgtaccagggcctgagcaccgccaccaaggatacctatg acgcactgcacatgcaggccctgccacctaga | |
| 162 | SRGGGGSGGGGSGGGGSLEMA | linker |
| 163 | GSRGGGGSGGGGSGGGGSLEMA | linker |
| 164 | ggatctgcgatcgctccggtgcccgtcagtgggcagagcgcacatcgccacagtccc cgagaagttgggggagggtcggcaattgaaccggtgcctagagaaggtggcgcggg gtaaactgggaaagtgatgtcgtgtactggctccgccttttcccgagggtgggggag aaccgtatataagtgcagtagtcgccgtgaacgttcttttcgcaacggggtttgcgc cagaacacagctgaagcttcgaggggctcgcatctctccttcacgcgcccgccgccct acctgaggccgccatccacgccggttgagtcgcgtctgccgcctcccgcctgtggtg cctcctgaactgcgtccgccgtctaggtaagtttaaagctcaggtcgagaccgggcct ttgtccggcgctcccttggagcctacctagactcagccggctctccacgctttgcctg accctgcttgctcaactctacgtctttgtttcgttttctgttctgcgccgttacagat ccaagctgtgaccggcgcctac | EF1alpha promoter with HTLV1 enhancer |
| 165 | aatcaacctctggattacaaaatttgtgaaagattgactggtattcttaactatgttg ctccttttacgctatgtggatacgctgctttaatgcctttgtatcatgctattgcttc ccgtatggctttcattttctcctccttgtataaatcctggttgctgtctctttatgag gagttgtggcccgttgtcaggcaacgtggcgtggtgtgcactgtgtttgctgacgcaa ccccactggttggggcattgccaccacctgtcagctccttttcgggactttcgcttt cccctccctattgccacggcggaactcatcgccgcctgcctgcccgctgctggaca ggggctcggctgtgggcactgacaattccgtggtgttgtcgggaaatcatcgtcct ttccttggctgctcgcctgtgttgccacctggattctgcgcgggacgtccttctgcta cgtcccttcggccctcaatccagcggaccttccttcccgcggcctgctgccggctctg cggcctcttccgcgtcttcgccttcgccctcagacgagtcggatctccctttgggccg cctccccgc | Woodchuck Hepatitis Virus (WHP) Posttranscriptional Regulatory Element (WPRE) |
| 166 | GSGEGRGSLLTCGDVEENPGP | T2A peptide (aa) |
| 167 | GSGQCTNYALLKLAGDVESNPGP | E2A peptide (aa) |
| 168 | GSGVKQTLNFDLLKLAGDVESNPGP | F2A peptide (aa) |
| 169 | ctcgagggcggcggagagggcagaggaagtcttctaacatgcggtgacgtggaggaga atcccggccctagg | T2A peptide (nt) |
| 170 | gagctggagcagccgccaccgccgccgccgagggagccccgggacggcagcccctggg cgcagggtcgctgttctcggagtccgacccaggcgactcacgcccactggtgcgac ccggacagcctgggactgacccgccgcccaggcgaggctgcagccagagggctggga agggatcgcgctcgcggcatccagaggcggccaggcggaggcgagggagcaggttaga gggacaaagagctttgcagacgtccccggcgtcctgcgagcgccagcggccgggacga ggcggccgggagcccgggaagagcccgtggatgttctgcgcgcggcctgggagccgcc gccgccgccgcctcagcgagaggaggaatgcaccggccgccgccgcgggacgcgc cgccgctcctggcgctgctggccgcgctgctgctggccgcacgcggggctgctgccca agaaacagagctgtcagtcagtgctgaattagtgcctacctcatcatggaacatctca agtgaactcaacaaagattcttacctgaccccttgatgaaccaatgaataacatcacca cgtctctgggccagacagcagaactgcactgcaaagtctctgggaatccacctcccac catccgctggttcaaaaatgatgctcctgtggtccaggagccccggaggctctccttt cggtccaccatctatggctctcggctgcggattagaaacctcgacaccacagacacag gctacttccagtgcgtggcaacaaacggcaaggaggtggtttcttccactggagtctt gtttgtcaagtttggcccccctcccactgcaagtccaggatactcagatgagtatgaa gaagatggattctgtcagccatacagagggattgcatgtgcaagatttattggcaacc gcaccgtctatatggagtctttgcacatgcaagggggaaatagaaaatcagatccacagc tgccttcactatgattggcacttccagtcacttatctgataagtgttctcagttcgcc attccttccctgtgccactatgccttcccgtactgcgatgaaacttcatccgtcccaa agcccgtgacttgtgtcgcgatgaatgtgaaatcctggagaatgtcctgtgtcaaac agagtacattttgcaagatcaaatcccatgattctgatgaggctgaaactgccaaac tgtgaagatctcccccagccagagagcccagaagctgcgaactgtatccggattggaa ttcccatggcagatcctataaataaaaatcacaagtgttataacagcacaggtgtgga ctaccggggaccgtcagtgtgaccaaatcagggcgccagtgccagcctggaattcc cagtatcccacacacacactttcaccgcccttcgtttcccagagctgaatggaggcc attcctactgccgcaacccagggaatcaaaaggaagctccctggtgcttcaccttgga | human ROR1 (nt) GenBank: M97675.1 |

| SEQ ID NO: | Sequence | Description |
|---|---|---|
| | tgaaaactttaagtctgatctgtgtgacatcccagcttgcgattcaaaggattccaag<br>gagaagaataaaatggaaatcctgtacatactagtgccaagtgtggccattcccctgg<br>ccattgcttactcttcttcttcatttgcgtctgtcggaataaccagaagtcatcgtc<br>ggcaccagtccagaggcaaccaaaacacgtcagaggtcaaaatgtgggagatgtcaatg<br>ctgaatgcatataaacccaagagcaaggctaaagagctacctcttctgctgtacgct<br>ttatggaagaatttgggtgagtgtgcctttggaaaaatctataaaggccatctctatct<br>cccaggcatggaccatgctcagctggttgctatcaagaccttgaaagactataacaac<br>ccccagcaatggatggaattcaacaagaagcctcctaatggcagaactgcaccacc<br>ccaatattgtctgccttctaggtgccgtcactcaggaacaacctgtgtgcatgctttt<br>tgagtatattaatcaggggatctccatgagttcctcatcatgagatccccacactct<br>gatgttggctgcagcagtgatgaagatgggactgtgaaatccagcctggaccacggag<br>attttctgcacattgcaattcagattgcagctggcatggaatacctgtctagtcactt<br>ctttgtccacaaggaccttgcagctcgcaatattttaatcggagagcaacttcatgta<br>aagatttcagacttggggcttccagagaaatttactccgctgattactacagggtcc<br>agagtaagtccttgctgcccattcgctggatgccccctgaagccatcatgtatggcaa<br>attctcttctgattcagatatctggtcctttggggttgtcttgtgggagattttcagt<br>tttggactccagccatattatggattcagtaaccaggaagtgattgagatggtgagaa<br>aacggcagctcttaccatgctctgaagactgcccacccagaatgtacagcctcatgac<br>agagtgctggaatgagattccttctaggagaccaagatttaaagatattcacgtccgg<br>cttcggtcctgggagggactctcaagtcacacaagctctactactccttcaggggga<br>atgccaccacacagacaacctccctcagtgccagcccagtgagtaatctcagtaaccc<br>cagatatcctaattacatgttcccgagccagggtattacaccacagggccagattgct<br>ggtttcattggcccgccaatacctcagaaccagcgattcattcccatcaatggatacc<br>caataccctcctggatatgcagcgtttccagctgcccactaccagcaacaggtcctcc<br>cagagtgattcagcactgcccacctcccaagagtcggtccccaagcagtgccagtggg<br>tcgactagcactggccatgtgactagcttgccctcatcaggatccaatcaggaagcaa<br>atattcctttactaccacacatgtcaattccaaatcatcctggtggaatgggtatcac<br>cgttttttggcaacaaatctcaaaaaccctacaaaattgactcaaagcaagcatcttta<br>ctaggagacgccaatattcatggacacaccgaatctatgatttctgcagaactgtaaa<br>atgcacaacttttgtaaatgtggtatacaggacaaactagacggccgtagaaaagatt<br>tatattcaaatgtttttattaaagtaaggttctcatttagcagacatcgcaacaagta<br>ccttctgtgaagtttcactgtgtcttaccaagcaggacagacactcggccag | |
| 171 | QETELSVSAELVPTSSWNTSSEIDKGSYLTLDEPMNNITTSLGQTAELHCKVSGNPPP<br>SIRWFKNDAPVVQEPRRISFRATNYGSRLRIRNLDTTDTGYFQCVATNGKKVVSTTGV<br>LFVKFGPPPTASPGSSDEYEEDGFCQPYRGIACARFIGNRTVYMESLHMQGEIENQIT<br>AAFTMIGTSSHLSDKCSQFAIPSLCHYAFPYCDETSSVPKPRDLCRDECEVLENVLCQ<br>TEYIFARSNPMILMRLKLPNCEDLPQPESPEAANCIRIGIPMADPINKNHKCYNSTGV<br>DYRGTVSVTKSGRQCPWNSQYPHTHSFTALRFPELNGGHSYCRNPGNQKEAPWCFTL<br>DENFKSDLCDIPACDSKDSKEKNKMEILYILVPSVAIPLATAFLEFFICVCRNNQKSS<br>SPPVQRQPKPVRGQNVEMSMLNAYKPKSKAKELPLSAVREMEELGECTEGKIYKGHLY<br>LPGMDHAQLVAIKTLKDYNNPQQWTEFQQEASLMAELHHPNIVCLLGAVTQEQPVCML<br>FEYMNQGDLHEFLIMRSPHSDVGCSSDEDGTVKSSLDHGDFLHIAIQIAAGMEYLSSH<br>FFVHKDLAARNILIGEQLHVKISDLGLSREIYSADYYRVQSKSSLPIRWMPPEAIMYG<br>KFSSDSDIWSFGVVLWEIFSFGLQPYYGFSNQEVIEMVRKRQLLPCSEDCPPRMYSLM<br>TECWNEIPSRRPRFKDIHVRLRSWEGLSSHTSSTTPSGGNATTQTTSLSASPVSNLSN<br>PRFPNYMFPSQGITPQGQIAGFIGPAIPQNQRFIPINGYPIPPGYAAFPAAHYQPAGP<br>PRVIQHCPPPKSRSPSSASGSTSTGHVASLPSSGSNQEANVPLLPHMSIPNHPGGMGI<br>TVFGNKSQKPYKIDSKQSSLLGDSHIHGHTESMISAEV | Mouse ROR1; GenBank No. NP_038873 |
| 172 | QVQLQQSGAELVRPGASVTLSCKASGYTFSDYEMHWVIQTPVHGLEWIGAIDPETGGT<br>AYNQKFKGKAILTADKSSSTAYMELRSLTSEDSAVYYCTGYYDYDSFTYWGQGTLVTV<br>SA | 2A2 V$_H$ |
| 173 | DIVMTQSQKIMSTTVGDRVS1TCKASQNVDAAVAWYQQKPGQSPKLLIYSASNRYTGV<br>PDRFTGSGSGTDFTLTISNMQSEDLADYFCQQYDIYPYTFGGGTKLEIK | 2A2 V$_L$ |
| 174 | QVQLQESGPGLVKPSQTLSLTCTVSGYAFTAYNIHWVRQAPGQGLEWMGSFDPYDGGS<br>SYNQKFKDRLTISKDTSKNQVVLTMTNMDPVDTATYYCARGWYYFDYWGHGTLVTVSS | 99961 humanized V$_H$ |
| 175 | QVQLQESGPGLVKPSQTLSLTCTVSGYAFTAYNIHWVRQAPGQGLEWMGSFDPYDGGS<br>SYNQKFKDRLTISKDTSKNQVVLTMTNMDPVDTATYYCARGWYYFDYWGHGTLVTVSS | 99961 humanized V$_H$ |
| 176 | QVQLQESGPGLVKPSQTLSLTCTVSGYAFTAYNIHWIRQPPGKGLEWIGSFDPYDGGS<br>SYNQKFKDRLTISKDTSKNQVVLTMTNMDPVDTATYYCARGWYYFDYWGHGTLVTVSS | 99961 humanized V$_H$ |
| 177 | QVQLQESGPGLVKPSQTLSLTCTVSGYAFTAYNIHWIRQPPGKGLEWIGSFDPYDGGS<br>SYNQKFKDRLTISKDTSKNQVVLTMTNMDPVDTATYYCARGWYYFDYWGHGTLVTVSS | 99961 humanized V$_H$ |

-continued

| SEQ ID NO: | Sequence | Description |
|---|---|---|
| 178 | DIVMTQTPLSLPVTPGEPASISCRASKSISKYLAWYQQKPGQAPRLLIYSGSTLQSGT PPRFSGSGYGTDFTLTINNIESEDAAYYFCQQHDESPYTFGEGTKVEIK | 99961 humanized $V_L$ |
| 179 | DVVMTQSPLSLPVTLGQPASISCRASKSISKYLAWYQQKPGKAPKLLIYSGSTLQSGT PPRFSGSGYGTDFTLTINNIESEDAAYYFCQQHDESPYTFGEGTKVEIK | 99961 humanized $V_L$ |
| 180 | DIVMTQTPLSLPVTPGEPASISCRASKSISKYLAWYQQKPGQAPRLLIYSGSTLQSGT PPRFSGSGYGTDFTLTINNIESEDAAYYFCQQHDESPYTFGEGTKVEIK | 99961 humanized $V_L$ |
| 181 | DVVMTQSPLSLPVTLGQPASISCRASKSISKYLAWYQQKPGKAPKLLIYSGSTLQSGT PPRFSGSGYGTDFTLTINNIESEDAAYYFCQQHDESPYTFGEGTKVEIK | 99961 humanized $V_L$ |
| 182 | agagtcaagttttccaggtccgccgacgctccagcctaccagcaggggcagaaccagc tgtacaacgagctgaacctgggcagaagggaagagtacgacgtcctggataagcggag aggccgggaccctgagatgggcggcaagcctcggcggaagaaccccagaaggcctg tataacgaactgcagaaagacaagatggccgaggcctacagcgagatcggcatgaag ggcgagcgaggcgggcaagggccacgacggcctgtatcagggcctgtccaccgccac caaggatacctacgacgccctgcacatgcaggccctgcccccaagg | CD3-zeta derived intracellular signaling domain (nt) |
| 183 | aggagtaagaggagcaggctcctgcacagtgactacatgaacatgactccccgccgcc ccggggcccaccccgcaagcattaccagccctatgccccaccacgcgacttcgcagccta tcgctcc | CD28 endodomain (nt) |
| 184 | QVQLQESGPGLVKPSETLSLTCTVSGGSISNYYWSWIRQPAGKGLEWIGRIYTSGSTN YNPSLKSRVTMSVDTSKNQFSLKLSSLTAADTAIYYCARYYDILTGFEDYWGQGTLVT VSSGGGGSGGGGSGGGGSVIWMTQSPSLLSASTGDSVTISCRMSQDISSYLAWYQQKP GKAPELLIYAASSLQSGVPSRFSGSGSGTDFTLTISSLQSEDFATYYCQQYDSFPPTF GQGTKVEFKRESKYGPPCPPCPMFWVLVVVGGVLACYSLLVTVAFIIFWVKRGRKKLL YIFKQPFMRPVQTTQEEDGCSCRFPEEEEGGCELRVKFSRSADAPAYQQGQNQLYNEL NLGRREEYDVLDKRRGRDPEMGGKPRRKNPQEGLYNELQKDKMAEAYSEIGMKGERRR GKGHDGLYQGLSTATKDTYDALHMQALPPR | anti-ROR1 CAR (aa) |
| 185 | QLQLQESGPGLVKPSETLSLTCTVSGGSINSTTSYWAWIRQPPGKGLEWIGTIFYSGK TYNNPSLKSRVTMSVDTSKNHFSLKVNSVTAADTAVYYCARFDYEGHDAFDIWGQGTM VTVSSGGGGSGGGGSGGGGSEIVMTQSPATLSLSPGERATLSCRASQSITSDYLSWYQ QKPGQAPRLLIYGASTRATGIPARFSGSGSGTDFTLTISSLQPEDFVVYYCQQDYNLY TFGQGTKLEIKRESKYGPPCPPCPMFWVLVVVGGVLACYSLLVTVAFIIFWVKRGRKK LLYIFKQPFMRPVQTTQEEDGCSCRFPEEEEGGCELRVKFSRSADAPAYQQGQNQLYN ELNLGRREEYDVLDKRRGRDPEMGGKPRRKNPQEGLYNELQKDKMAEAYSEIGMKGER RRGKGHDGLYQGLSTATKDTYDALHMQALPPR | anti-ROR1 CAR (aa) |
| 186 | QVQLQESGPGLVKPSETLSLTCTVSGGSISNYYWSWIRQPAGKGLEWIGRIYTSGSTN YNPSLKSRVTMSVDTSKNQFSLKLSSLTAADTAIYYCARYYDILTGFEDYWGQGTLVT VSSGGGGSGGGGSGGGGSVIWMTQSPSLLSASTGDSVTISCRMSQDISSYLAWYQQKP GKAPELLIYAASSLQSGVPSRFSGSGSGTDFTLTISSLQSEDFATYYCQQYDSFPPTF GQGTKVEFKRESKYGPPCPPCPGQPREPQVYTLPPSQEEMTKNQVSLTCLVKGFYPSD IAVEWESNGQPENNYKTTPPVLDSDGSFELYSRLTVDKSRWQEGNVFSCSVMHEALHN HYTQKSLSLSLGKMFWVLVVVGGVLACYSLLVTVAFIIFWVKRGRKKLLYIFKQPFMR PVQTTQEEDGCSCRFPEEEEGGCELRVKFSRSADAPAYQQGQNQLYNELNLGRREEYD VLDKRRGRDPEMGGKPRRKNPQEGLYNELQKDKMAEAYSEIGMKGERRRGKGHDGLYQ GLSTATKDTYDALHMQALPPR | anti-ROR1 CAR (aa) |
| 187 | QVQLVQSGAEVKKPGASVKVSCKASGYTFTSYGISWVRQAPGQGLEWMGWISAYNGNT KYAQKLQGRVTMTTDTSTSTAYMELRSLRSDDTAVYYCARDEDILTGYNYYGMDVWGQ GTTVTVSSGGGGSGGGGSGGGGSQLVLTQSPSASASLGASVKLTCTLSSGHSSYAIAW HQQQPEKGPRYLMKLNSDGSHSKGDGIPDRFSGSSSGAERYLTISSLQSEDEADYYCQ TWGTGIRVFGGGTKLTVLGESKYGPPCPPCPGQPREPQVYTLPPSQEEMTKNQVSLTC LVKGFYPSDIAVEWESNGQPENNYKTTPPVLDSDGSFELYSRLTVDKSRWQEGNVFSC SVMHEALHNHYTQKSLSLSLGKMFWVLVVVGGVLACYSLLVTVAFIIFWVKRGRKKLL YIFKQPFMRPVQTTQEEDGCSCRFPEEEEGGCELRVKFSRSADAPAYQQGQNQLYNEL NLGRREEYDVLDKRRGRDPEMGGKPRRKNPQEGLYNELQKDKMAEAYSEIGMKGERRR GKGHDGLYQGLSTATKDTYDALHMQALPPR | anti-ROR1 CAR (aa) |
| 188 | QLQLQESGPGLVKPSETLSLTCTVSGGSINSTTSYWAWIRQPPGKGLEWIGTIFYSGK TYNNPSLKSRVTMSVDTSKNHFSLKVNSVTAADTAVYYCARFDYEGHDAFDIWGQGTM VTVSSGGGGSGGGGSGGGGSEIVMTQSPATLSLSPGERATLSCRASQSITSDYLSWYQ QKPGQAPRLLIYGASTRATGIPARFSGSGSGTDFTLTISSLQPEDFVVYYCQQDYNLY TFGQGTKLEIKRESKYGPPCPPCPGQPREPQVYTLPPSQEEMTKNQVSLTCLVKGFYP SDIAVEWESNGQPENNYKTTPPVLDSDGSFELYSRLTVDKSRWQEGNVFSCSVMHEAL | anti-ROR1 CAR (aa) |

| SEQ ID NO: | Sequence | Description |
|---|---|---|
| | HNHYTQKSLSLSLGKMFWVLVVVGGVLACYSLLVTVAFIIFWVKRGRKKLLYIFKQPF<br>MRPVQTTQEEDGCSCRFPEEEEGGCELRVKFSRSADAPAYQQGQNQLYNELNLGRREE<br>YDVLDKRRGRDPEMGGKPRRKNPQEGLYNELQKDKMAEAYSEIGMKGERRRGKGHDGL<br>YQGLSTATKDTYDALHMQALPPR | |
| 189 | QVQLLQSGAEVKKPGASVKVSCKASGYTFTSYGISWVRQAPGQGLEWMGWISAYTGNT<br>RYAQKLQGRVTMTTDTSTSTAYMELRSLRSDDTAVYYCAREEGATTDYDYYGMDVWGQ<br>GTAVTVSSGGGGSGGGGSGGGGSQLVLTQSPSASASLGASVKLTCTLSSGHSSYAIAW<br>HQQQPEKGPRYLMKLNSDGSHSKGDGIPDRFSGSSSGAERYLTISSLQSEDEADYYCQ<br>TWGTGIRVFGGGTKLTVLGESKYGPPCPPCPGQPREPQVYTLPPSQEEMTKNQVSLTC<br>LVKGFYPSDIAVEWESNGQPENNYKTTPPVLDSDGSFELYSRLTVDKSRWQEGNVFSC<br>SVMHEALHNHYTQKSLSLSLGKMFWVLVVVGGVLACYSLLVTVAFIIFWVKRGRKKLL<br>YIFKQPFMRPVQTTQEEDGCSCRFPEEEEGGCELRVKFSRSADAPAYQQGQNQLYNEL<br>NLGRREEYDVLDKRRGRDPEMGGKPRRKNPQEGLYNELQKDKMAEAYSEIGMKGERRR<br>GKGHDGLYQGLSTATKDTYDALHMQALPPR | anti-ROR1 CAR (aa) |
| 190 | atgcctctgctgctgcttctgcctcttctttgggctggtgctctggct | CD33 signal sequence (nt) (O/SSE) |
| 191 | atgccgctgctgctactgctgcccctgctgtgggcaggggccctggct | CD33 signal sequence (nt) GenBank: M23197.1 |
| 192 | gaatctaagtacggaccgccctgccccccttgccctatg | Spacer (IgG4 hinge)(nt) |
| 193 | GAATCTAAGTACGGACCGCCTTGTCCTCCATGTCCTGGCCAGCCAAGAGAACCCCAGG<br>TGTACACACTGCCTCCAAGCCAAGAGGAAATGACCAAGAACCAGGTGTCCCTGACCTG<br>CCTGGTCAAGGGCTTCTACCCTTCCGATATCGCCGTGGAATGGGAGAGCAATGGCCAG<br>CCTGAGAACAACTACAAGACCACACCTCCTGTGCTGGACAGCGACGGCTCATTCTTCC<br>TGTACAGCCGGCTGACCGTGGACAAGAGCAGATGGCAAGAGGGCAACGTGTTCAGCTG<br>CAGCGTGATGCACGAGGCCCTGCACAACCACTACACCCAGAAGTCTCTGAGCCTGAGC<br>CTGGGCAAG | Hinge-C$_H$3 spacer (nt) |
| 194 | ESKYGPPCPPCPAPPVAGPSVFLFPPKPKDTLMISRTPEVTCVVVDVSQEDPEVQFNW<br>YVDGVEVHNAKTKPREEQFQSTYRVVSVLTVLHQDWLNGKEYKCKVSNKGLPSSIEKT<br>ISKAKGQPREPQVYTLPPSQEEMTKNQVSLTCLVKGFYPSDIAVEWESNGQPENNYKT<br>TPPVLDSDGSFFLYSRLTVDKSRWQEGNVFSCSVMHEALHNHYTQKSLSLSLGKM | IgG4/IgG2 hinge-IgG2/IgG4 C$_H$2-IgG4 C$_H$3 spacer (aa) |
| 195 | gaatctaagtacggaccgccctgccctccctgccctgctcctcctgtggctggaccaa<br>ggtgttcctgctttccacctaagcctaaagatacccgtgatgatttcccgcacacctga<br>agtgacttgcgtggtcgtggacgtgagccaggaggatccagaagtgcagttcaactgg<br>tacgtggacggcgtggaagttccacaatgctaagactaaaccccgagaggaacagtttc<br>agtcaacttaccgggtcgtgagcgtgctgaccgtcctgcatcaggattggctgaacgg<br>gaaggagtataagtgcaaagtgtctaataagggactgcctagctccatcgagaaaaca<br>attagtaaggcaaaagggcagcctcgagaaccacaggtgtatacccctgcccctagcc<br>aggaggaaatgaccaagaaccaggtgtccctgacatgtctggtcaaaggcttctatcc<br>aagtgacatcgccgtgagtgggaatcaaatgggcagcccgagaacaattacaagacc<br>acaccaccccgtgctggactctgatggaagtttctttctgtattccaggctgaccgtgg<br>ataaatctcgctggcaggagggcaacgtgttctcttgcagtgtcatgcacgaagccct<br>gcacaatcattatacacagaagtcactgagcctgtccctgggcaaaatg | IgG4/IgG2 hinge-IgG2/IgG4 C$_H$2-IgG4 C$_H$3 spacer (nt) |
| 196 | gagtctaaatacggaccgccttgtcctccttgtcccgctcctcctgttgccggacctt<br>ccgtgttcctgtttcctccaaagcctaaggacaccctgatgatcagcaggacccctga<br>agtgacctgcgtggtggtggatgtgtcccaagaggatcccgaggtgcagttcaactgg<br>tatgtggacggcgtggaagtgcacaacgccaagaccaagcctagagaggaacagttcc<br>agagcacctacagagtggtgtccgtgctgacagtgctgcaccaggattggctgaacgg<br>caaagagtacaagtgcaaggtgtccaacaagggcctgcctagcagcatcgagaaaacc<br>atctccaaggccaagggccagccaagagagcccaggtttacacactgcctccaagcc<br>aagaggaaatgaccaagaatcaggtgtccctgacatgcctggtcaagggcttctaccc<br>ctccgatatcgccgtgaatgggagagcaatggccagcctgagaacaactacaagacc<br>acacctcctgtgctggacagcgacggcagtttcttcctgtatagtagactcaccgtgg<br>ataaatcaagatggcaagagggcaacgtgttcagctgcagcgtgatgcacgaggccct<br>gcacaaccactacacccagaaaagcctgagcctgtctctgggcaagatg | IgG4/IgG2 hinge-IgG2/IgG4 C$_H$2-IgG4 C$_H$3 spacer (nt) O/SSE |
| 197 | ttttgggtgctggtcgtggtcggaggggtgctggcctgttacagcctgctggtgacag<br>tcgctttcatcatcttctgggtg | CD28 transmembrane domain (nt) |

| SEQ ID NO: | Sequence | Description |
|---|---|---|
| 198 | ttctgggtgctcgtggtcgttggcggagtgctggcctgttacagcctgctggttaccg tggccttcatcatctttggggtc | CD28 transmembrane domain (nt) (O/SSE) |
| 199 | FRSTIYGSRLRIRNL | ROR1 epitope 1 |
| 200 | LSVSAELVPTSSW | ROR1 epitope 2 |
| 201 | HCKVSGNPPPTIRW | ROR1 epitope 3 |
| 202 | WFKNDAPVVQEPRRLSFRSTIYGSRL | ROR1 epitope 4 |
| 203 | VSSTGVLFV | ROR1 epitope 5 |
| 204 | LFVKFGPPPTASP | ROR1 epitope 6 |
| 205 | DEYEEDGFCQP | ROR1 epitope 7 |
| 206 | QPYRGIACARFIGN | ROR1 epitope 8 |
| 207 | SQFAIPSLCHYAFP | ROR1 epitope 9 |
| 208 | AFPYCDETSSVP | ROR1 epitope 10 |
| 209 | NVLCQTEYIFARSNPMILMR | ROR1 epitope 11 |
| 210 | LKLPNCEDLPQP | ROR1 epitope 12 |
| 211 | PESPEAANCIRIGIP | ROR1 epitope 13 |
| 212 | VDYRGTVSVTKSGR | ROR1 epitope 14 |
| 213 | SQYPHTHTFTALRF | ROR1 epitope 15 |
| 214 | DSKEKNKMEILYILV | ROR1 epitope 16 |
| 215 | MHRPRRGTRPPLLALLAALLLAARGAAAQETELSVSAELVPTSSWNISSELNKDSYLTLDEPM NNITTSLGQTAELHCKVSGNPPPTIRWFKNDAPVVQEPRRLSFRSTIYGSRLRIRNLDTTDTGY FQCVATNGKEVSSTGVLFVKFGPPPTASPGYSDEYEEDGFCQPYRGIACARFIGNRTVYMESL HMQGEIENQITAAFTMIGTSSHLSDKCSQFAIPSLCHYAFPYCDETSSVPKPRDLCRDECEILE NVLCQTEYIFARSNPMILMRLKLPNCEDLPQPESPEAANCIRIGIPMADPINKNHKCYNSTGVD YRGTVSVTKSGRQCQPWNSQYPHTHTFTALRFPELNGGHSYCRNPGNQKEAPWCFTLDENFKSD LCDIPACDSKDSKEKNKMEILYILVPSVAIPLAIALLFFFICVCRNNQKSSSAPVQRQPKHVRG QNVEMSMLNAYKPKSKAKELPLSAVRFMEELGECAFGKIYKGHLYLPGMDHAQLVAIKTLKDYN NPQQWTEFQQEASLMAELHHPNIVCLLGAVTQEQPVCMLFEYINQGDLHEFLIMRSPHSDVGCS SDEDGTVKSSLDHGDFLHIAIQIAAGMEYLSSHFFVHKDLAARNILIGEQLHVKISDLGLSREI YSADYYRVQSKSLLPIRWMPPEAIMYGKFSSDSDIWSFGVVLWEIFSFGLQPYYGFSNQEVIEM VRKRQLLPCSEDCPPRMYSLMTECWNEIPSRRPRFKDIHVRLRSWEGLSSHTSSTTPSGGNATT QTTSLSASPVSNLSNPRYPNYMFPSQGITPQGQIAGFIGPPIPQNQRFIPINGYPIPPGYAAFP AAHYQPTGPPRVIQHCPPPKSRSPSSASGSTGHVTSLPSSGSNQEANIPLLPHMSIPNHPGG MGITVFGNKSQKPYKIDSKQASLLGDANIHGHTESMISAEL | human ROR1 (Homo sapiens) (Uniprot Q01973) |
| 216 | MHRPRRGTRPPLLALLAALLLAARGAAAQETELSVSAELVPTSSWNISSELNKDSYLTLDEPM NNITTSLGQTAELHCKVSGNPPPTIRWFKNDAPVVQEPRRLSFRSTIYGSRLRIRNLDTTDTGY FQCVATNGKEVSSTGVLFVKFGPPPTASPGYSDEYEEDGFCQPYRGIACARFIGNRTVYMESL HMQGEIENQITAAFTMIGTSSHLSDKCSQFAIPSLCHYAFPYCDETSSVPKPRDLCRDECEILE | Rhesus macaque ROR1 (Macaca mulatta) |

| SEQ ID NO: | Sequence | Description |
|---|---|---|
| | NVLCQTEYIFARSNPMILMRLKLPNCEDLPQPESPEAANCIRIGIPMADPINKNHKCYNSTGVD<br>YRGTVSVTKSGRQCQPWNSQYPHTHTFTALRFPELNGGHSYCRNPGNQKEAPWCFTLDENFKSD<br>LCDIPACDSKDSKEKNKMEILYILVPSVAIPLAIALLFFFICVCRNNQKSSSPPVQRQPKHVRG<br>QNVEMSMLNAYKPKSKAKELPLSAVRFMEELGECAFGKIYKGHLYLPGMDHAQLVAIKTLKDYN<br>NPQQWTEFQQEASLMAELHHPNIVCLLGAVTQEQPVCMLFEYMNQGDLHEFLIMRSPHSDVGCS<br>SDEDGTVKSSLDHGDFLHIAIQIAAGMEYLSSHFFVHKDLAARNILIGEQLHVKISDLGLSREI<br>YSADYYRVQSKSLLPIRWMPPEAIMYGKFSSDSDIWSFGVVLWEIFSFGLQPYYGFSNQEVIEM<br>VRKRQLLPCSEDCPPRMYSLMTECWNEIPSRRPRFKDIHVRLRSWEGLSSHTSSTTPSGGNATT<br>QTTSLSASPVSNLSNPRYPNYIFPSQGITPQGQIAGFIGPPIPQNQRFIPINGYPIPPGYAAFP<br>AAHYQPTGPPRVIQHCPPPKSRSPSSASGSTSTGHVTSLPSGSNQEANIPLLPHMSIPNHPGG<br>MGITVFGNKSQKPYKIDAKQASLLGDANIHGHTESMISAEL | ROR1<br>(Uniprot<br>F6RUP2) |
| 217 | MLRTAHKLLYLILPLSFSLPFFFFSETELSVSAELVPTSSWNISSELNKDSYLTLDEPMNNITT<br>SLGQTAELHCKVSGNPPPTIRWFKNDAPVVQEPRRLSFRSTIYGSRLRIRNLDTTDTGYFQCVA<br>TNGKEVVSSTGVLFVKFGKDEYEEDGFCQPYRGIACARFIGNRTVYMESLHMQGEIENQITAAF<br>TMIGTSSHLSDKCSQFAIPSLCHYAFPYCDETSSVPKPRDLCRDECEILENVLCQTEYIFARSN<br>PMILMRLKLPNCEDLPQPESPEAANCIRIGIPMADPINKNHKCYNSTGVDYRGTVSVTKSGRQC<br>QPWNSQYPHTHTFTALRFPELNGGHSYCRNPGNQKEAPWCFTLDENFKSDLCDIPACDSKDSKE<br>KNKMEILYILVPSVAIPLAIALLFFFICVCRNNQKSSSPPVQRQPKHVRGQNVEMSMLNAYKPK<br>SKAKELPLSAVRFMEELGECAFGKIYKGHLYLPGMDHAQLVAIKTLKDYNNPQQWTEFQQEASL<br>MAELHHPNIVCLLGAVTQEQPVCMLFEYMNQGDLHEFLIMRSPHSDVGCSSDEDGTVKSSLDHG<br>DFLHIAIQIAAGMEYLSSHFFVHKDLAARNILIGEQLHVKISDLGLSREIYSADYYRVQSKSLL<br>PIRWMPPEAIMYGKFSSDSDIWSFGVVLWEIFSFGLQPYYGFSNQEVIEMVRKRQLLPCSEDCP<br>PRMYSLMTECWNEIPSRRPRFKDIHVRLRSWEGLSSHTSSTTPSGGNATTQTTSLSASPVSNLS<br>NPRYPNYIFPSQGITPQGQIAGFIGPPIPQNQRFIPINGYPIPPGYAAFPAAHYQPTGPPRVIQ<br>HCPPPKSRSPSSASGSTSTGHVTSLPSSGSNQEANIPLLPHMSIPNHPGGMGITVFGNKSQKPY<br>KIDAKQASLLGDANIHGHTESMISAEL | cynomolgus<br>macaque<br>(macaca<br>fasicularis)<br>ROR1<br>(Uniprot<br>A0A2K5WT<br>X7) |
| 218 | SYLTLDEPMNNITTSLGQTAELHCKVSGNPPPTIRWFKNDAPVVQEPRRLSFRSTIYGSRLRIR<br>NLDTTDTGYFQCVATNGKEVVSSTGVLFVKFGPPPTASPGYSDEYEEDGFCQPYRGIACARFIG<br>NRTVYMESLHMQGEIENQITAAFTMIGTSSHLSDKCSQFAIPSLCHYAFPYCDETSSVPKPRDL<br>CRDECEILENVLCQTEYIFARSNPMILMRLKLPNCEDLPQPESPEAANCIRIGIPMADPINKNH<br>KCYNSTGVDYRGTVSVTKSGRQCQPWNSQYPHTHTFTALRFPELNGGHSYCRNPGNQKEAPWCF<br>TLDENFKSDLCDIPACDSKDSKEKNKMEILYILVPSVAIPLAIALLFFFICVCRNNQKSSSPPV<br>QRQPKHVRGQNVEMSMLNAYKPKSKAKELPLSAVRFMEELGECAFGKIYKGHLYLPGMDHAQLV<br>AIKTLKDYNNPQQWTEFQQEASLMAELHHPNIVCLLGAVTQEQPVCMLFEYMNQGDLHEFLIMR<br>SPHSDVGCSSDEDGTVKSSLDHGDFLHIAIQIAAGMEYLSSHFFVHKDLAARNILIGEQLHVKI<br>SDLGLSREIYSADYYRVQSKSLLPIRWMPPEAIMYGKFSSDSDIWSFGVVLWEIFSFGLQPYYG<br>FSNQEVIEMVRKRQLLPCSEDCPPRMYSLMTECWNEIPSRRPRFKDIHVRLRSWEGLSSHTSST<br>TPSGGNATTQTTSLSASPVSNLSNPRYPNYIFPSQGITPQGQIAGFIGPPIPQNQRFIPINGYP<br>IPPGYAAFPAAHYQPTGPPRVIQHCPPPKSRSPSSASGSTSTGHVTSLPSSGSNQEANIPLLPH<br>MSIPNHPGGMGITVFGNKSQKPYKIDAKQASLLGDANIHGHTESMISAEL | cynomolgus<br>macaque<br>(macaca<br>fasicularis)<br>ROR1<br>(Uniprot<br>A0A2K5WT<br>X4) |
| 219 | MHRPRRRGTRPPPLALLAALLLAARGADAQETELSVSAELVPTSSWNTSSEIDKGSYLTLDEPM<br>NNITTSLGQTAELHCKVSGNPPPSIRWFKNDAPVVQEPRRISFRATNYGSRLRIRNLDTTDTGY<br>FQCVATNGKKVVSTTGVLFVKFGPPPTASPGSSDEYEEDGFCQPYRGIACARFIGNRTVYMESL<br>HMQGEIENQITAAFTMIGTSSHLSDKCSQFAIPSLCHYAFPYCDETSSVPKPRDLCRDECEVLE<br>NVLCQTEYIFARSNPMILMRLKLPNCEDLPQPESPEAANCIRIGIPMADPINKNHKCYNSTGVD<br>YRGTVSVTKSGRQCQPWNSQYPHTHSFTALRFPELNGGHSYCRNPGNQKEAPWCFTLDENFKSD<br>LCDIPACDSKDSKEKNKMEILYILVPSVAIPLAIAFLFFFICVCRNNQKSSSPPVQRQPKPVRG<br>QNVEMSMLNAYKPKSKAKELPLSAVRFMEELGECTFGKIYKGHLYLPGMDHAQLVAIKTLKDYN<br>NPQQWTEFQQEASLMAELHHPNIVCLLGAVTQEQPVCMLFEYMNQGDLHEFLIMRSPHSDVGCS<br>SDEDGTVKSSLDHGDFLHIAIQIAAGMEYLSSHFFVHKDLAARNILIGEQLHVKISDLGLSREI<br>YSADYYRVQSKSSLPIRWMPPEAIMYGKFSSDSDIWSFGVVLWEIFSFGLQPYYGFSNQEVIEM<br>VRKRQLLPCSEDCPPRMYSLMTECWNEIPSRRPRFKDIHVRLRSWEGLSSHTSSTTPSGGNATT<br>QTTSLSASPVSNLSNPRFPNYMFPSQGITPQGQIAGFIGPAIPQNQRFIPINGYPIPPGYAAFP<br>AAHYQPAGPPRVIQHCPPPKSRSPSSASGSTSTGHVASLPSSGSNQEANVPLLPHMSIPNHPGG<br>MGITVFGNKSQKPYKIDSKQSSLLGDSHIHGHTESMISAEV | mouse (mus<br>musculus)<br>ROR1<br>(Uniprot<br>Q9Z139) |

The invention claimed is:

1. An anti-receptor tyrosine kinase-like orphan receptor 1 (ROR1) antibody or antigen-binding fragment thereof comprising: a heavy chain variable ($V_H$) region and a light chain variable ($V_L$) region, wherein:
   the $V_H$ region comprises a heavy chain complementarity determining region 1 (CDR-H1), a heavy chain complementarity determining region 2 (CDR-H2) and a heavy chain complementarity determining region 3 (CDR-H3) contained within SEQ ID NO: 112, and the $V_L$ region comprises a light chain complementarity determining region 1 (CDR-L1), a light chain complementarity determining region 2 (CDR-L2) and a light chain complementarity determining region 3 (CDR-L3) contained within SEQ ID NO:115;
   the $V_H$ region comprises a CDR-H1, a CDR-H2 and a CDR-H3 contained within SEQ ID NO: 121, and the $V_L$ region comprises a CDR-L1, a CDR-L2 and a CDR-L3 contained within SEQ ID: NO 124;
   the $V_H$ region comprises a CDR-H1, a CDR-H2 and a CDR-H3 contained within SEQ ID NO: 103, and the $V_L$ region comprises a CDR-L1, a CDR-L2 and a CDR-L3 contained within SEQ ID: NO 106; or
   the $V_H$ region comprises a CDR-H1, a CDR-H2 and a CDR-H3 contained within SEQ ID NO: 130, and the $V_L$ region comprises a CDR-L1, a CDR-L2 and a CDR-L3 contained within SEQ ID: NO 106.

2. An anti-ROR1 antibody or antigen-binding fragment thereof comprising: a heavy chain variable ($V_H$) region, and a light chain variable ($V_L$) region, wherein the $V_H$ region comprises a heavy chain complementarity determining region 1 (CDR-H1), a heavy chain complementarity determining region 2 (CDR-H2) and a heavy chain complementarity determining region 3 (CDR-H3) comprising the sequence set forth in SEQ ID NOS: 67, 71 and 73, respectively, and the $V_L$ region comprises a light chain complementarity determining region 1 (CDR-L1), a light chain complementarity determining region 2 (CDR-L2) and a light chain complementarity determining region 3 (CDR-L3) comprising the sequence set forth in SEQ ID NOS: 75, 77 and 79, respectively;
   the $V_H$ region comprises a CDR-H1, a CDR-H2 and a CDR-H3 comprising the sequence set forth in SEQ ID NOS: 82, 86 and 88, respectively, and the $V_L$ region comprises a CDR-L1, a CDR-L2 and a CDR-L3 comprising the sequence set forth in SEQ ID NOS: 90, 92 and 94, respectively;
   the $V_H$ region comprises a CDR-H1, a CDR-H2 and a CDR-H3 comprising the sequence set forth in SEQ ID NOS: 52, 56 and 58, respectively, and the $V_L$ region comprises a CDR-L1, a CDR-L2 and a CDR-L3 comprising the sequence set forth in SEQ ID NOS: 60, 62 and 64, respectively; or
   the $V_H$ region comprises a CDR-H1, a CDR-H2 and a CDR-H3 comprising the sequence set forth in SEQ ID NOS: 52, 97 and 99, respectively, and the $V_L$ region comprises a CDR-L1, a CDR-L2 and a CDR-L3 comprising the sequence set forth in SEQ ID NOS: 60, 62 and 64, respectively.

3. The anti-ROR1 antibody or antigen-binding fragment thereof of claim 2, wherein the $V_H$ region comprises a CDR-H1, a CDR-H2 and a CDR-H3 comprising the sequence set forth in SEQ ID NOS: 67, 71 and 73, respectively, and the $V_L$ region comprises a CDR-L1, a CDR-L2 and a CDR-L3 comprising the sequence set forth in SEQ ID NOS: 75, 77 and 79, respectively.

4. The anti-ROR1 antibody or antigen-binding fragment thereof of claim 2, wherein:
   the $V_H$ region comprises an amino acid sequence having at least 85% identity to SEQ ID NO: 112, and the $V_L$ region comprises an amino acid sequence having at least 85% identity to SEQ ID NO: 115;
   the $V_H$ region comprises an amino acid sequence having at least 85% identity to SEQ ID NO: 121, and the $V_L$ region comprises an amino acid sequence having at least 85% identity to SEQ ID NO: 124;
   the $V_H$ region comprises an amino acid sequence having at least 85% identity to SEQ ID NO: 103, and the $V_L$ region comprises an amino acid sequence having at least 85% identity to SEQ ID NO: 106; or
   the $V_H$ region comprises an amino acid sequence having at least at or about 85% identity to SEQ ID NO: 130, and the $V_L$ region comprises an amino acid sequence having at least 85% identity to SEQ ID NO:106.

5. The anti-ROR1 antibody or antigen-binding fragment thereof of claim 2, wherein the $V_H$ region and the $V_L$ region comprise the sequence set forth in SEQ ID NOS: 112 and 115, respectively.

6. The anti-ROR1 antibody or antigen-binding fragment thereof of claim 2, wherein the antibody is a full length antibody.

7. The anti-ROR1 antibody or antigen-binding fragment thereof of claim 2, wherein the anti-ROR1 antibody or antigen binding fragment thereof is an antigen-binding fragment thereof, and wherein the antigen-binding fragment thereof comprises a single chain Fv (scFv).

8. The anti-ROR1 antibody or antigen-binding fragment thereof of claim 7, wherein the scFv comprises an amino acid sequence having at least 85% sequence identity to SEQ ID NO: 118, 127, 109 or 134.

9. The anti-ROR1 antibody or antigen-binding fragment thereof of claim 7, wherein the scFv comprises the sequence set forth in SEQ ID NO: 118.

10. A single chain cell-surface protein, comprising the anti-ROR1 antibody or antigen-binding fragment thereof of claim 2.

11. A conjugate, comprising the anti-ROR1 antibody or antigen-binding fragment thereof of claim 2.

12. An anti-ROR1 chimeric antigen receptor (CAR) comprising an extracellular antigen-binding domain comprising the anti-ROR1 antibody or antigen-binding fragment thereof of claim 2, a transmembrane region and an intracellular signaling region.

13. The anti-ROR1 chimeric antigen receptor of claim 12, further comprising a spacer between the extracellular antigen-binding domain and the transmembrane region.

14. The anti-ROR1 chimeric antigen receptor of claim 13, wherein the spacer comprises at least a portion of a hinge region of an immunoglobulin or a variant thereof.

15. The anti-ROR1 chimeric antigen receptor of claim 14, wherein the at least a portion of a hinge region comprises all or a portion of an IgG4 hinge region.

16. The anti-ROR1 chimeric antigen receptor of claim 13, wherein the spacer comprises an amino acid sequence having at least 85% identity to SEQ ID NO: 1, 26, 27, 29, 31, 32, 33 or 135.

17. The anti-ROR1 chimeric antigen receptor of claim 13, wherein the spacer comprises the sequence set forth in SEQ ID NO: 135.

18. The anti-ROR1 chimeric antigen receptor of claim 13, wherein the chimeric antigen receptor comprises from its N to C terminus in order: the extracellular antigen-binding domain, the spacer, the transmembrane region and the intracellular signaling region.

19. The anti-ROR1 chimeric antigen receptor of claim 12, wherein the transmembrane region comprises a transmembrane domain from CD28.

20. The anti-ROR1 chimeric antigen receptor of claim 12, wherein the transmembrane region comprises an amino acid sequence having at least 90% sequence identity to SEQ ID NO: 8.

21. The anti-ROR1 chimeric antigen receptor of claim 12, wherein the intracellular signaling region comprises a cytoplasmic signaling domain of a CD3-zeta (CD3ζ) chain.

22. The anti-ROR1 chimeric antigen receptor of claim 21, wherein the intracellular signaling region is or comprises the sequence set forth in SEQ ID NO: 13.

23. The anti-ROR1 chimeric antigen receptor of claim 12, wherein the intracellular signaling region comprises an amino acid sequence having at least at 90% sequence identity to SEQ ID NO: 13, 14 or 15.

24. The anti-ROR1 chimeric antigen receptor of claim 12, wherein the intracellular signaling region further comprises a costimulatory signaling region.

25. The anti-ROR1 chimeric antigen receptor of claim 24, wherein the costimulatory signaling region is between the transmembrane region and the intracellular signaling region.

26. The anti-ROR1 chimeric antigen receptor of claim 24, wherein the costimulatory signaling region comprises an intracellular signaling domain of a T cell costimulatory molecule or a signaling portion thereof.

27. The anti-ROR1 chimeric antigen receptor of claim 26, wherein the costimulatory signaling region comprises an intracellular signaling domain of CD28, 4-1BB, or ICOS.

28. The anti-ROR1 chimeric antigen receptor of claim 27, wherein the costimulatory signaling region comprises an intracellular signaling domain of a human CD28.

29. The anti-ROR1 chimeric antigen receptor of claim 27, wherein the costimulatory signaling region comprises an intracellular signaling domain of a human 4-1BB.

30. The anti-ROR1 chimeric antigen receptor of claim 27, wherein the costimulatory signaling region comprises an amino acid sequence having at least 90% sequence identity to SEQ ID NO: 12.

31. The anti-ROR1 chimeric antigen receptor of claim 24, wherein the antigen-binding domain is an scFv and the chimeric antigen receptor comprises from its N to C terminus in order: an extracellular antigen-binding domain comprising the scFv, a spacer comprising a modified IgG4 hinge-CH3; a transmembrane domain an intracellular signaling region comprising a cytoplasmic signaling domain of a CD3-zeta (CD3ζ) chain; and an intracellular signaling domain of a costimulatory signaling region.

32. The anti-ROR1 chimeric antigen receptor of claim 12, wherein the anti-ROR1 chimeric antigen receptor comprises a sequence that exhibits at least 85% sequence identity to the sequence set forth in SEQ ID NO: 184, 185, 186, 187, 188 or 189.

33. The anti-ROR1 chimeric antigen receptor of claim 32, wherein the anti-ROR1 chimeric antigen receptor comprises a sequence that exhibits at least 85% sequence identity to the sequence set forth in SEQ ID NO: 184.

34. The anti-ROR1 chimeric antigen receptor of claim 33, wherein the anti-ROR1 chimeric antigen receptor comprises the sequence set forth in SEQ ID NO: 184.

35. A polynucleotide comprising a nucleic acid encoding the anti-ROR1 chimeric antigen receptor of claim 12.

36. A vector, comprising the polynucleotide of claim 35.

37. A cell comprising the polynucleotide of claim 35.

38. A cell comprising the anti-ROR1 chimeric antigen receptor of claim 12.

39. The cell of claim 38, that is a lymphocyte.

40. The cell of claim 39, that is an NK cell or a T cell.

41. The cell of claim 40, wherein the cell is a T cell and the T cell is a CD4+ T cell or a CD8+ T cell.

42. The cell of claim 41, wherein the cell is a primary cell obtained from a subject.

43. A composition comprising the cell of claim 38.

44. A method of treatment comprising administering the cell of claim 38 to a subject having a disease or disorder associated with ROR1.

45. A polynucleotide comprising a nucleic acid encoding the anti-ROR1 antibody or antigen-binding domain thereof of claim 2.

46. A cell comprising the polynucleotide of claim 45.

47. A vector comprising the polynucleotide of claim 45.

48. A composition comprising the anti-ROR1 antibody or antigen-binding fragment thereof of any of claim 2.

49. A method of treatment comprising administering the anti-ROR1 antibody or antigen-binding fragment thereof of claim 2 to a subject having a disease or disorder associated with ROR1.

* * * * *

SEQUENCE LISTING

<160> NUMBER OF SEQ ID NOS: 219

<210> SEQ ID NO 1
<211> LENGTH: 12
<212> TYPE: PRT
<213> ORGANISM: artificial sequence
<220> FEATURE:
<223> OTHER INFORMATION: Spacer (IgG4 hinge)

<400> SEQUENCE: 1

Glu Ser Lys Tyr Gly Pro Pro Cys Pro Pro Cys Pro
1               5                   10

<210> SEQ ID NO 2
<211> LENGTH: 36
<212> TYPE: DNA
<213> ORGANISM: artificial sequence
<220> FEATURE:
<223> OTHER INFORMATION: Spacer (IgG4 hinge)

<400> SEQUENCE: 2
gaatctaagt acggaccgcc ctgccccct tgccct                                    36

<210> SEQ ID NO 3
<211> LENGTH: 119
<212> TYPE: PRT
<213> ORGANISM: artificial sequence
<220> FEATURE:
<223> OTHER INFORMATION: Hinge-CH3 spacer

<400> SEQUENCE: 3

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
                20                  25                  30

Asn Gln Val Ser Leu Thr Cys Leu Val Lys Gly Phe Tyr Pro Ser Asp
            35                  40                  45

Ile Ala Val Glu Trp Glu Ser Asn Gly Gln Pro Glu Asn Asn Tyr Lys
        50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Glu Gly Asn Val Phe Ser
                85                  90                  95

Cys Ser Val Met His Glu Ala Leu His Asn His Tyr Thr Gln Lys Ser
            100                 105                 110

Leu Ser Leu Ser Leu Gly Lys
        115

<210> SEQ ID NO 4
<211> LENGTH: 357
<212> TYPE: DNA
<213> ORGANISM: artificial sequence
<220> FEATURE:
<223> OTHER INFORMATION: Hinge-CH3 spacer

<400> SEQUENCE: 4
gaatctaagt acggaccgcc ttgtcctcca gtgtcctggcc agccaagaga accccaggtg        60
tacacactgc ctccaagcca agaggaaatg accaagaacc aggtgtccct gacctgcctg        120
gtcaagggct ctacccttc cgatatcgcc gtggaatggg agagcaatgg ccagcctgag        180
aacaactaca agaccacacc tcctgtgctg gacagcgacg gctcattctt cctgtacagc        240
cggctgaccg tggacaagag cagatggcaa gagggcaacg tgttcagctg cagcgtgatg        300
cacgaggccc tgcacaacca ctacacccag aagtctctga gcctgagcct gggcaag          357

<210> SEQ ID NO 5
<211> LENGTH: 282
<212> TYPE: PRT
<213> ORGANISM: artificial sequence

```
<220> FEATURE:
<223> OTHER INFORMATION: IgD-hinge-Fc

<400> SEQUENCE: 5

Arg Trp Pro Glu Ser Pro Lys Ala Gln Ala Ser Ser Val Pro Thr Ala
1               5                   10                  15

Gln Pro Gln Ala Glu Gly Ser Leu Ala Lys Ala Thr Thr Ala Pro Ala
            20                  25                  30

Thr Thr Arg Asn Thr Gly Arg Gly Gly Glu Glu Lys Lys Lys Glu Lys
        35                  40                  45

Glu Lys Glu Glu Gln Glu Glu Arg Glu Thr Lys Thr Pro Glu Cys Pro
    50                  55                  60

Ser His Thr Gln Pro Leu Gly Val Tyr Leu Leu Thr Pro Ala Val Gln
65                  70                  75                  80

Asp Leu Trp Leu Arg Asp Lys Ala Thr Phe Thr Cys Phe Val Val Gly
                85                  90                  95

Ser Asp Leu Lys Asp Ala His Leu Thr Trp Glu Val Ala Gly Lys Val
            100                 105                 110

Pro Thr Gly Gly Val Glu Glu Gly Leu Leu Glu Arg His Ser Asn Gly
        115                 120                 125

Ser Gln Ser Gln His Ser Arg Leu Thr Leu Pro Arg Ser Leu Trp Asn
    130                 135                 140

Ala Gly Thr Ser Val Thr Cys Thr Leu Asn His Pro Ser Leu Pro Pro
145                 150                 155                 160

Gln Arg Leu Met Ala Leu Arg Glu Pro Ala Ala Gln Ala Pro Val Lys
                165                 170                 175

Leu Ser Leu Asn Leu Leu Ala Ser Ser Asp Pro Pro Glu Ala Ala Ser
            180                 185                 190

Trp Leu Leu Cys Glu Val Ser Gly Phe Ser Pro Pro Asn Ile Leu Leu
        195                 200                 205

Met Trp Leu Glu Asp Gln Arg Glu Val Asn Thr Ser Gly Phe Ala Pro
    210                 215                 220

Ala Arg Pro Pro Pro Gln Pro Gly Ser Thr Thr Phe Trp Ala Trp Ser
225                 230                 235                 240

Val Leu Arg Val Pro Ala Pro Pro Ser Pro Gln Pro Ala Thr Tyr Thr
                245                 250                 255

Cys Val Val Ser His Glu Asp Ser Arg Thr Leu Leu Asn Ala Ser Arg
            260                 265                 270

Ser Leu Glu Val Ser Tyr Val Thr Asp His
        275                 280

<210> SEQ ID NO 6
<211> LENGTH: 24
<212> TYPE: PRT
<213> ORGANISM: artificial sequence
<220> FEATURE:
<223> OTHER INFORMATION: T2A

<400> SEQUENCE: 6

Leu Glu Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 7
<211> LENGTH: 357
<212> TYPE: PRT
```

<213> ORGANISM: artificial sequence
<220> FEATURE:
<223> OTHER INFORMATION: tEGFR

<400> SEQUENCE: 7

```
Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
    210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
    290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
                325                 330                 335

Thr Gly Met Val Gly Ala Leu Leu Leu Leu Val Val Ala Leu Gly
            340                 345                 350

Ile Gly Leu Phe Met
        355
```

<210> SEQ ID NO 8
<211> LENGTH: 27
<212> TYPE: PRT

```
<213> ORGANISM: homo sapiens
<220> FEATURE:
<221> NAME/KEY: MISC_FEATURE
<223> OTHER INFORMATION: CD28
<300> PUBLICATION INFORMATION:
<308> DATABASE ACCESSION NUMBER: P10747
<309> DATABASE ENTRY DATE: 1989-07-01
<313> RELEVANT RESIDUES IN SEQ ID NO: (153)..(179)

<400> SEQUENCE: 8

Phe Trp Val Leu Val Val Val Gly Gly Val Leu Ala Cys Tyr Ser Leu
 1               5                  10                  15

Leu Val Thr Val Ala Phe Ile Ile Phe Trp Val
             20                  25

<210> SEQ ID NO 9
<211> LENGTH: 66
<212> TYPE: PRT
<213> ORGANISM: homo sapiens
<220> FEATURE:
<221> NAME/KEY: MISC_FEATURE
<223> OTHER INFORMATION: CD28
<300> PUBLICATION INFORMATION:
<308> DATABASE ACCESSION NUMBER: P10747
<309> DATABASE ENTRY DATE: 1989-07-01
<313> RELEVANT RESIDUES IN SEQ ID NO: (114)..(179)

<400> SEQUENCE: 9

Ile Glu Val Met Tyr Pro Pro Pro Tyr Leu Asp Asn Glu Lys Ser Asn
 1               5                  10                  15

Gly Thr Ile Ile His Val Lys Gly Lys His Leu Cys Pro Ser Pro Leu
             20                  25                  30

Phe Pro Gly Pro Ser Lys Pro Phe Trp Val Leu Val Val Val Gly Gly
         35                  40                  45

Val Leu Ala Cys Tyr Ser Leu Leu Val Thr Val Ala Phe Ile Ile Phe
     50                  55                  60

Trp Val
65

<210> SEQ ID NO 10
<211> LENGTH: 41
<212> TYPE: PRT
<213> ORGANISM: homo sapiens
<220> FEATURE:
<221> NAME/KEY: MISC_FEATURE
<223> OTHER INFORMATION: CD28
<300> PUBLICATION INFORMATION:
<308> DATABASE ACCESSION NUMBER: P10747
<309> DATABASE ENTRY DATE: 1989-07-01
<313> RELEVANT RESIDUES IN SEQ ID NO: (180)..(220)

<400> SEQUENCE: 10

Arg Ser Lys Arg Ser Arg Leu Leu His Ser Asp Tyr Met Asn Met Thr
 1               5                  10                  15

Pro Arg Arg Pro Gly Pro Thr Arg Lys His Tyr Gln Pro Tyr Ala Pro
             20                  25                  30

Pro Arg Asp Phe Ala Ala Tyr Arg Ser
         35                  40

<210> SEQ ID NO 11
<211> LENGTH: 41
<212> TYPE: PRT
<213> ORGANISM: homo sapiens
<220> FEATURE:
<221> NAME/KEY: MISC_FEATURE
<223> OTHER INFORMATION: CD28 (LL to GG)
```

<400> SEQUENCE: 11

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 12
<211> LENGTH: 42
<212> TYPE: PRT
<213> ORGANISM: homo sapiens
<220> FEATURE:
<221> NAME/KEY: MISC_FEATURE
<223> OTHER INFORMATION: 4-1BB
<300> PUBLICATION INFORMATION:
<308> DATABASE ACCESSION NUMBER: Q07011.1
<309> DATABASE ENTRY DATE: 1995-02-01
<313> RELEVANT RESIDUES IN SEQ ID NO: (214)..(255)

<400> SEQUENCE: 12

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 13
<211> LENGTH: 112
<212> TYPE: PRT
<213> ORGANISM: homo sapiens
<220> FEATURE:
<221> NAME/KEY: MISC_FEATURE
<223> OTHER INFORMATION: CD3 zeta

<400> SEQUENCE: 13

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 14
<211> LENGTH: 112
<212> TYPE: PRT
<213> ORGANISM: homo sapiens
<220> FEATURE:
<221> NAME/KEY: MISC_FEATURE
<223> OTHER INFORMATION: CD3 zeta

<400> SEQUENCE: 14

```
Arg Val Lys Phe Ser Arg Ser Ala Glu Pro Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 15
<211> LENGTH: 112
<212> TYPE: PRT
<213> ORGANISM: homo sapiens
<220> FEATURE:
<221> NAME/KEY: MISC_FEATURE
<223> OTHER INFORMATION: CD3 zeta

<400> SEQUENCE: 15

```
Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 16
<211> LENGTH: 335
<212> TYPE: PRT
<213> ORGANISM: artificial sequence
<220> FEATURE:
<223> OTHER INFORMATION: tEGFR

<400> SEQUENCE: 16

```
Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60
```

```
Val Lys Glu Ile Thr Gly Phe Leu Leu Ile Gln Ala Trp Pro Glu Asn
 65                  70                  75                  80

Arg Thr Asp Leu His Ala Phe Glu Asn Leu Glu Ile Ile Arg Gly Arg
                 85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
            115                 120                 125

Ile Ile Ser Gly Asn Lys Asn Leu Cys Tyr Ala Asn Thr Ile Asn Trp
130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
            195                 200                 205

Leu Glu Gly Glu Pro Arg Glu Phe Val Glu Asn Ser Glu Cys Ile Gln
210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His
            275                 280                 285

Pro Asn Cys Thr Tyr Gly Cys Thr Gly Pro Gly Leu Glu Gly Cys Pro
290                 295                 300

Thr Asn Gly Pro Lys Ile Pro Ser Ile Ala Thr Gly Met Val Gly Ala
305                 310                 315                 320

Leu Leu Leu Leu Leu Val Val Ala Leu Gly Ile Gly Leu Phe Met
                325                 330                 335

<210> SEQ ID NO 17
<211> LENGTH: 18
<212> TYPE: PRT
<213> ORGANISM: artificial sequence
<220> FEATURE:
<223> OTHER INFORMATION: T2A

<400> SEQUENCE: 17

Glu Gly Arg Gly Ser Leu Leu Thr Cys Gly Asp Val Glu Glu Asn Pro
1               5                   10                  15

Gly Pro

<210> SEQ ID NO 18
<211> LENGTH: 22
<212> TYPE: PRT
<213> ORGANISM: artificial sequence
<220> FEATURE:
<223> OTHER INFORMATION: P2A

<400> SEQUENCE: 18

Gly Ser Gly Ala Thr Asn Phe Ser Leu Leu Lys Gln Ala Gly Asp Val
1               5                   10                  15
```

```
Glu Glu Asn Pro Gly Pro
            20

<210> SEQ ID NO 19
<211> LENGTH: 19
<212> TYPE: PRT
<213> ORGANISM: artificial sequence
<220> FEATURE:
<223> OTHER INFORMATION: P2A

<400> SEQUENCE: 19

Ala Thr Asn Phe Ser Leu Leu Lys Gln Ala Gly Asp Val Glu Glu Asn
1               5                   10                  15

Pro Gly Pro

<210> SEQ ID NO 20
<211> LENGTH: 20
<212> TYPE: PRT
<213> ORGANISM: artificial sequence
<220> FEATURE:
<223> OTHER INFORMATION: E2A

<400> SEQUENCE: 20

Gln Cys Thr Asn Tyr Ala Leu Leu Lys Leu Ala Gly Asp Val Glu Ser
1               5                   10                  15

Asn Pro Gly Pro
            20

<210> SEQ ID NO 21
<211> LENGTH: 22
<212> TYPE: PRT
<213> ORGANISM: artificial sequence
<220> FEATURE:
<223> OTHER INFORMATION: F2A

<400> SEQUENCE: 21

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 22
<211> LENGTH: 10
<212> TYPE: PRT
<213> ORGANISM: artificial sequence
<220> FEATURE:
<223> OTHER INFORMATION: linker
<220> FEATURE:
<221> NAME/KEY: REPEAT
<222> LOCATION: (5)..(9)
<223> OTHER INFORMATION: SGGGG is repeated 5 times

<400> SEQUENCE: 22

Pro Gly Gly Gly Ser Gly Gly Gly Gly Pro
1               5                   10

<210> SEQ ID NO 23
<211> LENGTH: 17
<212> TYPE: PRT
<213> ORGANISM: artificial sequence
<220> FEATURE:
<223> OTHER INFORMATION: linker
```

```
<400> SEQUENCE: 23

Gly Ser Ala Asp Asp Ala Lys Lys Asp Ala Ala Lys Lys Asp Gly Lys
1               5                   10                  15

Ser

<210> SEQ ID NO 24
<211> LENGTH: 18
<212> TYPE: PRT
<213> ORGANISM: artificial sequence
<220> FEATURE:
<223> OTHER INFORMATION: linker

<400> SEQUENCE: 24

Gly Ser Thr Ser Gly Ser Gly Lys Pro Gly Ser Gly Glu Gly Ser Thr
1               5                   10                  15

Lys Gly

<210> SEQ ID NO 25
<211> LENGTH: 5
<212> TYPE: PRT
<213> ORGANISM: artificial sequence
<220> FEATURE:
<223> OTHER INFORMATION: hinge
<220> FEATURE:
<221> NAME/KEY: VARIANT
<222> LOCATION: (1)..(1)
<223> OTHER INFORMATION: X is glycine, cysteine or arginine
<220> FEATURE:
<221> NAME/KEY: VARIANT
<222> LOCATION: (4)..(4)
<223> OTHER INFORMATION: X is cysteine or threonine

<400> SEQUENCE: 25

Xaa Pro Pro Xaa Pro
1               5

<210> SEQ ID NO 26
<211> LENGTH: 15
<212> TYPE: PRT
<213> ORGANISM: artificial sequence
<220> FEATURE:
<223> OTHER INFORMATION: hinge

<400> SEQUENCE: 26

Glu Pro Lys Ser Cys Asp Lys Thr His Thr Cys Pro Pro Cys Pro
1               5                   10                  15

<210> SEQ ID NO 27
<211> LENGTH: 12
<212> TYPE: PRT
<213> ORGANISM: artificial sequence
<220> FEATURE:
<223> OTHER INFORMATION: hinge

<400> SEQUENCE: 27

Glu Arg Lys Cys Cys Val Glu Cys Pro Pro Cys Pro
1               5                   10

<210> SEQ ID NO 28
<211> LENGTH: 61
<212> TYPE: PRT
<213> ORGANISM: artificial sequence
<220> FEATURE:
<223> OTHER INFORMATION: hinge
```

<400> SEQUENCE: 28

Glu Leu Lys Thr Pro Leu Gly Asp Thr His Thr Cys Pro Arg Cys Pro
1               5                   10                  15

Glu Pro Lys Ser Cys Asp Thr Pro Pro Cys Pro Arg Cys Pro Glu
            20                  25                  30

Pro Lys Ser Cys Asp Thr Pro Pro Cys Pro Arg Cys Pro Glu Pro
        35                  40                  45

Lys Ser Cys Asp Thr Pro Pro Cys Pro Arg Cys Pro
    50                  55                  60

<210> SEQ ID NO 29
<211> LENGTH: 12
<212> TYPE: PRT
<213> ORGANISM: artificial sequence
<220> FEATURE:
<223> OTHER INFORMATION: hinge

<400> SEQUENCE: 29

Glu Ser Lys Tyr Gly Pro Pro Cys Pro Ser Cys Pro
1               5                   10

<210> SEQ ID NO 30
<211> LENGTH: 36
<212> TYPE: DNA
<213> ORGANISM: artificial sequence
<220> FEATURE:
<223> OTHER INFORMATION: Spacer (IgG4hinge) O/SSE

<400> SEQUENCE: 30
gagtctaaat acggaccgcc ttgtcctcct tgtccc                                36

<210> SEQ ID NO 31
<211> LENGTH: 9
<212> TYPE: PRT
<213> ORGANISM: artificial sequence
<220> FEATURE:
<223> OTHER INFORMATION: hinge

<400> SEQUENCE: 31

Tyr Gly Pro Pro Cys Pro Pro Cys Pro
1               5

<210> SEQ ID NO 32
<211> LENGTH: 10
<212> TYPE: PRT
<213> ORGANISM: artificial sequence
<220> FEATURE:
<223> OTHER INFORMATION: hinge

<400> SEQUENCE: 32

Lys Tyr Gly Pro Pro Cys Pro Pro Cys Pro
1               5                   10

<210> SEQ ID NO 33
<211> LENGTH: 14
<212> TYPE: PRT
<213> ORGANISM: artificial sequence
<220> FEATURE:
<223> OTHER INFORMATION: hinge

<400> SEQUENCE: 33

Glu Val Val Val Lys Tyr Gly Pro Pro Cys Pro Pro Cys Pro
1               5                   10

<210> SEQ ID NO 34
<211> LENGTH: 228
<212> TYPE: PRT
<213> ORGANISM: artificial sequence
<220> FEATURE:
<223> OTHER INFORMATION: Hinge-CH2-CH3 spacer

<400> SEQUENCE: 34

```
Glu Ser Lys Tyr Gly Pro Pro Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Gln Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Leu Pro Ser Ser
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Leu Gly Lys
225
```

<210> SEQ ID NO 35
<211> LENGTH: 684
<212> TYPE: DNA
<213> ORGANISM: artificial sequence
<220> FEATURE:
<223> OTHER INFORMATION: Hinge-CH2-CH3 spacer

<400> SEQUENCE: 35

```
gaatctaagt acggaccgcc ttgtcctcca tgtcctgctc ctccagttgc cggaccttcc      60
gtgttcctgt ttcctccaaa gcctaaggac accctgatga tcagcagaac ccctgaagtg    120
acctgcgtgg tggtggacgt gtcccaagag gatcctgagg tgcagttcaa ctggtatgtg    180
gacggcgtga agtgcacaa cgccaagacc aagcctagag aggaacagtt ccagagcacc     240
tacagagtgg tgtccgtgct gacagtgctg caccaggatt ggctgaacgg caaagagtac    300
aagtgcaagg tgtccaacaa gggcctgcct agcagcatcg agaaaaccat cagcaaggcc    360
aagggccagc caagagaacc ccaggtgtac acactgcctc caagccaaga ggaaatgacc    420
```

```
aagaaccagg tgtccctgac ctgcctggtc aagggcttct acccttccga tatcgccgtg    480
gaatgggaga gcaatggcca gcctgagaac aactacaaga ccacacctcc tgtgctggac    540
agcgacggct cattcttcct gtacagccgg ctgaccgtgg acaagagcag atggcaagag    600
ggcaacgtgt tcagctgcag cgtgatgcac gaggccctgc acaaccacta cacccagaag    660
tctctgagcc tgagcctggg caag                                           684
```

<210> SEQ ID NO 36
<211> LENGTH: 229
<212> TYPE: PRT
<213> ORGANISM: artificial sequence
<220> FEATURE:
<223> OTHER INFORMATION: Hinge-CH2-CH3 spacer

<400> SEQUENCE: 36

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```

<210> SEQ ID NO 37
<211> LENGTH: 228
<212> TYPE: PRT
<213> ORGANISM: artificial sequence
<220> FEATURE:
<223> OTHER INFORMATION: IgG4/IgG2 hinge- IgG2/IgG4 CH2- IgG4 CH3 spacer

<400> SEQUENCE: 37

```
Glu Ser Lys Tyr Gly Pro Pro Cys Pro Pro Cys Pro Ala Pro Pro Val
1               5                   10                  15
```

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Val Glu
50                  55                  60

Val His Asn Ala Lys Thr Lys Pro Arg Glu Glu Gln Phe Gln Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Leu Pro Ser Ser
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Leu Gly Lys
225

<210> SEQ ID NO 38
<211> LENGTH: 684
<212> TYPE: DNA
<213> ORGANISM: artificial sequence
<220> FEATURE:
<223> OTHER INFORMATION: IgG4/IgG2 hinge- IgG2/IgG4 CH2- IgG4 CH3 spacer

<400> SEQUENCE: 38
gaatctaagt acggaccgcc ctgccctccc tgccctgctc ctcctgtggc tggaccaagc      60
gtgttcctgt ttccacctaa gcctaaagat accctgatga tttcccgcac acctgaagtg    120
acttgcgtgg tcgtggacgt gagccaggag gatccagaag tgcagttcaa ctggtacgtg    180
gacggcgtgg aagtccacaa tgctaagact aaaccccgag aggaacagtt tcagtcaact    240
taccgggtcg tgagcgtgct gaccgtcctg catcaggatt ggctgaacgg aaggagtat    300 aagtgcaaag tgtctaataa gggactgcct agctccatcg agaaaacaat tagtaaggca    360
aaagggcagc ctcgagaacc acaggtgtat accctgcccc ctagccagga ggaaatgacc    420
aagaaccagg tgtccctgac atgtctggtc aaaggcttct atccaagtga catcgccgtg    480
gagtgggaat caaatgggca gcccgagaac aattacaaga ccacaccacc cgtgctggac    540
tctgatggaa gtttctttct gtattccagg ctgaccgtgg ataaatctcg ctggcaggag    600
ggcaacgtgt tctcttgcag tgtcatgcac gaagccctgc acaatcatta tacacagaag    660
tcactgagcc tgtccctggg caaa                                            684

<210> SEQ ID NO 39

```
<211> LENGTH: 5
<212> TYPE: PRT
<213> ORGANISM: artificial sequence
<220> FEATURE:
<223> OTHER INFORMATION: 4GS linker

<400> SEQUENCE: 39

Gly Gly Gly Gly Ser
1               5

<210> SEQ ID NO 40
<211> LENGTH: 4
<212> TYPE: PRT
<213> ORGANISM: artificial sequence
<220> FEATURE:
<223> OTHER INFORMATION: 3GS linker

<400> SEQUENCE: 40

Gly Gly Gly Ser
1

<210> SEQ ID NO 41
<211> LENGTH: 15
<212> TYPE: PRT
<213> ORGANISM: artificial sequence
<220> FEATURE:
<223> OTHER INFORMATION: (4GS)3 linker

<400> SEQUENCE: 41

Gly Gly Gly Gly Ser Gly Gly Gly Gly Ser Gly Gly Gly Gly Ser
1               5                   10                  15

<210> SEQ ID NO 42
<211> LENGTH: 16
<212> TYPE: PRT
<213> ORGANISM: artificial sequence
<220> FEATURE:
<223> OTHER INFORMATION: CD33 Signal Peptide

<400> SEQUENCE: 42

Met Pro Leu Leu Leu Leu Leu Pro Leu Leu Trp Ala Gly Ala Leu Ala
1               5                   10                  15

<210> SEQ ID NO 43
<211> LENGTH: 20
<212> TYPE: PRT
<213> ORGANISM: artificial sequence
<220> FEATURE:
<223> OTHER INFORMATION: human IgG-kappa signal peptide

<400> SEQUENCE: 43

Met Val Leu Gln Thr Gln Val Phe Ile Ser Leu Leu Leu Trp Ile Ser
1               5                   10                  15

Gly Ala Tyr Gly
            20

<210> SEQ ID NO 44
<211> LENGTH: 60
<212> TYPE: DNA
<213> ORGANISM: artificial sequence
<220> FEATURE:
<223> OTHER INFORMATION: human IgG-kappa signal sequence

<400> SEQUENCE: 44
atggtgctgc agacccaggt gttcatcagc ctgctgctgt ggatctccgg agcatacgga     60
```

-continued

<210> SEQ ID NO 45
<211> LENGTH: 22
<212> TYPE: PRT
<213> ORGANISM: artificial sequence
<220> FEATURE:
<223> OTHER INFORMATION: GMCSFR alpha chain signal peptide

<400> SEQUENCE: 45

Met Leu Leu Leu Val Thr Ser Leu Leu Cys Glu Leu Pro His Pro
1               5                   10                  15

Ala Phe Leu Leu Ile Pro
            20

<210> SEQ ID NO 46
<211> LENGTH: 66
<212> TYPE: DNA
<213> ORGANISM: artificial sequence
<220> FEATURE:
<223> OTHER INFORMATION: GMCSFR alpha chain signal sequence

<400> SEQUENCE: 46
atgcttctcc tggtgacaag ccttctgctc tgtgagttac cacacccagc attcctcctg      60
atccca                                                                66

<210> SEQ ID NO 47
<211> LENGTH: 18
<212> TYPE: PRT
<213> ORGANISM: artificial sequence
<220> FEATURE:
<223> OTHER INFORMATION: CD8 alpha signal peptide

<400> SEQUENCE: 47

Met Ala Leu Pro Val Thr Ala Leu Leu Leu Pro Leu Ala Leu Leu Leu
1               5                   10                  15

His Ala

<210> SEQ ID NO 48
<211> LENGTH: 326
<212> TYPE: PRT
<213> ORGANISM: homo sapiens
<220> FEATURE:
<221> NAME/KEY: MISC_FEATURE
<223> OTHER INFORMATION: IgG2 Fc (Uniprot P01859)

<400> SEQUENCE: 48

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

```
Thr Leu Met Ile Ser Arg Thr Pro Glu Val Thr Cys Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 49
<211> LENGTH: 327
<212> TYPE: PRT
<213> ORGANISM: homo sapiens
<220> FEATURE:
<221> NAME/KEY: MISC_FEATURE
<223> OTHER INFORMATION: IgG4 Fc (Uniprot P01861)

<400> SEQUENCE: 49

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160
```

```
Gly Val Glu Val His Asn Ala Lys Thr Lys Pro Arg Glu Glu Gln Phe
            165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 50
<211> LENGTH: 7
<212> TYPE: PRT
<213> ORGANISM: artificial sequence
<220> FEATURE:
<223> OTHER INFORMATION: CDR-H1

<400> SEQUENCE: 50

Gly Tyr Thr Phe Thr Ser Tyr
1               5

<210> SEQ ID NO 51
<211> LENGTH: 10
<212> TYPE: PRT
<213> ORGANISM: artificial sequence
<220> FEATURE:
<223> OTHER INFORMATION: CDR-H1

<400> SEQUENCE: 51

Gly Tyr Thr Phe Thr Ser Tyr Gly Ile Ser
1               5                   10

<210> SEQ ID NO 52
<211> LENGTH: 5
<212> TYPE: PRT
<213> ORGANISM: artificial sequence
<220> FEATURE:
<223> OTHER INFORMATION: CDR-H1

<400> SEQUENCE: 52

Ser Tyr Gly Ile Ser
1               5

<210> SEQ ID NO 53
<211> LENGTH: 8
<212> TYPE: PRT
<213> ORGANISM: artificial sequence
<220> FEATURE:
```

```
<223> OTHER INFORMATION: CDR-H1

<400> SEQUENCE: 53

Gly Tyr Thr Phe Thr Ser Tyr Gly
1               5

<210> SEQ ID NO 54
<211> LENGTH: 6
<212> TYPE: PRT
<213> ORGANISM: ARTIFICIAL SEQUENCE
<220> FEATURE:
<223> OTHER INFORMATION: CDR-H2

<400> SEQUENCE: 54

Ser Ala Tyr Asn Gly Asn
1               5

<210> SEQ ID NO 55
<211> LENGTH: 10
<212> TYPE: PRT
<213> ORGANISM: ARTIFICIAL SEQUENCE
<220> FEATURE:
<223> OTHER INFORMATION: CDR-H2

<400> SEQUENCE: 55

Trp Ile Ser Ala Tyr Asn Gly Asn Thr Lys
1               5                   10

<210> SEQ ID NO 56
<211> LENGTH: 17
<212> TYPE: PRT
<213> ORGANISM: ARTIFICIAL SEQUENCE
<220> FEATURE:
<223> OTHER INFORMATION: CDR-H2

<400> SEQUENCE: 56

Trp Ile Ser Ala Tyr Asn Gly Asn Thr Lys Tyr Ala Gln Lys Leu Gln
1               5                   10                  15

Gly

<210> SEQ ID NO 57
<211> LENGTH: 8
<212> TYPE: PRT
<213> ORGANISM: ARTIFICIAL SEQUENCE
<220> FEATURE:
<223> OTHER INFORMATION: CDR-H2

<400> SEQUENCE: 57

Ile Ser Ala Tyr Asn Gly Asn Thr
1               5

<210> SEQ ID NO 58
<211> LENGTH: 15
<212> TYPE: PRT
<213> ORGANISM: ARTIFICIAL SEQUENCE
<220> FEATURE:
<223> OTHER INFORMATION: CDR-H3

<400> SEQUENCE: 58

Asp Glu Asp Ile Leu Thr Gly Tyr Asn Tyr Tyr Gly Met Asp Val
1               5                   10                  15

<210> SEQ ID NO 59
<211> LENGTH: 17
<212> TYPE: PRT
<213> ORGANISM: ARTIFICIAL SEQUENCE
```

```
<220> FEATURE:
<223> OTHER INFORMATION: CDR-H3

<400> SEQUENCE: 59

Ala Arg Asp Glu Asp Ile Leu Thr Gly Tyr Asn Tyr Tyr Gly Met Asp
1               5                   10                  15
Val

<210> SEQ ID NO 60
<211> LENGTH: 12
<212> TYPE: PRT
<213> ORGANISM: ARTIFICIAL SEQUENCE
<220> FEATURE:
<223> OTHER INFORMATION: CDR-L1

<400> SEQUENCE: 60

Thr Leu Ser Ser Gly His Ser Ser Tyr Ala Ile Ala
1               5                   10

<210> SEQ ID NO 61
<211> LENGTH: 7
<212> TYPE: PRT
<213> ORGANISM: ARTIFICIAL SEQUENCE
<220> FEATURE:
<223> OTHER INFORMATION: CDR-L1

<400> SEQUENCE: 61

Ser Gly His Ser Ser Tyr Ala
1               5

<210> SEQ ID NO 62
<211> LENGTH: 11
<212> TYPE: PRT
<213> ORGANISM: ARTIFICIAL SEQUENCE
<220> FEATURE:
<223> OTHER INFORMATION: CDR-L2

<400> SEQUENCE: 62

Leu Asn Ser Asp Gly Ser His Ser Lys Gly Asp
1               5                   10

<210> SEQ ID NO 63
<211> LENGTH: 7
<212> TYPE: PRT
<213> ORGANISM: ARTIFICIAL SEQUENCE
<220> FEATURE:
<223> OTHER INFORMATION: CDR-L2

<400> SEQUENCE: 63

Leu Asn Ser Asp Gly Ser His
1               5

<210> SEQ ID NO 64
<211> LENGTH: 9
<212> TYPE: PRT
<213> ORGANISM: ARTIFICIAL SEQUENCE
<220> FEATURE:
<223> OTHER INFORMATION: CDR-L3

<400> SEQUENCE: 64

Gln Thr Trp Gly Thr Gly Ile Arg Val
1               5

<210> SEQ ID NO 65
<211> LENGTH: 7
<212> TYPE: PRT
```

```
<213> ORGANISM: ARTIFICIAL SEQUENCE
<220> FEATURE:
<223> OTHER INFORMATION: CDR-H1

<400> SEQUENCE: 65

Gly Gly Ser Ile Ser Asn Tyr
1               5

<210> SEQ ID NO 66
<211> LENGTH: 10
<212> TYPE: PRT
<213> ORGANISM: ARTIFICIAL SEQUENCE
<220> FEATURE:
<223> OTHER INFORMATION: CDR-H1

<400> SEQUENCE: 66

Gly Gly Ser Ile Ser Asn Tyr Tyr Trp Ser
1               5                   10

<210> SEQ ID NO 67
<211> LENGTH: 5
<212> TYPE: PRT
<213> ORGANISM: ARTIFICIAL SEQUENCE
<220> FEATURE:
<223> OTHER INFORMATION: CDR-H1

<400> SEQUENCE: 67

Asn Tyr Tyr Trp Ser
1               5

<210> SEQ ID NO 68
<211> LENGTH: 8
<212> TYPE: PRT
<213> ORGANISM: ARTIFICIAL SEQUENCE
<220> FEATURE:
<223> OTHER INFORMATION: CDR-H1

<400> SEQUENCE: 68

Gly Gly Ser Ile Ser Asn Tyr Tyr
1               5

<210> SEQ ID NO 69
<211> LENGTH: 5
<212> TYPE: PRT
<213> ORGANISM: ARTIFICIAL SEQUENCE
<220> FEATURE:
<223> OTHER INFORMATION: CDR-H2

<400> SEQUENCE: 69

Tyr Thr Ser Gly Ser
1               5

<210> SEQ ID NO 70
<211> LENGTH: 9
<212> TYPE: PRT
<213> ORGANISM: ARTIFICIAL SEQUENCE
<220> FEATURE:
<223> OTHER INFORMATION: CDR-H2

<400> SEQUENCE: 70

Arg Ile Tyr Thr Ser Gly Ser Thr Asn
1               5

<210> SEQ ID NO 71
<211> LENGTH: 16
<212> TYPE: PRT
<213> ORGANISM: ARTIFICIAL SEQUENCE
```

<220> FEATURE:
<223> OTHER INFORMATION: CDR-H2

<400> SEQUENCE: 71

Arg Ile Tyr Thr Ser Gly Ser Thr Asn Tyr Asn Pro Ser Leu Lys Ser
1               5                   10                  15

<210> SEQ ID NO 72
<211> LENGTH: 7
<212> TYPE: PRT
<213> ORGANISM: ARTIFICIAL SEQUENCE
<220> FEATURE:
<223> OTHER INFORMATION: CDR-H2

<400> SEQUENCE: 72

Ile Tyr Thr Ser Gly Ser Thr
1               5

<210> SEQ ID NO 73
<211> LENGTH: 11
<212> TYPE: PRT
<213> ORGANISM: ARTIFICIAL SEQUENCE
<220> FEATURE:
<223> OTHER INFORMATION: CDR-H3

<400> SEQUENCE: 73

Tyr Tyr Asp Ile Leu Thr Gly Phe Phe Asp Tyr
1               5                   10

<210> SEQ ID NO 74
<211> LENGTH: 13
<212> TYPE: PRT
<213> ORGANISM: ARTIFICIAL SEQUENCE
<220> FEATURE:
<223> OTHER INFORMATION: CDR-H3

<400> SEQUENCE: 74

Ala Arg Tyr Tyr Asp Ile Leu Thr Gly Phe Phe Asp Tyr
1               5                   10

<210> SEQ ID NO 75
<211> LENGTH: 11
<212> TYPE: PRT
<213> ORGANISM: ARTIFICIAL SEQUENCE
<220> FEATURE:
<223> OTHER INFORMATION: CDR-L1

<400> SEQUENCE: 75

Arg Met Ser Gln Asp Ile Ser Ser Tyr Leu Ala
1               5                   10

<210> SEQ ID NO 76
<211> LENGTH: 6
<212> TYPE: PRT
<213> ORGANISM: ARTIFICIAL SEQUENCE
<220> FEATURE:
<223> OTHER INFORMATION: CDR-L1

<400> SEQUENCE: 76

Gln Asp Ile Ser Ser Tyr
1               5

<210> SEQ ID NO 77
<211> LENGTH: 7
<212> TYPE: PRT
<213> ORGANISM: ARTIFICIAL SEQUENCE
<220> FEATURE:

<223> OTHER INFORMATION: CDR-L2

<400> SEQUENCE: 77

Ala Ala Ser Ser Leu Gln Ser
1               5

<210> SEQ ID NO 78
<211> LENGTH: 3
<212> TYPE: PRT
<213> ORGANISM: ARTIFICIAL SEQUENCE
<220> FEATURE:
<223> OTHER INFORMATION: CDR-L2

<400> SEQUENCE: 78

Ala Ala Ser
1

<210> SEQ ID NO 79
<211> LENGTH: 9
<212> TYPE: PRT
<213> ORGANISM: ARTIFICIAL SEQUENCE
<220> FEATURE:
<223> OTHER INFORMATION: CDR-L3

<400> SEQUENCE: 79

Gln Gln Tyr Asp Ser Phe Pro Pro Thr
1               5

<210> SEQ ID NO 80
<211> LENGTH: 9
<212> TYPE: PRT
<213> ORGANISM: ARTIFICIAL SEQUENCE
<220> FEATURE:
<223> OTHER INFORMATION: CDR-H1

<400> SEQUENCE: 80

Gly Gly Ser Ile Asn Ser Thr Thr Ser
1               5

<210> SEQ ID NO 81
<211> LENGTH: 12
<212> TYPE: PRT
<213> ORGANISM: ARTIFICIAL SEQUENCE
<220> FEATURE:
<223> OTHER INFORMATION: CDR-H1

<400> SEQUENCE: 81

Gly Gly Ser Ile Asn Ser Thr Thr Ser Tyr Trp Ala
1               5                   10

<210> SEQ ID NO 82
<211> LENGTH: 7
<212> TYPE: PRT
<213> ORGANISM: ARTIFICIAL SEQUENCE
<220> FEATURE:
<223> OTHER INFORMATION: CDR-H1

<400> SEQUENCE: 82

Ser Thr Thr Ser Tyr Trp Ala
1               5

<210> SEQ ID NO 83
<211> LENGTH: 10
<212> TYPE: PRT
<213> ORGANISM: ARTIFICIAL SEQUENCE
<220> FEATURE:
<223> OTHER INFORMATION: CDR-H1

```
<400> SEQUENCE: 83

Gly Gly Ser Ile Asn Ser Thr Thr Ser Tyr
1               5                   10

<210> SEQ ID NO 84
<211> LENGTH: 4
<212> TYPE: PRT
<213> ORGANISM: ARTIFICIAL SEQUENCE
<220> FEATURE:
<223> OTHER INFORMATION: CDR-H2

<400> SEQUENCE: 84

Tyr Ser Gly Lys
1

<210> SEQ ID NO 85
<211> LENGTH: 9
<212> TYPE: PRT
<213> ORGANISM: ARTIFICIAL SEQUENCE
<220> FEATURE:
<223> OTHER INFORMATION: CDR-H2

<400> SEQUENCE: 85

Thr Ile Phe Tyr Ser Gly Lys Thr Tyr
1               5

<210> SEQ ID NO 86
<211> LENGTH: 16
<212> TYPE: PRT
<213> ORGANISM: ARTIFICIAL SEQUENCE
<220> FEATURE:
<223> OTHER INFORMATION: CDR-H2

<400> SEQUENCE: 86

Thr Ile Phe Tyr Ser Gly Lys Thr Tyr Asn Asn Pro Ser Leu Lys Ser
1               5                   10                  15

<210> SEQ ID NO 87
<211> LENGTH: 7
<212> TYPE: PRT
<213> ORGANISM: ARTIFICIAL SEQUENCE
<220> FEATURE:
<223> OTHER INFORMATION: CDR-H2

<400> SEQUENCE: 87

Ile Phe Tyr Ser Gly Lys Thr
1               5

<210> SEQ ID NO 88
<211> LENGTH: 11
<212> TYPE: PRT
<213> ORGANISM: ARTIFICIAL SEQUENCE
<220> FEATURE:
<223> OTHER INFORMATION: CDR-H3

<400> SEQUENCE: 88

Phe Asp Tyr Gly Phe His Asp Ala Phe Asp Ile
1               5                   10

<210> SEQ ID NO 89
<211> LENGTH: 13
<212> TYPE: PRT
<213> ORGANISM: ARTIFICIAL SEQUENCE
<220> FEATURE:
<223> OTHER INFORMATION: CDR-H3
```

```
<400> SEQUENCE: 89

Ala Arg Phe Asp Tyr Gly Phe His Asp Ala Phe Asp Ile
1               5                   10

<210> SEQ ID NO 90
<211> LENGTH: 12
<212> TYPE: PRT
<213> ORGANISM: ARTIFICIAL SEQUENCE
<220> FEATURE:
<223> OTHER INFORMATION: CDR-L1

<400> SEQUENCE: 90

Arg Ala Ser Gln Ser Ile Thr Ser Asp Tyr Leu Ser
1               5                   10

<210> SEQ ID NO 91
<211> LENGTH: 7
<212> TYPE: PRT
<213> ORGANISM: ARTIFICIAL SEQUENCE
<220> FEATURE:
<223> OTHER INFORMATION: CDR-L1

<400> SEQUENCE: 91

Gln Ser Ile Thr Ser Asp Tyr
1               5

<210> SEQ ID NO 92
<211> LENGTH: 7
<212> TYPE: PRT
<213> ORGANISM: ARTIFICIAL SEQUENCE
<220> FEATURE:
<223> OTHER INFORMATION: CDR-L2

<400> SEQUENCE: 92

Gly Ala Ser Thr Arg Ala Thr
1               5

<210> SEQ ID NO 93
<211> LENGTH: 3
<212> TYPE: PRT
<213> ORGANISM: ARTIFICIAL SEQUENCE
<220> FEATURE:
<223> OTHER INFORMATION: CDR-L2

<400> SEQUENCE: 93

Gly Ala Ser
1

<210> SEQ ID NO 94
<211> LENGTH: 8
<212> TYPE: PRT
<213> ORGANISM: ARTIFICIAL SEQUENCE
<220> FEATURE:
<223> OTHER INFORMATION: CDR-L3

<400> SEQUENCE: 94

Gln Gln Asp Tyr Asn Leu Tyr Thr
1               5

<210> SEQ ID NO 95
<211> LENGTH: 6
<212> TYPE: PRT
<213> ORGANISM: ARTIFICIAL SEQUENCE
<220> FEATURE:
<223> OTHER INFORMATION: CDR-H2
```

```
<400> SEQUENCE: 95

Ser Ala Tyr Thr Gly Asn
1               5

<210> SEQ ID NO 96
<211> LENGTH: 10
<212> TYPE: PRT
<213> ORGANISM: ARTIFICIAL SEQUENCE
<220> FEATURE:
<223> OTHER INFORMATION: CDR-H2

<400> SEQUENCE: 96

Trp Ile Ser Ala Tyr Thr Gly Asn Thr Arg
1               5                   10

<210> SEQ ID NO 97
<211> LENGTH: 17
<212> TYPE: PRT
<213> ORGANISM: ARTIFICIAL SEQUENCE
<220> FEATURE:
<223> OTHER INFORMATION: CDR-H2

<400> SEQUENCE: 97

Trp Ile Ser Ala Tyr Thr Gly Asn Thr Arg Tyr Ala Gln Lys Leu Gln
1               5                   10                  15

Gly

<210> SEQ ID NO 98
<211> LENGTH: 8
<212> TYPE: PRT
<213> ORGANISM: ARTIFICIAL SEQUENCE
<220> FEATURE:
<223> OTHER INFORMATION: CDR-H2

<400> SEQUENCE: 98

Ile Ser Ala Tyr Thr Gly Asn Thr
1               5

<210> SEQ ID NO 99
<211> LENGTH: 15
<212> TYPE: PRT
<213> ORGANISM: ARTIFICIAL SEQUENCE
<220> FEATURE:
<223> OTHER INFORMATION: CDR-H3

<400> SEQUENCE: 99

Glu Glu Gly Ala Thr Thr Asp Tyr Asp Tyr Tyr Gly Met Asp Val
1               5                   10                  15

<210> SEQ ID NO 100
<211> LENGTH: 17
<212> TYPE: PRT
<213> ORGANISM: ARTIFICIAL SEQUENCE
<220> FEATURE:
<223> OTHER INFORMATION: CDR-H3

<400> SEQUENCE: 100

Ala Arg Glu Glu Gly Ala Thr Thr Asp Tyr Asp Tyr Tyr Gly Met Asp
1               5                   10                  15

Val

<210> SEQ ID NO 101
<211> LENGTH: 372
<212> TYPE: DNA
```

<213> ORGANISM: ARTIFICIAL SEQUENCE
<220> FEATURE:
<223> OTHER INFORMATION: VH

<400> SEQUENCE: 101

```
caggttcagc tggtgcagtc tggagctgag gtgaagaagc ctggggcctc agtgaaggtc    60
tcctgcaagg cttctggtta cacctttacc agctatggta tcagctgggt gcgacaggcc   120
cctggacaag gcttgagtg gatgggatgg atcagcgctt acaatggtaa cacaaagtat   180
gcacagaagc tccagggcag agtcaccatg accacagaca catccacgag cacagcctac   240
atggagctga ggagcctgag atctgacgac acggccgtgt attactgtgc gagagatgag   300
gatattttga ctggttacaa ctactacggt atggacgtct ggggccaagg gaccacggtc   360
accgtctcct ca                                                        372
```

<210> SEQ ID NO 102
<211> LENGTH: 372
<212> TYPE: DNA
<213> ORGANISM: ARTIFICIAL SEQUENCE
<220> FEATURE:
<223> OTHER INFORMATION: VH O/SSE

<400> SEQUENCE: 102

```
caggtgcagc tggttcaatc tggcgccgaa gtgaagaaac caggcgccct tgtgaaggtg    60
tcctgcaagg ccagcggcta cacctttacc agctacggca tcagctgggt ccgacaggct   120
cctggacaag gcttggaatg gatgggctgg atcagcgcct acaacggcaa caccaaatac   180
gcccagaaac tgcagggcag agtgaccatg accaccgaca ccagcacaag caccgcctac   240
atggaactgc ggagcctgag atccgatgac accgccgtgt actactgcgc cagagatgag   300
gacatcctga ccggctacaa ctactacggc atggacgtgt ggggccaggg cacaacagtg   360
acagtttctt ct                                                        372
```

<210> SEQ ID NO 103
<211> LENGTH: 124
<212> TYPE: PRT
<213> ORGANISM: ARTIFICIAL SEQUENCE
<220> FEATURE:
<223> OTHER INFORMATION: VH

<400> SEQUENCE: 103

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Gly Ile Ser Trp Val Arg Gln Ala Pro Gly Gln Gly Leu Glu Trp Met
        35                  40                  45
Gly Trp Ile Ser Ala Tyr Asn Gly Asn Thr Lys Tyr Ala Gln Lys Leu
    50                  55                  60
Gln Gly Arg Val Thr Met Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Asp Glu Asp Ile Leu Thr Gly Tyr Asn Tyr Tyr Gly Met Asp
            100                 105                 110
Val Trp Gly Gln Gly Thr Thr Val Thr Val Ser Ser
        115                 120
```

```
<210> SEQ ID NO 104
<211> LENGTH: 336
<212> TYPE: DNA
<213> ORGANISM: ARTIFICIAL SEQUENCE
<220> FEATURE:
<223> OTHER INFORMATION: VL

<400> SEQUENCE: 104
cagcttgtgc tgactcaatc gccctctgcc tctgcctccc tgggagcctc ggtcaagctc      60
acctgcactc tgagcagtgg gcacagcagc tacgccatcg catggcatca gcagcagcca     120
gagaagggcc ctcggtactt gatgaagctt aacagtgatg gcagccacag caagggggac     180
gggatccctg atcgcttctc aggctccagc tctggggctg agcgctacct caccatctcc     240
agcctccagt ctgaggatga ggctgactat tactgtcaga cctggggcac tggcattcgg     300
gtgttcggtg gaggaaccaa actgactgtc ctaggc                               336

<210> SEQ ID NO 105
<211> LENGTH: 336
<212> TYPE: DNA
<213> ORGANISM: ARTIFICIAL SEQUENCE
<220> FEATURE:
<223> OTHER INFORMATION: VL O/SSE

<400> SEQUENCE: 105
caactggtgc tgacacagtc tcctagcgcc tctgcttctc tgggagccag cgtgaagctg      60
acctgtacac tgtctagcgg ccacagcagc tacgccattg cttggcatca gcagcagccc     120
gagaagggcc ctagatacct gatgaagctg aacagcgacg gcagccactc taaaggcgac     180
ggcatccccg atagattcag cggcagttct agcggagccg agcgctacct gacaatcagc     240
tctctgcaat ccgaggacga ggccgactac tactgtcaga catggggcac cggcatcaga     300
gtgtttggcg gaggcaccaa gctgacagtg cttgga                               336

<210> SEQ ID NO 106
<211> LENGTH: 112
<212> TYPE: PRT
<213> ORGANISM: ARTIFICIAL SEQUENCE
<220> FEATURE:
<223> OTHER INFORMATION: VL

<400> SEQUENCE: 106

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gly His Ser Ser Tyr Ala
            20                  25                  30

Ile Ala Trp His Gln Gln Gln Pro Glu Lys Gly Pro Arg Tyr Leu Met
        35                  40                  45

Lys Leu Asn Ser Asp Gly Ser His Ser Lys Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gln Thr Trp Gly
                85                  90                  95

Thr Gly Ile Arg Val Phe Gly Gly Gly Thr Lys Leu Thr Val Leu Gly
            100                 105                 110

<210> SEQ ID NO 107
<211> LENGTH: 753
<212> TYPE: DNA
<213> ORGANISM: ARTIFICIAL SEQUENCE
```

<220> FEATURE:
<223> OTHER INFORMATION: scFv (VH-VL)

<400> SEQUENCE: 107

```
caggttcagc tggtgcagtc tggagctgag gtgaagaagc ctggggcctc agtgaaggtc      60
tcctgcaagg cttctggtta ccctttacc agctatggta tcagctgggt gcgacaggcc     120
cctggacaag gcttgagtg gatgggatgg atcagcgctt acaatggtaa cacaaagtat     180
gcacagaagc tccagggcag agtcaccatg accacagaca catccacgag cacagcctac     240
atggagctga ggagcctgag atctgacgac acggccgtgt attactgtgc gagagatgag     300
gatattttga ctggttacaa ctactacggt atggacgtct ggggccaagg gaccacggtc     360
accgtctcct caggtggtgg tggtagcggc ggcggcggct ctggtggtgg tggatcccag     420
cttgtgctga ctcaatcgcc ctctgcctct gcctcctgg gagcctcggt caagctcacc     480
tgcactctga gcagtgggca cagcagctac gccatcgcat ggcatcagca gcagccagag     540
aagggccctc ggtacttgat gaagcttaac agtgatggca ccacagcaa ggggacggg     600
atccctgatc gcttctcagg ctccagctct ggggctgagc gctacctcac catctccagc     660
ctccagtctg aggatgaggc tgactattac tgtcagacct ggggcactgg cattcgggtg     720
ttcggtggag gaaccaaact gactgtccta ggc                                  753
```

<210> SEQ ID NO 108
<211> LENGTH: 753
<212> TYPE: DNA
<213> ORGANISM: ARTIFICIAL SEQUENCE
<220> FEATURE:
<223> OTHER INFORMATION: scFv (VH-VL) O/SSE

<400> SEQUENCE: 108

```
caggtgcagc tggttcaatc tggcgccgaa gtgaagaaac caggcgcctc tgtgaaggtg      60
tcctgcaagg ccagcggcta caccttacc agctacggca tcagctgggt ccgacaggct     120
cctggacaag gcttggaatg gatgggctgg atcagcgcct acaacggcaa caccaaatac     180
gcccagaaac tgcagggcag agtgaccatg accaccgaca ccagcacaag caccgcctac     240
atggaactgc ggagcctgag atccgatgac accgccgtgt actactgcgc cagagatgag     300
gacatcctga ccggctacaa ctactacggc atggacgtgt ggggccaggg cacaacagtg     360
acagtttctt ctggcggcgg aggatctggc ggaggtggaa gcggaggcgg tggatctcaa     420
ctggtgctga cacagtctcc tagcgcctct gcttctctgg agccagcgt gaagctgacc     480
tgtacactgt ctagcggcca cagcagctac gccattgctt ggcatcagca gcagcccgag     540
aagggcccta gatacctgat gaagctgaac agcgacggca ccactctaa aggcgacggc     600
atccccgata gattcagcgg cagttctagc ggagccgagc gctacctgac aatcagctct     660
ctgcaatccg aggacgaggc cgactactac tgtcagacat ggggcaccgg catcagagtg     720
tttggcggag gcaccaagct gacagtgctt gga                                  753
```

<210> SEQ ID NO 109
<211> LENGTH: 251
<212> TYPE: PRT
<213> ORGANISM: ARTIFICIAL SEQUENCE
<220> FEATURE:
<223> OTHER INFORMATION: scFv (VH-VL)

<400> SEQUENCE: 109

```
Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Lys Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Glu Asp Ile Leu Thr Gly Tyr Asn Tyr Tyr Gly Met Asp
                100                 105                 110

Val Trp Gly Gln Gly Thr Thr Val Thr Val Ser Ser Gly Gly Gly Gly
            115                 120                 125

Ser Gly Gly Gly Gly Ser Gly Gly Gly Ser Gln Leu Val Leu Thr
    130                 135                 140

Gln Ser Pro Ser Ala Ser Ala Ser Leu Gly Ala Ser Val Lys Leu Thr
145                 150                 155                 160

Cys Thr Leu Ser Ser Gly His Ser Ser Tyr Ala Ile Ala Trp His Gln
                165                 170                 175

Gln Gln Pro Glu Lys Gly Pro Arg Tyr Leu Met Lys Leu Asn Ser Asp
                180                 185                 190

Gly Ser His Ser Lys Gly Asp Gly Ile Pro Asp Arg Phe Ser Gly Ser
            195                 200                 205

Ser Ser Gly Ala Glu Arg Tyr Leu Thr Ile Ser Ser Leu Gln Ser Glu
    210                 215                 220

Asp Glu Ala Asp Tyr Tyr Cys Gln Thr Trp Gly Thr Gly Ile Arg Val
225                 230                 235                 240

Phe Gly Gly Gly Thr Lys Leu Thr Val Leu Gly
                245                 250

<210> SEQ ID NO 110
<211> LENGTH: 357
<212> TYPE: DNA
<213> ORGANISM: ARTIFICIAL SEQUENCE
<220> FEATURE:
<223> OTHER INFORMATION: VH

<400> SEQUENCE: 110
caggtgcagc tgcaggagtc gggcccagga ctggtgaagc cttcggagac cctgtccctc      60
acctgcactg tctctggagg ctccatcagt aattactact ggagctggat ccggcagccc     120
gccgggaagg gactggagtg gattgggcgt atctatacca gtgggagcac caactacaac     180
ccctccctca agagtcgagt caccatgtca gtagacacgt ccaagaacca gttctccctg     240
aagctgagtt ctttgaccgc cgcggacacg gccatatatt actgtgcgag gtattacgat     300
attttgactg gttctcttga ctactggggc cagggaaccc tggtcaccgt ctcctca       357

<210> SEQ ID NO 111
<211> LENGTH: 357
<212> TYPE: DNA
<213> ORGANISM: ARTIFICIAL SEQUENCE
<220> FEATURE:
<223> OTHER INFORMATION: VH O/SSE
```

<400> SEQUENCE: 111

```
caggttcagc tgcaagagtc tggccctggc ctggtcaagc ctagcgaaac actgagcctg    60
acctgtaccg tgtctggcgg cagcatctcc aactactact ggtcctggat cagacagcct   120
gccggcaaag gcctggaatg gatcggcaga atctacacca gcggcagcac caactacaac   180
cccagcctga gtccagagt gaccatgagc gtggacacca gcaagaacca gttctccctg    240
aagctgagca gcctgacagc cgccgatacc gccatctact actgtgcccg gtactacgat   300
atcctgaccg gcttcttcga ctactggggc cagggaacac tggtcacagt ttctagc      357
```

<210> SEQ ID NO 112
<211> LENGTH: 119
<212> TYPE: PRT
<213> ORGANISM: ARTIFICIAL SEQUENCE
<220> FEATURE:
<223> OTHER INFORMATION: VH

<400> SEQUENCE: 112

```
Gln Val Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Ser Asn Tyr
            20                  25                  30
Tyr Trp Ser Trp Ile Arg Gln Pro Ala Gly Lys Gly Leu Glu Trp Ile
        35                  40                  45
Gly Arg Ile Tyr Thr Ser Gly Ser Thr Asn Tyr Asn Pro Ser Leu Lys
    50                  55                  60
Ser Arg Val Thr Met Ser Val Asp Thr Ser Lys Asn Gln Phe Ser Leu
65                  70                  75                  80
Lys Leu Ser Ser Leu Thr Ala Ala Asp Thr Ala Ile Tyr Tyr Cys Ala
                85                  90                  95
Arg Tyr Tyr Asp Ile Leu Thr Gly Phe Phe Asp Tyr Trp Gly Gln Gly
            100                 105                 110
Thr Leu Val Thr Val Ser Ser
        115
```

<210> SEQ ID NO 113
<211> LENGTH: 324
<212> TYPE: DNA
<213> ORGANISM: ARTIFICIAL SEQUENCE
<220> FEATURE:
<223> OTHER INFORMATION: VL

<400> SEQUENCE: 113

```
gtcatctgga tgacccagtc tccatcctta ctctctgcat ctacaggaga cagtgtcacc    60
atcagttgtc ggatgagtca ggacattagc agttatttag cctggtatca gcaaaaacca   120
gggaaagccc ctgagctcct gatctatgct gcatccagtt tgcaaagtgg ggtcccatca   180
aggttcagtg cagtggatc tgggacagac ttcactctca ccatcagttc cctgcagtct   240
gaagattttg ctacttatta ctgtcaacag tatgatagtt tccctccgac gttcggccaa   300
gggaccaagg tggaattcaa acgg                                           324
```

<210> SEQ ID NO 114
<211> LENGTH: 324
<212> TYPE: DNA
<213> ORGANISM: ARTIFICIAL SEQUENCE
<220> FEATURE:
<223> OTHER INFORMATION: VL O/SSE

<400> SEQUENCE: 114

```
gtgatttgga tgacacagag ccctagcctg ctgagcgcca gcacaggcga tagcgtgacc      60
atcagctgca gaatgagcca ggacatcagc agctacctgg cttggtatca gcagaagcct     120
ggcaaggccc ctgaactgct gatctatgcc gcttccagtc tgcagagcgg cgtgccatct     180
agattttccg gcagcggctc tggcaccgac ttcaccctga caatcagctc cctgcagtcc     240
gaggacttcg ccacctacta ttgccagcag tacgacagct cccctccaac ctttggccag     300
ggcaccaagg tggaattcaa gcgc                                            324
```

<210> SEQ ID NO 115
<211> LENGTH: 108
<212> TYPE: PRT
<213> ORGANISM: ARTIFICIAL SEQUENCE
<220> FEATURE:
<223> OTHER INFORMATION: VL

<400> SEQUENCE: 115

```
Val Ile Trp Met Thr Gln Ser Pro Ser Leu Leu Ser Ala Ser Thr Gly
1               5                   10                  15
Asp Ser Val Thr Ile Ser Cys Arg Met Ser Gln Asp Ile Ser Ser Tyr
            20                  25                  30
Leu Ala Trp Tyr Gln Gln Lys Pro Gly Lys Ala Pro Glu Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Ser
65                  70                  75                  80
Glu Asp Phe Ala Thr Tyr Tyr Cys Gln Gln Tyr Asp Ser Phe Pro Pro
                85                  90                  95
Thr Phe Gly Gln Gly Thr Lys Val Glu Phe Lys Arg
            100                 105
```

<210> SEQ ID NO 116
<211> LENGTH: 726
<212> TYPE: DNA
<213> ORGANISM: ARTIFICIAL SEQUENCE
<220> FEATURE:
<223> OTHER INFORMATION: scFv (VH-VL)

<400> SEQUENCE: 116

```
caggtgcagc tgcaggagtc gggcccagga ctggtgaagc cttcggagac cctgtccctc      60
acctgcactg tctctggagg ctccatcagt aattactact ggagctggat ccggcagccc     120
gccgggaagg gactggagtg gattggcgt atctatacca gtgggagcac caactacaac     180
cctccctca agagtcgagt caccatgtca gtagacacgt ccaagaacca gttctccctg     240
aagctgagtt ctttgaccgc cgcggacacg gccatatatt actgtgcgag gtattacgat     300
attttgactg gtttctttga ctactgggc cagggaaccc tggtcaccgt ctcctcaggt     360
ggtggtggta gcggcggcgg cggctctggt ggtggtggat ccgtcatctg atgacccag     420
tctccatcct tactctctgc atctacagga gacagtgtca ccatcagttg tcggatgagt     480
caggacatta gcagttattt agcctggtat cagcaaaaac cagggaaagc ccctgagctc     540
ctgatctatg ctgcatccag tttgcaaagt ggggtcccat caaggttcag tggcagtgga     600
```

```
tctgggacag acttcactct caccatcagt tccctgcagt ctgaagattt tgctacttat    660
tactgtcaac agtatgatag tttccctccg acgttcggcc aagggaccaa ggtggaattc    720
aaacgg                                                                726
```

<210> SEQ ID NO 117
<211> LENGTH: 726
<212> TYPE: DNA
<213> ORGANISM: ARTIFICIAL SEQUENCE
<220> FEATURE:
<223> OTHER INFORMATION: scFv (VH-VL) O/SSE

<400> SEQUENCE: 117

```
caggttcagc tgcaagagtc tggccctggc ctggtcaagc ctagcgaaac actgagcctg     60
acctgtaccg tgtctggcgg cagcatctcc aactactact ggtcctggat cagacagcct    120
gccggcaaag gcctggaatg gatcggcaga atctacacca gcggcagcac caactacaac    180
cccagcctga agtccagagt gaccatgagc gtggacacca gcaagaacca gttctccctg    240
aagctgagca gcctgacagc cgccgatacc gccatctact actgtgcccg gtactacgat    300
atcctgaccg gcttcttcga ctactggggc cagggaacac tggtcacagt ttctagcgga    360
ggcggaggat ctggtggcgg aggaagtggc ggaggcggtt ctgtgatttg gatgacacag    420
agccctagcc tgctgagcgc cagcacaggc gatagcgtga ccatcagctg cagaatgagc    480
caggacatca gcagctacct ggcttggtat cagcagaagc tggcaaggc ccctgaactg     540 ctgatctatg ccgcttccag tctgcagagc ggcgtgccat ctagattttc cggcagcggc    600
tctggcaccg acttcaccct gacaatcagc tccctgcagt ccgaggactt cgccacctac    660
tattgccagc agtacgacag cttccctcca acctttggcc agggcaccaa ggtggaattc    720
aagcgc                                                                726
```

<210> SEQ ID NO 118
<211> LENGTH: 242
<212> TYPE: PRT
<213> ORGANISM: ARTIFICIAL SEQUENCE
<220> FEATURE:
<223> OTHER INFORMATION: scFv (VH-VL)

<400> SEQUENCE: 118

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Asn Tyr
            20                  25                  30

Tyr Trp Ser Trp Ile Arg Gln Pro Ala Gly Lys Gly Leu Glu Trp Ile
        35                  40                  45

Gly Arg Ile Tyr Thr Ser Gly Ser Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Leu Thr Ala Ala Asp Thr Ala Ile Tyr Tyr Cys Ala
                85                  90                  95

Arg Tyr Tyr Asp Ile Leu Thr Gly Phe Phe Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Val Ile Trp Met Thr Gln Ser Pro Ser Leu
    130                 135                 140
```

| | | | | | | | | | | | |
|---|---|---|---|---|---|---|---|---|---|---|---|
| Leu | Ser | Ala | Ser | Thr | Gly | Asp | Ser | Val | Thr | Ile | Ser | Cys | Arg | Met | Ser |
| 145 | | | | 150 | | | | | 155 | | | | | 160 | |

Leu Ser Ala Ser Thr Gly Asp Ser Val Thr Ile Ser Cys Arg Met Ser
145                 150                 155                 160

Gln Asp Ile Ser Ser Tyr Leu Ala Trp Tyr Gln Gln Lys Pro Gly Lys
                165                 170                 175

Ala Pro Glu Leu Leu Ile Tyr Ala Ala Ser Ser Leu Gln Ser Gly Val
            180                 185                 190

Pro Ser Arg Phe Ser Gly Ser Gly Ser Gly Thr Asp Phe Thr Leu Thr
        195                 200                 205

Ile Ser Ser Leu Gln Ser Glu Asp Phe Ala Thr Tyr Tyr Cys Gln Gln
    210                 215                 220

Tyr Asp Ser Phe Pro Pro Thr Phe Gly Gln Gly Thr Lys Val Glu Phe
225                 230                 235                 240

Lys Arg

<210> SEQ ID NO 119
<211> LENGTH: 363
<212> TYPE: DNA
<213> ORGANISM: ARTIFICIAL SEQUENCE
<220> FEATURE:
<223> OTHER INFORMATION: VH

<400> SEQUENCE: 119

```
cagctgcagc tgcaggagtc gggcccagga ctggtgaagc cttcggagac cctgtccctc      60
acctgcactg tctctggtgg ctccatcaac agtactactt cctactgggc ctggatccgc     120
cagcccccag ggaaggggct ggagtggatt gggactatct tttatagtgg aaaaacctac     180
aacaacccgt ccctcaagag tcgagtcacc atgtccgtag acacgtccaa gaaccacttc     240
tccctgaagg tgaactctgt gaccgccgca gacacggctg tgtattactg cgaggttt      300
gactacggtt tcatgatgc ttttgatatc tggggccagg gacaatggt caccgtctct      360
tca                                                                   363
```

<210> SEQ ID NO 120
<211> LENGTH: 363
<212> TYPE: DNA
<213> ORGANISM: ARTIFICIAL SEQUENCE
<220> FEATURE:
<223> OTHER INFORMATION: VH O/SSE

<400> SEQUENCE: 120

```
cagctccagc tgcaagaatc tggacctggc ctggtcaagc ccagcgagac actgtctctg      60
acctgtacag tgtccggcgg cagcatcaat agcaccacaa gctactgggc ctggatcaga     120
cagcctcctg gcaaaggcct ggaatggatc ggcaccatct tctacagcgg caagacctac     180
aacaacccca gcctgaagtc cagagtgacc atgagcgtgg acaccagcaa gaaccacttc     240
agcctgaaag tgaacagcgt gacagccgcc gataccgccg tgtactactg cgccagattc     300
gactacggct ccacgacgc cttcgacatc tggggccagg gcacaatggt cacagtttct     360
agc                                                                   363
```

<210> SEQ ID NO 121
<211> LENGTH: 121
<212> TYPE: PRT
<213> ORGANISM: ARTIFICIAL SEQUENCE
<220> FEATURE:
<223> OTHER INFORMATION: VH

<400> SEQUENCE: 121

| Gln | Leu | Gln | Leu | Gln | Glu | Ser | Gly | Pro | Gly | Leu | Val | Lys | Pro | Ser | Glu |
| 1 | | | | 5 | | | | | 10 | | | | | 15 | |

| Thr | Leu | Ser | Leu | Thr | Cys | Thr | Val | Ser | Gly | Gly | Ser | Ile | Asn | Ser | Thr |
| | | | 20 | | | | | 25 | | | | | 30 | | |

| Thr | Ser | Tyr | Trp | Ala | Trp | Ile | Arg | Gln | Pro | Pro | Gly | Lys | Gly | Leu | Glu |
| | | 35 | | | | | 40 | | | | | 45 | | | |

| Trp | Ile | Gly | Thr | Ile | Phe | Tyr | Ser | Gly | Lys | Thr | Tyr | Asn | Asn | Pro | Ser |
| 50 | | | | | 55 | | | | | 60 | | | | | |

| Leu | Lys | Ser | Arg | Val | Thr | Met | Ser | Val | Asp | Thr | Ser | Lys | Asn | His | Phe |
| 65 | | | | 70 | | | | | 75 | | | | | 80 | |

| Ser | Leu | Lys | Val | Asn | Ser | Val | Thr | Ala | Ala | Asp | Thr | Ala | Val | Tyr | Tyr |
| | | | | 85 | | | | | 90 | | | | | 95 | |

| Cys | Ala | Arg | Phe | Asp | Tyr | Gly | Phe | His | Asp | Ala | Phe | Asp | Ile | Trp | Gly |
| | | | 100 | | | | | 105 | | | | | 110 | | |

| Gln | Gly | Thr | Met | Val | Thr | Val | Ser | Ser |
| | | | 115 | | | | | 120 |

```
<210> SEQ ID NO 122
<211> LENGTH: 324
<212> TYPE: DNA
<213> ORGANISM: ARTIFICIAL SEQUENCE
<220> FEATURE:
<223> OTHER INFORMATION: VL

<400> SEQUENCE: 122
gaaattgtaa tgacacagtc tccagccacc ctgtctttgt ctccagggga aagagccacc      60
ctctcctgca gggccagtca gagtattacc agcgactact tatcctggta ccaacaaaaa     120
cctgggcagg ctcccaggct cctcatctat ggtgcatcca ccaggccac tggcatccca      180 gccaggttca gtggcagtgg gtctgggaca gacttcactc tcaccatcag cagcctgcag     240
cctgaagatt ttgtagttta ttactgtcag caggattata acttgtacac ttttggccag     300
gggaccaagc tggagatcaa acgg                                             324

<210> SEQ ID NO 123
<211> LENGTH: 324
<212> TYPE: DNA
<213> ORGANISM: ARTIFICIAL SEQUENCE
<220> FEATURE:
<223> OTHER INFORMATION: VL O/SSE

<400> SEQUENCE: 123
gagattgtga tgacacagag ccccgccact ctgagcctta gtcctggcga aagagccaca      60
ctgagctgca gagccagcca gagcatcacc agcgattacc tgagctggta tcagcagaag     120
cccggacagg ctcccagact gctgatctat ggcgcctcta caagagccac cggcattccc     180
gcccgctttt ctggctctgg aagcggcacc gacttcaccc tgaccatatc tagcctgcag     240
cctgaggact cgtggtgta ctattgccag caggactaca acctgtacac cttcggccag      300
gggaccaagc tggaaatcaa gaga                                             324

<210> SEQ ID NO 124
<211> LENGTH: 108
<212> TYPE: PRT
<213> ORGANISM: ARTIFICIAL SEQUENCE
<220> FEATURE:
<223> OTHER INFORMATION: VL
```

-continued

<400> SEQUENCE: 124

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Ile Thr Ser Asp
            20                  25                  30

Tyr Leu Ser Trp Tyr Gln Lys Pro Gly Gln Ala Pro Arg Leu Leu
        35                  40                  45

Ile Tyr Gly Ala Ser Thr Arg Ala Thr Gly Ile Pro Ala Arg Phe Ser
50                  55                  60

Gly Ser Gly Ser Gly Thr Asp Phe Thr Leu Thr Ile Ser Ser Leu Gln
65                  70                  75                  80

Pro Glu Asp Phe Val Val Tyr Tyr Cys Gln Gln Asp Tyr Asn Leu Tyr
                85                  90                  95

Thr Phe Gly Gln Gly Thr Lys Leu Glu Ile Lys Arg
            100                 105

<210> SEQ ID NO 125
<211> LENGTH: 732
<212> TYPE: DNA
<213> ORGANISM: ARTIFICIAL SEQUENCE
<220> FEATURE:
<223> OTHER INFORMATION: scFv (VH-VL)

<400> SEQUENCE: 125

```
cagctgcagc tgcaggagtc gggcccagga ctggtgaagc cttcggagac cctgtccctc      60
acctgcactg tctctggtgg ctccatcaac agtactactt cctactgggc ctggatccgc     120
cagcccccag ggaaggggct ggagtggatt gggactatct tttatagtgg aaaacctac      180
aacaacccgt ccctcaagag tcgagtcacc atgtccgtag acacgtccaa gaaccacttc     240
tccctgaagg tgaactctgt gaccgccgca gacacggctg tgtattactg tgcgaggttt     300
gactacggtt ttcatgatgc ttttgatatc tggggccagg ggacaatggt caccgtctct     360
tcaggtggtg gtggtagcgg cggcggcggc tctggtggtg gtggatccga aattgtaatg     420
acacagtctc cagccaccct gtctttgtct ccaggggaaa gagccaccct ctcctgcagg     480
gccagtcaga gtattaccag cgactactta tcctggtacc aacaaaaacc tgggcaggct     540
cccaggctcc tcatctatgg tgcatccacc agggccactg gcatcccagc caggttcagt     600
ggcagtgggt ctgggacaga cttcactctc accatcagca gcctgcagcc tgaagatttt     660
gtagtttatt actgtcagca ggattataac ttgtacactt ttggccaggg gaccaagctg     720
gagatcaaac gg                                                         732
```

<210> SEQ ID NO 126
<211> LENGTH: 732
<212> TYPE: DNA
<213> ORGANISM: ARTIFICIAL SEQUENCE
<220> FEATURE:
<223> OTHER INFORMATION: scFv (VH-VL) O/SSE

<400> SEQUENCE: 126

```
cagctccagc tgcaagaatc tggacctggc ctggtcaagc ccagcgagac actgtctctg      60
acctgtacag tgtccggcgg cagcatcaat agcaccacaa gctactgggc ctggatcaga     120
cagcctcctg gcaaaggcct ggaatggatc ggcaccatct tctacagcgg caagacctac     180
aacaacccca gcctgaagtc cagagtgacc atgagcgtgg acaccagcaa gaaccacttc     240
agcctgaaag tgaacagcgt gacagccgcc gataccgccg tgtactactg cgccagattc     300
```

```
gactacggct tccacgacgc cttcgacatc tggggccagg gcacaatggt cacagtttct    360
agcggaggcg gaggatctgg tggcggagga agtggcggag gcggttctga gattgtgatg    420
acacagagcc ccgccactct gagccttagt cctggcgaaa gagccacact gagctgcaga    480
gccagccaga gcatcaccag cgattacctg agctggtatc agcagaagcc cggacaggct    540
cccagactgc tgatctatgg cgcctctaca agagccaccg gcattcccgc cgctttttct    600
ggctctggaa gcggaccga cttcacccta accatatcta gcctgcagcc tgaggacttc    660
gtggtgtact attgccagca ggactacaac ctgtacacct tcggccaggg gaccaagctg    720
gaaatcaaga ga                                                        732
```

```
<210> SEQ ID NO 127
<211> LENGTH: 244
<212> TYPE: PRT
<213> ORGANISM: ARTIFICIAL SEQUENCE
<220> FEATURE:
<223> OTHER INFORMATION: scFv (VH-VL)

<400> SEQUENCE: 127
```

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Asn Ser Thr
            20                  25                  30

Thr Ser Tyr Trp Ala Trp Ile Arg Gln Pro Pro Gly Lys Gly Leu Glu
        35                  40                  45

Trp Ile Gly Thr Ile Phe Tyr Ser Gly Lys Thr Tyr Asn Asn Pro Ser
    50                  55                  60

Leu Lys Ser Arg Val Thr Met Ser Val Asp Thr Ser Lys Asn His Phe
65                  70                  75                  80

Ser Leu Lys Val Asn Ser Val Thr Ala Ala Asp Thr Ala Val Tyr Tyr
                85                  90                  95

Cys Ala Arg Phe Asp Tyr Gly Phe His Asp Ala Phe Asp Ile Trp Gly
            100                 105                 110

Gln Gly Thr Met Val Thr Val Ser Ser Gly Gly Gly Ser Gly Gly
        115                 120                 125

Gly Gly Ser Gly Gly Gly Ser Glu Ile Val Met Thr Gln Ser Pro
    130                 135                 140

Ala Thr Leu Ser Leu Ser Pro Gly Glu Arg Ala Thr Leu Ser Cys Arg
145                 150                 155                 160

Ala Ser Gln Ser Ile Thr Ser Asp Tyr Leu Ser Trp Tyr Gln Gln Lys
                165                 170                 175

Pro Gly Gln Ala Pro Arg Leu Leu Ile Tyr Gly Ala Ser Thr Arg Ala
            180                 185                 190

Thr Gly Ile Pro Ala Arg Phe Ser Gly Ser Gly Ser Gly Thr Asp Phe
        195                 200                 205

Thr Leu Thr Ile Ser Ser Leu Gln Pro Glu Asp Phe Val Val Tyr Tyr
    210                 215                 220

Cys Gln Gln Asp Tyr Asn Leu Tyr Thr Phe Gly Gln Gly Thr Lys Leu
225                 230                 235                 240

Glu Ile Lys Arg

```
<210> SEQ ID NO 128
<211> LENGTH: 372
<212> TYPE: DNA
<213> ORGANISM: ARTIFICIAL SEQUENCE
<220> FEATURE:
```

<223> OTHER INFORMATION: VH

<400> SEQUENCE: 128

```
caggttcagc tgctgcagtc tggagctgag gtgaagaagc tggggcctc agtgaaggtc      60
tcctgcaagg cttctggtta cacctttacc agctatggta tcagctgggt gcgacaggcc    120
cctggacaag ggcttgagtg gatgggatgg atcagcgctt acactggtaa cacaaggtat    180
gcacagaagc tccagggcag agtcaccatg accacagaca catccacgag cacagcctac    240
atggagctga ggagcctgag atctgacgac acggccgtgt attactgtgc gagagaagaa    300
ggagctacta cggactacga ctactacggt atggacgtct ggggccaagg gactgcggtc    360
accgtctcct ca                                                        372
```

<210> SEQ ID NO 129
<211> LENGTH: 372
<212> TYPE: DNA
<213> ORGANISM: ARTIFICIAL SEQUENCE
<220> FEATURE:
<223> OTHER INFORMATION: VH O/SSE

<400> SEQUENCE: 129

```
caggttcagc tgcttcagtc tggcgccgaa gtgaagaaac tggcgcctc tgtgaaggtg      60
tcctgcaagg ccagcggcta cacctttacc agctacggca tcagctgggt ccgacaggct    120
cctggacaag gcttggaatg gatgggctgg atcagcgcct acaccggcaa taccagatac    180
gcccagaaac tgcagggcag agtgaccatg accaccgaca ccagcacaag caccgcctac    240
atggaactgc ggagcctgag atccgatgac accgccgtgt actactgcgc cagagaagaa    300
ggcgccacca ccgactacga ctactacggc atggatgtgt ggggccaggg aacagccgtg    360
acagtttctt ct                                                        372
```

<210> SEQ ID NO 130
<211> LENGTH: 124
<212> TYPE: PRT
<213> ORGANISM: ARTIFICIAL SEQUENCE
<220> FEATURE:
<223> OTHER INFORMATION: VH

<400> SEQUENCE: 130

Gln Val Gln Leu Leu Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Thr Gly Asn Thr Arg Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Glu Gly Ala Thr Thr Asp Tyr Asp Tyr Tyr Gly Met Asp
            100                 105                 110

Val Trp Gly Gln Gly Thr Ala Val Thr Val Ser Ser
        115                 120

<210> SEQ ID NO 131
<211> LENGTH: 336

<212> TYPE: DNA
<213> ORGANISM: artificial sequence
<220> FEATURE:
<223> OTHER INFORMATION: VL O/SSE

<400> SEQUENCE: 131

```
caactggttc tgacacagag cccaagcgcc tctgcatctc tgggagcttc cgtgaagctg    60
acctgcacac tgtctagcgg ccacagcagc tatgccattg cctggcatca gcaacagccc   120
gagaagggcc ctagatacct gatgaagctg aacagcgacg gcagccactc taaaggcgac   180
ggcatccccg atagattcag cggcagttct agcggagccg agcgctacct gacaatcagc   240
tctctgcaat ccgaggacga ggccgattac tactgtcaga catggggcac cggcatcaga   300
gtgtttggcg gcggaacaaa gctgaccgtg ctgggc                             336
```

<210> SEQ ID NO 132
<211> LENGTH: 696
<212> TYPE: DNA
<213> ORGANISM: artificial sequence
<220> FEATURE:
<223> OTHER INFORMATION: scFv (VH-VL)

<400> SEQUENCE: 132

```
caggttcagc tgctgcagtc tggagctgag gtgaagaagc ctggggcctc agtgaaggtc    60
tcctgcaagg cttctggtta caccttacc agctatggta tcagctgggt gcgacaggcc   120
cctggacaag ggcttgagtg gatgggatgg atcagcgctt acactggtaa cacaaggtat   180
gcacagaagc tccagggcag agtcaccatg accacagaca catccacgag cacagcctac   240
atggagctga ggagcctgag atctgacgac acggccgtgt attactgtgc gagagaagaa   300
ggagctacta cggactacga ctactacggt atggacgtct ggggccaagg gactgcggtc   360
accgtctcct caggtggtgg tggtagcggc ggcggcggct ctggtggtgg tggatcccag   420
cttgtgctga ctcaatcgcc ctctgcctct gcctccctgg agcctcggt caagctcacc   480
tgcactctga gcagtgggca cagcagctac gccatcgcat ggcatcagca gcagccagag   540
aagggccctc ggtacttgat gaagcttaac agtgatggca ccacagcaa ggggacggg   600
atccctgatc gcttctcagg ctccagctct ggggctgagc gctacctcac catctccagc   660
ctccagtctg aggatgaggc tgactattac tgtcag                             696
```

<210> SEQ ID NO 133
<211> LENGTH: 753
<212> TYPE: DNA
<213> ORGANISM: artificial sequence
<220> FEATURE:
<223> OTHER INFORMATION: scFv (VH-VL) O/SSE

<400> SEQUENCE: 133

```
caggttcagc tgcttcagtc tggcgccgaa gtgaagaaac ctggcgcctc tgtgaaggtg    60
tcctgcaagg ccagcggcta cacctttacc agctacggca tcagctgggt ccgacaggct   120
cctggacaag gcttggaatg gatgggctgg atcagcgcct acaccggcaa taccagatac   180
gcccagaaac tgcagggcag agtgaccatg accaccgaca ccagcacaag caccgcctac   240
atggaactgc ggagcctgag atccgatgac accgccgtgt actactgcgc cagagaagaa   300
ggcgccacca ccgactacga ctactacggc atggatgtgt ggggccaggg aacagccgtg   360
acagtttctt ctggtggcgg aggatctggc ggaggtggaa gcggcggagg cggatctcaa   420
ctggttctga cacagagccc aagcgcctct gcatctctgg gagcttccgt gaagctgacc   480
```

```
tgcacactgt ctagcggcca cagcagctat gccattgcct ggcatcagca acagcccgag    540
aagggcccta gatacctgat gaagctgaac agcgacggca gccactctaa aggcgacggc    600
atccccgata gattcagcgg cagttctagc ggagccgagc gctacctgac aatcagctct    660
ctgcaatccg aggacgaggc cgattactac tgtcagacat ggggcaccgg catcagagtg    720
tttggcggcg aacaaagct gaccgtgctg ggc                                  753
```

<210> SEQ ID NO 134
<211> LENGTH: 251
<212> TYPE: PRT
<213> ORGANISM: artificial sequence
<220> FEATURE:
<223> OTHER INFORMATION: scFv (VH-VL)

<400> SEQUENCE: 134

```
Gln Val Gln Leu Leu Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Thr Gly Asn Thr Arg Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Glu Gly Ala Thr Thr Asp Tyr Asp Tyr Tyr Gly Met Asp
            100                 105                 110

Val Trp Gly Gln Gly Thr Ala Val Thr Val Ser Ser Gly Gly Gly Gly
        115                 120                 125

Ser Gly Gly Gly Gly Ser Gly Gly Gly Gly Ser Gln Leu Val Leu Thr
    130                 135                 140

Gln Ser Pro Ser Ala Ser Ala Ser Leu Gly Ala Ser Val Lys Leu Thr
145                 150                 155                 160

Cys Thr Leu Ser Ser Gly His Ser Ser Tyr Ala Ile Ala Trp His Gln
                165                 170                 175

Gln Gln Pro Glu Lys Gly Pro Arg Tyr Leu Met Lys Leu Asn Ser Asp
            180                 185                 190

Gly Ser His Ser Lys Gly Asp Gly Ile Pro Asp Arg Phe Ser Gly Ser
        195                 200                 205

Ser Ser Gly Ala Glu Arg Tyr Leu Thr Ile Ser Ser Leu Gln Ser Glu
    210                 215                 220

Asp Glu Ala Asp Tyr Tyr Cys Gln Thr Trp Gly Thr Gly Ile Arg Val
225                 230                 235                 240

Phe Gly Gly Gly Thr Lys Leu Thr Val Leu Gly
                245                 250
```

<210> SEQ ID NO 135
<211> LENGTH: 13
<212> TYPE: PRT
<213> ORGANISM: artificial sequence
<220> FEATURE:
<223> OTHER INFORMATION: IgG4 hinge spacer

<400> SEQUENCE: 135

Glu Ser Lys Tyr Gly Pro Pro Cys Pro Pro Cys Pro Met
1               5                   10

<210> SEQ ID NO 136
<211> LENGTH: 39
<212> TYPE: DNA
<213> ORGANISM: artificial sequence
<220> FEATURE:
<223> OTHER INFORMATION: IgG4 hinge spacer O/SSE

<400> SEQUENCE: 136
gagtctaaat acggaccgcc ttgtcctcct tgtcccatg                          39

<210> SEQ ID NO 137
<211> LENGTH: 357
<212> TYPE: DNA
<213> ORGANISM: artificial sequence
<220> FEATURE:
<223> OTHER INFORMATION: Hinge-CH3 spacer O/SSE

<400> SEQUENCE: 137
gagtctaaat acggaccgcc ttgtcctcct tgtcccggcc agccaagaga gccccaggtt    60
tacacactgc ctccaagcca agaggaaatg accaagaatc aggtgtccct gacatgcctg   120
gtcaagggct ctaccccctc cgatatcgcc gtggaatggg agagcaatgg ccagcctgag   180
aacaactaca agaccacacc tcctgtgctg gacagcgacg gcagtttctt cctgtatagt   240
agactcaccg tggataaatc aagatggcaa gagggcaacg tgttcagctg cagcgtgatg   300
cacgaggccc tgcacaacca ctacacccag aaaagcctga gcctgtctct gggcaag     357

<210> SEQ ID NO 138
<211> LENGTH: 120
<212> TYPE: PRT
<213> ORGANISM: artificial sequence
<220> FEATURE:
<223> OTHER INFORMATION: Hinge-CH3 spacer

<400> SEQUENCE: 138

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
            20                  25                  30

Asn Gln Val Ser Leu Thr Cys Leu Val Lys Gly Phe Tyr Pro Ser Asp
        35                  40                  45

Ile Ala Val Glu Trp Glu Ser Asn Gly Gln Pro Glu Asn Asn Tyr Lys
    50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Glu Gly Asn Val Phe Ser
                85                  90                  95

Cys Ser Val Met His Glu Ala Leu His Asn His Tyr Thr Gln Lys Ser
            100                 105                 110

Leu Ser Leu Ser Leu Gly Lys Met
        115                 120

<210> SEQ ID NO 139
<211> LENGTH: 360
<212> TYPE: DNA
<213> ORGANISM: artificial sequence
<220> FEATURE:
<223> OTHER INFORMATION: Hinge-CH3 spacer O/SSE

<400> SEQUENCE: 139

```
gagtctaaat acggaccgcc ttgtcctcct tgtcccggcc agccaagaga gccccaggtt    60
tacacactgc ctccaagcca agaggaaatg accaagaatc aggtgtccct gacatgcctg   120
gtcaagggct tctacccctc cgatatcgcc gtggaatggg agagcaatgg ccagcctgag   180
aacaactaca agaccacacc tcctgtgctg gacagcgacg gcagtttctt cctgtatagt   240
agactcaccg tggataaatc aagatggcaa gagggcaacg tgttcagctg cagcgtgatg   300
cacgaggccc tgcacaacca ctacacccag aaaagcctga cctgtctct gggcaagatg    360
```

<210> SEQ ID NO 140
<211> LENGTH: 684
<212> TYPE: DNA
<213> ORGANISM: artificial sequence
<220> FEATURE:
<223> OTHER INFORMATION: IgG4/IgG2 hinge- IgG2/IgG4 CH2- IgG4 CH3 spacer
      O/SSE

<400> SEQUENCE: 140

```
gagtctaaat acggaccgcc ttgtcctcct tgtcccgctc ctcctgttgc cggaccttcc    60
gtgttcctgt ttcctccaaa gcctaaggac accctgatga tcagcaggac ccctgaagtg   120
acctgcgtgg tggtggatgt gtcccaagag gatcccgagg tgcagttcaa ctggtatgtg   180
gacggcgtgg aagtgcacaa cgccaagacc aagcctagag aggaacagtt ccagagcacc   240
tacagagtgg tgtccgtgct gacagtgctg caccaggatt ggctgaacgg caaagagtac   300
aagtgcaagg tgtccaacaa gggcctgcct agcagcatcg agaaaaccat ctccaaggcc   360
aagggccagc caagagagcc ccaggtttac acactgcctc caagccaaga ggaaatgacc   420
aagaatcagg tgtccctgac atgcctggtc aagggcttct acccctccga tatcgccgtg   480
gaatgggaga gcaatggcca gcctgagaac aactacaaga ccacacctcc tgtgctggac   540
agcgacggca gtttcttcct gtatagtaga ctcaccgtgg ataaatcaag atggcaagag   600
ggcaacgtgt tcagctgcag cgtgatgcac gaggccctgc acaaccacta cacccagaaa   660
agcctgagcc tgtctctggg caag                                          684
```

<210> SEQ ID NO 141
<211> LENGTH: 72
<212> TYPE: DNA
<213> ORGANISM: artificial sequence
<220> FEATURE:
<223> OTHER INFORMATION: T2A O/SSE

<400> SEQUENCE: 141

```
cttgaaggtg gtggcgaagg cagaggcagc ctgcttacat gcggagatgt ggaagagaac    60
cccggaccta ga                                                        72
```

<210> SEQ ID NO 142
<211> LENGTH: 248
<212> TYPE: PRT
<213> ORGANISM: artificial sequence
<220> FEATURE:
<223> OTHER INFORMATION: R12 VH-VL scFv

<400> SEQUENCE: 142

Gln Glu Gln Leu Val Glu Ser Gly Gly Arg Leu Val Thr Pro Gly Gly
1               5                   10                  15

```
Ser Leu Thr Leu Ser Cys Lys Ala Ser Gly Phe Asp Phe Ser Ala Tyr
            20                  25                  30

Tyr Met Ser Trp Val Arg Gln Ala Pro Gly Lys Gly Leu Glu Trp Ile
        35                  40                  45

Ala Thr Ile Tyr Pro Ser Ser Gly Lys Thr Tyr Tyr Ala Thr Trp Val
    50                  55                  60

Asn Gly Arg Phe Thr Ile Ser Ser Asp Asn Ala Gln Asn Thr Val Asp
65                  70                  75                  80

Leu Gln Met Asn Ser Leu Thr Ala Ala Asp Arg Ala Thr Tyr Phe Cys
                85                  90                  95

Ala Arg Asp Ser Tyr Ala Asp Asp Gly Ala Leu Phe Asn Ile Trp Gly
            100                 105                 110

Pro Gly Thr Leu Val Thr Ile Ser Ser Gly Gly Gly Ser Gly Gly
        115                 120                 125

Gly Gly Ser Gly Gly Gly Ser Glu Leu Val Leu Thr Gln Ser Pro
    130                 135                 140

Ser Val Ser Ala Ala Leu Gly Ser Pro Ala Lys Ile Thr Cys Thr Leu
145                 150                 155                 160

Ser Ser Ala His Lys Thr Asp Thr Ile Asp Trp Tyr Gln Gln Leu Gln
                165                 170                 175

Gly Glu Ala Pro Arg Tyr Leu Met Gln Val Gln Ser Asp Gly Ser Tyr
            180                 185                 190

Thr Lys Arg Pro Gly Val Pro Asp Arg Phe Ser Gly Ser Ser Ser Gly
        195                 200                 205

Ala Asp Arg Tyr Leu Ile Ile Pro Ser Val Gln Ala Asp Glu Ala
    210                 215                 220

Asp Tyr Tyr Cys Gly Ala Asp Tyr Ile Gly Gly Tyr Val Phe Gly Gly
225                 230                 235                 240

Gly Thr Gln Leu Thr Val Thr Gly
                245

<210> SEQ ID NO 143
<211> LENGTH: 745
<212> TYPE: DNA
<213> ORGANISM: artificial sequence
<220> FEATURE:
<223> OTHER INFORMATION: R12 VH-VL scFv

<400> SEQUENCE: 143
caagaacagc tggtggaatc tggcggcaga ctggttacac tggcggaag cctgacactg      60 agctgtaaag ccagcggctt cgacttcagc gcctactaca tgagctgggt ccgacaggcc    120
cctggcaaag gactggaatg gatcgccaca atctacccca gctccggcaa gacctactac    180
gccacatggg tcaacggccg gttcaccatc agcagcgaca acgcccagaa caccgtggac    240
ctgcagatga actctctgac agccgccgac cgggccacct acttttgtgc cagagatagc    300
tacgccgacg acggcgccct gttcaatatt tggggacctg gcacactcgt gaccatctct    360
agcggaggcg aggaagtggt ggcggagga tcaggcggtg gtggatctga actggtgctg    420
acacagagcc cctctgtgtc tgctgctctg ggaagccctg ccaagatcac atgtaccctg    480
agcagcgccc acaagaccga caccatcgac tggtatcagc agctgcaggg cgaagcccct    540
agatacctga tgcaggttca gagcgacggc agctacacca aaagacctgg cgtgcccgat    600
```

```
agattcagcg gcagttcttc tggcgccgat cgctacctga tcatcccttc tgtgcaagcc    660
gacgatgagg ccgactatta ctgcggagcc gattacatcg gcggctacgt tttcggtggc    720
ggcacacagt tgacagtgac aggcg                                          745
```

<210> SEQ ID NO 144
<211> LENGTH: 908
<212> TYPE: PRT
<213> ORGANISM: homo sapiens
<220> FEATURE:
<221> NAME/KEY: MISC_FEATURE
<223> OTHER INFORMATION: human ROR1 GenBank: AAA60275.1

<400> SEQUENCE: 144

```
Gln Glu Thr Glu Leu Ser Val Ser Ala Glu Leu Val Pro Thr Ser Ser
1               5                   10                  15

Trp Asn Ile Ser Ser Glu Leu Asn Lys Asp Ser Tyr Leu Thr Leu Asp
            20                  25                  30

Glu Pro Met Asn Asn Ile Thr Thr Ser Leu Gly Gln Thr Ala Glu Leu
        35                  40                  45

His Cys Lys Val Ser Gly Asn Pro Pro Pro Thr Ile Arg Trp Phe Lys
    50                  55                  60

Asn Asp Ala Pro Val Val Gln Glu Pro Arg Arg Leu Ser Phe Arg Ser
65                  70                  75                  80

Thr Ile Tyr Gly Ser Arg Leu Arg Ile Arg Asn Leu Asp Thr Thr Asp
                85                  90                  95

Thr Gly Tyr Phe Gln Cys Val Ala Thr Asn Gly Lys Glu Val Val Ser
            100                 105                 110

Ser Thr Gly Val Leu Phe Val Lys Phe Gly Pro Pro Pro Thr Ala Ser
        115                 120                 125

Pro Gly Tyr Ser Asp Glu Tyr Glu Glu Asp Gly Phe Cys Gln Pro Tyr
    130                 135                 140

Arg Gly Ile Ala Cys Ala Arg Phe Ile Gly Asn Arg Thr Val Tyr Met
145                 150                 155                 160

Glu Ser Leu His Met Gln Gly Glu Ile Glu Asn Gln Ile Thr Ala Ala
                165                 170                 175

Phe Thr Met Ile Gly Thr Ser Ser His Leu Ser Asp Lys Cys Ser Gln
            180                 185                 190

Phe Ala Ile Pro Ser Leu Cys His Tyr Ala Phe Pro Tyr Cys Asp Glu
        195                 200                 205

Thr Ser Ser Val Pro Lys Pro Arg Asp Leu Cys Arg Asp Glu Cys Glu
    210                 215                 220

Ile Leu Glu Asn Val Leu Cys Gln Thr Glu Tyr Ile Phe Ala Arg Ser
225                 230                 235                 240

Asn Pro Met Ile Leu Met Arg Leu Lys Leu Pro Asn Cys Glu Asp Leu
                245                 250                 255

Pro Gln Pro Glu Ser Pro Glu Ala Ala Asn Cys Ile Arg Ile Gly Ile
            260                 265                 270

Pro Met Ala Asp Pro Ile Asn Lys Asn His Lys Cys Tyr Asn Ser Thr
        275                 280                 285

Gly Val Asp Tyr Arg Gly Thr Val Ser Val Thr Lys Ser Gly Arg Gln
    290                 295                 300

Cys Gln Pro Trp Asn Ser Gln Tyr Pro His Thr His Thr Phe Thr Ala
305                 310                 315                 320
```

```
Leu Arg Phe Pro Glu Leu Asn Gly Gly His Ser Tyr Cys Arg Asn Pro
                325                 330                 335

Gly Asn Gln Lys Glu Ala Pro Trp Cys Phe Thr Leu Asp Glu Asn Phe
                340                 345                 350

Lys Ser Asp Leu Cys Asp Ile Pro Ala Cys Asp Ser Lys Asp Ser Lys
                355                 360                 365

Glu Lys Asn Lys Met Glu Ile Leu Tyr Ile Leu Val Pro Ser Val Ala
                370                 375                 380

Ile Pro Leu Ala Ile Ala Leu Leu Phe Phe Phe Ile Cys Val Cys Arg
385                 390                 395                 400

Asn Asn Gln Lys Ser Ser Ala Pro Val Gln Arg Gln Pro Lys His
                405                 410                 415

Val Arg Gly Gln Asn Val Glu Met Ser Met Leu Asn Ala Tyr Lys Pro
                420                 425                 430

Lys Ser Lys Ala Lys Glu Leu Pro Leu Ser Ala Val Arg Phe Met Glu
                435                 440                 445

Glu Leu Gly Glu Cys Ala Phe Gly Lys Ile Tyr Lys Gly His Leu Tyr
                450                 455                 460

Leu Pro Gly Met Asp His Ala Gln Leu Val Ala Ile Lys Thr Leu Lys
465                 470                 475                 480

Asp Tyr Asn Asn Pro Gln Gln Trp Thr Glu Phe Gln Gln Glu Ala Ser
                485                 490                 495

Leu Met Ala Glu Leu His His Pro Asn Ile Val Cys Leu Leu Gly Ala
                500                 505                 510

Val Thr Gln Glu Gln Pro Val Cys Met Leu Phe Glu Tyr Ile Asn Gln
                515                 520                 525

Gly Asp Leu His Glu Phe Leu Ile Met Arg Ser Pro His Ser Asp Val
                530                 535                 540

Gly Cys Ser Ser Asp Glu Asp Gly Thr Val Lys Ser Ser Leu Asp His
545                 550                 555                 560

Gly Asp Phe Leu His Ile Ala Ile Gln Ile Ala Ala Gly Met Glu Tyr
                565                 570                 575

Leu Ser Ser His Phe Phe Val His Lys Asp Leu Ala Ala Arg Asn Ile
                580                 585                 590

Leu Ile Gly Glu Gln Leu His Val Lys Ile Ser Asp Leu Gly Leu Ser
                595                 600                 605

Arg Glu Ile Tyr Ser Ala Asp Tyr Tyr Arg Val Gln Ser Lys Ser Leu
                610                 615                 620

Leu Pro Ile Arg Trp Met Pro Pro Glu Ala Ile Met Tyr Gly Lys Phe
625                 630                 635                 640

Ser Ser Asp Ser Asp Ile Trp Ser Phe Gly Val Val Leu Trp Glu Ile
                645                 650                 655

Phe Ser Phe Gly Leu Gln Pro Tyr Tyr Gly Phe Ser Asn Gln Glu Val
                660                 665                 670

Ile Glu Met Val Arg Lys Arg Gln Leu Leu Pro Cys Ser Glu Asp Cys
                675                 680                 685

Pro Pro Arg Met Tyr Ser Leu Met Thr Glu Cys Trp Asn Glu Ile Pro
                690                 695                 700

Ser Arg Arg Pro Arg Phe Lys Asp Ile His Val Arg Leu Arg Ser Trp
705                 710                 715                 720

Glu Gly Leu Ser Ser His Thr Ser Ser Thr Thr Pro Ser Gly Gly Asn
                725                 730                 735
```

```
Ala Thr Thr Gln Thr Thr Ser Leu Ser Ala Ser Pro Val Ser Asn Leu
                740                 745                 750

Ser Asn Pro Arg Tyr Pro Asn Tyr Met Phe Pro Ser Gln Gly Ile Thr
            755                 760                 765

Pro Gln Gly Gln Ile Ala Gly Phe Ile Gly Pro Pro Ile Pro Gln Asn
        770                 775                 780

Gln Arg Phe Ile Pro Ile Asn Gly Tyr Pro Ile Pro Pro Gly Tyr Ala
785                 790                 795                 800

Ala Phe Pro Ala Ala His Tyr Gln Pro Thr Gly Pro Pro Arg Val Ile
                805                 810                 815

Gln His Cys Pro Pro Pro Lys Ser Arg Ser Pro Ser Ser Ala Ser Gly
                820                 825                 830

Ser Thr Ser Thr Gly His Val Thr Ser Leu Pro Ser Ser Gly Ser Asn
            835                 840                 845

Gln Glu Ala Asn Ile Pro Leu Leu Pro His Met Ser Ile Pro Asn His
        850                 855                 860

Pro Gly Gly Met Gly Ile Thr Val Phe Gly Asn Lys Ser Gln Lys Pro
865                 870                 875                 880

Tyr Lys Ile Asp Ser Lys Gln Ala Ser Leu Leu Gly Asp Ala Asn Ile
                885                 890                 895

His Gly His Thr Glu Ser Met Ile Ser Ala Glu Leu
            900                 905

<210> SEQ ID NO 145
<211> LENGTH: 520
<212> TYPE: PRT
<213> ORGANISM: homo sapiens
<220> FEATURE:
<221> NAME/KEY: MISC_FEATURE
<223> OTHER INFORMATION: human ROR1 isoform 2

<400> SEQUENCE: 145

Gln Glu Thr Glu Leu Ser Val Ser Ala Glu Leu Val Pro Thr Ser Ser
1               5                   10                  15

Trp Asn Ile Ser Ser Glu Leu Asn Lys Asp Ser Tyr Leu Thr Leu Asp
                20                  25                  30

Glu Pro Met Asn Asn Ile Thr Thr Ser Leu Gly Gln Thr Ala Glu Leu
            35                  40                  45

His Cys Lys Val Ser Gly Asn Pro Pro Pro Thr Ile Arg Trp Phe Lys
        50                  55                  60

Asn Asp Ala Pro Val Val Gln Glu Pro Arg Arg Leu Ser Phe Arg Ser
65                  70                  75                  80

Thr Ile Tyr Gly Ser Arg Leu Arg Ile Arg Asn Leu Asp Thr Thr Asp
                85                  90                  95

Thr Gly Tyr Phe Gln Cys Val Ala Thr Asn Gly Lys Glu Val Val Ser
            100                 105                 110

Ser Thr Gly Val Leu Phe Val Lys Phe Gly Pro Pro Pro Thr Ala Ser
        115                 120                 125

Pro Gly Tyr Ser Asp Glu Tyr Glu Glu Asp Gly Phe Cys Gln Pro Tyr
    130                 135                 140

Arg Gly Ile Ala Cys Ala Arg Phe Ile Gly Asn Arg Thr Val Tyr Met
145                 150                 155                 160

Glu Ser Leu His Met Gln Gly Glu Ile Glu Asn Gln Ile Thr Ala Ala
                165                 170                 175

Phe Thr Met Ile Gly Thr Ser Ser His Leu Ser Asp Lys Cys Ser Gln
            180                 185                 190
```

```
Phe Ala Ile Pro Ser Leu Cys His Tyr Ala Phe Pro Tyr Cys Asp Glu
            195                 200                 205

Thr Ser Ser Val Pro Lys Pro Arg Asp Leu Cys Arg Asp Glu Cys Glu
        210                 215                 220

Ile Leu Glu Asn Val Leu Cys Gln Thr Glu Tyr Ile Phe Ala Arg Ser
225                 230                 235                 240

Asn Pro Met Ile Leu Met Arg Leu Lys Leu Pro Asn Cys Glu Asp Leu
                245                 250                 255

Pro Gln Pro Glu Ser Pro Glu Ala Ala Asn Cys Ile Arg Ile Gly Ile
            260                 265                 270

Pro Met Ala Asp Pro Ile Asn Lys Asn His Lys Cys Tyr Asn Ser Thr
        275                 280                 285

Gly Val Asp Tyr Arg Gly Thr Val Ser Val Thr Lys Ser Gly Arg Gln
290                 295                 300

Cys Gln Pro Trp Asn Ser Gln Tyr Pro His Thr His Thr Phe Thr Ala
305                 310                 315                 320

Leu Arg Phe Pro Glu Leu Asn Gly Gly His Ser Tyr Cys Arg Asn Pro
                325                 330                 335

Gly Asn Gln Lys Glu Ala Pro Trp Cys Phe Thr Leu Glu Asn Phe
            340                 345                 350

Lys Ser Asp Leu Cys Asp Ile Pro Ala Cys Asp Ser Lys Asp Ser Lys
        355                 360                 365

Glu Lys Asn Lys Met Glu Ile Leu Tyr Ile Leu Val Pro Ser Val Ala
            370                 375                 380

Ile Pro Leu Ala Ile Ala Leu Leu Phe Phe Phe Ile Cys Val Cys Arg
385                 390                 395                 400

Asn Asn Gln Lys Ser Ser Ser Ala Pro Val Gln Arg Gln Pro Lys His
                405                 410                 415

Val Arg Gly Gln Asn Val Glu Met Ser Met Leu Asn Ala Tyr Lys Pro
            420                 425                 430

Lys Ser Lys Ala Lys Glu Leu Pro Leu Ser Ala Val Arg Phe Met Glu
        435                 440                 445

Glu Leu Gly Glu Cys Ala Phe Gly Lys Ile Tyr Lys Gly His Leu Tyr
            450                 455                 460

Leu Pro Gly Met Asp His Ala Gln Leu Val Ala Ile Lys Thr Leu Lys
465                 470                 475                 480

Asp Tyr Asn Asn Pro Gln Gln Trp Thr Glu Phe Gln Gln Glu Ala Ser
                485                 490                 495

Leu Met Ala Glu Leu His His Pro Asn Ile Val Cys Leu Leu Gly Ala
            500                 505                 510

Val Thr Gln Glu Gln Pro Val Cys
        515                 520

<210> SEQ ID NO 146
<211> LENGTH: 364
<212> TYPE: PRT
<213> ORGANISM: homo sapiens
<220> FEATURE:
<221> NAME/KEY: MISC_FEATURE
<223> OTHER INFORMATION: human ROR1 isoform 3

<400> SEQUENCE: 146

Gln Glu Thr Glu Leu Ser Val Ser Ala Glu Leu Val Pro Thr Ser Ser
1               5                   10                  15
```

```
Trp Asn Ile Ser Ser Glu Leu Asn Lys Asp Ser Tyr Leu Thr Leu Asp
             20                  25                  30

Glu Pro Met Asn Asn Ile Thr Thr Ser Leu Gly Gln Thr Ala Glu Leu
         35                  40                  45

His Cys Lys Val Ser Gly Asn Pro Pro Thr Ile Arg Trp Phe Lys
     50                  55                  60

Asn Asp Ala Pro Val Val Gln Glu Pro Arg Arg Leu Ser Phe Arg Ser
 65              70                  75                  80

Thr Ile Tyr Gly Ser Arg Leu Arg Ile Arg Asn Leu Asp Thr Thr Asp
                 85                  90                  95

Thr Gly Tyr Phe Gln Cys Val Ala Thr Asn Gly Lys Glu Val Val Ser
            100                 105                 110

Ser Thr Gly Val Leu Phe Val Lys Phe Gly Pro Pro Thr Ala Ser
        115                 120                 125

Pro Gly Tyr Ser Asp Glu Tyr Glu Glu Asp Gly Phe Cys Gln Pro Tyr
    130                 135                 140

Arg Gly Ile Ala Cys Ala Arg Phe Ile Gly Asn Arg Thr Val Tyr Met
145                 150                 155                 160

Glu Ser Leu His Met Gln Gly Glu Ile Glu Asn Gln Ile Thr Ala Ala
                165                 170                 175

Phe Thr Met Ile Gly Thr Ser Ser His Leu Ser Asp Lys Cys Ser Gln
                180                 185                 190

Phe Ala Ile Pro Ser Leu Cys His Tyr Ala Phe Pro Tyr Cys Asp Glu
            195                 200                 205

Thr Ser Ser Val Pro Lys Pro Arg Asp Leu Cys Arg Asp Glu Cys Glu
    210                 215                 220

Ile Leu Glu Asn Val Leu Cys Gln Thr Glu Tyr Ile Phe Ala Arg Ser
225                 230                 235                 240

Asn Pro Met Ile Leu Met Arg Leu Lys Leu Pro Asn Cys Glu Asp Leu
                245                 250                 255

Pro Gln Pro Glu Ser Pro Glu Ala Ala Asn Cys Ile Arg Ile Gly Ile
                260                 265                 270

Pro Met Ala Asp Pro Ile Asn Lys Asn His Lys Cys Tyr Asn Ser Thr
    275                 280                 285

Gly Val Asp Tyr Arg Gly Thr Val Ser Val Thr Lys Ser Gly Arg Gln
                290                 295                 300

Cys Gln Pro Trp Asn Ser Gln Tyr Pro His Thr His Thr Phe Thr Ala
305                 310                 315                 320

Leu Arg Phe Pro Glu Leu Asn Gly Gly His Ser Tyr Cys Arg Asn Pro
                325                 330                 335

Gly Asn Gln Lys Glu Ala Pro Trp Cys Phe Thr Leu Asp Glu Asn Phe
                340                 345                 350

Lys Ser Asp Leu Cys Asp Ile Pro Ala Cys Gly Lys
        355                 360

<210> SEQ ID NO 147
<211> LENGTH: 84
<212> TYPE: DNA
<213> ORGANISM: artificial sequence
<220> FEATURE:
<223> OTHER INFORMATION: CD28 transmembrane domain
```

<400> SEQUENCE: 147

```
atgttttggg tgctggtcgt ggtcggaggg gtgctggcct gttacagcct gctggtgaca    60
gtcgctttca tcatcttctg ggtg                                           84
```

<210> SEQ ID NO 148
<211> LENGTH: 84
<212> TYPE: DNA
<213> ORGANISM: artificial sequence
<220> FEATURE:
<223> OTHER INFORMATION: CD28 transmembrane domain (O/SSE)

<400> SEQUENCE: 148

```
atgttctggg tgctcgtggt cgttggcgga gtgctggcct gttacagcct gctggttacc    60
gtggccttca tcatcttttg ggtc                                           84
```

<210> SEQ ID NO 149
<211> LENGTH: 28
<212> TYPE: PRT
<213> ORGANISM: artificial sequence
<220> FEATURE:
<223> OTHER INFORMATION: CD28 transmembrane domain

<400> SEQUENCE: 149

Met Phe Trp Val Leu Val Val Val Gly Gly Val Leu Ala Cys Tyr Ser
1               5                   10                  15

Leu Leu Val Thr Val Ala Phe Ile Ile Phe Trp Val
            20                  25

<210> SEQ ID NO 150
<211> LENGTH: 336
<212> TYPE: DNA
<213> ORGANISM: artificial sequence
<220> FEATURE:
<223> OTHER INFORMATION: CD3-zeta derived intracellular signaling domain
      (O/SSE)

<400> SEQUENCE: 150

```
agagtgaagt tcagcagatc cgccgacgct ccagcctatc agcagggcca aaaccagctg    60
tacaacgagc tgaacctggg gagaagagaa gagtacgacg tgctggataa gcggagaggc   120
agagatcctg aaatgggcgg caagcccaga cggaagaatc ctcaagaggg cctgtataat   180
gagctgcaga agacaagat ggccgaggcc tacagcgaga tcggaatgaa gggcgagcgc    240
agaagaggca aggacacga tggactgtac cagggcctga gcaccgccac caaggatacc   300
tatgacgcac tgcacatgca ggccctgcca cctaga                             336
```

<210> SEQ ID NO 151
<211> LENGTH: 1074
<212> TYPE: DNA
<213> ORGANISM: artificial sequence
<220> FEATURE:
<223> OTHER INFORMATION: truncated EGFR (tEGFR) sequence

<400> SEQUENCE: 151

```
atgcttctcc tggtgacaag ccttctgctc tgtgagttac cacacccagc attcctcctg    60
atcccacgca aagtgtgtaa cggaataggt attggtgaat ttaaagactc actctccata   120
aatgctacga atattaaaca cttcaaaaac tgcacctcca tcagtggcga tctccacatc   180
ctgccggtgg catttagggg tgactccttc acacatactc ctcctctgga tccacaggaa   240
ctggatattc tgaaaaccgt aaaggaaatc acagggtttt tgctgattca ggcttggcct   300
```

```
gaaaacagga cggacctcca tgcctttgag aacctagaaa tcatacgcgg caggaccaag    360
caacatggtc agttttctct tgcagtcgtc agcctgaaca taacatcctt gggattacgc    420
tccctcaagg agataagtga tggagatgtg ataatttcag gaaacaaaaa tttgtgctat    480
gcaaatacaa taaactggaa aaaactgttt gggacctccg tcagaaaaac caaaattata    540
agcaacagag gtgaaaacag ctgcaaggcc acaggccagg tctgccatgc cttgtgctcc    600
cccgagggct gctggggccc ggagcccagg gactgcgtct cttgccggaa tgtcagccga    660
ggcagggaat gcgtggacaa gtgcaacctt ctggagggtg agccaaggga gtttgtggag    720
aactctgagt gcatacagtg ccacccagag tgcctgcctc aggccatgaa catcacctgc    780
acaggacggg gaccagacaa ctgtatccag tgtgcccact acattgacgg cccccactgc    840
gtcaagacct gcccggcagg agtcatggga gaaaacaaca ccctggtctg aagtacgca    900 gacgccggcc atgtgtgcca cctgtgccat ccaaactgca cctacggatg cactgggcca    960
ggtcttgaag ctgtccaac gaatgggcct aagatcccgt ccatcgccac tgggatggtg   1020
ggggccctcc tcttgctgct ggtggtggcc ctggggatcg gcctcttcat gtga         1074

<210> SEQ ID NO 152
<211> LENGTH: 1074
<212> TYPE: DNA
<213> ORGANISM: artificial sequence
<220> FEATURE:
<223> OTHER INFORMATION: truncated EGFR (tEGFR) sequence (O/SSE)

<400> SEQUENCE: 152
atgctgctcc tcgtgacaag cctgctcctg tgtgaactcc ctcatccagc ttttctgctc     60
attcctcgga aagtgtgcaa cggcatcggc atcggagagt tcaaggacag cctgagcatc    120
aatgccacca acatcaagca cttcaagaat tgcaccagca tcagcggcga cctgcacatt    180
ctgcctgtgg cctttagagg cgacagcttc acccacacac ctccactgga tccccaagag    240
ctggatatcc tgaaaaccgt gaaagagatt accggattcc tcctgatcca gcctggcca    300 gagaacagaa ccgatctgca cgccttcgag aacctcgaga tcatcagagg ccggaccaaa    360
cagcacggcc agtttagcct ggctgtggtg tctctgaaca tcaccagtct gggcctgaga    420
agcctgaaag aaatctccga cggcgacgtg atcatctccg gaaacaagaa cctgtgctac    480
gccaacacca tcaactggaa gaagctgttc ggcacctccg gccagaaaac aaagatcatc    540
tctaaccggg gcgagaacag ctgcaaggcc accggacaag tttgtcacgc cctgtgtagc    600
cctgaaggct gttggggacc cgaacctaga gactgtgtgt cctgccggaa tgtgtcccgg    660
ggcagagaat gtgtggataa gtgcaacctg ctggaaggcg agccccgcga gtttgtggaa    720
aacagcgagt gcatccagtg tcaccccgag tgtctgcccc aggccatgaa cattacatgc    780
accggcagag gccccgacaa ctgtattcag tgcgcccact acatcgacgg ccctcactgc    840
gtgaaaacat gtccagctgg cgtgatggga gagaacaaca ccctcgtgtg aagtatgcc    900 gacgccggac atgtgtgcca cctgtgtcac cctaattgca cctacggctg taccggacct    960
ggcctggaag gatgccctac aaacggccct aagatcccca gcattgccac cggaatggtt   1020
ggagccctgc tgcttctgtt ggtggtggcc ctcggaatcg gcctgttcat gtga         1074

<210> SEQ ID NO 153
<211> LENGTH: 357
<212> TYPE: PRT
<213> ORGANISM: artificial sequence
<220> FEATURE:
```

<223> OTHER INFORMATION: truncated EGFR (tEGFR) sequence

<400> SEQUENCE: 153

```
Met Leu Leu Leu Val Thr Ser Leu Leu Leu Cys Glu Leu Pro His Pro
1               5                   10                  15
Ala Phe Leu Leu Ile Pro Arg Lys Val Cys Asn Gly Ile Gly Ile Gly
            20                  25                  30
Glu Phe Lys Asp Ser Leu Ser Ile Asn Ala Thr Asn Ile Lys His Phe
        35                  40                  45
Lys Asn Cys Thr Ser Ile Ser Gly Asp Leu His Ile Leu Pro Val Ala
    50                  55                  60
Phe Arg Gly Asp Ser Phe Thr His Thr Pro Pro Leu Asp Pro Gln Glu
65                  70                  75                  80
Leu Asp Ile Leu Lys Thr Val Lys Glu Ile Thr Gly Phe Leu Leu Ile
                85                  90                  95
Gln Ala Trp Pro Glu Asn Arg Thr Asp Leu His Ala Phe Glu Asn Leu
            100                 105                 110
Glu Ile Ile Arg Gly Arg Thr Lys Gln His Gly Gln Phe Ser Leu Ala
        115                 120                 125
Val Val Ser Leu Asn Ile Thr Ser Leu Gly Leu Arg Ser Leu Lys Glu
    130                 135                 140
Ile Ser Asp Gly Asp Val Ile Ile Ser Gly Asn Lys Asn Leu Cys Tyr
145                 150                 155                 160
Ala Asn Thr Ile Asn Trp Lys Lys Leu Phe Gly Thr Ser Gly Gln Lys
                165                 170                 175
Thr Lys Ile Ile Ser Asn Arg Gly Glu Asn Ser Cys Lys Ala Thr Gly
            180                 185                 190
Gln Val Cys His Ala Leu Cys Ser Pro Glu Gly Cys Trp Gly Pro Glu
        195                 200                 205
Pro Arg Asp Cys Val Ser Cys Arg Asn Val Ser Arg Gly Arg Glu Cys
    210                 215                 220
Val Asp Lys Cys Asn Leu Leu Glu Gly Glu Pro Arg Glu Phe Val Glu
225                 230                 235                 240
Asn Ser Glu Cys Ile Gln Cys His Pro Glu Cys Leu Pro Gln Ala Met
                245                 250                 255
Asn Ile Thr Cys Thr Gly Arg Gly Pro Asp Asn Cys Ile Gln Cys Ala
            260                 265                 270
His Tyr Ile Asp Gly Pro His Cys Val Lys Thr Cys Pro Ala Gly Val
        275                 280                 285
Met Gly Glu Asn Asn Thr Leu Val Trp Lys Tyr Ala Asp Ala Gly His
    290                 295                 300
Val Cys His Leu Cys His Pro Asn Cys Thr Tyr Gly Cys Thr Gly Pro
305                 310                 315                 320
Gly Leu Glu Gly Cys Pro Thr Asn Gly Pro Lys Ile Pro Ser Ile Ala
                325                 330                 335
Thr Gly Met Val Gly Ala Leu Leu Leu Leu Val Val Ala Leu Gly
            340                 345                 350
Ile Gly Leu Phe Met
        355
```

<210> SEQ ID NO 154
<211> LENGTH: 126
<212> TYPE: DNA
<213> ORGANISM: artificial sequence
<220> FEATURE:

<223> OTHER INFORMATION: 4-1BB intracellular co-signaling sequence

<400> SEQUENCE: 154

| aagcggggga gaaagaaact gctgtatatt ttcaaacagc cctttatgag acctgtgcag | 60 |
| actacccagg aggaagacgg atgcagctgt aggtttcccg aggaagagga aggaggctgt | 120 |
| gagctg | 126 |

<210> SEQ ID NO 155
<211> LENGTH: 126
<212> TYPE: DNA
<213> ORGANISM: artificial sequence
<220> FEATURE:
<223> OTHER INFORMATION: 4-1BB intracellular co-signaling sequence (O/SSE)

<400> SEQUENCE: 155

| aagcggggca gaaagaagct gctctacatc ttcaagcagc ccttcatgcg gcccgtgcag | 60 |
| accacacaag aggaagatgg ctgctcctgc agattccccg aggaagaaga aggcggctgc | 120 |
| gagctg | 126 |

<210> SEQ ID NO 156
<211> LENGTH: 1308
<212> TYPE: DNA
<213> ORGANISM: artificial sequence
<220> FEATURE:
<223> OTHER INFORMATION: anti-ROR1 CAR

<400> SEQUENCE: 156

| caggttcagc tgcaagagtc tggccctggc ctggtcaagc ctagcgaaac actgagcctg | 60 |
| acctgtaccg tgtctggcgg cagcatctcc aactactact ggtcctggat cagacagcct | 120 |
| gccggcaaag gcctggaatg gatcggcaga atctacacca gcggcagcac caactacaac | 180 |
| cccagcctga gtccagagt gaccatgagc gtggacacca gcaagaacca gttctccctg | 240 |
| aagctgagca gcctgacagc cgccgatacc gccatctact actgtgcccg gtactacgat | 300 |
| atcctgaccg gcttcttcga ctactgggc cagggaacac tggtcacagt ttctagcgga | 360 |
| ggcggaggat ctggtggcgg aggaagtggc ggaggcggtt ctgtgatttg gatgacacag | 420 |
| agccctagcc tgctgagcgc cagcacaggc gatagcgtga ccatcagctg cagaatgagc | 480 |
| caggacatca gcagctacct ggcttggtat cagcagaagc tggcaaggc ccctgaactg | 540 |
| ctgatctatg ccgcttccag tctgcagagc ggcgtgccat ctagattttc cggcagcggc | 600 |
| tctggcaccg acttcaccct gacaatcagc tccctgcagt ccgaggactt cgccacctac | 660 |
| tattgccagc agtacgacag cttccctcca acctttggcc agggcaccaa ggtggaattc | 720 |
| aagcgcgagt ctaaatacgg accgccttgt cctccttgtc ccatgttctg ggtgctcgtg | 780 |
| gtcgttggcg gagtgctggc ctgttacagc ctgctggtta ccgtggcctt catcatcttt | 840 |
| tgggtcaagc ggggcagaaa gaagctgctc tacatcttca gcagcccctt catgcggccc | 900 |
| gtgcagacca cacaagagga agatggctgc tcctgcagat ccccgagga agaagaaggc | 960 |
| ggctgcgagc tgagagtgaa gttcagcaga tccgccgacg ctccagccta tcagcagggc | 1020 |
| caaaaccagc tgtacaacga gctgaacctg ggagaagag aagagtacga cgtgctggat | 1080 |
| aagcggagag gcagagatcc tgaaatgggc ggcaagccca cggaagaa tcctcaagag | 1140 |

```
ggcctgtata atgagctgca gaaagacaag atggccgagg cctacagcga gatcggaatg      1200
aagggcgagc gcagaagagg caagggacac gatggactgt accagggcct gagcaccgcc      1260
accaaggata cctatgacgc actgcacatg caggccctgc acctaga                    1308
```

<210> SEQ ID NO 157
<211> LENGTH: 1314
<212> TYPE: DNA
<213> ORGANISM: artificial sequence
<220> FEATURE:
<223> OTHER INFORMATION: anti-ROR1 CAR

<400> SEQUENCE: 157

```
cagctccagc tgcaagaatc tggacctggc ctggtcaagc ccagcgagac actgtctctg        60
acctgtacag tgtccggcgg cagcatcaat agcaccacaa gctactgggc ctggatcaga       120
cagcctcctg gcaaaggcct ggaatggatc ggcaccatct tctacagcgg caagacctac       180
aacaacccca gcctgaagtc cagagtgacc atgagcgtgg acaccagcaa gaaccacttc       240
agcctgaaag tgaacagcgt gacagccgcc gataccgccg tgtactactg cgccagattc       300
gactacggct tccacgacgc cttcgacatc tggggccagg gcacaatggt cacagtttct       360
agcggaggcg aggatctggt ggcggagga agtgccggag gcggttctga gattgtgatg       420
acacagagcc ccgccactct gagccttagt cctggcgaaa gagccacact gagctgcaga       480
gccagccaga gcatcaccag cgattacctg agctggtatc agcagaagcc cggacaggct       540
cccagactgc tgatctatgg cgcctctaca gagccaccg gcattcccgc ccgcttttct       600
ggctctggaa gcggcaccga cttcaccctg accatatcta gcctgcagcc tgaggacttc       660
gtggtgtact attgccagca ggactacaac ctgtacacct cggccagg gaccaagctg        720 gaaatcaaga gagagtctaa atacggaccg ccttgtcctc cttgtcccat gttctgggtg       780
ctcgtggtcg ttggcggagt gctggcctgt tacagcctgc tggttaccgt ggccttcatc       840
atctttgggg tcaagcgggg cagaaagaag ctgctctaca tcttcaagca gcccttcatg       900
cggcccgtgc agaccacaca agaggaagat ggctgctcct gcagattccc cgaggaagaa       960
gaaggcggct gcgagctgag agtgaagttc agcagatccg ccgacgctcc agcctatcag      1020
cagggccaaa accagctgta caacgagctg aacctgggga aagagaaga gtacgacgtg      1080 ctggataagc ggagaggcag agatcctgaa atggcggca agcccagacg aagaatcct       1140 caagagggcc tgtataatga gctgcagaaa gacaagatgg ccgaggccta cagcgagatc      1200
ggaatgaagg gcgagcgcag aagaggcaag gacacgatg gactgtacca gggcctgagc      1260
accgccacca aggatacct tgacgcactg cacatgcagg ccctgccacc taga             1314
```

<210> SEQ ID NO 158
<211> LENGTH: 1629
<212> TYPE: DNA
<213> ORGANISM: artificial sequence
<220> FEATURE:
<223> OTHER INFORMATION: anti-ROR1 CAR

<400> SEQUENCE: 158

```
caggttcagc tgcaagagtc tggccctggc ctggtcaagc ctagcgaaac actgagcctg        60
acctgtaccg tgtctggcgg cagcatctcc aactactact ggtcctggat cagacagcct       120
gccggcaaag gctggaatg gatcggcaga atctacacca cggcagcac caactacaac       180 cccagcctga gtccagagt gaccatgagc gtggacacca gcaagaacca gttctcccctg      240
```

| | |
|---|---|
| aagctgagca gcctgacagc cgccgatacc gccatctact actgtgcccg gtactacgat | 300 |
| atcctgaccg gcttcttcga ctactggggc cagggaacac tggtcacagt ttctagcgga | 360 |
| ggcggaggat ctggtggcgg aggaagtggc ggaggcggtt ctgtgatttg gatgacacag | 420 |
| agccctagcc tgctgagcgc cagcacaggc gatagcgtga ccatcagctg cagaatgagc | 480 |
| caggacatca gcagctacct ggcttggtat cagcagaagc tggcaaggc ccctgaactg | 540 |
| ctgatctatg ccgcttccag tctgcagagc ggcgtgccat ctagattttc ggcagcggc | 600 |
| tctggcaccg acttcaccct gacaatcagc tccctgcagt ccgaggactt cgccacctac | 660 |
| tattgccagc agtacgacag cttccctcca acctttggcc agggcaccaa ggtggaattc | 720 |
| aagcgcgagt ctaaatacgg accgccttgt cctccttgtc ccggccagcc aagagagccc | 780 |
| caggtttaca cactgcctcc aagccaagag gaaatgacca gaatcaggt gtccctgaca | 840 |
| tgcctggtca agggcttcta cccctccgat atcgccgtgg aatgggagag caatggccag | 900 |
| cctgagaaca actacaagac cacacctcct gtgctggaca gcgacggcag tttcttcctg | 960 |
| tatagtagac tcaccgtgga taaatcaaga tggcaagagg gcaacgtgtt cagctgcagc | 1020 |
| gtgatgcacg aggccctgca caaccactac acccagaaaa gcctgagcct gtctctgggc | 1080 |
| aagatgttct gggtgctcgt ggtcgttggc ggagtgctgg cctgttacag cctgctggtt | 1140 |
| accgtggcct tcatcatctt ttgggtcaag cggggcagaa agaagctgct ctacatcttc | 1200 |
| aagcagcccc tcatgcggcc cgtgcagacc acacaagagg aagatggctg ctcctgcaga | 1260 |
| ttccccgagg aagaagaagg cggctgcgag ctgagagtga agttcagcag atccgccgac | 1320 |
| gctccagcct atcagcaggg ccaaaaccag ctgtacaacg agctgaacct ggggagaaga | 1380 |
| gaagagtacg acgtgctgga taagcggaga ggcagagatc ctgaaatggg cggcaagccc | 1440 |
| agacggaaga atcctcaaga gggcctgtat aatgagctgc agaaagacaa gatggccgag | 1500 |
| gcctacagcg agatcggaat gaagggcgag cgcagaagag gcaagggaca cgatggactg | 1560 |
| taccagggcc tgagcaccgc caccaaggat acctatgacg cactgcacat gcaggccctg | 1620 |
| ccacctaga | 1629 |

<210> SEQ ID NO 159
<211> LENGTH: 1656
<212> TYPE: DNA
<213> ORGANISM: artificial sequence
<220> FEATURE:
<223> OTHER INFORMATION: anti-ROR1 CAR

<400> SEQUENCE: 159

| | |
|---|---|
| caggtgcagc tggttcaatc tggcgccgaa gtgaagaaac caggcgcctc tgtgaaggtg | 60 |
| tcctgcaagg ccagcggcta cacctttacc agctacggca tcagctgggt ccgacaggct | 120 |
| cctggacaag gcttggaatg gatgggctgg atcagcgcct acaacggcaa caccaaatac | 180 |
| gcccagaaac tgcagggcag agtgaccatg accaccgaca ccagcacaag caccgcctac | 240 |
| atggaactgc ggagcctgag atccgatgac accgccgtgt actactgcgc cagagatgag | 300 |
| gacatcctga ccggctacaa ctactacggc atggacgtgt ggggccaggg cacaacagtg | 360 |
| acagtttctt ctggcggcgg aggatctggc ggaggtggaa gcggaggcgg tggatctcaa | 420 |
| ctggtgctga cacagtctcc tagcgcctct gcttctctgg gagccagcgt gaagctgacc | 480 |
| tgtacactgt ctagcggcca cagcagctac gccattgctt ggcatcagca gcagcccgag | 540 |
| aagggcccta gatacctgat gaagctgaac agcgacggca gccactctaa aggcgacggc | 600 |
| atccccgata gattcagcgg cagttctagc ggagccgagc gctacctgac aatcagctct | 660 |

```
ctgcaatccg aggacgaggc cgactactac tgtcagacat ggggcaccgg catcagagtg      720
tttggcggag gcaccaagct gacagtgctt ggagagtcta aatacggacc gccttgtcct      780
ccttgtcccg gccagccaag agagcccag gtttacacac tgcctccaag ccaagaggaa       840
atgaccaaga atcaggtgtc cctgacatgc ctggtcaagg gcttctaccc ctccgatatc      900
gccgtggaat gggagagcaa tggccagcct gagaacaact acaagaccac acctcctgtg     960
ctggacagcg acggcagttt cttcctgtat agtagactca ccgtggataa atcaagatgg    1020
caagagggca acgtgttcag ctgcagcgtg atgcacgagg ccctgcacaa ccactacacc    1080
cagaaaagcc tgagcctgtc tctgggcaag atgttctggg tgctcgtggt cgttggcgga    1140
gtgctggcct gttacagcct gctggttacc gtggccttca tcatcttttg ggtcaagcgg    1200
ggcagaaaga agctgctcta catcttcaag cagcccttca tgcggcccgt gcagaccaca    1260
caagaggaag atggctgctc ctgcagattc cccgaggaag aagaggcgg ctgcgagctg      1320 agagtgaagt tcagcagatc cgccgacgct ccagcctatc agcagggcca aaaccagctg    1380
tacaacgagc tgaacctggg gagaagagaa gagtacgacg tgctggataa gcggagaggc    1440
agagatcctg aaatgggcgg caagcccaga cggaagaatc ctcaagaggg cctgtataat    1500
gagctgcaga aagacaagat ggccgaggcc tacagcgaga tcggaatgaa gggcgagcgc    1560
agaagaggca aggacacga tggactgtac cagggcctga gcaccgccac caaggatacc    1620
tatgacgcac tgcacatgca ggccctgcca cctaga                             1656
```

<210> SEQ ID NO 160
<211> LENGTH: 1635
<212> TYPE: DNA
<213> ORGANISM: artificial sequence
<220> FEATURE:
<223> OTHER INFORMATION: anti-ROR1 CAR

<400> SEQUENCE: 160

```
cagctccagc tgcaagaatc tggacctggc ctggtcaagc ccagcgagac actgtctctg       60
acctgtacag tgtccggcgg cagcatcaat agcaccacaa gctactgggc ctggatcaga     120
cagcctcctg gcaaaggcct ggaatggatc ggcaccatct tctacagcgg caagacctac     180
aacaacccca gcctgaagtc cagagtgacc atgagcgtgg acaccagcaa gaaccacttc     240
agcctgaaag tgaacagcgt gacagccgcc gataccgccg tgtactactg cgccagattc     300
gactacggct tccacgacgc cttcgacatc tggggccagg gcacaatggt cacagtttct     360
agcggaggcg gaggatctgg tggcggagga agtggcggag gcggttctga gattgtgatg     420
acacagagcc ccgccactct gagccttagt cctggcgaaa gagccacact gagctgcaga     480
gccagccaga gcatcaccag cgattacctg agctggtatc agcagaagcc cggacaggct     540
cccagactgc tgatctatgg cgcctctaca agagccaccg gcattcccgc ccgcttttct     600
ggctctggaa gcggcaccga cttcaccctg accatatcta gcctgcagcc tgaggacttc     660
gtggtgtact attgccagca ggactacaac ctgtacacct cggccaggg gaccaagctg     720 gaaatcaaga gagagtctaa atacggaccg ccttgtcctc cttgtcccgg ccagccaaga    780 gagcccagg tttacacact gcctccaagc caagaggaaa tgaccaagaa tcaggtgtcc     840
ctgacatgcc tggtcaaggg cttctacccc tccgatatcg ccgtggaatg ggagagcaat    900
ggccagcctg agaacaacta caagaccaca cctcctgtgc tggacagcga cggcagtttc    960
ttcctgtata gtagactcac cgtggataaa tcaagatggc aagagggcaa cgtgttcagc   1020
```

```
tgcagcgtga tgcacgaggc cctgcacaac cactacaccc agaaaagcct gagcctgtct   1080
ctgggcaaga tgttctgggt gctcgtggtc gttggcggag tgctggcctg ttacagcctg   1140
ctggttaccg tggccttcat catctttttgg gtcaagcggg gcagaaagaa gctgctctac   1200
atcttcaagc agcccttcat gcggcccgtg cagaccacac aagaggaaga tggctgctcc   1260
tgcagattcc ccgaggaaga agaaggcggc tgcgagctga gagtgaagtt cagcagatcc   1320
gccgacgctc cagcctatca gcagggccaa aaccagctgt acaacgagct gaacctgggg   1380
agaagagaag agtacgacgt gctggataag cggagaggca gagatcctga aatgggcggc   1440
aagcccagac ggaagaatcc tcaagagggc ctgtataatg agctgcagaa agacaagatg   1500
gccgaggcct acagcgagat cggaatgaag ggcgagcgca agagggcaa gggacacgat   1560 ggactgtacc agggcctgag caccgccacc aaggatacct atgacgcact gcacatgcag   1620
gccctgccac ctaga                                                    1635

<210> SEQ ID NO 161
<211> LENGTH: 1656
<212> TYPE: DNA
<213> ORGANISM: anti-ROR1 CAR

<400> SEQUENCE: 161
caggttcagc tgcttcagtc tggcgccgaa gtgaagaaac ctggcgcctc tgtgaaggtg     60
tcctgcaagg ccagcggcta caccttttacc agctacggca tcagctgggt ccgacaggct    120
cctggacaag gcttggaatg gatgggctgg atcagcgcct acaccggcaa taccagatac    180
gcccagaaac tgcagggcag agtgaccatg accaccgaca ccagcacaag caccgcctac    240
atggaactgc ggagcctgag atccgatgac accgccgtgt actactgcgc cagagaagaa    300
ggcgccacca ccgactacga ctactacggc atggatgtgt ggggccaggg aacagccgtg    360
acagtttctt ctggtggcgg aggatctggc ggaggtggaa gcggcggagg cggatctcaa    420
ctggttctga cacagagccc aagcgcctct gcatctctgg gagcttccgt gaagctgacc    480
tgcacactgt ctagcggcca cagcagctat gccattgcct ggcatcagca acagcccgag    540
aagggcccta gataccctgat gaagctgaac agcgacggca ccactctaa aggcgacggc    600 atccccgata gattcagcgg cagttctagc ggagccgagc gctacctgac aatcagctct    660
ctgcaatccg aggacgaggc cgattactac tgtcagacat ggggcaccgg catcagagtg    720
tttggcggcg gaacaaagct gaccgtgctg ggcgagtcta atacggacc gccttgtcct    780 ccttgtcccg gccagccaag agagcccag gtttacacac tgcctccaag ccaagaggaa    840
atgaccaaga atcaggtgtc cctgacatgc ctggtcaagg gcttctaccc ctccgatatc    900
gccgtggaat gggagagcaa tggccagcct gagaacaact acaagaccac acctcctgtg    960
ctggacagcg acggcagttt cttcctgtat agtagactca ccgtggataa atcaagatgg   1020
caagagggca acgtgttcag ctgcagcgtg atgcacgagg ccctgcacaa ccactacacc   1080
cagaaaagcc tgagcctgtc tctgggcaag atgttctggg tgctcgtggt cgttggcgga   1140
gtgctggcct gttacagcct gctggttacc gtggccttca tcatctttttg ggtcaagcgg   1200 ggcagaaaga agctgctcta catcttcaag cagcccttca tgcggcccgt gcagaccaca   1260
caagaggaag atggctgctc ctgcagattc cccgaggaag aagaaggcgg ctgcgagctg   1320
agagtgaagt tcagcagatc cgccgacgct ccagcctatc agcagggcca aaaccagctg   1380
tacaacgagc tgaacctggg gagaagagaa gagtacgacg tgctggataa gcggagaggc   1440
agagatcctg aaatgggcgg caagcccaga cggaagaatc ctcaagaggg cctgtataat   1500
```

```
gagctgcaga aagacaagat ggccgaggcc tacagcgaga tcggaatgaa gggcgagcgc    1560
agaagaggca agggacacga tggactgtac cagggcctga gcaccgccac caaggatacc    1620
tatgacgcac tgcacatgca ggccctgcca cctaga                              1656
```

<210> SEQ ID NO 162
<211> LENGTH: 21
<212> TYPE: PRT
<213> ORGANISM: artificial sequence
<220> FEATURE:
<223> OTHER INFORMATION: linker

<400> SEQUENCE: 162

```
Ser Arg Gly Gly Gly Gly Ser Gly Gly Gly Gly Ser Gly Gly Gly Gly
1               5                   10                  15

Ser Leu Glu Met Ala
            20
```

<210> SEQ ID NO 163
<211> LENGTH: 22
<212> TYPE: PRT
<213> ORGANISM: artificial sequence
<220> FEATURE:
<223> OTHER INFORMATION: linker

<400> SEQUENCE: 163

```
Gly Ser Arg Gly Gly Gly Gly Ser Gly Gly Gly Gly Ser Gly Gly Gly
1               5                   10                  15

Gly Ser Leu Glu Met Ala
            20
```

<210> SEQ ID NO 164
<211> LENGTH: 544
<212> TYPE: DNA
<213> ORGANISM: artificial sequence
<220> FEATURE:
<223> OTHER INFORMATION: EF1alpha promoter with HTLV1 ehancer

<400> SEQUENCE: 164

```
ggatctgcga tcgctccggt gcccgtcagt gggcagagcg cacatcgccc acagtccccg     60
agaagttggg gggaggggtc ggcaattgaa ccggtgccta gagaaggtgg cgcggggtaa    120
actgggaaag tgatgtcgtg tactggctcc gcctttttcc cgagggtggg ggagaaccgt    180
atataagtgc agtagtcgcc gtgaacgttc tttttcgcaa cgggtttgcc gccagaacac    240
agctgaagct cgaggggct cgcatctctc cttcacgcgc ccgccgccct acctgaggcc    300
gccatccacg ccggttgagt cgcgttctgc cgcctcccgc ctgtggtgcc tcctgaactg    360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctac                                                                544
```

<210> SEQ ID NO 165
<211> LENGTH: 588
<212> TYPE: DNA
<213> ORGANISM: artificial sequence
<220> FEATURE:
<223> OTHER INFORMATION: Woodchuck Hepatitis Virus (WHP)
        Posttranscriptional Regulatory Element (WPRE)

-continued

```
<400> SEQUENCE: 165
atcaacctct ggattacaaa atttgtgaaa gattgactgg tattcttaac tatgttgctc    60
cttttacgct atgtggatac gctgctttaa tgcctttgta tcatgctatt gcttcccgta   120
tggctttcat tttctcctcc ttgtataaat cctggttgct gtctctttat gaggagttgt   180
ggcccgttgt caggcaacgt ggcgtggtgt gcactgtgtt tgctgacgca accccactg   240 gttgggcat tgccaccacc tgtcagctcc tttccgggac tttcgctttc ccctcccta   300 ttgccacggc ggaactcatc gccgcctgcc ttgcccgctg ctggacaggg gctcggctgt   360
tgggcactga caattccgtg gtgttgtcgg ggaaatcatc gtcctttcct ggctgctcg    420 cctgtgttgc cacctggatt ctgcgcggga cgtccttctg ctacgtccct tcggccctca   480
atccagcgga ccttccttcc cgcggcctgc tgccggctct gcggcctctt ccgcgtcttc   540
gccttcgccc tcagacgagt cggatctccc tttgggccgc ctcccccgc                588

<210> SEQ ID NO 166
<211> LENGTH: 21
<212> TYPE: PRT
<213> ORGANISM: artificial sequence
<220> FEATURE:
<223> OTHER INFORMATION: T2A peptide

<400> SEQUENCE: 166

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 167
<211> LENGTH: 23
<212> TYPE: PRT
<213> ORGANISM: artificial sequence
<220> FEATURE:
<223> OTHER INFORMATION: E2A peptide

<400> SEQUENCE: 167

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 168
<211> LENGTH: 25
<212> TYPE: PRT
<213> ORGANISM: artificial sequence
<220> FEATURE:
<223> OTHER INFORMATION: F2A peptide

<400> SEQUENCE: 168

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 169
<211> LENGTH: 72
<212> TYPE: DNA
<213> ORGANISM: artificial sequence
<220> FEATURE:
<223> OTHER INFORMATION: T2A peptide
```

-continued

<400> SEQUENCE: 169

```
ctcgagggcg gcggagaggg cagaggaagt cttctaacat gcggtgacgt ggaggagaat    60
cccggcccta gg                                                        72
```

<210> SEQ ID NO 170
<211> LENGTH: 3358
<212> TYPE: DNA
<213> ORGANISM: homo sapiens
<220> FEATURE:
<221> NAME/KEY: misc_feature
<223> OTHER INFORMATION: human ROR1 GenBank: M97675.1

<400> SEQUENCE: 170

```
gagctggagc agccgccacc gccgccgccg agggagcccc gggacggcag cccctgggcg     60
cagggtgcgc tgttctcgga gtccgaccca gggcgactca cgcccactgg tgcgacccgg    120
acagcctggg actgacccgc cggcccaggc gaggctgcag ccagagggct gggaagggat    180
cgcgctcgcg gcatccagag gcggccaggc ggaggcgagg gagcaggtta gagggacaaa    240
gagctttgca gacgtccccg gcgtcctgcg agcgccagcg gccgggacga ggcggccggg    300
agcccgggaa gagcccgtgg atgttctgcg cgcggcctgg gagccgccgc cgccgccgcc    360
tcagcgagag gaggaatgca ccggccgcgc cgccgcggga cgcgcccgcc gctcctggcg    420
ctgctggccg cgctgctgct ggccgcacgc ggggctgctg cccaagaaac agagctgtca    480
gtcagtgctg aattagtgcc tacctcatca tggaacatct caagtgaact caacaaagat    540
tcttacctga cccttgatga accaatgaat aacatcacca cgtctctggg ccagacagca    600
gaactgcact gcaaagtctc tgggaatcca cctcccacca tccgctggtt caaaaatgat    660
gctcctgtgg tccaggagcc ccggaggctc tcctttcggt ccaccatcta tggctctcgg    720
ctgcggatta gaaacctcga caccacagac acaggctact ccagtgcgt ggcaacaaac    780 ggcaaggagg tggtttcttc cactggagtc ttgtttgtca gtttggccc cctcccact     840 gcaagtccag atactcaga tgagtatgaa aagatggat tctgtcagcc atacagaggg    900
attgcatgtg caagatttat tggcaaccgc accgtctata tggagtcttt gcacatgcaa    960
ggggaaatag aaaatcagat cacagctgcc ttcactatga ttggcacttc cagtcactta   1020
tctgataagt gttctcagtt cgccattcct tccctgtgcc actatgcctt cccgtactgc   1080
gatgaaactt catccgtccc aaagcccgt gacttgtgtc gcgatgaatg tgaaatcctg   1140
gagaatgtcc tgtgtcaaac agagtacatt tttgcaagat caaatcccat gattctgatg   1200
aggctgaaac tgccaaactg tgaagatctc cccagccag agagcccaga agctgcgaac   1260
tgtatccgga ttggaattcc catggcagat cctataaata aaaatcacaa gtgttataac   1320
agcacaggtg tggactaccg ggggaccgtc agtgtgacca atcagggcg ccagtgccag   1380 ccatggaatt cccagtatcc ccacacacac actttcaccg ccccttcgtt cccagagctg   1440
aatggaggcc attcctactg ccgcaaccca gggaatcaaa aggaagctcc ctggtgcttc   1500
accttggatg aaaactttaa gtctgatctg tgtgacatcc cagcttgcga ttcaaaggat   1560
tccaaggaga agaataaaat ggaaatcctg tacatactag tgccaagtgt ggccattccc   1620
ctggccattg ctttactctt cttcttcatt tgcgtctgtc ggaataacca gaagtcatcg   1680
tcggcaccag tccagaggca accaaaaacac gtcagaggtc aaaatgtgga gatgtcaatg   1740
ctgaatgcat ataaacccaa gagcaaggct aagagctac ctctttctgc tgtacgcttt   1800
atggaagaat tgggtgagtg tgcctttgga aaaatctata aaggccatct ctatctccca   1860
```

```
ggcatggacc atgctcagct ggttgctatc aagaccttga aagactataa caaccccag      1920
caatggatgg aatttcaaca agaagcctcc ctaatggcag aactgcacca ccccaatatt      1980
gtctgccttc taggtgccgt cactcaggaa caacctgtgt gcatgctttt tgagtatatt      2040
aatcagggg atctccatga gttcctcatc atgagatccc cacactctga tgttggctgc       2100
agcagtgatg aagatgggac tgtgaaatcc agcctggacc acggagattt tctgcacatt      2160
gcaattcaga ttgcagctgg catggaatac ctgtctagtc acttctttgt ccacaaggac      2220
cttgcagctc gcaatatttt aatcggagag caacttcatg taaagatttc agacttgggg     2280
cttteecagag aaatttactc cgctgattac tacagggtcc agagtaagtc cttgctgccc     2340
attcgctgga tgcccctga agccatcatg tatggcaaat tctcttctga ttcagatatc      2400
tggtcctttg gggttgtctt gtgggagatt ttcagttttg actccagcc atattatgga      2460
ttcagtaacc aggaagtgat tgagatggtg agaaaacggc agctcttacc atgctctgaa     2520
gactgcccac ccagaatgta cagcctcatg acagagtgct ggaatgagat tccttctagg     2580
agaccaagat ttaaagatat tcacgtccgg cttcggtcct gggagggact ctcaagtcac     2640
acaagctcta ctactccttc aggggggaaat gccaccacac agacaacctc cctcagtgcc    2700
agcccagtga gtaatctcag taaccccaga tatcctaatt acatgttccc gagccagggt     2760
attacaccac agggccagat tgctggtttc attggcccgc caatacctca gaaccagcga     2820
ttcattccca tcaatggata cccaatacct cctggatatg cagcgtttcc agctgcccac     2880
taccagccaa caggtcctcc cagagtgatt cagcactgcc cacctcccaa gagtcggtcc     2940
ccaagcagtg ccagtgggtc gactagcact ggccatgtga ctagcttgcc ctcatcagga    3000
tccaatcagg aagcaaatat tcctttacta ccacacatgt caattccaaa tcatcctggt    3060
ggaatgggta tcaccgtttt tggcaacaaa tctcaaaaac cctacaaaat tgactcaaag   3120
caagcatctt tactaggaga cgccaatatt catggacaca ccgaatctat gatttctgca   3180
gaactgtaaa atgcacaact tttgtaaatg tggtatacag acaaactag acggccgtag    3240
aaaagattta tattcaaatg ttttattaa agtaaggttc tcatttagca gacatcgcaa    3300
caagtacctt ctgtgaagtt tcactgtgtc ttaccaagca ggacagacac tcggccag     3358
```

<210> SEQ ID NO 171
<211> LENGTH: 908
<212> TYPE: PRT
<213> ORGANISM: mus musculus
<220> FEATURE:
<221> NAME/KEY: MISC_FEATURE
<223> OTHER INFORMATION: Mouse ROR1; GenBank No. NP_038873

<400> SEQUENCE: 171

Gln Glu Thr Glu Leu Ser Val Ser Ala Glu Leu Val Pro Thr Ser Ser
1               5                   10                  15

Trp Asn Thr Ser Ser Glu Ile Asp Lys Gly Ser Tyr Leu Thr Leu Asp
            20                  25                  30

Glu Pro Met Asn Asn Ile Thr Thr Ser Leu Gly Gln Thr Ala Glu Leu
        35                  40                  45

His Cys Lys Val Ser Gly Asn Pro Pro Ser Ile Arg Trp Phe Lys
    50                  55                  60

Asn Asp Ala Pro Val Val Gln Glu Pro Arg Arg Ile Ser Phe Arg Ala
65                  70                  75                  80

Thr Asn Tyr Gly Ser Arg Leu Arg Ile Arg Asn Leu Asp Thr Thr Asp
                85                  90                  95

```
Thr Gly Tyr Phe Gln Cys Val Ala Thr Asn Gly Lys Lys Val Val Ser
            100                 105                 110

Thr Thr Gly Val Leu Phe Val Lys Phe Gly Pro Pro Thr Ala Ser
        115                 120                 125

Pro Gly Ser Ser Asp Glu Tyr Glu Glu Asp Gly Phe Cys Gln Pro Tyr
    130                 135                 140

Arg Gly Ile Ala Cys Ala Arg Phe Ile Gly Asn Arg Thr Val Tyr Met
145                 150                 155                 160

Glu Ser Leu His Met Gln Gly Glu Ile Glu Asn Gln Ile Thr Ala Ala
                165                 170                 175

Phe Thr Met Ile Gly Thr Ser His Leu Ser Asp Lys Cys Ser Gln
            180                 185                 190

Phe Ala Ile Pro Ser Leu Cys His Tyr Ala Phe Pro Tyr Cys Asp Glu
    195                 200                 205

Thr Ser Ser Val Pro Lys Pro Arg Asp Leu Cys Arg Asp Glu Cys Glu
    210                 215                 220

Val Leu Glu Asn Val Leu Cys Gln Thr Glu Tyr Ile Phe Ala Arg Ser
225                 230                 235                 240

Asn Pro Met Ile Leu Met Arg Leu Lys Leu Pro Asn Cys Glu Asp Leu
            245                 250                 255

Pro Gln Pro Glu Ser Pro Glu Ala Ala Asn Cys Ile Arg Ile Gly Ile
    260                 265                 270

Pro Met Ala Asp Pro Ile Asn Lys Asn His Lys Cys Tyr Asn Ser Thr
    275                 280                 285

Gly Val Asp Tyr Arg Gly Thr Val Ser Val Thr Lys Ser Gly Arg Gln
    290                 295                 300

Cys Gln Pro Trp Asn Ser Gln Tyr Pro His Thr His Ser Phe Thr Ala
305                 310                 315                 320

Leu Arg Phe Pro Glu Leu Asn Gly Gly His Ser Tyr Cys Arg Asn Pro
            325                 330                 335

Gly Asn Gln Lys Glu Ala Pro Trp Cys Phe Thr Leu Asp Glu Asn Phe
            340                 345                 350

Lys Ser Asp Leu Cys Asp Ile Pro Ala Cys Asp Ser Lys Asp Ser Lys
            355                 360                 365

Glu Lys Asn Lys Met Glu Ile Leu Tyr Ile Leu Val Pro Ser Val Ala
    370                 375                 380

Ile Pro Leu Ala Ile Ala Phe Leu Phe Phe Ile Cys Val Cys Arg
385                 390                 395                 400

Asn Asn Gln Lys Ser Ser Ser Pro Pro Val Gln Arg Gln Pro Lys Pro
            405                 410                 415

Val Arg Gly Gln Asn Val Glu Met Ser Met Leu Asn Ala Tyr Lys Pro
            420                 425                 430

Lys Ser Lys Ala Lys Glu Leu Pro Leu Ser Ala Val Arg Phe Met Glu
            435                 440                 445

Glu Leu Gly Glu Cys Thr Phe Gly Lys Ile Tyr Lys Gly His Leu Tyr
    450                 455                 460

Leu Pro Gly Met Asp His Ala Gln Leu Val Ala Ile Lys Thr Leu Lys
465                 470                 475                 480

Asp Tyr Asn Asn Pro Gln Gln Trp Thr Glu Phe Gln Gln Glu Ala Ser
            485                 490                 495

Leu Met Ala Glu Leu His His Pro Asn Ile Val Cys Leu Leu Gly Ala
            500                 505                 510
```

Val Thr Gln Glu Gln Pro Val Cys Met Leu Phe Glu Tyr Met Asn Gln
            515                 520                 525

Gly Asp Leu His Glu Phe Leu Ile Met Arg Ser Pro His Ser Asp Val
        530                 535                 540

Gly Cys Ser Ser Asp Glu Asp Gly Thr Val Lys Ser Ser Leu Asp His
545                 550                 555                 560

Gly Asp Phe Leu His Ile Ala Ile Gln Ile Ala Ala Gly Met Glu Tyr
                565                 570                 575

Leu Ser Ser His Phe Phe Val His Lys Asp Leu Ala Ala Arg Asn Ile
            580                 585                 590

Leu Ile Gly Glu Gln Leu His Val Lys Ile Ser Asp Leu Gly Leu Ser
        595                 600                 605

Arg Glu Ile Tyr Ser Ala Asp Tyr Tyr Arg Val Gln Ser Lys Ser Ser
    610                 615                 620

Leu Pro Ile Arg Trp Met Pro Pro Glu Ala Ile Met Tyr Gly Lys Phe
625                 630                 635                 640

Ser Ser Asp Ser Asp Ile Trp Ser Phe Gly Val Val Leu Trp Glu Ile
                645                 650                 655

Phe Ser Phe Gly Leu Gln Pro Tyr Tyr Gly Phe Ser Asn Gln Glu Val
            660                 665                 670

Ile Glu Met Val Arg Lys Arg Gln Leu Leu Pro Cys Ser Glu Asp Cys
        675                 680                 685

Pro Pro Arg Met Tyr Ser Leu Met Thr Glu Cys Trp Asn Glu Ile Pro
    690                 695                 700

Ser Arg Arg Pro Arg Phe Lys Asp Ile His Val Arg Leu Arg Ser Trp
705                 710                 715                 720

Glu Gly Leu Ser Ser His Thr Ser Ser Thr Thr Pro Ser Gly Gly Asn
                725                 730                 735

Ala Thr Thr Gln Thr Thr Ser Leu Ser Ala Ser Pro Val Ser Asn Leu
            740                 745                 750

Ser Asn Pro Arg Phe Pro Asn Tyr Met Phe Pro Ser Gln Gly Ile Thr
        755                 760                 765

Pro Gln Gly Gln Ile Ala Gly Phe Ile Gly Pro Ala Ile Pro Gln Asn
    770                 775                 780

Gln Arg Phe Ile Pro Ile Asn Gly Tyr Pro Ile Pro Pro Gly Tyr Ala
785                 790                 795                 800

Ala Phe Pro Ala Ala His Tyr Gln Pro Ala Gly Pro Pro Arg Val Ile
                805                 810                 815

Gln His Cys Pro Pro Lys Ser Arg Ser Pro Ser Ser Ala Ser Gly
            820                 825                 830

Ser Thr Ser Thr Gly His Val Ala Ser Leu Pro Ser Ser Gly Ser Asn
        835                 840                 845

Gln Glu Ala Asn Val Pro Leu Leu Pro His Met Ser Ile Pro Asn His
    850                 855                 860

Pro Gly Gly Met Gly Ile Thr Val Phe Gly Asn Lys Ser Gln Lys Pro
865                 870                 875                 880

Tyr Lys Ile Asp Ser Lys Gln Ser Ser Leu Leu Gly Asp Ser His Ile
                885                 890                 895

His Gly His Thr Glu Ser Met Ile Ser Ala Glu Val
            900                 905

<210> SEQ ID NO 172
<211> LENGTH: 118

```
<212> TYPE: PRT
<213> ORGANISM: artificial sequence
<220> FEATURE:
<223> OTHER INFORMATION: 2A2 VH

<400> SEQUENCE: 172

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Ser Asp Tyr
            20                  25                  30

Glu Met His Trp Val Ile Gln Thr Pro Val His Gly Leu Glu Trp Ile
        35                  40                  45

Gly Ala Ile Asp Pro Glu Thr Gly Gly Thr Ala Tyr Asn Gln Lys Phe
    50                  55                  60

Lys Gly Lys Ala Ile Leu Thr Ala Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Gly Tyr Tyr Asp Tyr Asp Ser Phe Thr Tyr Trp Gly Gln Gly Thr
            100                 105                 110

Leu Val Thr Val Ser Ala
        115

<210> SEQ ID NO 173
<211> LENGTH: 107
<212> TYPE: PRT
<213> ORGANISM: artificial sequence
<220> FEATURE:
<223> OTHER INFORMATION: 2A2 VL

<400> SEQUENCE: 173

Asp Ile Val Met Thr Gln Ser Gln Lys Ile Met Ser Thr Thr Val Gly
1               5                   10                  15

Asp Arg Val Ser Ile Thr Cys Lys Ala Ser Gln Asn Val Asp Ala Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Leu Thr Ile Ser Asn Met Gln Ser
65                  70                  75                  80

Glu Asp Leu Ala Asp Tyr Phe Cys Gln Gln Tyr Asp Ile Tyr Pro Tyr
                85                  90                  95

Thr Phe Gly Gly Gly Thr Lys Leu Glu Ile Lys
            100                 105

<210> SEQ ID NO 174
<211> LENGTH: 116
<212> TYPE: PRT
<213> ORGANISM: artificial sequence
<220> FEATURE:
<223> OTHER INFORMATION: 99961 humanized VH

<400> SEQUENCE: 174

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ala Phe Thr Ala Tyr
            20                  25                  30
```

```
Asn Ile His Trp Val Arg Gln Ala Pro Gly Gln Gly Leu Glu Trp Met
            35                  40                  45

Gly Ser Phe Asp Pro Tyr Asp Gly Gly Ser Ser Tyr Asn Gln Lys Phe
        50                  55                  60

Lys Asp Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Gly Trp Tyr Tyr Phe Asp Tyr Trp Gly His Gly Thr Leu Val
            100                 105                 110

Thr Val Ser Ser
        115

<210> SEQ ID NO 175
<211> LENGTH: 116
<212> TYPE: PRT
<213> ORGANISM: artificial sequence
<220> FEATURE:
<223> OTHER INFORMATION: 99961 humanized VH

<400> SEQUENCE: 175

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ala Phe Thr Ala Tyr
            20                  25                  30

Asn Ile His Trp Val Arg Gln Ala Pro Gly Gln Gly Leu Glu Trp Met
            35                  40                  45

Gly Ser Phe Asp Pro Tyr Asp Gly Gly Ser Ser Tyr Asn Gln Lys Phe
        50                  55                  60

Lys Asp Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Gly Trp Tyr Tyr Phe Asp Tyr Trp Gly His Gly Thr Leu Val
            100                 105                 110

Thr Val Ser Ser
        115

<210> SEQ ID NO 176
<211> LENGTH: 116
<212> TYPE: PRT
<213> ORGANISM: artificial sequence
<220> FEATURE:
<223> OTHER INFORMATION: 99961 humanized VH

<400> SEQUENCE: 176

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ala Phe Thr Ala Tyr
            20                  25                  30

Asn Ile His Trp Ile Arg Gln Pro Pro Gly Lys Gly Leu Glu Trp Ile
            35                  40                  45

Gly Ser Phe Asp Pro Tyr Asp Gly Gly Ser Ser Tyr Asn Gln Lys Phe
        50                  55                  60

Lys Asp Arg Leu Thr Ile Ser Lys Asp Thr Ser Lys Asn Gln Val Val
65                  70                  75                  80
```

```
Leu Thr Met Thr Asn Met Asp Pro Val Asp Thr Ala Thr Tyr Tyr Cys
                85                  90                  95

Ala Arg Gly Trp Tyr Tyr Phe Asp Tyr Trp Gly His Gly Thr Leu Val
            100                 105                 110

Thr Val Ser Ser
        115

<210> SEQ ID NO 177
<211> LENGTH: 116
<212> TYPE: PRT
<213> ORGANISM: artificial sequence
<220> FEATURE:
<223> OTHER INFORMATION: 99961 humanized VH

<400> SEQUENCE: 177

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ala Phe Thr Ala Tyr
            20                  25                  30

Asn Ile His Trp Ile Arg Gln Pro Pro Gly Lys Gly Leu Glu Trp Ile
            35                  40                  45

Gly Ser Phe Asp Pro Tyr Asp Gly Ser Ser Tyr Asn Gln Lys Phe
    50                  55                  60

Lys Asp Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Gly Trp Tyr Tyr Phe Asp Tyr Trp Gly His Gly Thr Leu Val
            100                 105                 110

Thr Val Ser Ser
        115

<210> SEQ ID NO 178
<211> LENGTH: 107
<212> TYPE: PRT
<213> ORGANISM: artificial sequence
<220> FEATURE:
<223> OTHER INFORMATION: 99961 humanized VL

<400> SEQUENCE: 178

Asp Ile Val Met Thr Gln Thr Pro Leu Ser Leu Pro Val Thr Pro Gly
1               5                   10                  15

Glu Pro Ala Ser Ile Ser Cys Arg Ala Ser Lys Ser Ile Ser Lys Tyr
            20                  25                  30

Leu Ala Trp Tyr Gln Gln Lys Pro Gly Gln Ala Pro Arg Leu Leu Ile
            35                  40                  45

Tyr Ser Gly Ser Thr Leu Gln Ser Gly Ile Pro Pro Arg Phe Ser Gly
        50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Gln Gln His Asp Glu Ser Pro Tyr
                85                  90                  95

Thr Phe Gly Glu Gly Thr Lys Val Glu Ile Lys
            100                 105

<210> SEQ ID NO 179
<211> LENGTH: 107
<212> TYPE: PRT
```

-continued

```
<213> ORGANISM: artificial sequence
<220> FEATURE:
<223> OTHER INFORMATION: 99961 humanized VL

<400> SEQUENCE: 179

Asp Val Val Met Thr Gln Ser Pro Leu Ser Leu Pro Val Thr Leu Gly
1               5                   10                  15

Gln Pro Ala Ser Ile Ser Cys Arg Ala Ser Lys Ser Ile Ser Lys Tyr
            20                  25                  30

Leu Ala Trp Tyr Gln Gln Lys Pro Gly Lys Ala Pro Lys Leu Leu Ile
        35                  40                  45

Tyr Ser Gly Ser Thr Leu Gln Ser Gly Ile Pro Pro Arg Phe Ser Gly
50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Gln Gln His Asp Glu Ser Pro Tyr
                85                  90                  95

Thr Phe Gly Glu Gly Thr Lys Val Glu Ile Lys
            100                 105

<210> SEQ ID NO 180
<211> LENGTH: 107
<212> TYPE: PRT
<213> ORGANISM: artificial sequence
<220> FEATURE:
<223> OTHER INFORMATION: 99961 humanized VL

<400> SEQUENCE: 180

Asp Ile Val Met Thr Gln Thr Pro Leu Ser Leu Pro Val Thr Pro Gly
1               5                   10                  15

Glu Pro Ala Ser Ile Ser Cys Arg Ala Ser Lys Ser Ile Ser Lys Tyr
            20                  25                  30

Leu Ala Trp Tyr Gln Gln Lys Pro Gly Gln Ala Pro Arg Leu Leu Ile
        35                  40                  45

Tyr Ser Gly Ser Thr Leu Gln Ser Gly Ile Pro Pro Arg Phe Ser Gly
50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Gln Gln His Asp Glu Ser Pro Tyr
                85                  90                  95

Thr Phe Gly Glu Gly Thr Lys Val Glu Ile Lys
            100                 105

<210> SEQ ID NO 181
<211> LENGTH: 107
<212> TYPE: PRT
<213> ORGANISM: artificial sequence
<220> FEATURE:
<223> OTHER INFORMATION: 99961 humanized VL

<400> SEQUENCE: 181

Asp Val Val Met Thr Gln Ser Pro Leu Ser Leu Pro Val Thr Leu Gly
1               5                   10                  15

Gln Pro Ala Ser Ile Ser Cys Arg Ala Ser Lys Ser Ile Ser Lys Tyr
            20                  25                  30

Leu Ala Trp Tyr Gln Gln Lys Pro Gly Lys Ala Pro Lys Leu Leu Ile
        35                  40                  45

Tyr Ser Gly Ser Thr Leu Gln Ser Gly Ile Pro Pro Arg Phe Ser Gly
50                  55                  60
```

Ser Gly Tyr Gly Thr Asp Phe Thr Leu Thr Ile Asn Asn Ile Glu Ser
65                  70                  75                  80

Glu Asp Ala Ala Tyr Tyr Phe Cys Gln Gln His Asp Glu Ser Pro Tyr
                85                  90                  95

Thr Phe Gly Glu Gly Thr Lys Val Glu Ile Lys
            100                 105

<210> SEQ ID NO 182
<211> LENGTH: 336
<212> TYPE: DNA
<213> ORGANISM: artificial sequence
<220> FEATURE:
<223> OTHER INFORMATION: CD3-zeta derived intracellular signaling domain

<400> SEQUENCE: 182
agagtcaagt tttccaggtc cgccgacgct ccagcctacc agcagggca gaaccagctg      60 tacaacgagc tgaacctggg cagaagggaa gagtacgacg tcctggataa gcggagaggc     120
cgggaccctg agatgggcgg caagcctcgg cggaagaacc cccaggaagg cctgtataac     180
gaactgcaga agacaagat ggccgaggcc tacagcgaga tcggcatgaa gggcgagcgg     240
aggcggggca aggccacga cggcctgtat cagggcctgt ccaccgccac caaggatacc     300
tacgacgccc tgcacatgca ggccctgccc ccaagg                              336

<210> SEQ ID NO 183
<211> LENGTH: 123
<212> TYPE: DNA
<213> ORGANISM: artificial sequence
<220> FEATURE:
<223> OTHER INFORMATION: CD28 endodomain

<400> SEQUENCE: 183
aggagtaaga ggagcaggct cctgcacagt gactacatga acatgactcc ccgccgcccc      60
gggcccaccc gcaagcatta ccagccctat gccccaccac gcgacttcgc agcctatcgc     120
tcc                                                                  123

<210> SEQ ID NO 184
<211> LENGTH: 436
<212> TYPE: PRT
<213> ORGANISM: artificial sequence
<220> FEATURE:
<223> OTHER INFORMATION: anti-ROR1 CAR

<400> SEQUENCE: 184

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Asn Tyr
                20                  25                  30

Tyr Trp Ser Trp Ile Arg Gln Pro Ala Gly Lys Gly Leu Glu Trp Ile
            35                  40                  45

Gly Arg Ile Tyr Thr Ser Gly Ser Thr Asn Tyr Asn Pro Ser Leu Lys
        50                  55                  60

Ser Arg Val Thr Met Ser Val Asp Thr Ser Lys Asn Gln Phe Ser Leu
65                  70                  75                  80

Lys Leu Ser Ser Leu Thr Ala Ala Asp Thr Ala Ile Tyr Tyr Cys Ala
                85                  90                  95

Arg Tyr Tyr Asp Ile Leu Thr Gly Phe Phe Asp Tyr Trp Gly Gln Gly
            100                 105                 110

Thr Leu Val Thr Val Ser Ser Gly Gly Gly Ser Gly Gly Gly
            115                 120                 125

Ser Gly Gly Gly Gly Ser Val Ile Trp Met Thr Gln Ser Pro Ser Leu
130                 135                 140

Leu Ser Ala Ser Thr Gly Asp Ser Val Thr Ile Ser Cys Arg Met Ser
145                 150                 155                 160

Gln Asp Ile Ser Ser Tyr Leu Ala Trp Tyr Gln Gln Lys Pro Gly Lys
                165                 170                 175

Ala Pro Glu Leu Leu Ile Tyr Ala Ala Ser Ser Leu Gln Ser Gly Val
            180                 185                 190

Pro Ser Arg Phe Ser Gly Ser Gly Ser Gly Thr Asp Phe Thr Leu Thr
        195                 200                 205

Ile Ser Ser Leu Gln Ser Glu Asp Phe Ala Thr Tyr Tyr Cys Gln Gln
210                 215                 220

Tyr Asp Ser Phe Pro Pro Thr Phe Gly Gln Gly Thr Lys Val Glu Phe
225                 230                 235                 240

Lys Arg Glu Ser Lys Tyr Gly Pro Pro Cys Pro Pro Cys Pro Met Phe
                245                 250                 255

Trp Val Leu Val Val Val Gly Gly Val Leu Ala Cys Tyr Ser Leu Leu
            260                 265                 270

Val Thr Val Ala Phe Ile Ile Phe Trp Val Lys Arg Gly Arg Lys Lys
        275                 280                 285

Leu Leu Tyr Ile Phe Lys Gln Pro Phe Met Arg Pro Val Gln Thr Thr
290                 295                 300

Gln Glu Glu Asp Gly Cys Ser Cys Arg Phe Pro Glu Glu Glu Glu Gly
305                 310                 315                 320

Gly Cys Glu Leu Arg Val Lys Phe Ser Arg Ser Ala Asp Ala Pro Ala
                325                 330                 335

Tyr Gln Gln Gly Gln Asn Gln Leu Tyr Asn Glu Leu Asn Leu Gly Arg
            340                 345                 350

Arg Glu Glu Tyr Asp Val Leu Asp Lys Arg Arg Gly Arg Asp Pro Glu
        355                 360                 365

Met Gly Gly Lys Pro Arg Arg Lys Asn Pro Gln Glu Gly Leu Tyr Asn
370                 375                 380

Glu Leu Gln Lys Asp Lys Met Ala Glu Ala Tyr Ser Glu Ile Gly Met
385                 390                 395                 400

Lys Gly Glu Arg Arg Arg Gly Lys Gly His Asp Gly Leu Tyr Gln Gly
                405                 410                 415

Leu Ser Thr Ala Thr Lys Asp Thr Tyr Asp Ala Leu His Met Gln Ala
            420                 425                 430

Leu Pro Pro Arg
        435

<210> SEQ ID NO 185
<211> LENGTH: 438
<212> TYPE: PRT
<213> ORGANISM: artificial sequence
<220> FEATURE:
<223> OTHER INFORMATION: anti-ROR1 CAR

<400> SEQUENCE: 185

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Asn Ser Thr
            20                  25                  30

-continued

Thr Ser Tyr Trp Ala Trp Ile Arg Gln Pro Pro Gly Lys Gly Leu Glu
        35                  40                  45

Trp Ile Gly Thr Ile Phe Tyr Ser Gly Lys Thr Tyr Asn Asn Pro Ser
 50                  55                  60

Leu Lys Ser Arg Val Thr Met Ser Val Asp Thr Ser Lys Asn His Phe
 65                  70                  75                  80

Ser Leu Lys Val Asn Ser Val Thr Ala Ala Asp Thr Ala Val Tyr Tyr
                85                  90                  95

Cys Ala Arg Phe Asp Tyr Gly Phe His Asp Ala Phe Asp Ile Trp Gly
            100                 105                 110

Gln Gly Thr Met Val Thr Val Ser Ser Gly Gly Gly Ser Gly Gly
        115                 120                 125

Gly Gly Ser Gly Gly Gly Ser Glu Ile Val Met Thr Gln Ser Pro
    130                 135                 140

Ala Thr Leu Ser Leu Ser Pro Gly Glu Arg Ala Thr Leu Ser Cys Arg
145                 150                 155                 160

Ala Ser Gln Ser Ile Thr Ser Asp Tyr Leu Ser Trp Tyr Gln Gln Lys
                165                 170                 175

Pro Gly Gln Ala Pro Arg Leu Leu Ile Tyr Gly Ala Ser Thr Arg Ala
            180                 185                 190

Thr Gly Ile Pro Ala Arg Phe Ser Gly Ser Gly Ser Gly Thr Asp Phe
        195                 200                 205

Thr Leu Thr Ile Ser Ser Leu Gln Pro Glu Asp Phe Val Val Tyr Tyr
    210                 215                 220

Cys Gln Gln Asp Tyr Asn Leu Tyr Thr Phe Gly Gln Gly Thr Lys Leu
225                 230                 235                 240

Glu Ile Lys Arg Glu Ser Lys Tyr Gly Pro Pro Cys Pro Pro Cys Pro
                245                 250                 255

Met Phe Trp Val Leu Val Val Val Gly Gly Val Leu Ala Cys Tyr Ser
            260                 265                 270

Leu Leu Val Thr Val Ala Phe Ile Ile Phe Trp Val Lys Arg Gly Arg
        275                 280                 285

Lys Lys Leu Leu Tyr Ile Phe Lys Gln Pro Phe Met Arg Pro Val Gln
    290                 295                 300

Thr Thr Gln Glu Glu Asp Gly Cys Ser Cys Arg Phe Pro Glu Glu Glu
305                 310                 315                 320

Glu Gly Gly Cys Glu Leu Arg Val Lys Phe Ser Arg Ser Ala Asp Ala
                325                 330                 335

Pro Ala Tyr Gln Gln Gly Gln Asn Gln Leu Tyr Asn Glu Leu Asn Leu
            340                 345                 350

Gly Arg Arg Glu Glu Tyr Asp Val Leu Asp Lys Arg Gly Arg Asp
        355                 360                 365

Pro Glu Met Gly Gly Lys Pro Arg Arg Lys Asn Pro Gln Glu Gly Leu
    370                 375                 380

Tyr Asn Glu Leu Gln Lys Asp Lys Met Ala Glu Ala Tyr Ser Glu Ile
385                 390                 395                 400

Gly Met Lys Gly Glu Arg Arg Arg Gly Lys Gly His Asp Gly Leu Tyr
                405                 410                 415

Gln Gly Leu Ser Thr Ala Thr Lys Asp Thr Tyr Asp Ala Leu His Met
            420                 425                 430

Gln Ala Leu Pro Pro Arg
        435

```
<210> SEQ ID NO 186
<211> LENGTH: 543
<212> TYPE: PRT
<213> ORGANISM: artificial sequence
<220> FEATURE:
<223> OTHER INFORMATION: anti-ROR1 CAR

<400> SEQUENCE: 186
```

| | | | | | | | | | | | | | | | |
|---|---|---|---|---|---|---|---|---|---|---|---|---|---|---|---|
| Gln | Val | Gln | Leu | Gln | Glu | Ser | Gly | Pro | Gly | Leu | Val | Lys | Pro | Ser | Glu |
| 1 | | | | 5 | | | | | 10 | | | | | 15 | |
| Thr | Leu | Ser | Leu | Thr | Cys | Thr | Val | Ser | Gly | Gly | Ser | Ile | Ser | Asn | Tyr |
| | | | 20 | | | | | 25 | | | | | 30 | | |
| Tyr | Trp | Ser | Trp | Ile | Arg | Gln | Pro | Ala | Gly | Lys | Gly | Leu | Glu | Trp | Ile |
| | | 35 | | | | | 40 | | | | | 45 | | | |
| Gly | Arg | Ile | Tyr | Thr | Ser | Gly | Ser | Thr | Asn | Tyr | Asn | Pro | Ser | Leu | Lys |
| | 50 | | | | | 55 | | | | | 60 | | | | |
| Ser | Arg | Val | Thr | Met | Ser | Val | Asp | Thr | Ser | Lys | Asn | Gln | Phe | Ser | Leu |
| 65 | | | | | 70 | | | | | 75 | | | | | 80 |
| Lys | Leu | Ser | Ser | Leu | Thr | Ala | Ala | Asp | Thr | Ala | Ile | Tyr | Tyr | Cys | Ala |
| | | | | 85 | | | | | 90 | | | | | 95 | |
| Arg | Tyr | Tyr | Asp | Ile | Leu | Thr | Gly | Phe | Phe | Asp | Tyr | Trp | Gly | Gln | Gly |
| | | | 100 | | | | | 105 | | | | | 110 | | |
| Thr | Leu | Val | Thr | Val | Ser | Ser | Gly | Gly | Gly | Gly | Ser | Gly | Gly | Gly | Gly |
| | | | 115 | | | | | 120 | | | | | 125 | | |
| Ser | Gly | Gly | Gly | Gly | Ser | Val | Ile | Trp | Met | Thr | Gln | Ser | Pro | Ser | Leu |
| | 130 | | | | | 135 | | | | | 140 | | | | |
| Leu | Ser | Ala | Ser | Thr | Gly | Asp | Ser | Val | Thr | Ile | Ser | Cys | Arg | Met | Ser |
| 145 | | | | | 150 | | | | | 155 | | | | | 160 |
| Gln | Asp | Ile | Ser | Ser | Tyr | Leu | Ala | Trp | Tyr | Gln | Gln | Lys | Pro | Gly | Lys |
| | | | | 165 | | | | | 170 | | | | | 175 | |
| Ala | Pro | Glu | Leu | Leu | Ile | Tyr | Ala | Ala | Ser | Ser | Leu | Gln | Ser | Gly | Val |
| | | | 180 | | | | | 185 | | | | | 190 | | |
| Pro | Ser | Arg | Phe | Ser | Gly | Ser | Gly | Ser | Gly | Thr | Asp | Phe | Thr | Leu | Thr |
| | | 195 | | | | | 200 | | | | | 205 | | | |
| Ile | Ser | Ser | Leu | Gln | Ser | Glu | Asp | Phe | Ala | Thr | Tyr | Tyr | Cys | Gln | Gln |
| | 210 | | | | | 215 | | | | | 220 | | | | |
| Tyr | Asp | Ser | Phe | Pro | Pro | Thr | Phe | Gly | Gln | Gly | Thr | Lys | Val | Glu | Phe |
| 225 | | | | | 230 | | | | | 235 | | | | | 240 |
| Lys | Arg | Glu | Ser | Lys | Tyr | Gly | Pro | Pro | Cys | Pro | Pro | Cys | Pro | Gly | Gln |
| | | | | 245 | | | | | 250 | | | | | 255 | |
| Pro | Arg | Glu | Pro | Gln | Val | Tyr | Thr | Leu | Pro | Pro | Ser | Gln | Glu | Glu | Met |
| | | | 260 | | | | | 265 | | | | | 270 | | |
| Thr | Lys | Asn | Gln | Val | Ser | Leu | Thr | Cys | Leu | Val | Lys | Gly | Phe | Tyr | Pro |
| | | 275 | | | | | 280 | | | | | 285 | | | |
| Ser | Asp | Ile | Ala | Val | Glu | Trp | Glu | Ser | Asn | Gly | Gln | Pro | Glu | Asn | Asn |
| | 290 | | | | | 295 | | | | | 300 | | | | |
| Tyr | Lys | Thr | Thr | Pro | Pro | Val | Leu | Asp | Ser | Asp | Gly | Ser | Phe | Phe | Leu |
| 305 | | | | | 310 | | | | | 315 | | | | | 320 |
| Tyr | Ser | Arg | Leu | Thr | Val | Asp | Lys | Ser | Arg | Trp | Gln | Glu | Gly | Asn | Val |
| | | | | 325 | | | | | 330 | | | | | 335 | |
| Phe | Ser | Cys | Ser | Val | Met | His | Glu | Ala | Leu | His | Asn | His | Tyr | Thr | Gln |
| | | | 340 | | | | | 345 | | | | | 350 | | |
| Lys | Ser | Leu | Ser | Leu | Ser | Leu | Gly | Lys | Met | Phe | Trp | Val | Leu | Val | Val |
| | | 355 | | | | | 360 | | | | | 365 | | | |

```
Val Gly Gly Val Leu Ala Cys Tyr Ser Leu Leu Val Thr Val Ala Phe
            370                 375                 380

Ile Ile Phe Trp Val Lys Arg Gly Arg Lys Lys Leu Leu Tyr Ile Phe
385                 390                 395                 400

Lys Gln Pro Phe Met Arg Pro Val Gln Thr Thr Gln Glu Glu Asp Gly
                405                 410                 415

Cys Ser Cys Arg Phe Pro Glu Glu Glu Gly Gly Cys Glu Leu Arg
            420                 425                 430

Val Lys Phe Ser Arg Ser Ala Asp Ala Pro Ala Tyr Gln Gln Gly Gln
            435                 440                 445

Asn Gln Leu Tyr Asn Glu Leu Asn Leu Gly Arg Arg Glu Glu Tyr Asp
            450                 455                 460

Val Leu Asp Lys Arg Arg Gly Arg Asp Pro Glu Met Gly Gly Lys Pro
465                 470                 475                 480

Arg Arg Lys Asn Pro Gln Glu Gly Leu Tyr Asn Glu Leu Gln Lys Asp
                485                 490                 495

Lys Met Ala Glu Ala Tyr Ser Glu Ile Gly Met Lys Gly Glu Arg Arg
                500                 505                 510

Arg Gly Lys Gly His Asp Gly Leu Tyr Gln Gly Leu Ser Thr Ala Thr
            515                 520                 525

Lys Asp Thr Tyr Asp Ala Leu His Met Gln Ala Leu Pro Pro Arg
            530                 535                 540

<210> SEQ ID NO 187
<211> LENGTH: 552
<212> TYPE: PRT
<213> ORGANISM: artificial sequence
<220> FEATURE:
<223> OTHER INFORMATION: anti-ROR1 CAR

<400> SEQUENCE: 187

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Lys Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Glu Asp Ile Leu Thr Gly Tyr Asn Tyr Tyr Gly Met Asp
            100                 105                 110

Val Trp Gly Gln Gly Thr Thr Val Thr Val Ser Ser Gly Gly Gly Gly
        115                 120                 125

Ser Gly Gly Gly Gly Ser Gly Gly Gly Gly Ser Gln Leu Val Leu Thr
    130                 135                 140

Gln Ser Pro Ser Ala Ser Ala Ser Leu Gly Ala Ser Val Lys Leu Thr
145                 150                 155                 160

Cys Thr Leu Ser Ser Gly His Ser Ser Tyr Ala Ile Ala Trp His Gln
                165                 170                 175

Gln Gln Pro Glu Lys Gly Pro Arg Tyr Leu Met Lys Leu Asn Ser Asp
            180                 185                 190
```

Gly Ser His Ser Lys Gly Asp Gly Ile Pro Asp Arg Phe Ser Gly Ser
        195                 200                 205

Ser Ser Gly Ala Glu Arg Tyr Leu Thr Ile Ser Ser Leu Gln Ser Glu
    210                 215                 220

Asp Glu Ala Asp Tyr Tyr Cys Gln Thr Trp Gly Thr Gly Ile Arg Val
225                 230                 235                 240

Phe Gly Gly Gly Thr Lys Leu Thr Val Leu Gly Glu Ser Lys Tyr Gly
                245                 250                 255

Pro Pro Cys Pro Pro Cys Pro Gly Gln Pro Arg Glu Pro Gln Val Tyr
            260                 265                 270

Thr Leu Pro Pro Ser Gln Glu Met Thr Lys Asn Gln Val Ser Leu
            275                 280                 285

Thr Cys Leu Val Lys Gly Phe Tyr Pro Ser Asp Ile Ala Val Glu Trp
290                 295                 300

Glu Ser Asn Gly Gln Pro Glu Asn Asn Tyr Lys Thr Thr Pro Pro Val
305                 310                 315                 320

Leu Asp Ser Asp Gly Ser Phe Phe Leu Tyr Ser Arg Leu Thr Val Asp
                325                 330                 335

Lys Ser Arg Trp Gln Glu Gly Asn Val Phe Ser Cys Ser Val Met His
            340                 345                 350

Glu Ala Leu His Asn His Tyr Thr Gln Lys Ser Leu Ser Leu Ser Leu
            355                 360                 365

Gly Lys Met Phe Trp Val Leu Val Val Val Gly Gly Val Leu Ala Cys
        370                 375                 380

Tyr Ser Leu Leu Val Thr Val Ala Phe Ile Ile Phe Trp Val Lys Arg
385                 390                 395                 400

Gly Arg Lys Lys Leu Leu Tyr Ile Phe Lys Gln Pro Phe Met Arg Pro
                405                 410                 415

Val Gln Thr Thr Gln Glu Glu Asp Gly Cys Ser Cys Arg Phe Pro Glu
            420                 425                 430

Glu Glu Glu Gly Gly Cys Glu Leu Arg Val Lys Phe Ser Arg Ser Ala
            435                 440                 445

Asp Ala Pro Ala Tyr Gln Gln Gly Gln Asn Gln Leu Tyr Asn Glu Leu
    450                 455                 460

Asn Leu Gly Arg Arg Glu Glu Tyr Asp Val Leu Asp Lys Arg Arg Gly
465                 470                 475                 480

Arg Asp Pro Glu Met Gly Gly Lys Pro Arg Arg Lys Asn Pro Gln Glu
                485                 490                 495

Gly Leu Tyr Asn Glu Leu Gln Lys Asp Lys Met Ala Glu Ala Tyr Ser
            500                 505                 510

Glu Ile Gly Met Lys Gly Glu Arg Arg Arg Gly Lys Gly His Asp Gly
            515                 520                 525

Leu Tyr Gln Gly Leu Ser Thr Ala Thr Lys Asp Thr Tyr Asp Ala Leu
    530                 535                 540

His Met Gln Ala Leu Pro Pro Arg
545                 550

<210> SEQ ID NO 188
<211> LENGTH: 545
<212> TYPE: PRT
<213> ORGANISM: artificial sequence
<220> FEATURE:
<223> OTHER INFORMATION: anti-ROR1 CAR

<400> SEQUENCE: 188

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Asn Ser Thr
            20                  25                  30

Thr Ser Tyr Trp Ala Trp Ile Arg Gln Pro Pro Gly Lys Gly Leu Glu
        35                  40                  45

Trp Ile Gly Thr Ile Phe Tyr Ser Gly Lys Thr Tyr Asn Asn Pro Ser
50                  55                  60

Leu Lys Ser Arg Val Thr Met Ser Val Asp Thr Ser Lys Asn His Phe
65                  70                  75                  80

Ser Leu Lys Val Asn Ser Val Thr Ala Ala Asp Thr Ala Val Tyr Tyr
            85                  90                  95

Cys Ala Arg Phe Asp Tyr Gly Phe His Asp Ala Phe Asp Ile Trp Gly
        100                 105                 110

Gln Gly Thr Met Val Thr Val Ser Ser Gly Gly Gly Ser Gly Gly
            115                 120                 125

Gly Gly Ser Gly Gly Gly Gly Ser Glu Ile Val Met Thr Gln Ser Pro
130                 135                 140

Ala Thr Leu Ser Leu Ser Pro Gly Glu Arg Ala Thr Leu Ser Cys Arg
145                 150                 155                 160

Ala Ser Gln Ser Ile Thr Ser Asp Tyr Leu Ser Trp Tyr Gln Gln Lys
            165                 170                 175

Pro Gly Gln Ala Pro Arg Leu Leu Ile Tyr Gly Ala Ser Thr Arg Ala
        180                 185                 190

Thr Gly Ile Pro Ala Arg Phe Ser Gly Ser Gly Ser Gly Thr Asp Phe
        195                 200                 205

Thr Leu Thr Ile Ser Ser Leu Gln Pro Glu Asp Phe Val Val Tyr Tyr
210                 215                 220

Cys Gln Gln Asp Tyr Asn Leu Tyr Thr Phe Gly Gln Gly Thr Lys Leu
225                 230                 235                 240

Glu Ile Lys Arg Glu Ser Lys Tyr Gly Pro Pro Cys Pro Pro Cys Pro
            245                 250                 255

Gly Gln Pro Arg Glu Pro Gln Val Tyr Thr Leu Pro Pro Ser Gln Glu
        260                 265                 270

Glu Met Thr Lys Asn Gln Val Ser Leu Thr Cys Leu Val Lys Gly Phe
        275                 280                 285

Tyr Pro Ser Asp Ile Ala Val Glu Trp Glu Ser Asn Gly Gln Pro Glu
290                 295                 300

Asn Asn Tyr Lys Thr Thr Pro Pro Val Leu Asp Ser Asp Gly Ser Phe
305                 310                 315                 320

Phe Leu Tyr Ser Arg Leu Thr Val Asp Lys Ser Arg Trp Gln Glu Gly
            325                 330                 335

Asn Val Phe Ser Cys Ser Val Met His Glu Ala Leu His Asn His Tyr
        340                 345                 350

Thr Gln Lys Ser Leu Ser Leu Ser Leu Gly Lys Met Phe Trp Val Leu
        355                 360                 365

Val Val Val Gly Gly Val Leu Ala Cys Tyr Ser Leu Leu Val Thr Val
        370                 375                 380

Ala Phe Ile Ile Phe Trp Val Lys Arg Gly Arg Lys Lys Leu Leu Tyr
385                 390                 395                 400
```

```
Ile Phe Lys Gln Pro Phe Met Arg Pro Val Gln Thr Thr Gln Glu Glu
                405                 410                 415

Asp Gly Cys Ser Cys Arg Phe Pro Glu Glu Glu Gly Gly Cys Glu
            420                 425                 430

Leu Arg Val Lys Phe Ser Arg Ser Ala Asp Ala Pro Ala Tyr Gln Gln
                435                 440                 445

Gly Gln Asn Gln Leu Tyr Asn Glu Leu Asn Leu Gly Arg Arg Glu Glu
450                 455                 460

Tyr Asp Val Leu Asp Lys Arg Arg Gly Arg Asp Pro Glu Met Gly Gly
465                 470                 475                 480

Lys Pro Arg Arg Lys Asn Pro Gln Glu Gly Leu Tyr Asn Glu Leu Gln
                485                 490                 495

Lys Asp Lys Met Ala Glu Ala Tyr Ser Glu Ile Gly Met Lys Gly Glu
                500                 505                 510

Arg Arg Arg Gly Lys Gly His Asp Gly Leu Tyr Gln Gly Leu Ser Thr
                515                 520                 525

Ala Thr Lys Asp Thr Tyr Asp Ala Leu His Met Gln Ala Leu Pro Pro
                530                 535                 540

Arg
545

<210> SEQ ID NO 189
<211> LENGTH: 552
<212> TYPE: PRT
<213> ORGANISM: artificial sequence
<220> FEATURE:
<223> OTHER INFORMATION: anti-ROR1 CAR

<400> SEQUENCE: 189

Gln Val Gln Leu Leu Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Thr Gly Asn Thr Arg Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Glu Gly Ala Thr Thr Asp Tyr Asp Tyr Tyr Gly Met Asp
                100                 105                 110

Val Trp Gly Gln Gly Thr Ala Val Thr Val Ser Ser Gly Gly Gly Gly
            115                 120                 125

Ser Gly Gly Gly Gly Ser Gly Gly Gly Gly Ser Gln Leu Val Leu Thr
130                 135                 140

Gln Ser Pro Ser Ala Ser Ala Ser Leu Gly Ala Ser Val Lys Leu Thr
145                 150                 155                 160

Cys Thr Leu Ser Ser Gly His Ser Ser Tyr Ala Ile Ala Trp His Gln
                165                 170                 175

Gln Gln Pro Glu Lys Gly Pro Arg Tyr Leu Met Lys Leu Asn Ser Asp
                180                 185                 190

Gly Ser His Ser Lys Gly Asp Gly Ile Pro Asp Arg Phe Ser Gly Ser
                195                 200                 205
```

```
Ser Ser Gly Ala Glu Arg Tyr Leu Thr Ile Ser Ser Leu Gln Ser Glu
210                 215                 220
Asp Glu Ala Asp Tyr Tyr Cys Gln Thr Trp Gly Thr Gly Ile Arg Val
225                 230                 235                 240
Phe Gly Gly Gly Thr Lys Leu Thr Val Leu Gly Glu Ser Lys Tyr Gly
                245                 250                 255
Pro Pro Cys Pro Pro Cys Pro Gly Gln Pro Arg Glu Pro Gln Val Tyr
            260                 265                 270
Thr Leu Pro Pro Ser Gln Glu Glu Met Thr Lys Asn Gln Val Ser Leu
        275                 280                 285
Thr Cys Leu Val Lys Gly Phe Tyr Pro Ser Asp Ile Ala Val Glu Trp
290                 295                 300
Glu Ser Asn Gly Gln Pro Glu Asn Asn Tyr Lys Thr Thr Pro Pro Val
305                 310                 315                 320
Leu Asp Ser Asp Gly Ser Phe Phe Leu Tyr Ser Arg Leu Thr Val Asp
                325                 330                 335
Lys Ser Arg Trp Gln Glu Gly Asn Val Phe Ser Cys Ser Val Met His
            340                 345                 350
Glu Ala Leu His Asn His Tyr Thr Gln Lys Ser Leu Ser Leu Ser Leu
        355                 360                 365
Gly Lys Met Phe Trp Val Leu Val Val Gly Gly Val Leu Ala Cys
370                 375                 380
Tyr Ser Leu Leu Val Thr Val Ala Phe Ile Ile Phe Trp Val Lys Arg
385                 390                 395                 400
Gly Arg Lys Lys Leu Leu Tyr Ile Phe Lys Gln Pro Phe Met Arg Pro
                405                 410                 415
Val Gln Thr Thr Gln Glu Glu Asp Gly Cys Ser Cys Arg Phe Pro Glu
            420                 425                 430
Glu Glu Glu Gly Gly Cys Glu Leu Arg Val Lys Phe Ser Arg Ser Ala
        435                 440                 445
Asp Ala Pro Ala Tyr Gln Gln Gly Gln Asn Gln Leu Tyr Asn Glu Leu
    450                 455                 460
Asn Leu Gly Arg Arg Glu Glu Tyr Asp Val Leu Asp Lys Arg Arg Gly
465                 470                 475                 480
Arg Asp Pro Glu Met Gly Gly Lys Pro Arg Arg Lys Asn Pro Gln Glu
                485                 490                 495
Gly Leu Tyr Asn Glu Leu Gln Lys Asp Lys Met Ala Glu Ala Tyr Ser
            500                 505                 510
Glu Ile Gly Met Lys Gly Glu Arg Arg Arg Gly Lys Gly His Asp Gly
        515                 520                 525
Leu Tyr Gln Gly Leu Ser Thr Ala Thr Lys Asp Thr Tyr Asp Ala Leu
    530                 535                 540
His Met Gln Ala Leu Pro Pro Arg
545                 550

<210> SEQ ID NO 190
<211> LENGTH: 48
<212> TYPE: DNA
<213> ORGANISM: artificial sequence
<220> FEATURE:
<223> OTHER INFORMATION: CD33 signal sequence (O/SSE)

<400> SEQUENCE: 190
atgcctctgc tgctgcttct gcctcttctt tgggctggtg ctctggct                    48
```

<210> SEQ ID NO 191
<211> LENGTH: 48
<212> TYPE: DNA
<213> ORGANISM: artificial sequence
<220> FEATURE:
<223> OTHER INFORMATION: CD33 signal sequence GenBank: M23197.1

<400> SEQUENCE: 191
atgccgctgc tgctactgct gcccctgctg tgggcagggg ccctggct                48

<210> SEQ ID NO 192
<211> LENGTH: 39
<212> TYPE: DNA
<213> ORGANISM: artificial sequence
<220> FEATURE:
<223> OTHER INFORMATION: Spacer (IgG4 hinge)

<400> SEQUENCE: 192
gaatctaagt acggaccgcc ctgccccct tgccctatg                           39

<210> SEQ ID NO 193
<211> LENGTH: 357
<212> TYPE: DNA
<213> ORGANISM: artificial sequence
<220> FEATURE:
<223> OTHER INFORMATION: Hinge-CH3 spacer

<400> SEQUENCE: 193
gaatctaagt acggaccgcc ttgtcctcca tgtcctggcc agccaagaga accccaggtg    60
tacacactgc ctccaagcca agaggaaatg accaagaacc aggtgtccct gacctgcctg   120
gtcaagggct ctaccttc cgatatcgcc gtggaatggg agagcaatgg ccagcctgag    180
aacaactaca agaccacacc tcctgtgctg acagcgacg gctcattctt cctgtacagc    240
cggctgaccg tggacaagag cagatggcaa gagggcaacg tgttcagctg cagcgtgatg    300
cacgaggccc tgcacaacca ctacacccag aagtctctga gcctgagcct gggcaag      357

<210> SEQ ID NO 194
<211> LENGTH: 229
<212> TYPE: PRT
<213> ORGANISM: artificial sequence
<220> FEATURE:
<223> OTHER INFORMATION: IgG4/IgG2 hinge- IgG2/IgG4 CH2- IgG4 CH3 spacer

<400> SEQUENCE: 194

Glu Ser Lys Tyr Gly Pro Pro Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Gln Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Leu Pro Ser Ser
            100                 105                 110

Ile Glu Lys Thr Ile Ser Lys Ala Lys Gly Gln Pro Arg Glu Pro Gln
        115                 120                 125

```
Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Leu Gly Lys Met
225

<210> SEQ ID NO 195
<211> LENGTH: 687
<212> TYPE: DNA
<213> ORGANISM: artificial sequence
<220> FEATURE:
<223> OTHER INFORMATION: IgG4/IgG2 hinge- IgG2/IgG4 CH2- IgG4 CH3 spacer

<400> SEQUENCE: 195
gaatctaagt acggaccgcc ctgccctccc tgccctgctc ctcctgtggc tggaccaagc     60
gtgttcctgt ttccacctaa gcctaaagat accctgatga tttcccgcac acctgaagtg    120
acttgcgtgg tcgtggacgt gagccaggag gatccagaag tgcagttcaa ctggtacgtg    180
gacggcgtgg aagtccacaa tgctaagact aaaccccgag aggaacagtt tcagtcaact    240
taccgggtcg tgagcgtgct gaccgtcctg catcaggatt ggctgaacgg aaggagtat    300 aagtgcaaag tgtctaataa gggactgcct agctccatcg agaaaacaat tagtaaggca    360
aaagggcagc ctcgagaacc acaggtgtat accctgcccc ctagccagga ggaaatgacc    420
aagaaccagg tgtccctgac atgtctggtc aaaggcttct atccaagtga catcgccgtg    480
gagtgggaat caaatgggca gcccgagaac aattacaaga ccacaccacc cgtgctggac    540
tctgatggaa gtttctttct gtattccagg ctgaccgtgg ataaatctcg ctggcaggag    600
ggcaacgtgt tctcttgcag tgtcatgcac gaagccctgc acaatcatta cacagaag     660 tcactgagcc tgtccctggg caaaatg                                        687

<210> SEQ ID NO 196
<211> LENGTH: 687
<212> TYPE: DNA
<213> ORGANISM: artificial sequence
<220> FEATURE:
<223> OTHER INFORMATION: IgG4/IgG2 hinge- IgG2/IgG4 CH2- IgG4 CH3 spacer
      O/SSE

<400> SEQUENCE: 196
gagtctaaat acggaccgcc ttgtcctcct tgtcccgctc ctcctgttgc cggaccttcc     60
gtgttcctgt ttcctccaaa gcctaaggac accctgatga tcagcaggac ccctgaagtg    120
acctgcgtgg tggtggatgt gtcccaagag gatcccgagg tgcagttcaa ctggtatgtg    180
gacggcgtgg aagtgcacaa cgccaagacc aagcctagag aggaacagtt ccagagcacc    240
tacagagtgg tgtccgtgct gacagtgctg caccaggatt ggctgaacgg caaagagtac    300
aagtgcaagg tgtccaacaa gggcctgcct agcagcatcg agaaaaccat ctccaaggcc    360
```

```
aagggccagc caagagagcc ccaggtttac acactgcctc caagccaaga ggaaatgacc      420
aagaatcagg tgtccctgac atgcctggtc aagggcttct acccctccga tatcgccgtg      480
gaatgggaga gcaatggcca gcctgagaac aactacaaga ccacacctcc tgtgctggac      540
agcgacggca gtttcttcct gtatagtaga ctcaccgtgg ataaatcaag atggcaagag      600
ggcaacgtgt tcagctgcag cgtgatgcac gaggccctgc acaaccacta cacccagaaa      660
agcctgagcc tgtctctggg caagatg                                          687
```

<210> SEQ ID NO 197
<211> LENGTH: 81
<212> TYPE: DNA
<213> ORGANISM: artificial sequence
<220> FEATURE:
<223> OTHER INFORMATION: CD28 transmembrane domain

<400> SEQUENCE: 197

```
ttttgggtgc tggtcgtggt cggaggggtg ctggcctgtt acagcctgct ggtgacagtc       60
gctttcatca tcttctgggt g                                                81
```

<210> SEQ ID NO 198
<211> LENGTH: 81
<212> TYPE: DNA
<213> ORGANISM: artificial sequence
<220> FEATURE:
<223> OTHER INFORMATION: CD28 transmembrane domain (O/SSE)

<400> SEQUENCE: 198

```
ttctgggtgc tcgtggtcgt tggcggagtg ctggcctgtt acagcctgct ggttaccgtg       60
gccttcatca tcttttgggt c                                                81
```

<210> SEQ ID NO 199
<211> LENGTH: 15
<212> TYPE: PRT
<213> ORGANISM: artificial sequence
<220> FEATURE:
<223> OTHER INFORMATION: ROR1 epitope 1

<400> SEQUENCE: 199

Phe Arg Ser Thr Ile Tyr Gly Ser Arg Leu Arg Ile Arg Asn Leu
1               5                   10                  15

<210> SEQ ID NO 200
<211> LENGTH: 13
<212> TYPE: PRT
<213> ORGANISM: artificial sequence
<220> FEATURE:
<223> OTHER INFORMATION: ROR1 epitope 2

<400> SEQUENCE: 200

Leu Ser Val Ser Ala Glu Leu Val Pro Thr Ser Ser Trp
1               5                   10

<210> SEQ ID NO 201
<211> LENGTH: 14
<212> TYPE: PRT
<213> ORGANISM: artificial sequence
<220> FEATURE:
<223> OTHER INFORMATION: ROR1 epitope 3

<400> SEQUENCE: 201

His Cys Lys Val Ser Gly Asn Pro Pro Pro Thr Ile Arg Trp
1               5                   10

```
<210> SEQ ID NO 202
<211> LENGTH: 26
<212> TYPE: PRT
<213> ORGANISM: artificial sequence
<220> FEATURE:
<223> OTHER INFORMATION: ROR1 epitope 4

<400> SEQUENCE: 202

Trp Phe Lys Asn Asp Ala Pro Val Val Gln Glu Pro Arg Arg Leu Ser
1               5                   10                  15

Phe Arg Ser Thr Ile Tyr Gly Ser Arg Leu
            20                  25

<210> SEQ ID NO 203
<211> LENGTH: 9
<212> TYPE: PRT
<213> ORGANISM: artificial sequence
<220> FEATURE:
<223> OTHER INFORMATION: ROR1 epitope 5

<400> SEQUENCE: 203

Val Ser Ser Thr Gly Val Leu Phe Val
1               5

<210> SEQ ID NO 204
<211> LENGTH: 13
<212> TYPE: PRT
<213> ORGANISM: artificial sequence
<220> FEATURE:
<223> OTHER INFORMATION: ROR1 epitope 6

<400> SEQUENCE: 204

Leu Phe Val Lys Phe Gly Pro Pro Pro Thr Ala Ser Pro
1               5                   10

<210> SEQ ID NO 205
<211> LENGTH: 11
<212> TYPE: PRT
<213> ORGANISM: artificial sequence
<220> FEATURE:
<223> OTHER INFORMATION: ROR1 epitope 7

<400> SEQUENCE: 205

Asp Glu Tyr Glu Glu Asp Gly Phe Cys Gln Pro
1               5                   10

<210> SEQ ID NO 206
<211> LENGTH: 14
<212> TYPE: PRT
<213> ORGANISM: artificial sequence
<220> FEATURE:
<223> OTHER INFORMATION: ROR1 epitope 8

<400> SEQUENCE: 206

Gln Pro Tyr Arg Gly Ile Ala Cys Ala Arg Phe Ile Gly Asn
1               5                   10

<210> SEQ ID NO 207
<211> LENGTH: 14
<212> TYPE: PRT
<213> ORGANISM: artificial sequence
<220> FEATURE:
<223> OTHER INFORMATION: ROR1 epitope 9
```

```
<400> SEQUENCE: 207

Ser Gln Phe Ala Ile Pro Ser Leu Cys His Tyr Ala Phe Pro
1               5                   10

<210> SEQ ID NO 208
<211> LENGTH: 12
<212> TYPE: PRT
<213> ORGANISM: artificial sequence
<220> FEATURE:
<223> OTHER INFORMATION: ROR1 epitope 10

<400> SEQUENCE: 208

Ala Phe Pro Tyr Cys Asp Glu Thr Ser Ser Val Pro
1               5                   10

<210> SEQ ID NO 209
<211> LENGTH: 20
<212> TYPE: PRT
<213> ORGANISM: artificial sequence
<220> FEATURE:
<223> OTHER INFORMATION: ROR1 epitope 11

<400> SEQUENCE: 209

Asn Val Leu Cys Gln Thr Glu Tyr Ile Phe Ala Arg Ser Asn Pro Met
1               5                   10                  15

Ile Leu Met Arg
            20

<210> SEQ ID NO 210
<211> LENGTH: 12
<212> TYPE: PRT
<213> ORGANISM: artificial sequence
<220> FEATURE:
<223> OTHER INFORMATION: ROR1 epitope 12

<400> SEQUENCE: 210

Leu Lys Leu Pro Asn Cys Glu Asp Leu Pro Gln Pro
1               5                   10

<210> SEQ ID NO 211
<211> LENGTH: 15
<212> TYPE: PRT
<213> ORGANISM: artificial sequence
<220> FEATURE:
<223> OTHER INFORMATION: ROR1 epitope 13

<400> SEQUENCE: 211

Pro Glu Ser Pro Glu Ala Ala Asn Cys Ile Arg Ile Gly Ile Pro
1               5                   10                  15

<210> SEQ ID NO 212
<211> LENGTH: 14
<212> TYPE: PRT
<213> ORGANISM: artificial sequence
<220> FEATURE:
<223> OTHER INFORMATION: ROR1 epitope 14

<400> SEQUENCE: 212

Val Asp Tyr Arg Gly Thr Val Ser Val Thr Lys Ser Gly Arg
1               5                   10

<210> SEQ ID NO 213
<211> LENGTH: 14
<212> TYPE: PRT
<213> ORGANISM: artificial sequence
```

```
<220> FEATURE:
<223> OTHER INFORMATION: ROR1 epitope 15

<400> SEQUENCE: 213

Ser Gln Tyr Pro His Thr His Thr Phe Thr Ala Leu Arg Phe
1               5                   10

<210> SEQ ID NO 214
<211> LENGTH: 15
<212> TYPE: PRT
<213> ORGANISM: artificial sequence
<220> FEATURE:
<223> OTHER INFORMATION: ROR1 epitope 16

<400> SEQUENCE: 214

Asp Ser Lys Glu Lys Asn Lys Met Glu Ile Leu Tyr Ile Leu Val
1               5                   10                  15

<210> SEQ ID NO 215
<211> LENGTH: 937
<212> TYPE: PRT
<213> ORGANISM: homo sapiens
<220> FEATURE:
<221> NAME/KEY: MISC_FEATURE
<223> OTHER INFORMATION: ROR1 (Uniprot Q01973)

<400> SEQUENCE: 215

Met His Arg Pro Arg Arg Arg Gly Thr Arg Pro Pro Leu Leu Ala Leu
1               5                   10                  15

Leu Ala Leu Leu Leu Ala Ala Arg Gly Ala Ala Ala Gln Glu Thr
                20                  25                  30

Glu Leu Ser Val Ser Ala Glu Leu Val Pro Thr Ser Ser Trp Asn Ile
            35                  40                  45

Ser Ser Glu Leu Asn Lys Asp Ser Tyr Leu Thr Leu Asp Glu Pro Met
        50                  55                  60

Asn Asn Ile Thr Thr Ser Leu Gly Gln Thr Ala Glu Leu His Cys Lys
65                  70                  75                  80

Val Ser Gly Asn Pro Pro Pro Thr Ile Arg Trp Phe Lys Asn Asp Ala
                85                  90                  95

Pro Val Val Gln Glu Pro Arg Arg Leu Ser Phe Arg Ser Thr Ile Tyr
            100                 105                 110

Gly Ser Arg Leu Arg Ile Arg Asn Leu Asp Thr Thr Asp Thr Gly Tyr
        115                 120                 125

Phe Gln Cys Val Ala Thr Asn Gly Lys Glu Val Val Ser Ser Thr Gly
    130                 135                 140

Val Leu Phe Val Lys Phe Gly Pro Pro Thr Ala Ser Pro Gly Tyr
145                 150                 155                 160

Ser Asp Glu Tyr Glu Glu Asp Gly Phe Cys Gln Pro Tyr Arg Gly Ile
                165                 170                 175

Ala Cys Ala Arg Phe Ile Gly Asn Arg Thr Val Tyr Met Glu Ser Leu
            180                 185                 190

His Met Gln Gly Glu Ile Glu Asn Gln Ile Thr Ala Ala Phe Thr Met
        195                 200                 205

Ile Gly Thr Ser Ser His Leu Ser Asp Lys Cys Ser Gln Phe Ala Ile
    210                 215                 220

Pro Ser Leu Cys His Tyr Ala Phe Pro Tyr Cys Asp Glu Thr Ser Ser
225                 230                 235                 240

Val Pro Lys Pro Arg Asp Leu Cys Arg Asp Glu Cys Glu Ile Leu Glu
                245                 250                 255
```

-continued

```
Asn Val Leu Cys Gln Thr Glu Tyr Ile Phe Ala Arg Ser Asn Pro Met
            260                 265                 270

Ile Leu Met Arg Leu Lys Leu Pro Asn Cys Glu Asp Leu Pro Gln Pro
            275                 280                 285

Glu Ser Pro Glu Ala Ala Asn Cys Ile Arg Ile Gly Ile Pro Met Ala
290                 295                 300

Asp Pro Ile Asn Lys Asn His Lys Cys Tyr Asn Ser Thr Gly Val Asp
305                 310                 315                 320

Tyr Arg Gly Thr Val Ser Val Thr Lys Ser Gly Arg Gln Cys Gln Pro
                325                 330                 335

Trp Asn Ser Gln Tyr Pro His Thr His Thr Phe Thr Ala Leu Arg Phe
            340                 345                 350

Pro Glu Leu Asn Gly Gly His Ser Tyr Cys Arg Asn Pro Gly Asn Gln
            355                 360                 365

Lys Glu Ala Pro Trp Cys Phe Thr Leu Asp Glu Asn Phe Lys Ser Asp
            370                 375                 380

Leu Cys Asp Ile Pro Ala Cys Asp Ser Lys Asp Ser Lys Glu Lys Asn
385                 390                 395                 400

Lys Met Glu Ile Leu Tyr Ile Leu Val Pro Ser Val Ala Ile Pro Leu
                405                 410                 415

Ala Ile Ala Leu Leu Phe Phe Phe Ile Cys Val Cys Arg Asn Asn Gln
            420                 425                 430

Lys Ser Ser Ser Ala Pro Val Gln Arg Gln Pro Lys His Val Arg Gly
            435                 440                 445

Gln Asn Val Glu Met Ser Met Leu Asn Ala Tyr Lys Pro Lys Ser Lys
            450                 455                 460

Ala Lys Glu Leu Pro Leu Ser Ala Val Arg Phe Met Glu Glu Leu Gly
465                 470                 475                 480

Glu Cys Ala Phe Gly Lys Ile Tyr Lys Gly His Leu Tyr Leu Pro Gly
                485                 490                 495

Met Asp His Ala Gln Leu Val Ala Ile Lys Thr Leu Lys Asp Tyr Asn
            500                 505                 510

Asn Pro Gln Gln Trp Thr Glu Phe Gln Gln Glu Ala Ser Leu Met Ala
            515                 520                 525

Glu Leu His His Pro Asn Ile Val Cys Leu Leu Gly Ala Val Thr Gln
530                 535                 540

Glu Gln Pro Val Cys Met Leu Phe Glu Tyr Ile Asn Gln Gly Asp Leu
545                 550                 555                 560

His Glu Phe Leu Ile Met Arg Ser Pro His Ser Asp Val Gly Cys Ser
                565                 570                 575

Ser Asp Glu Asp Gly Thr Val Lys Ser Ser Leu Asp His Gly Asp Phe
            580                 585                 590

Leu His Ile Ala Ile Gln Ile Ala Ala Gly Met Glu Tyr Leu Ser Ser
            595                 600                 605

His Phe Phe Val His Lys Asp Leu Ala Ala Arg Asn Ile Leu Ile Gly
            610                 615                 620

Glu Gln Leu His Val Lys Ile Ser Asp Leu Gly Leu Ser Arg Glu Ile
625                 630                 635                 640

Tyr Ser Ala Asp Tyr Tyr Arg Val Gln Ser Lys Ser Leu Leu Pro Ile
                645                 650                 655

Arg Trp Met Pro Pro Glu Ala Ile Met Tyr Gly Lys Phe Ser Ser Asp
            660                 665                 670
```

```
Ser Asp Ile Trp Ser Phe Gly Val Val Leu Trp Glu Ile Phe Ser Phe
            675                 680                 685

Gly Leu Gln Pro Tyr Tyr Gly Phe Ser Asn Gln Glu Val Ile Glu Met
    690                 695                 700

Val Arg Lys Arg Gln Leu Leu Pro Cys Ser Glu Asp Cys Pro Pro Arg
705                 710                 715                 720

Met Tyr Ser Leu Met Thr Glu Cys Trp Asn Glu Ile Pro Ser Arg Arg
                725                 730                 735

Pro Arg Phe Lys Asp Ile His Val Arg Leu Arg Ser Trp Glu Gly Leu
                740                 745                 750

Ser Ser His Thr Ser Ser Thr Thr Pro Ser Gly Gly Asn Ala Thr Thr
            755                 760                 765

Gln Thr Thr Ser Leu Ser Ala Ser Pro Val Ser Asn Leu Ser Asn Pro
    770                 775                 780

Arg Tyr Pro Asn Tyr Met Phe Pro Ser Gln Gly Ile Thr Pro Gln Gly
785                 790                 795                 800

Gln Ile Ala Gly Phe Ile Gly Pro Pro Ile Pro Gln Asn Gln Arg Phe
                805                 810                 815

Ile Pro Ile Asn Gly Tyr Pro Ile Pro Pro Gly Tyr Ala Ala Phe Pro
                820                 825                 830

Ala Ala His Tyr Gln Pro Thr Gly Pro Pro Arg Val Ile Gln His Cys
            835                 840                 845

Pro Pro Pro Lys Ser Arg Ser Pro Ser Ser Ala Ser Gly Ser Thr Ser
    850                 855                 860

Thr Gly His Val Thr Ser Leu Pro Ser Ser Gly Ser Asn Gln Glu Ala
865                 870                 875                 880

Asn Ile Pro Leu Leu Pro His Met Ser Ile Pro Asn His Pro Gly Gly
                885                 890                 895

Met Gly Ile Thr Val Phe Gly Asn Lys Ser Gln Lys Pro Tyr Lys Ile
                900                 905                 910

Asp Ser Lys Gln Ala Ser Leu Leu Gly Asp Ala Asn Ile His Gly His
            915                 920                 925

Thr Glu Ser Met Ile Ser Ala Glu Leu
    930                 935

<210> SEQ ID NO 216
<211> LENGTH: 937
<212> TYPE: PRT
<213> ORGANISM: Macaca mulatta
<220> FEATURE:
<221> NAME/KEY: MISC_FEATURE
<223> OTHER INFORMATION: ROR1 (Uniprot F6RUP2)

<400> SEQUENCE: 216

Met His Arg Pro Arg Arg Arg Gly Thr Arg Pro Pro Leu Leu Ala Leu
1               5                   10                  15

Leu Ala Ala Leu Leu Leu Ala Ala Arg Gly Ala Ala Ala Gln Glu Thr
                20                  25                  30

Glu Leu Ser Val Ser Ala Glu Leu Val Pro Thr Ser Ser Trp Asn Ile
            35                  40                  45

Ser Ser Glu Leu Asn Lys Asp Ser Tyr Leu Thr Leu Asp Glu Pro Met
        50                  55                  60

Asn Asn Ile Thr Thr Ser Leu Gly Gln Thr Ala Glu Leu His Cys Lys
65                  70                  75                  80

Val Ser Gly Asn Pro Pro Pro Thr Ile Arg Trp Phe Lys Asn Asp Ala
                85                  90                  95
```

```
Pro Val Val Gln Glu Pro Arg Leu Ser Phe Arg Ser Thr Ile Tyr
            100                 105                 110

Gly Ser Arg Leu Arg Ile Arg Asn Leu Asp Thr Thr Asp Thr Gly Tyr
            115                 120                 125

Phe Gln Cys Val Ala Thr Asn Gly Lys Glu Val Val Ser Ser Thr Gly
        130                 135                 140

Val Leu Phe Val Lys Phe Gly Pro Pro Thr Ala Ser Pro Gly Tyr
145                 150                 155                 160

Ser Asp Glu Tyr Glu Glu Asp Gly Phe Cys Gln Pro Tyr Arg Gly Ile
                165                 170                 175

Ala Cys Ala Arg Phe Ile Gly Asn Arg Thr Val Tyr Met Glu Ser Leu
            180                 185                 190

His Met Gln Gly Glu Ile Glu Asn Gln Ile Thr Ala Ala Phe Thr Met
        195                 200                 205

Ile Gly Thr Ser Ser His Leu Ser Asp Lys Cys Ser Gln Phe Ala Ile
        210                 215                 220

Pro Ser Leu Cys His Tyr Ala Phe Pro Tyr Cys Asp Glu Thr Ser Ser
225                 230                 235                 240

Val Pro Lys Pro Arg Asp Leu Cys Arg Asp Glu Cys Glu Ile Leu Glu
                245                 250                 255

Asn Val Leu Cys Gln Thr Glu Tyr Ile Phe Ala Arg Ser Asn Pro Met
            260                 265                 270

Ile Leu Met Arg Leu Lys Leu Pro Asn Cys Glu Asp Leu Pro Gln Pro
        275                 280                 285

Glu Ser Pro Glu Ala Ala Asn Cys Ile Arg Ile Gly Ile Pro Met Ala
        290                 295                 300

Asp Pro Ile Asn Lys Asn His Lys Cys Tyr Asn Ser Thr Gly Val Asp
305                 310                 315                 320

Tyr Arg Gly Thr Val Ser Val Thr Lys Ser Gly Arg Gln Cys Gln Pro
                325                 330                 335

Trp Asn Ser Gln Tyr Pro His Thr His Thr Phe Thr Ala Leu Arg Phe
            340                 345                 350

Pro Glu Leu Asn Gly Gly His Ser Tyr Cys Arg Asn Pro Gly Asn Gln
        355                 360                 365

Lys Glu Ala Pro Trp Cys Phe Thr Leu Asp Glu Asn Phe Lys Ser Asp
        370                 375                 380

Leu Cys Asp Ile Pro Ala Cys Asp Ser Lys Asp Ser Lys Glu Lys Asn
385                 390                 395                 400

Lys Met Glu Ile Leu Tyr Ile Leu Val Pro Ser Val Ala Ile Pro Leu
                405                 410                 415

Ala Ile Ala Leu Leu Phe Phe Phe Ile Cys Val Cys Arg Asn Asn Gln
            420                 425                 430

Lys Ser Ser Ser Pro Pro Val Gln Arg Gln Pro Lys His Val Arg Gly
        435                 440                 445

Gln Asn Val Glu Met Ser Met Leu Asn Ala Tyr Lys Pro Lys Ser Lys
        450                 455                 460

Ala Lys Glu Leu Pro Leu Ser Ala Val Arg Phe Met Glu Glu Leu Gly
465                 470                 475                 480

Glu Cys Ala Phe Gly Lys Ile Tyr Lys Gly His Leu Tyr Leu Pro Gly
                485                 490                 495

Met Asp His Ala Gln Leu Val Ala Ile Lys Thr Leu Lys Asp Tyr Asn
            500                 505                 510
```

```
Asn Pro Gln Gln Trp Thr Glu Phe Gln Gln Glu Ala Ser Leu Met Ala
            515                 520                 525

Glu Leu His His Pro Asn Ile Val Cys Leu Leu Gly Ala Val Thr Gln
        530                 535                 540

Glu Gln Pro Val Cys Met Leu Phe Glu Tyr Met Asn Gln Gly Asp Leu
545                 550                 555                 560

His Glu Phe Leu Ile Met Arg Ser Pro His Ser Asp Val Gly Cys Ser
            565                 570                 575

Ser Asp Glu Asp Gly Thr Val Lys Ser Ser Leu Asp His Gly Asp Phe
        580                 585                 590

Leu His Ile Ala Ile Gln Ile Ala Ala Gly Met Glu Tyr Leu Ser Ser
            595                 600                 605

His Phe Phe Val His Lys Asp Leu Ala Ala Arg Asn Ile Leu Ile Gly
        610                 615                 620

Glu Gln Leu His Val Lys Ile Ser Asp Leu Gly Leu Ser Arg Glu Ile
625                 630                 635                 640

Tyr Ser Ala Asp Tyr Tyr Arg Val Gln Ser Lys Ser Leu Leu Pro Ile
            645                 650                 655

Arg Trp Met Pro Pro Glu Ala Ile Met Tyr Gly Lys Phe Ser Ser Asp
            660                 665                 670

Ser Asp Ile Trp Ser Phe Gly Val Val Leu Trp Glu Ile Phe Ser Phe
            675                 680                 685

Gly Leu Gln Pro Tyr Tyr Gly Phe Ser Asn Gln Glu Val Ile Glu Met
        690                 695                 700

Val Arg Lys Arg Gln Leu Leu Pro Cys Ser Glu Asp Cys Pro Pro Arg
705                 710                 715                 720

Met Tyr Ser Leu Met Thr Glu Cys Trp Asn Glu Ile Pro Ser Arg Arg
            725                 730                 735

Pro Arg Phe Lys Asp Ile His Val Arg Leu Arg Ser Trp Glu Gly Leu
            740                 745                 750

Ser Ser His Thr Ser Ser Thr Thr Pro Ser Gly Gly Asn Ala Thr Thr
        755                 760                 765

Gln Thr Thr Ser Leu Ser Ala Ser Pro Val Ser Asn Leu Ser Asn Pro
770                 775                 780

Arg Tyr Pro Asn Tyr Ile Phe Pro Ser Gln Gly Ile Thr Pro Gln Gly
785                 790                 795                 800

Gln Ile Ala Gly Phe Ile Gly Pro Pro Ile Pro Gln Asn Gln Arg Phe
            805                 810                 815

Ile Pro Ile Asn Gly Tyr Pro Ile Pro Pro Gly Tyr Ala Ala Phe Pro
            820                 825                 830

Ala Ala His Tyr Gln Pro Thr Gly Pro Pro Arg Val Ile Gln His Cys
        835                 840                 845

Pro Pro Pro Lys Ser Arg Ser Pro Ser Ser Ala Ser Gly Ser Thr Ser
850                 855                 860

Thr Gly His Val Thr Ser Leu Pro Ser Ser Gly Ser Asn Gln Glu Ala
865                 870                 875                 880

Asn Ile Pro Leu Leu Pro His Met Ser Ile Pro Asn His Pro Gly Gly
            885                 890                 895

Met Gly Ile Thr Val Phe Gly Asn Lys Ser Gln Lys Pro Tyr Lys Ile
            900                 905                 910
```

-continued

```
Asp Ala Lys Gln Ala Ser Leu Leu Gly Asp Ala Asn Ile His Gly His
        915                 920                 925

Thr Glu Ser Met Ile Ser Ala Glu Leu
        930                 935

<210> SEQ ID NO 217
<211> LENGTH: 923
<212> TYPE: PRT
<213> ORGANISM: macaca fasicularis
<220> FEATURE:
<221> NAME/KEY: MISC_FEATURE
<223> OTHER INFORMATION: ROR1 (Uniprot A0A2K5WTX7)

<400> SEQUENCE: 217

Met Leu Arg Thr Ala His Lys Leu Leu Tyr Leu Ile Leu Pro Leu Ser
1               5                   10                  15

Phe Ser Leu Pro Phe Phe Phe Ser Glu Thr Glu Leu Ser Val Ser
            20                  25                  30

Ala Glu Leu Val Pro Thr Ser Ser Trp Asn Ile Ser Ser Glu Leu Asn
        35                  40                  45

Lys Asp Ser Tyr Leu Thr Leu Asp Glu Pro Met Asn Asn Ile Thr Thr
50                  55                  60

Ser Leu Gly Gln Thr Ala Glu Leu His Cys Lys Val Ser Gly Asn Pro
65                  70                  75                  80

Pro Pro Thr Ile Arg Trp Phe Lys Asn Asp Ala Pro Val Val Gln Glu
                85                  90                  95

Pro Arg Arg Leu Ser Phe Arg Ser Thr Ile Tyr Gly Ser Arg Leu Arg
            100                 105                 110

Ile Arg Asn Leu Asp Thr Thr Asp Thr Gly Tyr Phe Gln Cys Val Ala
        115                 120                 125

Thr Asn Gly Lys Glu Val Val Ser Ser Thr Gly Val Leu Phe Val Lys
130                 135                 140

Phe Gly Lys Asp Glu Tyr Glu Glu Asp Gly Phe Cys Gln Pro Tyr Arg
145                 150                 155                 160

Gly Ile Ala Cys Ala Arg Phe Ile Gly Asn Arg Thr Val Tyr Met Glu
                165                 170                 175

Ser Leu His Met Gln Gly Glu Ile Glu Asn Gln Ile Thr Ala Ala Phe
            180                 185                 190

Thr Met Ile Gly Thr Ser Ser His Leu Ser Asp Lys Cys Ser Gln Phe
        195                 200                 205

Ala Ile Pro Ser Leu Cys His Tyr Ala Phe Pro Tyr Cys Asp Glu Thr
210                 215                 220

Ser Ser Val Pro Lys Pro Arg Asp Leu Cys Arg Asp Glu Cys Glu Ile
225                 230                 235                 240

Leu Glu Asn Val Leu Cys Gln Thr Glu Tyr Ile Phe Ala Arg Ser Asn
                245                 250                 255

Pro Met Ile Leu Met Arg Leu Lys Leu Pro Asn Cys Glu Asp Leu Pro
            260                 265                 270

Gln Pro Glu Ser Pro Glu Ala Ala Asn Cys Ile Arg Ile Gly Ile Pro
        275                 280                 285

Met Ala Asp Pro Ile Asn Lys Asn His Lys Cys Tyr Asn Ser Thr Gly
290                 295                 300

Val Asp Tyr Arg Gly Thr Val Ser Val Thr Lys Ser Gly Arg Gln Cys
305                 310                 315                 320
```

-continued

```
Gln Pro Trp Asn Ser Gln Tyr Pro His Thr His Thr Phe Thr Ala Leu
            325                 330                 335

Arg Phe Pro Glu Leu Asn Gly Gly His Ser Tyr Cys Arg Asn Pro Gly
            340                 345                 350

Asn Gln Lys Glu Ala Pro Trp Cys Phe Thr Leu Asp Glu Asn Phe Lys
            355                 360                 365

Ser Asp Leu Cys Asp Ile Pro Ala Cys Asp Ser Lys Asp Ser Lys Glu
    370                 375                 380

Lys Asn Lys Met Glu Ile Leu Tyr Ile Leu Val Pro Ser Val Ala Ile
385                 390                 395                 400

Pro Leu Ala Ile Ala Leu Leu Phe Phe Ile Cys Val Cys Arg Asn
            405                 410                 415

Asn Gln Lys Ser Ser Ser Pro Val Gln Arg Gln Pro Lys His Val
            420                 425                 430

Arg Gly Gln Asn Val Glu Met Ser Met Leu Asn Ala Tyr Lys Pro Lys
            435                 440                 445

Ser Lys Ala Lys Glu Leu Pro Leu Ser Ala Val Arg Phe Met Glu Glu
    450                 455                 460

Leu Gly Glu Cys Ala Phe Gly Lys Ile Tyr Lys Gly His Leu Tyr Leu
465                 470                 475                 480

Pro Gly Met Asp His Ala Gln Leu Val Ala Ile Lys Thr Leu Lys Asp
            485                 490                 495

Tyr Asn Asn Pro Gln Gln Trp Thr Glu Phe Gln Gln Glu Ala Ser Leu
            500                 505                 510

Met Ala Glu Leu His His Pro Asn Ile Val Cys Leu Leu Gly Ala Val
            515                 520                 525

Thr Gln Glu Gln Pro Val Cys Met Leu Phe Glu Tyr Met Asn Gln Gly
            530                 535                 540

Asp Leu His Glu Phe Leu Ile Met Arg Ser Pro His Ser Asp Val Gly
545                 550                 555                 560

Cys Ser Ser Asp Glu Asp Gly Thr Val Lys Ser Ser Leu Asp His Gly
            565                 570                 575

Asp Phe Leu His Ile Ala Ile Gln Ile Ala Ala Gly Met Glu Tyr Leu
            580                 585                 590

Ser Ser His Phe Phe Val His Lys Asp Leu Ala Ala Arg Asn Ile Leu
            595                 600                 605

Ile Gly Glu Gln Leu His Val Lys Ile Ser Asp Leu Gly Leu Ser Arg
610                 615                 620

Glu Ile Tyr Ser Ala Asp Tyr Tyr Arg Val Gln Ser Lys Ser Leu Leu
625                 630                 635                 640

Pro Ile Arg Trp Met Pro Pro Glu Ala Ile Met Tyr Gly Lys Phe Ser
            645                 650                 655

Ser Asp Ser Asp Ile Trp Ser Phe Gly Val Val Leu Trp Glu Ile Phe
            660                 665                 670

Ser Phe Gly Leu Gln Pro Tyr Tyr Gly Phe Ser Asn Gln Glu Val Ile
            675                 680                 685

Glu Met Val Arg Lys Arg Gln Leu Leu Pro Cys Ser Glu Asp Cys Pro
690                 695                 700

Pro Arg Met Tyr Ser Leu Met Thr Glu Cys Trp Asn Glu Ile Pro Ser
705                 710                 715                 720

Arg Arg Pro Arg Phe Lys Asp Ile His Val Arg Leu Arg Ser Trp Glu
            725                 730                 735
```

Gly Leu Ser Ser His Thr Ser Ser Thr Pro Ser Gly Gly Asn Ala
            740                 745                 750

Thr Thr Gln Thr Thr Ser Leu Ser Ala Ser Pro Val Ser Asn Leu Ser
        755                 760                 765

Asn Pro Arg Tyr Pro Asn Tyr Ile Phe Pro Ser Gln Gly Ile Thr Pro
    770                 775                 780

Gln Gly Gln Ile Ala Gly Phe Ile Gly Pro Ile Pro Gln Asn Gln
785                 790                 795                 800

Arg Phe Ile Pro Ile Asn Gly Tyr Pro Ile Pro Gly Tyr Ala Ala
                805                 810                 815

Phe Pro Ala Ala His Tyr Gln Pro Thr Gly Pro Pro Arg Val Ile Gln
            820                 825                 830

His Cys Pro Pro Pro Lys Ser Arg Ser Pro Ser Ser Ala Ser Gly Ser
        835                 840                 845

Thr Ser Thr Gly His Val Thr Ser Leu Pro Ser Ser Gly Ser Asn Gln
    850                 855                 860

Glu Ala Asn Ile Pro Leu Leu Pro His Met Ser Ile Pro Asn His Pro
865                 870                 875                 880

Gly Gly Met Gly Ile Thr Val Phe Gly Asn Lys Ser Gln Lys Pro Tyr
                885                 890                 895

Lys Ile Asp Ala Lys Gln Ala Ser Leu Leu Gly Asp Ala Asn Ile His
            900                 905                 910

Gly His Thr Glu Ser Met Ile Ser Ala Glu Leu
        915                 920

<210> SEQ ID NO 218
<211> LENGTH: 882
<212> TYPE: PRT
<213> ORGANISM: macaca fasicularis
<220> FEATURE:
<221> NAME/KEY: MISC_FEATURE
<223> OTHER INFORMATION: ROR1 (Uniprot A0A2K5WTX4)

<400> SEQUENCE: 218

Ser Tyr Leu Thr Leu Asp Glu Pro Met Asn Asn Ile Thr Thr Ser Leu
1               5                   10                  15

Gly Gln Thr Ala Glu Leu His Cys Lys Val Ser Gly Asn Pro Pro Pro
            20                  25                  30

Thr Ile Arg Trp Phe Lys Asn Asp Ala Pro Val Val Gln Glu Pro Arg
        35                  40                  45

Arg Leu Ser Phe Arg Ser Thr Ile Tyr Gly Ser Arg Leu Arg Ile Arg
    50                  55                  60

Asn Leu Asp Thr Thr Asp Thr Gly Tyr Phe Gln Cys Val Ala Thr Asn
65                  70                  75                  80

Gly Lys Glu Val Val Ser Ser Thr Gly Val Leu Phe Val Lys Phe Gly
                85                  90                  95

Pro Pro Pro Thr Ala Ser Pro Gly Tyr Ser Asp Glu Tyr Glu Asp
            100                 105                 110

Gly Phe Cys Gln Pro Tyr Arg Gly Ile Ala Cys Ala Arg Phe Ile Gly
        115                 120                 125

Asn Arg Thr Val Tyr Met Glu Ser Leu His Met Gln Gly Glu Ile Glu
    130                 135                 140

Asn Gln Ile Thr Ala Ala Phe Thr Met Ile Gly Thr Ser Ser His Leu
145                 150                 155                 160

Ser Asp Lys Cys Ser Gln Phe Ala Ile Pro Ser Leu Cys His Tyr Ala
                165                 170                 175

```
Phe Pro Tyr Cys Asp Glu Thr Ser Ser Val Pro Lys Pro Arg Asp Leu
            180                 185                 190

Cys Arg Asp Glu Cys Glu Ile Leu Glu Asn Val Leu Cys Gln Thr Glu
        195                 200                 205

Tyr Ile Phe Ala Arg Ser Asn Pro Met Ile Leu Met Arg Leu Lys Leu
    210                 215                 220

Pro Asn Cys Glu Asp Leu Pro Gln Pro Glu Ser Pro Glu Ala Ala Asn
225                 230                 235                 240

Cys Ile Arg Ile Gly Ile Pro Met Ala Asp Pro Ile Asn Lys Asn His
                245                 250                 255

Lys Cys Tyr Asn Ser Thr Gly Val Asp Tyr Arg Gly Thr Val Ser Val
            260                 265                 270

Thr Lys Ser Gly Arg Gln Cys Gln Pro Trp Asn Ser Gln Tyr Pro His
        275                 280                 285

Thr His Thr Phe Thr Ala Leu Arg Phe Pro Glu Leu Asn Gly Gly His
    290                 295                 300

Ser Tyr Cys Arg Asn Pro Gly Asn Gln Lys Glu Ala Pro Trp Cys Phe
305                 310                 315                 320

Thr Leu Asp Glu Asn Phe Lys Ser Asp Leu Cys Asp Ile Pro Ala Cys
                325                 330                 335

Asp Ser Lys Asp Ser Lys Glu Lys Asn Lys Met Glu Ile Leu Tyr Ile
            340                 345                 350

Leu Val Pro Ser Val Ala Ile Pro Leu Ala Ile Ala Leu Leu Phe Phe
        355                 360                 365

Phe Ile Cys Val Cys Arg Asn Asn Gln Lys Ser Ser Ser Pro Pro Val
    370                 375                 380

Gln Arg Gln Pro Lys His Val Arg Gly Gln Asn Val Glu Met Ser Met
385                 390                 395                 400

Leu Asn Ala Tyr Lys Pro Lys Ser Lys Ala Lys Glu Leu Pro Leu Ser
                405                 410                 415

Ala Val Arg Phe Met Glu Glu Leu Gly Glu Cys Ala Phe Gly Lys Ile
            420                 425                 430

Tyr Lys Gly His Leu Tyr Leu Pro Gly Met Asp His Ala Gln Leu Val
        435                 440                 445

Ala Ile Lys Thr Leu Lys Asp Tyr Asn Asn Pro Gln Gln Trp Thr Glu
    450                 455                 460

Phe Gln Gln Glu Ala Ser Leu Met Ala Glu Leu His Pro Asn Ile
465                 470                 475                 480

Val Cys Leu Leu Gly Ala Val Thr Gln Glu Gln Pro Val Cys Met Leu
                485                 490                 495

Phe Glu Tyr Met Asn Gln Gly Asp Leu His Glu Phe Leu Ile Met Arg
            500                 505                 510

Ser Pro His Ser Asp Val Gly Cys Ser Ser Asp Glu Asp Gly Thr Val
        515                 520                 525

Lys Ser Ser Leu Asp His Gly Asp Phe Leu His Ile Ala Ile Gln Ile
    530                 535                 540

Ala Ala Gly Met Glu Tyr Leu Ser Ser His Phe Phe Val His Lys Asp
545                 550                 555                 560

Leu Ala Ala Arg Asn Ile Leu Ile Gly Glu Gln Leu His Val Lys Ile
                565                 570                 575

Ser Asp Leu Gly Leu Ser Arg Glu Ile Tyr Ser Ala Asp Tyr Tyr Arg
            580                 585                 590
```

```
Val Gln Ser Lys Ser Leu Leu Pro Ile Arg Trp Met Pro Glu Ala
            595                 600                 605
Ile Met Tyr Gly Lys Phe Ser Ser Asp Ser Asp Ile Trp Ser Phe Gly
610                 615                 620
Val Val Leu Trp Glu Ile Phe Ser Phe Gly Leu Gln Pro Tyr Tyr Gly
625                 630                 635                 640
Phe Ser Asn Gln Glu Val Ile Glu Met Val Arg Lys Arg Gln Leu Leu
                645                 650                 655
Pro Cys Ser Glu Asp Cys Pro Arg Met Tyr Ser Leu Met Thr Glu
            660                 665                 670
Cys Trp Asn Glu Ile Pro Ser Arg Arg Pro Arg Phe Lys Asp Ile His
            675                 680                 685
Val Arg Leu Arg Ser Trp Glu Gly Leu Ser Ser His Thr Ser Ser Thr
690                 695                 700
Thr Pro Ser Gly Gly Asn Ala Thr Thr Gln Thr Thr Ser Leu Ser Ala
705                 710                 715                 720
Ser Pro Val Ser Asn Leu Ser Asn Pro Arg Tyr Pro Asn Tyr Ile Phe
                725                 730                 735
Pro Ser Gln Gly Ile Thr Pro Gln Gly Gln Ile Ala Gly Phe Ile Gly
            740                 745                 750
Pro Pro Ile Pro Gln Asn Gln Arg Phe Ile Pro Ile Asn Gly Tyr Pro
            755                 760                 765
Ile Pro Pro Gly Tyr Ala Ala Phe Pro Ala Ala His Tyr Gln Pro Thr
770                 775                 780
Gly Pro Pro Arg Val Ile Gln His Cys Pro Pro Lys Ser Arg Ser
785                 790                 795                 800
Pro Ser Ser Ala Ser Gly Ser Thr Ser Thr Gly His Val Thr Ser Leu
                805                 810                 815
Pro Ser Ser Gly Ser Asn Gln Glu Ala Asn Ile Pro Leu Leu Pro His
            820                 825                 830
Met Ser Ile Pro Asn His Pro Gly Gly Met Gly Ile Thr Val Phe Gly
            835                 840                 845
Asn Lys Ser Gln Lys Pro Tyr Lys Ile Asp Ala Lys Gln Ala Ser Leu
850                 855                 860
Leu Gly Asp Ala Asn Ile His Gly His Thr Glu Ser Met Ile Ser Ala
865                 870                 875                 880
Glu Leu
```

<210> SEQ ID NO 219
<211> LENGTH: 937
<212> TYPE: PRT
<213> ORGANISM: mus musculus
<220> FEATURE:
<221> NAME/KEY: MISC_FEATURE
<223> OTHER INFORMATION: ROR1 (Uniprot Q9Z139)

<400> SEQUENCE: 219

```
Met His Arg Pro Arg Arg Arg Gly Thr Arg Pro Pro Leu Ala Leu
1               5                   10                  15
Leu Ala Leu Leu Leu Ala Ala Arg Gly Ala Asp Ala Gln Glu Thr
            20                  25                  30
Glu Leu Ser Val Ser Ala Glu Leu Val Pro Thr Ser Ser Trp Asn
            35                  40                  45
Ser Ser Glu Ile Asp Lys Gly Ser Tyr Leu Thr Leu Asp Glu Pro Met
50                  55                  60
```

-continued

```
Asn Asn Ile Thr Thr Ser Leu Gly Gln Thr Ala Glu Leu His Cys Lys
 65                  70                  75                  80

Val Ser Gly Asn Pro Pro Ser Ile Arg Trp Phe Lys Asn Asp Ala
                 85                  90                  95

Pro Val Val Gln Glu Pro Arg Arg Ile Ser Phe Arg Ala Thr Asn Tyr
                100                 105                 110

Gly Ser Arg Leu Arg Ile Arg Asn Leu Asp Thr Thr Asp Thr Gly Tyr
                115                 120                 125

Phe Gln Cys Val Ala Thr Asn Gly Lys Lys Val Val Ser Thr Thr Gly
            130                 135                 140

Val Leu Phe Val Lys Phe Gly Pro Pro Thr Ala Ser Pro Gly Ser
145                 150                 155                 160

Ser Asp Glu Tyr Glu Glu Asp Gly Phe Cys Gln Pro Tyr Arg Gly Ile
                165                 170                 175

Ala Cys Ala Arg Phe Ile Gly Asn Arg Thr Val Tyr Met Glu Ser Leu
            180                 185                 190

His Met Gln Gly Glu Ile Glu Asn Gln Ile Thr Ala Ala Phe Thr Met
            195                 200                 205

Ile Gly Thr Ser Ser His Leu Ser Asp Lys Cys Ser Gln Phe Ala Ile
210                 215                 220

Pro Ser Leu Cys His Tyr Ala Phe Pro Tyr Cys Asp Glu Thr Ser Ser
225                 230                 235                 240

Val Pro Lys Pro Arg Asp Leu Cys Arg Asp Glu Cys Glu Val Leu Glu
                245                 250                 255

Asn Val Leu Cys Gln Thr Glu Tyr Ile Phe Ala Arg Ser Asn Pro Met
            260                 265                 270

Ile Leu Met Arg Leu Lys Leu Pro Asn Cys Glu Asp Leu Pro Gln Pro
            275                 280                 285

Glu Ser Pro Glu Ala Ala Asn Cys Ile Arg Ile Gly Ile Pro Met Ala
            290                 295                 300

Asp Pro Ile Asn Lys Asn His Lys Cys Tyr Asn Ser Thr Gly Val Asp
305                 310                 315                 320

Tyr Arg Gly Thr Val Ser Val Thr Lys Ser Gly Arg Gln Cys Gln Pro
                325                 330                 335

Trp Asn Ser Gln Tyr Pro His Thr His Ser Phe Thr Ala Leu Arg Phe
                340                 345                 350

Pro Glu Leu Asn Gly Gly His Ser Tyr Cys Arg Asn Pro Gly Asn Gln
                355                 360                 365

Lys Glu Ala Pro Trp Cys Phe Thr Leu Asp Glu Asn Phe Lys Ser Asp
370                 375                 380

Leu Cys Asp Ile Pro Ala Cys Asp Ser Lys Asp Ser Lys Glu Lys Asn
385                 390                 395                 400

Lys Met Glu Ile Leu Tyr Ile Leu Val Pro Ser Val Ala Ile Pro Leu
                405                 410                 415

Ala Ile Ala Phe Leu Phe Phe Ile Cys Val Cys Arg Asn Asn Gln
                420                 425                 430

Lys Ser Ser Ser Pro Pro Val Gln Arg Gln Pro Lys Pro Val Arg Gly
            435                 440                 445

Gln Asn Val Glu Met Ser Met Leu Asn Ala Tyr Lys Pro Lys Ser Lys
            450                 455                 460

Ala Lys Glu Leu Pro Leu Ser Ala Val Arg Phe Met Glu Glu Leu Gly
465                 470                 475                 480
```

-continued

Glu Cys Thr Phe Gly Lys Ile Tyr Lys Gly His Leu Tyr Leu Pro Gly
                485                 490                 495

Met Asp His Ala Gln Leu Val Ala Ile Lys Thr Leu Lys Asp Tyr Asn
            500                 505                 510

Asn Pro Gln Gln Trp Thr Glu Phe Gln Gln Glu Ala Ser Leu Met Ala
        515                 520                 525

Glu Leu His His Pro Asn Ile Val Cys Leu Leu Gly Ala Val Thr Gln
    530                 535                 540

Glu Gln Pro Val Cys Met Leu Phe Glu Tyr Met Asn Gln Gly Asp Leu
545                 550                 555                 560

His Glu Phe Leu Ile Met Arg Ser Pro His Ser Asp Val Gly Cys Ser
                565                 570                 575

Ser Asp Glu Asp Gly Thr Val Lys Ser Ser Leu Asp His Gly Asp Phe
            580                 585                 590

Leu His Ile Ala Ile Gln Ile Ala Ala Gly Met Glu Tyr Leu Ser Ser
        595                 600                 605

His Phe Phe Val His Lys Asp Leu Ala Ala Arg Asn Ile Leu Ile Gly
    610                 615                 620

Glu Gln Leu His Val Lys Ile Ser Asp Leu Gly Leu Ser Arg Glu Ile
625                 630                 635                 640

Tyr Ser Ala Asp Tyr Tyr Arg Val Gln Ser Lys Ser Ser Leu Pro Ile
                645                 650                 655

Arg Trp Met Pro Pro Glu Ala Ile Met Tyr Gly Lys Phe Ser Ser Asp
            660                 665                 670

Ser Asp Ile Trp Ser Phe Gly Val Leu Trp Glu Ile Phe Ser Phe
        675                 680                 685

Gly Leu Gln Pro Tyr Tyr Gly Phe Ser Asn Gln Glu Val Ile Glu Met
    690                 695                 700

Val Arg Lys Arg Gln Leu Leu Pro Cys Ser Glu Asp Cys Pro Pro Arg
705                 710                 715                 720

Met Tyr Ser Leu Met Thr Glu Cys Trp Asn Glu Ile Pro Ser Arg Arg
                725                 730                 735

Pro Arg Phe Lys Asp Ile His Val Arg Leu Arg Ser Trp Glu Gly Leu
            740                 745                 750

Ser Ser His Thr Ser Ser Thr Thr Pro Ser Gly Gly Asn Ala Thr Thr
        755                 760                 765

Gln Thr Thr Ser Leu Ser Ala Ser Pro Val Ser Asn Leu Ser Asn Pro
    770                 775                 780

Arg Phe Pro Asn Tyr Met Phe Pro Ser Gln Gly Ile Thr Pro Gln Gly
785                 790                 795                 800

Gln Ile Ala Gly Phe Ile Gly Pro Ala Ile Pro Gln Asn Gln Arg Phe
                805                 810                 815

Ile Pro Ile Asn Gly Tyr Pro Ile Pro Pro Gly Tyr Ala Ala Phe Pro
            820                 825                 830

Ala Ala His Tyr Gln Pro Ala Gly Pro Pro Arg Val Ile Gln His Cys
        835                 840                 845

Pro Pro Pro Lys Ser Arg Ser Pro Ser Ser Ala Ser Gly Ser Thr Ser
850                 855                 860

Thr Gly His Val Ala Ser Leu Pro Ser Ser Gly Ser Asn Gln Glu Ala
865                 870                 875                 880

Asn Val Pro Leu Leu Pro His Met Ser Ile Pro Asn His Pro Gly Gly
                885                 890                 895

```
-continued

Met Gly Ile Thr Val Phe Gly Asn Lys Ser Gln Lys Pro Tyr Lys Ile
            900                 905                 910

Asp Ser Lys Gln Ser Ser Leu Leu Gly Asp Ser His Ile His Gly His
        915                 920                 925

Thr Glu Ser Met Ile Ser Ala Glu Val
    930                 935
```